US011185562B2

(12) United States Patent
Cook et al.

(10) Patent No.: US 11,185,562 B2
(45) Date of Patent: Nov. 30, 2021

(54) COMPOSITIONS AND METHODS FOR INHIBITION OF PATHOGENIC BACTERIAL GROWTH

(71) Applicant: Seres Therapeutics, Inc., Cambridge, MA (US)

(72) Inventors: David N. Cook, Brooklyn, NY (US); Han Zhang, Cambridge, MA (US); Anthony Mario D'Onofrio, Northborough, MA (US); David Arthur Berry, Brookline, MA (US); Mary-Jane Lombardo McKenzie, Arlington, MA (US); John Grant Aunins, Doylestown, PA (US); Gregory McKenzie, Arlington, MA (US); Toshiro K. Ohsumi, Cambridge, MA (US)

(73) Assignee: Seres Therapeutics, Inc., Cambridge, MA (US)

( * ) Notice: Subject to any disclaimer, the term of this patent is extended or adjusted under 35 U.S.C. 154(b) by 324 days.

(21) Appl. No.: 14/765,814

(22) PCT Filed: Feb. 4, 2014

(86) PCT No.: PCT/US2014/014744
§ 371 (c)(1),
(2) Date: Aug. 4, 2015

(87) PCT Pub. No.: WO2014/121301
PCT Pub. Date: Aug. 7, 2014

(65) Prior Publication Data
US 2016/0243172 A1 Aug. 25, 2016

Related U.S. Application Data

(60) Provisional application No. 61/760,574, filed on Feb. 4, 2013, provisional application No. 61/760,584, filed on Feb. 4, 2013, provisional application No. 61/760,585, filed on Feb. 4, 2013, provisional application No. 61/760,606, filed on Feb. 4, 2013, provisional application No. 61/926,918, filed on Jan. 13, 2014.

(51) Int. Cl.
A61K 35/741 (2015.01)
A61K 35/742 (2015.01)
A61K 9/00 (2006.01)
A61K 45/06 (2006.01)
A61K 9/48 (2006.01)
C12N 1/20 (2006.01)
A61K 35/74 (2015.01)
A61K 35/744 (2015.01)
A61K 35/745 (2015.01)
A61K 35/747 (2015.01)
A61K 35/37 (2015.01)

(52) U.S. Cl.
CPC .......... A61K 35/741 (2013.01); A61K 9/0053 (2013.01); A61K 9/48 (2013.01); A61K 9/4816 (2013.01); A61K 35/37 (2013.01); A61K 35/74 (2013.01); A61K 35/742 (2013.01); A61K 35/744 (2013.01); A61K 35/745 (2013.01); A61K 35/747 (2013.01); A61K 45/06 (2013.01); C12N 1/20 (2013.01); Y02A 50/30 (2018.01)

(58) Field of Classification Search
None
See application file for complete search history.

(56) References Cited

U.S. PATENT DOCUMENTS

| | | | |
|---|---|---|---|
| 3,009,861 | A | 11/1961 | Alderton et al. |
| 3,009,864 | A | 11/1961 | Gordon-Aldterton et al. |
| 3,228,838 | A | 1/1966 | Rinfret |
| 3,608,030 | A | 11/1971 | Grant |
| 4,077,227 | A | 3/1978 | Larson |
| 4,205,132 | A | 5/1980 | Sandine |
| 4,655,047 | A | 4/1987 | Temple |
| 4,689,226 | A | 8/1987 | Nurmi |
| 4,839,281 | A | 6/1989 | Gorbach et al. |
| 5,196,205 | A | 3/1993 | Borody |
| 5,425,951 | A | 6/1995 | Goodrich |
| 5,436,002 | A | 7/1995 | Payne |
| 5,443,826 | A | 8/1995 | Borody |
| 5,599,795 | A | 2/1997 | McCann |
| 5,648,206 | A | 7/1997 | Goodrich |

(Continued)

FOREIGN PATENT DOCUMENTS

| | | |
|---|---|---|
| CN | 102131928 A | 7/2011 |
| CN | 102940652 A | 2/2013 |

(Continued)

OTHER PUBLICATIONS

Wilson et al. Infect. Immunol. 1988, vol. 56, No. 10, pp. 2610-2614.*

(Continued)

Primary Examiner — Vera Afremova
(74) Attorney, Agent, or Firm — Sterne, Kessler, Goldstein & Fox P.L.L.C.

(57) ABSTRACT

Compositions for methods of preventing or reducing pathogenic bacterial growth, proliferation, and/or colonization are described containing one or more types of non-pathogenic bacteria to be introduced into the gastrointestinal tract and effectively compete with pathogenic bacteria for monomeric or polymeric carbohydrate nutrients, and/or amino acid nutrients, and/or vitamin nutrients.

16 Claims, 46 Drawing Sheets
Specification includes a Sequence Listing.

(56) References Cited

U.S. PATENT DOCUMENTS

| | | | |
|---|---|---|---|
| 5,951,977 A | 9/1999 | Nisbet et al. | |
| 5,965,128 A | 10/1999 | Doyle et al. | |
| 6,589,771 B1 | 7/2003 | Marshall | |
| 6,645,530 B1 | 11/2003 | Borody | |
| 7,326,551 B2 | 2/2008 | Maupin-Furlow et al. | |
| 7,427,398 B2 | 9/2008 | Baillon et al. | |
| 7,628,982 B2 | 12/2009 | Klaviniskis | |
| 7,632,520 B2 | 12/2009 | Khandelwal | |
| 7,708,988 B2 | 5/2010 | Farmer | |
| 7,731,976 B2 | 6/2010 | Cobb | |
| 7,763,420 B2 | 7/2010 | Stritzker et al. | |
| 7,981,411 B2 | 7/2011 | Nadeau et al. | |
| 7,998,473 B2 | 8/2011 | Boileau et al. | |
| 8,021,654 B2 | 9/2011 | Rehberger et al. | |
| 8,034,601 B2 | 10/2011 | Boileau | |
| 8,039,006 B2 | 10/2011 | Prato | |
| 8,147,482 B2 | 4/2012 | Shimizu | |
| 8,187,590 B2 | 5/2012 | Farmer | |
| 8,236,508 B2 | 8/2012 | Mutharasan | |
| 8,388,996 B2 | 3/2013 | Gehling | |
| 8,460,648 B2 * | 6/2013 | Borody | A61K 35/741 424/184.1 |
| 8,906,668 B2 | 12/2014 | Henn et al. | |
| 8,968,721 B2 * | 3/2015 | Harel | A23L 33/135 424/93.1 |
| 9,011,834 B1 | 4/2015 | McKenzie et al. | |
| 9,028,841 B2 | 5/2015 | Henn et al. | |
| 9,180,147 B2 | 11/2015 | McKenzie et al. | |
| 9,408,872 B2 | 8/2016 | Borody | |
| 9,446,080 B2 | 9/2016 | McKenzie et al. | |
| 9,610,307 B2 | 4/2017 | Berry et al. | |
| 9,808,519 B2 | 11/2017 | Honda et al. | |
| 10,238,694 B2 * | 3/2019 | Honda | A61K 45/06 |
| 10,258,655 B2 | 4/2019 | Henn et al. | |
| 2001/0036453 A1 | 11/2001 | Reid | |
| 2004/0028689 A1 * | 2/2004 | Borody | A61K 35/741 424/184.1 |
| 2004/0170617 A1 | 9/2004 | Finegold | |
| 2005/0048515 A1 | 3/2005 | Garner | |
| 2005/0180962 A1 | 8/2005 | Raz | |
| 2006/0046246 A1 | 3/2006 | Zeng et al. | |
| 2006/0067924 A1 | 3/2006 | Lee et al. | |
| 2006/0188523 A1 | 8/2006 | Pei | |
| 2006/0233830 A1 | 10/2006 | Wong | |
| 2007/0141139 A1 | 6/2007 | Vandenberg | |
| 2008/0213752 A1 | 9/2008 | Stave et al. | |
| 2009/0197249 A1 | 8/2009 | Gillevet | |
| 2010/0074872 A1 | 3/2010 | Blaser et al. | |
| 2010/0215745 A1 | 8/2010 | Lazzari et al. | |
| 2011/0081320 A1 | 4/2011 | Westall et al. | |
| 2011/0113863 A1 | 5/2011 | Fuhrmann et al. | |
| 2011/0189132 A1 | 8/2011 | Garner et al. | |
| 2011/0280840 A1 | 11/2011 | Blaser | |
| 2011/0280847 A1 | 11/2011 | Sorg et al. | |
| 2012/0020950 A1 | 1/2012 | Davis et al. | |
| 2012/0021429 A1 | 1/2012 | Rublee | |
| 2012/0021921 A1 | 1/2012 | Scott | |
| 2012/0058094 A1 | 3/2012 | Blaser | |
| 2012/0064592 A1 | 3/2012 | O'Mullan et al. | |
| 2012/0128633 A1 | 5/2012 | Veiga et al. | |
| 2012/0128634 A1 | 5/2012 | Veiga | |
| 2012/0148629 A1 | 6/2012 | Holvoet et al. | |
| 2012/0149584 A1 | 6/2012 | Olle | |
| 2012/0165215 A1 | 6/2012 | Andersen | |
| 2012/0177650 A1 | 7/2012 | Borody | |
| 2012/0207726 A1 | 8/2012 | Lipkin | |
| 2012/0238468 A1 | 9/2012 | Tuk | |
| 2012/0264637 A1 | 10/2012 | Brodie | |
| 2012/0276149 A1 | 11/2012 | Littman | |
| 2012/0276201 A1 | 11/2012 | Trachtman | |
| 2012/0315249 A1 | 12/2012 | Olmstead | |
| 2013/0017999 A1 | 1/2013 | Fremont | |
| 2013/0022575 A1 | 1/2013 | Cassity | |
| 2013/0045274 A1 | 2/2013 | Hlavka | |
| 2013/0045874 A1 | 2/2013 | Ehrlich | |
| 2013/0065862 A1 | 3/2013 | Johnson et al. | |
| 2013/0115232 A1 | 5/2013 | Ferrara et al. | |
| 2013/0121968 A1 | 5/2013 | Quay | |
| 2013/0149339 A1 | 6/2013 | Honda | |
| 2013/0149375 A1 | 6/2013 | Geall | |
| 2013/0195820 A1 | 8/2013 | Wacklin et al. | |
| 2013/0266539 A1 | 10/2013 | Borody | |
| 2014/0045744 A1 | 2/2014 | Gordon | |
| 2014/0135398 A1 | 5/2014 | Matar et al. | |
| 2014/0147417 A1 | 5/2014 | Sadowsky et al. | |
| 2014/0147425 A1 | 5/2014 | Henn et al. | |
| 2014/0199281 A1 | 7/2014 | Henn et al. | |
| 2014/0328803 A1 | 11/2014 | McKenzie et al. | |
| 2014/0341921 A1 | 11/2014 | Honda et al. | |
| 2014/0342438 A1 | 11/2014 | Allen-Vercoe et al. | |
| 2014/0363397 A1 * | 12/2014 | Allen-Vercoe | A61K 35/745 424/93.3 |
| 2015/0011415 A1 | 1/2015 | Levin et al. | |
| 2015/0093360 A1 | 4/2015 | McKenzie et al. | |
| 2015/0190435 A1 | 7/2015 | Henn et al. | |
| 2016/0271188 A1 | 9/2016 | Berry et al. | |
| 2017/0165302 A1 | 6/2017 | Henn et al. | |

FOREIGN PATENT DOCUMENTS

| | | |
|---|---|---|
| DE | 102006062250 A1 | 6/2008 |
| EA | 006847 B1 | 4/2006 |
| EP | 0033584 A3 | 1/1981 |
| EP | 0446069 A1 | 9/1991 |
| EP | 0456418 A2 | 11/1991 |
| EP | 0433299 A4 | 4/1992 |
| EP | 1107772 B1 | 4/2006 |
| EP | 1631312 B1 | 9/2008 |
| EP | 2337569 A2 | 6/2011 |
| EP | 2338989 A1 | 6/2011 |
| EP | 2519108 A1 | 11/2012 |
| EP | 2684469 A1 | 1/2014 |
| EP | 0479820 B1 | 7/2014 |
| EP | 2626076 A1 | 8/2014 |
| EP | 2750682 B1 | 5/2016 |
| JP | 6-56679 A | 3/1994 |
| JP | 2007-332083 A | 12/2007 |
| JP | 2010-539179 T | 12/2010 |
| JP | 5 019563 B2 | 9/2012 |
| RU | 2035186 C1 | 5/1995 |
| RU | 2439145 C2 | 1/2012 |
| WO | WO 90/01335 A1 | 2/1990 |
| WO | WO 1997/008598 A1 | 4/1994 |
| WO | WO-9408598 A1 | 4/1994 |
| WO | WO 1997/009886 A1 | 3/1997 |
| WO | WO 98/26787 A1 | 6/1998 |
| WO | WO 2000/010582 A2 | 3/2000 |
| WO | WO 01/93904 A1 | 12/2001 |
| WO | WO 2002/007741 A1 | 1/2002 |
| WO | WO 02/43649 A2 | 6/2002 |
| WO | WO 2005/017095 A2 | 2/2005 |
| WO | WO 2005/110445 A2 | 11/2005 |
| WO | WO 2006/012586 A2 | 2/2006 |
| WO | WO 2007/036230 A1 | 4/2007 |
| WO | WO 2007/136553 A2 | 11/2007 |
| WO | WO 2008/076696 A2 | 6/2008 |
| WO | WO 2008/083157 A2 | 7/2008 |
| WO | WO 2010/030997 A1 | 3/2010 |
| WO | WO 2010/062369 A2 | 6/2010 |
| WO | WO 2010/124387 A2 | 11/2010 |
| WO | WO 2010/151842 A2 | 12/2010 |
| WO | WO 2011/005756 A1 | 1/2011 |
| WO | WO 2011/022542 A2 | 2/2011 |
| WO | WO 2011022660 A1 | 2/2011 |
| WO | WO 2011/033310 A1 | 3/2011 |
| WO | WO 2011/043654 A1 | 4/2011 |
| WO | WO 2011/046616 A3 | 4/2011 |
| WO | WO 2011/060123 A1 | 5/2011 |
| WO | WO 2011/094027 A1 | 8/2011 |
| WO | WO 2011/103123 A2 | 8/2011 |
| WO | WO 2011/107482 A2 | 9/2011 |
| WO | WO 2011/113801 A1 | 9/2011 |
| WO | WO 2011107481 A2 | 9/2011 |
| WO | WO 2011/152566 A2 | 12/2011 |

(56) References Cited

FOREIGN PATENT DOCUMENTS

| | | |
|---|---|---|
| WO | WO 2012/009712 A2 | 1/2012 |
| WO | WO 2012/016287 A2 | 2/2012 |
| WO | WO 2012/033814 A2 | 3/2012 |
| WO | WO 2012/045150 A1 | 4/2012 |
| WO | WO 2012/064981 A2 | 5/2012 |
| WO | WO 2012/108830 A1 | 8/2012 |
| WO | WO 2012/116289 A2 | 8/2012 |
| WO | WO 2012/122478 A1 | 9/2012 |
| WO | WO 2012/122522 A2 | 9/2012 |
| WO | WO 2012/142605 A1 | 10/2012 |
| WO | WO 2012/148991 A1 | 11/2012 |
| WO | WO 2012/159023 A2 | 11/2012 |
| WO | WO 2013/016636 A1 | 1/2013 |
| WO | WO 2013/019896 A1 | 2/2013 |
| WO | WO 2013/032328 A1 | 3/2013 |
| WO | WO 2013/037067 A1 | 3/2013 |
| WO | WO 2013/037068 A1 | 3/2013 |
| WO | WO 2013/050792 A1 | 4/2013 |
| WO | WO 2013/053836 A1 | 4/2013 |
| WO | WO 2013/080561 A1 | 6/2013 |
| WO | WO 2013/166031 A1 | 11/2013 |
| WO | WO 2013/171515 A1 | 11/2013 |
| WO | WO 2013/176774 A1 | 11/2013 |
| WO | WO 2013/177596 A2 | 11/2013 |
| WO | WO 2014/082050 A1 | 5/2014 |
| WO | WO 2015/095241 A2 | 6/2014 |
| WO | WO 2014/121298 A2 | 8/2014 |
| WO | WO 2014/121301 A1 | 8/2014 |
| WO | WO 2014/121302 A2 | 8/2014 |
| WO | WO 2014/121304 A1 | 8/2014 |
| WO | WO 2014/145958 A2 | 9/2014 |
| WO | WO 2014/153194 A2 | 9/2014 |
| WO | WO 2014/177667 A1 | 11/2014 |
| WO | WO 2015/077794 A1 | 5/2015 |
| WO | WO-2017091783 A2 | 6/2017 |
| WO | WO-2017160711 A1 | 9/2017 |
| WO | WO 2008/077614 A2 | 7/2018 |
| WO | WO-2019089643 A1 | 5/2019 |

OTHER PUBLICATIONS

Yamaakawa et al. J Med. Microbiol. 1996, vol. 44, No. 2, pp. 111-114.*
Theriot et al. Nature Communications. Jan. 2014, 5:3114, DOI:10.1038/ncomms4114, pp. 1-10.*
Bergey's Manual of Determinative Bacteriology, 1994, pp. 527, 531, 577 and 579.*
Yuli Song et al. "*Clostridium bolteae* sp. nov., Isolated from Human Sources". System. Appl. Microbiol., 2003, 26, pp. 84-89.*
Cai-Xia Pei et al. Anaerobe, 2010, 16, pp. 426-432.*
Dezfulian, M. et al., "Selective Medium for Isolation of Clostridium botulinum from Human Feces," Journal of Clinical Microbiology, Mar. 1981, pp. 526-531, vol. 13, No. 3.
Dowell, V.R et al., "Coproexamination for Botulinal Toxin and Clostridium botulinum," JAMA, Oct. 24, 1977, pp. 1829-1832, vol. 238, No. 7.
Gupta, R.K. et al., "Differentiation Between Heat Resistance and Octyl Alcohol Resistance of the Cells of Bacillus Cereus T.," Biochemical and Biophysical Research Communications, 1970, pp. 23-30, vol. 38, No. 1.
Johnston, R. et al., "Method to Facilitate the Isolation of Clostridium botulinum Type E," J. Bacteriol., 1964, pp. 1521-1522, vol. 88.
Naaber P. et al., "Inhibition of *Clostridium difficile* Strains by Intestinal *Lactobacillus* Species" Journal of Medical Microbiology, 2004, pp. 551-554, vol. 53.
New Zealand Examination Report, New Zealand Application No. 709392, dated Jun. 9, 2016, 7 pages.
Russell, A.D., "The Destruction of Bacterial Spores," 1982, pp. 191-193.
Australian First Examination Report, Australian Application No. 2013347805, dated Apr. 13, 2017, 3 pages.

Chiu, C-H. et al., "Rapid Identification of *Salmonella serovars* in Feces by Specific Detection of Virulence Genes, invA and spvC, by an Enrichment Broth Culture-Multiplex PCR Combination Assay," Journal of Clinical Microbiology, Oct. 1996, pp. 2619-2622, vol. 34, No. 10.
Coleman, W.H., "Mechanism of Killing Spores of *Bacillus cereus* and *Bacillus megaterium* by Wet Heat," The Society for Applied Microbiology, Letters in Applied Microbiology, 2010. pp. 507-514, vol. 50.
Dendukuri, N., "Probiotic Therapy for the Prevention and Treatment of Clostridium Difficile—Associated Diarrhea: A Systematic Review," Canadian Medical Association Journal, Jul. 19, 2005, pp. 167-170, vol. 173, No. 2.
European Extended Search Report, European Application No. 14746341.8, dated Sep. 28, 2016, 10 pages.
European Partial Supplementary Report, European Application No. 14745792.3, dated Sep. 20, 2016, 11 pages.
European Partial Supplementary Report, European Application No. 14745749.3, dated Oct. 14, 2016, 6 pages.
European Extended Search Report, European Application No. 14746455.6, dated Nov. 24, 2016, 10 pages.
European Extended Search Report, European Application No. 14745792.3, dated Dec. 23, 2016, 17 pages.
European Extended Search Report, European Application No. 14745749.3, dated Jan. 23, 2017, 13 pages.
European Extended Search Report, European Application No. 13856249.1, dated Jan. 26, 2017, 19 pages.
Israel Office Action, Israel Application No. 238973, dated Apr. 20, 2017, 4 pages (with concise explanation of relevance).
Janda, J.M. et al., "16S rRNA Gene Sequencing for Bacterial Identification in the Diagnostic Laboratory: Pluses, Perils and Pitfalls," Journal of Clinical Microbiology, Sep. 2007, pp. 2761-2764, vol. 45, No. 9.
Johnson, S. et al., "Is Primary Prevention of Clostridium Difficile Infection Possible with Specific Probiotics?" International Journal of Infectious Diseases, Nov. 2012, pp. e786-e792, vol. 16, No. 11.
McFarland, L.V. et al., "Pharmaceutical Probiotics for the Treatment of Anaerobic and Other Infections," Anaerobe, Jan. 1997, pp. 73-78, vol. 3, No. 2-3.
New Zealand Third Examination Report, New Zealand Application No. 711771, dated Nov. 4, 2016, 4 pages.
Russian First Office Action, Russian Patent Application No. 2015124366, dated Dec. 13, 2016, 12 pages.
Russian Second Office Action, Russian Patent Application No. 2015137399, dated Mar. 14, 2017, 8 pages.
Setlow, B. et al., "Mechanisms of Killing Spores of *Bacillus subtilis* by Acid, Alkali and Ethanol," Journal of Applied Microbiology, 2002, pp. 362-375, vol. 92.
United States Office Action, U.S. Appl. No. 14/777,252, filed Nov. 3, 2016, 16 pages.
United States Office Action, U.S. Appl. No. 14/765,810, filed Jan. 23, 2017, 20 pages.
United States Office Action, U.S. Appl. No. 14/776,676, filed Mar. 23, 2017, 9 pages.
United States Office Action, U.S. Appl. No. 14/777,252, filed May 11, 2017, 9 pages.
Australian First Examination Report, Australian Application No. 2014232370, dated Oct. 19, 2017, 4 pages.
Australian First Examination Report, Australian Application No. 2014212004, dated Sep. 21, 2017, 6 pages.
Chinese First Office Action, Chinese Application No. 201480019395.8, dated Jul. 17, 2017, 29 pages.
European Partial Supplementary Search Report, European Application No. 14870947.0, dated Jul. 11, 2017, 14 pages.
European Extended Search Report, European Application No. 14870947.0, dated Oct. 17, 2017, 11 pages.
European Examination Report, European Application No. 14745749.3, dated Oct. 31, 2017, 3 pages.
European Examination Report, European Application No. 14746455.6, dated Oct. 31, 2017, 6 pages.
European Examination Report, European Application No. 14763266.5, dated Nov. 13, 2017, 4 pages.

(56) References Cited

OTHER PUBLICATIONS

European Examination Report, European Application No. 14768281.9, dated Dec. 18, 2017, 4 pages.
European Examination Report, European Application No. 14745792.3, dated Dec. 21, 2017, 6 pages.
Japanese First Office Action, Japanese Application No. P2015-544179, dated Sep. 19, 2017, 8 pages.
Japanese Office Action, Japanese Application No. 2015-556241, dated Sep. 26, 2017, 12 pages.
Japanese Office Action, Japanese Application No. 2015-556240, dated Oct. 3, 2017, 8 pages.
Kim, J.Y. et al., "Effect of Oral Probiotics (Bifidobacterium lactis AD011 and Lactobacillus acidophilus AD031) Administration on Ovalbumin-Induced Food Allergy Mouse Model," J. Microbiol. Biotechnol., 2008, pp. 1393-1400, vol. 18, No. 8.
Li, A-D. et al., "Clinical Features and Bacterial Culture on Stools of Patients with Acute Diarrhea," Chinese Journal of Health Laboratory Technology, Mar. 10, 2012, pp. 559-561, vol. 2, No. 6.
New Zealand Examination Report, New Zealand Application No. 713298, dated Sep. 26, 2017, 5 pages.
Pharmacy, 2011, pp. 79-86, vol. 62, No. 3. [With English Main Sub-Points].
Plassart, C. et al., "First Case of Intra-Abdominal Infection with Clostridium Disporicum," Anaerobe, 2013, pp. 77-78, vol. 19.
Prioult, G. et al., "Effect of Probiotic Bacteria on Induction and Maintenance of Oral Tolerance to β-Lactoglobulin in Gnotobiotic Mice," Clinical and Diagnostic Laboratory Immunology, Sep. 2003, pp. 787-792, vol. 10, No. 5.
Rehman, A. et al., "Effect of Probiotics and Antibiotics on the Intestinal Homeostasis in a Computer Controlled Model of the Large Intestine," BMC Microbiology, 2012, 10 pages, vol. 12, No. 47.
United States Office Action, U.S. Appl. No. 14/777,252, dated Aug. 29, 2017, 16 pages.
United States Office Action, U.S. Appl. No. 15/104,873, dated Oct. 17, 2017, 7 pages.
United States Office Action, U.S. Appl. No. 15/039,007, dated Nov. 1, 2017, 13 pages.
United States Office Action, U.S. Appl. No. 14/765,812, dated Dec. 7, 2017, 10 pages.
United States Office Action, U.S. Appl. No. 14/765,810, dated Jan. 8, 2018, 8 pages.
United States Office Action, U.S. Appl. No. 14/765,810, dated Jan. 25, 2018, 11 pages.
Yuguchi Hiroya et al., "Hakkonyuu/nyuusankin inryou to chounaikinsou "Fermented Milk/Lactic Acid Bacteria Beverages and Intestinal Bacterial Flora,"" New Food Industry, UDA, Moritaka, New Food Industry K.K., 1987, pp. 71-88, vol. 29, No. 7. [With English Subtitle Translations].
European Extended Search Report, European Application No. 14768281.9, dated Jul. 18, 2016, 10 pages.
European Extended Search Report, European Application No. 14763266.5, dated Aug. 16, 2016, 7 pages.
Joosten, H. et al., "*Salmonelle* Detection in Probiotic Products," International Journal of Food Microbiology, Jul. 2006, pp. 104-107, vol. 110, No. 1.
Kollmann, M. et al., Design Principles of a Bacterial Signalling Network, Nature, Nov. 24, 2005, pp. 504-507, vol. 438, No. 7067.
Logan, N.A., "Bacillus and Relatives in Foodborne Illness," Journal of Applied Microbiology, Mar. 20, 2012, pp. 417-429, vol. 112, No. 3.
Sleator, R.D. et al.."Designer Probiotics: A Potential Therapeutic for Clostridium difficile?" Journal of Medical Microbiology, Jun. 2008, pp. 793-794, vol. 57, No. 6.
Stefka, A.T. et al., "Commensal Bacteria Protect Against Food Allergen Sensitization," PNAS, Sep. 9, 2014, pp. 13145-13150, vol. 111, No. 36.
United States Office Action, U.S. Appl. No. 14/884,655, dated Aug. 17, 2016, 9 pages.
United States Office Action, U.S. Appl. No. 14/765,812, dated Aug. 25, 2016, 10 pages.
European Examination Report, European Application No. 14821918.1, dated Jan. 29, 2018, 4 pages.
Hickson, M. et al., "Probiotics in the Prevention of Antibiotic-Associated Diarrhoea and Clostridium Difficile Infection," Therapeutic Advances in Gastroenterology, 2011, pp. 185-197, vol. 4, No. 3.
Japanese Office Action, Japanese Application No. P2016-502561, dated Feb. 6, 2018, 10 pages.
Jordan, F. et al., "Network Ecology: Topological Constraints on Ecosystem Dynamics," Physics of Life Reviews, Dec. 2004, pp. 139-172, vol. 1, Issue 3 (Abstract Only).
New Zealand Third Examination Report, New Zealand Application No. 713298, dated Feb. 15, 2018, 6 pages.
New Zealand Fourth Examination Report, New Zealand Application No. 713298, dated Mar. 15, 2018, 2 pages.
Papadimitriou, K. et al., "Discovering Probiotic Microorganisms: In Vitro, In Vivo, Genetic and Omics Approaches," Frontiers in Microbiology, Feb. 17, 2015, pp. 1-28, vol. 6, Article 58.
Pillai, A. et al., "Probiotics for Treatment of Clostridium Difficile—Associated Colitis in Adults (Review)," Cochrane Database of Systematic Reviews, The Cochrane Collaboration, John Wiley & Sons, Ltd., 2010, 18 pages.
Russian Second Office Action, Russian Application No. 2015124366, dated Feb. 12, 2018, 10 pages.
European Examination Report, European Application No. 14746341.8, dated Jun. 13, 2017, 11 pages.
New Zealand First Examination Report, New Zealand Application No. 713298, dated Feb. 28, 2017, 6 pages.
Aas, J., Gessert, C.E., and Bakken, J.S. (2003). Recurrent Clostridium difficile colitis: case series involving 18 patients treated with donor stool administered via a nasogastric tube. Clinical Infectious Diseases 36(5), 580-585.
Abrams, R.S., "Open-Label, Uncontrolled Trial of Bowel Sterilization and Repopulation with Normal Bowel Flora for Treatment of Inflammatory Bowel Disease," Current Therapeutic Research, Dec. 1997, pp. 1001-1012, vol. 58, No. 12.
Achtman, M., and Wagner, M. (2008). Microbial diversity and the genetic nature of microbial species. Nat. Rev. Microbiol. 6(6), 431-440.
Accoceberry, I. et al., "One-Step Purification of *Enterocytozoon bieneusi* Spores from Human Stools by Immunoaffinity Expanded-Bed Adsorption," Journal of Clinical Microbiology, May 2001, pp. 1974-1951, vol. 39, No. 5.
Allen-Vercoe, E., Reid, G., Viner, N., Gloor, G.B., Hota, S., Kim, P., Lee, C., O'Doherty, K., Vanner, S.J., Weese, J.S., et al. (2012). A Canadian Working Group report on fecal microbial therapy: microbial ecosystems therapeutics. Can. J. Gastroenterol. 26(7), 457-462.
Allen-Vercoe, E., Strauss, J., and Chadee, K. (2011). Fusobacterium nucleatum: an emerging gut pathogen? Gut Microbes 2(5), 294-298.
Anderson, K.F., Lonsway, D.R., Rasheed, J.K., Biddle, J., Jensen, B., Mcdougal, L.K., Carey, R.B., Thompson, A., Stocker, S., Limbago, B., et al. (2007). Evaluation of Methods to Identify the Klebsiella pneumoniae Carbapenemase in Enterobacteriaceae. J. Clin. Microbiol. 45(8), 2723-2725.
Arumugam, M., Raes, J., Pelletier, E., Paslier, D.L., Yamada, T., Mende, D.R., Fernandes, G.R., Tap, J., Bruls, T., Batto, J.-M., et al. (2011). Enterotypes of the human gut microbiome. Nature 473(7346), 174-180.
Atarashi, K., Tanoue, T Oshima, K., Suda, W., Nagano, Y., Nishikawa, H., Fukuda, S., Saito, T., Narushima, S., Hase, K., et al. (2013). Treg induction by a rationally selected mixture of *Clostridia* strains from the human microbiota. Nature 500(7461), 232-236.
Atarashi, K., Tanoue, T., Shima, T., Imaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331(6015), 337-341.
Backhed, F. et al., (2004). The gut microbiota as an environmental factor that regulates fat storage, PNAS, Nov. 2, 2014, pp. 15718-15723, vol. 101, No. 44.
Bader, J., Albin, A., and Stahl, U. (2012). Spore-forming bacteria and their utilisation as probiotics. Benef Microbes 3(1), 67-75.

(56) References Cited

OTHER PUBLICATIONS

Bakken, J.S. (2009). Fecal bacteriotherapy for recurrent Clostridium difficile infection. Anaerobe 15(6), 285-289.

Bakken, J.S., Borody, T., Brandt, L.J., Brill, J.V., Demarco, D.C., Franzos, M.A., Kelly, C., Khoruts, A., Louie, T., Martinelli, L.P., et al. K2011). Treating Clostridium difficile infection with fecal microbiota transplantation. Clin. Gastroenterol. Hepatol. 9(12), 1044-1049.

Barreau, M., Pagnier, I., and La Scola, B. (2013). Improving the identification of anaerobes in the clinical microbiology laboratory through MALDI-TOF mass spectrometry. Anaerobe 22, 123-125.

Bauer, T.M. et al., "Derivation and Validation of Guidelines for Stool Cultures for Enteropathogenic Bacteria Other Than Clostridium difficile in Hospitalized Adults," The Journal of the American Medical Association, Jan. 17, 2001, pp. 313-319, vol. 285.

Ben-Amor, K., Heilig, H., Smidt, H., Vaughan, E.E., Abee, T., and De Vos, W.M. (2005). Genetic diversity of viable, injured, and dead fecal bacteria assessed by fluorescence-activated cell sorting and 16S rRNA gene analysis. Applied and Environmental Microbiology 71(8), 4679-4689.

Berstad, A. et al., "Fecal Fat Determination with a Modified Titration Method," Scandinavian Journal of Gastroenterology, 2010, pp. 603-607, vol. 45.

Bhatia, A. et al., "Proionibacterium Acnes and Chronic Diseases," The Infectious Etiology of Chronic Diseases: Defining the Relationship, Enhancing the Research, and Mitigating the Effects: Workshop Summary., Knobler, S.L. et al. (eds.), 2004, pp. 74-80, may be downloaded at<URL:http://www.nap.edu/catalog/11026.html>.

Bidawid, S., Farber, J.M., Sattar, S.A., and Hayward, S. (2000). Heat inactivation of hepatitis A virus in dairy foods. J. Food Prot. 63(4), 522-528.

Bloedt, K., Riecker, M., Poppert, S., and Wellinghausen, N. (2009). Evaluation of new selective culture media and a rapid fluorescence in situ hybridization assay for identification of Clostridium difficile from stool samples. J Med Microbiol 58(7), 874-877.

Bokulich, N.A., Subramanian, S., Faith, J.J., Gevers, D., Gordon, J.I., Knight, R., Mills, D.A., and Caporaso, J.G. (2013). Quality-filtering vastly improves diversity estimates from Illumina amplicon sequencing. Nat Methods 10(1), 57-59.

Bolivar, I. et al., "Bacterial Diversity in Oral Samples of Children in Niger with Acute Noma, Acute Necrotizing Gingivitis and Healthy Controls," PLOS Neglected Tropical Diseases, Mar. 2012, pp. 1-11, vol. 6, No. 3, E1556; Uncultured *Catonella* sp. partial 16S rRNA Gene, Clone 402A04(oral): Nucleotide: NCBI: GenBank: AM420133.1, last accessed Mar. 12, 2014, pp. 12-13.

Borody, T.J. et al. (2011). Fecal microbiota transplantation (FMT) in multiple Sclerosis. Poster abstract at American College of Gastroenterology Annual Scientific Meeting and Postgraduate Course Oct. 28, 2011.

Borody, T.J., and Khoruts, A. (2012). Fecal microbiota transplantation and emerging applications. Nat Rev Gastroenterol Hepatol 9(2), 88-96.

Borriello, S.P. (1990). The influence of the normal flora on Clostridium difficile colonisation of the gut. Ann. Med. 22(1), 61-67.

Borriello, S.P., and Barclay, F.E. (1985). Protection of hamsters against *Clostridium difficile* ileocaecitis by prior colonisation with non-pathogenic strains. J Med Microbiol 19(3), 339-350.

Borriello, S.P., and Barclay, F.E. (1986). An in-vitro model of colonisation resistance to Clostridium difficile infection. Journal of Medical Microbiology 21(4), 299-309.

Borriello, S.P., and Honour, P. (1981). Simplified procedure for the routine isolation of Clostridium difficile from faeces. J Clin Pathol 34(10), 1124-1127.

Boyles, W.A., and Lincoln, R.E. (1958). Separation and concentration of bacterial spores and vegetative cells by foam flotation. Appl Microbiol 6(5), 327-334.

Brandt, L.J. (2012). Fecal Transplantation for the Treatment of Clostridium difficile Infection. Gastroenterol Hepatol (N Y) 8(3), 191-194.

Brandt, L.J., Aroniadis, O.C., Mellow, M Kanatzar, A., Kelly, C., Park, T., Stollman, N., Rohlke, F., and Surawicz, C. (2012). Long-Term Follow-Up of Colonoscopic Fecal Microbiota Transplant for Recurrent Clostridium difficile Infection. The American Journal of Gastroenterology 107(7), 1079-1087.

Bräuniger, S., Peters, J., Borchers, U., and Kao, M. (2000). Further studies on thermal resistance of bovine parvovirus against moist and dry heat. International Journal of Hygiene and Environmental Health 203(1), 71-75.

Broda, D.M., De Lacy, K.M., and Bell, R.G. (1998). Efficacy of heat and ethanol spore treatments for the isolation of psychrotrophic *Clostridium* spp. associated with the spoilage of chilled vacuum-packed meats. International Journal of Food Microbiology 39(1-2), 61-68.

Brosius, J. et al., "Complete Nucleotide Sequence of a 16S Ribosomal RNA Gene from *Eschericia coli*," Proc. Natl. Acad. Sci., Oct. 1978, pp. 4801-4805, vol. 75, No. 10.

Bueche, M., Wunderlin, T., Roussel-Delif, L., Junier, T., Sauvain, L., Jeanneret, N., and Junier, P. (2013). Quantification of Endospore-Forming Firmicutes by Quantitative PCR with the Functional Gene spo0A. Applied and Environmental Microbiology 79(17), 5302-5312.

Buffie, C.G., and Pamer, E.G. (2013). Microbiota-mediated colonization resistance against intestinal pathogens. Nature Reviews Immunology 13(11), 790-801.

Burke, C.J., Hsu, T.A., and Volkin, D.B. (1999). Formulation, stability, and delivery of live attenuated vaccines for human use. Crit Rev Ther Drug Carrier Syst 16(1), 1-83.

Cani, P.D., Possemiers, S., Wiele, T.V. De, Guiot, Y., Everard, A., Rottier, O., Geurts, L., Naslain, D., Neyrinck, A., Lambert, D.M., et al. (2009). Changes in gut microbiota control inflammation in obese mice through a mechanism involving GLP-2-driven improvement of gut permeability. Gut 58(8), 1091-1103.

Carvalho, A.S., Silva, J., Ho, P., Teixeira, P., Malcata, F.X., and Gibbs, P. (2008). Effects of Various Sugars Added to Growth and Drying Media upon Thermotolerance and Survival throughout Storage of Freeze-Dried *Lactobacillus delbrueckii* ssp. bulgaricus. Biotechnology Progress 20(1), 248-254.

Champagne, C.P., Mondou, F., Raymond, Y., and Roy, D. (1996). Effect of polymers and storage temperature on the stability of freeze-dried lactic acid bacteria. Food Research International 29(5-6), 555-562.

Chang, J.Y., Antonopoulos, D.A., Kalra, A., Tonelli, A., Khalife, W.T., Schmidt, T.M., and Young, V.B. (2008). Decreased diversity of the fecal Microbiome in recurrent Clostridium difficile-associated diarrhea. J. Infect. Dis. 197(3), 435-438.

Chapman, C.M.C., Gibson, G.R., and Rowland, I. (2012). In vitro evaluation of single- and multi-strain probiotics: Inter-species inhibition between probiotic strains, and inhibition of pathogens. Anaerobe 18(4), 405-413.

Chen, X., Katchar, K., Goldsmith, J.D., Nanthakumar, N., Cheknis, A., Gerding, D.N., and Kelly, C.P. (2008). A Mouse Model of *Clostridium difficile*—Associated Disease. Gastroenterology 135(6), 1984-1992.

Chow, J., Tang, H., and Mazmanian, S.K. (2011). Pathobionts of the Gastrointestinal Microbiota and Inflammatory Disease. Curr Opin Immunol 23(4), 473-480.

Claesson, M.J., Wang, Q., O'Sullivan, O., Greene-Diniz, R., Cole, J.R., Ross, R.P., and O'Toole, P.W. (2010). Comparison of two next-generation sequencing technologies for resolving highly complex microbiota composition using tandem variable 16S rRNA gene regions. Nucleic Acids Res 38(22), e200.

Clemente, J.C., Ursell, L.K., Parfrey, L.W., and Knight, R. (2012). The impact of the gut microbiota on human health: an integrative view. Cell 148(6), 1258-1270.

D'Souza, D.H., and Su, X. (2010). Efficacy of chemical treatments against murine norovirus, feline calicivirus, and MS2 bacteriophage. Foodborne Pathogens and Disease 7(3), 319-326.

David, L.A., Maurice, C.F., Carmody, R.N., Gootenberg, D.B., Button, J.E., Wolfe, B.E., Ling, A.V., Devlin, A.S., Varma, Y., Fischbach, M.A., et al. (2013). Diet rapidly and reproducibly alters the human gut microbiome. Nature advance online publication.

(56) References Cited

OTHER PUBLICATIONS

De Angelis, M., Piccolo, M., Vannini, L., Siragusa, S., De Giacomo, A., Serrazzanetti, D.I., Cristofori, F., Guerzoni, M.E., Gobbetti, M., and Francavilla, R. (2013). Fecal Microbiota and Metabolome of Children with Autism and Pervasive Developmental Disorder Not Otherwise Specified. PLoS ONE 8(10), e76993.

De Vos, W.M. (2013). Fame and future of faecal transplantations—developing nextgeneration therapies with synthetic microbiomes: Fame and future of faecal transplantations. Microbial Biotechnology 6(4), 316-325.

Defined Fecal Microbiota Transplantation for Clostridium difficile Diarrhea <http://clinicaltrials.gov/ct2/show/NCT01868373> Accessed Mar. 26, 2014.

Derrien, M. (2004). *Akkermansia muciniphila* gen. nov., sp. nov., a human intestinal mucin-degrading bacterium. International Journal of Systematic and Evolutionary Microbiology 54(5), 1469-1476.

Dethlefsen, L., Huse, S., Sogin, M.L., and Relman, D.A. (2008). The Pervasive Effects of an Antibiotic on the Human Gut Microbiota, as Revealed by Deep 16S rRNA Sequencing. PLoS Biology 6(11), e280.

Detmer, A., and Glenting, J. (2006). Live bacterial vaccines—a review and identification of potential hazards. Microb Cell Fact 5, 23.

Dharmani, P., De Simone, C., and Chadee, K. (2013). The Probiotic Mixture VSL#3 Accelerates Gastric Ulcer Healing by Stimulating Vascular Endothelial Growth Factor. PLoS ONE 8(3), e58671.

Dietrich, G., Collioud, A., and Rothen, S.A. (2008). Developing and Manufacturing Attenuated Live Bacterial Vaccines. <http://www.biopharminternational.com/biopharm/Vaccine+Manufacturing+Articles/Developing-and-Manufacturing-Attenuated-Live-Bacte/ArticleStandard/Article/detail/557306> Accessed Mar. 25, 2014.

Dragon, D.C., and Rennie, R.P. (2001). Evaluation of spore extraction and purification methods for selective recovery of viable Bacillus anthracis spores. Lett. Appl. Microbiol. 33(2), 100-105.

Duc, L. (2003). Germination of the spore in the gastrointestinal tract provides a novel route for heterologous antigen delivery. Vaccine 21(27-30), 4215-4224.

Duc, L.H., Hong, H.A., Fairweather, N., Ricca, E., and Cutting, S.M. (2003). Bacterial Spores as Vaccine Vehicles. Infection and Immunity 71(5), 2810-2818.

Dumas, M.E. et al., (2006). Metabolic profiling reveals a contribution of gut microbiota to fatty liver phenotype in insulin-resistant mice, PNAS, Aug. 15, 2006, pp. 12511-12516, vol. 103, No. 33.

Dutta, S.K., Girotra, M., Garg, S., Dutta, A., Von Rosenvinge, E.C., Maddox, C., Song, Y., Bartlett, J.G., Vinayek, R., and Fricke, W.F. (2014). Efficacy of Combined Jejunal and Colonic Fecal Microbiota Transplantation for Recurrent Clostridium difficile Infection. Clinical Gastroenterology and Hepatology.

Edwards, A.D., and Slater, N.K.H. (2008). Formulation of a live bacterial vaccine for stable room temperature storage results in loss of acid, bile and bile salt resistance. Vaccine 26(45), 5675-5678.

Eiseman, B., Silen, W., Bascom, G.S., and Kauvar, A.J. (1958). Fecal enema as an adjunct in the treatment of pseudomembranous enterocolitis. Surgery 44(5), 854-859.

Elving, J., Emmoth, E Albihn, A., Vinneras, B., and Ottoson, J. (2012). Composting for Avian Influenza Virus Elimination. Applied and Environmental Microbiology 78(9), 3280-3285.

Emanuelsson, F., Claesson, B.E.B., Ljungström, L., Tvede, M., and Ung, K.-A. (2014). Faecal microbiota transplantation and bacteriotherapy for recurrent Clostridium difficile infection: A retrospective evaluation of 31 patients. Scandinavian Journal of Infectious Diseases 46(2), 89-97.

Endt, K., Stecher, B., Chaffron, S., Slack, E., Tchitchek, N., Benecke, A., Van Maele, L., Sirard, J.-C., Mueller, A.J., Heikenwalder, M., et al. K2010). The Microbiota Mediates Pathogen Clearance from the Gut Lumen after Non-Typhoidal *Salmonella* Diarrhea. PLoS Pathog 6(9), e1001097.

Everard, A., Belzer, C., Geurts, L., Ouwerkerk, J.P., Druart, C., Bindels, L.B., Guiot, Y., Derrien, M., Muccioli, G.G., Delzenne, N.M., et al. (2013). Cross-talk between Akkermansia muciniphila and intestinal epithelium controls diet-induced obesity. Proceedings of the National Academy of Sciences 110(22), 9066-9071.

Fairhead, H., Setlow, B., Waites, W.M., and Setlow, P. (1994). Small, acidsoluble proteins bound to DNA protect *Bacillus subtilis* spores from being killed by freeze-drying. Applied and Environmental Microbiology 60(7), 2647-2649.

Faith, J.J., Ahern, P.P., Ridaura, V.K., Cheng, J., and Gordon, J.I. (2014). Identifying Gut Microbe-Host Phenotype Relationships Using Combinatorial Communities in Gnotobiotic Mice. Sci Transl Med 6(220), 220ra11-220ra11.

Fakhry, S., Sorrentini, I., Ricca, E., De Felice, M., and Baccigalupi, L. (2008). Characterization of spore forming Bacilli isolated from the human gastrointestinal tract. Journal of Applied Microbiology 105(6), 2178-2186.

Faust, et al., "Microbial Co-occurrence Relationships in the Human Microbiome," PLoS Computational Biology, Jul. 2012, e1002606, 17 pages, vol. 8, No. 7.

Fell JR., N.F., Pellegrino, P.M., and Gillespie, J.B. (2001). Mitigating phosphate interference in bacterial endospore detection by Tb dipicolinate photoluminescence. Analytica Chimica Acta 426(1), 43-50.

Fichtel, J., Köster, J., Rullkötter, J., and Sass, H. (2007). Spore dipicolinic acid contents used for estimating the number of endospores in sediments. FEMS Microbiology Ecology 61(3), 522-532.

Fischbach, M.A., Bluestone, J.A., and Lim, W.A. (2013). Cell-Based Therapeutics: The Next Pillar of Medicine. Sci Transl Med 5(179), 179ps7.

Fonseca, F., Béal, C., and Corrieu, G. (2001). Operating Conditions That Affect the Resistance of Lactic Acid Bacteria to Freezing and Frozen Storage. Cryobiology 43(3), 189-198.

Franz, C.M.A.P., Huch, M., Abriouel, H., Holzapfel, W., and Gálvez, A. (2011). Enterococci as probiotics and their implications in food safety. International Journal of Food Microbiology 151(2), 125-140.

Friedman-Moraco, R.J., Mehta, A.K., Lyon, G.M., and Kraft, C.S. (2014). Fecal Microbiota Transplantation for Refractory Clostridium difficile Colitis in Solid Organ Transplant Recipients: Fecal Microbiota Transplantation in Solid Organ Transplant Recipients. American Journal of Transplantation 14(2), 477-480.

Fuentes, S., Van Nood, E., Tims, S., Heikamp-De Jong, I., Ter Braak, C.J., Keller, J.J., Zoetendal, E.G., and De Vos, W.M. (2014). Reset of a critically disturbed microbial ecosystem: faecal transplant in recurrent Clostridium difficile infection. The ISME Journal.

GenBank HQ819637, "Uncultured Organism Clone ELU0180-T56-S-NIPCRAMgANa_000311 Small Subunit Ribosomal RNA Gene, Partial Sequence," Jul. 30, 2012, 1 page, [Online] [Retrieved on Aug. 21, 2014] Retrieved from the Internet<URL:http://www.ncbi.nlm.nih.gov/nuccore/HQ819637>.

Gevers, D., Kugathasan, S., Denson, L.A., Vázquex-Baeza, Y., Van Treuren, W., Ren, B., Schwager, E., Knights, D., Song, S.J., Yassour, M., et al. (2014). The Treatment-Naive Microbiome in New-Onset Crohn's Disease. Cell Host & Microbe 15(3), 382-392.

Gilligan, P.H. (2013). Identification of Pathogens by Classical Clinical Tests. In the Prokaryotes, E. Rosenberg, E.F. DeLong, S. Lory, E. Stackebrandt, and F. Thompson, eds. (Springer Berlin Heidelberg), pp. 57-89.

Goodman, A.L., Kallstrom, G., Faith, J.J., Reyes, A., Moore, A., Dantas, G., and Gordon, J.I. (2011). From the Cover: Extensive personal human gut microbiota culture collections characterized and manipulated in gnotobiotic mice. Proceedings of the National Academy of Sciences 108(15), 6252-6257.

Goodman, N.S., Gottfried, R.J., and Rogoff, M.H. (1967). Biphasic system for separation of spores and crystals of Bacillus thuringiensis. Journal of Bacteriology 94(2), 485.

Gough, E. et al., "Systematic Review of Intestinal Microbiota Transplantation (Fecal Bacteriotherapy) for Recurrent Clostridium Dfficile Infection," Clin. Infect. Dis., Nov. 15, 2011, pp. 994-1002, vol. 53, No. 10.

Gould, G.W., and Sale, A.J. (1970). Initiation of germination of bacterial spores by hydrostatic pressure. J. Gen. Microbiol. 60(3), 335-346.

Grabow, W.O., Clay, C.G., Dhaliwal, W., Vrey, M.A., and Müller, E.E. (1999). Elimination of viruses, phages, bacteria and

(56) References Cited

OTHER PUBLICATIONS

Cryptosporidium by a new generation Aquaguard point-of-use water treatment unit. Zentralbl Hyg Umweltmed 202(5), 399-410.
Greenway, F., Wang, S., and Heiman, M. (2014). A novel cobiotic containing a prebiotic and an antioxidant augments the glucose control and gastrointestinal tolerability of metformin: a case report. Beneficial Microbes 5(1), 29-32.
Grehan, M.J., Borody, T.J., Leis, S.M., Campbell, J., Mitchell, H., and Wettstein, A. (2010). Durable alteration of the colonic microbiota by the administration of donor fecal flora. J. Clin. Gastroenterol. 44(8), 551-561.
Grimoud, J. et al., "In Vitro Screening of Probiotic Lactic Acid Bacteria and Prebiotic Glucooligosaccharides to Select Effective Synbiotics," Anaerobe, Clinical Microbiology, Oct. 2010, pp. 493-500, vol. 16, No. 5.
Hamilton, M.J., Weingarden, A.R., Sadowsky, M.J., and Khoruts, A. (2012). Standardized frozen preparation for transplantation of fecal microbiota for recurrent Clostridium difficile infection. Am. J. Gastroenterol. 107(5), 761-767.
Hamilton, M.J., Weingarden, A.R., Unno, T Khoruts, A., and Sadowsky, M.J. (2013). High-throughput DNA sequence analysis reveals stable engraftment of gut microbiota following transplantation of previously frozen fecal bacteria. Gut Microbes 4(2), 125-135.
Harmsen, H. J. M., Gibson, G. R., Elfferich, P., Raangs, G. C., Wildeboer-Veloo, A. C. M., Argaiz, A., Roberfroid, M. B., and Welling, G. W. (2000). Comparison of viable cell counts and fluorescence in situ hybridization using specific rRNA-based probes for the quantification of human fecal bacteria. FEMS Microbiology Letters 183(1), 125-129.
Harrison, F., "Bacterial Cooperation in the Wild and in the Clinic: Are Pathogen Social Behaviours Relevant Outside the Laboratory?" Bioessays, Dec. 27, 2012, pp. 108-112, vol. 35, No. 2.
Hasan, J.A., Japal, K.M., Christensen, E.R., and Samalot-Freire, L.C. (2011). In vitro production of Clostridium difficile spores for use in the efficacy evaluation of disinfectants: a precollaborative investigation. J AOAC Int 94(1), 259-272.
Hayashi, Y. et al., "Western Blot (Immunoblot) Assay of Small Round-Structured Virus Associated with an Acute Gastroenteritis Outbreak in Tokyo," Journal of Clinical Microbiology, Aug. 1989, pp. 1728-1733, vol. 27.
Hell, M., Bernhofer, C., Stalzer, P., Kern, J.M., and Claassen, E. (2013). Probiotics in Clostridium difficile infection: reviewing the need for a multistrain probiotic. Beneficial Microbes 4(1), 39-51.
Hemmerling, A., Harrison, W., Schroeder, A., Park, J., Korn, A., Shiboski, S., Foster-Rosales, A., and Cohen, C.R. (2010). Phase 2a Study Assessing Colonization Efficiency, Safety, and Acceptability of Lactobacillus crispatus CTV-05 in Women With Bacterial Vaginosis: Sexually Transmitted Diseases 37(12), 745-750.
Herron, P.R., and Wellington, E.M.H. (1990). New Method for Extraction of *Streptomycete* Spores from Soil and Application to the Study of Lysogeny in Sterile Amended and Nonsterile Soil. Appl Environ Microbiol 56(5), 1406-1412.
Hewitt, J., Rivera-Aban, M., and Greening, G.E. (2009). Evaluation of murine norovirus as a surrogate for human norovirus and hepatitis A virus in heat inactivation studies. Journal of Applied Microbiology 107(1), 65-71.
Hindle, A.A., and Hall, E.A.H. (1999). Dipicolinic acid (DPA) assay revisited and appraised for spore detection. The Analyst 124(11), 1599-1604.
Hirsch, E.B., and Tam, V.H. (2010). Detection and treatment options for Klebsiella pneumoniae carbapenemases (KPCs): an emerging cause of multidrug-resistant infection. J. Antimicrob. Chemother. 65(6), 1119-1125.
Hofsten, B.V. (1966). Partition of *Escherichia coli* in an aqueous polymer two-phase system. Experimental Cell Research 41(1), 117-123.
Holmes, E., Kinross, J., Gibson, G.R., Burcelin, R., Jia, W., Pettersson, S., and Nicholson, J.K. (2012). Therapeutic Modulation of Microbiota-Host Metabolic Interactions. Science Translational Medicine 4(137), 137rv6-137rv6.
Hoppe, B., Groothoff, J.W., Hulton, S.-A., Cochat, P., Niaudet, P., Kemper, M.J., Deschênes, G., Unwin, R., and Milliner, D. (2011). Efficacy and safety of Oxalobacterformigenes to reduce urinary oxalate in primary hyperoxaluria. Nephrol. Dial. Transplant. 26(11), 3609-3615.
Hoyles, L., Honda, H., Logan, N.A., Halket, G., La Ragione, R.M., and McCartney, A.L. (2012). Recognition of greater diversity of *Bacillus* species and related bacteria in human faeces. Res. Microbiol. 163(1), 3-13.
Hurst, C.J., and Gerba, C.P. (1989). Fate of viruses during wastewater sludge treatment processes. Critical Reviews in Environmental Control 18(4), 317-343.
Iizuka, M. et al., "Elemental Diet Modulates the Growth of Clostridium difficile in the Gut Flora," Aliment Pharmacol. Ther., Jul. 2004, pp. 151-157, vol. 20, Suppl. 1.
Itoh, K., and Mitsuoka, T. (1985). Characterization of Clostridia isolated from faeces of limited flora mice and their effect on caecal size when associated with germ-free mice. Laboratory Animals 19(2), 111-118.
Itoh, K., Lee, W.K., Kawamura, H., Mitsuoka, T., and Magaribuchi, T. (1987). Intestinal bacteria antagonistic to *Clostridium difficile* in mice. Lab Anim 21(1), 20-25.
Itoh, K., Urano, T., and Mitsuoka, T. (1986). Colonization resistance against Pseudomonas aeruginosa in gnotobiotic mice. Lab Anim 20(3), 197-201.
Jalanka-Tuovinen, J., Salojarvi, J., Salonen, A., Immonen, O., Garsed, K., Kelly, F.M., Zaitoun, A., Palva, A., Spiller, R.C., and De Vos, W.M. (2013). Faecal microbiota composition and host-microbe cross-talk following gastroenteritis and in postinfectious irritable bowel syndrome. Gut 0, 1-9.
Jeffs, L.B., and Khachatourians, G.G. (1997). Estimation of spore hydrophobicity for members of the genera Beauveria, Metarhizium, and Tolypocladium by salt-mediated aggregation and sedimentation. Canadian Journal of Microbiology 43(1), 23-28.
Jensen, N.S., and Canale-Parola, E. (1986). *Bacteroides pectinophilus* sp. nov. and *Bacteroides galacturonicus* sp. nov.: two pectinolytic bacteria from the human intestinal tract. Appl. Environ. Microbiol. 52(4), 880-887.
Jones, M.L., Martoni, C.J., and Prakash, S. (2012a). Cholesterol lowering and inhibition of sterol absorption by Lactobacillus reuteri NCIMB 30242: a randomized controlled trial. Eur J Clin Nutr 66(11), 1234-1241.
Jones, M.L., Martoni, C.J., Parent, M., and Prakash, S. (2012b). Cholesterol-lowering efficacy of a microencapsulated bile salt hydrolase-active Lactobacillus reuteri NCIMB 30242 yoghurt formulation in hypercholesterolaemic adults. British Journal of Nutrition 107(10), 1505-1513.
Jorgensen, J.H., and Ferraro, M.J. (2009). Antimicrobial Susceptibility Testing a Review of General Principles and Contemporary Practices. Clin Infect Dis., Medical Microbiology, 49(11), 1749-1755.
Jorup-Rönström, C., Håkanson, A., Sandell, S., Edvinsson, O., Midtvedt, T., Persson, A.-K., and Norin, E. (2012). Fecal transplant against relapsing Clostridium difficile—associated diarrhea in 32 patients. Scand. J. Gastroenterol. 47(5), 548-552.
Jousimies-Somer, H., Summanen, P., Citron, D.M., Baron, E.J., Wexler, H.M., and Finegold, S.M. (2002). Wadsworth-KLT Anaerobic Bacteriology Manual, 6th edition (California: Star), pp. 55-74, 81-132, 165-185.
Kailasapathy, K. (2002). Microencapsulation of probiotic bacteria: technology and potential applications. Curr Issues Intest Microbiol 3(2), 39-48.
Kamiya, S., Yamakawa, K., Ogura, H., and Nakamura, S. (1989). Recovery of spores of *Clostridium difficile* altered by heat or alkali. J Med Microbiol 28(3), 217-221.
Kanamoto, T. et al., "Genetic Heterogeneities and Phenotypic Characteristics of Strains of the Genus *Abiotrophia* and Proposal of *Abiotrophia para-adiacens* sp. nov.," Journal of Clinical Microbiology, Feb. 2000, pp. 492-498, vol. 38, No. 2 *Abiotropia para-*

(56) References Cited

OTHER PUBLICATIONS

*adjacens* gene for 16S rRNA, partial sequence, strain: Nucleotide NCBI: GenBank: AB022027.1, last accessed Mar. 12, 2014, p. 8.
Kanehisa Laboratories. KEGG: Kyoto encyclopedia of genes and genomes. <http://www.genome.jp/kegg/> Accessed 27th Match 2014.
Karasawa, T. et al., "A Defined Growth Medium for Clostridium difficile," Microbiology, Feb. 1995, pp. 371-375, vol. 151, No. 2.
Kazamias, M. et al., "Enhanced Fermentation of Mannitol and Release of Cytotoxin by Clostridium difficile in Alkaline Culture Media," Applied and Environmental Microbiology, Jun. 1995, pp. 2425-2427, vol. 61, No. 6.
Kelly, D., Campbell, J.I., King, T.P., Grant, G., Jansson, E.A., Coutts, A.G.P., Pettersson, S., and Conway, S. (2003). Commensal anaerobic gut bacteria attenuate inflammation by regulating nuclear-cytoplasmic shuttling of PPAR-γ and RelA. Nature Immunology 5(1), 104-112.
Khoruts, A. (2013). How Does Fecal Microbiota Transplantation Treat Clostridium difficile Infection? <https://www.genome.gov/Multimedia/Slides/HumanMicrobiomeScience2013/39_Khoruts.pdf> Accessed Mar. 21, 2014.
Khoruts, A., and Sadowsky, M.J. (2011). Therapeutic transplantation of the distal gut microbiota. Mucosal Immunol 4(1), 4-7.
Khoruts, A., Dicksved, J., Jansson, J.K., and Sadowsky, M.J. (2010). Changes in the composition of the human fecal microbiome after bacteriotherapy for recurrent Clostridium difficile—associated diarrhea. J. Clin. Gastroenterol. 44(5), 354-360.
Kim, B., Kim, N.J., Kim, M., Kim, Y.S., Woo, J., and Ryu, J. (2003). Bacteraemia Due to Tribe Proteeae: A Review of 132 Cases During a Decade (1991-2000). Scandinavian Journal of Infectious Diseases 35(2), 98-103.
Klayraung, S., Viernstein, H., and Okonogi, S. (2009). Development of tablets containing probiotics: Effects of formulation and processing parameters on bacterial viability. International Journal of Pharmaceutics 370(1-2), 54-60.
Kong, Q., He, G.-Q., Jia, J.-L., Zhu, Q.-L., and Ruan, H. (2011). Oral Administration of Clostridium butyricum for Modulating Gastrointestinal Microflora in Mice. Curr Microbiol 62(2), 512-517.
Konstantinidis, K.T., Ramette, A., and Tiedje, J.M. (2006). The bacterial species definition in the genomic era. Philos Trans R Soc Lond B Biol Sci 361(1475), 1929-1940.
Koonin, E.V. (2002). Chapter 22 The clusters of orthologous groups (COGS) database: Phylogenetic classification of proteins from complete genomes. <http://www.ncbi.nlm.nih.gov/books/NBK21090/pdf/ch22.pdf> Accessed 27th Match 2014.
Koransky, J.R., Allen, S.D., and Dowell, V.R., Jr (1978). Use of ethanol for selective isolation of sporeforming microorganisms. Appl. Environ. Microbiol. 35(4), 762-765.
Kort, R., O'Brien, A.C., Stokkum, I.H.M. Van, Oomes, S.J.C.M., Crielaard, W., Hellingwerf, K.J., and Brul, S. (2005). Assessment of Heat Resistance of Bacterial Spores from Food Product Isolates by Fluorescence Monitoring of Dipicolinic Acid Release. Appl. Environ. Microbiol. 71(7), 3556-3564.
Kucerova, Z., Moura, H., Leitch, G.J., Sriram, R., Bern, C., Kawai, V., Vargas, D., Gilman, R.H., Ticona, E., and Vivar, A. (2004). Purification of *Enterocytozoon bieneusi* spores from stool specimens by gradient and cell sorting techniques. Journal of Clinical Microbiology 42(7), 3256-3261.
Kumar, M. et al., "Cholesterol-Lowering Probiotics as Potential Biotherapeutics for Metabolic Diseases," Experimental Diabetes Research, 2012, Article ID 902917, 14 pages, vol. 2012.
Kump, P.K., Gröchenig, H.-P., Lackner, S., Trajanoski, S., Reicht, G., Hoffmann, K.M., Deutschmann, A., Wenzl, H.H., Petritsch, W., Krejs, G.J., et al. (2013). Alteration of intestinal dysbiosis by fecal microbiota transplantation does not induce remission in patients with chronic active ulcerative colitis. Inflamm. Bowel Dis. 19(10), 2155-2165.
Kunde, S., Pham, A., Bonczyk, S., Crumb, T., Duba, M., Conrad, H., Jr, Cloney, D., and Kugathasan, S. (2013). Safety, tolerability, and clinical response after fecal transplantation in children and young adults with ulcerative colitis. J. Pediatr. Gastroenterol. Nutr. 56(6), 597-601.
Landy, J., Al-Hassi, H.O., Mclaughlin, S.D., Walker, A.W., Ciclitira, P.J., Nicholls, R.J., Clark, S.K., and Hart, A.L. (2011). Review article: faecal transplantation therapy for gastrointestinal disease. Alimentary Pharmacology & Therapeutics 34(4), 409-415.
Lawley, T.D., Clare, S., Walker, A.W., Stares, M.D., Connor, T.R., Raisen, C., Goulding, D., Rad, R., Schreiber, F., Brandt, C., et al. (2012). Targeted Restoration of the Intestinal Microbiota with a Simple, Defined Bacteriotherapy Resolves Relapsing Clostridium difficile Disease in Mice. PLoS Pathog 8(10), e1002995.
Lawson, P.A., Song, Y., Liu, C Molitoris, D.R., Vaisanen, M.-L., Collins, M.D., and Finegold, S.M. (2004). *Anaerotruncus colihominis* gen. nov., sp. nov., from human faeces. Int J Syst Evol Microbiol 54(2), 413-417.
Lee, I.-K., and Liu, J.-W. (2006). Clinical characteristics and risk factors for mortality in Morganella morganii bacteremia. J Microbiol Immunol Infect 39(4), 328-334.
Lee, J.S., Cha, D.S., and Park, H.J. (2004). Survival of Freeze-Dried Lactobacillus bulgaricus KFRI 673 in Chitosan-Coated Calcium Alginate Microparticles. J. Agric. Food Chem. 52(24), 7300-7305.
Lee, M., Hesek, D., Shah, I.M., Oliver, A.G., Dworkin, J., and Mobashery, S. (2010). Synthetic peptidoglycan motifs for germination of bacterial spores. Chembiochem 11(18), 2525-2529.
Lehar, J. (2007). Chemical combination effects predict connectivity in biological systems, Molecular Systems Biology, pp. 1-14, vol. 3, Article No. 80.
Lemon, K.P., Armitage, G.C., Relman, D.A., and Fischbach, M.A. (2012). Microbiota-Targeted Therapies: An Ecological Perspective. Science Translational Medicine 4(137), 137rv5-137rv5.
Leslie, S.B., Israeli, E., Lighthart, B., Crowe, J.H., and Crowe, L.M. (1995). Trehalose and sucrose protect both membranes and proteins in intact bacteria during drying. Applied and Environmental Microbiology 61(10), 3592-3597.
Liggins, M., Ramirez, N., Magnuson, N., and Abel-Santos, E. (2011). Progesterone analogs influence germination of *Clostridium sordellii* and *Clostridium difficile* spores in vitro. J. Bacteriol. 193(11), 2776-2783.
Lindsay, J.A., Beaman, T.C., and Gerhardt, P. (1985). Protoplast water content of bacterial spores determined by buoyant density sedimentation. J. Bacteriol. 163(2), 735-737.
Liu, K., Linder, C.R., and Warnow, T. (2011). RAxML and FastTree: Comparing Two Methods for Large-Scale Maximum Likelihood Phylogeny Estimation. PLoS ONE 6(11), e27731.
Livingston, S.J., Kominos, S.D., and Yee, R.B. (1978). New medium for selection and presumptive identification of the Bacteroides fragilis group. J. Clin. Microbiol. 7(5), 448-453.
Lopetuso, L.R., Scaldaferri, F., Petito, V., and Gasbarrini, A. (2013). Commensal Clostridia: leading players in the maintenance of gut homeostasis. Gut Pathogens 5(1), 23.
Lodish, H. et al., "Viruses: Structure, Function, and Uses," Molecular Cell Biology, $4^{th}$ Edition, 2000, pp. 1-12.
Lozupone, C., Faust, K., Raes, J., Faith, J.J., Frank, D.N., Zaneveld, J., Gordon, J.I., and Knight, R. (2012). Identifying genomic and metabolic features that can underlie early successional and opportunistic lifestyles of human gut symbionts. Genome Res 22(10), 1974-1984.
Malik, K.A. (1988). A new freeze-drying method for the preservation of nitrogen-fixing and other fragile bacteria. Journal of Microbiological Methods 8(5), 259-271.
Manichanh, C. (2006). Reduced diversity of faecal microbiota in Crohn's disease revealed by a metagenomic approach. Gut 55(2), 205-211.
Matsuda, K., et al., "Sensitive Quantitative Detection of Commensal Bacteria by rRNA-Targeted Reverse Transcription-PCR," Applied and Environmental Microbiology, Jan. 2007, pp. 32-39, vol. 73, No. 1.
Mbithi, J.N., Springthorpe, V.S., and Sattar, S.A. (1990). Chemical disinfection of hepatitis A virus on environmental surfaces. Applied and Environmental Microbiology 56(11), 3601-3604.

(56) References Cited

OTHER PUBLICATIONS

McGuire, G., Denham, M.C., and Balding, D.J. (2001). Models of Sequence Evolution for DNA Sequences Containing Gaps. Mol Biol Evol 18(4), 481-490.

McNulty, N.P., Yatsunenko, T., Hsiao, A., Faith, J.J., Muegge, B.D., Goodman, A.L., Henrissat, B., Oozeer, R., Cools-Portier, S., Gobert, G., et al. (2011). The impact of a consortium of fermented milk strains on the gut microbiome of gnotobiotic mice and monozygotic twins. Sci Transl Med 3(106), 106ra106.

Mevissen-Verhage, E.A., Marcelis, J.H., Vos, M.N. De, Amerongen, W.C.H., and Verhoef, J. (1987). *Bifidobacterium, Bacteroides, and Clostridium* spp. in fecal samples from breast-fed and bottle-fed infants with and without iron supplement. J. Clin. Microbiol. 25(2), 285-289.

Miller, R.S., and Hoskins, L.C. (1981). Mucin degradation in human colon ecosystems. Fecal population densities of mucin-degrading bacteria estimated by a "most probable number" method. Gastroenterology 81(4), 759-765.

Miyamoto-Shinohara, Y., Sukenobe, J., Imaizumi, T., Nakahara, T., and Others (2008). Survival of freeze-dried bacteria. The Journal of General and Applied Microbiology 54(1), 9.

Momose, Y. et al., "16S rRNA Gene Sequence-Based Analysis of Clostridia Related to Conversion of Germfree Mice to the Normal State," Journal of Applied Microbiology, 2009, pp. 2088-2097, vol. 107.

Morgan, C.A., Herman, N., White, P.A., and Vesey, G. (2006). Preservation of micro-organisms by drying; A review. Journal of Microbiological Methods 66(2), 183-193.

Murri, M., Leiva, I., Gomez-Zumaquero, J.M., Tinahones, F.J., Cardona, F., Soriguer, F., and Queipo-Ortuño, M.I. (2013). Gut microbiota in children with type 1 diabetes differs from that in healthy children: a case-control study. BMC Med 11(1), 1-12.

Myllyluoma, E. et al., "Effects of Multispecies Probiotic Combination on Helicobacter pylori Infection in Vitro," Clinical and Vaccine Immunology, Sep. 2008, pp. 1472-1482, vol. 15, No. 9.

New Zealand First Examination Report, New Zealand Application No. 709392, Oct. 5, 2015, 7 pages.

Nicholson, W.L., and Law, J.F. (1999). Method for purification of bacterial endospores from soils: UV resistance of natural Sonoran desert soil populations of *Bacillus* spp. with reference to *B. subtilis* strain 168. Journal of Microbiological Methods 35(1), 13-21.

NIH human microbiome project, <http://www.hmpdacc.org/> Accessed 27th Match 2014.

Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).

Nitert, M.D., Barrett, H.L., Foxcroft, K., Tremellen, A., Wilkinson, S., Lingwood, B., Tobin, J.M., McSweeney, C., O'Rourke, P., McIntyre, H.D., et al. (2013). SPRING: an RCT study of probiotics in the prevention of gestational diabetes mellitus in overweight and obese women. BMC Pregnancy and Childbirth 13(1), 50.

Noack, J., Kleessen, B., Proll, J., Dongowski, G., and Blaut, M. (1998). Dietary guar gum and pectin stimulate intestinal microbial polyamine synthesis in rats. J. Nutr. 128(8), 1385-1391.

Nyangale, et al., "Gut Microbial Activity, Implications for Health and Disease: the Potential Role of Metabolite Analysis," J. Proteome Res., 2012, pp. 5573-5585. vol. 11, No. 12.

O'Hara, C.M., Brenner, F.W., and Miller, J.M. (2000). Classification, identification, and clinical significance of Proteus, Providencia, and Morganella. Clin. Microbiol. Rev. 13(4), 534-546.

Okada, Y., Setoyama, H., Matsumoto, S., Imaoka, A., Nanno, M., Kawaguchi, M., and Umesaki, Y. (1994). Effects of fecal microorganisms and their chloroform-resistant variants derived from mice, rats, and humans on immunological and physiological characteristics of the intestines of ex-germfree mice. Infect. Immun. 62(12), 5442-5446.

Olle, B. (2013). Medicines from microbiota. Nat. Biotechnol. 31(4), 309-315.

OpenBiome. Quality metrics. <http://static.squarespace.com/static/50e0c29ae4b0a05702af7e6a/t/52e19b89e4b0b28f802c9b4e/1390517129976/OpenBiome%20Quality%20Metrics.pdf> Accessed Mar. 21, 2014.

Owens, C., Broussard, E., and Surawicz, C. (2013). Fecal microbiota transplantation and donor standardization. Trends in Microbiology 21(9), 443-445.

Paine, R.T. (1969). A note on trophic complexity and community stability. American Naturalist 103(929), 91-93.

Palmfeldt, J., and Hahn-Hägerdal, B. (2000). Influence of culture pH on survival of *Lactobacillus reuteri* subjected to freeze-drying. International Journal of Food Microbiology 55(1), 235-238.

Pamer, E.G. (2014). Fecal microbiota transplantation: effectiveness, complexities, and lingering concerns. Mucosal Immunology 7(2), 210-214.

Paredes-Sabja, D., Udompijitkul, P., and Sarker, M.R. (2009). Inorganic phosphate and sodium ions are cogerminants for spores of *Clostridium perfringens* type A food poisoning-related isolates. Appl. Environ. Microbiol. 75(19), 6299-6305.

Path Vaccine and Pharmaceutical Technologies Group. Summary of stability data for investigational formulations of vaccines. <http://www.path.org/publications/files/TS_vaccine_stability_table_invest.pdf> Accessed Mar. 21, 2014.

PCT International Search Report and Written Opinion, PCT Application No. PCT/US14/14744, dated May 21, 2014, 36 pages.

PCT International Search Report and Written Opinion, PCT Application No. PCT/US14/14747, dated Jun. 13, 2014, 27 pages.

PCT International Search Report and Written Opinion, PCT Application No. PCT/US14/14738, dated Jul. 30, 2014, 32 pages.

PCT International Search Report and Written Opinion, PCT Application No. PCT/US14/14745, dated Jul. 30, 2014, 31 pages.

PCT Invitation to Pay Additional Fees, PCT Application No. PCT/US14/14745, dated May 16, 2014, 2 pages.

PCT International Search Report and Written Opinion, PCT Application No. PCT/US13/71758, dated May 5, 2014, 45 pages.

PCT Invitation to Pay Additional Fees, PCT Application No. PCT/US14/70684, dated Mar. 24, 2015, 2 pages.

PCT International Search Report and Written Opinion, PCT Application No. PCT/US2014/067491, dated Apr. 2, 2015, 14 pages.

PCT International Search Report and Written Opinion, PCT Application No. PCT/US14/70684, dated Jun. 10, 2015, 24 pages.

PCT Invitation to Pay Additional Fees, PCT Application No. PCT/US13/71758, dated Feb. 25, 2014, 4 pages.

PCT Invitation to Pay Additional Fees, PCT Application No. PCT/US2014/014738, dated May 16, 2014, 2 pages.

PCT International Search Report and Written Opinion, PCT Application No. PCT/US2014/030817, dated Dec. 5, 2014, 16 pages.

PCT Invitation to Pay Additional Fees, PCT Application No. PCT/US2014/030817, dated Sep. 8, 2014, 5 pages.

PCT International Search Report and Written Opinion, PCT Application No. PCT/US2014/029539, dated Oct. 10, 2014, 17 pages.

PCT Invitation to Pay Additional Fees, PCT Application No. PCT/US14/29539, dated Jul. 31, 2014, 3 pages.

Peck, M.W. et al., "Development and Application of a New Method for Specific and Sensitive Enumeration of Spores of Nonproteolytic Clostridium Botulinum Types B, E and F in Foods and Food Materials," Applied and Environmental Microbiology, Oct. 2010, pp. 6607-6614, vol. 76, No. 19.

Pehkonen, K.S., Roos, Y.H., Miao, S., Ross, R.P., and Stanton, C. (2008). State transitions and physicochemical aspects of cryoprotection and stabilization in freeze-drying of Lactobacillus rhamnosus GG (LGG). Journal of Applied Microbiology 104(6), 1732-1743.

Peighambardoust, S.H., Golshan Tafti, A., and Hesari, J. (2011). Application of spray drying for preservation of lactic acid starter cultures: a review. Trends in Food Science & Technology 22(5), 215-224.

Pellegrino, P.M., Fell JR., N.F., and Gillespie, J.B. (2002). Enhanced spore detection using dipicolinate extraction techniques. Analytica Chimica Acta 455(2), 167-177.

Perez, F., Pultz, M.J., Endimiani, A., Bonomo, R.A., and Donskey, C.J. (2011). Effect of antibiotic treatment on establishment and

(56) References Cited

OTHER PUBLICATIONS elimination of intestinal colonization by KPC-producing Klebsiella pneumoniae in mice. Antimicrob. Agents Chemother. 55(6), 2585-2589.
Perez, J., Springthorpe, V.S., and Sattar, S.A. (2011). Clospore: a liquid medium for producing high titers of semi-purified spores of *Clostridium difficile*. J AOAC Int 94(2), 618-626.
Peterson, D.A. et al., "Metagenomic Approaches for Defining the Pathogenesis of Inflammatory Bowel Diseases," Cell Host Microbe, Jun. 2008, pp. 417-427, vol. 3, No. 6.
Petrof, E.O., Claud, E.C., Gloor, G.B., and Allen-Vercoe, E. (2013a). Microbial ecosystems therapeutics: a new paradigm in medicine? Beneficial Microbes 4(1), 53-65.
Petrof, E.O., Gloor, G.B., Vanner, S.J., Weese, S.J., Carter, D., Daigneault, M.C., Brown, E.M., Schroeter, K., and Allen-Vercoe, E. (2013b). Stool substitute transplant therapy for the eradication of Clostridium difficile infection: "RePOOPulating" the gut, Microbiome, Jan. 9, 2013, p. 3, vol. 1, No. 1.
Picot, A., and Lacroix, C. (2004). Encapsulation of bifidobacteria in whey protein-based microcapsules and survival in simulated gastrointestinal conditions and in yoghurt. International Dairy Journal 14(6), 505-515.
Pinn, D. et al. (2013). Follow-up Study of Fecal Microbiota Transplantation (FMT) for the Treatment of Refractory Irritable Bowel Syndrome (IBS). Abstract ACG 2013.
Postgate, J.R., and Hunter, J.R. (1961). On the Survival of Frozen Bacteria. J Gen Microbiol 26(3), 367-378.
Prilassnig, M. et al., "Are Probiotics Detectable in Human Feces After Oral Uptake by Healthy Volunteers?" The Middle European Journal of Medicine, Aug. 2007, pp. 456-462, vol. 119, Nos. 15-16.
Pultz, N.J., Hoyen, C.K., and Donskey, C.J. (2004). Inhibition of methicillin-resistant *Staphylococcus aureus* by an in vitro continuous-flow culture containing human stool microflora. FEMS Microbiology Letters 241(2), 201-205.
Queenan, A.M., and Bush, K. (2007). Carbapenemases: the Versatile β-Lactamases. Clin. Microbiol. Rev. 20(3), 440-458.
Quigley, E.M.M. et al., "Small Intestinal Bacterial Overgrowth: Roles of Antibiotics, Prebiotics and Probiotics," Gastroenterology, Feb. 2006, pp. 78-90, vol. 130.
Raibaud, P., Ducluzeau, R., Dubos, F., Hudault, S., Bewa, H., and Muller, M.C. (1980). Implantation of bacteria from the digestive tract of man and various animals into gnotobiotic mice. Am J Clin Nutr 33(11), 2440-2447.
Ramirez, N., and Abel-Santos, E. (2010). Requirements for germination of *Clostridium sordellii* spores in vitro. J. Bacteriol. 192(2), 418-425.
Rao, A.V., Shiwnarain, N., and Maharaj, I. (1989). Survival of Microencapsulated Bifidobacterium pseudolongum in Simulated Gastric and Intestinal Juices. Canadian Institute of Food Science and Technology Journal 22(4), 345-349.
Reeves, A.E., Koenigsknecht, M.J., Bergin, I.L., and Young, V.B. (2012). Suppression of Clostridium difficile in the Gastrointestinal Tracts of Germfree Mice Inoculated with a Murine Isolate from the Family Lachnospiraceae. Infection and Immunity 80(11), 3786-3794.
Rexroad, J., Wiethoff, C.M., Jones, L.S., and Middaugh, C.R. (2002). Lyophilization and the thermostability of vaccines. Cell Preservation Technology 1(2), 91-104.
Ridaura, V.K., Faith, J.J., Rey, F.E., Cheng, J., Duncan, A.E., Kau, A.L., Griffin, N.W., Lombard, V., Henrissat, B., Bain, J.R., et al. (2013). Gut Microbiota from Twins Discordant for Obesity Modulate Metabolism in Mice. Science 341(6150), 1241214-1241214.
Rode, L.J., and Foster, J.W. (1961). Germination of bacterial spores with alkyl primary amines1. J Bacteriol 81(5), 768-779.
Roffe, C. (1996). Biotherapy for antibiotic-associated and other diarrhoeas. J. Infect. 32(1), 1-10.
Rohlke, F., Surawicz, C.M., and Stollman, N. (2010). Fecal flora reconstitution for recurrent Clostridium difficile infection: results and methodology. J. Clin. Gastroenterol. 44(8), 567-570.

Rosen, D.L., Sharpless, C., and Mcgown, L.B. (1997). Bacterial Spore Detection and Determination by Use of Terbium Dipicolinate Photoluminescence. Anal. Chem. 69(6), 1082-1085.
Sack, D.A., Shimko, J., Sack, R.B., Gomes, J.G., Macleod, K., O'Sullivan, D., and Spriggs, D. (1997). Comparison of alternative buffers for use with a new live oral cholera vaccine, Peru-15, in outpatient volunteers. Infect. Immun. 65(6), 2107-2111.
Sacks, L.E., and Alderton, G. (1961). Behavior of bacterial spores in aqueous polymer two-phase systems. J. Bacteriol. 82, 331-341.
Sahlström, L., Bagge, E., Emmoth, E., Holmqvist, A., Danielsson-Tham, M.-L., and Albihn, A. (2008). A laboratory study of survival of selected Microorganisms after heat treatment of biowaste used in biogas plants. Bioresour. Technol. 99(16), 7859-7865.
Santivarangkna, C., Kulozik, U., and Foerst, P. (2007). Alternative Drying Processes for the Industrial Preservation of Lactic Acid Starter Cultures. Biotechnology Progress 23(2), 302-315.
Sattar, S.A., Jason, T., Bidawid, S., and Farber, J. (2000). Foodborne spread of hepatitis A: recent studies on virus survival, transfer and inactivation. The Canadian Journal of Infectious Diseases 11(3), 159.
Savaiano, D.A., Ritter, A.J., Klaenhammer, T., Walker, M.R., Carlson, H.L.F., and Ruckle, J. (2012). A Novel High Purity Short-Chain Galacto-Oligosaccharide (RP-G28) Improves Lactose Digestion and Symptoms of Lactose Intolerance. Gastroenterology 142(5), S-182.
Savaiano, D.A., Ritter, A.J., Klaenhammer, T.R., Walker, W.A., James, G.M., Longcore, A.T., Chandler, J.R., and Foyt, H.L. (2013). Improving lactose digestion and symptoms of lactose intolerance with a novel galacto-oligosaccharide (RP-G28): a randomized, double-blind clinical trial. Nutrition Journal 12(1), 160.
Seale, R.B., Flint, S.H., Mcquillan, A.J., and Bremer, P.J. (2008). Recovery of Spores from Thermophilic Dairy Bacilli and Effects of Their Surface Characteristics on Attachment to Different Surfaces. Appl Environ Microbiol 74(3), 731-737.
Seo, M., Inoue, I., Tanaka, M., Matsuda, N., Nakano, T., Awata, T., Katayama, S., Alpers, D.H., and Komoda, T. (2013). Clostridium butyricum MIYAIRI 588 improves high-fat diet-induced non-alcoholic fatty liver disease in rats. Dig. Dis. Sci. 58(12), 3534-3544.
Setlow, B., Cowan, A. E., and Setlow, P. (2003). Germination of spores of Bacillus subtilis with dodecylamine. Journal of Applied Microbiology 95(3), 637-648.
Setlow, B., Yu, J., Li, Y.-Q., and Setlow, P. (2013). Analysis of the germination kinetics of individual Bacillus subtilis spores treated with hydrogen peroxide or sodium hypochlorite. Letters in Applied Microbiology 57(4), 259-265.
Shafaat, H.S., and Ponce, A. (2006). Applications of a Rapid Endospore Viability Assay for Monitoring UV Inactivation and Characterizing Arctic Ice Cores. Appl Environ Microbiol 72(10), 6808-6814.
Shah, I.M., Laaberki, M.-H., Popham, D.L., and Dworkin, J. (2008). A eukaryotic-like Ser/Thr kinase signals bacteria to exit dormancy in response to peptidoglycan fragments. Cell 135(3), 486-496.
Shah, N.P., "Symposium: Probiotic Bacteria: Probiotic Bacteria: Selective Enumeration and Survival in Dairy Foods," Oct. 7, 1999, 14 pages.
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, S. (2012). Clostridium difficile in inflammatory Bowel Disease: a dangerous mix (Clostridium difficile Symposium, Miriam Hospital, Providence, RI).
Shahinas, D., Silverman, M., Sittler, T., Chiu, C., Kim, P., Allen-Vercoe, E., Weese, S., Wong, A., Low, D.E., and Pillai, D.R. (2012). Toward an Understanding of Changes in Diversity Associated with Fecal Microbiome Transplantation Based on 16S rRNA Gene Deep Sequencing. mBio 3(5), e00338-12-e00338-12.
Sharpe, E.S., Nickerson, K.W., Bulla JR, L.A., and Aronson, J.N. (1975). Separation of spores and parasporal crystals of Bacillus thuringiensis in gradients of certain x-ray contrasting agents. Applied Microbiology 30(6), 1052.

(56) References Cited

OTHER PUBLICATIONS

Sheu, T.-Y., Marshall, R.T., and Heymann, H. (1993). Improving Survival of Culture Bacteria in Frozen Desserts by Microentrapment. Journal of Dairy Science V6(7), 1902-1907.

Siaterlis, A., Deepika, G., and Charalampopoulos, D. (2009). Effect of culture medium and cryoprotectants on the growth and survival of probiotic lactobacilli during freeze drying. Letters in Applied Microbiology 48(3), 295-301.

Sigma-Tau. VSL#3. <http://www.vsl3.com/> Accessed Mar. 21, 2014.

Skaar, E., "The Battle for Iron Between Bacterial Pathogens and Their Vertebrate Hosts," PLoS Pathog., Aug. 12, 2010, pp. 1-4, vol. 6, No. 8.

Snitkin, E.S., Zelazny, A.M., Thomas, P.J., Stock, F Henderson, D.K., Palmore, T.N., and Segre, J.A. (2012). Tracking a Hospital Outbreak of Carbapenem-Resistant Klebsiella pneumoniae with Whole-Genome Sequencing. Sci Transl Med 4(148), 148ra116-148ra116.

Solanki, H.K., Pawar, D.D., Shah, D.A., Prajapati, V.D., Jani, G.K., Mulla, A.M., and Thakar, P.M. (2013). Development of Microencapsulation Delivery System for Long-Term Preservation of Probiotics as Biotherapeutics Agent. BioMed Research International 2013, 1-21.

SOP No. MB-28-00. <http://www.epa.gov/pesticides/methods/MB-28-00.pdf> Accessed 27th Match 2014.

Sorg, J.A., and Sonenshein, A.L. (2008). Bile Salts and Glycine as Cogerminants for Clostridium difficile Spores. J Bacteriol 190(7), 2505-2512.

Sow, H., Desbiens, M., Morales-Rayas, R., Ngazoa, S.E., and Jean, J. (2011). Heat Inactivation of Hepatitis A Virus and a Norovirus Surrogate in Soft-Shell Clams (Mya arenaria). Foodborne Pathogens and Disease 8(3), 387-393.

Stams, A.J.M., Van Dijk, J.B., Dijkema, C., and Plugge, C.M. (1993). Growth of Syntrophic Propionate-Oxidizing Bacteria with Fumarate in the Absence of Methanogenic Bacteria. Appl Environ Microbiol 59(4), 1114-1119.

Stevens, K.A., and Jaykus, L.-A. (2004). Bacterial Separation and Concentration from Complex Sample Matrices: A Review. Critical Reviews in Microbiology 30(1), 7-24.

Su, W.J., Waechter, M.J., Bourlioux, P., Dolegeal, M., Fourniat, J., and Mahuzier, G. (1987). Role of volatile fatty acids in colonization resistance to Clostridium difficile in gnotobiotic mice. Infect. Immun. 55(7), 1686-1691.

Talwalkar, A., and Kailasapathy, K. (2003). Effect of microencapsulation on oxygen toxicity in probiotic bacteria. Australian Journal of Dairy Technology 58(1), 36-39.

Tamir, H., and Gilvarg, C. (1966). Density Gradient Centrifugation for the Separation of Sporulating Forms of Bacteria. J. Biol. Chem. 241(5), 1085-1090.

Tanaka, M. et al., "Increased Fasting Plasma Ghrelin Levels in Patients with Bulimia Nervosa," European Journal of Endocrinology, Jun. 2002, pp. 1-3, vol. 146.

Taur, Y., and Pamer, E.G. (2014). Harnessing Microbiota to Kill a Pathogen: Fixing the microbiota to treat Clostridium difficile infections. Nature Medicine 20(3), 246-247.

Taur, Y., Xavier, J.B., Lipuma, L., Ubeda, C., Goldberg, J., Gobourne, A., Lee, Y.J., Dubin, K.A., Socci, N.D., Viale, A., et al. (2012). Intestinal Domination and the Risk of Bacteremia in Patients Undergoing Allogeneic Hematopoietic Stem Cell Transplantation. Clin Infect Dis 55(7), 905-914.

The Human Microbiome Project Consortium (2012). Structure, function and diversity of the healthy human microbiome. Nature 486(7402), 207-214.

Tisa, L.S., Koshikawa, T., and Gerhardt, P. (1982). Wet and dry bacterial spore densities determined by buoyant sedimentation. Applied and Environmental Microbiology 43(6), 1307-1310.

Tvede, M., and Rask-Madsen, J. (1989). Bacteriotherapy for chronic relapsing Clostridium difficile diarrhoea in six patients. Lancet 1 (8648), 1156-1160.

Ubeda, C., Bucci, V., Caballero, S., Djukovic, A., Toussaint, N.C., Equinda, M., Lipuma, L., Ling, L., Gobourne, A., No. D., et al. (2013). Intestinal Microbiota Containing Barnesiella Species Cures Vancomycin-Resistant Enterococcus faecium Colonization. Infect. Immun. 81(3), 965-973.

Ubeda, C., Taur, Y., Jenq, R.R., Equinda, M.J., Son, T., Samstein, M., Viale, A., Socci, N.D., Van Den Brink, M.R.M., Kamboj, M., et al. (2010). Vancomycin-resistant Enterococcus domination of intestinal microbiota is enabled by antibiotic treatment in mice and precedes bloodstream invasion in humans. Journal of Clinical Investigation 120(12), 4332-4341.

United States Office Action, U.S. Appl. No. 14/313,828, dated Aug. 13, 2014, 5 pages.

United States Office Action, U.S. Appl. No. 14/313,828, dated Dec. 10, 2014, 7 pages.

United States Office Action, U.S. Appl. No. 14/313,828, dated May 15, 2015, 11 pages.

United States Office Action, U.S. Appl. No. 14/221,190, dated Jul. 22, 2014, 19 pages.

United States Office Action, U.S. Appl. No. 14/091,201, dated Mar. 25, 2014, 19 pages.

United States Office Action, U.S. Appl. No. 14/197,044, dated Aug. 13, 2014, 5 pages.

United States Office Action, U.S. Appl. No. 14/592,481, dated Dec. 22, 2015, 21 pages.

Van Der Woude, M.W., and Baumler, A.J. (2004). Phase and Antigenic Variation in Bacteria. Clin Microbiol Rev 17(3), 581-611.

Van Kregten, E., Westerdaal, N.A., and Willers, J.M. (1984). New, simple medium for selective recovery of Klebsiella pneumoniae and Klebsiella oxytoca from human feces. J Clin Microbiol 20(5), 936-941.

Van Nood, E., Vrieze, A., Nieuwdorp, M., Fuentes, S., Zoetendal, E.G., De Vos, W.M., Visser, C.E., Kuijper, E.J., Bartelsman, J.F.W. M., Tijssen, J.G.P., et al. (2013). Duodenal Infusion of Donor Feces for Recurrent Clostridium difficile. New England Journal of Medicine 368(5), 407-415.

Vandenplas, Y., Veereman, G., Van Der Werff Ten Bosch, J., Goossens, A., Pierard, D., Samsom, J.N., and Escher, J.C. (2014). Fecal Microbial Transplantation in a One-Year-Old Girl with Early Onset Colitis—Caution Advised: Journal of Pediatric Gastroenterology and Nutrition 1.

Vidal, M., Forestier, C., Charbonnel, N., Henard, S., Rabaud, C., and Lesens, O. (2010). Probiotics and Intestinal Colonization by Vancomycin-Resistant Enterococci in Mice and Humans. J Clin Microbiol 48(7), 2595-2598.

Villano, S.A., Seiberling, M., Tatarowicz, W., Monnot-Chase, E., and Gerding, D.N. (2012). Evaluation of an Oral Suspension of VP20621, Spores of Nontoxigenic Clostridium difficile Strain M3, in Healthy Subjects. Antimicrobial Agents and Chemotherapy 56(10), 5224-5229.

Wagman, J., and Weneck, E.J. (1963). Preservation of bacteria by circulating-gas freeze drying. Applied Microbiology 11(3), 244-248.

Waites, W.M., and Wyatt, L.R. (1971). Germination of spores of Clostridium bifermentans by certain amino acids, lactate and pyruvate in the presence of sodium or potassium ions. J. Gen. Microbiol. 67(2), 215-222.

Waites, W.M., and Wyatt, L.R. (1974). The effect of pH, germinants and temperature on the germination of spores of Clostridium bifermentans. J. Gen. Microbiol. 80(1), 253-258.

Walker, A.W., and Lawley, T.D. (2012). Therapeutic modulation of intestinal dysbiosis. Pharmacological Research 69(1), 75-86.

Wang, M., et al., "Comparison of Bacterial Diversity Along The Human Intestinal Tract by Direct Cloning and Sequencing of 16S rRNA Genes," FEMS Microbiology Ecology, 2005, pp. 219-231, vol. 54.

Wang, S., and Curtiss III, R. (2014). Development of Streptococcus pneumoniae Vaccines Using Live Vectors. Vaccines 2(1), 49-88.

Weingarden, A.R., Chen, C., Bobr, A., Yao, D Lu, Y., Nelson, V.M., Sadowsky, M.J., and Khoruts, A. (2013). Microbiota transplantation restores normal fecal bile acid composition in recurrent Clostridium difficile infection. AJP: Gastrointestinal and Liver Physiology 306(4), G310-G319.

(56) References Cited

OTHER PUBLICATIONS

Wiencek, K.M. et al., "Hydrophobicity of Bacillus and Clostridium Spores," Applied and Environmental Microbiology, Sep. 1990, pp. 2600-2605, vol. 56, No. 9.

Wilson, K.H., and Sheagren, J.N. (1983). Antagonism of toxigenic Clostridium difficile by nontoxigenic C. difficile. Journal of Infectious Diseases 147(4), 733.

Wilson, K.H., Silva, J., and Fekety, F.R. (1981). Suppression of Clostridium difficile by Normal Hamster Cecal Flora and Prevention of Antibiotic-Associated Cecitis. Infect Immun 34(2), 626-628.

Wilson, K. et al., "Role of Competition for Nutrients in Suppression of Clostridium difficile by the Colonic Microflora," Infection and Immunity, Oct. 1988, pp. 2610-2614m vol. 56, No. 10.

Woo, T.D.H., Oka, K., Takahashi, M., Hojo, F., Osaki, T., Hanawa, T., Kurata, S., Yonezawa, H., and Kamiya, S. (2011). Inhibition of the cytotoxic effect of Clostridium difficile in vitro by Clostridium butyricum MIYAIRI 588 strain. J. Med. Microbiol. 60(Pt 11), 1617-1625.

Wróbel, B. (2008). Statistical measures of uncertainty for branches in phylogenetic trees inferred from molecular sequences by using model-based methods. J. Appl. Genet. 49(1), 49-67.

Wroblewski, D., Hannett, G.E., Bopp, D.J., Dumyati, G.K., Halse, T.A., Dumas, N.B., and Musser, K.A. (2009). Rapid Molecular Characterization of Clostridium difficile and Assessment of Populations of C. difficile in Stool Specimens. Journal of Clinical Microbiology 47(7), 2142-2148.

Yamakawa, K. et al., "Enhancement of Clostridium difficile Toxin Production in Biotin-Limited Conditions," J. Med. Microbiol., Feb. 1996, pp. 111-114, vol. 44, No. 2.

Yamamura, H., Hayakawa, M., and Iimura, Y. (2003). Application of sucrose-gradient centrifugation for selective isolation of *Nocardia* spp. from soil. Journal of Applied Microbiology 95(4), 677-685.

Yang, W.-W., and Ponce, A. (2009). Rapid endospore viability assay of Clostridium sporogenes spores. International Journal of Food Microbiology 133(3), 213-216.

Yang, W.-W., and Ponce, A. (2011). Validation of a Clostridium Endospore Viability Assay and Analysis of Greenland Ices and Atacama Desert Soils. Appl. Environ. Microbiol. 77(7), 2352-2358.

Yang, W.-W., Crow-Willard, E.N., and Ponce, A. (2009). Production and characterization of pure Clostridium spore suspensions. J. Appl. Microbiol. 106(1), 27-33.

Yang, W.W. (2010). Fast Viability Assessment of Clostridium Spores Survival in Extreme Environments. PhD thesis California Institute of Technology.

YI, X., and Setlow, P. (2010). Studies of the Commitment Step in the Germination of Spores of *Bacillus* Species. J. Bacteriol. 192(13), 3424-3433.

Yung, P.T., and Ponce, A. (2008). Fast Sterility Assessment by Germinable-Endospore Biodosimetry. Appl. Environ. Microbiol. 74(24), 7669-7674.

Yunoki, M., Tsujikawa, M., Urayama, T., Sasaki, Y., Morita, M., Tanaka, H., Hattori, S., Takechi, K., and Ikuta, K. (2003). Heat sensitivity of human parvovirus B19. Vox Sanguinis 84(3), 164-169.

Zeng, Y., Fan, H., Chiueh, G., Pham, B., Martin, R., Lechuga-Ballesteros, D., Truong, V.L., Joshi, S.B., and Middaugh, C.R. (2009). Towards development of stable formulations of a live attenuated bacterial vaccine: a preformulation study facilitated by a biophysical approach. Hum Vaccin 5(5), 322-331.

Zhao, J., Krishna, V., Moudgil, B., and Koopman, B. (2008). Evaluation of endospore purification methods applied to Bacillus cereus. Separation and Purification Technology 61(3), 341-347.

Halmann, M. et al., "Stages in Germination of Spores of Bacillus Lichenformis," J. Bacteriol., 1962, pp. 1187-1193, vol. 84.

McFarland, L.V., "Use of Probiotics to Correct Dysbiosis of Normal Microbiota Following Disease or Disruptive Events: A Systematic Review," BMJ Open, 2014, pp. 1-18, vol. 4.

Mierau, I. et al., "Industrial-Scale Production and Purification of a Heterologous Protein in Lactococcus Lactis Using the Nisin-Controlled Gene Expression System NICE: The Case of Lysostaphin," Microbial Cell Factories, May 27, 2005, pp. 1-9, vol. 4, No. 15.

New Zealand First Examination Report, New Zealand Application No. 711771, dated Nov. 23, 2015, 6 pages.

New Zealand First Examination Report, New Zealand Application No. 711773, dated Nov. 24, 2015, 6 pages.

"Potentials of Probiotics in Pig Nutrition," AllAboutFeed News, Jan. 31, 2007, 6 pages.

Robinson, I.M. et al., "Emendation of Acetivibrio and Description of Acetivibrio ethanolgignens, a New Species from the Colons of Pigs with Dysentery," International Journal of Systematic Bacteriology, Jul. 1981, pp. 333-338, vol. 31, No. 3.

Russian Office Action, Russian Application No. 2015137399, dated Mar. 22, 2016, 8 pages.

United States Office Action, U.S. Appl. No. 15/068,438, dated Apr. 28, 2016, 9 pages.

United States Office Action, U.S. Appl. No. 14/884,655, dated May 5, 2016, 10 pages.

Van Immerseel, F. et al., "Butyric Acid-Producing Anaerobic Bacteria as a Novel Probiotic Treatment Approach for Inflammatory Bowel Disease," Journal of Medical Microbiology, JMM Editorial, 2010, pp. 141-143.

Hazenberg, M.P. et al., "Conversion of Germ-Free Mice to the Normal State by Clostridia," Zeitschrift fur Versuchstierkunde, 1976, pp. 185-190, vol. 18, No. 4.

Manichanh, C. et al., "Reshaping the Gut Microbiome with Bacterial Transplantation and Antibiotic Intake," Genome Research, 2010, pp. 1411-1419, vol. 20.

Thompson-Chagoyan, O.C. et al., "Aetiology of Inflammatory Bowel Disease (IBD): Role of Intestinal Microbiota and Gut-Associated Lymphoid Tissue Immune Response," Clinical Nutrition, Feb. 2005, pp. 339-352, vol. 24, No. 3.

Wilson, K.H. et al., "Interaction of Clostridium difficile and *Escherichia coli* with Microfloras in Continuous-Flow Cultures and Gnotobiotic Mice," Infection and Immunity, Nov. 1986, pp. 354-358, vol. 54, No. 2.

Chinese First Office Action, Chinese Application No. 201380071190.X, dated Jul. 4, 2018, 11 pages (with concise explanation of relevance).

European Summons to Attend Oral Proceedings Pursuant to Rule 115(1) EPC, European Application No. 14768281.9, dated Jul. 11, 2018, 9 pages.

Mexican Office Action, Mexican Application No. MX/a/2015/006491, dated Jun. 25, 2018, 8 pages, (with concise explanation of relevance).

Mexican Office Action, Mexican Application No. MX/a/2015/009991, dated Jul. 16, 2018, (with concise explanation of relevance).

Sheptulin, A.A., "Refractory and Relapsing Forms of Clostridium difficile—Associated Colitis," www.gastro-j.ru, 2011, pp. 50-53 (with English abstract).

Chinese Second Office Action, Chinese Application No. 201480019395.8, dated Apr. 4, 2018 (with concise explanation of relevance), 14 pages.

El-Houssieny, R. et al., "Recovery and Detection of Microbial Contaminants in Some Non-Sterile Pharmaceutical Products," Archives of Clinical Microbiology, 2013, pp. 1-14, vol. 4, No. 6: 1.

European Examination Report, European Application No. 14746341.8, dated Apr. 18, 2018, 8 pages.

European Examination Report, European Application No. 13856249.1, dated May 23, 2018, 6 pages.

Holdeman, L.V. et al., "Human Fecal Flora: Variation in Bacterial Composition Within Individuals and a Possible Effect of Emotional Stress," Applied and Environmental Microbiology, Mar. 1976, pp. 359-375, vol. 31, No. 3.

Japanese Office Action, Japanese Application No. 2015-556240, dated Jun. 5, 2018, 5 pages.

Manafi, M. Handbook of Culture Media for Food and Water Microbiology, 3rd Edition, Janet E.L. Corry et al., 2012, pp. 223-260.

Technical Data, HiMedia Laboratories Pvt. Ltd., M581BP, 2011, pp. 1-2.

United States Office Action, U.S. Appl. No. 15/359,439, dated Jun. 15, 2018, 14 pages.

(56) References Cited

OTHER PUBLICATIONS

United States Office Action, U.S. Appl. No. 14/776,676, dated Jun. 22, 2018, 16 pages.
United States Office Action, U.S. Appl. No. 15/039,007, dated Jun. 12, 2018, 9 pages.
Cruz et al., "Immunosuppressive and Nonimmunosuppressive Cyclosporine Analogs Are Toxic to the Opportunistic Fungal Pathogen Cryptococcus neoformans via Cyclophilin-Dependent Inhibition of Calcineurin," Antimicrob. Agents Chemother. 44(1): 143-149, American Society for Microbiology (2000).
Fitzpatrick, L.R., "Probiotics for the treatment of Clostridium difficile associated disease", World Journal of Gastrointestinal Pathophysiology, 4(3): 47, 1 Baishideng Publishing Group, United States (2013).
Marcus et al., "Deoxycholic acid and the pathogenesis of gall stones," Gut, 29, 522-533, BMJ Publishing Group, England (1988).
Rasti et al., "Inhibition of Clostridium scindens and Clostridium hiranonis growth by Bifidobacterium pseudocatenulatum G4 in simulated colonic pH ," Journal of Food Agriculture and Environment 11 (2): 127-131, WFL Publisher Ltd, Poland (2013).
Vogt et al. "Chemical communication in the gut: Effects of microbiota-generated metabolites on gastrointestinal bacterial pathogens," Anaerobe 34 106-115, Elsevier, Netherlands (2015).
Gut definition. Merriam Webster Dictionary. https://www.merriam-webster.com/dictionary/gut, retrieved Mar. 9, 2020.
Office Action dated Jul. 10, 2018, in United States Application No., Pamer, E. et al., filed Nov. 18, 2016, 16 pages.
Office Action dated Feb. 26, 2019, in U.S. Appl. No. 15/312,610, Pamer, E. et al., filed Nov. 18, 2016, 22 pages.
Office Action dated Dec. 21, 2018, in U.S. Appl. No. 15/986,369, Pamer, E. et al., filed May 22, 2018, 16 pages.
Office Action dated Sep. 20, 2019, in U.S. Appl. No. 15/986,369, Pamer, E. et al., filed May 22, 2018, 11 pages.
Notice of Allowance dated Jan. 13, 2020, in U.S. Appl. No. 15/986,369, Pamer, E. et al., filed May 22, 2018, 7 pages.
Stackebrandt et al. "Taxonomic Note: A Place for DNA-DNA Reassociation and 16S rRNA Sequence Analysis in the Present Species Definition in Bacteriology," International Journal of Systematic Bacteriology 44(4): 846-849, International Union of Microbiological Societies (Oct. 1994).
14th International Congress of Immunology, Kobe, Japan, International Immunology, Aug. 2010, 3 pages, vol. 22, Issue Suppl 1 Pt 3.
Andoh, A., et al., "Terminal Restriction Fragment Polymorphism Analyses of Fecal Microbiota in Five Siblings Including Two with Ulcerative Colitis," Gastroenterology 2(5):343-345, Springer Japan (Oct. 2009).
Anonymous, "Ecobiotic Drugs," Seres Therapeutics, Oct. 22, 2015, <http://web.archive.org/web/20151 022091731/http://web.archive.org/web/20151ecobiotic-drugs, retrieved Mar. 7, 2017 (3 pages).
Anonymous, "Microbiome Therapeutics Platform," Seres Therapeutics, Retrieved on [Oct. 23, 2015], Retrieved from (http://web.arch ive.org/web/20151023063153/), Retrieved from (http://www.serestherapeutics.com/ou rscience/microbiome-therapeutics-platform), Retrieved on [Mar. 7, 2017], 3 pages.
Anonymous, "Product Pipeline," Seres Therapeutics, Oct. 22, 2015], Retrived from (< http: web.="" arch="" ive.org="" web="" 20="" 151="" 022091722="" http:="" http://www.serestherapeutics.com/pipeline/products) < /http: > , Retrieved on [Mar. 7, 2017], (3 pages).
Application as Filed WO 2011/152566, Filed Jun. 3, 2011, 151 pages.
Autoimmune Disease List, There Are More Than 100 Autoimmune Diseases, American Autoimmune Related Diseases Association, AARDA, Inc., 2014, 4 pages.
Babel, N.et al., "Analysis of T Cell Receptor Repertoire by Newly Established CDR3 High-Throughput Sequencing Allows for Monitoring/Tracing of Antigen-Specific T Cells in Peripheral Blood and Tissue," pp. 063-40, 14th ICI Abstract Book, 14th International Congress of Immunology, 2010, 3 pages.

Belkaid, Y, and Rouse, B,T., "Natural Regulatory T Cells in Infectious Disease," Nature Immunology 6(4):353-360, Nature America Inc, United States (Apr. 2005).
Borody, T,J., et al., "Treatment of Ulcerative Colitis Using Fecal Bacteriotherapy," Journal of Clinical Gastroenterology 37(1):42-47, Wolters Kluwer Health, Inc, United States (Jul. 2003).
Browne, H,P., et al., "Culturing of 'unculturable' Human Microbiota Reveals Novel Taxa and Extensive Sporulation," Nature 533(7604):543-546, Nature Publishing Group, England (May 2016).
Cato, E.P., et al., "Clostridium Oroticum Comb. Nov. Amended Description," International Journal of Systematic and Evolutionary Microbiology 17(1):9-13, (Jan. 1968).
Collins, M,D., et al., "The Phylogeny of the Genus Clostridium: Proposal of Five New Genera and Eleven New Species Combinations," International Journal of Systematic Bacteriology 44(4):812-826, Society for General Microbiology, England (Oct. 1994).
Cover Page of Science, Jan. 21, 2011, 1 page.
Dabard J., et al., "Ruminococcin A, a New Iantibiotic Produced by a *Ruminococcus gnavus* Strain Isolated from Human Feces,"Applied and Environmental Microbiology, 67(9):4111-4118, American Society for Microbiology, United States (Sep. 2001).
Dewhirst, F.E., et al., "Phylogeny of the Defined Murine Microbiota: Altered Schaedler Flora," Applied and Environmental Microbiology 65(8):3287-3292, American Society for Microbiology, United States (Aug. 1999).
Eeckhaut, V., et al., "The Anaerobic Butyrate-producing Strain Butyricicoccus Pullicaecorum Decreases Colonic Inflammation and Ulceration in a Tnbs-induced Colitis Rat Model," 5th Probiotics, Prebiotics and New Foods Congress, 2009,1 page.
Elhage, R. et al., "Emerging Trends in "Smart Probiotics": Functional Consideration for the Development of Novel Health and Industrial Applications," Frontiers in Microbiology, Sep. 2017, pp. 1-11, vol. 8, Article 1889.
European Examination Report for EP Application No. EP 11728077.6, dated Sep. 18, 2015, 4 pages.
Foditsch, C., et al., "Isolation and Characterization of Faecalibacterium prausnitzii from Calves and Piglets," PLOS One, 9(12):e116465, Public Library of Science, United States ( Dec. 31, 2014).
Frank, D.N., et al., "Molecular-phylogenetic Characterization of Microbial Community Imbalances in Human Inflammatory Bowel Diseases," Proceedings of the National Academy of Sciences of the United States of America 104(34):13780-13785, National Academy of Sciences, United States (Aug. 2007).
Gaboriau-Routhiau, V., et al., "The Key Role of Segmented Filamentous Bacteria in the Coordinated Maturation of Gut Helper T Cell Responses," Immunity 31(4):677-689, Cell Press, United States (Oct. 2009).
Geuking, M.B., et al., "Intestinal Bacterial Colonization Induces Mutualistic Regulatory T Cell Responses," Immunity 34(5):794-806, Cell Press, United States (May 2011).
Hansen, A.K. et al., Handbook of Laboratory Animal Bacteriology, Second Edition, CRC Press, 2015, p. 158 (3 total pages).
Hata, D.J. et al., "Blood Group B Degrading Activity of Ruminococcus Gnavus Alpha- Galactosidase," Artif. Cells Blood Substit. Immobil. Biotechnol., May 2004, pp. 263-274, vol. 32, No. 2.
Honda, K., et al., "Regulations of T cell reponses by intestinal commensal bacteria," Journal of Intestinal Microbiology 25(2):103-104, (Apr. 2011).
ICI Wrap-up Report Immunology in the 21st Century: Defeating Infection, Autoimmunity, Allergy and Cancer, 14th International Congress of Immunology, Aug. 22-27, 2010, Japan, 1 page.
International Preliminary Report on Patentability for Application No. PCT/US2016/063697, dated May 29, 2018, Button et al., "Designed Bacterial Compositions," filed Nov. 23, 2016, 26 pages.
International Search Report and Written Opinion for Application No. PCT/US2016/041538, dated Sep. 23, 2016, Cook., et al., "Methods of Treating Colitis," filed Jul. 8, 2016, 11 Pages.
International Search Report and Written Opinion for International Application No. PCT/US2016/063697, European Patent Office, HV Rijswijk, dated May 19, 2017, 24 pages.
International Statistical Classification of Diseases and Related Health Problems 1 O'h Review, Chapter 1: Certain Infectious and Parasitic Diseases (AOO-B99), 2016, 2 pages.

(56) References Cited

OTHER PUBLICATIONS

Ivanov, I.I., et al., "Specific Microbiota Direct the Differentiation of Il-17-Producing T-Helper Cells in the Mucosa of the Small Intestine," Cell Host Microbe 4(4):337-349, Cell Press, United States (Oct. 2008) including supplemental data.
Janeway, C.A. et al., "Autoimmune Responses are Directed Against Self Antigens," Immunobiology: The Immune System in Health and Disease, 51th Edition, Garland Science, 2001, pp. 1-14.
Janeway, C.A. et al., Immuno Biology, 61th Edition, Garland Science Publishing, 2005, p. 414.
Jarry, A., et al., "Mucosal IL-10 and TGF-Beta Play Crucial Roles in Preventing LPS-driven, IFN-gamma-mediated Epithelial Damage in Human Colon Explants," The Journal of Clinical Investigation, 118(3):1132-1142, American Society for Clinical Investigation, United States (Mar. 2008).
Jawetz, et al., "Chapter 11: Spore-Forming Gram-Positive Bacilli: Bacillus and *Clostridium* Species," Jawetz, Melnick&Adelberg's Medical Microbiology, 26e:1-15 (Mar. 7, 2017).
Kakihana, K., et al., "Fecal Microbiota Transplantation for Patients with Steroid-Resistant Acute Graft-Versus-Host Disease of the Gut," Blood 128(16):2083-2088, American Society of Hematology, United States (Oct. 2016).
Kelly, D., et al., "Commensal Gut Bacteria: Mechanisms of Immune Modulation ," Trends in Immunology 26(6):326-333, Elsevier Science Ltd, England (Jun. 2005).
Keynan, Y., et al., "The Role of Regulatory T Cells in Chronic and Acute Viral Infections," Clinical Infectious Diseases 46(7):1046-1052, Oxford University Press, United states (Apr. 2008).
Krogius-Kurikka, L., et al., "Sequence Analysis of Percent G+C Fraction Libraries of Human Faecal Bacterial DNA Reveals a High Number of Actinobacteria," BMC Microbiology 9:68, BioMed Central, England (Apr. 2009).
Lau, S.K.P., et al., "Bacteraemia Caused By Anaerotruncus Colihominis and Emended Description of the Species," Clinical Pathology 59(7):748-752, BMJ Pub. Group, England (Jul. 2006).
Lawson, P.A., "Anaerotruncus," Bergey's Manual of Systematics of Archaea and Bacteria, Bergey's Manual Trust, 2009, pp. 1-4.
Louis, P and Flint, H.J., "Diversity, Metabolism and Microbial Ecology of Butyrate-producing Bacteria From the Human Large Intestine," FEMS Microbiology Letters 294(1):1-8, Oxford University Press, England (May 2009).
Machine Translation of PCT Specification, PCT Application No. PCT/JP2010/071746, Filed Dec. 3, 2010, 79 pages.
Maizels, R.M. and Smith, K.A., "Regulatory T Cells in Infection," Advances in Immunology 112:73-136, Academic Press, United states (2011).
Maslowski, K.M et al., "Diet, Gut Microbiota and Immune Responses," Nature Immunology, Jan. 2011, pp. 5-9, vol. 12, No. 1.
Nitzan, O., et al., "Role of Antibiotics for Treatment of Inflammatory Bowel Disease," World Journal of Gastroenterology, 22(3):1078-1087, Baishideng Publishing Group, United States (Jan. 2016).
Russell et al., "Early Outcomes After Allogeneic Stem Cell Transplantation for Leukemia and Myelodysplasia Without Protective Isolation: A 1 0-year Experience," Biol. Blood Marrow Transplant 6(2): 109-114 (2000).
Non-Patent Literature Submitted with Notice of Opposition to a European Patent, Jul. 18, 2017, European Patent No. EP2575835: Other Evidence, E102635, 1 page.
Office Action dated Feb. 25, 2014, in European Patent Application No. 11728077.6 filed Jun. 3, 2011.
Office Action dated Sep. 18, 2015, in European Patent Application No. 11728077.6 filed Jun. 3, 2011.
O'Garra, A., et al., "IL-10-producing and Naturally Occurring CD4+ Tregs: Limiting Collateral Damage," The Journal of Clinical Investigation 114(10):1372-1378, American Society for Clinical Investigation, United states (Nov. 2004).
Priority Document JP 2010-129134 for PCT Application No. PCT/JP2011/063302, Filed June 4, 2010, 42 pages.
Priority Document PCT/JP2010/071746 for PCT Application No. PCT/JP2011/063302, Filed Dec. 3, 2010, 107 pages.

Qiu, X., et al., "Faecalibacterium prausnitzii Upregulates Regulatory T Cells and Anti-Inflammatory Cytokines in Treating TNBS-Induced Colitis," Crohn's and Colitis 7(11):e558-e568, Elsevier Science, England (Dec. 2013 ).
Response dated Jan. 28, 2015 in Examination, European Application No. 11728077.6, 3 pages.
Response to Official Communication dated Sep. 18, 2018, European Application No. 11728077.6, filed Nov. 18, 2015, 2 pages.
Roberts, B., "Generation and Development of Defined Microbial Drug Products," Vendata Biosciences, 17 pages (2016).
Rosero, J.A., et al., "Reclassification of Eubacterium Rectale (Hauduroy et al. 1937) Prévot 1938 in a New Genus *Agathobacter* Gen. Nov. As Agathobacter Rectalis Comb. Nov., and Description of *Agathobacter ruminis* Sp. Nov., Isolated From the Rumen Contents of Sheep and Cows," International Journal of Systematic and Evolutionary Microbiology, 66(2):768-773, Microbiology Society, England (Feb. 2016).
Rossen, N.G., et al., "Findings From a Randomized Controlled Trial of Fecal Transplantation for Patients With Ulcerative Colitis.," Gastroenterology, 149(1):110-118, W.B. Saunders, United States (Jul. 2015).
Rossi, O., et al., "Faecalibacterium Prausnitzii A2-165 has a High Capacity to Induce IL-10 in Human and Murine Dendritic Cells and Modulates T Cell Responses," Scientific Reports 6:12 pages, (Jan. 2015).
Sanchez, A.M. and Yang, Y., "The Role of Natural Regulatory T Cells in Infection," Immunologic Research 49(1-3):124-134, Humana Press, United states (Apr. 2011 ).
Sartor, R.B., "Therapeutic Correction of Bacterial Dysbiosis Discovered by Molecular Techniques," Proceedings of the National Academy of Sciences of the United States of America 105(43):16413-16414, National Academy of Sciences, United states (Oct. 2008).
Seki, H., et al., "Prevention of Antibiotic-Associated Diarrhea in Children by Clostridium Butyricum MIYAIRI," Pediatrics International, 45(1):86-90, Blackwell Science Asia, Australia (Feb. 2003).
Sghir, A., et al., "Quantification of Bacterial Groups Within Human Fecal Flora by Oligonucleotide Probe Hybridization," Applied and Environmental Microbiology 66(5):2263-2266, American Society for Microbiology, United States (May 2000).
Sokol, H., et al., "Faecalibacterium Prausnitzii Is an Anti-Inflammatory Commensal Bacterium Identified by Gut Microbiota Analysis of Crohn Disease Patients," Proceedings of the National Academy of Sciences 105(43):16731-16736, National Academy of Sciences, United States (Oct. 2008).
Sokol, H., et al., "Low Counts of Faecalibacterium Prausnitzii in Colitis Microbiota," Inflammatory Bowel Diseases 15(8):1183-1189, Lippincott Williams & Wilkins, cited States (Aug. 2009).
Takaishi, H., et al., "Imbalance in Intestinal Microflora Constitution Could Be Involved in the Pathogenesis of Inflammatory Bowel Disease," International Journal of Medical Microbiology 298(5-6):463-572, Urban & Fischer Verlag, Germany (Jul. 2008).
Wachsman, J.T., et al., "Characterization of an Orotic Acid Fermenting Bacterium, Zymobacterium Oroticum, Nov. Gen., Nov. Spec," Bacteriology 68(4):400-404, American Society for Microbiology, United States (Oct. 1954).
Warren, Y.A., et al., "*Clostridium aldenense* Sp. Nov. and *Clostridium citroniae* Sp. Nov. Isolated from human clinical Infections," Journal of Clinical Microbiology 44(7):2416-2422, American Society for Microbiology, United States (Jul. 2006 ).
Wells, C.L. et al., Chapter 18: Clostridia: Sporeforming Anaerobic Bacilli, Medical Microbiology, 4th Edition, 1996, pp. 1-20.
Wortman et al., "Design and evaluation of SER-262: A fermentation-derived microbiometherapeutic for the prevention of recurrence in patients with primary Clostridium difficile infection," Seres Therapeutics, Cambridge, MA, Jun. 1, 2016, Retrived from (http://serestherapeutics.com/sites/default/files/wortman_asm_poster_final_poster_ser_262.pdf), Retrieved on [Nov. 5, 2019], 1 page.
Ze, X., et al., "Ruminococcus Bromii Is a Keystone Species for the Degradation of Resistant Starch in the Human Colon, "The ISME Journal, 6(8):1535-1543, Nature Publishing Group, England (Aug. 2012).
Zhou, D., et al., "Total Fecal Microbiota Transplantation Alleviates Highfat Diet-Induced Steatohepatitis in Mice via Beneficial Regu-

(56) References Cited

OTHER PUBLICATIONS lation of Gut Microbiota," Scientific Reports 7(1):11 pages, Nature Publishing Group, England (May 2017).
Britton et al., "Role of the intenstinal Microbiota in Reistance to Colonization by Clostridium Difficile," Gastroenterology 146:1547-1553 (2014).
Buffie et al., "Precision microbiome reconstitution restores bile acid mediated resistances to Clostridium difficile," Nature 517:205-8 (2015).
Partial Supplementary European Search Report dated Jan. 4, 2018 in Application No. 15796000.6.
Abt et al., "Commensal Bacteria Calibrate the activation threshold of Innate Antiviral Immunity," Immunity 37(1):158-70 (2012).
Barrasa et al., "Bile acids in the colon, from healthy to cytotoxic molecules," Toxicology In Vitro 27:964-977 (2013).
Bartlett et al., "Antibiotic-Associated Pseudomembranous Colitis Due To Toxin-Producing Clostridia," N. Engl. J. Med. 298(I0):53I-534 (1978).
Basler et al., "Tit-for-tat: Type VI secretion system counterattack during bacterial cell-cell interactions," Cell, I52(4):884-894 (2013).
Basler et al., "Type VI secretion requires a dynamic contractile phage tail-like structure," Nature, 483(7388):182-186 (2013).
Bernstein et al., "Bile acids as carcinogens in human gastrointestinal cancers," Mutation Res 589:47-65 (2005).
Brandl et al., "Vancomycin-resistant enterococci exploit anti biotic-induced innate immune deficit,". Nature 455(7214):804-807 (2008).
Buffie et al., "Profound Alterations of Intestinal Microbiota following a Single Dose of Clindamycin Results in Sustained Susceptibility to Clostridium difficile—Induced Colitis," Infection and Immunity 80:62-73 (2012).
Caporaso et al., "QIIME allows analysis of high-throughput community sequencing data," Nat Methods. 7(5):335-336 (2010).
Caporaso et al., "Ultra-high-throughput microbial community analysis on the Illumina HiSeq and MiSeq platforms," The ISME Journal 6:1621-1624 (2012).
Carlier et al., "Proposal to unify Clostridium orbiscindens Winter et al. 1991 and Eubacterium plautii (Seguin 1928) Hofstad and Aasjord 1982, with description of Flavonifractor plautii gen. nov., comb, nov., and reassignment of Bacteroides capillosus to Pseudojlavonifractor capillosus gen. nov., comb, nov.," Int J Syst Evol Microbial 60:585-590 (2010).
Chang et al., "Decreased Diversity of the Fecal Microbiome in Recurrent Clostridium difficile—Associated Diarrhea," J Infect Dis 197:43 5-43 8 (2008).
Chen et al., "A Mouse Model of Clostridium difficile—Associated Disease," Gastroenterology 13 5: 1984-1992 (2008).
Chen et al., "Overview of Clostridium difficile infection: implications for China," Gastroenterology Report 1:153-158 (2013).
Chung et al., "Gut Immune Maturation Depends on Colonization with a Host-Specific Microbiota," Cell 149(7): 1578-1593 (2012).
Cohen, Statistical Power Analysis for the Behavioral Sciences, Second Edition (Routledge, Hillsdale, NJ, 1988).
De Aguiar Vallim et al., "Pleiotropic Roles of Bile Acids in Metabolism," Cell Metab. 17(5):657-669 (2013).
Dethlefsen et al., "Incomplete recovery and individualized responses of the human distal gut microbiota to repeated antibiotic perturbation," PNAS 108(Suppl. 1 ):4554-4561 (2011).
Diehl et al., "Microbiota Restricts Trafficking of Bacteria to Mesenteric Lymph Nodes by CX(3)CR1(hi) Cells," Nature 494(7435): 116-120 (2013).
Duan et al., "Microbial colonization drives expansion of IL-1 receptor 1 expressing, IL-17 producing gamma/delta T cells," Cell Host Microbe, 7(2): 140-150 (2010).
Edgar et al., "UCHIME 1m proves sensitivity and speed of chimera detection," Bioinformatics 27(16):2194-2200 (2011).
Farache et al., "Luminal Bacteria Recruit CD103(+) Dendritic Cells into the Intestinal Epithelium to Sample Bacterial Antigens for Presentation," Immunity, 38(3):581-595 (2013).

Ferreira et al., "The Intestinal Microbiota Plays a Role in *Salmonella*—Induced Colitis Independent ofPathogen Colonization," PLoS One 6(5):e20338 (2011).
Giel et al., "Metabolism of Bile Salts in Mice Influences Spore Germination in Clostridium dif.ficile," PLoS ONE, 5(1):e8740 (2010).
Hall, "Building Phylogenetic Trees from Molecular Data with MEGA," Mol. Biol. Evol. 30(5): 1229-1235 (2013).
Hand et al., "Acute Gastrointestinal Infection Induces Long-Lived Microbiota-Specific T Cell Responses," Science, 337(6101): 1553-1556 (2012).
Heeg et al., "Spores of Clostridium difficile Clinical Isolates Display a Diverse Germination Response to Bile Salts," PLoS One 7(2):e32381 (2012).
Hill et al., "Commensal bacteria-derived signals regulate basophil hematopoiesis and allergic inflammation," Nat Med., 18(4):538-546 (2012).
Huse et al., "Exploring Microbial Diversity and Taxonomy Using ssu rRNA Hypervariable Tag Sequencing," PLoS Genet 4(11):e1000255 (2008).
International Search Report dated Sep. 8, 2015 in International Application No. PCT/US15/31627.
Ivanov et al., "Induction of intestinal Th 17 cells by segmented filamentous bacteria," Cell, 139(3):485-498 (2009).
Kang et al., "Clostridium scindens baiCD and baiH genes encode stereo-specific 7alpha/7beta-hydroxy-3-oxo-delta4-cholenoic acid oxidoreductases," Biochim Biophys Acta 1781(1-2): 16-25 (2008).
Kinnebrew et al., "Early Clostridium difficile Infection during Allogeneic Hematopoietic Stem Cell Transplantation," PLoS One 9(3):e90158 (2014).
Kitahara et al., "Assignment of *Eubacterium* sp. VPI 12708 and related strains with high bile acid 7a-dehydroxylating activity to Clostridium scindens and proposal of *Clostridiumhylemonae* sp. nov., isolated from human faeces," Int J Syst Evol Microbial 50:971-978 (2000).
Koeth et al., "Intestinal microbiota metabolism of L-camitine, a nutrient in red meat, promotes atherosclerosis," Nat Med. 19(5):576-585 (2013).
Krishna et al., "Risk Factors, preemptive therapy, and antiperistaltic agents for Clostridium difficile infection in cancer patients," Transplant Infect Dis., 15:493-501 (2013).
Kyne et al., "Health Care Costs and Mortality Associated with Nosocomial Diarrhea Due to Clostridium difficile," Clin Infect Dis 34:346-353 (2002).
Langille et al., "Predictive functional profiling of microbial communities using 16S rRNA marker gene sequences," NatBiotechnol31(9):814-821 (2013).
Lathrop et al., "Peripheral education of the immune system by colonic commensal microbiota," Nature, 478(7368):250-254 (2012).
Lawley et al., "Targeted Restoration of the Intestinal Microbiota with a Simple, Defined Bacteriotherapy Resolves Relapsing Clostridium difficile Disease in Mice," PLoS Pathog 8(10):e1002995 (2012).
Liu et al., "Reclassification of Clostridium coccoides, Ruminococcus hansenii, Ruminococcus hydrogenotrophicus, Ruminococcus luti, Ruminococcus producta and Ruminococcus schinkii as Blautia coccoides gen. nov., comb, nov., Blautia hansenii comb, nov., Blautia hydrogenotrophica comb, nov., Blautia luti comb, nov., Blautia producta comb, nov., Blautia schinkii comb. nov. and description of *Blautia wexlerae* sp. nov., isolated from human faeces," Int J Syst Evol Microbial 58:1896-1902 (2008).
Louie et al., "Tolevamer, a Novel Nonantibiotic Polymer, Compared with Vancomycin in the Treatment of Mild to Moderately Severe Clostridium difficile—Associated Diarrhea," Clin Infect Dis 43:411-420 (2006).
Lozupone et al., "UniFrac: a New Phylogenetic Method for Comparing Microbial communities," Appl Environ Microbial 71(12):8228-8235 (2005).
Macpherson et al., "Induction of Protective IgA by Intestinal Dendritic Cells Carrying Commensal Bacteria," Science, 303:1662-1665 (2004).

(56) References Cited

OTHER PUBLICATIONS

Manges et al., "Comparative Metagenomic Study of Alterations to the Intestinal Microbiota and Risk of Nosocomial Clostridum difficile-Associated Disease," Journal of Infectious Diseases, 202(12): 1877-1884 (2010).
Marsh et al., "Association of Relapse of Clostridium difficile Disease with BI/NAP1/027," J Clin Microbial 50(12):4078-4082 (2012).
Olszak et al., "Microbial Exposure During Early Life has Persistent Effects on Natural Killer T Cell Function," Science, 336(6080):489-493 (2012).
Ott et al., "Quantification of Intestinal Bacterial Populations by Real-Time PCR with a Universal Primer Set and Minor Groove Binder Probes: a Global Approach to the Enteric Flora," Journal of Clinical Microbiology, 42(6):2566-2572 (2004).
Out et al., "Bile acid sequestrants: more than simple resins," Curr Opin Lipidol 23:43-55 (2012).
Rakoff-Nahoum et al., "Recognition of Commensal Microflora by Toll-Like Receptors Is Required for Intestinal Homeostasis," Cell, 118:229-241 (2004).
Rea et al., "Effect of broad- and narrow-spectrum antimicrobials on Clostridium difficile and microbial diversity in a model of the distal colon," PNAS 108(Suppl. 1):4639-4644 (2011).
Rea et al., "Thuricin CD, a posttranslationally modified bacteriocin with a narrow spectrum of activity against Clostridium difficile," PNAS, 107(20):9352-9357 (2010).
Reeves et al., "The interplay between microbiome dynamics and pathogen dynamics in a murine model of Clostridium difficile infection," Gut Microbes 2(3): 145-158 (2011).
Ridlon et al., "Bile salt biotransfoimations by human intestinal bacteria," J Lipid Res 47:241-259 (2006).
Ridlon et al., "Clostridium scindens: a human gut microbe with a high potential to convert glucocorticoids into androgens," J. Lipid Res. 54:2437-2449 (2013).
Ridlon et al., "Identification and characterization of two bile-acid coenzyme A transferases from Clostridium scindens, a bile acid 7 a-dehydroxylating intestinal bacterium," J. Lipid Res. 53:66-76 (2012).
Ridlon, "Enzymology and Molecular Biology of Bile Acid 7alpha- and 7beta-Dehydroxylation by the Intestinal Bacteria Clostridium Scindens and Clostridium Hylemonae," VCU Theses and Dissertations, Paper 736 (2008).
Rupnik et al., "Clostridium difficile infection: new developments in epidemiology and pathogenesis," Nat Rev Microbial 7:526-536 (2009).
Schloss et al., "Introducing mothur: Open-Source, Platfoim-Independent, Community-Supported Software for Describing and Comparing Microbial Communities," Appl Environ Microbial 75(23):7537-7541 (2009).
Sheneman et al., "Clearcut: a fast implementation of relaxed neighbor joining," Bioinformatics 22(22):2823-2824 (2006).
Sorg et al., "Chenodeoxycholate IS an Inhibitor of Clostridium difficile Spore Germination," J Bacterial 191(3): 1115-1117 (2009).
Stein et al., "Ecological Modeling from Time-Series Inference: Insight into Dynamics and Stability ofIntestinal Microbiota," PLoS Comput Biol 9(12):e1003388 (2013).
Surawicz et al., "Treatment of refractory and recurrent Clostridium difficile infection," Nat Rev Gastroenterology & Hepatology 8:330-339 (2011).
Tumbaugh et al., "A core gut microbiome in obese and lean twins," Nature 457(7228): 480-484 (2009).
Ubeda et al., "Intestinal Microbiota Containing *Barnesiella* Species Cures Vancomycin-Resistant Enterococcus faecium Colonization," Infection and Immunity 81(3):965-973 (2013).
Ubeda et al., "Vancomycin-resistant Enterococcus domination of intestinal microbiota is enabled by antibiotic treatment in mice and precedes bloodstream invasion in humans," J Clin Invest 120(12):4332-4341 (2010).
Van Nood et al., "Duodenal Infusion of Donor Feces for Recurrent Clostridium difficile," N Engl. J Med 368(5):407-415 (2013).

Wells et al., "Development and application of a polymerase chain reaction assay for the detection and enumeration of bile acid 7a-dehydroxylating bacteria in human feces," Clinica Chimica Acta, 331:127-134 (2003).
Wells et al., "Identification and Characterization of a Bile Acid 7a-Dehydroxylation Operon in *Clostridium* sp. Strain T0-931, a Highly Active 7a-Dehydroxylating Strain Isolated from Human Feces," Applied and Environmental Microbiology 66(3): 1107-1113 (2000).
Wingender et al., "Intestinal Microbes Affect Phenotypes and Functions of Invariant Natural Killer T Cells in Mice," Gastroenterology, 143(2):418-428 (2012).
Yutin et al., "A genomic update on clostridial phylogeny: Gram-negative spore formers and other misplaced Clostridia," Environ Microbial. 15(10):2631-2641 (2013).
Zar et al., "A Comparison of Vancomycin and Metronidazole for the Treatment of Clostridium difficile—Associated Diarrhea, Stratified by Disease Severity," Clin. Infect. Dis. 45:302-307 (2007).
Zhao et al., "RAPSearch2: a fast and memory-efficient protein similarity search tool for next-generation sequencing data," Bioinformatics 28(1): 125-126 (2012).
Zilberberg et al., "Increase in Adult Clostridium difficile—related Hospitalizations and Case-Fatality Rate, United States, 2000-2005," Emerg Infect Dis 14(6):929-931 (2008).
Supplementary Partial European Search Report dated Jun. 14, 2018 in Application No. EP 15862844.
"Current Uses and Outcomes of Hematopoietic Stem Cell Transplantation 2012" CIBMTR Summary Slides, 2012.
Abubucker et al., "Metabolic Reconstruction for Metagenomic Data and Its Application to the Human Microbiome," PLoS Computational Biology 8(6):e1002358 (2012).
Ahern et al., "The interleukin-23 axis m intestinal inflammation," Immunological Reviews 226:147-159 (2008).
Ahmad et al., "Biomarkers of Myocardial Stress and Fibrosis as Predictors of Mode of Death in Patients with Chronic Heart Failure," JACC Heart Fail. 2(3):260-268 (2014).
Arpaia et al., "Metabolites produced by commensal bacteria promote peripheral regulatory T-cell generation," Nature 504:451-455 (2013).
ASBMT RFI 2016—Disease Classifications Corresponding to CIBMIR Classifications. 2016.
Bacigalupo et al., "Defining the Intensity of Conditioning Regimens: Working Definitions," Biol. Blood Marrow Transplant 15:1628-1633 (2009).
Bajaj et al., "Colonic mucosal microbiome differs from stool microbiome in cirrhosis and hepatic encephalopathy and is linked to cognition and inflammation," Am J Physiol Gastrointest Liver Physiol. 303 :G675-685 (2012).
Barrell et al., "Reduced-Intensity Conditioning Allogeneic Stem Cell Transplantation in Pediatric Patients and Subsequent Supportive Care," Oncol Nurs Forum 39(6):E451-458 (2012).
Beelen et al., "Influence of Intestinal Bacterial Decontamination Using Metronidazole and Ciprofloxacin or Ciprofloxacin Alone on the Development of Acute Graft-Versus-Host Disease After Marrow Transplantation in Patients with Hematologic Malignancies: Final Results and Long-Term Follow-Up of an Open-Label Prospective Randomized Trial," Blood 93(10):3267-3275 (1999).
Bolger et al., "Trimmomatic: a flexible trimmer for Illumina sequence data," Bioinformatics 30(15):2114-2120 (2014).
Chen et al., "Human Intestinal Lumen and Mucosa-Associated Microbiota in Patients with Colorectal Cancer," PLoS One 7(6):e39743 (2012).
Chromek et al., "The Antimicrobial Peptide Cathelicidin Protects Mice from *Escherichia coli* 0157:H7—Mediated Disease," PLoS ONE 7(10):e46476 (2012).
Clifford et al., "Detection of Bacterial 16S rRNA and Identification of Four Clinically Important Bacteria by Real-Time PCR," PLoS ONE 7(11):e48558 (2012).
Cooke et al., "An Experimental Model of Idiopathic Pneumonia Syndrome after Bone Marrow Transplantation: I. The Roles of Minor H Antigens and Endotoxin," Blood 8(8):3230-3239 (1996).

(56) References Cited

OTHER PUBLICATIONS

Cooke et al., "LPS antagonism reduces graft-versus-host disease and preserves graftversus-leukemia activity after experimental bone marrow transplantation," J. Clin. Invest. 107:1581-1589 (2001).
Copelan et al., "A Scheme for Defining Cause of Death and Its Application in the T-Cell Depletion Trial," Biol. Blood Marrow Transplant. 13: 1469-14 76 (2007).
Das et al., "Blockade of interleukin-23 signaling results in targeted protection of the colon and allows for separation of graft-versus-host and graft-versus-leukemia responses," Blood 115(25):5249-5258 (2010).
Das et al., "Interleukin-23 secretion by donor antigen-presenting cells is critical for organspecific pathology in graft-versus-host disease," Blood 113(10):2352-2362 (2009).
Derrien et al., "Modulation of Mucosal Immune Response, Tolerance, and Proliferation in Mice Colonized by the Mucin-Degrader Akkermansia muciniphila," Frontiers in Microbiology 2:166 (2011).
Derrien et al., "Mucin-bacterial interactions in the human oral cavity and digestive tract," Gut Microbes 1(4):254-268 (2010).
DeSantis et al., "Greengenes, a Chimera-Checked 16S rRNA Gene Database and Workbench Compatible with ARB," Appl. Environ Microbial. 72(7):5069-5072 (2006).
Duncker et al., "The D-alanine content of lipoteichoic acid is crucial for Lactobacillus plantarum—mediated protection from visceral pain perception in a rat colorectal distension model," Neurogastroenterology and Motility 20:843-850 (2008).
Eriguchi et al., "Graft versus-host disease disrupts intestinal microbial ecology by inhibiting Paneth cell production of a-defensins," Blood 120(1):223-231 (2012).
Freifeld et al., "Clinical Practice Guideline for the Use of Antimicrobial Agents in Neutropenic Patients with Cancer: 2010 Update by the Infectious Diseases Society of America," Clinical Infectious Diseases 52(4):e56-e93 (2011).
Furusawa et al., "Commensal microbe-derived butyrate induces the differentiation of colonic regulatory T cells," Nature 504:446-450 (2013).
Gallo et al., "Epithelial antimicrobial defence of the skin and intestine," Nat Rev Immunol. 12:503-516 (2012).
Ganesh et al., "Commensal Akkermansia muciniphila Exacerbates Gut Inflammation in *Salmonella typhimurium*—Infected Gnotobiotic Mice," PLoS ONE 8(9):e74963 (2013).
Goldberg et al., "T Cell-Depleted Stem Cell Transplantation for Adults with High-Risk Acute Lymphoblastic Leukemia: Long-Term Survival for Patients in First Complete Remission with a Decreased Risk of Graft-versus-Host Disease," Biol. Blood Marrow Transplant 19:208-213 (2013).
Grangette et al., "Enhanced antiinflammatory capacity of a Lactobacillus plantarum mutant synthesizing modified teichoic acids," PNAS 102(29): 10321-10326 (2005).
Hahn et al., "Risk factors for Acute Graft-Versus-Host Disease after Human Leukocyte Antigen-Identical Sibling Transplants for Adults With Leukemia," J Clin. Oncol. 26(35):5728-5734 (2008).
Hiemenz, "Management of Infections Complicating Allogeneic Hematopoietic Stem Cell Transplantation," Semin Hematol 46:289-312 (2009).
Holler et al., "Metagenomic Analysis of the Stool Microbiome in Patients Receiving Allogeneic Stem Cell Transplantation: Loss of Diversity Is Associated with Use of Systemic Antibiotics and More Pronounced m Gastrointestinal Graft-versus-Host Disease," Biol, Blood Marrow Transplant. 20:640-645 (2014).
Hong et al., "1H NMR-based Metabonomic Assessment of Probiotic Effects in a Colitis Mouse Model," Arch Pharm Res 33(7): 1091-1101 (2010).
Hue et al., "Interleukin-23 drives innate and T cell-mediated intestinal inflammation," JEM 203(11):2473-2483 (2006).
International Search Report dated Apr. 14, 2016 in International Application No. PCT/US2015/062734.
Jacobs et al., "1H NMR metabolite profiling of feces as a tool to assess the impact of nutrition on the human microbiome," NMR in Biomedicine 21:615-626 (2008).
Jaffe et al., "Prevention of Peritransplantation Viridans Streptococcal Bacteremia with Early Vancomycin Administration: A Single-Center Observational Cohort Study," Clin Infect Dis. 39:1625-1632 (2004).
Jagasia et al., "Risk factors for acute GVHD and survival after hematopoietic cell transplantation," Blood 119(1):296-307 (2012).
Jakubowski et al., "T Cell-Depleted Unrelated Donor Stem Cell Transplantation Provides Favorable Disease-Free Survival for Adults with Hematologic Malignancies," Biol. Blood Marrow Transplant 17:1335-1342 (2011).
Jenq et al., "Intestinal Blautia Is Associated with Reduced Death from Graft-versus-Host Disease," Biology of Blood and Marrow Transplantation 21:1373-1383 (2015).
Johansson et al., "The two mucus layers of colon are organized by the MUC2 mucin, whereas the outer layer is a legislator of host-microbial interactions," PNAS 108(Suppl.1):4659-4665 (2011).
Jones et al., "Mortality and Gross Pathology of Secondary Disease in Germfree Mouse Radiation Chimeras," Radial Res. 45(3):577-588 (1971).
Kamboj et al., "Clostridium difficile Infection after Allogeneic Hematopoietic Stem Cell Transplant: Strain Diversity and Outcomes Associated with NAP1/027," Biol. Blood Marrow Transplant 20:1626-1633 (2014).
Kamboj et al., "The Changing Epidemiology of Vancomycin-Resistant Enterococcus (VRE) Bacteremia m Allogeneic Hematopoietic Stem Cell Transplant (HSCT) Recipients," Biol Blood Marrow Transplant 16:1576-1581 (2010).
Langrish et al., "IL-12 and IL-23: master regulators of innate and adaptive immunity," Immunological Reviews 202:96-105 (2004).
LaRocco et al., "Infection in the Bone Marrow Transplant Recipient and Role of the Microbiology Laboratory in Clinical Transplantation," Clinical Microbiology Reviews 10(2):277-297 (1997).
Lindner et al., "Diversification of memory B cells drives the continuous adaptation of secretory antibodies to gut microbiota," Nature Immunology 16(8):880-890 (2015).
Lozupone et al., "UniFrac—An online tool for comparing microbial community diversity in a phylogenetic context," BMC Bioinfomatics 7:371 (2006).
MacMillan et al., "What predicts high risk acute graft-versus-host disease (GVHD) at onset?: identification of those at highest risk by a novel acute GVHD risk score," Br. J. Haematol 157:732-741 (2012).
Magurran, "Measuring Biological Diversity," Malden, MA: Blackwell Publishing; 2004.
Malard et al., "Impact of Cyclosporine—A Concentration on the Incidence of Severe Acute Graft-Versus-Host Disease after Allogeneic Stem Cell Transplantation," Biol. Blood Marrow Transplant 16:28-34 (2010).
Martin et al., "Increasingly Frequent Diagnosis of Acute Gastrointestinal Graft-versus-Host Disease after Allogeneic Hematopoietic Cell Transplantation," Biol. Blood Marrow Transplant. 10:320-327 (2004).
Maynard et al., "Reciprocal interactions of the intestinal microbiota and immune system," Nature 489:231-241 (2012).
Meyers, "Infection in Bone Marrow Transplant Recipients," The American Journal of Medicine 81(Suppl. 1A):27-38 (1986).
Narushima et al., "Characterization of the 17 strains of regulatory T cell-inducing humanderived Clostridia," Gut Microbes 5(3):333-339 (2014).
Parham et al., "A Receptor for the Heterodimeric Cytokine IL-23 is Composed of IL-12Rbeta1 and a Novel Cytokine Receptor Subunit, IL-23R1," J Immunol 168:5699-5708 (2002).
Park et al., "*Blautia faecis* sp. nov., isolated from human faeces," Int J Syst Evol Microbial. 63:599-603 (2013).
Passweg et al., "Influence of protective isolation on outcome of allogeneic bone marrow transplantation for leukemia," Bone Marrow Transplantation 21:1231-1238 (1998).
Pelaseyed et al., "The mucus and mucins of the goblet cells and enterocytes provide the first defense line of the gastrointestinal tract and interact with the immune system," Immunological Reviews 260:8-20 (2014).
Petersen et al., "Infectious Complications m Patients Undergoing Marrow Transplantation: A Prospective Randomized Study of the

(56) References Cited

OTHER PUBLICATIONS

Additional Effect of Decontamination and Laminar Airflow Isolation among Patients Receiving Prophylactic Systemic Antibiotics," Scand J. Infect Dis. 19(5):559-567 (1987).
Ponce et al., "Graft-versus-Host Disease after Double-Unit Cord Blood Transplantation Has Unique Features and an Association with Engrafting Unit-To-Recipient HLA Match," Biol. Blood Marrow Transplant 19:904-911 (2013).
Rowlings et al., "IBMTR Severity Index for grading acute graft-versus-host disease: retrospective comparison with Glucksberg grade," Br J Haematol. 97:855-864 (1997).
Office Action dated Nov. 13, 2019, in U.S. Appl. No. 15/603,916, Van Den Brink; M. et al., filed May 24, 2017, 21 pages.
Office Action dated May 14, 2019, in U.S. Appl. No. 15/603,916, Van Den Brink; M. et al., filed May 24, 2017, 25 pages.
Office Action dated Mar. 28, 2019, in U.S. Appl. No. 15/603,916, Van Den Brink; M. et al., filed May 24, 2017, 24 pages.
Office Action dated Dec. 9, 2019, in U.S. Appl. No. 16/223,008, Matthew R. Henn et al., filed Dec. 17, 2018, 18 pages.
Office Action dated Nov. 1, 2019, in U.S. Appl. No. 16/054,864, Gregory McKenzie et al., filed Aug. 3, 2018, 11 pages.
Office Action dated Mar. 15, 2019, in U.S. Appl. No. 16/054,864, Gregory McKenzie et al., filed Aug. 3, 2018, 10 pages.
Office Action dated Mar. 21, 2019, in U.S. Appl. No. 14/765,812, Noubar B. Afeyan et al., filed Aug. 4, 2015, 10 pages.
Office Action dated Dec. 11, 2019, in U.S. Appl. No. 14/765,812, Noubar B. Afeyan et al., filed Aug. 4, 2015, 10 pages.
Office Action dated Dec. 31, 2019, in U.S. Appl. No. 16/051,747, Geoffrey von Maltzahn et al., filed Aug. 1, 2018, 47 pages.
Office Action dated Apr. 7, 2020, in U.S. Appl. No. 16/054,864, Gregory McKenzie et al., filed Aug. 3, 2018, 16 pages.
Office Action dated Jul. 29, 2020, in U.S. Appl. No. 15/778,095, Julie Button et al., filed May 22, 2018, 40 pages.
Atarashi, K. et al., "Supporting Online Material for Induction of Colonic Regulatory T Cells by Indigenous *Clostridium* Species," Science 331(6015): 1-25, American Association for the Advancement of Science (2011).
Begley et al., "Bile Salt Hydrolase Activity in Probiotics," Appl. Environ. Microbial. 72(3): 1729-1738, American Society for Microbiology (2006).
Caballero, S. et al. "Distinct but Spatially Overlapping Intestinal Niches for Vancomycin-Resistant Enterococcus faecium and Carbapenem—Resistant Klebsiella Pneumoniae" PLOS Pathogens 11(9):e1005132, Public Library of Science, United States (2015).
Derrien, M., "Akkermansia Muciniphila Gen. Nov., Sp. Nov., a Human Intestinal Mucin-degrading Bacterium," International Journal of Systematic and Evolutionary Microbiology, 54(5):1469-1476, Microbiology Society, England (Sep. 2004).
Ezaki, T., et al., "16s Ribosomal DNA Sequences of Anaerobic Cocci and Proposal of Ruminococcus Hansenii Comb. Nov. and Ruminococcus Productus Comb. Nov," International Journal of Systematic Bacteriology 44(1):130-136, Society for General Microbiology, England (Jan. 1994).
Final Office Action dated Apr. 14, 2020, in U.S. Appl. No. 16/223,008, Henn, M.R. et al., filed Dec. 17, 2018, 11 pages.
Wood et al., "Kraken: ultrafast metagenomic sequence classification using exact alignments," Genome Biology 15:R46, BioMed Central, England (2014).
Yang, W. "Fast viability assessment of Clostridium spores: Survival in extreme environments." Diss. California Institute of Technology (2010).
Fuentes, S. et al. "Reset of a critically disturbed microbial ecosystem: faecal transplant in recurrent Clostridium difficile infection." The ISME journal: 1-13, Springer Nature Limited, United States (2014).
GenBank: Accession No. NR 118589.1.
Hayashi, H., et al., "Phylogenetic Analysis of the Human Gut Microbiota Using 16S rDNA Clone Libraries and Strictly Anaerobic Culture-based Methods," Microbiology and Immunology 46(8):535-548, Wiley-Blackwell, Australia (2002).

Kim, S.W. "Treatment of refractory or recurrent Clostridium difficile infection." The Korean Journal of Gastroenterology 60(2): 71-78, Korean Society of Gastroenterology, South Korea (2012).
Kron et al., "Adenovirus Vectors and Subviral Particles for Protein and Peptide Delivery," Curr Gene Ther 12:362-373, Bentham Science, United Arab Emirates (2012).
McAuliffe et al., "Genetic Analysis of Two Bile Salt Hydrolase Activities in Lactobacillus acidophilus NCFM," Appl. Environ Microbial. 71(8):4925-4929, American Society for Microbiology (2005).
Morris, G.N., et al., "*Clostridium scindens* sp. nov., A Human Intestinal Bacterium with Desmolytic Activity on Corticoids," International Journal of Systematic and Evolutionary Microbiology 35(4):478-481, Microbiology Society, England (Oct. 1985).
The Human Microbiome Project Consortium: "Structure, Function and Diversity of the Healthy Human Microbiome," Nature 486(7402):207-214, Nature Publishing, England (2013).
Wang, Q., et al., "Naive Bayesian Classifier for Rapid Assignment of rRNA Sequences Into the New Bacterial Taxonomy," Applied and Environmental Microbiology 73(16):5261-5267, American Society for Microbiology, United States (Aug. 2007).
Non Final Office Action dated Oct. 22, 2019, in U.S. Appl. No. 15/742,732, Cook, D. et al., filed Jan. 8, 2018, 10 pages.
Non-Final Office Action dated Oct. 29, 2019, in U.S. Appl. No. 15/990,539, Henn,M.R. et al., filed May 25, 2018, 25 pages.
Non-Final Office action dated Dec. 31, 2019, in U.S. Appl. No. 16/051,747, Maltzahn, G.V. et al., filed Aug. 1, 2018, 46 pages.
Non-Final Office Action dated Mar. 10, 2020, in U.S. Appl. No. 15/778,095, Button, J. et al., filed May 22, 2018, 28 pages.
Non-Final Office Action dated Mar. 23, 2020, in U.S. Appl. No. 15/990,539, Henn, M.R. et al., filed May 25, 2018, 10 pages.
Office Action dated Aug. 19, 2016, in U.S. Appl. No. 14/592,481, Henn, M.R., et al., filed Jan. 8, 2015, 6 pages.
Plassart, C., et al., "First Case of Intra-abdominal Infection With Clostridium Disporicum," Anaerobe 19:77-78, Academic Press, England (Feb. 2013).
Yen et al., "IL-23 is essential for T cell-mediated colitis and promotes inflammation via IL-17 and IL-6," The Journal of Clinical Investigation 116(5): 1310-1316, American Society for Clinical Investigation (2006).
Sakamoto et al., "*Eubacterium limosum* strain JCM 6421 16S ribosomal RNA gene, partial sequence" NCBI Reference Sequence, 2 pages, Nov. 23, 2016.
Salzman et al., "Analysis of 16S libraries of mouse gastrointestinal microflora reveals a large new group of mouse intestinal bacteria," Microbiology 148:3651-3660, Springer Publishing, United States (2002).
Schloss, P.D., et al., "Reducing the Effects of Pcr Amplification and Sequencing Artifacts on 16s rRNA-based Studies," PLoS One 6(12):e27310, Public Library of Science, United States (Dec. 2011).
Segata et al., "Metagenomic biomarker discovery and explanation," Genome Biol. 12:R60, BioMed Central, England (2011).
Shannon, "The Mathematical Theory of Communication," M.D. Computing 14( 4): 1-55, Springer Publishing, United States (1997).
Smith, P.M., et al., "The Microbial Metabolites, Short-Chain Fatty Acids, Regulate Colonic Treg Cell Homeostasis," Science 341(6145):1-10, American Association for the Advancement of Science, United States (Aug. 2013).
Solomkin et al., "Diagnosis and Management of Complicated Intra-abdominal Infection in Adults and Children: Guidelines by the Surgical Infection Society and the Infectious Diseases Society of America," Clin Infect Dis. 50:133-164 (2010).
Swidsinski et al., "Spatial Organization and Composition of the Mucosal Flora in Patients with Inflammatory Bowel Disease," Journal of Clinical Microbiology 43(7):3380-3389, American Society of Microbiology (2005).
Altschul, S. F., et al., "Basic Local Alignment Search Tool," *Journal of Molecular Biology* 215(3):403-410, Elsevier, United Kingdom (Oct. 1990).
Altschul, S. F., et al., "Gapped BLAST and PSI-BLAST: A New Generation of Protein Database Search Programs," *Nucleic Acids Research* 25(17):3389-3402, Oxford University Press, United Kingdom (Sep. 1997).

(56) References Cited

OTHER PUBLICATIONS

Casula, G., and Cutting, S. M., "Bacillus Probiotics: Spore Germination in the Gastrointestinal Tract," *Applied and Environmental Microbiology* 68(5):2344-2352, American Society for Microbiology, United States (May 2002).

Cunliffe, R. N. and Scott, B. B., "Review Article: Monitoring for Drug Side-effects in Inflammatory Bowel Disease," *Alimentary Pharmacology & Therapeutics* 16(4):647-662, Wiley-Blackwell, United Kingdom (Apr. 2002).

Delay, M. L., et al., "HLA-B27 misfolding and the unfolded protein response augment interleukin-23 production and are associated with Th17 activation in transgenic rats," *Arthritis and Rheumatism* 60(9):2633-2643, Wiley-Blackwell, United States (Sep. 2009).

Duc, L. H., et al., "Characterization of Bacillus Probiotics Available for Human Use," *Applied and Environmental Microbiology* 70(4):2161-2171, American Society for Microbiology, United States (Apr. 2004).

GenBank, "[Clostridium] bolteae ATCC BAA-613 C_bolteae-3.0.1_Cont299, whole genome shotgun sequence," Accession No. ABCC02000039.1, accessed at https://www.ncbi.nlm.nih.gov/nuccore/ABCC02000039.1 on Dec. 22, 2020, 99 pages.

GenBank, "Clostridium boltei partial 16S rRNA gene, strain 16351," Accession No. AJ508452.1, accessed at https://www.ncbi.nlm.nih.gov/nuccore/AJ508452, accessed on Dec. 22, 2020, 2 pages.

Gennaro, A. R., ed., "Table of Contents" in *Remington's Pharmaceutical Sciences*, 18th Edition, Mack Publishing Co., 5 pages, (1990).

Hong, H. A., et al., "The Use of Bacterial Spore Formers as Probiotics," *FEMS Microbiology Reviews* 29(4):813-835, Oxford University Press, United Kingdom (Sep. 2005).

Hylemon, P. B., et al., "Bile acids as regulatory molecules," *Journal of Lipid Research* 50(8):1509-1520, Lipid Research, Inc., United States (Aug. 2009).

International Search Report and Written Opinion for International Application No. PCT/US2019/025010, European Patent Office, Netherlands, dated Jul. 11, 2019, 12 pages.

Jousimies-Somer, H., et al., eds., "Chapter 4—Preliminary Identification Methods. General Considerations" in *Wadsworth-Ktl Anaerobic Bacteriology Manual*, $6^{th}$ Edition, pp. 55-185 (2002).

Kabeerdoss, J., et al., "Clostridium leptum group bacteria abundance and diversity in the fecal microbiota of patients with inflammatory bowel disease: a case-control study in India," *BMC Gastroenterology* 13:20, BioMed Central, United Kingdom (Jan. 2013).

Martinez-Montiel, M. P., et al., "Pharmacologic Therapy for Inflammatory Bowel Disease Refractory to Steroids," *Clinical and Experimental Gastroenterology* 8:257-269, Dove Medical Press, New Zealand (Aug. 2015).

M'Koma, A. E., "Inflammatory Bowel Disease: An Expanding Global Health Problem," *Clinical Medicine Insights. Gastroenterology* 6:33-47, SAGE Publications, United States (Aug. 2013).

Myers, E. W., and Miller, W., "Optimal alignments in linear space," *Computer Applications in the Biosciences* 4(1):11-17, IRL-Press Ltd., United Kingdom (1988).

Needleman, S. B. and Wunsch, C. D., "A General Method Applicable to the Search for Similarities in the Amino Acid Sequence of Two Proteins," *Journal of Molecular Biology* 48(3):443-453, Academic Press, United Kingdom (Mar. 1970).

Rheinwald, J. G., "Chapter 15 Serial Cultivation of Normal Human Epidermal Keratinocytes," *Methods in Cell Biology* 21A:229-254, Academic Press, United States (1980).

Thomas, C., et al., "Targeting Bile-acid Signalling for Metabolic Diseases," *Nature Reviews. Drug Discovery* 7(8):678-693, Nature Pub. Group, United Kingdom (Aug. 2008).

Zhu, C., et al., "Bile Acids in Regulation of Inflammation and Immunity: Friend or Foe?" *Clinical and Experimental Rheumatology* 34(4 Suppl 98):25-31, Clinical and Experimental Rheumatology S.A.S, Italy (Jul.-Aug. 2016).

\* cited by examiner

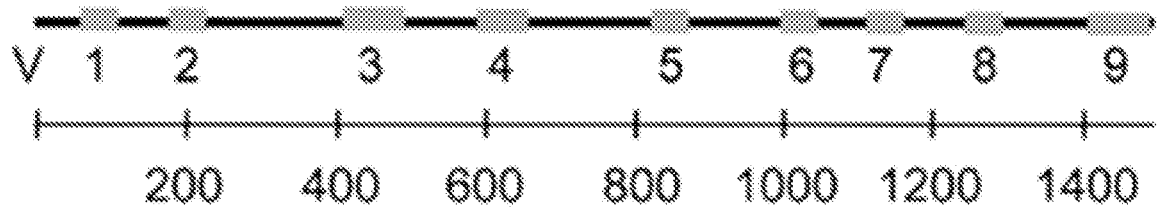

FIGURE 1A

| | |
|---|---|
| 1 | AAATTGAAGAGTTTGATCATGGCTCAGATTGAACGCTGGCGGCAGGCCTA |
| 51 | ACACATGCAAGTCGAACGGTAACAGGAAGAAGCTTGCTCTTTGCTGACGA |
| 101 | GTGGCGGACGGGTGAGTAATGTCTGGGAAACTGCCTGATGGAGGGGGATA |
| 151 | ACTACTGGAAACGGTAGCTAATACCGCATAACGTCGCAAGACCAAAGAGG |
| 201 | GGGACCTTCGGGCCTCTTGCCATCGGATGTGCCCAGATGGGATTAGCTAG |
| 251 | TAGGTGGGGTAACGGCTCACCTAGGCGACGATCCCTAGCTGGTCTGAGAG |
| 301 | GATGACCAGCCACACTGGAACTGAGACACGGTCCAGACTCCTACGGGAGG |
| 351 | CAGCAGTGGGGAATATTGCACAATGGGCGCAAGCCTGATGCAGCCATGCC |
| 401 | GCGTGTATGAAGAAGGCCTTCGGGTTGTAAAGTACTTTCAGCGGGGAGGA |
| 451 | AGGGAGTAAAGTTAATACCTTTGCTCATTGACGTTACCCGCAGAAGAAGC |
| 501 | ACCGGCTAACTCGTGCCCAGGCATGCGCAGGAATACGGAGGTGCAAGCGT |
| 551 | TAATCGGAATTACTGGGCGTAAAGCGCACGCAGGCGGTTTGTTAAGTCAG |
| 601 | ATGTGAAATCCCCGGGCTCAACCTGGGAACTGCATCTGATACTGGCAAGC |
| 651 | TTGAGTCTCGTAGAGGGGGGTAGAATTCCAGGTGTAGCGGTGAAATGCGT |
| 701 | AGAGATCTGGAGGAATACCGGTGGCGAAGGCGGCCCCCTGGACGAAGACT |
| 751 | CACGCTCAGGTGCGAAAGCGTGGGGAGCAAACAGGATTAGATACCCTGGT |
| 801 | AGTCCACGCCGTAAACGATGTCGACTTGGAGGTTGTGCCCTTGAGGCGTG |
| 851 | GCTTCCGGAGCTAACGCGTTAAGTCGACCGCCTGGGGAGTACGGCCGCAA |
| 901 | GGTTAAAACTCAAATGAATTGACGGGGGCCCGCACAAGCGGTGGAGCATG |
| 951 | TGGTTTAATTCGATGCAACGCGAAGAACCTTACCTGGTCTTGACATCCAC |
| 1001 | GGAAGTTTTCAGAGATGAGAATGTGCCTTCGGGAACCGTGAGACAGGTGC |
| 1051 | TGCATGGCTGTCGTCAGCTCGTGTTGTGAAATGTTGGGTTAAGTCCCGCA |
| 1101 | ACGAGCGCAACCCTTATCCTTTGTTGCCAGCGGTCCGGCCGGGAACTCAA |
| 1151 | AGGAGACTGCCAGTGATAAACTGGAGGAAGGTGGGGATGACGTCAAGTCA |
| 1201 | TCATGGCCCTTACGACCAGGGCTACACACGTGCTACAATGGCGCATACAA |
| 1251 | AGAGAAGCGACCTCGCGAGAGCAAGCGGACCTCATAAAGTGCGTCGTAGT |
| 1301 | CCGGATTGGAGTCTGCAACTCGACTCCATGAAGTCGGAATCGCTAGTAAT |
| 1351 | CGTGGATCAGAATGCCACGGTGAATACGTTCCCGGGCCTTGTACACACCG |
| 1401 | CCCGMCACACCATGGGAGTGGGTTGCAAAAGAAGTAGGTAGCTTAACCTT |
| 1451 | CGGGAGGGCGCTTACCACTTTGTGATTCATGACTGGGGTGAAGTCGTAAC |
| 1501 | AAGGTAACCGTAGGGGAACCTGCGGTTGGATCACCTCCTTA |

| Substrate | C. difficile 9689 | C. difficile 9689 | C. difficile 9689 | C. difficile 9689 | C. difficile 9689 | C. difficile 9689 | C. difficile 9689 | C. difficile 43593 | C. difficile 43593 | C. difficile 43593 | C. difficile 43255 | C. difficile 43255 | C. difficile 43255 | C. difficile 43255 | C. difficile 43255 | C. difficile 43255 | C. difficile 43255 |
|---|---|---|---|---|---|---|---|---|---|---|---|---|---|---|---|---|---|
| time (hr) | 20 | 20 | 20 | 20 | 44 | 44 | 44 | 20 | 20 | 96 | 20 | 20 | 20 | 20 | 96 | 20 | 96 |
| menadione (μM) | 0.05 | 0.05 | 0.16 | 0.05 | 0.05 | 0.16 | 0.05 | 0.05 | 0.5 | 0.5 | 0.05 | 0.16 | 0.05 | 0.5 | 0.5 | 0.5 | 0.5 |
| ferricyanide (mM) | 0.12 | 0.12 | 0.38 | 0.38 | 0.12 | 0.38 | 0.38 | 0.38 | 0.12 | 0.12 | 0.38 | 0.38 | 0.12 | 0.38 | 0.38 | 0.12 | 0.12 |
| L-Arabinose | + | + | + | + | + | + | + | + | + | + | + | - | + | + | + | + | + |
| N-Acetyl-D-Glucosamine | - | - | - | - | - | - | - | - | - | - | - | - | - | - | - | - | - |
| D-Saccharic Acid | - | - | - | - | - | - | + | - | - | - | - | - | - | - | - | - | - |
| Succinic Acid | - | - | - | - | - | - | - | - | - | - | - | - | - | - | - | - | - |
| D-Galactose | + | + | + | + | + | + | + | + | + | + | + | - | + | - | - | + | + |
| L-Aspartic Acid | + | - | - | - | + | - | - | - | - | - | - | - | - | - | - | - | - |
| L-Proline | - | - | - | - | - | - | - | - | - | - | - | - | - | - | - | - | - |
| D-Alanine | - | - | - | - | - | - | - | - | - | - | - | - | - | - | - | - | - |
| D-Trehalose | - | - | - | - | - | - | - | - | - | - | - | - | - | - | - | - | - |
| D-Mannose | + | + | + | + | + | + | + | + | + | + | + | - | + | - | - | - | + |
| Dulcitol | - | - | - | - | - | - | - | - | - | - | - | - | - | - | - | - | - |
| D-Serine | - | - | - | - | - | - | - | - | - | - | - | - | - | - | - | - | - |
| D-Sorbitol | - | - | - | - | - | - | - | - | - | - | - | - | - | - | - | - | - |
| Glycerol | - | - | - | - | - | - | + | - | - | - | - | - | - | - | - | - | - |
| L-Fucose | + | + | + | + | + | + | + | + | + | + | + | - | + | - | - | + | + |
| D-Glucuronic Acid | + | + | + | + | + | + | + | + | + | + | + | - | - | - | - | - | - |
| D-Gluconic Acid | - | - | - | - | - | - | - | - | - | - | - | - | - | - | - | - | - |
| D,L-alpha-Glycerol-Phosphate | - | - | - | - | - | - | - | - | - | - | - | - | - | - | - | - | - |
| D-Xylose | + | + | + | + | + | + | + | + | + | + | + | + | + | - | + | + | + |
| L-Lactic Acid | - | - | - | - | - | - | - | - | - | - | - | - | - | - | - | - | - |

FIG. 11 (continued)

| Species | C. difficile 9689 | C. difficile 9689 | C. difficile 9689 | C. difficile 9689 | C. difficile 9689 | C. difficile 9689 | C. difficile 9689 | C. difficile 43593 | C. difficile 43593 | C. difficile 43593 | C. difficile 43255 | C. difficile 43255 | C. difficile 43255 | C. difficile 43255 | C. difficile 43255 | C. difficile 43255 | C. difficile 43255 |
|---|---|---|---|---|---|---|---|---|---|---|---|---|---|---|---|---|---|
| Formic Acid | - | - | - | - | - | - | - | - | - | - | - | - | - | - | - | - | - |
| D-Mannitol | - | + | - | - | - | + | - | - | - | - | - | - | - | - | - | - | - |
| L-Glutamic Acid | - | - | + | - | - | + | - | - | - | + | - | - | - | - | - | - | - |
| D-Glucose-6-Phosphate | - | - | - | - | - | - | + | - | + | + | - | - | - | - | - | - | + |
| D-Galactonic Acid-gamma-Lactone | - | - | - | - | - | - | - | - | - | + | - | - | - | - | - | + | + |
| D,L-Malic Acid | + | + | + | + | + | + | + | + | + | + | + | + | + | + | + | + | - |
| D-Ribose | - | - | - | - | - | - | - | - | - | - | - | - | - | - | - | - | + |
| Tween 20 | + | + | + | + | + | + | - | + | + | + | + | - | - | - | - | - | - |
| L-Rhamnose | + | + | + | + | - | + | - | + | - | + | - | + | - | + | + | + | + |
| D-Fructose | - | - | - | - | - | - | - | - | - | - | - | - | - | - | - | - | + |
| Acetic Acid | + | + | + | - | - | + | + | - | - | - | - | - | - | - | + | - | - |
| alpha-D-Glucose | - | - | + | - | - | - | - | + | - | + | + | - | + | - | - | - | + |
| Maltose | - | + | + | + | - | + | - | - | - | - | - | - | - | - | - | - | - |
| D-Mellibiose | - | - | - | + | - | - | - | - | - | - | - | - | - | - | - | - | - |
| Thymidine | - | - | - | - | - | - | - | - | - | - | - | - | - | - | - | - | - |
| L-Asparagine | - | - | - | - | - | - | - | - | - | - | - | - | - | - | - | - | - |
| D-Aspartic Acid | - | - | + | - | - | - | - | - | - | - | - | - | - | - | - | - | - |
| D-Glucosaminic Acid | - | - | - | - | - | - | - | - | - | + | + | - | - | - | - | - | - |
| 1,2-Propanediol | - | + | + | - | - | - | - | - | - | + | - | - | - | - | - | - | - |
| Tween 40 | - | - | - | - | - | - | - | + | - | + | - | - | - | - | - | - | - |
| alpha-Keto-Glutaric Acid | - | - | - | - | - | - | - | - | - | - | - | - | - | - | - | - | - |
| alpha-Keto-Butyric Acid | + | - | - | - | - | + | - | - | - | + | - | - | - | - | - | - | - |
| alpha-Methyl-D-Galactoside | - | - | - | - | - | - | - | - | - | - | - | - | - | - | - | - | - |

FIG. 11 (continued)

| Species | Clostridium difficile 9689 | Clostridium difficile 9689 | Clostridium difficile 9689 | Clostridium difficile 9689 | Clostridium difficile 9689 | Clostridium difficile 9689 | Clostridium difficile 9689 | Clostridium difficile 43593 | Clostridium difficile 43593 | Clostridium difficile 43593 | Clostridium difficile 43255 | Clostridium difficile 43255 | Clostridium difficile 43255 | Clostridium difficile 43255 | Clostridium difficile 43255 | Clostridium difficile 43255 | Clostridium difficile 43255 |
|---|---|---|---|---|---|---|---|---|---|---|---|---|---|---|---|---|---|
| alpha-D-Lactose | - | + | - | + | + | - | + | - | - | - | - | - | - | - | - | - | - |
| Lactulose | - | - | - | + | - | - | - | - | - | - | - | - | - | - | - | - | - |
| Sucrose | - | - | - | - | - | - | - | - | - | - | - | - | - | - | - | - | - |
| Uridine | - | - | - | - | - | - | - | - | - | - | - | - | - | - | - | - | - |
| L-Glutamine | - | - | - | - | - | - | - | - | - | - | - | - | - | - | - | - | - |
| M-Tartaric Acid | - | - | - | - | - | - | - | - | - | - | - | - | - | - | - | - | - |
| D-Glucose-1-Phosphate | - | + | - | + | - | - | - | - | - | - | - | - | - | - | - | - | - |
| D-Fructose-6-Phosphate | + | - | + | + | - | + | - | + | + | + | - | - | - | - | + | + | + |
| Tween 80 | - | - | - | - | - | - | - | - | - | - | - | - | - | - | - | - | - |
| alpha-Hydroxy-Glutaric-gamma-lactone | - | - | - | - | - | - | - | - | - | - | - | - | - | - | - | - | - |
| alpha-Hydroxy Butyric Acid | - | - | - | - | - | - | - | - | - | - | - | - | - | - | - | - | - |
| beta-Methyl-D-Glucoside | - | - | - | - | - | - | - | - | - | - | - | - | - | - | - | - | - |
| Adonitol | - | - | - | - | - | - | - | - | - | - | - | - | - | - | - | - | - |
| Maltotriose | - | - | - | - | + | - | - | - | - | - | - | - | - | - | - | - | - |
| 2-Deoxy Adenosine | - | - | - | - | - | - | - | - | - | - | - | - | - | - | - | - | - |
| Adenosine | - | - | - | - | - | - | - | - | - | - | - | - | - | - | - | - | - |
| Glycyl-L-Aspartic Acid | - | - | - | - | - | - | - | - | - | - | - | - | - | - | - | - | - |
| Citric Acid | - | - | - | - | - | - | - | - | - | - | - | - | - | - | - | - | - |
| M-Inositol | - | - | - | - | - | - | - | - | - | - | - | - | - | - | - | - | - |
| D-Threonine | - | - | - | - | - | - | - | - | - | - | - | - | - | - | - | - | - |
| Fumaric Acid | - | - | - | - | - | - | - | - | - | - | - | - | - | - | - | - | - |
| Bromo Succinic Acid | - | - | - | - | - | - | - | - | - | - | - | - | - | - | - | - | - |
| Propionic Acid | - | - | - | - | - | - | - | - | - | - | - | - | - | - | - | - | - |

FIG. 11 (continued)

| Species | C. difficile 9689 | C. difficile 9689 | C. difficile 9689 | C. difficile 9689 | C. difficile 9689 | C. difficile 9689 | C. difficile 9689 | C. difficile 43593 | C. difficile 43593 | C. difficile 43593 | C. difficile 43255 | C. difficile 43255 | C. difficile 43255 | C. difficile 43255 | C. difficile 43255 | C. difficile 43255 | C. difficile 43255 |
|---|---|---|---|---|---|---|---|---|---|---|---|---|---|---|---|---|---|
| Mucic Acid | - | - | - | - | - | - | - | - | - | - | - | - | - | - | - | - | - |
| Glycolic Acid | - | - | - | - | - | - | - | - | - | - | - | - | - | - | - | - | - |
| Glyoxylic Acid | - | + | - | - | - | - | - | - | - | - | - | - | - | - | - | - | + |
| D-Cellobiose | - | - | + | + | + | + | - | - | - | - | - | - | - | - | - | - | - |
| Inosine | - | - | - | - | - | - | - | - | - | - | - | - | - | - | - | - | - |
| Glycyl-L-Glutamic Acid | - | - | - | - | - | - | - | - | - | - | - | - | - | - | - | - | - |
| Tricarballylic Acid | - | - | - | - | - | - | - | - | - | - | - | - | - | - | - | - | - |
| L-Serine | - | - | - | - | - | - | - | - | - | - | - | - | - | - | - | - | - |
| L-Threonine | - | - | - | - | - | - | - | - | - | - | - | - | - | - | - | - | - |
| L-Alanine | - | - | - | - | + | - | - | - | - | - | - | - | - | - | - | - | - |
| L-Alanyl-Glycine | - | - | - | - | - | - | - | - | - | - | - | - | - | - | - | - | - |
| Acetoacetic Acid | - | - | - | - | - | - | - | + | - | - | - | - | - | - | - | - | + |
| N-Acetyl-beta-D-Mannosamine | - | - | - | - | - | - | - | - | - | - | - | - | - | - | - | - | - |
| Mono Methyl Succinate | - | - | - | - | - | - | - | - | - | - | - | - | - | - | - | - | - |
| Methyl Pyruvate | + | - | - | - | - | - | - | - | - | - | - | + | - | - | - | - | - |
| D-Malic Acid | - | - | - | - | - | - | - | - | - | - | - | - | - | - | - | - | - |
| L-Malic Acid | - | - | - | - | - | - | - | - | - | - | - | - | - | - | - | - | - |
| Glycyl-L-Proline | - | - | - | - | - | - | - | - | - | - | - | - | - | - | - | - | - |
| p-Hydroxy Phenyl Acetic Acid | - | - | - | - | - | - | - | - | - | - | - | - | - | - | - | - | - |
| m-Hydroxy Phenyl Acetic Acid | - | - | - | - | - | - | - | - | - | - | - | - | - | - | - | - | - |
| Tyramine | - | - | - | - | - | - | - | - | - | - | - | - | - | - | - | - | - |
| D-Psicose | + | + | + | + | + | + | + | + | + | + | - | - | + | + | + | + | + |
| L-Lyxose | + | + | + | + | + | + | + | + | + | + | - | + | + | + | + | + | + |

FIG. 11 (continued)

| Species | Clostridium difficile 9689 | Clostridium difficile 9689 | Clostridium difficile 9689 | Clostridium difficile 9689 | Clostridium difficile 9689 | Clostridium difficile 9689 | Clostridium difficile 9689 | Clostridium difficile 43593 | Clostridium difficile 43593 | Clostridium difficile 43593 | Clostridium difficile 43255 | Clostridium difficile 43255 | Clostridium difficile 43255 | Clostridium difficile 43255 | Clostridium difficile 43255 | Clostridium difficile 43255 | Clostridium difficile 43255 |
|---|---|---|---|---|---|---|---|---|---|---|---|---|---|---|---|---|---|
| Glucuronamide | + | + | + | + | + | + | + | - | + | + | - | + | - | + | + | + | + |
| Pyruvic Acid | - | + | - | - | - | - | - | - | - | - | + | - | - | - | - | - | - |
| L-Galactonic Acid-gamma-Lactone | + | - | - | - | - | - | - | - | - | - | - | - | - | - | - | - | - |
| D-Galacturonic Acid | - | + | - | + | - | + | + | + | - | - | - | - | - | - | - | + | + |
| Pheylethyl-amine | - | - | - | - | - | - | - | - | - | - | - | - | - | - | - | - | - |
| 2-aminoethanol | - | - | - | - | - | - | - | - | - | - | - | - | - | - | - | - | - |
| Negative control | - | - | - | - | - | - | - | - | - | - | - | - | - | - | - | - | - |
| Chondroitin Sulfate C | - | - | - | - | - | - | - | - | - | - | - | - | - | - | - | - | - |
| alpha-Cyclodextrin | - | - | - | - | - | - | - | - | - | - | - | - | - | - | - | - | - |
| beta-Cyclodextrin | - | - | - | - | - | - | - | - | - | - | - | - | - | - | - | - | - |
| gamma-Cyclodextrin | - | - | - | - | - | - | - | - | - | + | - | - | - | - | - | - | - |
| Dextrin | - | + | + | + | + | + | + | - | - | - | + | + | + | + | - | - | - |
| Gelatin | - | - | - | - | - | - | - | - | - | - | - | - | - | - | - | - | - |
| Glycogen | - | + | - | - | - | - | - | - | - | - | - | + | + | - | - | - | - |
| Inulin | - | - | - | - | + | + | + | - | - | - | + | + | + | - | - | + | - |
| Laminarin | - | - | - | - | - | - | - | - | - | - | - | - | - | - | - | - | - |
| Mannan | - | - | - | - | - | - | - | - | - | - | - | - | - | - | - | - | - |
| Pectin | - | - | + | + | + | + | + | + | + | + | + | + | + | - | - | - | - |
| N-Acetyl-D-Galactosamine | + | - | - | - | - | - | - | - | - | - | - | - | - | - | - | - | - |
| N-Acetyl-Neuraminic Acid | - | - | - | + | + | + | + | + | + | - | - | - | + | - | + | + | + |
| beta-D-Allose | + | - | - | - | - | - | - | - | - | - | - | - | - | - | - | - | - |
| Amygdalin | - | - | - | - | - | - | - | - | - | - | - | - | - | - | - | - | - |
| D-Arabinose | - | + | + | + | + | + | + | + | + | + | + | + | + | + | + | + | + |

FIG. 11 (continued)

| Species | D-Arabitol | L-Arabitol | Arbutin | 2-Deoxy-D-Ribose | I-Erythritol | D-Fucose | 3-0-beta-D-Galacto-pyranosyl-D-Arabinose | Gentibiose | L-Glucose | Lactitol | D-Melezitose | Maltitol | alpha-Methyl-D-Glucoside | beta-Methyl-D-Galactoside | 3-Methyl Glucose | beta-Methyl-D-Glucoronic Acid | alpha-Methyl-D-Mannoside | beta-Metyl-D-Xyloside | Palatinose | D-Raffinose | Salicin | Sedoheptulosan | L-Sorbose |
|---|---|---|---|---|---|---|---|---|---|---|---|---|---|---|---|---|---|---|---|---|---|---|---|
| Clostridium difficile 9689 | - | - | + | - | + | + | + | - | - | - | - | - | - | + | - | - | - | + | - | - | - | + | - |
| Clostridium difficile 9689 | - | - | - | + | - | + | + | - | + | - | - | - | - | - | + | - | - | - | + | - | - | - | + |
| Clostridium difficile 9689 | - | - | - | + | - | + | - | + | - | - | - | + | - | - | + | - | - | - | + | - | - | - | + |
| Clostridium difficile 9689 | - | - | - | + | - | + | + | - | - | - | - | + | - | - | + | - | - | - | + | - | - | - | - |
| Clostridium difficile 9689 | - | - | - | + | - | + | - | + | - | + | - | - | - | - | + | - | - | - | + | - | - | - | + |
| Clostridium difficile 9689 | - | - | - | + | - | - | + | + | + | - | - | - | + | - | + | - | - | - | + | - | - | - | + |
| Clostridium difficile 9689 | - | - | - | + | - | + | + | + | + | - | - | - | + | - | + | - | - | - | + | - | - | - | + |
| Clostridium difficile 43593 | - | - | - | - | - | - | - | - | - | - | - | - | - | - | - | - | - | - | - | - | - | - | - |
| Clostridium difficile 43593 | - | - | - | + | - | - | - | - | - | - | - | + | - | - | + | - | - | - | + | - | - | - | - |
| Clostridium difficile 43593 | - | - | - | + | - | - | + | + | - | - | - | + | - | - | + | - | - | - | + | - | - | - | + |
| Clostridium difficile 43255 | - | - | - | + | - | - | - | - | - | - | - | - | - | - | - | - | - | - | - | - | - | - | - |
| Clostridium difficile 43255 | - | - | - | - | - | - | - | - | - | - | - | - | - | - | - | - | - | - | - | - | - | - | - |
| Clostridium difficile 43255 | - | - | - | - | + | - | - | - | - | - | - | - | - | - | - | - | - | - | - | - | - | - | - |
| Clostridium difficile 43255 | - | - | - | - | - | - | - | - | - | - | - | - | - | - | - | - | - | - | - | - | - | - | - |
| Clostridium difficile 43255 | - | - | - | + | - | - | - | - | - | - | - | - | - | - | + | - | - | - | - | - | + | - | + |
| Clostridium difficile 43255 | - | - | - | + | - | - | - | - | - | - | - | - | - | - | - | - | - | - | - | - | + | - | - |
| Clostridium difficile 43255 | - | - | - | + | - | + | + | + | + | - | - | - | - | - | + | - | - | - | + | - | - | - | + |

FIG. 11 (continued)

| Species | C. difficile 43255 | C. difficile 43255 | C. difficile 43255 | C. difficile 43255 | C. difficile 43255 | C. difficile 43255 | C. difficile 43255 | C. difficile 43593 | C. difficile 43593 | C. difficile 43593 | C. difficile 9689 | C. difficile 9689 | C. difficile 9689 | C. difficile 9689 | C. difficile 9689 | C. difficile 9689 | C. difficile 9689 |
|---|---|---|---|---|---|---|---|---|---|---|---|---|---|---|---|---|---|
| Stachyose | - | - | - | - | - | - | - | - | - | - | - | - | - | - | - | - | + |
| D-Tagatose | + | + | + | - | + | - | + | + | + | + | + | + | + | + | - | + | + |
| Turanose | + | - | - | - | - | - | - | + | - | + | + | + | + | - | - | - | - |
| Xylitol | - | - | - | - | - | - | - | - | - | - | - | - | - | - | - | - | - |
| N-Acetyl-D-Glucosaminitol | - | - | - | - | - | - | - | - | - | - | - | - | - | - | - | - | - |
| gamma-Amino Butyric Acid | - | - | - | - | - | - | - | - | - | - | - | - | - | - | - | - | - |
| delta-Amino Valeric Acid | - | - | - | - | - | - | - | - | - | - | - | - | - | - | - | - | - |
| Butyric Acid | - | - | - | - | - | - | - | - | - | - | - | - | - | - | - | - | - |
| Capric Acid | - | - | - | - | - | - | - | - | - | - | - | - | - | - | - | - | - |
| Caproic Acid | + | + | + | + | + | + | + | + | + | + | + | + | + | + | + | + | - |
| Citraconic Acid | - | - | - | - | - | - | - | - | - | - | - | - | - | - | - | - | - |
| Citramalic Acid | - | - | - | - | - | - | - | - | - | - | - | - | - | + | - | - | - |
| D-Glucosamine | - | - | - | - | - | - | - | - | - | - | - | - | - | - | - | - | + |
| 2-Hydroxy Benzoic Acid | - | - | - | - | - | - | - | - | - | - | - | - | - | - | - | - | - |
| 4-Hydroxy Benzoic Acid | - | - | - | - | - | - | - | - | - | - | - | - | - | - | - | - | + |
| beta-Hydroxy Butyric Acid | - | - | - | - | - | - | - | - | - | - | - | - | - | + | - | - | - |
| gamma-Hydroxy Butyric Acid | - | - | - | - | - | - | - | - | - | - | - | - | - | - | - | - | + |
| alpha-Keto Valeric Acid | + | + | + | + | + | + | + | + | + | + | + | + | + | + | - | + | + |
| Itaconic Acid | - | - | - | - | - | - | - | - | - | - | - | - | - | - | - | - | - |
| 5-Keto-D-Gluconic Acid | - | - | + | - | - | - | - | - | - | - | - | - | - | - | - | - | - |
| D-Lactic Acid Methyl Ester | - | - | - | - | - | - | - | - | - | - | - | - | - | - | - | - | - |
| Malonic Acid | - | - | - | - | - | - | - | - | - | - | - | - | - | - | - | - | - |
| Melibionic Acid | - | - | - | - | - | - | - | - | - | - | - | - | - | - | - | - | - |

FIG. 11 (continued)

| Species | C. difficile 43255 | C. difficile 43255 | C. difficile 43255 | C. difficile 43255 | C. difficile 43255 | C. difficile 43255 | C. difficile 43255 | C. difficile 43593 | C. difficile 43593 | C. difficile 43593 | C. difficile 9689 | C. difficile 9689 | C. difficile 9689 | C. difficile 9689 | C. difficile 9689 | C. difficile 9689 |
|---|---|---|---|---|---|---|---|---|---|---|---|---|---|---|---|---|
| Oxalic Acid | - | - | - | - | - | - | - | - | - | - | - | - | - | - | - | - |
| Oxalomalic Acid | + | - | - | - | - | - | - | + | - | - | - | - | - | - | - | - |
| Quinic Acid | - | - | - | - | - | - | - | - | - | - | - | - | - | - | - | - |
| D-Ribino-1,4-Lacton | - | - | - | - | - | - | - | - | - | - | - | - | - | - | - | + |
| Sebacic Acid | - | - | - | - | - | - | - | - | - | - | - | - | - | - | + | - |
| Sorbic Acid | + | + | + | + | - | - | - | + | - | - | - | - | + | - | - | - |
| Succinamic Acid | - | - | - | - | - | - | - | - | - | - | - | - | - | - | - | - |
| D-Tartaric Acid | - | - | - | - | - | - | - | - | - | - | - | - | - | - | - | - |
| L-Tartaric Acid | - | - | - | - | - | - | - | - | - | - | - | - | - | - | - | - |
| Acetamide | - | - | - | - | - | - | - | - | - | - | - | - | - | - | - | - |
| L-Alaninamide | - | - | - | - | - | - | - | - | - | - | - | - | + | - | - | - |
| N-Acetyl-L-Glutamic Acid | - | - | - | - | - | - | - | - | - | - | - | - | - | - | - | - |
| L-Arginine | - | - | - | - | - | - | - | - | - | - | - | - | - | - | - | - |
| Glycine | - | - | - | - | - | - | - | - | - | - | - | - | - | - | - | - |
| L-Histidine | + | - | - | - | - | - | - | - | - | - | - | - | - | - | - | - |
| L-Homserine | - | - | - | - | - | - | - | - | - | - | - | - | - | - | - | - |
| Hydroxy-L-Proline | - | - | - | - | - | - | - | - | - | - | - | - | - | - | - | - |
| L-Isoleucine | - | - | - | - | - | - | - | - | - | - | - | - | - | - | - | - |
| L-Leucine | - | - | - | - | - | - | - | - | - | - | - | - | - | - | - | - |
| L-Lysine | - | - | - | - | - | - | - | - | - | - | - | - | - | - | - | - |
| L-Methionine | - | - | - | - | - | - | - | - | - | - | - | - | - | - | - | - |
| L-Ornithine | - | - | - | - | - | - | - | - | - | - | - | - | - | - | - | - |
| L-Phenylalanine | - | - | - | - | - | - | - | - | - | - | - | - | - | - | - | - |

FIG. 11 (continued)

| Species | L-Pyroglutamic Acid | L-Valine | D,L-Carnithine | Sec-Butylamine | D,L-Octopamine | Putrescine | Dihydroxy Acetone | 2,3-Butanediol | 2,3-Butanone | 3-Hydroxy 2-Butanone |
|---|---|---|---|---|---|---|---|---|---|---|
| Clostridium difficile 9689 | - | - | - | + | - | + | - | - | - | - |
| Clostridium difficile 9689 | - | + | - | - | - | - | - | - | - | - |
| Clostridium difficile 9689 | - | - | - | - | - | - | + | - | - | - |
| Clostridium difficile 9689 | - | - | - | - | - | - | + | - | - | - |
| Clostridium difficile 9689 | - | - | - | - | - | - | + | - | + | - |
| Clostridium difficile 9689 | - | - | - | - | - | - | + | - | - | - |
| Clostridium difficile 43593 | - | - | - | - | - | - | + | - | - | - |
| Clostridium difficile 43593 | - | - | - | - | - | - | + | - | - | - |
| Clostridium difficile 43593 | - | - | - | - | - | - | + | - | + | - |
| Clostridium difficile 43255 | - | - | - | - | - | - | + | - | - | - |
| Clostridium difficile 43255 | - | - | - | - | - | - | + | - | - | - |
| Clostridium difficile 43255 | - | - | - | - | - | - | + | - | - | - |
| Clostridium difficile 43255 | - | - | - | - | - | - | + | - | - | - |
| Clostridium difficile 43255 | - | - | - | - | - | - | + | - | - | - |
| Clostridium difficile 43255 | - | - | - | - | - | + | + | - | - | - |
| Clostridium difficile 43255 | - | - | - | - | - | - | + | - | + | - |

FIG. 11 (continued)

| Species | Clostridium difficile 43255 | Clostridium difficile 43255 | Collinsella aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium prausnitzii | Faecalibacterium prausnitzii |
|---|---|---|---|---|---|---|---|---|---|---|---|---|---|---|---|---|---|
| time (hr) | 20 | 96 | 20 | 20 | 20 | 20 | 20 | 20 | 20 | 20 | 20 | 20 | 96 | 20 | 20 | 20 | 20 |
| menadione (uM) | 0.16 | 0.16 | 0.5 | 0.5 | 0.5 | 0.5 | 0.5 | 0.5 | 0.05 | 0.05 | 0.05 | 0.05 | 0.05 | 0.05 | 0.5 | 0.5 | 0.5 |
| ferricyanide (mM) | 0.12 | 0.12 | 0.12 | 0.12 | 0.12 | 0.12 | 0.12 | 0.12 | 0.12 | 0.38 | 0.38 | 0.12 | 0.12 | 0.38 | 0.12 | 0.12 | 0.06 |
| L-Arabinose | + | + | + | + | + | + | + | + | + | + | - | + | + | + | + | + | + |
| N-Acetyl-D-Glucosamine | - | - | + | + | + | + | + | - | + | - | - | - | - | - | - | - | - |
| D-Saccharic Acid | - | - | - | - | + | - | - | - | - | - | - | - | - | - | - | - | - |
| Succinic Acid | - | - | - | - | - | - | - | - | - | - | - | - | - | - | - | - | - |
| D-Galactose | + | + | + | + | + | + | + | + | + | + | - | + | + | + | + | + | + |
| L-Aspartic Acid | - | - | - | - | - | - | - | - | - | - | - | - | - | - | - | - | - |
| L-Proline | - | - | - | - | - | + | - | - | - | - | - | - | - | - | - | - | - |
| D-Alanine | - | - | - | - | - | + | - | - | - | - | - | - | - | - | - | - | - |
| D-Trehalose | - | - | - | + | - | - | - | - | + | - | - | - | - | - | + | - | - |
| D-Mannose | - | + | + | + | + | + | + | + | + | - | - | - | - | + | + | - | - |
| Dulcitol | - | - | - | - | - | - | - | - | - | - | - | - | - | - | - | - | - |
| D-Serine | - | - | - | - | - | - | - | - | - | - | - | - | - | - | - | - | - |
| D-Sorbitol | - | - | + | + | + | + | + | + | + | - | - | - | - | + | + | - | - |
| Glycerol | - | - | - | - | + | - | - | - | - | - | - | - | - | - | - | - | - |
| L-Fucose | - | + | - | - | + | + | + | - | + | + | - | + | + | + | + | - | + |
| D-Glucuronic Acid | + | + | + | - | + | + | + | + | + | + | - | - | + | + | + | - | + |
| D-Gluconic Acid | - | - | - | - | + | - | - | - | - | - | - | - | - | - | + | - | - |
| D, L-alpha-Glycerol-Phosphate | - | - | - | - | + | - | - | - | - | - | - | - | - | - | + | - | - |
| D-Xylose | + | + | + | + | + | + | + | + | + | + | + | + | + | + | + | + | + |
| L-Lactic Acid | - | - | - | - | + | - | - | - | - | - | - | - | - | - | + | - | - |

FIG. 11 (continued)

| Species | Clostridium difficile 43255 | Clostridium difficile 43255 | Collinsella aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium prausnitzii | Faecalibacterium prausnitzii |
|---|---|---|---|---|---|---|---|---|---|---|---|---|---|---|---|---|---|
| Formic Acid | - | - | - | - | - | - | - | - | - | - | - | - | - | - | + | - | - |
| D-Mannitol | - | - | - | + | - | + | - | - | + | - | - | - | - | - | + | - | - |
| L-Glutamic Acid | - | + | - | - | - | - | - | - | - | - | - | - | - | - | + | - | - |
| D-Glucose-6-Phosphate | + | + | - | - | - | + | - | - | + | - | - | + | - | - | - | - | - |
| D-Galactonic Acid-gamma-Lactone | + | - | + | - | - | - | + | - | + | - | - | + | + | - | + | + | + |
| D,L-Malic Acid | - | - | - | - | - | - | - | - | - | - | - | - | - | - | - | - | - |
| D-Ribose | + | + | + | + | + | + | + | + | + | + | + | + | + | + | + | + | + |
| Tween 20 | - | - | - | + | + | - | - | - | - | - | - | - | - | - | - | - | - |
| L-Rhamnose | + | + | + | + | + | + | + | + | + | - | - | + | + | + | + | - | + |
| D-Fructose | - | + | + | + | + | + | + | + | + | - | - | + | + | + | + | - | - |
| Acetic Acid | - | - | - | + | - | + | + | + | + | + | - | - | + | + | + | - | - |
| alpha-D-Glucose | - | + | + | + | + | + | + | + | + | + | - | + | + | + | + | - | - |
| Maltose | - | - | + | + | - | + | + | + | + | - | - | + | - | - | + | - | - |
| D-Mellibiose | - | - | + | + | - | + | + | + | + | - | - | + | - | - | + | - | - |
| Thymidine | - | - | + | + | - | + | - | - | + | - | - | - | - | - | + | - | - |
| L-Asparagine | - | - | - | - | - | - | - | - | - | - | - | - | - | - | - | - | - |
| D-Aspartic Acid | - | - | - | - | - | - | - | - | - | - | - | - | - | - | - | - | - |
| D-Glucosaminic Acid | - | - | - | - | - | - | - | - | - | - | - | - | - | - | - | - | - |
| 1,2-Propanediol | - | + | + | - | + | + | - | - | + | - | - | - | - | - | - | - | - |
| Tween 40 | - | - | - | - | + | - | + | + | - | - | - | - | - | - | - | - | - |
| alpha-Keto-Glutaric Acid | - | - | - | - | - | - | - | - | - | - | - | - | - | - | + | - | - |
| alpha-Keto-Butyric Acid | - | - | - | - | - | - | - | - | + | - | - | + | - | - | + | - | - |
| alpha-Methyl-D-Galactoside | - | - | - | - | - | - | - | + | - | - | - | - | - | - | + | - | - |

FIG. 11 (continued)

| Species | Clostridium difficile 43255 | Clostridium difficile 43255 | Collinsella_aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium_prausnitzii | Faecalibacterium_prausnitzii |
|---|---|---|---|---|---|---|---|---|---|---|---|---|---|---|---|---|---|
| alpha-D-Lactose | - | - | + | - | + | + | + | - | + | - | - | - | - | - | + | - | - |
| Lactulose | - | - | + | - | + | + | + | - | + | - | - | - | - | - | + | - | - |
| Sucrose | - | - | + | + | + | - | + | + | + | - | - | - | - | - | + | - | - |
| Uridine | - | - | - | + | + | + | - | - | - | - | - | - | - | - | + | - | - |
| L-Glutamine | - | - | - | - | - | - | - | - | - | - | - | - | - | - | - | - | - |
| M-Tartaric Acid | - | + | - | - | - | - | - | - | - | - | - | - | - | - | - | - | - |
| D-Glucose-1-Phosphate | - | - | - | - | - | - | - | - | - | - | - | + | - | - | - | - | + |
| D-Fructose-6-Phosphate | - | - | + | + | + | + | + | + | + | - | - | - | - | + | + | - | + |
| Tween 80 | - | - | - | - | - | - | - | - | - | - | - | - | - | - | - | - | - |
| alpha-Hydroxy-Glutaric-gamma-lactone | - | - | - | - | - | - | - | - | - | - | - | - | - | - | + | - | - |
| alpha-Hydroxy Butyric Acid | - | - | - | - | - | - | - | - | - | - | - | - | - | - | - | - | - |
| beta-Methyl-D-Glucoside | - | - | - | + | - | - | - | - | - | - | - | - | - | - | - | - | - |
| Adonitol | - | - | - | - | - | - | - | - | - | - | - | - | - | - | - | - | - |
| Maltotriose | - | - | + | + | + | + | + | + | + | - | - | - | - | - | + | - | - |
| 2-Deoxy Adenosine | - | - | - | + | + | + | + | - | + | - | - | - | - | - | + | - | - |
| Adenosine | - | - | - | + | + | + | - | - | - | - | - | - | - | - | + | - | - |
| Glycyl-L-Aspartic Acid | - | - | - | - | + | - | - | - | - | - | - | - | - | - | + | - | - |
| Citric Acid | - | - | - | - | - | - | - | - | - | - | - | - | - | - | - | - | - |
| M-Inositol | - | - | - | - | - | - | - | - | - | - | - | - | - | - | - | - | - |
| D-Threonine | - | - | - | - | - | - | - | - | - | - | - | - | - | - | + | - | - |
| Fumaric Acid | - | - | - | - | - | - | - | - | - | - | - | - | - | - | + | - | - |
| Bromo Succinic Acid | - | - | - | - | - | - | - | - | - | - | - | + | + | - | - | - | - |
| Propionic Acid | - | - | - | - | - | + | - | - | - | - | - | - | - | - | + | - | - |

FIG. 11 (continued)

| Species | Clostridium difficile 43255 | Clostridium difficile 43255 | Collinsella aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium prausnitzii | Faecalibacterium prausnitzii |
|---|---|---|---|---|---|---|---|---|---|---|---|---|---|---|---|---|---|
| Mucic Acid | - | - | - | - | + | - | - | - | - | - | - | - | - | - | + | - | - |
| Glycolic Acid | - | - | - | - | - | - | - | - | - | - | - | - | - | - | - | - | - |
| Glyoxylic Acid | - | - | - | - | - | - | - | - | - | - | + | - | - | - | - | - | - |
| D-Cellobiose | - | - | + | + | + | + | + | + | + | + | - | - | - | - | + | - | - |
| Inosine | - | - | - | + | + | + | - | - | + | - | - | - | - | - | + | - | - |
| Glycyl-L-Glutamic Acid | - | - | - | - | - | - | - | - | - | - | - | - | - | - | + | - | - |
| Tricarballylic Acid | - | - | - | - | - | - | - | - | - | - | - | - | - | - | - | - | - |
| L-Serine | - | - | - | - | - | + | - | - | - | - | - | - | - | - | + | - | - |
| L-Threonine | - | - | - | - | - | + | - | - | - | - | - | - | - | - | - | - | - |
| L-Alanine | - | - | - | - | - | + | - | - | - | - | - | - | - | - | + | - | - |
| L-Alanyl-Glycine | - | - | + | - | + | + | + | - | - | - | - | - | - | - | + | - | - |
| Acetoacetic Acid | - | - | - | + | + | - | + | - | - | - | + | - | - | - | + | - | - |
| N-Acetyl-beta-D-Mannosamine | - | - | - | - | - | - | - | - | - | - | - | - | - | - | - | - | - |
| Mono Methyl Succinate | - | - | - | - | - | + | - | - | - | - | - | - | - | - | - | - | - |
| Methyl Pyruvate | - | - | - | + | + | + | + | - | - | - | - | - | - | - | + | - | - |
| D-Malic Acid | - | - | - | - | - | - | - | - | - | - | - | - | - | - | - | - | - |
| L-Malic Acid | - | - | - | - | - | + | - | - | - | - | - | - | - | - | + | - | - |
| Glycyl-L-Proline | - | - | - | - | - | - | - | - | - | - | - | - | - | - | - | - | - |
| p-Hydroxy Phenyl Acetic Acid | - | - | - | - | - | - | - | - | - | - | - | - | - | - | - | - | - |
| m-Hydroxy Phenyl Acetic Acid | - | - | - | - | - | - | - | - | - | - | - | - | - | - | - | - | - |
| Tyramine | - | - | - | - | - | - | - | - | - | - | - | - | - | - | - | - | - |
| D-Psicose | + | - | - | + | + | + | + | + | + | + | - | + | + | + | + | - | + |
| L-Lyxose | + | + | + | + | + | + | + | + | + | + | - | + | + | + | + | + | + |

FIG. 11 (continued)

| Species | Clostridium difficile 43255 | Clostridium difficile 43255 | Collinsella aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium prausnitzii | Faecalibacterium prausnitzii |
|---|---|---|---|---|---|---|---|---|---|---|---|---|---|---|---|---|---|
| Glucuronamide | + | + | + | + | + | + | + | + | + | + | - | + | + | + | + | + | + |
| Pyruvic Acid | - | - | + | + | + | + | - | - | - | - | - | - | - | - | + | - | - |
| L-Galactonic Acid-gamma-Lactone | - | - | - | - | - | - | - | - | - | - | - | - | - | - | - | - | - |
| D-Galacturonic Acid | + | - | + | + | + | + | + | - | + | - | - | - | + | + | + | - | + |
| Pheylethyl-amine | - | - | - | - | - | - | - | - | - | - | - | - | - | - | - | - | - |
| 2-aminoethanol | - | - | - | - | - | - | - | - | - | - | - | - | - | - | - | - | - |
| Negative control | - | - | - | - | - | - | - | - | - | - | - | - | - | - | - | - | - |
| Chondroitin Sulfate C | - | - | - | - | - | - | - | - | + | - | - | - | - | - | - | - | - |
| alpha-Cyclodextrin | - | - | - | - | - | - | - | - | + | - | - | - | - | - | - | - | - |
| beta-Cyclodextrin | - | - | - | - | - | + | - | - | + | - | - | + | + | - | - | - | - |
| gamma-Cyclodextrin | - | - | - | - | - | - | - | - | - | - | - | - | - | - | - | - | - |
| Dextrin | + | - | + | + | - | + | + | - | + | + | + | + | + | + | - | - | - |
| Gelatin | - | - | - | - | + | - | - | - | + | - | - | - | - | - | - | - | - |
| Glycogen | - | - | - | - | - | - | - | - | - | - | - | - | - | - | + | - | - |
| Inulin | - | - | - | + | - | - | - | - | + | - | + | + | + | + | + | - | - |
| Laminarin | - | - | + | - | - | + | - | - | + | + | - | - | - | - | + | - | - |
| Mannan | - | - | - | - | - | + | - | - | + | - | - | - | - | - | + | - | - |
| Pectin | - | - | - | - | + | - | - | - | - | - | - | - | - | - | + | - | - |
| N-Acetyl-D-Galactosamine | + | - | + | + | + | + | + | + | + | + | + | + | + | + | + | + | + |
| N-Acetyl-Neuramic Acid | - | - | - | - | - | + | - | - | - | - | - | - | - | - | + | - | - |
| beta-D-Allose | + | + | - | - | - | - | - | - | - | - | - | - | - | - | + | + | + |
| Amygdalin | - | - | - | - | - | - | - | - | - | - | - | - | - | - | + | - | - |
| D-Arabinose | + | + | + | + | + | + | + | + | + | + | + | + | + | + | + | + | + |

FIG. 11 (continued)

| Species | Clostridium difficile 43255 | Clostridium difficile 43255 | Collinsella_aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium_prausnitzii | Faecalibacterium_prausnitzii |
|---|---|---|---|---|---|---|---|---|---|---|---|---|---|---|---|---|---|
| D-Arabitol | - | - | - | - | - | + | - | - | - | - | - | - | - | - | + | - | - |
| L-Arabitol | - | - | - | + | - | - | - | - | - | - | - | - | - | - | + | - | - |
| Arbutin | - | + | + | - | - | - | - | - | + | - | - | - | - | - | - | - | - |
| 2-Deoxy-D-Ribose | + | + | + | + | + | + | + | + | + | + | + | + | + | + | + | + | + |
| I-Erythritol | - | - | - | - | - | + | - | - | - | + | - | - | - | - | - | - | - |
| D-Fucose | - | + | + | + | + | + | + | + | + | + | + | - | + | + | + | + | + |
| 3-O-beta-D-Galacto-pyranosyl-D-Arabinose | - | + | + | + | + | + | + | + | + | + | - | - | - | - | + | - | - |
| Gentibiose | - | + | + | + | + | + | + | - | + | + | + | - | - | - | + | - | - |
| L-Glucose | - | + | + | + | + | + | + | + | + | - | + | - | - | - | + | - | + |
| Lactitol | - | + | - | - | + | - | - | - | + | - | + | - | - | - | + | - | - |
| D-Melezitose | - | - | - | - | - | - | - | - | - | - | - | - | - | - | + | - | - |
| Maltitol | - | - | + | + | + | + | + | + | + | + | + | + | + | + | + | + | + |
| alpha-Methyl-D-Glucoside | - | - | - | - | - | + | - | - | - | - | - | - | - | - | + | - | - |
| beta-Methyl-D-Galactoside | - | + | + | + | + | + | + | + | + | + | + | + | - | + | + | + | + |
| 3-Methyl Glucose | - | - | - | - | - | - | - | - | - | - | - | - | - | - | + | - | - |
| beta-Methyl-D-Glucoronic Acid | - | - | - | + | - | - | - | - | - | - | + | - | - | - | - | - | - |
| alpha-Methyl-D-Mannoside | - | - | + | - | - | - | - | - | + | - | - | - | - | - | + | - | + |
| beta-Metyl-D-Xyloside | - | - | - | - | - | + | - | - | + | - | - | - | - | - | + | - | - |
| Palatinose | + | - | + | - | + | - | - | + | - | + | + | - | - | - | + | + | - |
| D-Raffinose | - | - | + | + | - | + | - | - | + | - | - | - | - | - | + | + | + |
| Salicin | - | - | - | + | - | + | - | - | - | - | + | - | + | - | - | - | - |
| Sedoheptulosan | - | - | - | - | - | + | - | - | - | - | - | - | - | - | - | - | - |
| L-Sorbose | - | + | + | + | + | + | + | + | + | + | + | - | + | - | + | - | + |

FIG. 11 (continued)

| Species | Stachyose | D-Tagatose | Turanose | Xylitol | N-Acetyl-D-Glucosaminitol | gamma-Amino Butyric Acid | delta-Amino Valeric Acid | Butyric Acid | Capric Acid | Caproic Acid | Citraconic Acid | Citramalic Acid | D-Glucosamine | 2-Hydroxy Benzoic Acid | 4-Hydroxy Benzoic Acid | beta-Hydroxy Butyric Acid | gamma-Hydroxy Butyric Acid | alpha-Keto Valeric Acid | Itaconic Acid | 5-Keto-D-Gluconic Acid | D-Lactic Acid Methyl Ester | Malonic Acid | Melibionic Acid |
|---|---|---|---|---|---|---|---|---|---|---|---|---|---|---|---|---|---|---|---|---|---|---|---|
| Clostridium difficile 43255 | + | - | - | - | - | - | - | - | - | - | - | - | + | - | - | - | - | - | + | - | - | - | - |
| Clostridium difficile 43255 | - | + | + | - | - | - | - | - | - | - | - | - | + | - | - | - | - | + | - | - | - | - | - |
| Collinsella_aerofaciens | - | + | + | - | - | - | - | - | - | - | - | + | - | - | + | + | - | - | - | - | - | - | - |
| Clostridium innocuum | - | + | + | - | + | - | - | - | - | + | - | - | + | - | + | + | + | - | - | - | - | - | - |
| Coprococcus comes | + | + | + | - | - | - | - | - | - | - | - | + | - | - | - | + | + | - | - | - | - | - | - |
| Clostridium hylemonae | - | + | + | + | - | - | - | + | - | + | - | - | + | - | - | + | + | + | - | - | - | - | + |
| Ruminococcus gnavus | + | + | + | - | - | - | - | - | - | - | - | + | - | - | - | + | + | - | - | - | - | - | - |
| Eubacterium rectale | - | + | + | - | - | - | - | - | - | - | - | + | - | - | - | - | + | - | + | - | - | - | - |
| Clostridium butyricum | + | + | + | - | - | + | + | + | - | - | - | + | - | - | - | - | + | - | + | - | - | - | - |
| Clostridium symbiosum | - | + | + | - | - | - | - | - | - | - | - | + | - | - | - | - | + | - | + | - | - | - | - |
| Clostridium tertium | - | + | - | - | - | - | - | - | - | - | - | + | - | - | - | - | - | + | - | - | - | - | - |
| Clostridium tertium | - | + | - | - | - | - | - | - | - | - | - | + | - | - | - | - | + | - | - | + | - | - | - |
| Clostridium tertium | - | - | + | - | - | - | - | - | - | - | - | + | - | - | - | + | - | - | - | - | - | - | - |
| Clostridium orbiscindens | - | + | - | - | - | - | - | - | - | - | - | + | - | - | - | - | - | + | - | - | - | - | - |
| Blautia producta | + | + | + | + | - | - | - | - | - | + | - | - | + | - | - | - | - | + | - | + | + | - | + |
| Faecalibacterium_prausnitzii | - | + | - | - | - | - | - | - | - | - | - | + | - | - | - | - | - | + | - | - | - | - | - |
| Faecalibacterium_prausnitzii | - | + | - | - | - | - | - | - | - | - | - | + | - | - | - | - | - | + | - | - | - | - | - |

FIG. 11 (continued)

| Species | Clostridium difficile 43255 | Clostridium difficile 43255 | Collinsella aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium prausnitzii | Faecalibacterium prausnitzii |
|---|---|---|---|---|---|---|---|---|---|---|---|---|---|---|---|---|---|
| Oxalic Acid | - | - | - | - | - | - | - | - | - | - | - | - | - | - | - | - | - |
| Oxalomalic Acid | - | - | + | - | + | + | - | - | - | - | + | - | - | - | + | - | - |
| Quinic Acid | - | - | - | - | - | - | - | - | - | - | - | - | - | - | - | - | - |
| D-Ribino-1,4-Lacton | - | - | - | - | - | - | - | - | - | - | - | - | - | - | - | - | - |
| Sebacic Acid | + | - | - | - | - | - | - | - | - | - | - | - | - | - | - | - | - |
| Sorbic Acid | - | + | + | + | + | - | + | - | + | - | + | - | - | - | - | - | + |
| Succinamic Acid | - | - | - | - | - | - | - | - | - | - | - | - | - | - | - | - | - |
| D-Tartaric Acid | - | - | - | - | - | - | - | - | - | - | - | - | - | - | - | - | - |
| L-Tartaric Acid | - | - | - | - | - | - | - | - | - | - | - | - | - | - | - | - | - |
| Acetamide | - | - | - | - | - | - | - | - | - | - | - | - | - | - | - | - | - |
| L-Alaninamide | - | - | - | - | - | - | - | - | + | - | - | - | - | - | + | - | - |
| N-Acetyl-L-Glutamic Acid | - | - | - | - | - | - | - | - | + | - | - | - | - | - | - | - | - |
| L-Arginine | - | - | - | - | - | - | - | - | - | - | - | - | - | - | - | - | - |
| Glycine | - | - | - | - | - | - | - | - | - | - | - | - | - | - | - | - | - |
| L-Histidine | - | - | - | - | - | - | - | - | - | - | - | - | - | - | + | - | - |
| L-Homserine | - | - | - | - | - | - | - | - | - | - | - | - | - | - | - | - | - |
| Hydroxy-L-Proline | - | - | - | - | - | - | - | - | - | - | - | - | - | - | - | - | - |
| L-Isoleucine | - | - | - | - | - | - | - | - | - | - | - | - | - | - | - | - | - |
| L-Leucine | - | - | - | - | - | - | - | - | - | - | - | - | - | - | - | - | - |
| L-Lysine | - | - | - | - | - | - | - | - | - | - | - | - | - | - | - | - | - |
| L-Methionine | - | - | - | - | - | - | - | - | - | - | - | - | - | - | - | - | - |
| L-Ornithine | - | - | - | - | - | - | - | - | - | - | - | - | - | - | - | - | - |
| L-Phenylalanine | - | - | - | - | - | - | - | - | - | - | - | - | - | - | - | - | - |

FIG. 11 (continued)

| Species | Clostridium difficile 43255 | Clostridium difficile 43255 | Collinsella_aerofaciens | Clostridium innocuum | Coprococcus comes | Clostridium hylemonae | Ruminococcus gnavus | Eubacterium rectale | Clostridium butyricum | Clostridium symbiosum | Clostridium tertium | Clostridium tertium | Clostridium tertium | Clostridium orbiscindens | Blautia producta | Faecalibacterium_prausnitzii | Faecalibacterium_prausnitzii |
|---|---|---|---|---|---|---|---|---|---|---|---|---|---|---|---|---|---|
| L-Pyroglutamic Acid | - | - | - | - | - | - | - | - | - | - | - | - | - | - | - | - | - |
| L-Valine | - | - | - | - | - | - | - | - | - | - | - | - | - | - | - | - | - |
| D,L-Carnithine | - | - | - | - | - | - | - | - | - | - | - | - | - | - | - | - | - |
| Sec-Butylamine | - | - | - | - | - | - | - | - | + | - | - | - | - | - | - | - | - |
| D,L-Octopamine | + | - | - | - | - | + | - | - | + | - | - | - | - | - | - | - | - |
| Putrescine | + | + | + | + | + | + | + | + | + | + | + | + | + | + | + | + | + |
| Dihydroxy Acetone | - | - | - | - | - | - | - | - | + | - | - | - | - | - | - | - | - |
| 2,3-Butanediol | - | - | + | + | - | - | - | - | - | - | - | - | + | - | - | - | - |
| 3-Hydroxy 2-Butanone | - | - | - | - | - | - | - | - | + | - | - | - | - | - | - | - | - |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium_disporicum | Clostridium_disporicum | Clostridium_disporicum | Clostridium_mayombei | Clostridium_mayombei | Clostridium_mayombei | Clostridium_mayombei | Clostridium_mayombei | Clostridium_mayombei | Clostridium_mayombei | Clostridium_bolteae |
|---|---|---|---|---|---|---|---|---|---|---|---|---|---|---|---|---|---|
| time (hr) | 96 | 20 | 20 | 20 | 20 | 96 | 20 | 20 | 96 | 20 | 20 | 20 | 20 | 96 | 20 | 96 | 20 |
| menadione (uM) | 0.5 | 0.05 | 0.05 | 0.5 | 0.5 | 0.5 | 0.05 | 0.16 | 0.16 | 0.05 | 0.16 | 0.05 | 0.5 | 0.5 | 0.16 | 0.16 | 0.05 |
| ferricyanide (mM) | 0.06 | 0.38 | 0.38 | 0.12 | 0.06 | 0.06 | 0.38 | 0.12 | 0.12 | 0.38 | 0.38 | 0.24 | 0.38 | 0.38 | 0.12 | 0.12 | 0.38 |
| L-Arabinose | + | - | - | + | + | + | + | + | + | + | + | + | + | + | + | + | + |
| N-Acetyl-D-Glucosamine | - | - | - | - | - | - | - | - | - | - | - | - | - | - | - | - | - |
| D-Saccharic Acid | - | - | - | - | - | - | - | - | - | - | - | - | - | - | - | - | - |
| Succinic Acid | - | - | - | - | - | - | - | - | - | - | - | - | - | - | - | - | - |
| D-Galactose | + | - | - | + | + | + | + | + | + | - | - | - | - | - | + | + | - |
| L-Aspartic Acid | - | - | - | - | - | - | - | - | - | - | - | - | - | - | - | - | - |
| L-Proline | - | - | - | - | - | - | - | - | - | - | - | - | - | - | - | - | - |
| D-Alanine | - | - | - | - | - | - | - | - | - | - | - | - | - | - | - | - | - |
| D-Trehalose | - | - | - | - | - | - | - | - | - | - | - | - | - | - | - | - | - |
| D-Mannose | + | - | - | - | + | + | - | + | + | - | - | - | - | - | - | + | - |
| Dulcitol | - | - | - | - | - | - | - | - | - | - | - | - | - | - | - | - | - |
| D-Serine | - | - | - | - | - | + | - | + | + | - | - | - | - | - | - | - | - |
| D-Sorbitol | - | - | - | - | + | + | - | + | + | - | - | - | - | - | - | - | - |
| Glycerol | - | - | - | - | - | - | - | - | - | - | - | - | - | - | - | - | - |
| L-Fucose | + | - | - | + | + | + | - | - | - | - | - | - | - | - | - | + | - |
| D-Glucuronic Acid | + | - | - | + | + | + | - | - | - | - | - | - | - | - | - | + | - |
| D-Gluconic Acid | - | - | - | - | - | - | - | - | - | - | - | - | - | - | - | - | - |
| D,L-alpha-Glycerol-Phosphate | + | - | - | - | - | - | - | - | - | - | - | - | - | - | - | - | - |
| D-Xylose | + | - | + | - | - | - | + | + | + | + | - | + | + | + | - | + | + |
| L-Lactic Acid | - | - | - | - | - | - | - | - | - | - | - | - | - | - | - | - | - |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostridium disporicum | Clostridium mayombei | Clostridium mayombei | Clostridium mayombei | Clostridium mayombei | Clostridium mayombei | Clostridium mayombei | Clostridium bolteae |
|---|---|---|---|---|---|---|---|---|---|---|---|---|---|---|---|---|
| Formic Acid | - | - | - | - | - | - | - | - | - | - | - | - | - | - | - | - |
| D-Mannitol | + | - | - | - | - | - | - | - | - | - | - | - | - | - | - | - |
| L-Glutamic Acid | - | - | - | - | - | - | - | - | - | - | - | - | - | - | - | - |
| D-Glucose-6-Phosphate | + | - | - | + | + | + | - | - | - | - | - | - | - | - | - | - |
| D-Galactonic Acid-gamma-Lactone | + | - | - | - | - | + | - | + | + | - | - | - | - | - | + | - |
| D,L-Malic Acid | - | - | - | - | - | - | - | - | - | - | + | - | - | - | - | - |
| D-Ribose | + | + | + | + | + | + | + | + | + | + | + | + | + | + | + | + |
| Tween 20 | - | - | - | - | - | - | - | - | - | - | - | - | - | - | - | - |
| L-Rhamnose | + | - | - | - | + | + | - | + | + | - | - | - | + | + | + | - |
| D-Fructose | + | - | - | - | - | + | - | - | + | - | - | - | - | - | + | - |
| Acetic Acid | + | - | - | - | - | + | - | - | - | - | - | - | - | - | - | - |
| alpha-D-Glucose | + | - | - | - | + | + | - | - | + | - | - | - | - | - | + | - |
| Maltose | - | - | - | - | - | - | - | - | - | - | - | - | - | - | - | - |
| D-Mellibiose | - | - | - | - | - | - | - | - | - | - | - | - | - | - | + | - |
| Thymidine | - | - | - | - | - | - | - | - | - | - | - | - | - | - | - | - |
| L-Asparagine | - | - | - | - | - | - | - | - | - | - | - | - | - | - | - | - |
| D-Aspartic Acid | - | - | - | - | - | + | - | - | - | - | - | + | + | - | - | - |
| D-Glucosaminic Acid | - | - | - | - | - | - | - | - | - | - | - | - | - | - | - | - |
| 1,2-Propanediol | - | - | - | - | - | - | - | - | - | - | - | - | - | - | - | - |
| Tween 40 | - | - | - | - | - | - | - | - | - | - | - | - | - | - | - | - |
| alpha-Keto-Glutaric Acid | - | - | - | - | - | - | - | - | - | - | - | - | - | - | - | - |
| alpha-Keto-Butyric Acid | + | - | - | - | - | + | - | - | - | - | - | - | - | - | + | - |
| alpha-Methyl-D-Galactoside | - | - | - | - | - | - | - | - | - | - | - | - | - | - | - | - |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostridium disporicum | Clostridium mayombei | Clostridium mayombei | Clostridium mayombei | Clostridium mayombei | Clostridium mayombei | Clostridium mayombei | Clostridium mayombei | Clostridium bolteae |
|---|---|---|---|---|---|---|---|---|---|---|---|---|---|---|---|---|---|
| alpha-D-Lactose | - | - | - | - | - | - | - | - | - | - | - | - | - | - | - | - | - |
| Lactulose | - | - | - | - | - | + | - | - | - | - | - | - | - | - | - | - | - |
| Sucrose | - | - | - | - | - | - | - | - | - | - | - | - | - | - | - | - | - |
| Uridine | - | - | - | - | - | - | - | - | - | - | - | - | - | - | - | - | - |
| L-Glutamine | - | - | - | - | - | - | - | - | - | - | - | - | - | - | - | - | - |
| M-Tartaric Acid | - | - | - | - | - | - | - | - | - | - | - | - | - | - | - | - | - |
| D-Glucose-1-Phosphate | - | - | - | - | - | - | - | - | - | - | - | - | - | - | - | - | - |
| D-Fructose-6-Phosphate | + | - | - | - | + | + | - | + | + | - | - | - | + | + | + | - | - |
| Tween 80 | - | - | - | - | - | - | - | - | - | - | - | - | - | - | - | - | - |
| alpha-Hydroxy-Glutaric-gamma-lactone | - | - | - | - | - | - | - | - | - | - | - | - | - | - | - | - | - |
| alpha-Hydroxy Butyric Acid | - | - | - | - | - | - | - | - | - | - | - | - | - | - | - | - | - |
| beta-Methyl-D-Glucoside | - | - | - | - | - | + | - | - | - | - | - | - | - | - | - | - | - |
| Adonitol | - | - | - | - | - | - | - | - | - | - | - | - | - | - | - | - | - |
| Maltotriose | - | - | - | - | - | - | - | - | - | - | - | - | - | - | - | + | - |
| 2-Deoxy Adenosine | - | - | - | - | - | - | - | - | - | - | - | - | - | - | - | - | - |
| Adenosine | - | - | - | - | - | - | - | - | - | - | - | - | - | - | - | - | - |
| Glycyl-L-Aspartic Acid | - | - | - | - | - | - | - | - | - | - | - | - | - | - | - | - | - |
| Citric Acid | - | - | - | - | - | - | - | - | - | - | - | - | - | - | - | - | - |
| M-Inositol | - | - | - | - | - | - | - | - | - | - | - | - | - | - | - | - | - |
| D-Threonine | - | - | - | - | - | - | - | - | - | - | - | - | - | - | - | - | - |
| Fumaric Acid | - | - | - | - | - | - | - | - | - | - | - | - | - | - | - | - | - |
| Bromo Succinic Acid | - | - | - | - | - | - | - | - | - | - | - | - | - | - | - | - | - |
| Propionic Acid | + | - | - | - | - | + | - | - | - | - | - | - | - | - | - | - | - |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostridium disporicum | Clostridium mayombei | Clostridium mayombei | Clostridium mayombei | Clostridium mayombei | Clostridium mayombei | Clostridium mayombei | Clostridium FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium_disporicum | Clostridium_disporicum | Clostridium_disporicum | Clostridium_mayombei | Clostridium_mayombei | Clostridium_mayombei | Clostridium_mayombei | Clostridium_mayombei | Clostridium_mayombei | Clostridium_mayombei | Clostridium_bolteae |
|---|---|---|---|---|---|---|---|---|---|---|---|---|---|---|---|---|---|
| Glucuronamide | + | - | - | + | + | + | - | + | + | - | - | + | - | + | + | + | - |
| Pyruvic Acid | + | - | - | - | + | + | - | - | - | - | - | - | - | - | - | - | - |
| L-Galactonic Acid-gamma-Lactone | - | - | - | - | - | - | - | - | - | - | - | - | - | - | - | - | - |
| D-Galacturonic Acid | + | - | - | - | + | + | - | - | - | - | - | - | - | - | - | + | - |
| Pheylethyl-amine | - | - | - | - | - | + | - | - | - | - | - | - | - | - | - | - | - |
| 2-aminoethanol | - | - | - | - | - | + | - | - | - | - | - | - | - | - | - | - | - |
| Negative control | - | - | - | - | - | - | - | - | - | - | - | - | - | - | - | - | - |
| Chondroitin Sulfate C | - | - | - | - | - | - | - | - | - | - | - | - | - | - | + | - | - |
| alpha-Cyclodextrin | - | - | - | - | - | - | - | - | - | - | - | - | - | - | - | - | - |
| beta-Cyclodextrin | - | - | - | - | - | - | - | - | - | - | - | - | - | - | - | - | - |
| gamma-Cyclodextrin | - | - | - | - | - | - | - | - | - | - | - | - | - | - | - | - | - |
| Dextrin | - | - | - | - | - | + | - | - | - | - | - | - | - | - | - | - | - |
| Gelatin | - | - | - | - | - | - | - | - | - | - | - | - | - | - | - | - | - |
| Glycogen | - | - | - | + | - | + | - | - | - | + | - | - | - | - | - | - | - |
| Inulin | + | - | + | - | - | - | - | - | - | - | - | - | - | - | - | - | - |
| Laminarin | - | - | - | - | - | - | - | - | - | - | - | - | - | - | - | - | - |
| Mannan | - | - | - | - | - | - | - | - | - | - | - | - | - | - | - | - | - |
| Pectin | - | - | - | - | - | - | - | - | - | - | - | - | - | - | - | - | - |
| N-Acetyl-D-Galactosamine | - | - | - | + | + | + | + | + | + | - | + | - | + | - | + | + | - |
| N-Acetyl-Neuramic Acid | + | - | + | + | + | + | + | + | + | + | + | - | + | + | + | + | - |
| beta-D-Allose | - | - | - | - | - | - | - | - | - | - | - | + | - | - | - | - | - |
| Amygdalin | - | - | - | - | - | - | - | - | - | - | - | - | - | - | + | + | - |
| D-Arabinose | + | + | + | + | + | + | + | + | + | + | + | + | + | + | + | + | + |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostridium disporicum | Clostridium mayombei | Clostridium mayombei | Clostridium mayombei | Clostridium mayombei | Clostridium mayombei | Clostridium mayombei | Clostridium mayombei | Clost FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostridium disporicum | Clostridium mayombei | Clostridium mayombei | Clostridium mayombei | Clostridium mayombei | Clostridium mayombei | Clostridium mayombei | Clostridium mayombei | Clostridium boltaea |
|---|---|---|---|---|---|---|---|---|---|---|---|---|---|---|---|---|---|
| Stachyose | - | - | - | - | - | - | - | - | - | - | - | - | - | - | - | - | - |
| D-Tagatose | + | - | + | + | + | + | + | + | + | + | + | + | + | + | + | + | - |
| Turanose | - | - | - | - | - | + | + | - | - | - | - | - | - | - | - | + | - |
| Xylitol | - | - | - | - | - | - | - | - | - | - | - | - | - | - | - | - | - |
| N-Acetyl-D-Glucosaminitol | - | - | - | - | + | - | - | - | - | - | - | - | - | - | - | - | - |
| gamma-Amino Butyric Acid | - | - | - | - | + | - | - | - | - | - | - | - | - | - | - | - | - |
| delta-Amino Valeric Acid | - | - | - | - | + | - | - | - | - | - | - | - | - | - | - | - | - |
| Butyric Acid | + | - | - | - | - | - | - | - | - | - | - | - | - | - | - | + | - |
| Capric Acid | - | - | - | - | - | - | - | - | - | - | - | - | - | - | - | - | - |
| Caproic Acid | - | - | - | - | - | - | - | - | - | - | - | - | - | - | - | - | - |
| Citraconic Acid | - | - | - | - | - | - | - | - | - | - | - | - | - | - | - | - | - |
| Citramalic Acid | - | - | - | - | - | - | - | - | - | - | - | - | - | - | - | - | - |
| D-Glucosamine | + | + | + | + | + | + | + | + | + | + | + | + | + | + | + | + | + |
| 2-Hydroxy Benzoic Acid | - | - | - | - | - | - | - | - | - | - | - | - | - | - | - | - | - |
| 4-Hydroxy Benzoic Acid | - | - | - | - | - | - | - | - | - | - | - | - | - | - | - | - | - |
| beta-Hydroxy Butyric Acid | - | - | - | - | - | - | - | - | - | - | - | - | - | - | - | - | - |
| gamma-Hydroxy Butyric Acid | + | - | + | - | - | + | - | - | - | - | - | - | - | - | - | - | - |
| alpha-Keto Valeric Acid | - | - | - | - | - | - | - | - | - | - | - | - | - | - | - | - | - |
| Itaconic Acid | - | - | - | - | - | - | - | - | - | - | - | - | - | - | - | - | - |
| 5-Keto-D-Gluconic Acid | + | + | + | + | + | + | + | + | + | + | + | + | + | + | + | + | + |
| D-Lactic Acid Methyl Ester | - | - | - | - | - | - | - | - | - | - | - | - | - | - | - | - | - |
| Malonic Acid | - | - | - | - | - | - | - | - | - | - | - | - | - | - | - | - | - |
| Melibionic Acid | - | - | - | - | - | - | - | - | - | - | - | - | - | - | - | - | - |

FIG. 11 (continued)

| Species | Oxalic Acid | Oxalomalic Acid | Quinic Acid | D-Ribino-1,4-Lacton | Sebacic Acid | Sorbic Acid | Succinamic Acid | D-Tartaric Acid | L-Tartaric Acid | Acetamide | L-Alaninamide | N-Acetyl-L-Glutamic Acid | L-Arginine | Glycine | L-Histidine | L-Homserine | Hydroxy-L-Proline | L-Isoleucine | L-Leucine | L-Lysine | L-Methionine | L-Ornithine | L-Phenylalanine |
|---|---|---|---|---|---|---|---|---|---|---|---|---|---|---|---|---|---|---|---|---|---|---|---|
| Faecalibacterium_prausnitzii | - | + | - | - | - | + | - | - | - | - | - | - | - | - | - | - | - | - | - | + | + | + | - |
| Lachnospiraceae_bacterium_5_1_57FAA | - | - | - | - | - | - | - | - | - | - | - | - | - | - | - | - | - | - | - | - | - | - | - |
| Ruminococcus_bromii | - | - | - | - | - | - | - | - | - | - | - | - | - | - | - | - | - | - | - | - | - | - | - |
| Ruminococcus_bromii | - | - | - | - | - | - | - | - | - | - | - | - | - | - | - | - | - | - | - | - | - | - | - |
| Ruminococcus_bromii | - | - | - | - | - | + | - | - | - | - | - | - | - | - | - | - | - | - | - | - | - | - | - |
| Ruminococcus_bromii | - | + | - | - | - | + | - | - | - | - | - | - | - | + | + | + | + | + | + | + | + | + | + |
| Clostridium disporicum | - | - | - | - | - | - | - | - | - | - | - | - | - | - | - | - | - | - | - | - | - | - | - |
| Clostridium disporicum | - | - | - | - | - | + | - | - | - | - | - | - | - | - | - | - | - | - | - | - | - | - | - |
| Clostridium disporicum | - | - | - | - | - | + | - | - | - | - | - | - | - | - | - | - | - | - | - | - | - | - | - |
| Clostridium mayombei | - | - | - | - | - | - | - | - | - | - | - | - | - | - | - | - | - | - | - | - | - | - | - |
| Clostridium mayombei | - | - | - | - | - | - | - | - | - | - | - | - | - | - | - | - | - | - | - | - | - | - | - |
| Clostridium mayombei | - | - | - | - | - | - | - | - | - | - | - | - | - | - | - | - | - | - | - | - | - | - | - |
| Clostridium mayombei | - | - | - | - | - | + | - | - | - | - | - | - | - | - | - | - | - | - | - | - | - | - | - |
| Clostridium mayombei | - | - | - | - | - | + | - | - | - | - | - | - | - | - | - | - | - | - | - | - | - | - | - |
| Clostridium mayombei | - | - | - | - | - | + | - | - | - | - | - | - | - | - | - | - | - | - | - | - | - | - | - |
| Clostridium mayombei | - | + | - | - | - | + | - | - | - | - | - | - | - | - | - | - | - | - | - | - | - | - | - |
| Clostridium bolteae | - | - | - | - | - | - | - | - | - | - | - | - | - | - | - | - | - | - | - | - | - | - | - |

FIG. 11 (continued)

| Species | Faecalibacterium_prausnitzii | Lachnospiraceae_bacterium_5_1_57FAA | Ruminococcus_bromii | Ruminococcus_bromii | Ruminococcus_bromii | Ruminococcus_bromii | Clostridium disporicum | Clostridium disporicum | Clostrid FIG. 11 (continued)

| Species | Clostridium bolteae | Clostridium bolteae | Clostridium bolteae | Clostridium bolteae |
|---|---|---|---|---|
| time (hr) | 20 | 96 | 20 | 96 |
| menadione (uM) | 0.16 | 0.16 | 0.05 | 0.05 |
| ferricyanide (mM) | 0.12 | 0.12 | 0.12 | 0.12 |
| L-Arabinose | + | + | + | + |
| N-Acetyl-D-Glucosamine | - | + | - | - |
| D-Saccharic Acid | - | - | - | - |
| Succinic Acid | - | - | - | - |
| D-Galactose | + | + | + | + |
| L-Aspartic Acid | - | - | - | - |
| L-Proline | - | - | - | - |
| D-Alanine | - | - | - | - |
| D-Trehalose | - | + | - | - |
| D-Mannose | + | + | - | + |
| Dulcitol | - | - | - | - |
| D-Serine | - | - | - | - |
| D-Sorbitol | - | - | - | - |
| Glycerol | - | - | - | - |
| L-Fucose | + | + | - | + |
| D-Glucuronic Acid | - | + | - | + |
| D-Gluconic Acid | - | + | - | - |
| D,L-alpha-Glycerol-Phosphate | - | + | - | + |
| D-Xylose | + | + | + | + |
| L-Lactic Acid | - | - | - | - |

FIG. 11 (continued)

| Species | Clostridium bolteae | Clostridium bolteae | Clostridium bolteae | Clostridium bolteae |
|---|---|---|---|---|
| Formic Acid | - | - | - | - |
| D-Mannitol | - | - | - | - |
| L-Glutamic Acid | - | - | - | - |
| D-Glucose-6-Phosphate | - | + | - | + |
| D-Galactonic Acid-gamma-Lactone | - | + | - | + |
| D,L-Malic Acid | - | - | - | - |
| D-Ribose | + | - | + | - |
| Tween 20 | - | - | - | - |
| L-Rhamnose | + | + | + | + |
| D-Fructose | - | + | - | + |
| Acetic Acid | - | - | - | - |
| alpha-D-Glucose | - | + | - | + |
| Maltose | - | - | - | - |
| D-Mellibiose | - | - | - | - |
| Thymidine | - | + | - | - |
| L-Asparagine | - | - | - | - |
| D-Aspartic Acid | - | - | - | - |
| D-Glucosaminic Acid | - | - | - | - |
| 1,2-Propanediol | - | - | - | - |
| Tween 40 | - | - | - | - |
| alpha-Keto-Glutaric Acid | - | - | - | - |
| alpha-Keto-Butyric Acid | - | - | - | - |
| alpha-Methyl-D-Galactoside | - | - | - | - |

FIG. 11 (continued)

| Species | Clostridium bolteae | Clostridium bolteae | Clostridium bolteae | Clostridium bolteae |
|---|---|---|---|---|
| alpha-D-Lactose | - | - | - | - |
| Lactulose | - | - | - | - |
| Sucrose | - | - | - | - |
| Uridine | - | + | - | - |
| L-Glutamine | - | - | - | - |
| M-Tartaric Acid | - | - | - | - |
| D-Glucose-1-Phosphate | - | - | - | - |
| D-Fructose-6-Phosphate | + | + | - | + |
| Tween 80 | - | - | - | - |
| alpha-Hydroxy-Glutaric-gamma-lactone | - | - | - | - |
| alpha-Hydroxy Butyric Acid | - | - | - | - |
| beta-Methyl-D-Glucoside | - | - | - | - |
| Adonitol | - | - | - | - |
| Maltotriose | - | - | - | - |
| 2-Deoxy Adenosine | - | - | - | - |
| Adenosine | - | + | - | - |
| Glycyl-L-Aspartic Acid | - | - | - | - |
| Citric Acid | - | - | - | - |
| M-Inositol | - | - | - | - |
| D-Threonine | - | - | - | - |
| Fumaric Acid | - | - | - | - |
| Bromo Succinic Acid | - | - | - | - |
| Propionic Acid | - | + | - | - |

FIG. 11 (continued)

| Species | Clostridium bolteae | Clostridium bolteae | Clostridium bolteae | Clostridium bolteae |
|---|---|---|---|---|
| Mucic Acid | - | - | - | - |
| Glycolic Acid | - | - | - | - |
| Glyoxylic Acid | - | - | - | + |
| D-Cellobiose | - | - | - | - |
| Inosine | - | + | - | - |
| Glycyl-L-Glutamic Acid | - | - | - | - |
| Tricarballylic Acid | - | - | - | - |
| L-Serine | - | - | - | - |
| L-Threonine | - | - | - | - |
| L-Alanine | - | - | - | - |
| L-Alanyl-Glycine | - | - | - | - |
| Acetoacetic Acid | - | - | - | + |
| N-Acetyl-beta-D-Mannosamine | - | - | - | - |
| Mono Methyl Succinate | - | - | - | - |
| Methyl Pyruvate | - | + | - | - |
| D-Malic Acid | - | - | - | - |
| L-Malic Acid | - | - | - | - |
| Glycyl-L-Proline | - | - | - | - |
| p-Hydroxy Phenyl Acetic Acid | - | - | - | - |
| m-Hydroxy Phenyl Acetic Acid | - | - | - | - |
| Tyramine | - | - | - | - |
| D-Psicose | + | + | + | + |
| L-Lyxose | + | + | + | + |

FIG. 11 (continued)

| Species | Clostridium boltae | Clostridium boltae

FIG. 11 (continued)

| Species | Clostridium bolteae | Clostridium bolteae | Clostridium bolteae | Clostridium bolteae |
|---|---|---|---|---|
| D-Arabitol | - | - | - | - |
| L-Arabitol | - | - | - | - |
| Arbutin | - | - | - | - |
| 2-Deoxy-D-Ribose | + | + | - | + |
| I-Erythritol | - | - | + | - |
| D-Fucose | - | + | - | + |
| 3-O-beta-D-Galacto-pyranosyl-D-Arabinose | - | - | - | + |
| Gentibiose | - | + | - | + |
| L-Glucose | - | + | - | + |
| Lactitol | - | - | - | - |
| D-Melezitose | - | - | - | - |
| Maltitol | - | - | - | - |
| alpha-Methyl-D-Glucoside | - | - | - | - |
| beta-Methyl-D-Galactoside | - | - | - | - |
| 3-Methyl Glucose | + | + | - | + |
| beta-Methyl-D-Glucoronic Acid | - | - | - | - |
| alpha-Methyl-D-Mannoside | - | - | - | - |
| beta-Metyl-D-Xyloside | - | - | - | - |
| Palatinose | + | + | + | + |
| D-Raffinose | - | - | - | - |
| Salicin | - | - | - | - |
| Sedoheptulosan | - | - | - | - |
| L-Sorbose | - | + | - | + |

FIG. 11 (continued)

| Species | Clostridium bolteae | Clostridium bolteae | Clostridium bolteae | Clostridium bolteae |
|---|---|---|---|---|
| Stachyose | - | - | - | - |
| D-Tagatose | + | + | + | + |
| Turanose | - | + | - | + |
| Xylitol | - | - | - | - |
| N-Acetyl-D-Glucosaminitol | - | - | - | - |
| gamma-Amino Butyric Acid | - | - | - | - |
| delta-Amino Valeric Acid | - | - | - | - |
| Butyric Acid | - | - | - | + |
| Capric Acid | - | - | - | - |
| Caproic Acid | - | - | - | - |
| Citraconic Acid | - | - | - | - |
| Citramalic Acid | - | - | - | - |
| D-Glucosamine | + | + | + | + |
| 2-Hydroxy Benzoic Acid | - | - | - | - |
| 4-Hydroxy Benzoic Acid | - | - | - | - |
| beta-Hydroxy Butyric Acid | - | - | - | - |
| gamma-Hydroxy Butyric Acid | - | + | - | + |
| alpha-Keto Valeric Acid | - | - | - | - |
| Itaconic Acid | + | + | + | + |
| 5-Keto-D-Gluconic Acid | - | - | - | - |
| D-Lactic Acid Methyl Ester | - | - | - | - |
| Malonic Acid | - | - | - | - |
| Melibionic Acid | - | - | - | - |

FIG. 11 (continued)

| Species | Clostridium bolteae | Clostridium bolteae | Clostridium bolteae | Clostridium bolteae |
|---|---|---|---|---|
| Oxalic Acid | - | - | - | - |
| Oxalomalic Acid | - | + | - | + |
| Quinic Acid | - | - | - | - |
| D-Ribino-1,4-Lacton | - | - | - | - |
| Sebacic Acid | - | - | - | - |
| Sorbic Acid | - | + | - | + |
| Succinamic Acid | - | - | - | - |
| D-Tartaric Acid | - | - | - | - |
| L-Tartaric Acid | - | - | - | - |
| Acetamide | - | - | - | - |
| L-Alaninamide | - | - | - | - |
| N-Acetyl-L-Glutamic Acid | - | - | - | - |
| L-Arginine | - | - | - | - |
| Glycine | - | - | - | - |
| L-Histidine | - | - | - | - |
| L-Homserine | - | - | - | - |
| Hydroxy-L-Proline | - | - | - | - |
| L-Isoleucine | - | - | - | - |
| L-Leucine | - | - | - | - |
| L-Lysine | - | - | - | - |
| L-Methionine | - | - | - | - |
| L-Ornithine | - | - | - | - |
| L-Phenylalanine | - | - | - | - |

FIG. 11 (continued)

| | Clostridium boteae | Clostridium boteae | Clostridium boteae | Clostridium boteae |
|---|---|---|---|---|
| Species | | | | |
| L-Pyroglutamic

COMPOSITIONS AND METHODS FOR INHIBITION OF PATHOGENIC BACTERIAL GROWTH

RELATED APPLICATIONS

This application is the National Stage of International Application No. PCT/US14/14744, filed Feb. 4, 2014, which claims priority to U.S. Provisional Application No. 61/760,584, filed Feb. 4, 2013 and U.S. Provisional Application No. 61/760,585, filed Feb. 4, 2013 and U.S. Provisional Application No. 61/760,574, filed Feb. 4, 2013 and U.S. Provisional Application No. 61/760,606, filed Feb. 4, 2013 and U.S. Provisional Application No. 61/926,918, filed Jan. 13, 2014. These applications are all incorporated by reference in their entirety for all purposes.

REFERENCE TO A SEQUENCE LISTING

This application includes a Sequence Listing submitted electronically as a text file named 25969US_CRF_sequencelisting.txt, created on Oct. 15, 2015, with a size of 4,165,632 bytes. The sequence listing is incorporated by reference.

BACKGROUND

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population by about 3 years of age. Interactions between microbial strains in these populations and between microbes and the host, e.g. the host immune system, shape the community structure, with availability of and competition for resources affecting the distribution of microbes. Such resources may be food, location and the availability of space to grow or a physical structure to which the microbe may attach. For example, host diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections of the gut. For instance, subjects become more susceptible to pathogenic infections when the normal intestinal microbiota has been disturbed due to use of broad-spectrum antibiotics. Many of these diseases and disorders are chronic conditions that significantly decrease a subject's quality of life and can be ultimately fatal.

Manufacturers of probiotics have asserted that their preparations of bacteria promote mammalian health by preserving the natural microflora in the GI tract and reinforcing the normal controls on aberrant immune responses. See, e.g., U.S. Pat. No. 8,034,601. Probiotics, however, have been limited to a very narrow group of genera and a correspondingly limited number of species; as such, they do not adequately replace the missing natural microflora nor correct dysbioses of the GI tract in many situations. Additionally, such probiotics are insufficient to prevent, reduce or treat a pathogenic bacterial infection of the gastrointestinal tract, such as by *Clostridium difficile*, by reducing the population of the gastrointestinal tract by the pathogenic bacteria.

Thus practitioners have a need for methods and compositions for preventing or treating pathogenic bacterial infections. We have designed bacterial compositions of isolated bacterial strains with a plurality of beneficial properties, including the ability to metabolize nutrients at rates above and at concentrations below those of pathogenic bacteria, based on our understanding of those bacterial strains and our analysis of the properties that enhance the utility and commercialization of a microbial composition.

Therefore, in response to the need for durable, efficient, and effective compositions and methods for prevention, diagnosis and/or treatment of gastrointestinal diseases by way of restoring or enhancing microbiota functions, we address these and other shortcomings of the prior art by providing compositions and methods for treating subjects.

SUMMARY OF THE INVENTION

The present invention demonstrates effective compositions for and methods of preventing or reducing pathogenic bacterial growth, proliferation, and/or colonization, whereby bacterial compositions that contain one or more types of non-pathogenic bacteria are introduced into the gastrointestinal tract and effectively compete with pathogenic bacteria for monomeric or polymeric carbohydrate nutrients, and/or amino acid nutrients, and/or vitamin nutrients. Alternatively, organisms may prevent disease by metabolizing available germinants utilized by the pathogenic bacteria and prevent pathogenic spore germination. Alternatively, competition for overlapping nutrients among two or more types of non-pathogenic bacteria that are introduced into the gastrointestinal tract may leads to secretion of molecules inhibitory to a pathogen and/or pathobiont by one or multiple of the types of introduced non-pathogenic bacteria. In certain instances, the inhibitory compound may be a toxin, antibiotic, or a bacterocin (see Chiuchiolo et al. Growth-phase-dependent expression of the cyclopeptide antibiotic microcin J25 J Bacteriol. 2001 March; 183(5):1755-64).

BRIEF DESCRIPTION OF THE DRAWINGS

FIG. 1 illustrates variable regions mapped onto the 16s sequence (FIG. 1A) and annotated 16s sequence (SEQ ID NO: 2043) (FIG. 1B) with bolded variable regions according to an embodiment of the Invention.

FIG. 6 illustrates a linear range of DPA assay compared to CFU counts/ml.

FIG. 11 illustrates the results of a nutrient utilization assay with *Clostridium difficile* and potential competitors of the pathogen. Plus (+) indicates that it is a nutrient for the isolate tested. Minus (−) Indicates that it is not a nutrient for the isolate tested.

Figure 2:
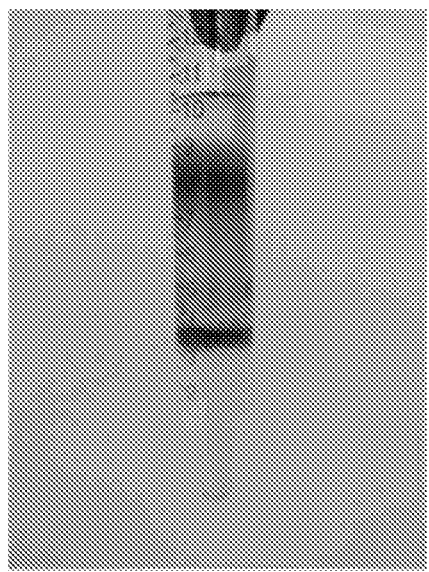
FIG. 2 is a photograph of a CsCl gradient demonstrating spore separation from other material.

The figures depict various embodiments of the present Invention for purposes of illustration only. One skilled in the art will readily recognize from the following discussion that alternative embodiments of the structures and methods illustrated herein may be employed without departing from the principles of the invention described herein.

DETAILED DESCRIPTION

Definitions

"Microbiota" refers to the community of microorganisms that occur (sustainably or transiently) in and on an animal subject, typically a mammal such as a human, including eukaryotes, archaea, bacteria, and viruses (including bacterial viruses i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

"Microbial Carriage" or simply "Carriage" refers to the population of microbes inhabiting a niche within or on humans. Carriage is often defined in terms of relative abundance. For example, OTU1 comprises 60% of the total microbial carriage, meaning that OTU1 has a relative abundance of 60% compared to the other OTUs in the sample from which the measurement was made. Carriage is most often based on genomic sequencing data where the relative abundance or carriage of a single OTU or group of OTUs is defined by the number of sequencing reads that are assigned to that OTU/s relative to the total number of sequencing reads for the sample.

"Microbial Augmentation" or simply "augmentation" refers to the establishment or significant increase of a population of microbes that are (i) absent or undetectable (as determined by the use of standard genomic and microbiological techniques) from the administered therapeutic microbial composition, (ii) absent, undetectable, or present at low frequencies in the host niche (as example: gastrointestinal tract, skin, anterior-nares, or vagina) before the delivery of the microbial composition, and (iii) are found after the administration of the microbial composition or significantly increase, for instance 2-fold, 5-fold, $1\times10^2$, $1\times10^3$, $1\times10^4$, $1\times10^5$, $1\times10^6$, $1\times10^7$, or greater than $1\times10^8$, in cases where they were present at low frequencies. The microbes that comprise an augmented ecology can be derived from exogenous sources such as food and the environment, or grow out from micro-niches within the host where they reside at low frequency.

The administration of the therapeutic microbial composition induces an environmental shift in the target niche that promotes favorable conditions for the growth of these commensal microbes. In the absence of treatment with a therapeutic microbial composition, the host can be constantly exposed to these microbes; however, sustained growth and the positive health effects associated with the stable population of increased levels of the microbes comprising the augmented ecology are not observed.

"Microbial Engraftment" or simply "engraftment" refers to the establishment of OTUs comprising a therapeutic microbial composition in a target niche that are absent in the treated host prior to treatment. The microbes that comprise the engrafted ecology are found in the therapeutic microbial composition and establish as constituents of the host microbial ecology upon treatment. Engrafted OTUs can establish for a transient period of time, or demonstrate long-term stability in the microbial ecology that populates the host post treatment with a therapeutic microbial composition. The engrafted ecology can induce an environmental shift in the target niche that promotes favorable conditions for the growth of commensal microbes capable of catalyzing a shift from a dysbiotic ecology to one representative of a health state.

"Ecological Niche" or simply "Niche" refers to the ecological space in which a an organism or group of organisms occupies. Niche describes how an organism or population or organisms responds to the distribution of resources, physical parameters (e.g., host tissue space) and competitors (e.g., by growing when resources are abundant, and when predators, parasites and pathogens are scarce) and how it in turn alters those same factors (e.g., limiting access to resources by other organisms, acting as a food source for predators and a consumer of prey).

"Dysbiosis" refers to a state of the microbiota or microbiome of the gut or other body area, including mucosal or skin surfaces in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a patient, or the shift to an ecological network that no longer provides a beneficial function to the host and therefore no longer promotes health.

The term "pathobiont" refer to specific bacterial species found in healthy hosts that may trigger immune-mediated pathology and/or disease in response to certain genetic or environmental factors. Chow et al., (2011) Curr Op Immunol. Pathobionts of the intestinal microbiota and inflammatory disease. 23: 473-80. Thus, a pathobiont is a pathogen that is mechanistically distinct from an acquired infectious organism. Thus, the term "pathogen" includes both acquired infectious organisms and pathobionts.

The terms "pathogen", "pathobiont" and "pathogenic" in reference to a bacterium or any other organism or entity includes any such organism or entity that is capable of causing or affecting a disease, disorder or condition of a host organism containing the organism or entity.

"Phylogenetic tree" refers to a graphical representation of the evolutionary relationships of one genetic sequence to another that is generated using a defined set of phylogenetic reconstruction algorithms (e.g. parsimony, maximum likelihood, or Bayesian). Nodes in the tree represent distinct ancestral sequences and the confidence of any node is provided by a bootstrap or Bayesian posterior probability, which measures branch uncertainty.

Operational taxonomic units," "OTU" (or plural, "OTUs") refer to a terminal leaf in a phylogenetic tree and Is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU (see e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940.). In embodiments involving the complete genome, MLSTs, specific genes, or sets of genes OTUs that share ≥95% average nucleotide identity are considered the same OTU (see e.g. Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940.). OTUs are frequently defined by comparing sequences between organisms. Generally, sequences with less than 95% sequence Identity are not considered to form part of the same OTU. OTUs may also be characterized by any combination of nucleotide markers or genes, in particular highly conserved genes (e.g., "housekeeping" genes), or a combination thereof. Such characterization employs, e.g., WGS data or a whole genome sequence.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses (i.e., phage)), fungal, mycoplasmal contaminants. In another embodiment, it means that fewer than $1\times10$-2%, $1\times10$-3%, $1\times10$-4%, $1\times10$-5%, $1\times10$-6%, $1\times10$-7%, $1\times10$-8 of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of 10-8 or 10-9), such as through multiple 10-fold serial dilutions. This can further be confirmed by showing that multiple isolated colonies have similar cell shapes and Gram staining behavior. Other methods for confirming adequate purity include genetic analysis (e.g. PCR, DNA sequencing), serology and antigen analysis, enzymatic and metabolic analysis, and methods using instrumentation such as flow cytometry with reagents that distinguish desired constituents from contaminants.

"Clade" refers to the OTUs or members of a phylogenetic tree that are downstream of a statistically valid node in a phylogenetic tree. The clade comprises a set of terminal leaves in the phylogenetic tree that is a distinct monophyletic evolutionary unit and that share some extent of sequence similarity.

In microbiology, "16S sequencing" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to a reference sequence and identifying the hypervariable regions based on similarity to the reference hypervariable regions, or alternatively, one can employ Whole Genome Shotgun (WGS) sequence characterization of microbes or a microbial community.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a gastrointestinal pathogen or may be at risk of developing or transmitting to others an infection due to a gastrointestinal pathogen.

The term "phenotype" refers to a set of observable characteristics of an individual entity. As example an Individual subject may have a phenotype of "health" or "disease". Phenotypes describe the state of an entity and all entities within a phenotype share the same set of characteristics that describe the phenotype. The phenotype of an Individual results in part, or in whole, from the interaction of the entities genome and/or microbiome with the environment.

The term "Network Ecology" refers to a consortium of OTUs that co-occur in some number of subjects. As used herein, a "network" is defined mathematically by a graph delineating how specific nodes (i.e. OTUs) and edges (connections between specific OTUs) relate to one another to define the structural ecology of a consortium of OTUs. Any given Network Ecology will possess inherent phylogenetic diversity and functional properties. A Network Ecology can also be defined in terms of function where for example the nodes would be comprised of elements such as, but not limited to, enzymes, clusters of orthologous groups (COGS; http://www.ncbi.nlm.nih.govlbooks/NBK21090/), or KEGG pathways (www.genome.jp/kegg/).

The terms "Network Class", "Core Network" and "Core Network Ecology" refer to a group of network ecologies that in general are computationally determined to comprise ecologies with similar phylogenetic and/or functional characteristics. A Core Network therefore contains important biological features, defined either phylogenetically or functionally, of a group (i.e., a cluster) of related network ecologies. One representation of a Core Network Ecology is a designed consortium of microbes, typically non-pathogenic bacteria, that represents core features of a set of phylogenetically or functionally related network ecologies seen in many different subjects. In many occurrences, a Core Network, while designed as described herein, exists as a Network Ecology observed in one or more subjects. Core Network ecologies are useful for reversing or reducing a dysbiosis in subjects where the underlying, related Network Ecology has been disrupted.

The term "Keystone OTU" refers to one or more OTUs that are common to many network ecologies and are members of networks ecologies that occur in many subjects (i.e. are pervasive). Due to the ubiquitous nature of Keystone OTUs, they are central to the function of network ecologies in healthy subjects and are often missing or at reduced levels in subjects with disease. Keystone OTUs may exist in low, moderate, or high abundance in subjects.

The term "non-Keystone OTU" refers to an OTU that is observed in a Network Ecology and is not a keystone OTU.

The term "Phylogenetic Diversity" refers to the biodiversity present in a given Network Ecology or Core Network Ecology based on the OTUs that comprise the network. Phylogenetic diversity is a relative term, meaning that a Network Ecology or Core Network that is comparatively more phylogenetically diverse than another network contains a greater number of unique species, genera, and taxonomic families. Uniqueness of a species, genera, or taxonomic family is generally defined using a phylogenetic tree that represents the genetic diversity all species, genera, or taxonomic families relative to one another. In another embodiment phylogenetic diversity may be measured using the total branch length or average branch length of a phylogenetic tree.

A "spore" or a population of "spores" includes bacteria (or other single-celled organisms) that are generally viable, more resistant to environmental influences such as heat and bacteriocidal agents than vegetative forms of the same bacteria, and typically capable of germination and outgrowth. "Spore-formers" or bacteria "capable of forming spores" are those bacteria containing the genes and other necessary abilities to produce spores under suitable environmental conditions.

A "spore population" refers to a plurality of spores present in a composition. Synonymous terms used herein include spore composition, spore preparation, ethanol treated spore fraction and spore ecology. A spore population may be purified from a fecal donation, e.g. via ethanol or heat treatment, or a density gradient separation or any combination of methods described herein to increase the purity, potency and/or concentration of spores in a sample. Alternatively, a spore population may be derived through culture methods starting from isolated spore former species or spore former OTUs or from a mixture of such species, either in vegetative or spore form.

In one embodiment, the spore preparation comprises spore forming species wherein residual non-spore forming species have been Inactivated by chemical or physical treatments including ethanol, detergent, heat, sonication, and the like; or wherein the non-spore forming species have been removed from the spore preparation by various separations steps including density gradients, centrifugation, filtration and/or chromatography; or wherein inactivation and separation methods are combined to make the spore preparation. In yet another embodiment, the spore preparation comprises spore forming species that are enriched over viable non-spore formers or vegetative forms of spore formers. In this embodiment, spores are enriched by 2-fold, 5-fold, 10-fold, 50-fold, 100-fold, 1000-fold, 10,000-fold or greater than 10,000-fold compared to all vegetative forms of bacteria. In yet another embodiment, the spores in the spore preparation undergo partial germination during processing and formulation such that the final composition comprises spores and vegetative bacteria derived from spore forming species.

The term "isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria include those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, or by passage through culture, and a purified bacterium or bacterial population may contain other materials up to about 10%, about 20%, about 30%, about 40%, about 50%, about 60%, about 70%, about 80%, about 90%, or above about 90% and still be considered "Isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

"Inhibition" of a pathogen encompasses the inhibition of any desired function or activity of the bacterial compositions of the present invention. Demonstrations of pathogen inhibition, such as decrease in the growth of a pathogenic bacterium or reduction in the level of colonization of a pathogenic bacterium are provided herein and otherwise recognized by one of ordinary skill in the art. Inhibition of a pathogenic bacterium's "growth" may include inhibiting the increase in size of the pathogenic bacterium and/or inhibiting the proliferation (or multiplication) of the pathogenic bacterium. Inhibition of colonization of a pathogenic bacterium may be demonstrated by measuring the amount or burden of a pathogen before and after a treatment. An "inhibition" or the act of "inhibiting" includes the total cessation and partial reduction of one or more activities of a pathogen, such as growth, proliferation, colonization, and function.

A "germinant" is a material or composition or physical-chemical process capable of inducing vegetative growth of a bacterium that is in a dormant spore form, or group of bacteria in the spore form, either directly or indirectly in a host organism and/or in vitro.

A "sporulation induction agent" is a material or physical-chemical process that is capable of inducing sporulation in a bacterium, either directly or indirectly, in a host organism and/or in vitro.

To "increase production of bacterial spores" includes an activity or a sporulation induction agent. "Production" includes conversion of vegetative bacterial cells into spores and augmentation of the rate of such conversion, as well as decreasing the germination of bacteria in spore form, decreasing the rate of spore decay in vivo, or ex vivo, or to increasing the total output of spores (e.g. via an increase in volumetric output of fecal material).

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

A "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin In vitamin supplements), vitamin C, vitamin D, vitamin E, vitamin K, K1 and K2 (i.e. MK-4, MK-7), folic acid and biotin) essential in minute amounts for normal growth and activity of the body and obtained naturally from plant and animal foods or synthetically made, pro-vitamins, derivatives, analogs.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

"Fermentation products" are compounds that are produced by bacteria or bacterial populations through carbohydrate metabolic processes. These metabolites include but are not limited to lactate, butyrate, acetate, ethanol, succinate, formate.

A substance that organisms use to live and grow. In this context, it includes but is not limited to vitamins, minerals, antioxidant, fermentation products, cofactors, proteins, amino acids, nucleotides, nucleic acids, lipids, carbohydrates and metabolic products of these molecules.

Compositions of the Invention

Bacterial Compostions

Provided are bacteria and combinations of bacteria of the human gut microbiota with the capacity to meaningfully provide functions of a healthy microbiota when administered to mammalian hosts. Without being limited to a specific mechanism, it is thought that such compositions inhibit the growth, proliferation, germination, and/or colonization of one or a plurality of pathogenic bacteria in the dysbiotic microbiotal niche, so that a healthy, diverse and protective microbiota colonizes and populates the intestinal lumen to establish or reestablish ecological control over pathogens or potential pathogens (e.g., some bacteria are pathogenic bacteria only when present In a dysbiotic environment). Inhibition of pathogens includes those pathogens such as *C. difficile, Salmonella* spp., enteropathogenic *E coli*, multi-drug resistant bacteria such as *Klebsiella*, and *E. coli*, Carbapenem-resistant Enterobacteriaceae (CRE), extended spectrum beta-lactam resistant Enterococci (ESBL), and vancomycin-resistant Enterococci (VRE).

As used herein, a "type" or more than one "types" of bacteria may be differentiated at the genus level, the species, level, the sub-species level, the strain level or by any other taxonomic method, as described herein and otherwise known in the art.

The present invention demonstrates effective methods of preventing or reducing pathogenic bacterial growth, proliferation, and/or colonization, whereby bacterial compositions that contain one or more types of non-pathogenic bacteria are introduced into the gastrointestinal tract and effectively compete with pathogenic bacteria for monomeric or polymeric carbohydrate nutrients, and/or amino acid nutrients, and/or vitamin nutrients. Alternatively, organisms may prevent disease by metabolizing available germinants utilized by the pathogenic bacteria and prevent pathogenic spore germination. Alternatively, competition for overlapping nutrients among two or more types of non-pathogenic bacteria that are introduced into the gastrointestinal tract may leads to secretion of molecules inhibitory to a pathogen and/or pathobiont by one or multiple of the types of introduced non-pathogenic bacteria. In certain instances, the inhibitory compound may be a toxin, antibiotic, or a bacterocin (see Chiuchiolo et al. Growth-phase-dependent expression of the cyclopeptide antibiotic microcin J25 J Bacteriol. 2001 March; 183(5):1755-64).

In one instance, the enteric bacterium *Clostridium difficile* (*C. difficile*) is an opportunistic pathogen whose infection frequently follows antibiotic treatment. Numerous investigations in animal models as well as clinical observations have demonstrated that the normal gut microbiota is capable of exerting ecological control over *C. difficile* that prevents it from colonizing the gut, and that this control is often perturbed following antibiotic treatment. One notable effect of antibiotic treatment is to change in the composition and availability nutrients in the gastrointestinal tract as a result of altering the gut microbiota. For instance, treatment of SPF mice with streptomycin leads to a transient 40-fold increase in sialic acid one day after antibiotic exposure, which declines by day three, a timeframe consistent with susceptibility to *C. difficile* infection [Ng K M, et al *Nature* (2013) 502: 96-9]. *C. difficile* is known to metabolize sialic acids such as N-acetyl-neuraminic acid, which is enzymatically released from mucin by commensal microbes along the intestinal epithelium. One experimental means of re-establishing control in animals has been to transplant the normal fecal flora of a healthy animal via an enteral route [for example, Wilson, K. H., J Silva, and FR Fekety (1981) Suppression of *Clostridium difficile* by normal hamster cecal flora and prevention of antibiotic-associated colitis. *Infect. Immun.* 34 (2): 626-8.] In humans, fecal microbiota transplantation (FMT) has shown similar beneficial results [for example, Shahinas, D, et al (2012) Toward an understanding of changes in diversity associated with fecal microbiome transplantation based on 16s rRNA gene deep sequencing. mBio 3].

In order to maintain steady-state concentrations in the gastrointestinal tract of a mammalian subject (where continuous dilution occurs as a result of the peristaltic wave), *C. difficile* is dependent upon the availability of a small number of nutrients, particularly carbohydrates such as glucose, mannitol, fructose, N-acetylglucosamine (NAG) and N-acetylneuraminic acid (NAN), amino acids, and vitamins such as biotin, pantothenate and pyridoxine. Free monosaccharide levels of NAG and NAN are low in the mammalian gastrointestinal tract; instead, NAG and NAN are present in higher order carbohydrate polymers such as mucins and inulin.

In one embodiment of the present invention, the bacterial compositions containing one or more types of non-pathogenic bacteria are introduced into the gastrointestinal tract to prevent or treat infection by utilizing the nutrients and/or metabolizing the germinants utilized by *C. difficile*. In some embodiments, the latter will be achieved when the introduced bacterial composition depletes one or more of the nutrients (e.g., carbohydrate or vitamin) utilized by *C. difficile* to a concentration that inhibits further growth of *C. difficile* or alternatively, reduces the rate of growth such that the introduced bacteria and/or other resident bacteria outcompete *C. difficile*.

In a first aspect, provided are compositions comprising an effective amount of a first type of bacteria and a second type of bacteria that overlap with *C. difficile* nutrition utilization, and/or are independently capable of proliferating in a nutrient medium having a threshold concentration of a nutrient below that concentration required for *Clostridium difficile* proliferation. In certain embodiments the first and second type of bacteria are Isolated, such as from the gastrointestinal tract of a healthy mammal, and are not identical to each other.

Exemplary nutrients include carbohydrates, amino acids, vitamins, minerals, and cofactors such as germinants. Exemplary minerals include iron, phosphate, copper, nickel, and magnesium. Additional nutrients include nitrogen sources, such as ammonia or urea. Table XXX5 contains representative nitrogen sources.

Exemplary fermentation products include lactate, butyrate, acetate, ethanol, succinate, and formate. Exemplary carbohydrate nutrients include glucose, mannitol, fructose, N-acetylglucosamine (NAG) and N-acetyineuraminic acid (NAN). The bacterial compositions contain bacteria that overlap with *C. difficile* nutrition utilization and/or and are Independently capable of proliferating in a nutrient medium having a threshold concentration of at least one of the following: glucose, mannitol, fructose, NAG and NAN below that concentration required for *Clostridium difficile* proliferation. In certain embodiments, the bacterial compositions include bacteria that are independently capable of proliferating in a nutrient medium having a threshold concentration of each of glucose, mannitol, fructose, NAG and NAN below the concentrations required for *Clostridium difficile* proliferation. The threshold concentration may be about 90%, about 80%, about 70%, about 60%, about 50%, about 40%, about 30%, about 20%, about 10% or less than about 10% of the concentration of that nutrient required for *Clostridium difficile* proliferation. In other embodiments, the bacterial compositions contain bacteria that can proliferate faster than *C. difficile* at a given nutrient concentration, effectively out-competing the *C. difficile* for a limited resource. For example, in a composition having two or more types of bacteria, these two types are independently capable of proliferating at a rate at least about 10%, 20%, 30%, 40%, 50%, 60%, 70%, 80%, 90%, 100%, 200%, 300%, or more than 300% greater than the proliferation rate of *Clostridium difficile* in a nutrient medium having a concentration of a nutrient such as glucose, mannitol, fructose, NAG and NAN, or a combination thereof. Alternatively, a composition is provided having two or more types of bacteria that are capable of growing to a maximal bacterial concentration in excess of the maximal bacterial concentration capable by *C. difficile*, as determined, e.g., by turbidity, colony counts, total biomass, or other means described herein or otherwise known in the art. In yet another embodiment, the bacterial composition is delivered at an efficacious dose such that the population of bacteria in the composition deplete glucose, mannitol, fructose, NAG and NAN and other carbohydrates necessary for *C. difficile* growth.

Exemplary vitamin nutrients include biotin, pantothenate, folic acid and pyridoxine. Table XXX1 contains representative vitamins, minerals, and cofactors. Without being limited to any particular mechanism, the bacteria present in the therapeutic composition are better able to transport one or more vitamins from the medium into the bacterial cell, or they are more efficient at utilizing the vitamin(s) once it is inside the cell.

The bacterial compositions comprise bacteria that overlap with *C. difficile* nutrition utilization requirements and/or are independently capable of proliferating in a nutrient medium having a threshold concentration of at least one of biotin, pantothenate and pyridoxine below that concentration required for *Clostridium difficile* proliferation. In certain embodiments, the bacterial compositions contain bacteria that are independently capable of proliferating in a nutrient medium having a threshold concentration of each of biotin, pantothenate and pyridoxine below the concentrations required for *Clostridium difficile* proliferation. The threshold concentration may be about 90%, about 80%, about 70%, about 60%, about 50%, about 40%, about 30%, about 20%, about 10% or less than about 10% of the concentration of that nutrient required for *Clostridium difficile* proliferation. In other embodiments, the bacterial compositions contain bacteria that can proliferate faster than *C. difficile* at a given nutrient concentration, effectively out-competing the *C. difficile* for a limited resource. For example, in a composition comprising two or more types of bacteria, these two types are independently capable of proliferating at a rate at least about 10%, 20%, 30%, 40%, 50%, 60%, 70%, 80%, 90%, 100%, 200%, 300%, or more than 300% greater than the proliferation rate of *Clostridium difficile* in a nutrient medium having a concentration of a nutrient such as biotin, pantothenate, pyridoxine, or a combination thereof. Alternatively, a composition is provided comprising two or more types of bacteria that are capable of growing to a maximal bacterial concentration in excess of the maximal bacterial concentration capable by *C. difficile*, as determined, e.g., by turbidity, colony counts, total biomass, or other means described herein or otherwise known in the art. In yet another embodiment, the bacterial composition is delivered at an efficacious dose such that the population of bacteria in the composition deplete biotin, pantothenate and pyridoxine and other vitamins necessary for *C. difficile* growth.

In another aspect, provided are compositions comprising effective amounts of one or more types of bacteria that compete with *C. difficile* for nutrients, e.g., polymeric carbohydrates, glycosylated proteins and/or vitamins. In a further aspect, provided are compositions comprising effective amounts of one or more types of bacteria that have rates of saccharification and consumption of the resulting products that exceed other bacterial species in the gastrointestinal tract. These compositions effectively eliminate polymeric carbohydrates from the local gastrointestinal environment, which would otherwise be hydrolyzed by resident bacterial species resulting in free glucose, NAG and/or NAN. Thus provided are bacterial compositions comprising first and second types of bacteria that are independently capable of saccharification at a rate at least 10% greater than *Clostridium difficile*. Also provided are bacterial compositions comprising first and second types of bacteria that are independently capable of saccharification at a rate at least about 10%, 20%, 30%, 40%, 50%, 60%, 70%, 80%, 90%, 100%, 200%, 300%, or more than 300% greater than any other bacterial species in the local environment that digests polymeric carbohydrates and releases the hydrolysis products into the media for consumption by, e.g., *Clostridium difficile*. Suitable carbohydrate polymers to target for selective digestion include a fructan, an arabinoxylan, a lactulose, and a galactooligosaccharide or a glycosylated protein such as a mucin.

Also provided are bacterial compositions comprising bacterial types capable of efficient saccharification of complex carbohydrates and metabolism of simple sugars. For example, provided is a composition comprising an effective amount of a first type of bacteria and a second type of bacteria formulated for oral administration to a mammalian subject, wherein the first type of bacteria is: (i) isolated, (ii) not identical to the second type of bacteria, and (iii) independently capable of saccharification at a rate at least 10% greater than *Clostridium difficile*, and wherein the second type of bacteria is: (i) isolated, (ii) not identical to the first type of bacteria, and (iii) independently capable of glycolysis of a nutrient selected from the group consisting of glucose, mannitol, fructose, NAG and NAN, at a rate at least 10% greater than *Clostridium difficile* or at a concentration at least 10% less than *Clostridium difficile*, or the combination thereof. In addition, provided is a composition comprising an effective amount of a first type of bacteria and a second type of bacteria formulated for oral administration to a mammalian subject, wherein the first type of bacteria is: (i) isolated, (ii) not identical to the second type of bacteria, and (iii) independently capable of saccharification of a necessary *C. difficile* nutrient, and wherein the second type of bacteria is: (i) isolated, (ii) not identical to the first type of bacteria, and (iii) independently capable of glycolysis of a nutrient selected from the group consisting of glucose, mannitol, fructose, NAG and NAN; and wherein the delivered bacteria effectively metabolize for nutrients to levels below that which is required for *C. difficile* growth.

Also provided are methods for the treatment of *Clostridium difficile* infection in a mammalian subject, by orally administering to the subject a composition comprising an effective amount of a first type of bacteria and a second type of bacteria formulated for oral administration to a mammalian subject, where the first type of bacteria is: (i) isolated, (ii) not identical to the second type of bacteria, and (iii) independently capable of saccharification at a rate at least 10% greater than *Clostridium difficile*, and where the second type of bacteria is: (I) isolated, (ii) not identical to the first type of bacteria, and (iii) independently capable of glycolysis of a nutrient selected from the group consisting of glucose, mannitol, fructose, N-acetylglucosamine (NAG) and N-acetyineuramic acid (NAN), at a rate at least 10% greater than *Clostridium difficile* or at a concentration at least 10% less than *Clostridium difficile*, or the combination thereof, under conditions such that the first type of bacteria and the second type of bacteria functionally populate the gastrointestinal tract of the subject and prevent the population of the gastrointestinal tract by *Clostridium difficile*.

Microbial, e.g., bacterial compositions may comprise two types of bacteria (termed "binary combinations" or "binary pairs") or greater than two types of bacteria. For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 2930, 31, 32, 33, 34, 35, 36, 37, 38, 39, or at least 40, at least 50 or greater than 50 types of bacteria, as defined by species or operational taxonomic unit (OTU), or otherwise as provided herein.

In another embodiment, the number of types of bacteria present in a bacterial composition is at or below a known value. For example, in such embodiments the bacterial composition comprises 50 or fewer types of bacteria, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of bacteria, 8 or fewer types of bacteria, 7 or fewer types of bacteria, 6 or fewer types of bacteria, 5 or fewer types of bacteria, 4 or fewer types of bacteria, or 3 or fewer types of bacteria. In another embodiment, a bacterial composition comprises from 2 to no more than 40, from 2 to no more than 30, from 2 to no more than 20, from 2 to no more than 15, from 2 to no more than 10, or from 2 to no more than 5 types of bacteria.

Bacterial Compositions Described by Species

Bacterial compositions may be prepared comprising at least two types of isolated bacteria, chosen from the species in Table 1.

In one embodiment, the microbial, e.g., bacterial composition comprises at least one and preferably more than one of the following: *Enterococcus faecalis* (previously known as *Streptococcus faecalis*), *Clostridium innocuum*, *Clostridium ramosum*, *Bacteroides ovatus*, *Bacteroides vulgatus*, *Bacteroides thetaoiotaomicron*, *Escherichia coli* (1109 and 1108-1), *Clostridium bifermentans*, and *Blautda producta* (previously known as *Peptostreptococcus productus*). In an alternative embodiment, at least one of the preceding species is not substantially present in the bacterial composition.

In one embodiment, the bacterial composition comprises at least one and preferably more than one of the following: *Enterococcus faecalis* (previously known as *Streptococcus faecalis*), *Clostridium Innocuum*, *Clostridium ramosum*, *Bacteroides ovatus*, *Bacteroides vulgatus*, *Bacteroides thetaoiotaomicron*, *Escherichia coli* (1109 and 1108-1), *Clostridium bifermentans*, and *Blautia producta* (previously known as *Peptostreptococcus productus*). In an alternative embodiment, at least one of the preceding species is not substantially present in the bacterial composition.

In another embodiment, the bacterial composition comprises at least one and preferably more than one of the following: *Acidaminococcus intestinalis, Bacteroides ovatus*, two strains of *Bifidobacterium adolescentis*, two strains of *Bifidobacterium longum, Blautia producta, Clostridium cocleatum, Collinsella aerofaciens*, two strains of *Dorea longicatena, Escherichia coli, Eubacterium desmolans, Eubacterium eligens, Eubacterium limosum*, four strains of *Eubacterium rectale, Eubacterium ventriosumi, Faecalibacterum prausnitzli, Lachnospira pectinoshiza, Lactobacillus casei, Lactobacillus casei/paracasei, Paracateroides distasonis, Raoultella sp.*, one strain of *Roseburia* (chosen from *Roseburia faecalis* or *Rosebura faecis*), *Roseburia Intestinalis*, two strains of *Ruminococcus torques*, two strains of *Ruminococcus obeum*, and *Streptococcus mitis*. In an alternative embodiment, at least one of the preceding species is not substantially present in the bacterial composition.

In yet another embodiment, the bacterial composition comprises at least one and preferably more than one of the following: *Barnesiella intestinihominis; Lactobacillus reuter*; a species characterized as one of *Enterococcus hiras, Enterococus faecium*, or *Enterococcus durans*; a species characterized as one of *Anserostipes caccae* or *Clostridium indolis*; a species characterized as one of *Staphylococcus warneri* or *Staphylococcus pasteuri*; and *Adlercreutzia equolifaciens*. In an alternative embodiment, at least one of the preceding species is not substantially present in the bacterial composition.

In other embodiments, the bacterial composition comprises at least one and preferably more than one of the following: *Clostridium absonum, Clostridium argentinense, Clostridium baratii, Clostridium bartlettii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertlum, Clostridium tetani, Clostridium wechii*, and *Clostridium villosum*. In an alternative embodiment, at least one of the preceding species is not substantially present in the bacterial composition.

In one embodiment, the bacterial composition comprises at least one and preferably more than one of the following: *Clostridium Innocuum, Clostridium bifermentans, Clostridium butyricum, Bacteroides fragilis, Bacteroides thetaiotaomicron, Bacteroides uniformis*, three strains of *Escherichia coli*, and *Lactobacillus* sp. In an alternative embodiment, at least one of the preceding species is not substantially present in the bacterial composition.

In one embodiment, the bacterial composition comprises at least one and preferably more than one of the following: *Clostridium bifermentans, Clostridium innocuum, Clostridium butyricum*, three strains of *Escherichia coli*, three strains of *Bacteroides*, and *Blautia producta*. In an alternative embodiment, at least one of the preceding species is not substantially present in the bacterial composition.

In one embodiment, the bacterial composition comprises at least one and preferably more than one of the following: *Bacteroides* sp., *Escherichia coli*, and non pathogenic Clostridia, including *Clostridium Innocuum, Clostridium bifermentans* and *Clostridium ramosum*. In an alternative embodiment, at least one of the preceding species is not substantially present in the bacterial composition.

In one embodiment, the bacterial composition comprises at least one and preferably more than one of the following: *Bacteroides* species, *Escherichia coli* and non-pathogenic Clostridia, such as *Clostridium butyricum, Clostridium bifermentans* and *Clostridium innocuum*. In an alternative embodiment, at least one of the preceding species is not substantially present in the bacterial composition.

In one embodiment, the bacterial composition comprises at least one and preferably more than one of the following: *Bacteroides caccae, Bacteroides capillosus, Bacteroides coagulans, Bacteroides distasonis, Bacteroldes eggerthili, Bacteroides forsythus, Bacteroides fragilis, Bacteroides fragilis-ryhm, Bacteroides gracilis, Bacteroides levii, Bacteroides macacae, Bacteroides merdae, Bacteroides ovatus, Bacteroides pneumosintes, Bacteroides putredinis, Bacteroides pyogenes, Bacteroides splanchnicus, Bacteroides stercoris, Bacteroides tectum, Bacteroides thetalotaomicron, Bacteroldes uniformis, Bacteroides ureolyticus*, and *Bacteroides vulgatus*. In an alternative embodiment, at least one of the preceding species is not substantially present in the bacterial composition.

In one embodiment, the bacterial composition comprises at least one and preferably more than one of the following: *Bacteroides, Eubacteria, Fusobacteria, Propionibacteria, Lactobacilli, anaerobic cocci, Ruminococcus, Escherichia coli, Gemmiger, Desulfomonas*, and *Peptostreptococcus*. In an alternative embodiment, at least one of the preceding species is not substantially present in the bacterial composition.

In one embodiment, the bacterial composition comprises at least one and preferably more than one of the following: *Bacteroides fragilis* ss. *Vulgatus, Eubacterium aerofaciens, Bacteroides fragilis* ss. *Thetaiotaomicron, Blautia producta* (previously known as *Peptostreptococcus productus* II), *Bacteroides fragilis* ss. *Distasonis, Fusobacterum prausnitzii, Coprococcus eutactus, Eubacterium aerofaciens* III, *Blautia producta* (previously known as *Peptostreptococcus productus* I), *Ruminococcus bronii, Bifdobacteium adolescentis, Gemmiger formicilis, Bifidobacterium longum, Eubacterium siraeum, Ruminococcus torques, Eubacterium rectale* III-H, *Eubacterium rectale* IV, *Eubacterium eligens, Bacteroides eggerthii, Clostridium leptum, Bacteroides fragilis* ss. A, *Eubacterium biforme, Bifidobacterium infantis, Eubacterium rectale* III-F, *Coprococcus comes, Bacteroides capillosus, Ruminococcus albus, Eubacterium formicigenerans, Eubacterium hallii, Eubacterium ventriosum* I, *Fusobacterium russii, Ruminococcus obeum, Eubacterium rectale* II, *Clostridium ramosum* I, *Lactobacillus leichmanii, Ruminococcus cailidus, Butyrivibro crossotus, Acidaminococcus fermentans, Eubacterium ventriosum, Bacteroides fragilis* ss. *fragilis, Bacteroides* AR, *Coprococcus catus, Eubacterium hadrum, Eubacterium cylindroides, Eubacterium ruminantium, Eubacterium* CH-1, *Staphylococcus epidermidis, Peptostreptococcus* BL, *Eubacterium limosum, Bacteroides praeacutus, Bacteroides* L, *Fusobacterium mortiferum* I, *Fusobacterium naviforme, Clostridium innocuum, Clostidium ramosum, Propionibacterlum acnes, Ruminococcus lavefaciens, Ruminococcus* AT, *Peptococcus* AU-1, *Eubacterium* AG, -AK, -AL, -AL-1, -AN; *Bacteroides fragilis* ss. *ovatus*, -ss. d, -ss. f; *Bacteroides* L-1, L-5; *Fusobacterium nucleatum, Fusobacterium mortiferum, Escherichia coli, Streptococcus morbiliorum, Peptococcus magnus, Peptococcus* G, AU-2; *Streptococcus intermedius, Ruminococcus lactaris, Ruminococcus* CO *Gemmiger* X, *Coprococcus* BH, -CC; *Eubacterium tenue, Eubacterium ramulus, Eubacterium* AE, -AG-H, -AG-M, -AJ, -BN-1; *Bacteroides clostridiiformis* ss. *clostridliformis, Bacteroides coagulans, Bacteroides orails, Bacteroides ruminicola* ss. *brevis*, -ss. *ruminicola, Bacteroides splanchnicus, Desuifomonas pigr, Bacteroides* L-4, -N-i; *Fusobacterium* H, *Lactobacillus* G, and *Succinivibrio* A. In an alternative embodiment, at least one of the preceding species is not substantially present in the bacterial composition.

Bacterial Compostions Described by Operational Taxonomic Unit (OTUs)

Bacterial compositions may be prepared comprising at least two types of isolated bacteria, chosen from the species in Table 1.

In one embodiment, the OTUs can be characterized by one or more of the variable regions of the 16S sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Bacterial Compositions Exclusive of Certain Bacterial Species or Strains

In one embodiment, the bacterial composition does not comprise at least one of *Enterococcus faecalis* (previously known as *Streptococcus faecalis*), *Clostridium innocuum, Clostridium ramosum, Bacteroides ovatus, Bacteroides vulgatus, Bacteroides thetaoiotaomicron, Escherichia coli* (1109 and 1108-1), *Clostridium bifermentans*, and *Blautia producta* (previously known as *Peptostreptococcus* productus).

In another embodiment, the bacterial composition does not comprise at least one of *Acidaminococcus intestinalis, Bacteroides ovatus*, two species of *Bifidobacterium adolescentis*, two species of *Bifidobacterium longum, Collinsella aerofaciens*, two species of *Dorea longicatena, Escherichia coli, Eubacterium eligens, Eubacterium limosum*, four species of *Eubacterium rectale, Eubacterium ventriosumi, Faecalibacterium prausnitzli, Lactobacillus casei, Lactobacillus paracasei, Paracateroides distasonis, Raoultella* sp., one species of *Roseburia* (chosen from *Roseburia faecalis* or *Roseburia faecis*), *Roseburia intestinalis*, two species of *Ruminococcus torques*, and *Streptococcus mitis*.

In yet another embodiment, the bacterial composition does not comprise at least one of *Barnesiella intestinihominis; Lactobacillus reuteri*; a species characterized as one of *Enterococcus hirae, Enterococus faecium*, or *Enterococcus durans*; a species characterized as one of Anaerostipes caccae or *Clostridium indolis*; a species characterized as one of *Staphylococcus warneri* or *Staphylococcus pasteuri; and Adlercreutzia equolifaciens*.

In other embodiments, the bacterial composition does not comprise at least one of *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium pili-* forme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii, and Clostridium villosum.

In another embodiment, the bacterial composition does not comprise at least one of Clostridium Innocuum, Clostridium bifermentans, Clostridium butyricum, Bacteroides fragilis, Bacteroides thetaiotaomicron, Bacteroides uniformis, three strains of Escherichia coli, and Lactobacillus sp.

In another embodiment, the bacterial composition does not comprise at least one of Clostridium bifermentans, Clostridium innocuum, Clostridium butyricum, three strains of Escherichia coli, three strains of Bacteroides, and Blautia producta (previously known as Peptostreptococcus productus).

In another embodiment, the bacterial composition does not comprise at least one of Bacteroides sp., Escherichia coli, and non pathogenic Clostridia, including Clostridium innocuum, Clostridium bifermentans and Clostridium ramosum.

In another embodiment, the bacterial composition does not comprise at least one of more than one Bacteroides species, Escherichia coli and non-pathogenic Clostridia, such as Clostridium butyricum, Clostridium bifermentans and Clostridium innocuum.

In another embodiment, the bacterial composition does not comprise at least one of Bacteroides caccae, Bacteroides capillosus, Bacteroides coagulans, Bacteroides distasonis, Bacteroides eggerthii, Bacteroides forsythus, Bacteroides fragilis, Bacteroides fragilis-ryhm, Bacteroides gracilis, Bacteroides levii, Bacteroides macacae, Bacteroides merdae, Bacteroides ovatus, Bacteroides pneumosintes, Bacteroides putredinis, Bacteroides pyogenes, Bacteroides splanchnicus, Bacteroides stercoris, Bacteroides tectum, Bacteroides thetaiotaomicron, Bacteroides uniformis, Bacteroides ureolyticus, and Bacteroides vulgatus.

In another embodiment, the bacterial composition does not comprise at least one of Bacteroides, Eubacteria, Fusobacteria, Propionibacteria, Lactobacilli, anaerobic cocci, Ruminococcus, Escherichia coli, Gemmiger, Desulfomonas, and Peptostreptococcus.

In another embodiment, the bacterial composition does not comprise at least one of Bacteroides fragilis ss. Vulgatus, Eubacterium aerofaciens, Bacteroides fragilis ss. Thetalotaomicron, Blautia producta (previously known as Peptostreptococcus productus II), Bacteroides fragilis ss. Distasonis, Fusobacterium prausnitzil, Coprococcus eutactus, Eubacterium aerofaciens III, Blautia producta (previously known as Peptostreptococcus productus I), Ruminococcus bromii, Bifidobacterium adolescentis, Gemmiger formicilis, Bifidobacterium longum, Eubacterium siraeum, Ruminococcus torques, Eubacterium rectale III-H, Eubacterium rectale IV, Eubacterium eligens, Bacteroides eggerthii, Clostridium leptum, Bacteroides fragilis ss. A, Eubacterium biforme, Bifidobacterium infantis, Eubacterium rectale III-F, Coprococcus comes, Bacteroides capillosus, Ruminococcus albus, Eubacterium formicigenerans, Eubacterium hallii, Eubacterium ventriosum I, Fusobacterium russii, Ruminococcus obeum, Eubacterium rectale II, Clostridium ramosum I, Lactobacillus leichmanii, Ruminococcus cailidus, Butyrivibrio crossotus, Acidaminococcus fermentans, Eubacterium ventriosum I, Bacteroides fragilis ss. fragilis, Bacteroides AR, Coprococcus catus, Eubacterium hadrum, Eubacterium cylindroides, Eubacterium ruminantium, Eubacterium CH-1, Staphylococcus epidermidis, Peptostreptococcus BL, Eubacterium limosum, Bacteroides praeacutus, Bacteroides L, Fusobacterium mortiferum I, Fusobacterium naviforme, Clostridium innocuum, Clostridium ramosum, Propionibacterium acnes, Ruminococcus flavefaciens, Ruminococcus AT, Peptococcus AU-1, Eubacterium AG, -AK, -AL, -AL-1, -AN; Bacteroides fragilis ss. ovatus, -ss. d, -ss. f; Bacteroides L-1, L-5; Fusobacterium nucleatum, Fusobacterium mortiferum, Escherichia coli, Streptococcus morbiliorum, Peptococcus magnus, Peptococcus G, AU-2; Streptococcus intermedius, Ruminococcus lactaris, Ruminococcus CO Gemmiger X, Coprococcus BH, -CC; Eubacterium tenue, Eubacterium ramulus, Eubacterium AE, -AG-H, -AG-M, -AJ, -BN-1; Bacteroides clostridliformis ss. clostridliformis, Bacteroides coagulans, Bacteroides orails, Bacteroides ruminicola ss. brevis, -ss. ruminicola, Bacteroides spianchnicus, Desuifomonas pigra, Bacteroides L-4, -N-i; Fusobacterium H, Lactobacillus G, and Succinivibrio A.

Inhibition of Bacterial Pathogens

In some embodiments, the bacterial composition provides a protective or therapeutic effect against infection by one or more GI pathogens of interest.

A list of exemplary bacterial pathogens Is provided in Table 1 as indicated by pathogen status.

In some embodiments, the pathogenic bacterium is selected from the group consisting of Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus, multi-drug resistant bacteria, extended spectrum beta-lactam resistant Enterococci (ESBL), Carbapenem-resistent Enterobacterlaceae (CRE), and vancomycin-resistant Enterococci (VRE).

In some embodiments, these pathogens include, but are not limited to, Aeromonas hydrophila, Campylobacter fetus, Pleslomonas shlgelloides, Bacillus cereus, Campylobacter jejuni, Clostridium botulinum, Clostridium difficile, Clostridium perfringens, enteroaggregative Escherichia coli, enterohemorrhagic Escherichia coli, enteroinvasive Escherichia coli, enterotoxigenic Escherichia coli (such as, but not limited to, LT and/or ST), Escherichia coli O157:H7, Helicobacter pylori, Klebsiella pneumonia, Lysteria monocytogenes, Plesiomonas shigelloides, Salmonella spp., Salmonella typhi, Salmonella paratyphi, Shigella spp., Staphylococcus spp., Staphylococcus aureus, vancomycin-resistant Enterococcus spp., Vibrio spp., Vibrio cholerae, Vibrio parahaemolyticus, Vibrio vulnificus, and Yersinia enterocolitica.

In one embodiment, the pathogen of interest is at least one pathogen chosen from Clostridium difficile, Salmonella spp., pathogenic Escherichia coli, vancomycin-resistant Enterococcus spp., and extended spectrum beta-lactam resistant Enterococci (ESBL).

Purified Spore Populations

In some embodiments, the bacterial compositions comprise purified spore populations. Purified spore populations contain combinations of commensal bacteria of the human gut microbiota with the capacity to meaningfully provide functions of a healthy microbiota when administered to a mammalian subject. Without being limited to a specific mechanism, it is thought that such compositions inhibit the growth of a pathogen such as C. difficile, Salmonella spp., enteropathogenic *E. coli*, and vancomycin-resistant *Enterococcus* spp., so that a healthy, diverse and protective microbiota can be maintained or, in the case of pathogenic bacterial infections such as *C. difficile* infection, repopulate the intestinal lumen to reestablish ecological control over potential pathogens. In some embodiments, yeast spores and other fungal spores are also purified and selected for therapeutic use.

Disclosed herein are therapeutic compositions containing non-pathogenic, germination-competent bacterial spores, spore forming organisms and non-spore forming organisms for the prevention, control, and treatment of gastrointestinal diseases, disorders and conditions and for general nutritional health. These compositions are advantageous in being suitable for safe administration to humans and other mammalian subjects and are efficacious in numerous gastrointestinal diseases, disorders and conditions and in general nutritional health.

Provided herein are therapeutic compositions containing a purified population of bacterial spores, spore forming organisms and non-spore forming organisms. As used herein, the terms "purify", "purified" and "purifying" refer to the state of a population (e.g., a plurality of known or unknown amount and/or concentration) of desired bacterial spores or bacteria, that have undergone one or more processes of purification, e.g., a selection or an enrichment of the desired bacterial spore, or alternatively a removal or reduction of residual habitat products as described herein. In some embodiments, a purified population has no detectable undesired activity or, alternatively, the level or amount of the undesired activity is at or below an acceptable level or amount. In other embodiments, a purified population has an amount and/or concentration of desired bacterial spores or bacteria at or above an acceptable amount and/or concentration. In other embodiments, the purified population of bacterial spores is enriched as compared to the starting material (e.g., liquid culture) from which the population is obtained. This enrichment may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material.

In certain embodiments, the purified populations have reduced or undetectable levels of one or more pathogenic activities, such as toxicity, an infection of the mammalian recipient subject, an immunomodulatory activity, an autoimmune response, a metabolic response, or an inflammatory response or a neurological response. Such a reduction in a pathogenic activity may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In other embodiments, the purified populations of bacterial spores have reduced sensory components as compared to fecal material, such as reduced odor, taste, appearance, and umami.

Provided are purified populations of bacterial spores that are substantially free of residual habitat products. In certain embodiments, this means that the bacterial spore composition no longer contains a substantial amount of the biological matter associated with the microbial community while living on or in the human or animal subject, and the purified population of spores may be 100% free, 99% free, 98% free, 97% free, 96% free, or 95% free of any contamination of the biological matter associated with the microbial community. Substantially free of residual habitat products may also mean that the bacterial spore composition contains no detectable cells from a human or animal, and that only microbial cells are detectable, in particular, only desired microbial cells are detectable. In another embodiment, it means that fewer than $1\times10^{-2}$%, $1\times10^{-3}$%, $1\times10^{-4}$%, $1\times10^{-5}$%, $1\times10^{-6}$%, $1\times10^{-7}$%, $1\times10^{-8}$% of the cells in the bacterial composition are human or animal, as compared to microbial cells. In another embodiment, the residual habitat product present in the purified population is reduced at least a certain level from the fecal material obtained from the mammalian donor subject, e.g., reduced by at least about 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999%.

In one embodiment, substantially free of residual habitat products or substantially free of a detectable level of a pathogenic material means that the bacterial composition contains no detectable viral (including bacterial viruses (i.e., phage)), fungal, or mycoplasmal or toxoplasmal contaminants, or a eukaryotic parasite such as a helminth. Alternatively, the purified spore populations are substantially free of an acellular material, e.g., DNA, viral coat material, or non-viable bacterial material.

As described herein, purified spore populations can be demonstrated by genetic analysis (e.g., PCR, DNA sequencing), serology and antigen analysis, and methods using Instrumentation such as flow cytometry with reagents that distinguish desired bacterial spores from non-desired, contaminating materials.

Exemplary biological materials include fecal materials such as feces or materials isolated from the various segments of the small and large intestines. Fecal materials are obtained from a mammalian donor subject, or can be obtained from more than one donor subject, e.g., 2, 3, 4, 5, 6, 7, 8, 9, 10, 15, 20, 25, 30, 35, 40, 45, 50, 75, 100, 200, 300, 400, 500, 750, 1000 or from greater than 1000 donors, where such materials are then pooled prior to purification of the desired bacterial spores.

In alternative embodiments, the desired bacterial spores are purified from a single fecal material sample obtained from a single donor, and after such purification are combined with purified spore populations from other purifications, either from the same donor at a different time, or from one or more different donors, or both.

Preferred bacterial genera include *Acetonema, Alkaliphilus, Alicyclobacillus, Amphibacillus, Ammonifex, Anaerobacter, Anaerofustis, Anaerostipes, Anaerotruncus, Anoxybacillus, Bacillus, Blautia, Brevibacillus, Bryantella, Caldicellulosiruptor, Caloramator, Candidatus, Carboxydibrachium, Carboxydothermus, Clostridium, Cohnella, Coprococcus, Dendrosporobacter Desulfitobacterium, Desulfosporosinus, Desulfotomaculum, Dorea, Eubacterium, Faecalibacterium, Filifactor, Geobacillus, Halobacteroides, Heliobacillus, Heliobacterium, Heliophilum, Heliorestis, Lachnoanaerobaculum, Lysinibacillus, Moorella, Oceanobacillus, Orenia* (S.), *Oxalophagus, Oxobacter, Paenibacillus, Pelospora, Pelotomaculum, Propionispora, Roseburia, Ruminococcus, Sarcina, Sporobacterium, Sporohalobacter, Sporolactobacillus, Sporomusa, Sporosarcina, Sporotomaculum, Subdoligranulum, Symbiobacterium, Syntrophobotulus, Syntrophospora, Terribacillus, Thermoanaerobacter,* and *Thermosinus.*

Preferred bacterial species are provided at Table X4. Where specific strains of a species are provided, one of skill in the art will recognize that other strains of the species can be substituted for the named strain.

In some embodiments, spore-forming bacteria are identified by the presence of nucleic acid sequences that modulate sporulation. In particular, signature sporulation genes are highly conserved across members of distantly related genera including *Clostridium* and *Bacillus*. Traditional approaches of forward genetics have identified many, if not all, genes that are essential for sporulation (spo). The developmental program of sporulation is governed in part by the successive action of four compartment-specific sigma factors (appearing in the order σF, σE, σG and σK), whose activities are confined to the forespore (σF and σG) or the mother cell (σE and σK).

Provided are spore populations containing more than one type of bacterium. As used herein, a "type" or more than one "types" of bacteria may be differentiated at the genus level, the species, level, the sub-species level, the strain level or by any other taxonomic method, as described herein and otherwise known in the art.

In some embodiments, all or essentially all of the bacterial species present in a purified population are isolated or originally isolated from a fecal material treated as described herein or otherwise known in the art. In alternative embodiments, one or more than one bacterial spores or types of bacteria are generated in culture and combined to form a purified population. In other alternative embodiments, one or more of these culture-generated populations are combined with a fecal material-derived population to generate a hybrid population. Bacterial compositions may contain at least two types of these preferred bacteria, including strains of the same species. For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more than 20 types of bacteria, as defined by species or operational taxonomic unit (OTU) encompassing such species.

Thus, provided herein are methods for production of a composition containing a population of bacterial spores suitable for therapeutic administration to a mammalian subject in need thereof. And the composition is produced by generally following the steps of: (a) providing a fecal material obtained from a mammalian donor subject; and (b) subjecting the fecal material to at least one purification treatment or step under conditions such that a population of bacterial spores is produced from the fecal material. The composition is formulated such that a single oral dose contains at least about $1\times10^4$ colony forming units of the bacterial spores, and a single oral dose will typically contain about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, or greater than $1\times10^{15}$ CFUs of the bacterial spores. The presence and/or concentration of a given type of bacteria spore may be known or unknown in a given purified spore population. If known, for example the concentration of spores of a given strain, or the aggregate of all strains, is e.g., $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, or greater than $1\times10^{15}$ viable bacterial spores per gram of composition or per administered dose.

In some formulations, the composition contains at least about 10%, 20%, 30%, 40%, 50%, 60%, 70%, 80%, 90% or greater than 90% spores on a mass basis. In some formulations, the administered dose does not exceed 200, 300, 400, 500, 600, 700, 800, 900 milligrams or 1, 1.1, 1.2, 1.3, 1.4, 1.5, 1.6, 1.7, 1.8, or 1.9 grams in mass.

The bacterial spore compositions are generally formulated for oral or gastric administration, typically to a mammalian subject. In particular embodiments, the composition is formulated for oral administration as a solid, semi-solid, gel, or liquid form, such as in the form of a pill, tablet, capsule, or lozenge. In some embodiments, such formulations contain or are coated by an enteric coating to protect the bacteria through the stomach and small intestine, although spores are generally resistant to the stomach and small intestines.

The bacterial spore compositions may be formulated to be effective in a given mammalian subject in a single administration or over multiple administrations. For example, a single administration is substantially effective to reduce *Cl. difficile* and/or *Cl. difficile* toxin content in a mammalian subject to whom the composition is administered. Substantially effective means that *Cl. difficile* and/or *Cl. difficile* toxin content in the subject is reduced by at least 10%, 20%, 30%, 40%, 50%, 60%, 70%, 80%, 90%, 95%, 98%, 99% or greater than 99% following administration of the composition.

Methods of the Invention

Methods for Determining 16S Sequences

OTUs can be defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing can be, but is not limited to being, performed using the Sanger method or using a next-generation sequencing method, such as an Illumina (sequencing by synthesis) method using barcoded primers allowing for multiplex reactions.

OTUs can be defined by a combination of nucleotide markers or genes, in particular highly conserved genes (e.g., "house-keeping" genes), or a combination thereof, full-genome sequence, or partial genome sequence generated using amplified genetic products, or whole genome sequence (WGS). Using well defined methods DNA extracted from a bacterial sample will have specific genomic regions amplified using PCR and sequenced to determine the nucleotide sequence of the amplified products. In the whole genome shotgun (WGS) method, extracted DNA will be directly sequenced without amplification. Sequence data can be generated using any sequencing technology Including, but not limited to Sanger, Illumina, 454 Life Sciences, Ion Torrent, ABI, Pacific Biosciences, and/or Oxford Nanopore.

Methods for Preparing a Bacterial Composition for Administration to a Subject

Methods for producing bacterial compositions can include three main processing steps, combined with one or more mixing steps. The steps include organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments that use a culturing step, the agar or broth can contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g. R. M. Atlas, *Handbook of Microbiological Media* (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use, this is often at 37° C. temperature, pH, and other parameter with values similar to the normal human niche. The environment can be actively controlled, passively controlled (e.g., via buffers), or allowed to drift. For example, for anaerobic bacterial compositions (e.g., gut microbiota), an anoxic/reducing environment can be employed. This can be accomplished by addition of reducing agents such as cysteine to the broth, and/or stripping it of oxygen. As an example, a culture of a bacterial composition can be grown at 37° C., pH 7, in the medium above, pre-reduced with 1 g/L cysteine☐HCl.

When the culture has generated sufficient biomass, it can be preserved for banking. The organisms can be placed into a chemical milieu that protects from freezing (adding 'cryoprotectants'), drying ('lyoprotectants'), and/or osmotic shock ('osmoprotectants'), dispensing into multiple (optionally Identical) containers to create a uniform bank, and then treating the culture for preservation. Containers are generally impermeable and have closures that assure isolation from the environment. Cryopreservation treatment Is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means, such as density gradient centrifugation preserved using the techniques described above. Bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production can be conducted using similar culture steps to banking, including medium composition and culture conditions. It can be conducted at larger scales of operation, especially for clinical development or commercial production. At larger scales, there can be several sub-cultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition can be cultivated to a concentration of $10^{10}$ CFU/mL, then concentrated 20-fold by tangential flow microfiltration; the spent medium can be exchanged by diafiltering with a preservative medium consisting of 2% gelatin, 100 mM trehalose, and 10 mM sodium phosphate buffer. The suspension can then be freeze-dried to a powder and titrated.

After drying, the powder can be blended to an appropriate potency, and mixed with other cultures and/or a filler such as microcrystalline cellulose for consistency and ease of handling, and the bacterial composition formulated as provided herein.

Methods of Treating a Subject

In some embodiments, the compositions disclosed herein are administered to a patient or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a patient, when a parent commands a minor user (such as a child) to consume a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The bacterial compositions offer a protective and/or therapeutic effect against infection by one or more GI pathogens of interest and can be administered after an acute case of infection has been resolved in order to prevent relapse, during an acute case of infection as a complement to antibiotic therapy if the bacterial composition is not sensitive to the same antibiotics as the GI pathogen, or to prevent infection or reduce transmission from disease carriers.

The present bacterial compositions can be useful in a variety of clinical situations. For example, the bacterial compositions can be administered as a complementary treatment to antibiotics when a patient is suffering from an acute infection, to reduce the risk of recurrence after an acute infection has subsided, or when a patient will be in dose proximity to others with or at risk of serious gastrointestinal infections (physicians, nurses, hospital workers, family members of those who are ill or hospitalized).

The present bacterial compositions can be administered to animals, including humans, laboratory animals (e.g., primates, rats, mice), livestock (e.g., cows, sheep, goats, pigs, turkeys, chickens), and household pets (e.g., dogs, cats, rodents).

In the present method, the bacterial composition can be administered enterically, in other words, by a route of access to the gastrointestinal tract. This includes oral administration, rectal administration (including enema, suppository, or colonoscopy), by an oral or nasal tube (nasogastric, nasojejunal, oral gastric, or oral jejunal), as detailed more fully herein.

Pretreatment Protocols

Prior to administration of the bacterial composition, the patient can optionally have a pretreatment protocol to prepare the gastrointestinal tract to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol can enhance the ability of the bacterial composition to affect the patient's microbiome.

As one way of preparing the patient for administration of the microbial ecosystem, at least one antibiotic can be administered to after the bacteria in the patient. As another way of preparing the patient for administration of the microbial ecosystem, a standard colon-cleansing preparation can be administered to the patient to substantially empty the contents of the colon, such as used to prepare a patient for a colonoscopy. By "substantially emptying the contents of the colon," this application means removing at least 75%, at least 80%, at least 90%, at least 95%, or about 100% of the contents of the ordinary volume of colon contents. Antibiotic treatment can precede the colon-cleansing protocol.

If a patient has received an antibiotic for treatment of an infection, or if a patient has received an antibiotic as part of a specific pretreatment protocol, in one embodiment, the antibiotic can be stopped in sufficient time to allow the antibiotic to be substantially reduced in concentration in the gut before the bacterial composition is administered. In one embodiment, the antibiotic can be discontinued 1, 2, or 3 days before the administration of the bacterial composition. In another embodiment, the antibiotic can be discontinued 3, 4, 5, 6, or 7 antibiotic half-lives before administration of the bacterial composition. In another embodiment, the antibiotic can be chosen so the constituents in the bacterial composition have an MIC50 that is higher than the concentration of the antibiotic in the gut.

MIC50 of a bacterial composition or the elements in the composition can be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic can be chosen so that the infection is sensitive to the antibiotic, but the constituents in the bacterial composition are not sensitive to the antibiotic.

Routes of Administration

The bacterial compositions of the invention are suitable for administration to mammals and non-mammalian animals in need thereof. In certain embodiments, the mammalian subject is a human subject who has one or more symptoms of a dysbiosis.

When a mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is diarrhea caused by *C. difficile* including recurrent *C. difficile* infection, ulcerative colitis, colitis, Crohn's disease, or irritable bowel disease. Beneficially, the therapeutic composition is administered only once prior to improvement of the disease, disorder or condition. In some embodiments, the therapeutic composition is administered at intervals greater than two days, such as once every three, four, five or six days, or every week or less frequently than every week. In other embodiments, the preparation can be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In certain embodiments, the bacterial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The bacterial composition can be administered to at least one region of the gastrointestinal tract, including the mouth, esophagus, stomach, small intestine, large intestine, and rectum. In some embodiments, it is administered to all regions of the gastrointestinal tract. The bacterial compositions can be administered orally in the form of medicaments such as powders, capsules, tablets, gels or liquids. The bacterial compositions can also be administered in gel or liquid form by the oral route or through a nasogastric tube, or by the rectal route in a gel or liquid form, by enema or instillation through a colonoscope or by a suppository.

If the composition is administered colonoscopically and, optionally, if the bacterial composition is administered by other rectal routes (such as an enema or suppository) or even if the subject has an oral administration, the subject can have a colon-cleansing preparation. The colon-cleansing preparation can facilitate proper use of the colonoscope or other administration devices, but even when it does not serve a mechanical purpose, It can also maximize the proportion of the bacterial composition relative to the other organisms previously residing in the gastrointestinal tract of the subject. Any ordinarily acceptable colon-cleansing preparation may be used such as those typically provided when a subject undergoes a colonoscopy.

Dosages and Schedule for Administration

In some embodiments, the bacteria and bacterial compositions are provided in a dosage form. In certain embodiments, the dosage form Is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In other embodiments, the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In certain embodiments, the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, 105 and $10^{12}$ microorganisms total can be administered to the patient in a given dosage form. In another embodiment, an effective amount can be provided in from 1 to 500 ml or from 1 to 500 grams of the bacterial composition having from 107 to $10^{11}$ bacteria per ml or per gram, or a capsule, tablet or suppository having from 1 mg to 1000 mg lyophilized powder having from 107 to $10^{11}$ bacteria. Those receiving acute treatment can receive higher doses than those who are receiving chronic administration (such as hospital workers or those admitted into long-term care facilities).

Any of the preparations described herein can be administered once on a single occasion or on multiple occasions, such as once a day for several days or more than once a day on the day of administration (including twice daily, three times daily, or up to five times daily). In another embodiment, the preparation can be administered intermittently according to a set schedule, e.g., once weekly, once monthly, or when the patient relapses from the primary illness. In one embodiment, the preparation can be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

Patient Selection

Particular bacterial compositions can be selected for individual patients or for patients with particular profiles. For example, 16S sequencing can be performed for a given patient to identify the bacteria present in his or her microbiota. The sequencing can either profile the patient's entire microbiome using 16S sequencing (to the family, genera, or species level), a portion of the patient's microbiome using 16S sequencing, or It can be used to detect the presence or absence of specific candidate bacteria that are biomarkers for health or a particular disease state, such as markers of multi-drug resistant organisms or specific genera of concern such as *Escherichia*. Based on the biomarker data, a particular composition can be selected for administration to a patient to supplement or complement a patient's microbiota in order to restore health or treat or prevent disease. In another embodiment, patients can be screened to determine the composition of their microbiota to determine the likelihood of successful treatment.

Combination Therapy

The bacterial compositions can be administered with other agents in a combination therapy mode, including anti-microbial agents and prebiotics. Administration can be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents can include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, fioxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticolds, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

A prebiotic is a selectively fermented ingredient that allows specific changes, both in the composition and/or activity in the gastrointestinal microbiota that confers benefits upon host well-being and health. Prebiotics can include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Methods for Testing Bacterial Compositions for Populating Effect

In Vivo Assay for Determining Whether a Bacterial Composition Populates a Subject's Gastrointestinal Tract In order to determine that the bacterial composition populates the gastrointestinal tract of a subject, an animal model, such as a mouse model, can be used. The model can begin by evaluating the microbiota of the mice. Qualitative assessments can be accomplished using 16S profiling of the microbial community in the feces of normal mice. It can also be accomplished by full genome sequencing, whole genome shotgun sequencing (WGS), or traditional microbiological techniques. Quantitative assessments can be conducted using quantitative PCR (qPCR), described below, or by using traditional microbiological techniques and counting colony formation.

Optionally, the mice can receive an antibiotic treatment to mimic the condition of dysbiosis. Antibiotic treatment can decrease the taxonomic richness, diversity, and evenness of the community, including a reduction of abundance of a significant number of bacterial taxa. Dethlefsen et at, The pervasive effects of an antibiotic on the human gut microbiota, as revealed by deep 16S rRNA sequencing, PLoS Biology 6(11):3280 (2008). At least one antibiotic can be used, and antibiotics are well known. Antibiotics can include aminoglycoside antibiotic (amikacin, arbekacin, gentamicin, kanamycin, neomycin, netilmicin, paromomycin, rhodostreptomycin, streptomycin, tobramycin, and apramycin), amoxicillin, ampicillin, Augmentin (an amoxicillin/clavulanate potassium combination), cephalosporin (cefaclor, defadroxil, cefazolin, cefixime, fefoxitin, cefprozil, ceftazimdime, cefuroxime, cephalexin), clavulanate potassium, clindamycin, colistin, gentamycin, kanamycin, metronidazole, or vancomycin. As an individual, nonlimiting specific example, the mice can be provided with drinking water containing a mixture of the antibiotics kanamycin, colistin, gentamycin, metronidazole and vancomycin at 40 mg/kg, 4.2 mg/kg, 3.5 mg/kg, 21.5 mg/kg, and 4.5 mg/kg (mg per average mouse body weight), respectively, for 7 days. Alternatively, mice can be administered ciprofloxacin at a dose of 15-20 mg/kg (mg per average mouse body weight), for 7 days.

If the mice are provided with an antibiotic, a wash out period of from one day to three days may be provided with no antibiotic treatment and no bacterial composition treatment.

Subsequently, the test bacterial composition is administered to the mice by oral gavage. The test bacterial composition may be administered in a volume of 0.2 ml containing 104 CFUs of each type of bacteria in the bacterial composition. Dose-response may be assessed by using a range of doses, including, but not limited to $10^2$, $10^3$, $10^4$, $10^5$, $10^6$, $10^7$, $10^8$, $10^9$, and/or $10^{10}$.

The mice can be evaluated using 16S sequencing, full genome sequencing, whole genome shotgun sequencing (WGS), or traditional microbiological techniques to determine whether the test bacterial composition has populated the gastrointestinal tract of the mice. For example only, one day, three days, one week, two weeks, and one month after administration of the bacterial composition to the mice, 16S profiling is conducted to determine whether the test bacterial composition has populated the gastrointestinal tract of the mice. Quantitative assessments, including qPCR and traditional microbiological techniques such as colony counting, can additionally or alternatively be performed, at the same time intervals.

Furthermore, the number of sequence counts that correspond exactly to those in the bacterial composition over time can be assessed to determine specifically which components of the bacterial composition reside In the gastrointestinal tract over a particular period of time. In one embodiment, the strains of the bacterial composition persist for a desired period of time. In another embodiment, the components of the bacterial composition persist for a desired period of time, while also increasing the ability of other microbes (such as those present in the environment, food, etc.) to populate the gastrointestinal tract, further increasing overall diversity, as discussed below.

Ability of Bacterial Compositions to Populate Different Regions of the Gastrointestinal Tract The present bacterial compositions can also be assessed for their ability to populate different regions on the gastrointestinal tract. In one embodiment, a bacterial composition can be chosen for its ability to populate one or more than one region of the gastrointestinal tract, including, but not limited to the stomach, the small intestine (duodenum, jejunum, and ileum), the large intestine (the cecum, the colon (the ascending, transverse, descending, and sigmoid colon), and the rectum).

An in vivo study can be conducted to determine which regions of the gastrointestinal tract a given bacterial composition will populate. A mouse model similar to the one described above can be conducted, except instead of assessing the feces produced by the mice, particular regions of the gastrointestinal tract can be removed and studied individually. For example, at least one particular region of the gastrointestinal tract can be removed and a qualitative or quantitative determination can be performed on the contents of that region of the gastrointestinal tract. In another embodiment, the contents can optionally be removed and the qualitative or quantitative determination may be conducted on the tissue removed from the mouse.

qPCR

As one quantitative method for determining whether a bacterial composition populates the gastrointestinal tract, quantitative PCR (qPCR) can be performed. Standard techniques can be followed to generate a standard curve for the bacterial composition of interest, either for all of the components of the bacterial composition collectively, individually, or in subsets (if applicable). Genomic DNA can be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's Instructions.

In some embodiments, qPCR can be conducted using HotMasterMix (5PRIME, Gaithersburg, Md.) and primers specific for the bacterial composition of interest, and may be conducted on a MicroAmpe Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels. The Cq value for each well on the FAM channel is determined by the CFX Manager™ software version 2.1. The $\log_{10}$(cfu/ml) of each experimental sample is calculated by inputting a given sample's Cq value into linear regression model generated from the standard curve comparing the Cq values of the standard curve wells to the known $\log_{10}$(cfu/ml) of those samples. The skilled artisan may employ alternative qPCR modes.

Methods for Characterization of Bacterial Compositions

In certain embodiments, provided are methods for testing certain characteristics of bacterial compositions. For example, the sensitivity of bacterial compositions to certain environmental variables is determined, e.g., in order to select for particular desirable characteristics in a given composition, formulation and/or use. For example, the constituents in the bacterial composition can be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

PH Sensitivity Testing

If a bacterial composition will be administered other than to the colon or rectum (i.e., for example, an oral route), optionally testing for pH resistance enhances the selection of bacterial compositions that will survive at the highest yield possible through the varying pH environments of the distinct regions of the GI tract. Understanding how the bacterial compositions react to the pH of the GI tract also assists in formulation, so that the number of bacteria in a dosage form can be increased if beneficial and/or so that the composition may be administered in an enteric-coated capsule or tablet or with a buffering or protective composition. As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This can be tested by exposing the bacterial composition to varying pH ranges for the expected gut transit times through those pH ranges. Therefore, as a nonlimiting example only, 18-hour cultures of bacterial compositions can be grown in standard media, such as gut microbiota medium ("GMM", see Goodman et al., Extensive personal human gut microbiota culture collections characterized and manipulated in gnotobiotic mice, PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile Acid Sensitivity Testing

Additionally, in some embodiments, testing for bile-acid resistance enhances the selection of bacterial compositions that will survive exposures to bile acid during transit through the GI tract. Bile acids are secreted into the small intestine and can, like pH, affect the survival of bacterial compositions. This can be tested by exposing the bacterial compositions to bile acids for the expected gut exposure time to bile acids. For example, bile acid solutions can be prepared at desired concentrations using 0.05 mM Tris at pH 9 as the solvent. After the bile acid is dissolved, the pH of the solution may be adjusted to 7.2 with 10% HCl. Bacterial compositions can be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria may be determined by culturing the bacteria and counting colonies on appropriate selective or non-selective media.

Antibiotic Sensitivity Testing

As a further optional sensitivity test, bacterial compositions can be tested for sensitivity to antibiotics. In one embodiment, bacterial compositions can be chosen so that the bacterial constituents are sensitive to antibiotics such that If necessary they can be eliminated or substantially reduced from the patient's gastrointestinal tract by at least one antibiotic targeting the bacterial composition.

Adherence to Gastrointestinal Cells

The bacterial compositions may optionally be tested for the ability to adhere to gastrointestinal cells. A method for testing adherence to gastrointestinal cells is described in U.S. Pat. No. 4,839,281.

Methods for Purifying Spores

Solvent Treatments

To purify the bacterial spores, the fecal material is subjected to one or more solvent treatments. A solvent treatment is a miscible solvent treatment (either partially miscible or fully miscible) or an immiscible solvent treatment. Miscibility is the ability of two liquids to mix with each to form a homogeneous solution. Water and ethanol, for example, are fully miscible such that a mixture containing water and ethanol in any ratio will show only one phase. Miscibility is provided as a wt/wt %, or weight of one solvent in 100 g of final solution. If two solvents are fully miscible in all proportions, their miscibility is 100%. Provided as fully miscible solutions with water are alcohols, e.g., methanol, ethanol, isopropanol, butanol, etc. The alcohols can be provided already combined with water; e.g., a solution containing 10%, 20%, 25%, 30%, 35%, 40%, 45%, 50%, 55%, 60%, 65%, 70%, 75%, 89%, 85%, 90%, 95% or greater than 95% Other solvents are only partially miscible, meaning that only some portion will dissolve in water. Diethyl ether, for example, is partially miscible with water. Up to 7 grams of diethyl ether will dissolve in 93 g of water to give a 7% (wt/wt %) solution. If more diethyl ether is added, a two phase solution will result with a distinct diethyl ether layer above the water. Other miscible materials include ethers, dimethoxyethane, or tetrahydrofuran In contrast, an oil such as an alkane and water are immiscible and form two phases. Further, immiscible treatments are optionally combined with a detergent, either an ionic detergent or a non-ionic detergent. Exemplary detergents Include Triton X-100, Tween 20, Tween 80, Nonidet P40, a pluronic, or a polyol.

Chromatography Treatments

To purify spore populations, the fecal materials are subjected to one or more chromatographic treatments, either sequentially or in parallel. In a chromatographic treatment, a solution containing the fecal material is contacted with a solid medium containing a hydrophobic interaction chromatographic (HIC) medium or an affinity chromatographic medium. In an alternative embodiment, a solid medium capable of absorbing a residual habitat product present in the fecal material is contacted with a solid medium that adsorbs a residual habitat product. In certain embodiments, the HIC medium contains sepharose or a derivatized sepharose such as butyl sepharose, octyl sepharose, phenyl sepharose, or butyl-s sepharose. In other embodiments, the affinity chromatographic medium contains material derivatized with mucin type I, II, III, IV, V, or VI, or oligosaccharides derived from or similar to those of mucins type I, II, III, IV, V, or VI. Alternatively, the affinity chromatographic medium contains material derivatized with antibodies that recognize spore-forming bacteria.

Mechanical Treatments

Provided herein is the physical disruption of the fecal material, particularly by one or more mechanical treatment such as blending, mixing, shaking, vortexing, impact pulverization, and sonication. As provided herein, the mechanical disrupting treatment substantially disrupts a non-spore material present in the fecal material and does not substantially disrupt a spore present in the fecal material. Mechanical treatments optionally include filtration treatments, where the desired spore populations are retained on a filter while the undesirable (non-spore) fecal components to pass through, and the spore fraction is then recovered from the filter medium. Alternatively, undesirable particulates and eukaryotic cells may be retained on a filter while bacterial cells including spores pass through. In some embodiments the spore fraction retained on the filter medium is subjected to a diafiltration step, wherein the retained spores are contacted with a wash liquid, typically a sterile saline-containing solution or other diluent, in order to further reduce or remove the undesirable fecal components.

Thermal Treatments

Provided herein is the thermal disruption of the fecal material. Generally, the fecal material is mixed in a saline-containing solution such as phosphate-buffered saline (PBS) and subjected to a heated environment, such as a warm room, incubator, water-bath, or the like, such that efficient heat transfer occurs between the heated environment and the fecal material. Preferably the fecal material solution is mixed during the incubation to enhance thermal conductivity and disrupt particulate aggregates. Thermal treatments can be modulated by the temperature of the environment and/or the duration of the thermal treatment. For example, the fecal material or a liquid comprising the fecal material is subjected to a heated environment, e.g., a hot water bath of at least about 20, 25, 30, 35, 40, 45, 50, 55, 60, 65, 70, 75, 80, 85, 90, 95, 100 or greater than 100 degrees Celsius, for at least about 1, 5, 10, 15, 20, 30, 45 seconds, or 1, 2, 3, 4, 5, 6, 7, 8, 9, 10, 15, 20, 25, 30, 40, or 50 minutes, or 1, 2, 3, 4, 5, 6, 7, 8, 9, 10 or more than 10 hours. In certain embodiments the thermal treatment occurs at two different temperatures, such as 30 seconds in a 100 degree Celsius environment followed by 10 minutes in a 50 degree Celsius environment. In preferred embodiments the temperature and duration of the thermal treatment are sufficient to kill or remove pathogenic materials while not substantially damaging or reducing the germination-competency of the spores.

Irradiation Treatments

Provided are methods of treating the fecal material or separated contents of the fecal material with ionizing radiation, typically gamma irradiation, ultraviolet irradiation or electron beam irradiation provided at an energy level sufficient to kill pathogenic materials while not substantially damaging the desired spore populations. For example, ultraviolet radiation at 254 nm provided at an energy level below about 22,000 microwatt seconds per cm$^2$ will not generally destroy desired spores.

Centrifugation and Density Separation Treatments

Provided are methods of separating desired spore populations from the other components of the fecal material by centrifugation. A solution containing the fecal material is subjected to one or more centrifugation treatments, e.g., at about 1000×g, 2000×g, 3000×g, 4000×g, 5000×g, 6000×g, 7000×g, 8000×g or greater than 8000×g. Differential centrifugation separates desired spores from undesired non-spore material; at low forces the spores are retained in solution, while at higher forces the spores are pelleted while smaller impurities (e.g., virus particles, phage) are retained in solution. For example, a first low force centrifugation pellets fibrous materials; a second, higher force centrifugation pellets undesired eukaryotic cells, and a third, still higher force centrifugation pellets the desired spores while small contaminants remain in suspension. In some embodiments density or mobility gradients or cushions (e.g., step cushions), such as Percoll, Ficoll, Nycodenz, Histodenz or sucrose gradients, are used to separate desired spore populations from other materials in the fecal material.

Also provided herein are methods of producing spore populations that combine two or more of the treatments described herein in order to synergistically purify the desired spores while killing or removing undesired materials and/or activities from the spore population. It is generally desirable to retain the spore populations under non-germinating and non-growth promoting conditions and media, in order to minimize the growth of pathogenic bacteria present in the spore populations and to minimize the germination of spores into vegetative bacterial cells.

Pharmaceutical Compositions and Formulations of the Invention

Formulations

Provided are formulations for administration to humans and other subjects in need thereof. Generally the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides Include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments, the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In other embodiments, the composition comprises at least one modified lipid, for example, a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In certain embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In other embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In another embodiment, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In other embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In another embodiment, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In other embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In other embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In another embodiment, the disintegrant is an effervescent disintegrant. Non-limiting examples of suitable effervescent disintegrants include sodium bicarbonate in combination with citric acid, and sodium bicarbonate in combination with tartaric acid.

In another embodiment, the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In other embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

In yet other embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The bacterial compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments, the core material comprises at least one of a solid, a liquid, and an emulsion. In other embodiments, the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In yet other embodiments, at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, insulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In another embodiment, the coating material comprises at least one of a fat and an oil. In other embodiments, the at least one of a fat and an oil is high temperature melting. In yet another embodiment, the at least one of a fat and an oil is hydrogenated or partially hydrogenated. In one embodiment, the at least one of a fat and an oil is derived from a plant. In other embodiments, the at least one of a fat and an oil comprises at least one of glycerides, free fatty acids, and fatty acid esters. In some embodiments, the coating material comprises at least one edible wax. The edible wax can be derived from animals, insects, or plants. Non-limiting examples include beeswax, lanolin, bayberry wax, caranuba wax, and rice bran wax. Tablets and pills can additionally be prepared with enteric coatings.

Alternatively, powders or granules embodying the bacterial compositions disclosed herein can be incorporated into a food product. In some embodiments, the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration Include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments, the food product can be a solid foodstuff. Suitable examples of a solid foodstuff include without limitation a food bar, a snack bar, a cookie, a brownie, a muffin, a cracker, an ice cream bar, a frozen yogurt bar, and the like.

In other embodiments, the compositions disclosed herein are incorporated into a therapeutic food. In some embodiments, the therapeutic food is a ready-to-use food that optionally contains some or all essential macronutrients and micronutrients. In another embodiment, the compositions disclosed herein are incorporated into a supplementary food that is designed to be blended into an existing meal. In one embodiment, the supplemental food contains some or all essential macronutrients and micronutrients. In another embodiment, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment, an enteric-coated capsule or tablet or with a buffering or protective composition can be used.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg Advanced *Organic Chemistry* $3^{rd}$ *Ed*. (Plenum Press) Vois A and B (1992).

Example 1: Species Identification

The identity of the bacterial species which grew up from a complex fraction can be determined in multiple ways. First, individual colonies can be picked into liquid media in a 96 well format, grown up and saved as 15% glycerol stocks at −80 C. Aliquots of the cultures can be placed into cell lysis buffer and colony PCR methods can be used to amplify and sequence the 16S rDNA gene (Example 2). Alternatively, colonies may be streaked to purity in several passages on solid media. Well separated colonies are streaked onto the fresh plates of the same kind and incubated for 48-72 hours at 37 C. The process is repeated multiple times in order to ensure purity. Pure cultures can be analyzed by phenotypic- or sequence-based methods, Including 16S rDNA amplification and sequencing as described in Examples 2 & 3. Sequence characterization of pure isolates or mixed communities e.g. plate scrapes and spore fractions can also include whole genome shotgun sequencing. The latter is valuable to determine the presence of genes associated with sporulation, antibiotic resistance, pathogenicity, and virulence. Colonies can also be scraped from plates en masse and sequenced using a massively parallel sequencing method as described in Examples 2 & 3 such that individual 16S signatures can be identified in a complex mixture. Optionally, the sample can be sequenced prior to germination (if appropriate DNA isolation procedures are used to lsye and release the DNA from spores) in order to compare the diversity of germinable species with the total number of species in a spore sample. As an alternative or complementary approach to 16S analysis, MALDI-TOF-mass spec can also be used for species identification (as reviewed in Anaerobe 22:123).

Example 2:16s Sequencing to Determine Operational Taxonomic Unit (OTU)

Method for Determining 16S Sequence

OTUs may be defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

In addition to the 16S rRNA gene, one may define an OTU by sequencing a selected set of genes that are known to be marker genes for a given species or taxonomic group of OTUs. These genes may alternatively be assayed using a PCR-based screening strategy. As example, various strains of pathogenic $Escherichia\ coli$ can be distinguished using DNAs from the genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv). The optimal genes to utilize for taxonomic assignment of OTUs by use of marker genes will be familiar to one with ordinary skill of the art of sequence based taxonomic identification.

Genomic DNA Extraction

Genomic DNA is extracted from pure microbial cultures using a hot alkaline lysis method. 1 µl of microbial culture is added to 9 µl of Lysis Buffer (25 mM NaOH, 0.2 mM EDTA) and the mixture is incubated at 95° C. for 30 minutes. Subsequently, the samples are cooled to 4° C. and neutralized by the addition of 10 µl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA isolation Kit (Mo Bio Laboratories, Carlsbad, Calif.) or by standard methods known to those skilled in the art.

Amplification of 16S Sequences for Downstream Sanger Sequencing

To amplify bacterial 16S rDNA (FIG. 1A), 2 µl of extracted gDNA is added to a 20 µl final volume PCR reaction. For full-length 16 sequencing the PCR reaction also contains 1× HotMasterMix (SPRIME, Gaithersburg, Md.), 250 nM of 27f (AGRGTTTGATCMTGGCTCAG (SEQ ID NO: 2033), IDT, Coralville, Iowa), and 250 nM of 1492r (TACGGYTACCTTGTTAYGACTT (SEQ ID NO: 2034), IDT, Coralville, Iowa), with PCR Water (Mo Bio Laboratories, Carlsbad, Calif.) for the balance of the volume. Alternatively, other universal bacterial primers or thermostable polymerases known to those skilled in the art are used. For example primers are available to those skilled in the art for the sequencing of the "V1-V9 regions" of the 16S rRNA (FIG. 1A). These regions refer to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the $E.\ coli$ system of nomenclature. Brosius et al., Complete nucleotide sequence of a 16S ribosomal RNA gene from $Escherichia\ coli$, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA (in FIG. 1A) by comparing the candidate sequence in question to the reference sequence (FIG. 1B) and identifying the hypervariable regions based on similarity to the reference hypervariable regions.

The PCR is performed on commercially available thermocyclers such as a BioRad MyCycler™ Thermal Cycler (BioRad, Hercules, Calif.). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

To remove nucleotides and oligonucleotides from the PCR products, 2 µl of HT ExoSap-IT (Affymetrix, Santa Clara, Calif.) is added to 5 µl of PCR product followed by a 15 minute incubation at 37° C. and then a 15 minute inactivation at 80° C.

Amplification of 16S Sequences for Downstream Characterization by Massively Parallel Sequencing Technologies Amplification performed for downstream sequencing by short read technologies such as Illumina require amplification using primers known to those skilled in the art that additionally include a sequence-based barcoded tag. As example, to amplify the 16s hypervariable region V4 region of bacterial 16S rDNA, 2 µl of extracted gDNA is added to a 20 µl final volume PCR reaction. The PCR reaction also contains 1× HotMasterMix (SPRIME, Gaithersburg, Md.), 200 nM of V4_515f_adapt (AATGATACGGCGAC-CACCGAGATCTACACTATGGTAATTGTGTGCCAGC-MGCCGCGGTAA (SEQ ID NO: 2035), IDT, Coralville, Iowa), and 200 nM of barcoded 806rbc (CAAGCAGAAGACGGCATACGAGAT_12bpGolayBarcode_AGTCAGTCAGCCGGACTACHVGGGTWTC-TAAT (SEQ ID NOS 2036 and 2037, respectively, in order of appearance), IDT, Coralville, Iowa), with PCR Water (Mo Bio Laboratories, Carlsbad, Calif.) for the balance of the volume. These primers incorporate barcoded adapters for Illumina sequencing by synthesis. Optionally, Identical replicate, triplicate, or quadruplicate reactions may be performed. Alternatively other universal bacterial primers or thermostable polymerases known to those skilled in the art are used to obtain different amplification and sequencing error rates as well as results on alternative sequencing technologies.

The PCR amplification is performed on commercially available thermocyclers such as a BioRad MyCycler™ Thermal Cycler (BioRad, Hercules, Calif.). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~1.5 kb product. PCR cleanup is performed as specified in the previous example.

Sanger Sequencing of Target Amplicons from Pure Homogeneous Samples

To detect nucleic acids for each sample, two sequencing reactions are performed to generate a forward and reverse sequencing read. For full-length 16s sequencing primers 27f and 1492r are used. 40 ng of ExoSap-IT-cleaned PCR products are mixed with 25 pmol of sequencing primer and Mo Bio Molecular Biology Grade Water (Mo Bio Laboratories, Carlsbad, Calif.) to 15 µl total volume. This reaction is submitted to a commercial sequencing organization such as Genewiz (South Plainfield, N.J.) for Sanger sequencing.

Massively Parallel Sequencing of Target Amplicons from Heterogenous Samples

DNA Quantification & Library Construction. The cleaned PCR amplification products are quantified using the Quant-iT™ PicoGreen® dsDNA Assay Kit (Life Technologies, Grand Island, N.Y.) according to the manufacturer's instructions. Following quantification, the barcoded cleaned PCR products are combined such that each distinct PCR product is at an equimolar ratio to create a prepared Illumina library.

Nucleic Acid Detection. The prepared library is sequenced on Illumina HiSeq or MiSeq sequencers (Illumina, San Diego, Calif.) with cluster generation, template hybridization, iso-thermal amplification, linearization, blocking and denaturization and hybridization of the sequencing primers performed according to the manufacturer's instructions. 16SV4SeqFw (TATGGTAAT-TGTGTGCCAGCMGCCGCGGTAA (SEQ ID NO: 2038)), 16SV4SeqRev (AGTCAGTCAGCCGGACTACHVGGG-TWTCTAAT (SEQ ID NO: 2037)), and 16SV4Index (ATT-AGAWACCCBDGTAGTCCGGCTGACTGACT (SEQ ID NO: 2039)) (IDT, Coralville, Iowa) are used for sequencing. Other sequencing technologies can be used such as but not limited to 454, Pacific Biosciences, Helicos, Ion Torrent, and Nanopore using protocols that are standard to someone skilled in the art of genomic sequencing.

Example 3: Sequence Read Annotation

Primary Read Annotation

Nucleic acid sequences are analyzed and annotations are to define taxonomic assignments using sequence similarity and phylogenetic placement methods or a combination of the two strategies. A similar approach can be used to annotate protein names, transcription factor names, and any other classification schema for nucleic acid sequences. Sequence similarity based methods include those familiar to individuals skilled in the art including, but not limited to BLAST, BLASTx, tBLASTn, tBLASTx, RDP-classifier, DNAcust, and various implementations of these algorithms such as Qiime or Mothur. These methods rely on mapping a sequence read to a reference database and selecting the match with the best score and e-value. Common databases include, but are not limited to the Human Microbiome Project, NCBI non-redundant database, Greengenes, RDP, and Silva. Phylogenetic methods can be used in combination with sequence similarity methods to improve the calling accuracy of an annotation or taxonomic assignment. Here tree topologies and nodal structure are used to refine the resolution of the analysis. In this approach we analyze nucleic acid sequences using one of numerous sequence similarity approaches and leverage phylogenetic methods that are well known to those skilled in the art, including but not limited to maximum likelihood phylogenetic reconstruction (see e.g. Liu K, Linder CR, and Wamow T. 2011. RAxML and FastTree: Comparing Two Methods for Large-Scale Maximum Likelihood Phylogeny Estimation. PLoS ONE 6: e27731. McGuire G, Denham MC, and Balding DJ. 2001. Models of sequence evolution for DNA sequences containing gaps. Mol. Biol. Evol 18: 481-490. Wróbel B. 2008. Statistical measures of uncertainty for branches in phylogenetic trees inferred from molecular sequences by using model-based methods. J. Appl. Genet. 49: 49-67.) Sequence reads are placed into a reference phylogeny comprised of appropriate reference sequences. Annotations are made based on the placement of the read in the phylogenetic tree. The certainty or significance of the OTU annotation is defined based on the OTU's sequence similarity to a reference nucleic acid sequence and the proximity of the OTU sequence relative to one or more reference sequences in the phylogeny. As an example, the specificity of a taxonomic assignment is defined with confidence at the level of Family, Genus, Species, or Strain with the confidence determined based on the position of bootstrap supported branches in the reference phylogenetic tree relative to the placement of the OTU sequence being interrogated.

Clade Assignments

The ability of 16S-V4 OTU identification to assign an OTU as a specific species depends in part on the resolving power of the 16S-V4 region of the 16S gene for a particular species or group of species. Both the density of available reference 16S sequences for different regions of the tree as well as the inherent variability in the 16S gene between different species will determine the definitiveness of a taxonomic annotation. Given the topological nature of a phylogenetic tree and the fact that tree represents hierarchical relationships of OTUs to one another based on their sequence similarity and an underlying evolutionary model, taxonomic annotations of a read can be rolled up to a higher level using a clade-based assignment procedure (Table 1). Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) within a 5% genetic similarity. OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, are likely to play similar functional roles in a microbial ecology such as that found in the human gut. Compositions substituting one species with another from the same clade are likely to have conserved ecological function and therefore are useful in the present invention.

Notably, 16S sequences of isolates of a given OTU are phylogenetically placed within their respective clades, sometimes in conflict with the microbiological-based assignment of species and genus that may have preceded 16S-based assignment. Discrepancies between taxonomic assignment based on microbiological characteristics versus genetic sequencing are known to exist from the literature.

Example 4: Germinating Spores

Mixtures of bacteria can include species that are In spore form. Germinating a spore fraction increases the number of viable bacteria that will grow on various media types. To germinate a population of spores, the sample is moved to the anaerobic chamber, resuspended in prereduced PBS, mixed and incubated for 1 hour at 37 C to allow for germination. Germinants can include amino-acids (e.g., alanine, glycine), sugars (e.g., fructose), nucleosides (e.g., Inosine), bile salts (e.g., cholate and taurocholate), metal cations (e.g., Mg2+, Ca2+), fatty acids, and long-chain alkyl amines (e.g., dodecylamine, Germination of bacterial spores with alkyl primary amines" J. Bacteriology, 1961.). Mixtures of these or more complex natural mixtures, such as rumen fluid or Oxgall, can be used to induce germination. Oxgall is dehydrated bovine bile composed of fatty acids, bile acids, inorganic salts, sulfates, bile pigments, cholesterol, mucin, lecithin, glycuronic acids, porphyrins, and urea. The germination can also be performed in a growth medium like prereduced BHIS/oxgall germination medium, in which BHIS (Brain heart infusion powder (37 g/L), yeast extract (5 g/L), L-cysteine HCl (1 g/L)) provides peptides, amino acids, inorganic ions and sugars in the complex BHI and yeast extract mixtures and Oxgall provides additional bile acid germinants.

In addition, pressure may be used to germinate spores. The selection of germinants can vary with the microbe being sought. Different species require different germinants and different isolates of the same species can require different germinants for optimal germination. Finally, it is important to dilute the mixture prior to plating because some germinants are inhibitory to growth of the vegetative-state microorganisms. For instance, it has been shown that alkyl amines must be neutralized with anionic lipophiles in order to promote optimal growth. Bile acids can also inhibit growth of some organisms despite promoting their germination, and must be diluted away prior to plating for viable cells.

For example, BHIS/oxgall solution is used as a germinant and contains 0.5×BHIS medium with 0.25% oxgall (dehydrated bovine bile) where 1×BHIS medium contains the following per L of solution: 6 g Brain Heart Infusion from solids, 7 g peptic digest of animal tissue, 14.5 g of pancreatic digest of casein, 5 g of yeast extract, 5 g sodium chloride, 2 g glucose, 2.5 g disodium phosphate, and 1 g cysteine. Additionally, Ca-DPA is a germinant and contains 40 mM CaCl2, and 40 mM dipicolinic acid (DPA). Rumen fluid (Bar Diamond, Inc.) is also a germinant. Simulated gastric fluid (Ricca Chemical) is a germinant and is 0.2% (w/v) Sodium Chloride in 0.7% (v/v) Hydrochloric Acid. Mucin medium is a germinant and prepared by adding the following items to 1 L of distilled sterile water: 0.4 g $KH_2PO_4$, 0.53 g $Na_2HPO_4$, 0.3 g $NH_4Cl$, 0.3 g NaCl, 0.1 g $MgCl_2 \times 6H_2O$, 0.11 g $CaCl_2$, 1 ml alkaline trace element solution, 1 ml acid trace element solution, 1 ml vitamin solution, 0.5 mg resazurin, 4 g $NaHCO_3$, 0.25 g $Na_2S \times 9H_2O$. The trace element and vitamin solutions prepared as described previously (Stams et al., 1993). All compounds were autoclaved, except the vitamins, which were filter-sterilized. The basal medium was supplemented with 0.7% (v/v) clarified, sterile rumen fluid and 0.25% (v/v) commercial hog gastric mucin (Type III; Sigma), purified by ethanol precipitation as described previously (Miller & Hoskins, 1981). This medium is referred herein as mucin medium.

Fetal Bovine Serum (Gibco) can be used as a germinant and contains 5% FBS heat inactivated, in Phosphate Buffered Saline (PBS, Fisher Scientific) containing 0.137M Sodium Chloride, 0.0027M Potassium Chloride, 0.0119M Phosphate Buffer. Thioglycollate is a germinant as described previously (Kamiya et al Journal of Medical Microbiology 1989) and contains 0.25M (pH10) sodium thioglycollate. Dodecylamine solution containing 1 mM dodecylamine in PBS is a germinant. A sugar solution can be used as a germinant and contains 0.2% fructose, 0.2% glucose, and 0.2% mannitol. Amino acid solution can also be used as a germinant and contains 5 mM alanine, 1 mM arginine, 1 mM histidine, 1 mM lysine, 1 mM proline, 1 mM asparagine, 1 mM aspartic acid, 1 mM phenylalanine. A germinant mixture referred to herein as Germix 3 can be a germinant and contains 5 mM alanine, 1 mM arginine, 1 mM histidine, 1 mM lysine, 1 mM proline, 1 mM asparagine, 1 mM aspartic acid, 1 mM phenylalanine, 0.2% taurocholate, 0.2% fructose, 0.2% mannitol, 0.2% glucose, 1 mM inosine, 2.5 mM Ca-DPA, and 5 mM KCl. BHIS medium+DPA is a germinant mixture and contains BHIS medium and 2 mM Ca-DPA. *Escherichia coli* spent medium supernatant referred to herein as EcSN is a germinant and is prepared by growing *E. coli* MG1655 in SweetB/Fos inulin medium anaerobically for 48 hr, spinning down cells at 20,000 rcf for 20 minutes, collecting the supernatant and heating to 60 C for 40 min. Finally, the solution is filter sterilized and used as a germinant solution.

Figure 3:
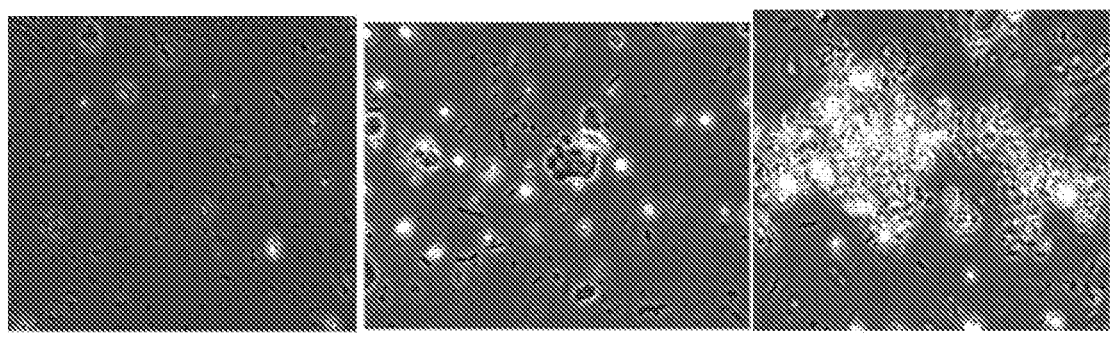
FIG. 3 illustrates population of fecal bacterial cell suspension (left) after CsCl separation (center) and after a CsCl and sucrose gradient (right) demonstrates enrichment of spores.

Example 5: The Purification and Isolation of a Spore Forming Fraction from Feces To purify and selectively isolate efficacious spores from fecal material a donation is first blended with saline using a homogenization device (e.g., laboratory blender) to produce a 20% slurry (w/v). 100% ethanol is added for an inactivation treatment that lasts 10 seconds to 1 hour. The final alcohol concentration can range from 30-90%, preferably 50-70%. High speed centrifugation (3200 rcf for 10 min) is performed to remove solvent and the pellet is retained and washed. Subsequently, once the washed pellet is resuspended, a low speed centrifugation step (200 rcf for 4 min) is performed to remove large particulate vegetative matter and the supernatant containing the spores is retained. High speed centrifugation (3200 rcf for 10 min) is performed on the supernatant to concentrate the spore material. The pellet is then washed and resuspended to generate a 20% slurry. This is the ethanol treated spore preparation. The concentrated slurry is then separated with a density based gradient e.g. a CsCl gradient, sucrose gradient or combination of the two generating a ethanol treated, gradient-purified spore preparation. For example, a CsCl gradient is performed by loading a 20% volume of spore suspension on top a 80% volume of a stepwise CsCl gradient (w/v) containing the steps of 64%, 50%, 40% CsCl (w/v) and centrifuging for 20 min at 3200 rcf. The spore fraction is then run on a sucrose step gradient with steps of 67%, 50%, 40%, and 30% (w/v). When centrifuged in a swinging bucket rotor for 10 min at 3200 rcf. The spores run roughly in the 30% and 40% sucrose fractions. The lower spore fraction (FIG. 2) is then removed and washed to produce a concentrated ethanol treated, gradient-purified spore preparation. Taking advantage of the refractive properties of spores observed by phase contrast microscopy (spores are bright and refractive while germinated spores and vegetative cells are dark) one can see an enrichment of the spore fraction from a fecal bacterial cell suspension (FIG. 3, left) compared to an ethanol treated, CsCl gradient purified, spore preparation (FIG. 3, center), and to an ethanol treated, CsCl gradient purified, sucrose gradient purified, spore preparation (FIG. 3, right).

Furthermore, growth of spores after treatment with a germinant can also be used to quantify a viable spore population. Briefly, samples were incubated with a germinant (Oxgall, 0.25% for up to 1 hour), diluted and plated anaerobically on BBA (Brucella Blood Agar) or similar media (e.g. see Examples 4 and 5). Individual colonies were picked and DNA isolated for full-length 16S sequencing to identify the species composition (e.g. see examples 2 and 3). Analysis revealed that 22 species were observed in total (Table 2) with a vast majority present in both the material purified with the gradient and without the gradient, indicating no or inconsequential shift in the ecology as a result of gradient purification. Spore yield calculations demonstrate an efficient recovery of 38% of the spores from the initial fecal material as measured by germination and plating of spores on BBA or measuring DPA count in the sample.

Example 6: Bacterial Compositions Prevent C. difficile Infection in a Mouse Model To test the therapeutic potential of the bacterial composition such as but not limited to a spore population, a prophylactic mouse model of C. difficile infection (model based on Chen, et al., A mouse model of Clostridium difficile associated disease, Gastroenterology 135(6):1984-1992) was used. Two cages of five mice each were tested for each arm of the experiment. All mice received an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and Vancomycin (0.056 mg/ml) in their drinking water on days −14 through −5 and a dose of 10 mg/kg Clindamycin by oral gavage on day −3. On day −1, they received either the test article or vehicle control via oral gavage. On day 0 they were challenged by administration of approximately 4.5 log 10 cfu of C. difficile (ATCC 43255) via oral gavage. Optionally a positive control group received vancomycin from day −1 through day 3 in addition to the antibiotic protocol and C. difficile challenge specified above. Feces were collected from the cages for analysis of bacterial carriage, mortality was assessed every day from day 0 to day 6 and the weight and subsequent weight change of the animal was assessed with weight loss being associated with C. difficile infection. Mortality and reduced weight loss of the test article compared to the vehicle were used to assess the success of the test article. Additionally, a C. difficile symptom scoring was performed each day from day −1 through day 6. Clinical Score was based on a 0-4 scale by combining scores for Appearance (0-2 pts based on normal, hunched, piloerection, or lethargic), and Clinical Signs (0-2 points based on normal, wet tail, cold-to-the-touch, or isolation from other animals).

In a naive control arm, animals were challenged with C. difficile. In the vancomycin positive control arm animals were dosed with C. difficile and treated with vancomycin from day −1 through day 3. The negative control was gavaged with PBS alone and no bacteria. The test arms of the experiment tested 1×, 0.1×, 0.01× dilutions derived from a single donor preparation of ethanol treated spores (e.g. see example 5) or the heat treated feces prepared by treating a 20% slurry for 30 min at 80 C. Dosing for CFU counts was determined from the final ethanol treated spores and dilutions of total spores were administered at 1×, 0.1×, 0.01× of the spore mixture for the ethanol treated fraction and a 1× dose for the heat treated fraction.

Weight loss and mortality were assessed on day 3. The negative control, treated with C. difficile only, exhibits 20% mortality and weight loss on Day 3, while the positive control of 10% human fecal suspension displays no mortality or weight loss on Day 3 (Table 3). EtOH-treated feces prevents mortality and weight loss at three dilutions, while the heat-treated fraction was protective at the only dose tested. These data indicate that the spore fraction is efficacious in preventing C. difficile infection in the mouse.

Example 7: The Prophylactic and Relapse Prevention Hamster Models

Figure 4:
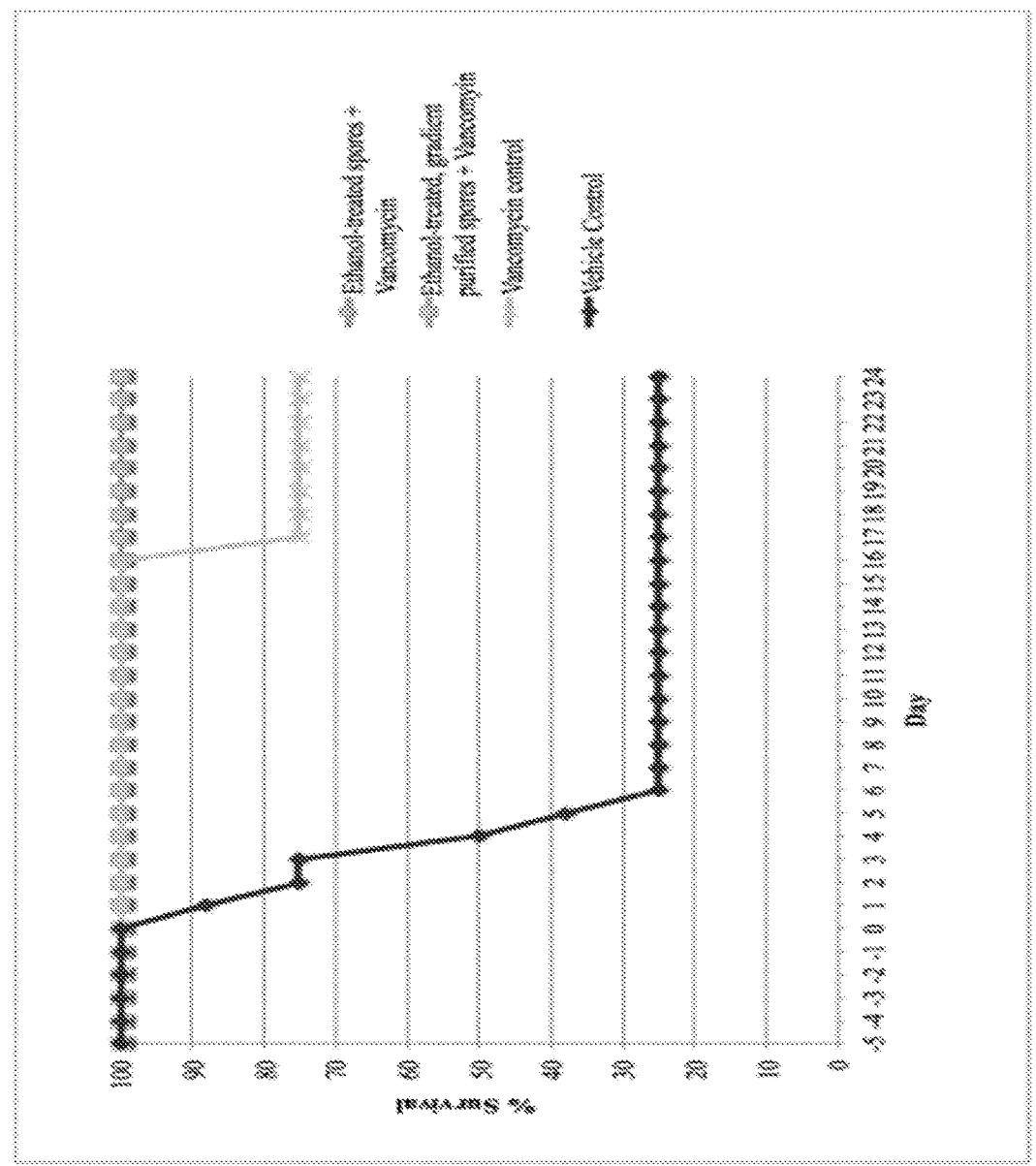
FIG. 4 illustrates a prophylaxis model with the ethanol treated spore preparation and the ethanol treated, gradient-purified spore preparation.

Previous studies with hamsters using toxigenic and non-toxigenic strains of C. difficile demonstrated the utility of the hamster model in examining relapse post antibiotic treatment and the effects of prophylaxis treatments with cecal flora in C. difficile infection (Wilson et al. 1981, Wilson et al. 1983, Borrello et al. 1985) and more broadly gastrointestinal Infectious disease. To demonstrate prophylactic use of a bacterial composition such as but not limited to a spore population, spore preparation, vegetative cell population, to ameliorate C. difficile infection, the following hamster model is used. In a prophylactic model, Clindamycin (10 mg/kg s.c.) is given on day −5, the bacterial composition or control is administered on day −3, and C. difficile challenge occurs on day 0. In the positive control arm, vancomycin is then administered on day 1-5 (and vehicle control is delivered on day −3). Feces are collected on day −5, −4, −1, 1, 3, 5, 7, 9 and fecal samples are assessed for pathogen carriage and reduction by microbiological methods, 16S sequencing approaches or other methods utilized by one skilled in the art. Mortality is assessed throughout the experiment through 21 days post *C. difficile* challenge. The percentage survival curves show that ethanol treated spores and ethanol treated, gradient-purified spores better protect the hamsters compared to the Vancomycin control, and vehicle control. The results are shown in FIG. 4, illustrating the prophylaxis model with the ethanol treated spore preparation and the ethanol treated, gradient-purified spore preparation.

In the relapse prevention model, hamsters are challenged with toxigenic *C. difficile* strains on day 0, and treated with clindamycin by oral gavage on day 1, and vancomycin dosing day 2-6. Test or control treatment was then administered on day 7, 8, and 9. The groups of hamsters for each arm consist of 8 hamsters per group. Fecal material is collected on day −1, 1, 3, 5, 7, 10 and 13 and hamster mortality is assessed throughout. Survival curves are used to assess the success of the test article e.g. ethanol treated or ethanol treated, gradient purified spores versus the control treatment in preventing hamster death. The survival curves demonstrate maximum efficacy for the ethanol treated, gradient-purified spores followed by the ethanol treated spores. Both treatments improved survival percentage over vancomycin treatment alone.

Figure 5:
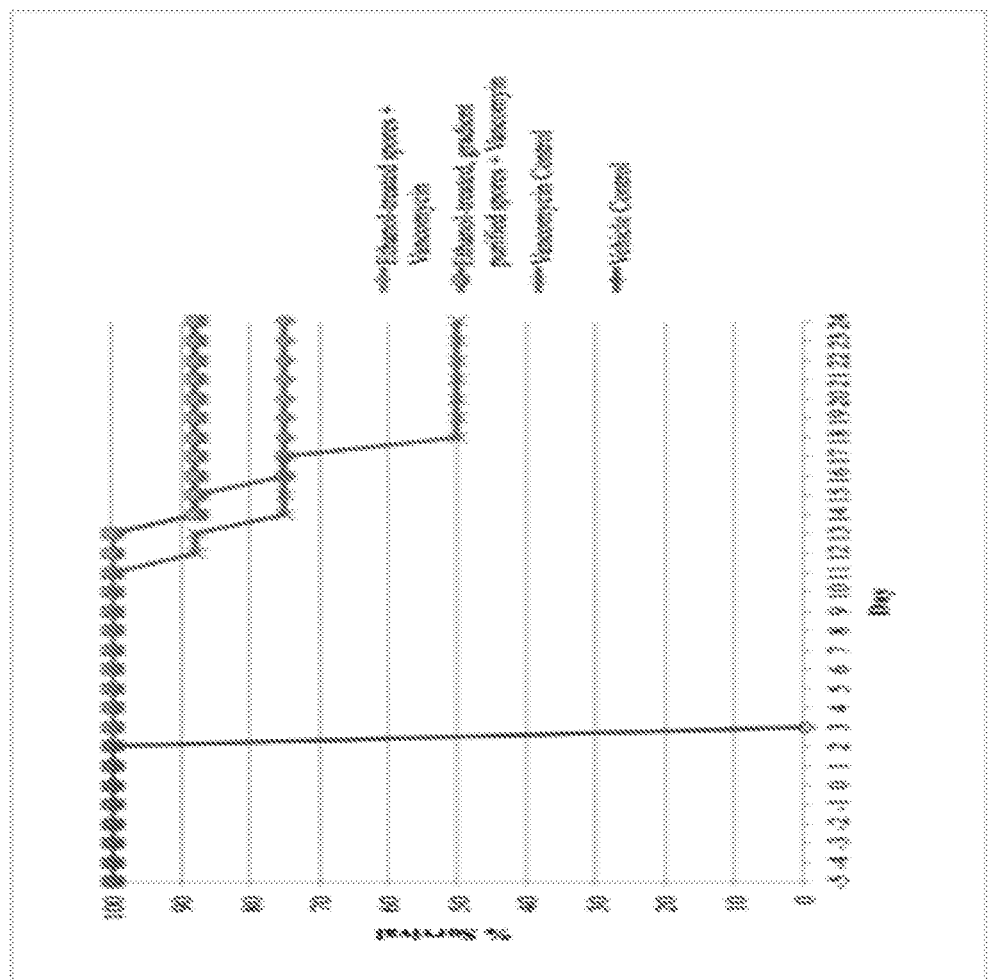
FIG. 5 illustrates a relapse prevention model with ethanol treated spores and ethanol treated, gradient purified spores.
Figure 7:
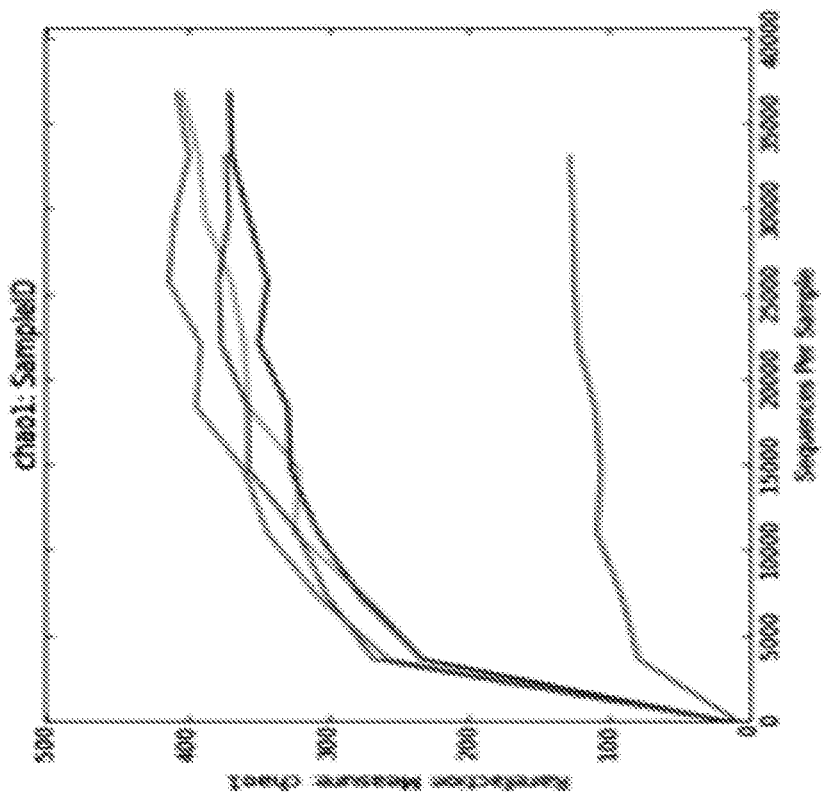
FIG. 7 illustrates bacterial diversity measured in the ethanol treated spore treatment sample and patient pre- and post-treatment samples.
Figure 8:
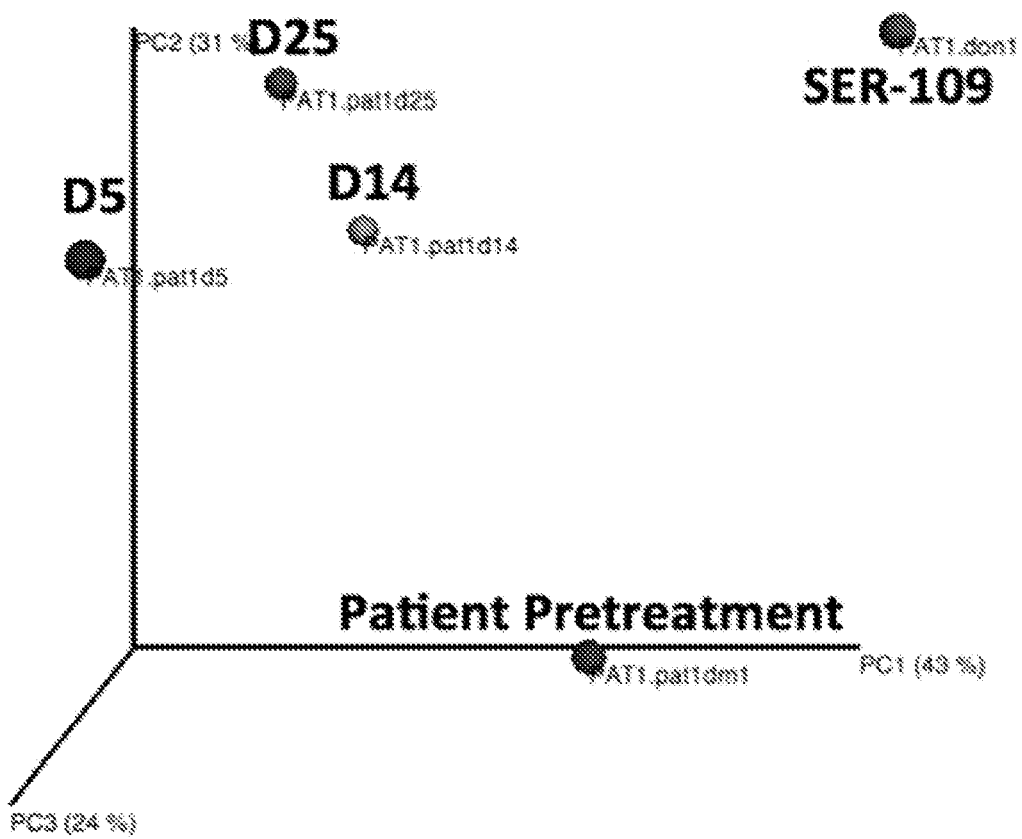
FIG. 8 Illustrates patient bacterial ecology is shifted by treatment with an ethanol treated spore treatment from a dysbiotic state to a state of health.

The results are shown in FIG. 5 illustrating the relapse prevention model with ethanol treated spores and ethanol treated, gradient purified spores Example 8: Clinical Treatment of Recurrent *C. difficile* in Patients To assess the efficacy of test articles like bacterial composition including but not limited to a ethanol treated spore preparations (e.g. see Example 5) to treat recurrent *C. difficile* in human patients, the following procedure was performed to take feces from a healthy donor, inactivate via the ethanol treated spore preparation protocol described below, and treat recurrent *C. difficile* in patients presenting with this indication. Non-related donors were screened for general health history for absence of chronic medical conditions (including inflammatory bowel disease; irritable bowel syndrome; Celiac disease; or any history of gastrointestinal malignancy or polyposis), absence of risk factors for transmissible infections, antibiotic non-use in the previous 6 months, and negative results in laboratory assays for blood-borne pathogens (HIV, HTLV, HCV, HBV, CMV, HAV and *Treponema pallidum*) and fecal bacterial pathogens (*Salmonella, Shigella, Yersinia, Campylobacter, E. coli* 0157), ova and parasites, and other infectious agents (Giardia, *Cryptosporidium Cyclospora, Isospora*) prior to stool donation.

Donor stool was frozen shortly after donation and sampled for testing. At the time of use, approximately 75 g of donor stool was thawed and resuspended in 500 mL of non-bacteriostatic normal saline and mixed in a single use glass or plastic blender. The resulting slurry was sequentially passed through sterile, disposable mesh screens that remove particles of size 600, 300 and 200 microns. The slurry was then centrifuged briefly (200 rcf for 4 min) to separate fibrous and particulate materials, and the supernatant (containing bacterial cells and spores) was transferred to a fresh container. Ethanol was added to a final concentration of 50% and the resulting ~1500 ml slurry was incubated at room temperature for 1 hr with continuous mixing to inactivate vegetative bacterial cells. Midway through inactivation the slurry was transferred to a new bottle to ensure complete contact with the ethanol. The solid matter was pelleted in a centrifuge and washed 3 times with normal saline to remove residual ethanol. The final pellet was resuspended in 100% sterile, USP glycerol at a minimum volume, and filled into approximately 30 size 0 delayed release capsules (hypromellose DRcaps, Capsugel, Inc.) at 0.65 mL suspension each. The capsules were Immediately capped and placed onto an aluminum freezing block held at −80° C. via dry ice to freeze. The frozen capsules were in turn over-capsulated with size 00 DRcaps to enhance capsule stability, labeled, and placed into <−65° C. storage immediately. The final product was stored at <−65° C. until the day and time of use. Encapsulated product may be stored for indefinitely at <−65° C. On the day of dosing capsules were warmed on wet ice for 1 to 2 hours to improve tolerability, and were then dosed with water ad libitum.

Patient 1 is a 45-year old woman with a history of *C. difficile* infection and diarrhea for at least 1 year prior to treatment. She has been previously treated with multiple courses of antibiotics followed each time by recurrence of *C. difficile*-associated diarrhea.

Patient 2 is an 81-year old female who has experienced recurrent *C. difficile* infection for 6 months prior to treatment despite adequate antibiotic therapy following each recurrence.

24 hours prior to starting oral treatment, CDAD antibiotic therapy was discontinued. Each patient received a colon preparation procedure intended to reduce the competing microbial burden in the gastrointestinal tract and to facilitate repopulation by the spore forming organisms in the investigational product.

On the morning of the first treatment day, the patients received a dose of delayed release capsules containing the investigational product with water ad libitum. Patients were requested to avoid food for 1 hour thereafter. The next day, the patient returned to the clinic to receive an additional dose. Patients were asked to avoid food for 4 hours prior to receiving their second dose and for 1 hour following dosing.

Both patients were followed closely for evidence of relapse or adverse symptoms following treatment. Patients were contacted by phone on Day 2, Day 4, and Weeks 1, 2 and 4 and each was queried about her general status and the condition of her CDAD and related symptoms. Stool samples were collected at baseline and Weeks 1, 2, 4 and 8 post-treatment to assess changes in the gut microbiota via 16S sequencing and spore count with methods explained previously (e.g. see Examples 2 and 3). Through 4 weeks post treatment, each patient has gradually improved with no evidence of *C. difficile* recurrence.

Six other patients with recurrent *C. difficile*-associated diarrhea were treated in a similar fashion, with no CDI recurrence and no requirement for resumption of antibiotics (total of 8 patients). Additionally, there were no treatment-related serious adverse events.

The above protocol could be modified to deliver other bacterial compositions e.g. vegetative cells, spore preparations, combinations thereof.

Example 9. Enrichment and Purification of Bacteria

To purify individual bacterial strains, dilution plates were selected in which the density enables distinct separation of single colonies. Colonies were picked with a sterile implement (either a sterile loop or toothpick) and re-streaked to BBA or other solid media. Plates were incubated at 37° C. for 3-7 days. One or more well-isolated single colonies of the major morphology type were re-streaked. This process was repeated at least three times until a single, stable colony morphology is observed. The isolated microbe was then cultured anaerobically in liquid media for 24 hours or longer to obtain a pure culture of $10^6$-$10^{10}$ cfu/ml. Liquid growth medium might include Brain Heart Infusion-based medium (Atlas, Handbook of Microbiological Media, 4th ed, ASM Press, 2010) supplemented with yeast extract, hemin, cysteine, and carbohydrates (for example, maltose, cellobiose, soluble starch) or other media described previously (e.g. see example 5). The culture was centrifuged at 10,000×g for 5 min to pellet the bacteria, the spent culture media was removed, and the bacteria were resuspended in sterile PBS. Sterile 75% glycerol was added to a final concentration of 20%. An aliquot of glycerol stock was titered by serial dilution and plating. The remainder of the stock was frozen on dry ice for 10-15 min and then placed at −80 C for long term storage.

Example 10. Cell Bank Preparation

Cell banks (RCBs) of bacterial strains were prepared as follows. Bacterial strains were struck from −80° C. frozen glycerol stocks to *Brucella* blood agar with Hemin or Vitamin K (Atlas, Handbook of Microbiological Media, 4th ed, ASM Press, 2010), M2GSC (Atlas, Handbook of Microbiological Media, 4th ed, ASM Press, 2010) or other solid growth media and Incubated for 24 to 48 h at 37° C. in an anaerobic chamber with a gas mixture of $H_2:CO_2:N_2$ of 10:10:80. Single colonies were then picked and used to inoculate 250 ml to 1 L of Wilkins-Chalgren broth, Brain-Heart Infusion broth, M2GSC broth or other growth media, and grown to mid to late exponential phase or into the stationary phase of growth. Alternatively, the single colonies may be used to inoculate a pilot culture of 10 ml, which were then used to inoculate a large volume culture. The growth media and the growth phase at harvest were selected to enhance cell titer, sporulation (if desired) and phenotypes that might be associated desired in vitro or in vivo. Optionally, Cultures were grown static or shaking, depending which yielded maximal cell titer. The cultures were then concentrated 10 fold or more by centrifugation at 5000 rpm for 20 min, and resuspended in sterile phosphate buffered saline (PBS) plus 15% glycerol. 1 ml aliquots were transferred into 1.8 ml cryovials which were then frozen on dry ice and stored at −80 C. The identity of a given cell bank was confirmed by PCR amplification of the 16S rDNA gene, followed by Sanger direct cycle sequencing, and comparison to a curated rDNA database to determine a taxonomic ID. Each bank was confirmed to yield colonies of a single morphology upon streaking to *Brucella* blood agar or M2GSC agar. When more than one morphology was observed, colonies were confirmed to be the expected species by PCR and sequencing analysis of the 16S rDNA gene. Variant colony morphologies can be observed within pure cultures, and in a variety of bacteria the mechanisms of varying colony morphologies have been well described (van der Woude, Clinical Microbiology Reviews, 17:518, 2004), including in *Clostridium* species (Wadsworth-KTL Anaerobic Bacteriology Manual, 6th Ed, Jousimie-Somer, et al 2002). For obligate anaerobes, RCBs were confirmed to lack aerobic colony forming units at a limit of detection of 10 cfu/ml.

Example 11. Titer Determination

The number of viable cells per ml was determined on the freshly harvested, washed and concentrated culture by plating serial dilutions of the RCB to *Brucella* blood agar or other solid media, and varied from 10W to $10^{10}$ cfu/ml. The impact of freezing on viability was determined by titering the banks after one or two freeze-thaw cycles on dry ice or at −80° C., followed by thawing in an anaerobic chamber at room temperature. Some strains displayed a 1-3 log drop in viable cfu/ml after the 1st and/or 2nd freeze thaw, while the viability of others were unaffected.

Example 12. Preparation of Bacterial Compositions

Individual strains were typically thawed on ice and combined in an anaerobic chamber to create mixtures, followed by a second freeze at −80° C. to preserve the mixed samples. When making combinations of strains for in vitro or in vivo assays, the cfu in the final mixture was estimated based on the second freeze-thaw titer of the individual strains. For experiments in rodents, strains may be combined at equal counts in order to deliver between 1e4 and 1e10 per strain. Additionally, some bacteria may not grow to sufficient titer to yield cell banks that allowed the production of compositions where all bacteria were present at 1e10.

Example 13. Provision of Gut Microbiome Sample Material

Fresh gut microbiome samples e.g. fecal samples were obtained from healthy human donors who have been screened for general good health and for the absence of infectious diseases, and meet inclusion and exclusion criteria, inclusion criteria include being in good general health, without significant medical history, physical examination findings, or clinical laboratory abnormalities, regular bowel movements with stool appearance typically Type 2, 3, 4, 5 or 6 on the Bristol Stool Scale, and having a BMI≥18 kg/m² and ≤25 kg/m². Exclusion criteria generally included significant chronic or acute medical conditions including renal, hepatic, pulmonary, gastrointestinal, cardiovascular, genitourinary, endocrine, immunologic, metabolic, neurologic or hematological disease, a family history of, inflammatory bowel disease including Crohn's disease and ulcerative colitis, Irritable bowel syndrome, colon, stomach or other gastrointestinal malignancies, or gastrointestinal polyposis syndromes, or recent use of yogurt or commercial probiotic materials in which an organism(s) is a primary component. Samples were collected directly using a commode specimen collection system, which contains a plastic support placed on the toilet seat and a collection container that rests on the support. Gut microbiome samples e.g. feces were deposited into the container, and the lid was then placed on the container and sealed tightly. The sample was then delivered on ice within 1-4 hours for processing. Samples were mixed with a sterile disposable tool, and 2-4 g aliquots were weighed and placed into tubes and flash frozen in a dry ice/ethanol bath. Aliquots are frozen at −80 degrees Celsius until use.

Optionally, the microbiome sample was suspended in a solution, and/or fibrous and/or particulate materials were removed. A frozen aliquot containing a known weight of sample was removed from storage at −80 degrees Celsius and allowed to thaw at room temperature. Sterile 1×PBS was added to create a 10% w/v suspension, and vigorous vortexing was performed to suspend the sample until the material appeared homogeneous. The sample was then left to sit for 10 minutes at room temperature to sediment fibrous and particulate matter. The suspension above the sediment was then carefully removed into a new tube and contains a purified spore population. Optionally, the suspension was then centrifuged at a low speed, e.g., 1000×g, for 5 minutes to pellet particulate matter including fibers. The pellet was discarded and the supernatant, which contained vegetative organisms and spores, was removed into a new tube. The supernatant was then centrifuged at 6000×g for 10 minutes to pellet the vegetative organisms and spores. The pellet was then resuspended in 1×PBS with vigorous vortexing until the sample material appears homogenous Example 14: Bacterial Compostions Populating the Out in a Mouse Model Two bacterial compositions were evaluated in a mouse model to demonstrate the ability to populate the gastrointestinal tract. Bacteria were grown as described in Example 12. Compositions were pre-made under anaerobic conditions and suspended in PBS+15% glycerol and stored at ≥−70° C. prior to use.

Groups of mice (10 females/group; 5 per cage) were pre-treated on Days −14 to −5 with an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and vancomycin (0.056 mg/ml) in their drinking water. On Day −3 they received 10 mg/kg Clindamycin by oral gavage. On Day −1, they were dosed with a microbial composition by oral gavage in a volume of 0.2 mL (Table ZA). Microbial compositions comprised approximately equal numbers of each OTU and were dosed at approximately $1\times10^9$, $1\times10^8$ and $1\times10^7$ per OTU for each composition (e.g. microbial composition 1, comprising 15 strains, was dosed at approximately $1.5\times10^{10}$, $1.5\times10^9$, and $1.5\times10^8$ total CFU). Fecal samples were collected from each cage on Day −1 (approximately 1 hour before dosing) and on Days 2, 3 and 4 post-dosing. Feces were stored frozen prior to processing and sequencing. Weight gain of mice treated with either microbial composition was similar to that of naive, control mice.

In parallel, groups of animals treated with the same microbial compositions on Day −1 were challenged on Day 0 with approximately 104-5 spores of Clostridium difficile (ATCC 43255) via oral gavage. Mortality for C. difficile challenged animals was assessed every day from Day 0 to Day 6 and the weight and subsequent weight change of the animal was assessed with weight loss being associated with C. difficile Infection. Mortality and reduced weight loss of the test article compared to the empty vehicle was used to assess the success of the test article.

TABLE ZA

| | OTU | Clade |
|---|---|---|
| Microbial Composition 1 | Clostridium__butyricum | clade__252 |
| | Clostridium__disporicum | clade__253 |
| | Clostridium__hylemonae | clade__260 |
| | Clostridium__orbiscindens | clade__494 |
| | Clostridium__symbiosum | clade__408 |
| | Collinsella__aerofaciens | clade__553 |
| | Coprococcus__comes | clade__262 |
| | Lachnospiraceae__bacterium__5__1__57FAA | clade__260 |
| | Ruminococcus__bromii | clade__537 |
| | Blautia__producta | clade__309 |
| | Clostridium__bolteae | clade__408 |
| | Clostridium__innocuum | clade__351 |
| | Clostridium__mayombei | clade__354 |
| | Clostridium__tertium | clade__252 |
| | Ruminococcus__gnavus | clade__360 |
| Microbial Composition 2 | Clostridium__disporicum | clade__253 |
| | Clostridium__orbiscindens | clade__494 |
| | Clostridium__symbiosum | clade__408 |
| | Collinsella__aerofaciens | clade__553 |
| | Eubacterium__rectale | clade__444 |
| | Lachnospiraceae__bacterium__5__1__57FAA | clade__260 |
| | Blautia__producta | clade__309 |
| | Clostridium__innocuum | clade__351 |
| | Clostridium__mayombei | clade__354 |

Fecal samples were processed by isolating and sequencing DNA according to *Example 2 and 3. The OTU assignment of fecal samples from Days −1, 2, 3 and 4 was determined by analyzing 16S-V4 sequence reads and assigning OTUs as described in *Example 2. Clades were assigned as described in ***Example 2. Total read counts were determined for each OTU or each clade by summing the results from cages of the same experimental group. Samples with 10 or fewer sequence reads for a given OTU or clade were considered to be below background and were not included in the summation process. Results are shown by OTU (Table TAB) and by clade (Table TAC).

TABLE TAB

Population of OTUs on Days 2, 3 and 4 following dosing with Microbial Compositions

| | $1 \times 10^9$ per OTU | | | | $1 \times 10^8$ per OTU | | | | $1 \times 10^7$ per OTU | | | |
|---|---|---|---|---|---|---|---|---|---|---|---|---|
| | −1 | 2 | 3 | 4 | −1 | 2 | 3 | 4 | −1 | 2 | 3 | 4 |
| Microbial comp 1 | | | | | | | | | | | | |
| Cl__butyricum | 0 | 106 | 51 | 32 | 0 | 10 | 0 | 34 | 195 | 0 | 0 | 0 |
| Cl__disporicum | 10 | 1746 | 1190 | 887 | 0 | 1746 | 769 | 1011 | 201 | 11175 | 1531 | 1152 |
| Cl__hylemonae | 0 | 258 | 258 | 84 | 0 | 203 | 164 | 77 | 0 | 265 | 214 | 90 |

TABLE TAB-continued

Population of OTUs on Days 2, 3 and 4 following dosing with Microbial Compositions

| | $1 \times 10^9$ per OTU | | | | $1 \times 10^8$ per OTU | | | | $1 \times 10^7$ per OTU | | | |
|---|---|---|---|---|---|---|---|---|---|---|---|---|
| | -1 | 2 | 3 | 4 | -1 | 2 | 3 | 4 | -1 | 2 | 3 | 4 |
| Cl_orbiscindens | 0 | 188 | 192 | 471 | 0 | 188 | 138 | 276 | 0 | 221 | 174 | 341 |
| Cl_symbiosum | 0 | 485 | 482 | 486 | 0 | 444 | 379 | 447 | 0 | 562 | 427 | 775 |
| Co_aerofaciens | 0 | 0 | 0 | 0 | 0 | 0 | 0 | 0 | 0 | 0 | 0 | 0 |
| C_comes | 0 | 0 | 0 | 0 | 0 | 0 | 0 | 0 | 0 | 0 | 0 | 0 |
| L_bacterium_5_1_57FAA | 0 | 341 | 336 | 354 | 0 | 351 | 182 | 356 | 0 | 256 | 240 | 300 |
| R_bromii | 0 | 0 | 0 | 0 | 0 | 0 | 0 | 0 | 0 | 0 | 0 | 0 |
| B_producta | 0 | 0 | 0 | 0 | 0 | 0 | 0 | 0 | 0 | 0 | 0 | 0 |
| Cl_bolteae | 0 | 0 | 0 | 0 | 0 | 0 | 0 | 0 | 0 | 0 | 0 | 0 |
| Cl_innocuum | 0 | 0 | 0 | 0 | 0 | 0 | 0 | 0 | 0 | 0 | 0 | 0 |
| Cl_mayombei | 0 | 0 | 0 | 0 | 0 | 0 | 0 | 0 | 0 | 0 | 0 | 0 |
| Cl_tertium | 0 | 0 | 0 | 0 | 0 | 0 | 0 | 0 | 0 | 0 | 0 | 0 |
| R_gnavus | 0 | 0 | 0 | 0 | 0 | 0 | 0 | 0 | 0 | 0 | 0 | 0 |
| Microbial comp 2 | | | | | | | | | | | | |
| Cl_disporicum | 29 | 11810 | 10948 | 14672 | 0 | 11349 | 13978 | 3942 | 0 | 11995 | 7005 | 6268 |
| Cl_orbiscindens | 0 | 510 | 408 | 764 | 0 | 332 | 545 | 544 | 0 | 310 | 319 | 432 |
| Cl_symbiosum | 0 | 559 | 508 | 375 | 0 | 665 | 494 | 450 | 0 | 396 | 639 | 650 |
| Co_aerofaciens | 0 | 0 | 0 | 0 | 0 | 0 | 1172 | 0 | 0 | 0 | 247 | 0 |
| E_rectale | 0 | 0 | 0 | 0 | 0 | 0 | 0 | 12 | 0 | 0 | 0 | 261 |
| L_bacterium_5_1_57FAA | 0 | 972 | 801 | 596 | 0 | 860 | 962 | 844 | 0 | 636 | 1901 | 1269 |
| B_producta | 0 | 0 | 0 | 0 | 0 | 0 | 0 | 0 | 0 | 0 | 0 | 0 |
| Cl_innocuum | 0 | 0 | 0 | 0 | 0 | 0 | 0 | 0 | 0 | 0 | 0 | 0 |
| Cl_mayombei | 0 | 0 | 0 | 0 | 0 | 0 | 0 | 0 | 0 | 0 | 0 | 0 |

TABLE TAC

Population of Clades on Days 2, 3 and 4 following dosing with Microbial Compositions

| | $1 \times 10^9$ per OTU $1 \times 10^9$ per OTU | | | | $1 \times 10^8$ per OTU $1 \times 10^8$ per OTU | | | | $1 \times 10^7$ per OTU $1 \times 10^7$ per OTU | | | |
|---|---|---|---|---|---|---|---|---|---|---|---|---|
| | -1 | 2 | 3 | 4 | -1 | 2 | 3 | 4 | -1 | 2 | 3 | 4 |
| Microbial comp 1 | | | | | | | | | | | | |
| clade_252 | 0 | 444 | 252 | 87 | 0 | 198 | 122 | 125 | 209 | 394 | 231 | 88 |
| clade_253 | 10 | 1746 | 1190 | 887 | 0 | 1746 | 769 | 1011 | 201 | 11175 | 1531 | 1152 |
| clade_260 | 0 | 599 | 594 | 438 | 0 | 554 | 346 | 433 | 0 | 521 | 454 | 390 |
| clade_262 | 0 | 14 | 151 | 51 | 0 | 0 | 0 | 0 | 0 | 12 | 21 | 57 |
| clade_309 | 0 | 11093 | 9750 | 4023 | 0 | 9991 | 5208 | 5145 | 19 | 9311 | 6369 | 4951 |
| clade_351 | 0 | 9064 | 10647 | 7751 | 0 | 6528 | 7259 | 8213 | 0 | 8903 | 10049 | 8701 |
| clade_354 | 0 | 0 | 0 | 0 | 0 | 0 | 0 | 31 | 173 | 0 | 0 | 0 |
| clade_360 | 0 | 14300 | 10220 | 11036 | 0 | 12553 | 12989 | 6889 | 0 | 9308 | 13483 | 9292 |
| clade_408 | 13 | 8892 | 12985 | 12101 | 23 | 3952 | 7260 | 10652 | 43 | 4079 | 8581 | 14929 |
| clade_494 | 0 | 226 | 227 | 565 | 0 | 188 | 184 | 411 | 0 | 221 | 200 | 351 |
| clade_537 | 0 | 0 | 68 | 225 | 0 | 0 | 0 | 0 | 0 | 0 | 0 | 55 |
| clade_553 | 0 | 0 | 0 | 0 | 0 | 0 | 0 | 0 | 0 | 0 | 0 | 0 |
| Microbial comp 2 | | | | | | | | | | | | |
| clade_253 | 29 | 11810 | 10948 | 14672 | 0 | 11349 | 13978 | 3942 | 0 | 11995 | 7005 | 6268 |
| clade_260 | 0 | 1125 | 1312 | 854 | 0 | 1049 | 1295 | 1250 | 0 | 792 | 2121 | 1637 |
| clade_309 | 54 | 12513 | 13731 | 7849 | 0 | 11610 | 12004 | 12672 | 0 | 7407 | 14111 | 10858 |
| clade_351 | 0 | 7651 | 9939 | 5936 | 0 | 8495 | 9724 | 9207 | 0 | 6005 | 9833 | 7655 |
| clade_354 | 149 | 0 | 127 | 429 | 0 | 0 | 0 | 39 | 12 | 0 | 0 | 0 |
| clade_408 | 18 | 2242 | 4989 | 10480 | 12 | 1688 | 5580 | 3789 | 0 | 1068 | 1561 | 6281 |
| clade_444 | 41 | 0 | 49 | 202 | 0 | 18 | 0 | 12 | 0 | 14 | 82 | 1578 |
| clade_494 | 0 | 510 | 465 | 1054 | 0 | 332 | 565 | 596 | 0 | 310 | 319 | 476 |
| clade_553 | 0 | 0 | 0 | 0 | 0 | 0 | 1172 | 0 | 0 | 0 | 247 | 0 |

Upon examining the OTU data in Table TAB, several patterns emerge. First, there are a group of OTUs with no sequence reads on Day −1 that show subsequent and large numbers of sequence reads on Days 2, 3, or 4; this group includes *Cl. butyricum, Cl. hylemonae, Cl. orbiscindens, Cl. symbiosum*, and *L. bacterium_5_1_57FAA*. *Cl. disporicum* is comparable to this group as it has sequence reads on Day −1 that are very close to background (10 and 29 in compositions 1 and 2, respectively), which subsequently increase by as much as 1000-fold on Days 2, 3 or 4. Second, there are OTUs such as Co. aerofaciens, *C. comes, R. bromil, B. producta, Cl. bolteae, Cl. mayombei, Cl. innocuum, Cl. tertium* and *R. gnavus* which are not detectable at the OTU level in either the Day −1 sample or in subsequent samples. In composition 2, Co. aerofaciens is detected transiently on Day 2 in the 1×10$^8$ and 1×10$^7$ dose groups; *E. rectale* in the same experimental groups is detected on Day 3, suggesting a possible relationship between transient population by Co. aerofaciens followed by *E. rectale* in these groups of mice. A striking observation is that the observed number of OTU sequence reads is not highly dose dependent. Overall, the data is consistent with a model whereby OTUs populate rapidly following oral administration.

The clade-based analysis in Table TAC was performed to more thoroughly evaluate the population of the GI tract. Clade-based analysis obscures some of the details afforded by an OTU analysis. For instance, *Cl. tertium* and *Cl. butyricum* are members of the same clade and thus a clade-based analysis cannot distinguish the dynamics of these individual OTUs. However, clade-based analysis has the compensatory benefit that it is sensitive to measuring population changes that can be missed by an OTU-based analysis. The ability of 16S-V4 OTU identification to assign an OTU as a specific species depends in part on the resolving power of the 16S-V4 region for a particular species or group of species. Both the density of available reference 16S sequences for different regions of the tree as well as the inherent variability in the 16S gene between different species will determine the definitiveness of a taxonomic annotation. So in some cases, the population of a species can be followed using clade-based assignments when OTU based-detection is insensitive in a complex population. For instance, the clade-based analysis in Table 1 supports the case that *R. bromii, B. producta, Cl. innocuum,* and *R. gnavus* were able to populate since each OTU is a sole member of a clade in the microbial compositions and sequence reads went from undetectable on Day −1 to well above background on Days 2, 3 or 4. 16S V4 sequencing and clade-based analysis could not determine whether *Cl. tertium* or *Cl. bolteae* populated due to the fact that other members of their clades (*Cl. butyricum* and *Cl. symbiosum*, respectively) were present and shown to populate at the OTU level in the mice.

In the mice challenged in parallel with *C. difficile*, animals were significantly protected as shown in Table TAD. Mice gavaged with vehicle (phosphate buffered saline) experienced 100% mortality while microbial compositions 1 and 2 protected at all dose levels with between 0 and 10% mortality by Day 6, the last day of the experiment. In addition, weight loss in animals treated with microbial compositions 1 and 2 was minimal compared to animals receiving the vehicle gavage. These data confirm that population of the gastrointestinal tract with microbial compositions confers a clinical benefit by restoring a state of dysbiosis so that animals can resist infection by a pathogen.

TABLE TAD

Mortality by experimental group in mice challenged with 10$^{4.5}$ *C. difficile* spores on Day 0

| Group | Dose (CFU per OTU) | Deaths (% mortality) |
|---|---|---|
| Vehicle control | N/A | 10 (100%) |
| Microbial composition 1 | 10$^9$ | 1 (10%) |
|  | 10$^8$ | 1 (10%) |
|  | 10$^7$ | 0 (0%) |
| Microbial composition 2 | 10$^9$ | 0 (0%) |
|  | 10$^8$ | 1 (10%) |
|  | 10$^7$ | 1 (10%) |

Example 15 Use of Biolog Assay to Determine Bacterial Strain Nutrient Utilization A screen was performed to test the ability of *Clostridium difficile* and potential competitor species to utilize a panel of 190 different carbon sources. The screen was carried out using PM1 and PM2 MicroPlates (Biolog #12111, #12112). IF-0a base media (Biolog #72268) and Biolog Redox Dye Mix D (Biolog #74224). For each strain, a 1 uL aliquot from −80° C. glycerol stock was streaked out for single colonies to solid *Brucella* Blood Agar plates (BBA) (Anaerobe Systems #AS-111) and incubated anaerobically at 37° C. for 24 hr. A single colony was then re-streaked to a BBA plate and incubated anaerobically at 37° C. for 24 hr. The MicroPlates were pre-reduced by incubating for at least 24 hr In a hydrogen free anaerobic environment before use. All liquid media and supplements used were pre-reduced by placing them in an anaerobic chamber with loose lids for at least 24 hr before use. Alternatively, combinations of bacteria can also be tested.

The base media for inoculation was prepared by adding 0.029 mL of 1M potassium ferricyanide to 0.240 mL of Dye Mix D followed by addition of 19.7 mL of IF-0a, 4 mL sterile water and 0.024 mL 0.5 mM menadione. For some species, the concentrations of potassium ferricyanide and menadione were adjusted to achieve the optimal redox balance or to test multiple redox conditions. Potassium ferricyanide was tested at a final concentration of 0.38, 0.12, 0.038 and 0.06 mM. Menadione was tested at a final concentration of 0.5, 0.16 and 0.05 µM. In total, this yields 9 redox conditions for testing. Reduction of the tetrazolium dye that forms the basis for the endpoint measurement was sensitive to the redox state of each bacterial culture, and thus to the ratio of menadione to potassium ferricyanide. It was therefore important to test various ratios for each bacterial Isolate and was also important in some cases to test a species at multiple menadione/potassium ferricyanide ratios in order to detect all conditions in which a possible nutrient utilization was detectable. Some species were tested beyond the 20 hr time point to detect all conditions resulting in a positive result. In these cases plates were read at 20, 44 or 96 hr.

Using a sterile, 1 µL microbiological loop, a loopful of biomass was scraped from the BBA plate and resuspended in the base media by vortexing. The OD was adjusted to 0.1 at 600 nm using a SpectraMax M5 plate reader. The bacterial suspension was then aliquoted into each well of the PM1 and PM2 plates (100 µL per well). The plates were incubated at 37° C. for 20 hr in a rectangular anaerobic jar (Mitsubishi) with 3 anaerobic, hydrogen-free gas packs (Mitsubishi AnaeroPack). After 20 hr, OD at 550 nm was read using a SpectraMax M5 plate reader. Wells were scored as a weak hit if the value was 1.5× above the negative control well, and a strong hit if the value was 2× above the negative control well. The results are shown in the Table in FIG. 11.

The following list of nutrient sources were tested: L-Arabinose, N-Acetyl-D-Glucosamine, D-Saccharic Acid, Succinic Acid, D-Galactose, L-Aspartic Acid, L-Proline, D-Alanine, D-Trehalose, D-Mannose, Dulcitol, D-Serine, D-Sorbitol, Glycerol, L-Fucose, D-Glucuronic Acid, D-Gluconic Acid, D, L-alpha-Glycerol-Phosphate, D-Xylose, L-Lactic Acid, Formic Acid, D-Mannitol, L-Glutamic Acid, D-Glucose-6-Phosphate, D-Galactonic Acid-gamma-Lactone, D,L-Malic Acid, D-Ribose, Tween 20, L-Rhamnose, D-Fructose, Acetic Acid, alpha-D-Glucose, Maltose, D-Melibiose, Thymidine, L-Asparagine, D-Aspartic Acid, D-Glucosaminic Acid, 1,2-Propanediol, Tween 40, alpha-Keto-Glutaric Acid, alpha-Keto-Butyric Acid, alpha-Methyl-D-Galactoside, alpha-D-Lactose, Lactulose, Sucrose, Uridine, L-Glutamine, M-Tartaric Acid, D-Glucose-1-Phosphate, D-Fructose-6-Phosphate, Tween 80, alpha-Hydroxy-Glutaric-gamma-lactone, alpha-Hydroxy Butyric Acid, beta-Methyl-D-Glucoside, Adonitol, Maltotriose, 2-Deoxy Adenosine, Adenosine, Glycyl-L-Aspartic Acid, Citric Acid, M-Inositol, D-Threonine, Fumaric Acid, Bromo Succinic Acid, Propionic Acid, Mucic Acid, Glycolic Acid, Glyoxylic Acid, D-Cellobiose, Inosine, Glycyl-L-Glutamic Acid, Tricarballylic Acid, L-Serine, L-Threonine, L-Alanine, L-Alanyl-Glycine, Acetoacetic Acid, N-Acetyl-beta-D-Mannosamine, Mono Methyl Succinate, Methyl Pyruvate, D-Malic Acid, L-Malic Acid, Glycyl-L-Proline, p-Hydroxy Phenyl Acetic Acid, m-Hydroxy Phenyl Acetic Acid, Tyramine, D-Psicose, L-Lyxose, Glucuronamide, Pyruvic Acid, L-Galactonic Acid-gamma-Lactone, D-Galacturonic Acid, Pheylethyl-amine, 2-aminoethanol, Chondroitin Sulfate C, alpha-Cyclodextrin, beta-Cyclodextrin, gamma-Cyclodextrin, Dextrin, Gelatin, Glycogen, Inulin, Laminarin, Mannan, Pectin, N-Acetyl-D-Galactosamine, N-Acetyl-Neuramic Acid, beta-D-Allose, Amygdalin, D-Arabinose, D-Arabitol, L-Arabitol, Arbutin, 2-Deoxy-D-Ribose, I-Erythritol, D-Fucose, 3-O-beta-D-Galacto-pyranosyl-D-Arabinose, Gentiobiose, L-Glucose, Lactitol, D-Melezitose, Maltitol, alpha-Methyl-D-Glucoside, beta-Methyl-D-Galactoside, 3-Methyl Glucose, beta-Methyl-D-Glucoronic Acid, alpha-Methyl-D-Mannoside, beta-Methyl-D-Xyloside, Palatinose, D-Raffinose, Salicin, Sedoheptulosan, L-Sorbose, Stachyose, D-Tagatose, Turanose, Xylitol, N-Acetyl-D-Glucosaminitol, gamma-Amino Butyric Acid, delta-Amino Valeric Acid, Butyric Acid, Capric Acid, Caproic Acid, Citraconic Acid, Citramalic Acid, D-Glucosamine, 2-Hydroxy Benzoic Acid, 4-Hydroxy Benzoic Acid, beta-Hydroxy Butyric Acid, gamma-Hydroxy Butyric Acid, alpha-Keto Valeric Acid, Itaconic Acid, 5-Keto-D-Gluconic Acid, D-Lactic Acid Methyl Ester, Malonic Acid, Mellbionic Acid, Oxalic Acid, Oxalomalic Acid, Quinic Acid, D-Ribino-1,4-Lacton, Sebacic Acid, Sorbic Acid, Succinamic Acid, D-Tartaric Acid, L-Tartaric Acid, Acetamide, L-Alaninamide, N-Acetyl-L-Glutamic Acid, L-Arginine, Glycine, L-Histidine, L-Homserine, Hydroxy-L-Proline, L-Isoleucine, L-Leucine, L-Lysine, L-Methionine, L-Omithine, L-Phenylalanine, L-Pyroglutamic Acid, L-Valine, D,L-Camithine, Sec-Butylamine, D,L-Octopamine, Putrescine, Dihydroxy Acetone, 2,3-Butanediol, 2,3-Butanone, 3-Hydroxy 2-Butanone.

Additionally, one of skill in the art could design nutrient utilization assays for an even broader set of nutrients using the using methods described above.

A similar screen can be performed to test the utilization of vitamins, amino acids, or cofactors. In these instances, Biolog MicroPlates for screening of vitamins, amino acids or cofactors that are of interest would be used in place of the PM1 and PM2 plates, for example PM5. Table XXX1 contains a list of representative vitamins, minerals, and cofactors. For each strain tested, a universal carbon source such as glucose will be used as a positive control to demonstrate reduction of the tetrazolium dye under the specific conditions of the assay.

Example 16: Use of Transcriptomics to Determine Bacterial Strain Nutrient Utilization Alternatively, the ability of a strain to utilize a particular carbon source can be determined by a transcriptomics based approach.

In this instance, a pure culture of *Clostidium difficile* is streaked to a *Brucella* Blood Agar plate (BBA) (Anaerobe Systems #AS-111) and incubated anaerobically at 37° C. for 24 hr. A single colony is then inoculated into a minimal defined base medium (as described in Karasawa, T, et al., *Microbiol* (1995)141: 371-5) substituting with a single carbon source such as fructose or mannitol. Several cultures can be tested in parallel altering the carbon source being tested. A control culture is also inoculated which lacks a carbon source. RNA is extracted from all cultures at 8, 14 and 38 hr. Extraction of total RNA is performed immediately using a FastPrep instrument and an RNA ProBlue kit (QBiogene). RNA quality is assessed by analysis on an Agilent Bioanalyser.

The *C. difficile* microarray based on the genome sequence of strain 630 can be found in ArrayExpress (accession number A-BUG-20). The microarray contains 3,679 coding sequences (CDSs). A Genisphere 3DNA Array 900 MPX microarray kit is used for cDNA synthesis, labeling, and hybridization. Ten micrograms of starting RNA is used for the cDNA synthesis reactions. The microarray slides are hybridized competitively with each cDNA.

The microarray slides are scanned using a ScanArray 4000 instrument (Packard Instrument Co.), and fluorescence intensities are quantified using ImaGene (BioDiscovery) software. Raw expression data from the arrays are analyzed with R and Limma (linear model for microarray data) software from the Bioconductor project. Further data processing and statistical analysis is performed by correcting background with the Normexp method, resulting in strictly positive values and reducing variability in the log ratios for genes with low hybridization signals. Each strain is then normalized by using the Loess method. In order to identify differentially expressed genes, Bayesian adjusted t statistics is performed. A gene is considered differentially expressed when the P value is <0.05. The 8 hr values are chosen as a reference for comparing values from later time points to Identify genes and pathways that are upregulated during the time course of the experiment. Alternatively, the values can be compared relative to a no carbon source control, or a glucose control, as glucose represses expression of genes involved in carbon utilization in many bacteria via catabolite repression.

Potential competitors of *Clostridium difficile* are tested in the same manner, singly or in combination, using custom microarray slides for each strain or species. Alternatively, an RNA-seq based approach can be used to identify and quantify the relative abundance of mRNA in each sample (can we insert a reference for how to perform an RNA-seq experiment?].

Example 17A: Use of In Vivo Transcriptomics to Determine Bacterial Strain Nutrient Utilization Alternatively, carbon source utilization of *Clostridium difficile* and potential competitors can be determined by a transcriptomics approach that detects the presence of mRNA levels in an in vivo mouse model. For example, in Ng et al (Nature 2013, 502:7469), *C. difficile* genes for catabolism of sialic acid and fucose were found to have increased levels of expression in vivo relative to when grown in vitro in growth medium, and in Janoir et al (I&I 201381:3757), expression of genes required for catabolism of glucose, sorbitol and fructose are induced in vivo relative to in vitro, suggesting their use during infection.

A group of mice are inoculated with *Clostridium difficile*, and subgroups are sacrificed after 8, 12 or 24 hr, at which time cecal contents are collected. Total nucleic acid is extracted from 50 µl aliquots of the cecal contents using a MasterPure RNA purification kit (Epicentre Biotechnologies, Madison, Wis.). DNA is removed using a Turbo DNA-free kit (Ambion, Austin, Tex.), using the rigorous protocol. Total RNA is quantified with a NanoDrop ND-1000 (Thermo Scientific, Wilmington, Del.), and integrity is analyzed using an RNA FlashGel (Lonza, Basel, Switzerland). Total RNA is enriched for mRNA using MicrobExpress (Ambion, Austin, Tex.). Enriched RNA is quantified using RiboGreen (Invitogen, Carlsbad, Calif.). One hundred nanograms of mRNA-enriched RNA is used for library preparation using SuperScript II (Invitrogen, Carlsbad, Calif.) and an mRNA-seq kit (Illumina, San Diego, Calif.). The cDNA library is sequenced using an Illumina HiSeq 2500. Reads are then mapped against the appropriate *C. difficile* reference genome. The 8 hr time point can be used as a reference to identify genes and pathways that are upregulated in vivo, or alternatively a control sample grown in vitro in a standard growth medium can be used as a reference. The pattern of upregulated catabolic genes defines a map of nutrients for which an effective anti-*C. difficile* consortium of organisms would compete.

The same process is repeated or performed in parallel for bacterial strains that are potential competitors of *C. difficile*. In an alternative version, combinations of bacterial strains can be inoculated into a mouse and analysed simultaneously from the same cecal sample using publicly available reference genomes from the human microbiome for read mapping. Species with potential ability to compete with *C. difficile* are selected based on their pattern of overlap for carbon sources analyzed.

Example 17B: Use of Literature Search to Determine Bacterial Strain Nutrient Utilization The nutrient utilization capabilities of a pathogen are also determined by means of a literature search. Compounds that can support growth of *C. difficile* were determined from scientific publications describing nutrients that are utilized by the organism (for example, Nakamura et al, 1982, Microbiol Immunol 26:107), from scientific papers describing a defined media that allows growth of the organism (for example, George et al, J. Clin. Microbiol. 1979, 9:214), reference manuals that compile data from the literature such as Bergey's Manual of Systematic Bacteriology (Bergey's Manual of Systematic Bacteriology: Vol. 3: The Firmicutes By Paul Vos, George Garrity, Dorothy Jones, Noel R. Krieg, Wolfgang Ludwig, Fred A. Rainey, Karl-Heinz Schleifer, William B. Whitman, 2009 Ed) or The Prokaryotes (The Prokaryotes: Vol. 4: Bacteria: Firmicutes, Cyanobacteria, 2006 Ed, edited by Martin Dworkin, Stanley Falkow). For example, Bergey's Manual indicates carbon sources typically used by *C. difficile*: glucose, cellobiose, fructose, mannitol, mannose, melezitose, salicin, sorbitol, sucrose, trehalose, xylose, proline, aspartic acid, serine, leucine, alanine, threonine, valine, phenylalanine, methionine, isoleucine. Note, not all strains use all of these carbon sources, making the testing of several individual strains useful.

Genomics studies describing analysis of reference genomes can suggest nutrients that are potentially used by a pathogen, based on the presence of metabolic pathways and transport proteins for given substrates. For example, Sebaihia et al., Nature Genetics, 2006 which presents the genome for the virulent *Clostridium difficile* strain 630, describes a 19 gene cluster for ethanolamine degradation suggesting ethanolamine is likely a carbon source used by *C. difficile*.

Transcriptomics studies, in which mRNA transcript levels are determined by microarray or RNA-seq methods, can reveal metabolic pathways that are upregulated in one condition relative to another. For example, for *Clostridium difficile* in Ng et al. (Nature 2013, 502:7469), genes for catabolism of sialic acid and fucose were found to have increased levels of expression In vivo relative to when grown In vitro in growth medium, and in Janoir et al. (I&I 201381:3757), expression of genes required for catabolism of glucose, sorbitol and fructose are induced In vivo relative to in vitro, suggesting their use during infection.

Metabolomic studies in mice infected with *C. difficile*, indicate that sorbitol, mannitol, arabitol, xylitol, gluconate, sucrose and lactate levels were elevated when the mice were made susceptible to *C. difficile* infection by treatment with antibiotics, implicating those as important nutrients in vivo (Theriot et al., 2013 (*Nature Communications*).

Example 18: Quantification of Spore Concentrations Using DPA Assay

Methods to assess spore concentration in complex mixtures typically require the separation and selection of spores and subsequent growth of individual species to determine the colony forming units. The art does not teach how to quantitatively germinate all the spores in a complex mixture as there are many species for which appropriate germinants have not been identified. Furthermore, sporulation is thought to be a stochastic process as a result of evolutionary selection, meaning that not all spores from a single species germinate with same response to germinant concentration, time and other environmental conditions. Alternatively, a key metabolite of bacterial spores, dipicolinic acid (DPA) has been developed to quantify spores particles in a sample and avoid interference from fecal contaminants. The assay utilizes the fact that DPA chelates Terbium 3+ to form a luminescent complex (Fichtel et al, FEMS Microbiology Ecology, 2007; Kort et al, Applied and Environmental Microbiology, 2005; Shafaat and Ponce, Applied and Environmental Microbiology, 2006; Yang and Ponce, International Journal of Food Microbiology, 2009; Hindle and Hall, Analyst, 1999). A time-resolved fluorescence assay detects terbium luminescence in the presence of DPA giving a quantitative measurement of DPA concentration in a solution.

To perform the assay 1 mL of the spore standard to be measured was transferred to a 2 mL microcentrifuge tube. The samples were centrifuged at 13000 RCF for 10 min and the sample is washed in 1 mL sterile deionized $H_2O$. Wash an additional time by repeating the centrifugation. Transfer the 1 mL solution to hungate tubes and autoclave samples on a steam cycle for 30 min at 250 C. Add 100 uL of 30 uM $TbCl_3$ solution (400 mM sodium acetate, pH 5.0, 30 µM TbCba) to the sample. Make serial dilutions of the autoclaved material and measure the fluorescence of each sample by exciting with 275 nm light and measuring the emission wavelength of 543 nm for an integration time of 1.25 ms and a 0.1 ms delay.

Figure 6:
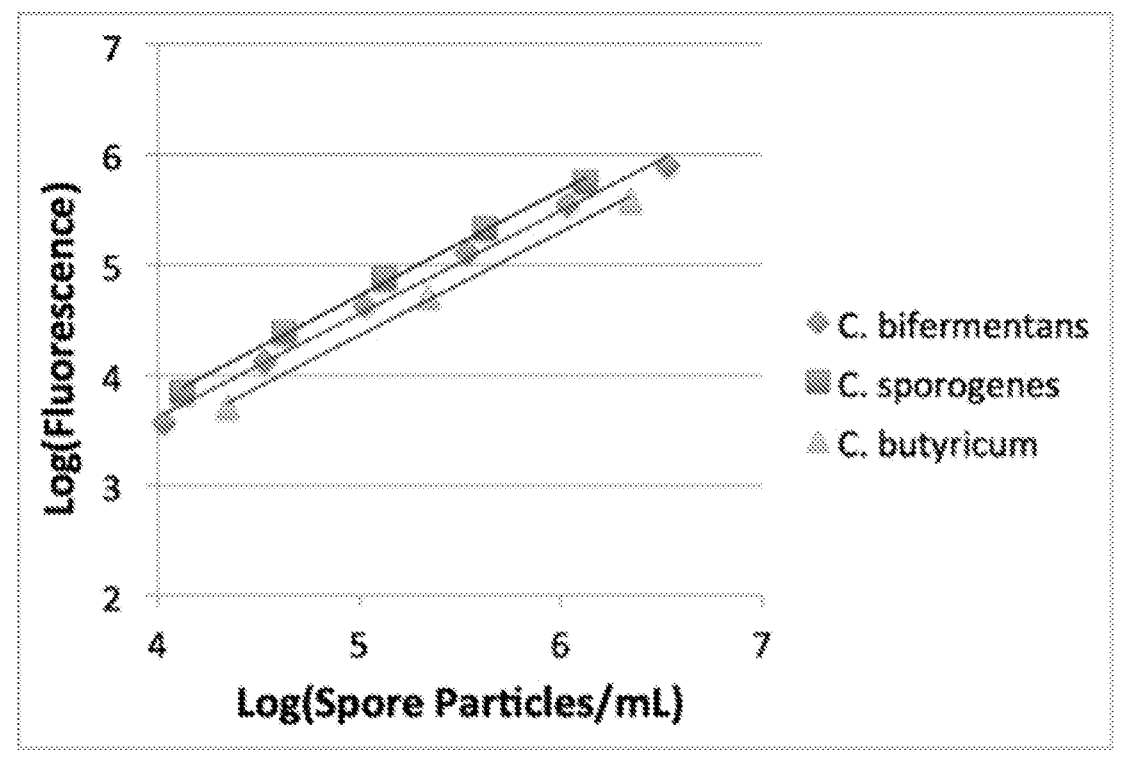

Purified spores are produced as described previously (e.g. see http://www.epa.gov/pesticides/methods/MB-28-00.pdf). Serial dilutions of purified spores from C. bifermentans, C. sporogenes, and C. butyricum cultures were prepared and measured by plating on BBA media and incubating overnight at 37 C to determine CFU/ml. FIG. 6 shows the linear correspondence across different spore producing bacteria across several logs demonstrating the DPA assay as means to assess spore content.

The discrepancy for complex spore populations between spore counts measured by germinable spore CFU and by DPA has Important Implications for determining the potency of an ethanol treated spore preparation for clinical use. Table AC shows spore content data from 3 different ethanol treated spore preparations used to successfully treat 3 patients suffering from recurrent *C. difficile* infection. The spore content of each spore preparation is characterized using the two described methods.

TABLE AC

Spore quantitation for ethanol treated spore preparations using spore CFU (SCFU) assay and DPA assay

| Preparation | SCFU/30 capsules | DPA SEq/30 capsules | Ratio SCFU/DPA |
|---|---|---|---|
| Preparation 1 | $4.0 \times 10^5$ | $6.8 \times 10^7$ | $5.9 \times 10^{-3}$ |
| Preparation 2 | $2.1 \times 10^7$ | $9.2 \times 10^8$ | 0.023 |
| Preparation 3 | $6.9 \times 10^9$ | $9.6 \times 10^9$ | 0.72 |

What is immediately apparent is that spore content varies greatly per 30 capsules. As measured by germinable SCFU, spore content varies by greater than 10,000-fold. As measured by DPA, spore content varies by greater than 100-fold. In the absence of the DPA assay, it would be difficult to set a minimum dose for administration to a patient. For instance, without data from the DPA assay, one would conclude that a minimum effective dose of spores is $4\times10^5$ or less using the SCFU assay (e.g. Preparation 1, Table AC). If that SCFU dose was used to normalize dosing in a clinical setting, however, then the actual spore doses given to patients would be much lower for other ethanol treated spore preparations as measured as by the DPA assay (Table AD).

TABLE AD

DPA doses in Table AC when normalized to $4 \times 10^5$ SCFU per dose

| Preparation | SCFU/30 capsules | DPA SEq/30 capsules | Fraction of Preparation 1 Dose |
|---|---|---|---|
| Preparation 1 | $4.0 \times 10^5$ | $6.8 \times 10^7$ | 1.0 |
| Preparation 2 | $4.0 \times 10^5$ | $1.8 \times 10^7$ | 0.26 |
| Preparation 3 | $4.0 \times 10^5$ | $5.6 \times 10^5$ | 0.0082 |

It becomes immediately obvious from the variability of SCFU and DPA counts across various donations that using SCFU as the measure of potency would lead to significant underdosing in certain cases. For instance, setting a dose specification of $4\times10^5$ SCFU (the apparent effective dose from donor Preparation 1) for product Preparation 3 would lead to a potential underdosing of more than 100-fold. This can be rectified only by setting potency specifications based on the DPA assay which better reflects total spore counts in an ethanol treated spore preparation. The unexpected finding of this work is that the DPA assay is uniquely suited to set potency and determine dosing for an ethanol treated spore preparation.

Example 19: Engraftment, Augmentation and Reduction of Pathogen Carriage in Patients Treated with Spore Compositions Complementary genomic and microbiological methods were used to characterize the composition of the microbiota from Patient 1, 2, 3, 4, and 5, 6, 7, 8, 9, and 10 at pretreatment (pretreatment) and on up to 4 weeks post-treatment.

To determine the OTUs that engraft from treatment with an ethanol treated spore preparation in the patients and how their microbiome changed in response, the microbiome was characterized by 16S-V4 sequencing prior to treatment (pretreatment) with an ethanol treated spore preparation and up to 25 days after receiving treatment. Alternatively, one might use a bacterial composition in the vegetative state, or a mixture of vegetative bacteria and bacterial spores. As example, the treatment of patient 1 with an ethanol treated spore preparation led to the engraftment of OTUs from the spore treatment and augmentation in the microbiome of the patient (FIG. 7 and FIG. 8). By day 25 following treatment, the total microbial carriage was dominated by species of the following taxonomic groups: *Bacteroides, Sutterella, Ruminococcus, Blautia, Eubacterium, Gemmiger/Faecalibacterium*, and the non-sporeforming *Lactobacillus* (see Table 16 and Table 1 for specific OTUs). The first two genera represent OTUs that do not form spores while the latter taxonomic groups represent OTUs that are believed to form spores.

Patient treatment with the ethanol treated spore preparation leads to the establishment of a microbial ecology that has greater diversity than prior to treatment (FIG. 7). Genomic-based microbiome characterization confirmed engraftment of a range of OTUs that were absent in the patient pretreatment (Table 16). These OTUs comprised both bacterial species that were capable and not capable of forming spores, and OTUs that represent multiple phylogenetic clades. Organisms absent in Patient 1 pre-treatment either engraft directly from the ethanol treated spore fraction or are augmented by the creation of a gut environment favoring a healthy, diverse microbiota. Furthermore, *Bacteroides fragilis* group species were increased by 4 and 6 logs in patients 1 and 2 (FIG. 9).

The results are shown in FIG. 7: Microbial diversity measured in the ethanol treated spore treatment sample and patient pre- and post-treatment samples. Total microbial diversity Is defined using the Chao1 Alpha-Diversity Index and Is measured at different genomic sampling depths to confirm adequate sequence coverage to assay the microbiome in the target samples. The patient pretreatment (purple) harbored a microbiome that was significantly reduced in total diversity as compared to the ethanol treated spore treatment (red) and patient post treatment at days 5 (blue), 14 (orange), and 25 (green).

The results are shown in FIG. 8. Patient microbial ecology is shifted by treatment with an ethanol treated spore treatment from a dysbiotic state to a state of health. Principle Coordinates Analysis based on the total diversity and structure of the microbiome (Bray-Curtis Beta-Diversity) of the patient pre- and post-treatment delineates that the engraftment of OTUs from the spore treatment and the augmentation of the patient microbial ecology leads to a microbial ecology that is distinct from both the pretreatment microbiome and the ecology of the ethanol treated spore treatment (Table 16).

Figure 9:
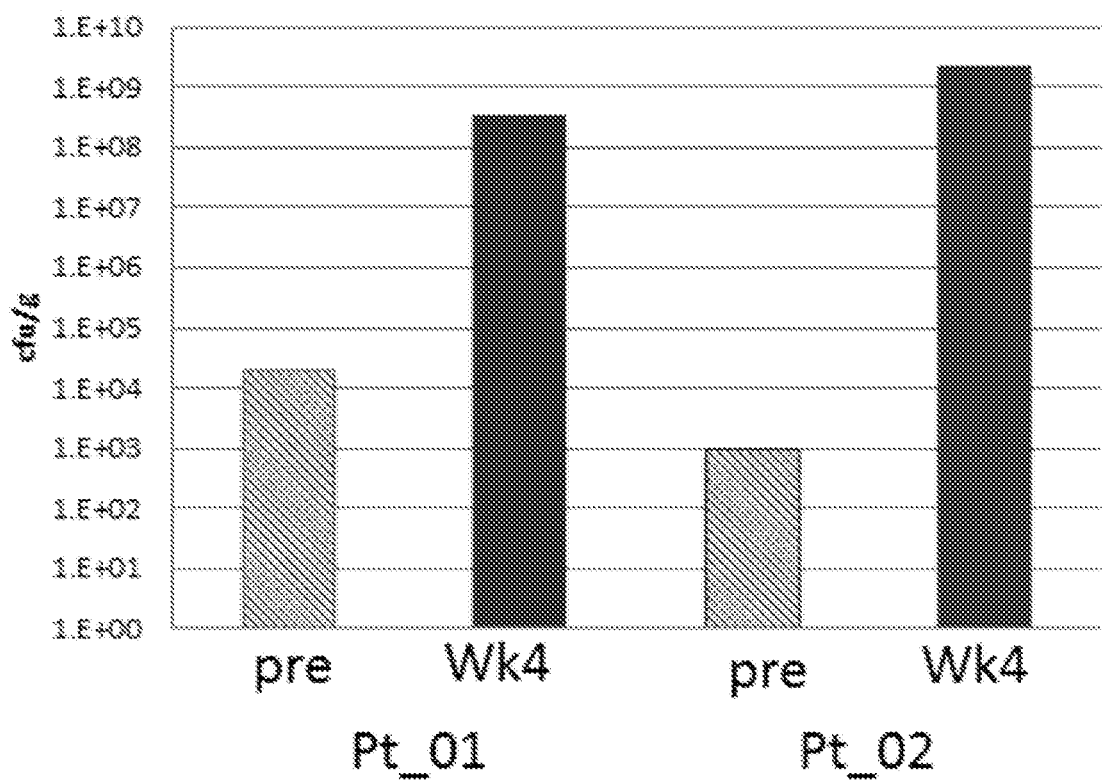
FIG. 9 illustrates Augmentation of *Bacteroides* species in patients.

Results are shown in FIG. 9 illustrating the augmentation of *Bacteroides* species in patients. Comparing the number of *Bacteroides fragilis* groups species per cfu/g of feces pretreatment and in week 4 post treatment reveals an increase of 4 logs or greater. The ability of 16S-V4 OTU identification to assign an OTU as a specific species depends in part on the resolution of the 16S-V4 region of the 16S gene for a particular species or group of species. Both the density of available reference 16S sequences for different regions of the tree as well as the inherent variability in the 16S gene between different species will determine the definitiveness of a taxonomic annotation to a given sequence read. Given the topological nature of a phylogenetic tree and that the tree represents hierarchical relationships of OTUs to one another based on their sequence similarity and an underlying evolutionary model, taxonomic annotations of a read can be rolled up to a higher level using a clade-based assignment procedure (Table 1). Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) within a 5% genetic similarity. OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, play similar functional roles in a microbial ecology such as that found in the human gut. Compositions substituting one species with another from the same clade are likely to have conserved ecological function and therefore are useful in the present invention.

Stool samples were aliquoted and resuspended 10× vol/wt in either 100% ethanol (for genomic characterization) or PBS containing 15% glycerol (for isolation of microbes) and then stored at −80° C. until needed for use. For genomic 16S sequence analysis colonies picked from plate isolates had their full-length 16S sequence characterized as described in Examples 2 and 3, and primary stool samples were prepared targeting the 16S-V4 region using the method for heterogeneous samples in Example 10.

Notably, 16S sequences of isolates of a given OTU are phylogenetically placed within their respective clades despite that the actual taxonomic assignment of species and genus may suggest they are taxonomically distinct from other members of the clades In which they fall. Discrepancies between taxonomic names given to an OTU is based on microbiological characteristics versus genetic sequencing are known to exist from the literature. The OTUs footnoted in this table are known to be discrepant between the different methods for assigning a taxonomic name.

Engraftment of OTUs from the ethanol treated spore preparation treatment into the patient as well as the resulting augmentation of the resident microbiome led to a significant decrease in and elimination of the carriage of pathogenic species other than *C. difficile* in the patient. 16S-V4 sequencing of primary stool samples demonstrated that at pretreatment, 20% of reads were from the genus *Klebsiella* and an additional 19% were assigned to the genus *Fusobacterium*. These striking data are evidence of a profoundly dysbiotic microbiota associated with recurrent *C. difficile* infection and chronic antibiotic use. In healthy individuals, *Klebsiella* is a resident of the human microbiome in only about 2% of subjects based on an analysis of HMP database (www.hmpdacc.org), and the mean relative abundance of *Klebsiella* is only about 0.09% in the stool of these people. It's surprising presence at 20% relative abundance in Patient 1 before treatment is an indicator of a proinflammatory gut environment enabling a "pathobiont" to overgrow and outcompete the commensal organisms normally found in the gut. Similarly, the dramatic overgrowth of *Fusobacterium* indicates a profoundly dysbiotic gut microbiota. One species of *Fusobacterium*, *F. nucleatum* (an OTU phylogenetically indistinguishable from *Fusobacterdum* sp. 3_1_33 based on 16S-V4), has been termed "an emerging gut pathogen" based on its association with IBD, Crohn's disease, and colorectal cancer in humans and its demonstrated causative role in the development of colorectal cancer in animal models [Allen-Vercoe, Gut Microbes (2011) 2:294-8]. Importantly, neither *Klebsiella* nor *Fusobacterium* was detected in the 16S-V4 reads by Day 25 (Table 18).

To further characterize the colonization of the gut by *Klebsiella* and other Enterobacteriaceae and to speciate these organisms, pretreatment and Day 25 fecal samples stored at −80 C as PBS-glycerol suspensions were plated on a variety of selective media including MacConkey lactose media (selective for gram negative enterobacteria) and Simmons Citrate Inositol media (selective for *Klebsiella* spp) [Van Cregten et al, J. Clin. Microbiol. (1984) 20: 936-41]. Enterobacteria identified in the patient samples included *K. pneumoniae*, *Klebsiella* sp. Co_9935 and *E. coli*. Strikingly, each *Klebsiella* species was reduced by 2-4 logs whereas *E. coli*, a normal commensal organism present in a healthy microbiota, was reduced by less than 1 log (Table 19). This decrease in *Klebsiella* spp. carriage is consistent across multiple patients. Four separate patients were evaluated for the presence of *Klebsiella* spp. pre treatment and 4 weeks post treatment. *Klebsiella* spp. were detected by growth on selective Simmons Citrate Inositol media as previously described. Serial dilution and plating, followed by determining cfu/mL titers of morphologically distinct species and 16S full length sequence identification of representatives of those distinct morphological classes, allowed calculation of titers of specific species.

The genus *Bacteroides* is an important member of the gastrointestinal microbiota; 100% of stool samples from the Human Microbiome Project contain at least one species of *Bacteroides* with total relative abundance in these samples ranging from 0.96% to 93.92% with a median relative abundance of 52.67% (www.hmodacc.org reference data set HMSMCP). *Bacteroides* in the gut has been associated with amino acid fermentation and degradation of complex polysaccharides. Its presence in the gut is enhanced by diets rich in animal-derived products as found in the typical western diet [David, L. A. et al, Nature (2013) doi:10.1038/nature12820]. Strikingly, prior to treatment, fewer than 0.008% of the 16S-V4 reads from Patient 1 mapped to the genus *Bacteroides* strongly suggesting that *Bacteroides* species were absent or that viable *Bacteroides* were reduced to an extremely minor component of the patient's gut microbiome. Post treatment, 242% of the 16S-V4 reads could be assigned to the genus *Bacteroides* within 5 days of treatment and by Day 25 post treatment 59.48% of the patients gut microbiome was comprised of *Bacteroides*. These results were confirmed microbiologically by the absence of detectable *Bacteroides* in the pretreatment sample plated on two different *Bacteroides* selective media: *Bacteroides* Bile Esculin (BBE) agar which is selective for *Bacteroides fragilis* group species [Livingston, S. J. et al *J. Clin. Microblol* (1978). 7: 448-453] and Polyamine Free Arabinose (PFA) agar [Noack et al. *J. Nutr.* (1998) 128: 1385-1391; modified by replacing glucose with arabinose]. The highly selective BBE agar had a limit of detection of <$2\times10^3$ cfu/g, while the limit of detection for *Bacteroides* on PFA agar was approximately $2\times10^7$ cfu/g due to the growth of multiple non-*Bacteroides* species in the pretreatment sample on that medium. Colony counts of *Bacteroides* species on Day 25 were up to $2\times10^{10}$ cfu/g, consistent with the 16S-V4 sequencing, demonstrating a profound reconstitution of the gut microbiota in Patient 1 (Table 20).

The significant abundance of *Bacteroides* in Patient 1 on Day 25 (and as early as Day 5 as shown by 16S-V4 sequencing) is remarkable. Viable *Bacteroides fragilis* group species were not present in the ethanol treated spore population based on microbiological plating (limit of detection of 10 cfu/ml). Thus, administration of the ethanol treated spore population to Patient 1 resulted not only in the engraftment of bacterial species such as but not limited to spore forming species, but also the restoration of high levels of ion-spore forming species commonly found in healthy individuals through the creation of a niche that allowed for the repopulation of *Bacteroides* species. These organisms were most likely either present at extremely low abundance in the GI tract of Patient 1, or present in a reservoir in the GI tract from which they could rebound to high titer. Those species may also be reinoculated via oral uptake from food following treatment. We term this healthy repopulation of the gut with OTUs that are not present in the bacterial composition such as but not limited to a spore population or ethanol treated spore population, "Augmentation." Augmentation is an important phenomenon in that it shows the ability to use an ethanol treated spore ecology or other bacterial composition to restore a healthy microbiota by seeding a diverse array or commensal organisms beyond the actual component organisms in the bacterial composition such as but not limited to an ethanol treated spore population itself; specifically the spore composition treatment itself and the engraftment of OTUs from the spore composition create a niche that enables the outgrowth of OTUs required to shift a dysbiotic microbiome to a microbial ecology that is associated with health. The diversity of *Bacteroides* species and their approximate relative abundance in the gut of Patient 1 is shown in Table 21, comprising at least 8 different species.

Figure 10:
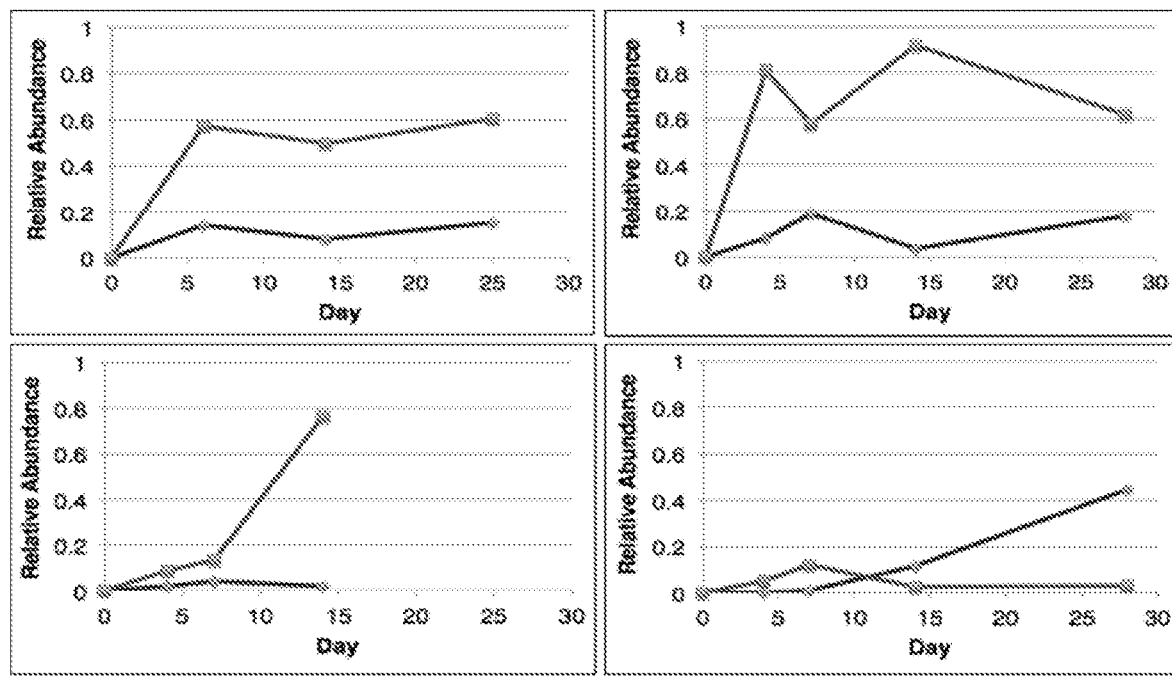
FIG. 10 illustrates species Engrafting versus Species Augmenting in patient's microbiomes after treatment with an ethanol-treated spore preparation.

The results are shown in FIG. 10; the figure illustrates Species Engrafting versus Species Augmenting in patients microbiomes after treatment with a bacterial composition such as but not limited to an ethanol-treated spore population. Relative abundance of species that engrafted or augmented as described were determined based on the number of 16S sequence reads. Each plot is from a different patient treated with the bacterial composition such as but not limited to an ethanol-treated spore population for recurrent *C. difficile.*

The impact of the bacterial composition such as but not limited to an ethanol treated spore population treatment on carriage of imipenem resistant Enterobacterdaceae was assessed by plating pretreatment and Day 28 clinical samples from Patients 2, 4 and 5 on MacConkey lactose plus 1 ug/mL of imipenem. Resistant organisms were scored by morphology, enumerated and DNA was submitted for full length 16S rDNA sequencing as described above. Isolates were Identified as *Morganella morganii, Providencia rettgert* and *Proteus pennerii.* Each of these are gut commensal organisms; overgrowth can lead to bacteremia and/or urinary tract infections requiring aggressive antibiotic treatment and, in some cases, hospitalization [Kim, B-N, et al Scan *J. Inf Dis* (2003) 35: 98-103; Lee, I-K and Liu, J-W *J. Microbiol Immunol Infect* (2006) 39: 328-334; O'Hara et al, *Clin Microbiol Rev* (2000) 13: 534]. The titer of organisms at pretreatment and Day 28 by patient is shown in Table 22. Importantly, administration of the bacterial composition such as but not limited to an ethanol treated spore preparation resulted in greater than 100-fold reduction in 4 of 5 cases of Enterobactenaceae carriage with multiple imipenem resistant organisms (Table 22).

In addition to speciation and enumeration, multiple isolates of each organism from Patient 4 were grown overnight in 96-well trays containing a 2-fold dilution series of imipenem in order to quantitatively determine the minimum Inhibitory concentration (MIC) of antibiotic. Growth of organisms was detected by light scattering at 600 nm on a SpectraMax M5e plate reader. In the clinical setting, these species are considered resistant to imipenem if they have an MIC of 1 ug/mL or greater. M. morganhiisolates from pretreatment samples from Patient D had MICs of 2-4 ug/mL and *P. pennerii* Isolates had MICs of 4-8 ug/mL. Thus the bacterial composition such as but not limited to an ethanol treated spores administered to Patient 4 caused the clearance of 2 imipenem resistant organisms (Table 16). While this example specifically uses a spore preparation, the methods herein describe how one skilled in the art would use a more general bacterial composition to achieve the same effects. The specific example should not be viewed as a limitation of the scope of this disclosure.

Example 20. Identifying the Core Ecology from the Bacterial Combination

Ten different bacterial compositions were made by the ethanol treated spore preparation methods from 6 different donors (as described herein). The spore preparations were used to treat 10 patients, each suffering from recurrent *C. difficile* infection. Patients were identified using the inclusion/exclusion criteria described herein, and donors were identified using the criteria described herein. None of the patients experienced a relapse of *C. difficile* in the 4 weeks of follow up after treatment, whereas the literature would predict that 70-80% of subjects would experience a relapse following cessation of antibiotic [Van Nood, et al, *NEJM* (2013)]. Thus, the ethanol treated spore preparations derived from multiple different donors and donations showed remarkable clinical efficacy. These ethanol treated spore preparations are a subset of the bacterial compositions described herein and the results should not be viewed as a limitation on the scope of the broader set of bacterial compositions.

To define the Core Ecology underlying the remarkable clinical efficacy of the bacterial compositions e.g. ethanol treated spore preparations, the following analysis was carried out. The OTU composition of the spore preparation was determined by 16S-V4 rDNA sequencing and computational assignment of OTUs per Example 12. A requirement to detect at least ten sequence reads in the ethanol treated spore preparation was set as a conservative threshold to define only OTUs that were highly unlikely to arise from errors during amplification or sequencing. Methods routinely employed by those familiar to the art of genomic-based microbiome characterization use a read relative abundance threshold of 0.005% (see e.g. Bokulich, A. et al. 2013.

Quality-filtering vastly improves diversity estimates from Illumina amplicon sequencing. Nature Methods 10: 57-59), which would equate to ≥2 reads given the sequencing depth obtained for the samples analyzed in this example, as cut-off which is substantially lower than the ≥10 reads used in this analysis. All taxonomic and clade assignments were made for each OTU as described in herein. The resulting list of OTUs, clade assignments, and frequency of detection in the spore preparations are shown in Table GB. OTUs that engraft in a treated patients and the percentage of patients in which they engraft are denoted, as are the clades, spore forming status, and Keystone OTU status. Bolded OTUs occur in 280% of the ethanol preps and engraft in ≥50% of the treated patients.

TABLE GB

OTUs detected by a minimum of ten 16S-V4 sequence reads in at least a one ethanol treated spore preparation (pan-microbiome).

| OTU | Clade | % of Spore Preps with OTU | % of Patients OTU Engrafts | Spore Former | Keystone OTU |
|---|---|---|---|---|---|
| Prevotella_maculosa | clade_104 | 10% | 0% | N | N |
| Prevotella_copri | clade_168 | 20% | 0% | N | N |
| Bacteroides_caccae | clade_170 | 30% | 0% | N | Y |
| Bifidobacterium_sp_TM_7 | clade_172 | 90% | 60% | N | N |
| Bifidobacterium_gallicum | clade_172 | 70% | 20% | N | N |
| Bifidobacterium_dentium | clade_172 | 50% | 0% | N | N |
| Lactobacillus_casei | clade_198 | 20% | 10% | N | N |
| Actinomyces_odontolyticus | clade_212 | 20% | 30% | N | N |
| Clostridium_colicanis | clade_223 | 10% | 10% | Y | N |
| Clostridiales_sp_SS3_4 | clade_246 | 100% | 70% | Y | N |
| Clostridium_sporogenes | clade_252 | 40% | 40% | Y | N |
| Clostridium_butyricum | clade_252 | 20% | 20% | Y | N |
| Clostridium_disporicum | clade_253 | 40% | 30% | Y | N |
| Clostridium_hylemonae | clade_260 | 100% | 50% | Y | N |
| Clostridium_scindens | clade_260 | 10% | 60% | Y | N |
| Coprococcus_comes | clade_262 | 90% | 80% | Y | Y |
| Lachnospiraceae_bacterium_1_4_56 FAA | clade_262 | 90% | 80% | Y | Y |
| Ruminococcus_torques | clade_262 | 30% | 70% | Y | Y |
| Parabacteroides_merdae | clade_286 | 30% | 20% | N | Y |
| Bifidobacterium_bifidum | clade_293 | 10% | 0% | N | N |
| Johnsonella_ignava | clade_298 | 10% | 10% | N | N |
| Blautia_glucerasea | clade_309 | 100% | 80% | Y | N |
| Blautia_sp_M25 | clade_309 | 100% | 70% | Y | Y |
| Lachnospiraceae_bacterium_6_1_63 FAA | clade_309 | 100% | 60% | Y | N |
| Eubacterium_cellulosolvens | clade_309 | 10% | 30% | Y | Y |
| Lactobacillus_fermentum | clade_313 | 10% | 0% | N | N |
| Sarcina_ventriculi | clade_353 | 10% | 10% | Y | N |
| Clostridium_bartlettii | clade_354 | 90% | 70% | Y | N |
| Clostridium_bifermentans | clade_354 | 70% | 70% | Y | N |
| Clostridium_mayombei | clade_354 | 50% | 50% | Y | N |
| Dorea_longicatena | clade_360 | 100% | 60% | Y | Y |
| Lachnospiraceae_bacterium_9_1_43 BFAA | clade_360 | 100% | 30% | Y | N |
| Lachnospiraceae_bacterium_2_1_58 FAA | clade_360 | 80% | 80% | Y | N |
| Lachnospiraceae_bacterium_2_1_46 FAA | clade_360 | 50% | 50% | Y | N |
| Lactobacillus_perolens | clade_373 | 10% | 0% | N | N |
| Bacteroides_dorei | clade_378 | 60% | 50% | N | Y |
| Eubacterium_biforme | clade_385 | 10% | 0% | Y | N |
| Peptoniphilus_sp_gpac077 | clade_389 | 10% | 20% | N | N |
| Coprococcus_catus | clade_393 | 100% | 70% | Y | Y |
| Eubacterium_hallii | clade_396 | 90% | 60% | Y | Y |
| Anaerosporobacter_mobilis | clade_396 | 40% | 60% | Y | N |
| Bacteroides_pectinophilus | clade_396 | 10% | 60% | Y | N |
| Lactobacillus_hominis | clade_398 | 10% | 0% | N | N |
| Lactococcus_lactis | clade_401 | 40% | 40% | N | N |
| Ruminococcus_champanellensis | clade_406 | 80% | 50% | Y | N |
| Ruminococcus_callidus | clade_406 | 10% | 10% | Y | N |
| Clostridium_clostridioforme | clade_408 | 100% | 60% | Y | Y |
| Eubacterium_hadrum | clade_408 | 100% | 90% | Y | Y |
| Clostridium_symbiosum | clade_408 | 30% | 50% | Y | Y |
| Anaerostipes_caccae | clade_408 | 10% | 50% | Y | N |
| Parasutterella_excrementihominis | clade_432 | 10% | 0% | N | N |
| Sutterella_stercoricanis | clade_432 | 10% | 0% | N | N |
| Eubacterium_rectale | clade_444 | 100% | 80% | Y | Y |
| Lachnobacterium_bovis | clade_444 | 100% | 80% | Y | N |
| Desulfovibrio_desulfuricans | clade_445 | 10% | 0% | N | Y |

TABLE GB-continued

OTUs detected by a minimum of ten 16S-V4 sequence reads in at least a one ethanol treated spore preparation (pan-microbiome).

| OTU | Clade | % of Spore Preps with OTU | % of Patients OTU Engrafts | Spore Former | Keystone OTU |
|---|---|---|---|---|---|
| Eubacterium_sp_oral_clone_JS001 | clade_476 | 80% | 70% | Y | N |
| Faecalibacterium_prausnitzii | clade_478 | 100% | 60% | Y | Y |
| Subdoligranulum_variabile | clade_478 | 100% | 80% | Y | Y |
| Coprobacillus_sp_D7 | clade_481 | 90% | 60% | Y | N |
| Clostridium_cocleatum | clade_481 | 60% | 20% | Y | N |
| Clostridium_spiroforme | clade_481 | 40% | 50% | Y | N |
| Eubacterium_ramulus | clade_482 | 80% | 60% | Y | N |
| Flavonifractor_plautii | clade_494 | 70% | 60% | Y | Y |
| Pseudoflavonifractor_capillosus | clade_494 | 60% | 60% | Y | Y |
| Ruminococcaceae_bacterium_D16 | clade_494 | 30% | 50% | Y | Y |
| Acetivibrio_cellulolyticus | clade_495 | 70% | 80% | Y | N |
| Clostridium_stercorarium | clade_495 | 40% | 50% | Y | N |
| Enterococcus_durans | clade_497 | 10% | 10% | N | N |
| Enterococcus_faecium | clade_497 | 10% | 10% | N | N |
| Dialister_invisus | clade_506 | 50% | 10% | N | N |
| Eubacterium_limosum | clade_512 | 20% | 0% | Y | N |
| Ruminococcus_flavefaciens | clade_516 | 60% | 60% | Y | N |
| Eubacterium_ventriosum | clade_519 | 30% | 60% | Y | Y |
| Bilophila_wadsworthia | clade_521 | 90% | 0% | N | Y |
| Lachnospira_pectinoschiza | clade_522 | 40% | 60% | Y | N |
| Eubacterium_eligens | clade_522 | 30% | 50% | Y | Y |
| Catonella_morbi | clade_534 | 20% | 0% | N | N |
| Clostridium_sporosphaeroides | clade_537 | 100% | 80% | Y | N |
| Ruminococcus_bromii | clade_537 | 60% | 30% | Y | Y |
| Clostridium_leptum | clade_537 | 40% | 70% | Y | Y |
| Clostridium_sp_YIT_12069 | clade_537 | 40% | 60% | Y | N |
| Clostridium_viride | clade_540 | 10% | 10% | Y | N |
| Megamonas_funiformis | clade_542 | 50% | 0% | N | N |
| Eubacterium_ruminantium | clade_543 | 80% | 90% | Y | N |
| Coprococcus_eutactus | clade_543 | 20% | 20% | Y | N |
| Collinsella_aerofaciens | clade_553 | 50% | 10% | Y | Y |
| Alkaliphilus_metalliredigenes | clade_554 | 40% | 10% | Y | N |
| Turicibacter_sanguinis | clade_555 | 80% | 40% | Y | N |
| Phascolarctobacterium_faecium | clade_556 | 20% | 0% | N | N |
| Clostridiales_bacterium_oral_clone_P4PA | clade_558 | 80% | 50% | N | N |
| Lutispora_thermophila | clade_564 | 100% | 0% | Y | N |
| Coriobacteriaceae_bacterium_JC110 | clade_566 | 70% | 0% | N | N |
| Eggerthella_sp_1_3_56FAA | clade_566 | 70% | 30% | N | N |
| Adlercreutzia_equolifaciens | clade_566 | 40% | 0% | N | N |
| Gordonibacter_pamelaeae | clade_566 | 30% | 0% | N | Y |
| Slackia_isoflavoniconvertens | clade_566 | 10% | 0% | N | N |
| Eubacterium_desmolans | clade_572 | 90% | 70% | Y | N |
| Papillibacter_cinnamivorans | clade_572 | 90% | 80% | Y | N |
| Clostridium_colinum | clade_576 | 30% | 30% | Y | N |
| Akkermansia_muciniphila | clade_583 | 60% | 10% | N | Y |
| Clostridiales_bacterium_oral_taxon_F32 | clade_584 | 60% | 30% | N | N |
| Prochlorococcus_marinus | clade_592 | 30% | 0% | N | N |
| Methanobrevibacter_wolinii | clade_595 | 30% | 0% | N | N |
| Bacteroides_fragilis | clade_65 | 20% | 30% | N | Y |
| Lactobacillus_delbrueckii | clade_72 | 10% | 0% | N | N |
| Escherichia_coli | clade_92 | 50% | 0% | N | Y |
| Clostridium_sp_D5 | clade_96 | 80% | 60% | Y | N |
| Streptococcus_thermophilus | clade_98 | 90% | 20% | N | Y |
| Streptococcus_sp_CM6 | clade_98 | 20% | 10% | N | N |
| Streptococcus_sp_oral_clone_ASCE05 | clade_98 | 10% | 0% | N | N |

Next, it was reasoned that for an OTU to be considered a member of the Core Ecology of the bacterial composition, that OTU must be shown to engraft in a patient. Engraftment is important for two reasons. First, engraftment is a sine qua non of the mechanism to reshape the microbiome and eliminate *C. difficile* colonization. OTUs that engraft with higher frequency are highly likely to be a component of the Core Ecology of the spore preparation or broadly speaking a set bacterial composition. Second, OTUs detected by sequencing a bacterial composition (as in Table GB) may include non-viable cells or other contaminant DNA molecules not associated with the composition. The requirement that an OTU must be shown to engraft in the patient eliminates OTUs that represent non-viable cells or contaminating sequences. Table GB also Identifies all OTUs detected in the bacterial composition that also were shown to engraft in at least one patient post-treatment. OTUs that are present in a large percentage of the bacterial composition e.g. ethanol spore preparations analyzed and that engraft in a large number of patients represent a subset of the Core Ecology that are highly likely to catalyze the shift from a dysbiotic disease ecology to a healthy microbiome.

A third lens was applied to further refine insights into the Core Ecology of the bacterial composition e.g. spore preparation. Computational-based, network analysis has enabled the description of microbial ecologies that are present in the microbiota of a broad population of healthy individuals. These network ecologies are comprised of multiple OTUs, some of which are defined as Keystone OTUs. Keystone OTUs are computationally defined as described herein. Keystone OTUs form a foundation to the microbially ecologies in that they are found and as such are central to the function of network ecologies in healthy subjects. Keystone OTUs associated with microbial ecologies associated with healthy subjects are often are missing or exist at reduced levels in subjects with disease. Keystone OTUs may exist in low, moderate, or high abundance in subjects. Table GB further notes which of the OTUs in the bacterial composition e.g. spore preparation are Keystone OTUs exclusively associated with individuals that are healthy and do not harbor disease.

There are several Important findings from this data. A relatively small number of species, 16 in total, are detected in all of the spore preparations from 6 donors and 10 donations. This is surprising because the HMP database (www.hmpdacc.org) describes the enormous variability of commensal species across healthy individuals. The presence of a small number of consistent OTUs lends support to the concept of a Core Ecology. The engraftment data further supports this conclusion. A regression analysis shows a significant correlation between frequency of detection in a spore preparation and frequency of engraftment in a donor: R=0.43 (p<0.001). While this may seem obvious, there is no a priori requirement that an OTU detected frequently in the bacterial composition e.g. spore preparation will or should engraft. For instance, *Lutispora thermophila*, a spore former found in all ten spore preparations, did not engraft in any of the patients. *Bilophila wadsworthia*, a gram negative anaerobe, is present in 9 of 10 donations, yet it does not engraft in any patient, indicating that it is likely a non-viable contaminant in the ethanol treated spore preparation. Finally, it is worth noting the high preponderance of previously defined Keystone OTUs among the most frequent OTUs in the spore preparations.

These three factors-prevalence in the bacterial composition such as but not limited to a spore preparation, frequency of engraftment, and designation as a Keystone OTUs-enabled the creation of a "Core Ecology Score" (CES) to rank individual OTUs. CES was defined as follows:

40% weighting for presence of OTU in spore preparation
multiplier of i for presence in 1-3 spore preparations
multiplier of 2.5 for presence in 4-8 spore preparations
multiplier of 5 for presences in ≥9 spore preparations
40% weighting for engraftment in a patient
multiplier of 1 for engraftment in 1-4 patients
multiplier of 2.5 for engraftment in 5-6 patients
multiplier of 5 for engraftment in ≥7 patients
20% weighting to Keystone OTUs
multiplier of 1 for a Keystone OTU
multiplier of 0 for a non-Keystone OTU Using this guide, the CES has a maximum possible score of 5 and a minimum possible score of 0.8. As an example, an OTU found in 8 of the 10 bacterial composition such as but not limited to a spore preparations that engrafted in 3 patients and was a Keystone OTU would be assigned the follow CES:

$$CES=(0.4\times2.5)+(0.4\times1)+(0.2\times Y)=1.6$$

Table GC ranks the top 20 OTUs by CES with the further requirement that an OTU must be shown to engraft to be a considered an element of a core ecology.

TABLE GC

Top 20 OTUs ranked by CES

| OTU | Clade | CES | Spore Former | Keystone OTU |
| --- | --- | --- | --- | --- |
| Eubacterium_hadrum | clade_408 | 4.2 | Y | Y |
| Eubacterium_rectale | clade_444 | 4.2 | Y | Y |
| Subdoligranulum_variabile | clade_478 | 4.2 | Y | Y |
| Blautia_sp_M25 | clade_309 | 4.2 | Y | Y |
| Coprococcus_catus | clade_393 | 4.2 | Y | Y |
| Lachnospiraceae_bacterium_1_4_56FAA | clade_262 | 4.2 | Y | Y |
| Coprococcus_comes | clade_262 | 4.2 | Y | Y |
| Blautia_glucerasea | clade_309 | 4.0 | Y | N |
| Lachnobacterium_bovis | clade_444 | 4.0 | Y | N |
| Clostridium_sporosphaeroides | clade_537 | 4.0 | Y | N |
| Clostridiales_sp_SS3_4 | clade_246 | 4.0 | Y | N |
| Papillibacter_cinnamivorans | clade_572 | 4.0 | Y | N |
| Clostridium_bartlettii | clade_354 | 4.0 | Y | N |
| Eubacterium_desmolans | clade_572 | 4.0 | Y | N |
| Clostridium_clostridioforme | clade_408 | 3.2 | Y | Y |
| Dorea_longicatena | clade_360 | 3.2 | Y | Y |
| Faecalibacterium_prausnitzii | clade_478 | 3.2 | Y | Y |
| Eubacterium_hallii | clade_396 | 3.2 | Y | Y |
| Clostridium_leptum | clade_537 | 3.2 | Y | Y |
| Lachnospiraceae_bacterium_6_1_63FAA | clade_309 | 3.0 | Y | N |

Example 21. Defining Efficacious Subsets of the Core Ecology

The number of organisms in the human gastrointestinal tract, as well as the diversity between healthy individuals, is indicative of the functional redundancy of a healthy gut microbiome ecology (see The Human Microbiome Consortia. 2012. Structure, function and diversity of the healthy human microbiome. Nature 486: 207-214). This redundancy makes it highly likely that subsets of the Core Ecology describe therapeutically beneficial components of the bacterial composition such as but not limited to an ethanol treated spore preparation and that such subsets may themselves be useful compositions for the treatment of *C. difficile* infection given the ecologies functional characteristics. Using the CES, Individual OTUs can be prioritized for evaluation as an efficacious subset of the Core Ecology.

Another aspect of functional redundancy is that evolutionarily related organisms (i.e. those close to one another on the phylogenetic tree, e.g. those grouped into a single clade) will also be effective substitutes in the Core Ecology or a subset thereof for treating C. difficile.

To one skilled in the art, the selection of appropriate OTU subsets for testing in vitro or in vivo (e.g. see Examples 6 or 7) is straightforward. Subsets may be selected by picking any 2, 3, 4, 5, 6, 7, 8, 9, 10, or more than 10 OTUs from Table GB, with a particular emphasis on those with higher CES, such as the OTUs described in Table GC. In addition, using the clade relationships defined in Example 2 and Table 1 above, related OTUs can be selected as substitutes for OTUs with acceptable CES values. These organisms can be cultured anaerobically in vitro using the appropriate media (selected from those described in Example 5 above), and then combined in a desired ratio. A typical experiment in the mouse C. difficile model utilizes at least $10^4$ and preferably at least $10^5$, $10^6$, $10^7$, $10^8$, $10^9$ or more than $10^{10}$ colony forming units of a each microbe in the composition. Variations in the culture yields may sometimes mean that organisms are combined in unequal ratios, e.g. 1:10, 1:100, 1:1,000, 1:10,000, 1:100,000, or greater than 1:100,000. What is important in these compositions is that each strain be provided in a minimum amount so that the strain's contribution to the efficacy of the Core Ecology subset can be measured. Using the principles and Instructions described here, it is straightforward for one of skill in the art to make clade-based substitutions to test the efficacy of subsets of the Core Ecology. Table GB describes the clades for each OTU detected in a spore preparation and Table 1 describes the OTUs that can be used for substitutions based on clade relationships.

Example 22: Prophylactic Use and Treatment in a Mouse Model of Vancomycin Resistant *Enterococcus* (VRE) Colonization The emergence and spread of highly antibiotic-resistant bacteria represent a major clinical challenge (Snitkin et al Science Translational Medicine, 2012). In recent years, the numbers of infections caused by organisms such as methicillin-resistant *Staphylococcus aureus*, carbapenem-resistant Enterobacteriaceae, vancomycin-resistant *Enterococcus* (VRE), and *Clostridium difficile* have increased markedly, and many of these strains are acquiring resistance to the few remaining active antibiotics. Most infections produced by highly antibiotic-resistant bacteria are acquired during hospitalizations, and preventing patient-to-patient transmission of these pathogens is one of the major challenges confronting hospitals and clinics. Most highly antibiotic-resistant bacterial strains belong to genera that colonize mucosal surfaces, usually at low densities. The highly complex microbiota that normally colonizes mucosal surfaces inhibits expansion of and domination by bacteria such as Enterobacteriaceae and Enterococcaceae. Destruction of the normal flora by antibiotic administration, however, disinhibition antibiotic-resistant members of these bacterial families, leading to their expansion to very high densities (Ubeda et al Journal of Clinical Investigation 2010). High-density colonization by these organisms can be calamitous for the susceptible patient, resulting in bacteremia and sepsis (Taur et al, Clinical Infectious Disease, 2012).

To test prophylactic use and treatment of a bacterial composition test article, a VRE infection mouse model is used as previously described (Ubeda et al, Infectious Immunity 2013, Ubeda et al, Journal of clinical Investigation, 2010). Briefly, experiments are done with 7-week-old C57BL/6J female mice purchased from Jackson Laboratory, housed with irradiated food, and provided with acidified water. Mice are individually housed to avoid contamination between mice due to coprophagia. For experimental infections with VRE, mice are treated with ampicillin (0.5 g/liter) in their drinking water, which is changed every 3 days.

In the treatment model, on day 1, mice are Infected by means of oral gavage with $10^8$ CFU of the vancomycin-resistant *Enterococcus faecium* strain purchased from ATCC (ATCC 700221). One day after infection (day 1), antibiotic treatment is stopped and VRE levels are determined at different time points by plating serial dilutions of fecal pellets on Enterococcosel agar plates (Difco) with vancomycin (8 ug/ml; Sigma). VRE colonies are identified by appearance and confirmed by Gram staining or other methods previously described (e.g. see example 1, 2 and 3). In addition, as previously described (Ubeda et al, Journal of Clinical Investigation 2010), PCR of the vanA gene, which confers resistance to vancomycin, confirms the presence of VRE in infected mice. The bacterial composition test article such as but not limited to an ethanol treated, gradient purified spore preparation (as described herein), fecal suspension, or antibiotic treatment is delivered in PBS on days 1-3 while the negative control contains only PBS and is also delivered on days 1-3 by oral gavage. Fresh fecal stool pellets are obtained daily for the duration of the experiment from days −7 to day 10. The samples are immediately frozen and stored at −80° C. DNA was extracted using standard techniques and analyzed with 16S or comparable methods (e.g. see example 2 and 3).

In the colonization model, ampicillin is administered as described above for day −7 to day 1, treatment with the test article or vehicle control is administered on day 0-2 and the VRE resistant bacteria at $10^8$ CFU are administered on day 14. Fecal samples are taken throughout the experiment daily from −7 to day 21 and submitted for 16S sequencing as previously described (e.g. see examples 2 and 3).

In both models titers of VRE in feces are used to evaluate the success of the test article versus the negative control. Furthermore, microbiota composition is assessed for the ability of the bacterial composition test article to induce a healthy microbiome.

Example 23: Prophylactic Use and Treatment of a Mouse Model of Carbapenem Resistant *Klebsiella* (CRKB) Colonization The emergence of *Klebsiella pneumoniae* strains with decreased susceptibility to carbapenems is a significant threat to hospitalized patients. Resistance to carbapenems in these organisms is most frequently mediated by *K. pneumoniae* carbapenemase (KPC), a class A beta-lactamase that also confers resistance to broad-spectrum cephalosporins and commercially available beta-lactam/beta-lactamase inhibitor combinations (Queenan et al, Clinical Microbiology Review, 2007). KPC-producing *K. pneumoniae* (KPC-Kp) strains often harbor resistance determinants against several other classes of antimicrobials, including aminoglycosides and fluoroquinolones, resulting in truly multidrug-resistant (MDR) organisms (Hirsch et al, Journal of Antimicrobial Chemotherapy, 2009). Considering the limited antimicrobial options, Infections caused by KPC-Kp pose a tremendous therapeutic challenge and are associated with poor clinical outcomes A treatment protocol in a mouse model as previously described (e.g. Perez et al, Antimicrobial Agents Chemotherapy, 2011) is used to evaluate the bacterial composition (test article) for treating carbapenem resistant *Klebsiella* and reducing carriage in the GI tract. Female CF1 mice (Harlan Sprague-Dawley, Indianapolis, Ind.) are used and are individually housed and weighed between 25 and 30 g.

The thoroughly characterized strain of *K. pneumoniae*, VA-367 (8, 9, 25) is used in this study. This clinical isolate is genetically related to the KPC-Kp strain circulating in the Eastern United States. Characterization of the resistance mechanisms in *K. pneumoniae* VA-367 with PCR and DNA sequence analysis revealed the presence of blaKPC-3, blaTEM-1, blaSHV-11, and bIaSHV-12 as well as qnrB19 and aac(6')-lb. Additionally, PCR and DNA sequencing revealed disruptions in the coding sequences of the following outer membrane protein genes: ompK35, ompK36, and ompK37. Antibiotic susceptibility testing (AST) was performed with the agar dilution method and interpreted according to current recommendations from the Clinical and Laboratory Standards Institute (CLSI). A modified Hodge test were performed, according to a method described previously (e.g. see Anderson et al, Journal of Clinical Microbiology, 2007) with ertapenem, meropenem, and imipenem. Tigecycline and polymyxin E were evaluated by Etest susceptibility assays (AB bioMerieux, Solna, Sweden). Results for tigecycline were interpreted as suggested by the U.S. Food and Drug Administration (FDA) and according to CLSI recommendations (criteria for *Pseudomonas*) for polymyxin E.

Mice (10 per group) are assigned to either a bacterial composition (test article), ethanol treated, spore preparation (e.g. as described herein), antibiotic clindamycin, piperacillin-tazobactam, tigecycline, ertapenem, cefepime, ciprofloxacin, or combination thereof or control group receiving only the vehicle. They are administered the test article daily from day −10 to day 0, On day 0, 103 CFU of KPC-Kp VA-367 diluted in 0.5 ml phosphate-buffered saline (PBS) was administered by oral gavage using a stainless-steel feeding tube (Perfektum; Popper & Sons, New Hyde Park, N.Y.). Stool samples were collected 1, 4, 6, and 11 days after the administration of KPC-Kp in order to measure the concentration of carbapenem-resistant *K. pneumoniae*. Stool samples (100 mg diluted in 800 ml of PBS) are plated onto MacConkey agar with and without 0.5 ug/ml of imipenem, and the number of CFU per gram of stool was determined. Alternatively other methods may be used to measure the levels of carbapenem-resistant *K. pneumoniae* e.g. pcr, antigen testing, as one who's skilled in the art could perform.

Stool samples were collected after 5 days of treatment to assess the effects of the antibiotics on the stool microflora and to measure antibiotic levels in stool. To assess the effects on the microflora, fresh stool samples as previously described (e.g. see examples 2 and 3). Additional experiments are performed to examine whether the administration the bacterial composition (test article) resulted in the elimination or persistence of colonization with KPC-Kp VA-367.

Mice are treated with subcutaneous clindamycin to reduce the normal intestinal flora 1 day before receiving 104 CFU of KPC-Kp VA-367 by oral gavage, and the mice continued to receive subcutaneous clindamycin every other day for 7 days. Concurrently, for 7 days after oral gavage with KPC-Kp, mice received oral gavage of normal saline (control group), or the bacterial composition as specified. An additional dose of subcutaneous clindamycin was administered 20 days after the administration of KPC-Kp VA-367 to assess whether low levels of carbapenem-resistant *K. pneumoniae* were present that could be augmented by the elimination of the anaerobic microflora. Stool samples were collected at baseline and at 3, 6, 8, 11, 16, and 21 days after KPC-Kp VA-367 was given by gavage. The bacterial composition will be examined by the reduction of CRKB in feces.

Example 24. Identification of Keystone OTUs and Functions

The human body is an ecosystem in which the microbiota, and the microbiome, play a significant role in the basic healthy function of human systems (e.g. metabolic, immunological, and neurological). The microbiota and resulting microbiome comprise an ecology of microorganisms that co-exist within single subjects interacting with one another and their host (i.e., the mammalian subject) to form a dynamic unit with inherent biodiversity and functional characteristics. Within these networks of interacting microbes (i.e. ecologies), particular members can contribute more significantly than others; as such these members are also found in many different ecologies, and the loss of these microbes from the ecology can have a significant impact on the functional capabilities of the specific ecology. Robert Paine coined the concept "Keystone Species" in 1969 (see Paine RT. 1969. A note on trophic complexity and community stability. The American Naturalist 103: 91-93.) to describe the existence of such lynchpin species that are integral to a given ecosystem regardless of their abundance in the ecological community. Paine originally describe the role of the starfish *Pisaster ochraceus* in marine systems and since the concept has been experimentally validated in numerous ecosystems.

Keystone OTUs and/or Functions are computationally-derived by analysis of network ecologies elucidated from a defined set of samples that share a specific phenotype. Keystone OTUs and/or Functions are defined as all Nodes within a defined set of networks that meet two or more of the following criteria. Using Criterion 1, the node is frequently observed in networks, and the networks in which the node is observed are found in a large number of individual subjects; the frequency of occurrence of these Nodes in networks and the pervasiveness of the networks in individuals Indicates these Nodes perform an important biological function in many individuals. Using Criterion 2, the node is frequently observed in networks, and each the networks in which the node is observed contain a large number of Nodes—these Nodes are thus "super-connectors", meaning that they form a nucleus of a majority of networks and as such have high biological significance with respect to their functional contributions to a given ecology. Using Criterion 3, the node is found in networks containing a large number of Nodes (i.e. they are large networks), and the networks in which the node is found occur in a large number of subjects; these networks are potentially of high Interest as It is unlikely that large networks occurring in many individuals would occur by chance alone strongly suggesting biological relevance. Optionally, the required thresholds for the frequency at which a node is observed in network ecologies, the frequency at which a given network is observed across subject samples, and the size of a given network to be considered a Keystone node are defined by the 50th, 70th, 80th, or 90th percentiles of the distribution of these variables. Optionally, the required thresholds are defined by the value for a given variable that is significantly different from the mean or median value for a given variable using standard parametric or non-parametric measures of statistical significance. In another embodiment a Keystone node is defined as one that occurs in a sample phenotype of interest such as but not limited to "health" and simultaneously does not occur in a sample phenotype that is not of interest such as but not limited to "disease. Optionally, a Keystone Node is defined as one that is shown to be significantly different from what is observed using permuted test datasets to measure significance.

Example 25: Method of Preparing the Bacterial Composition for Administration to a Patient Two strains for the bacterial composition are independently cultured and mixed together before administration. Both strains are independently be grown at 37° C., pH 7, In a GMM or other animal-products-free medium, pre-reduced with 1 g/L cysteineYHCl. After each strain reaches a sufficient biomass, it is preserved for banking by adding 15% glycerol and then frozen at −80° C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

Example 26: Use of Microbiological Assay to Determine Bacterial Strain Germinant Utilization In the case of pathogenic sporulating bacteria, typically bacterial spores must germinate and initiate vegetative cell growth in order to trigger disease symptoms. An example is *C. difficile*, which is highly infectious when in the dormant, spore phase, but must germinate and grow in order to cause the symptoms of *Clostridium difficile*-associated disease (CDAD) (Burns et al., Research in Microbiology, Volume 161, Issue 9, November 2010, Pages 730-734). Preventing pathogenic spore germination by using sets of strains to metabolize available germinants is therefore a viable strategy for preventing disease caused by sporulating bacteria.

One method to isolate and identify single strains or sets of strains that utilize similar nutrients and germinants to a given pathogen involves selecting for such microbes from complex communities of bacteria. Plating a complex community of bacteria on plates that are selective for the pathogenic vegetative or spore of interest can lead to the isolation of species with similar nutrient and germinant utilization profiles.

Fecal suspensions from samples that tested negative for the presence of *C. difficile* were left untreated or treated with 50% ethanol for 1 hour to select for bacterial spores and eliminate vegetative bacteria. These samples were then plated on commercially available plates for the selective isolation of *C. difficile* (chromID® *C. difficile* plates from Biomerieux, or *Clostridium difficile* selective agar (CDSA) plates from BD). These plates contain mixtures of germinants which support *C. difficile* germination and nutrients which support *C. difficile* vegetative growth. Individual colonies of strains that grew on these plates were picked for Identification via 16S ribosomal sequencing. These strains utilize essential nutrients and germinants necessary for *C. difficile* germination and growth, and thus represent candidates for use in multi-strain bacterial compositions to treat and prevent CDAD.

Treatment 3 consists of 15 organisms that comprise *C. disporicum, C. mayombei, C. tertium, C. innocuum*, and *Collineslia aerofaciens* each of which was shown to utilized similar nutrients and germinants as *C. difficile* in the present example (Table X). This treatment prevented *C. difficile*-associated mortality, weight loss, and clinical symptoms upon challenge with the pathogen.

TABLE X

Species isolated from a fecal suspension after ethanol treatment and plating on media agars that are selective for *C. difficile*

| Plate Type | Treatment | OTUs Isolated from Fecal Suspension on Designated Plate Type |
|---|---|---|
| ChromID ® *C. difficile* Agar | Ethanol Treated | Clostridium__celatum<br>Clostridium__citroniae<br>Clostridium__disporicum<br>Clostridium__hathewayi<br>Clostridium__mayombei<br>Clostridium__tertium |
| CDSA | Ethanol Treated | Clostridium__sp__HGF2<br>Clostridium__innocuum |
| CDSA | Untreated | Bacteroides__sp__3__2__5<br>Clostridium__sp__HGF2<br>Collinsella__aerofaciens<br>Enterobacter__cloacae<br>Enterobacter__sp__247BMC<br>Enterococcus__faecium<br>Enterococcus__faecium<br>Enterococcus__faecium<br>Lactobacillus__rhamnosus |

Example 27: Use of Biolog Assay to Determine Bacterial Strain Germinant Utilization Bacterial species that inhibit the germination of spores of a pathogen can be determined by finding a competitor species or combination of competitor species that overlap for germination requirements. As an example, the method described in Example 15 can be used to find a list of germination requirements for a spore forming pathogen. Potential competitors can be tested in parallel and chosen based on the level of overlap for germination requirements when the bacteria are grown from spores. For this assay, a culture consisting of pure spores is used as the inoculating material. A pure spore sample is prepared by treating a culture of a spore forming species with 50% ethanol for 1 hr with mixing. After incubation in ethanol the suspension is pelleted in a centrifuge at 12,000 rpm for 5 min. The spores are then resuspended in PBS. Germination from spores are tested in parallel with and without added germinants. After incubation for 1 hr to allow germination, each sample is serially diluted and plated for titer. Nutrients are scored as germinants if titer is higher in the presence of the nutrient. A combination of competitors which overlap sufficiently with the germination requirements of the pathogen can be selected as a set with potential to prevent germination of the pathogen.

Example 28: Inhibition of a Pathogen by Identifying Compositions that Modify its Germinants Required for Sporulation

*C. difficile* is a spore former whose germination is induced by primary bile salts, including cholate, taurocholate, glycocholate and other taurocholate derivatives [Sorg and Sonnenshein (2008) *J Bact* 190: 2505-2512; Theriot, C. M. et al., (2013) *Nat Communications DOI:* 10.1038/ncomms4114]. Many commensal organisms encode enzymes that dehydroxylate primary bile salts to secondary bile salts, including lithocholate, deoxycholate isomers, and various conjugated bile salts. An overnight culture of the commensal of interest is incubated in a growth media containing added taurocholate or cholate. Concentrations of between 0.001% and 0.1% are tested with each growth media in a 96 well measuring growth by monitoring $OD_{600}$ in order to find a concentration of each bile salt that is not inhibitory to growth of the commensal organism of interest. For each condition in which growth was observed, an aliquot is analyzed. The microbes are removed by centrifugation, and the supernatant tested using LC-electrospray-triple quadrupole mass spectrometry, or an equivalent method, to detect the production of secondary bile acids from taurocholate and cholate. A set of reference standards, including commercially available primary and secondary bile acids, is prepared and run in parallel. A microbial composition is then selected by combining two or more commensals capable of metabolizing taurocholate and cholate and tested for the ability to prevent *C. difficile* infection in the mouse as described in the examples herein.

Example 29: Determination of Nutrient Utilization by a Pathogen

The specific nutrient utilization capabilities of a pathogen can be determined by use of one, or a combination of methods described above. In one instance, a list of compounds which allow, enhance or are necessary for the growth of *Clostridium difficile* was determined using the method described in Example 15 above. Wells that had a final value of 1.5× the negative control well under any of the conditions tested were scored as a growth requirement. Three strains of the same pathogen species were tested using a variety of redox buffer conditions, and compounds that supported growth of any of the strains were considered a growth substrate for the pathogen species.

Example 30: Determination of Nutrient Utilization by a Potential Competitor

The specific nutrient utilization capabilities of a bacterial species which is a potential pathogen competitor can be determined by use of one or, a combination of methods described above. In one instance, a list of compounds which allow, enhance or are necessary for the growth of a potential pathogen competitor species was determined by using the method described in Example 15 above. Wells that had a final absorbance value of at least 1.5× the negative control well under any of the conditions tested were scored as a nutrient that the competitor is capable of utilizing. A potential competitor of the pathogen or combination of competitors can be chosen based on the level of overlap with nutrient utilization capabilities of the pathogen. As a general principle, the greater the overlap, the greater potential the isolate or set of isolates has as a competitor to the pathogen.

Example 31: Use of Minimum Nutrient Threshold Quantification to Identify Potential Competitors The minimum concentration of a nutrient or other growth requirement necessary for growth can be determined by growth in a minimal defined media assay. In this assay, a minimal defined media is constructed that lacks at least one constituent necessary for growth. The specific missing nutrient is titrated into the defined media by two fold dilutions along a row of a 96-well plate. The potential competitor of a particular pathogen is then inoculated into all wells of the plate, and the growth rate is determined as a function of the test nutrient concentration. The plate is incubated for 48 hr and growth is measured by optical density (OD) at 600 nm. The well with the lowest concentration of nutrient that allows growth is determined to be the minimum threshold concentration. Potential competitors of the pathogen can be chosen by virtue of having a minimum threshold concentration below that of the pathogen.

Example 32: Use of Proliferation Rate Quantification to Identify Potential Competitors The proliferation rate of a bacterial species can be determined by inoculating the species being tested into a defined media and measuring the titer at several points over a time course. In one example, a pathogen or potential competitor of the pathogen is inoculated into a minimal defined media containing the nutrient being tested. For Instance, *Clostridium difficile* growth rates can be measured in defined media containing a single carbon source (Theriot et al., 2013 (*Nature Communications*)). A variety of carbon sources are tested, with glucose as a positive control and no carbohydrate media as negative controls. The defined media used for the assay contains 0.5% (wt/vol) of the test carbohydrate, no other carbon source, and 0.125 mg/A biotin, 1 mg/A pyridoxine and pantothenate, 75 mg/l histidine, glycine and tryptophan, 150 mg/l arginine, methionine and threonine, 225 mg/I valine and isoleucine, 300 mg/l leucine, 400 mg/l cysteine, and 450 mg/l proline.

Specifically, for each carbon source tested, *C. difficile* is cultured for 14 hours in brain heart infusion medium at 37 degrees and then subcultured 1:3 into defined media containing 0.5% glucose with the described vitamins and amino acids, grown for 3 hours, centrifuged for 10 min at 2000×g, and resuspended in equal volume of anaerobically equilibrated PBS buffer. 100 µl of the suspension is used to inoculate defined media containing 0.5% test carbohydrate and described vitamins and amino acids. Samples are incubated shaking at 200 r.p.m. $OD_{600}$ is monitored hourly for 24 hours in a Thermo Scientific Spectronic 20D+ apparatus. The specific growth rate is determined as growth rate=In (X/Xo)/T, where X is the OD600 value during the linear portion of growth and T is time (hours). Values are reported as the mean of 3 independent cultures conducted twice (see Table XX).

TABLE XX

Carbon utilization of *C. difficile*

| Carbon source | Growth rate (1/hrs) |
|---|---|
| Sorbitol | 0.62 ± 0.06 |
| Mannitol | 0.66 ± 0.10 |
| Arabitol | 0.58 ± 0.09 |
| Xylitol | no growth observed |
| Gluconate | 0.54 ± 0.01 |

TABLE XX-continued

Carbon utilization of *C. difficile*

| Carbon source | Growth rate (1/hrs) |
|---|---|
| Sucrose | 0.52 ± 0.04 |
| Lactate | 0.55 ± 0.05 |
| Raffinose | 0.56 ± 0.03 |
| Stachyose | 0.55 ± 0.03 |
| Galactose | no growth observed |
| Fructose | 0.66 ± 0.12 |
| Glucose control | 0.73 ± 0.09 |
| Amino Acids, No Carbohydrates | 0.54 ± 0.02 |
| No Amino Acids, No Carbohydrates | no growth observed |

Alternatively, progress of growth can be determined by taking a small aliquot at each timepoint, serially diluting and plating to a nutrient rich solid media to count colonies.

Comparison can be made between the pathogen and potential competitor species to define competitors with high potential to compete with *C. difficile*. High potential competitor candidates will have a growth rate that is faster than that of the pathogen microbe.

Example 33: Use of In Vitro Assay to Test Potential Bacterial Competitor Consortia for Functionality An in vitro assay is performed to test the ability of a chosen species or combination of species to inhibit the growth of a pathogen such as *Clostridium difficile* in media that is otherwise suitable for growth of the pathogen. A liquid media suitable for growth of the pathogen is chosen, such as Brain Heart Infusion Broth (BHI) for *C. difficile*. The potential competitor species or a combination of competitor species are inoculated into 3 mL of the media and incubated anaerobically for 24 hr at 37° C. After incubation the cells are pelleted in a centrifuge at 10,000 rcf for 5 min. Supernatant is removed and filtered through a 0.22 μm filter to remove all cells. *C. difficile* or another pathogen of interest is then inoculated into the filtered spent supernatant and grown anaerobically at 37° C. for 24 hr. A control culture in fresh media is incubated in parallel. After incubation, the titer of *C. difficile* is determined by serially diluting and plating to *Brucella* Blood Agar (BBA) plates and incubated anaerobically for 24 hr at 37° C. Colonies are counted to determine the final titer of the pathogen after incubation in competitor conditioned media and control media. The percent reduction in final titer is calculated and considered inhibitory if a statistically significant reduction in growth is measured. Alternatively, the inhibition of pathogen growth is monitored by $OD_{600}$ measurement of the test and control cultures.

Example 34: Selection of Species to Test In Vivo for Pathogen Inhibition

Based on the principles of identifying bacterial compositions of species that compete for resources with a pathogen or pathobiont, one builds sets of species that are likely to displace a pathogen or pathobiont in a host gut. Mechanisms include competition between a set of organisms and a pathogen or pathobiont based on nutrient utilization, minimum nutrient threshold for a given important nutrient or subset of Important nutrients, proliferation rate, germinant requirements or general mechanisms understood through the in vitro competition assay. Additional other mechanisms are recognized by one skilled in the art in light of the teachings described herein and thus the mechanisms described should not be viewed as limiting the scope of this disclosure. The bacterial combinations can then be prepared as described and tested in vivo in an appropriate host model as described herein.

Example 35: Use of In Vivo Mouse Model to Test Potential Bacterial Competitor Consortia for Functionality Combinations of bacterial species to test in a mouse model of *Clostridium difficile* associated disease were chosen by use of a screen for nutrient utilization of both the pathogen and 17 potential competitors of the pathogen using the methods described herein. The use of nutrients used by each of the potential competitors was cross-referenced to the list of nutrients used by any of the *Clostridium difficile* strains tested under any condition tested. The 17 strains were rank-ordered for overlap with the list of *Clostridium difficile* nutrients. Two and three species combinations were chosen from the top three species (*Clostridium hylemonae, Blautia producta, Clostridium butyricum*) ranked for overlap with *Clostridium difficile* nutrients. Four species combinations were chosen from species that ranked in the top 50% when rank ordered for overlap with *Clostridium difficile* nutrients. A three species combination with reduced overlap was also chosen based on a rank ordering of nutrient utilization by *Clostridium difficile*.

To test the therapeutic potential of the bacterial compositions a prophylactic mouse model of *C. difficile* infection (model based on Chen, et al., A mouse model of *Clostridium difficile* associated disease, Gastroenterology 135(6):1984-1992) was used. Two cages of five mice each were tested for each arm of the experiment. All mice received an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and Vancomycin (0.056 mg/ml) in their drinking water on days −14 through −5 and a dose of 10 mg/kg Clindamycin by oral gavage on day −3. On day −1, they received either the test article or vehicle control via oral gavage. On day 0 they were challenged by administration of approximately 4.5 log 10 cfu of *C. difficile* (ATCC 43255) via oral gavage. A positive control group receives Vancomycin from day −1 through day 3 in addition to the antibiotic protocol and *C. difficile* challenge specified above. Feces were collected from the cages for analysis of bacterial carriage, mortality was assessed every day from day 0 to day 6 and the weight and subsequent weight change of the animal was assessed with weight loss being associated with *C. difficile* infection. Mortality and reduced weight loss of the test article compared to the empty vehicle were used to assess the success of the test article. Additionally, a *C. difficile* symptom scoring was performed each day from day −1 through day 6. Symptom scoring was based on Appearance (0-2 pts based on normal, hunched, piloerection, or lethargic), Respiration (0-2 pts based on normal, rapid or shallow, with abdominal breathing), Clinical Signs (0-2 points based on normal, wet tail, cold-to-the-touch, or isolation from other animals).

In addition to compiling the cumulative mortality for each arm, the average minimum relative weight is calculated as the mean of each mouse's minimum weight relative to Day −1 and the average maximum clinical score is calculated as the mean of each mouse's maximum combined clinical score with a score of 4 assigned in the case of death. The treatments are specified in Table W and the results are reported in Table Y.

TABLE W

Treatment compositions tested C. difficile mouse model.

| Treatment | Vehicle (PBS) | 10% Fecal Suspension | Collinsella_aerofaciens | Clostridium_tertium | Clostridium_disporicum | Clostridium_innocuum |
|---|---|---|---|---|---|---|
| 1 | x | | | | | |
| 2 | | x | | | | |
| 6 | | | | | | |
| 3 | | | x | x | x | x |
| 9 | | | | | | |
| 8 | | | | | | |
| 7 | | | | | | |
| 4 | | | x | | | |
| 5 | | | x | | | x |

| Treatment | Clostridium_mayombei | Clostridium_butyricum | Coprococcus_comes | Clostridium_hylemonae | Clostridium_bolteae |
|---|---|---|---|---|---|
| 1 | | | | | |
| 2 | | | | | |
| 6 | | x | | x | |
| 3 | x | x | x | x | x |
| 9 | | | | | |
| 8 | | x | | | |
| 7 | | x | | x | |
| 4 | | x | | x | |
| 5 | | | x | | |

| Treatment | Clostridium_symbiosum | Clostridium_orbiscindens | Lachnospiraceae_bacterium_5_1_57FAA | Blautia_producta |
|---|---|---|---|---|
| 1 | | | | |
| 2 | | | | |
| 6 | | | | x |
| 3 | x | x | x | x |
| 9 | | x | x | |
| 8 | | | | x |
| 7 | | | | |
| 4 | | | | x |
| 5 | | | | |

| Treatment | Ruminococcus_gnavus | Ruminococcus_bromii | Eubacterium_rectale |
|---|---|---|---|
| 1 | | | |
| 2 | | | |
| 6 | | | |
| 3 | x | x | |
| 9 | | | x |
| 8 | | | |
| 7 | | | |
| 4 | | | |
| 5 | | x | |

TABLE Y

Results of bacterial compositions tested in a C. difficile mouse model.

| Treatment | Dose | Cumulative Mortality (%) | Avg. Minimum Relative Weight | Avg. Maximum Clinical Score (Death = 4) |
|---|---|---|---|---|
| 1 | — | 40 | 0.87 | 2.8 |
| 2 | 5.8e8 cfu | 0 | 0.99 | 0 |
| 3 | 1e8 cfu/OTU | 0 | 0.98 | 0 |
| 4 | 1e8 cfu/OTU | 10 | 0.84 | 2.1 |
| 5 | 1e8 cfu/OTU | 10 | 0.84 | 2.2 |
| 6 | 1e8 cfu/OTU | 0 | 0.87 | 2 |
| 7 | 1e8 cfu/OTU | 20 | 0.91 | 1.7 |
| 8 | 1e8 cfu/OTU | 40 | 0.82 | 2.8 |
| 9 | 1e8 cfu/OTU | 0 | 0.90 | 1 |

Example 36: Selection of Media for Growth

It is important to select appropriate media to support growth, including preferred carbon sources. For example, some organisms prefer complex sugars such as cellobiose over simple sugars. Examples of media used are below. In the case of plating on solid media, multiple dilutions are plated out to ensure that some plates will have well isolated colonies on them for analysis, or alternatively plates with dense colonies may scraped and suspended in PBS to generate a mixed diverse community. Liquid media include (can be adapted to solid media by addition of 1.5% agar):

Gifu Anaerobic Medium (GAM, Nissui) without dextrose supplemented with fructooligosaccharides/inulin (0.4%), mannitol (0.4%), inulin (0.4%), or fructose (0.4%), or a combination thereof.

"Sweet GAM [Gifu Anaerobic Medium (GAM, Nissui)] modified, supplemented with glucose, cellobiose, maltose, L-arabinose, fructose, fructooligosaccharides/inulin, mannitol and sodium lactate)

Brucella Blood Broth (BBA, Atlas, Handbook of Microbiological Media, 4th ed, ASM Press, 2010)

"PEA sheep blood (Anaerobe Systems; 5% Sheep Blood with Phenylethyl Alcohol)

Egg Yolk Broth (Atlas, Handbook of Microbiological Media, 4th ed, ASM Press, 2010)

Sulfite polymyxin milk (Mevissen-Verhage et al., J. Clin. Microbiol. 25:285-289 (1987))

Mucin Broth (Derrien et al., IJSEM 54: 1469-1476 (2004))

Polygalacturonate Broth (Jensen & Canale-Parola, Appl. Environ. Microbiol. 52:880-997 (1986))

M2GSC (Atlas, Handbook of Microbiological Media, 4th ed, ASM Press, 2010)

M2 Broth (Atlas, Handbook of Microbiological Media, 4th ed, ASM Press, 2010) supplemented with starch (1%), mannitol (0.4%), lactate (1.5 g/L) or lactose (0.4%)

Sweet B—Brain Heart Infusion Broth (Atlas, Handbook of Microbiological Media, 4th ed, ASM Press, 2010) supplemented with yeast extract (0.5%), hemin, cysteine (0.1%), maltose (0.1%), cellobiose (0.1%), soluble starch (sigma, 1%), MOPS (50 mM, pH 7).

PY-salicin (peptone-yeast extract agar supplemented with salicin) (Atlas, Handbook of Microbiological Media, 4th ed, ASM Press, 2010).

Modified Brain Heart Infusion (M-BHI) [[sweet and sour]] contains the following per L: 37.5 g Brain Heart Infusion powder (Remel), 5 g yeast extract, 2.2 g meat extract, 1.2 g liver extract, 1 g cystein HCl, 0.3 g sodium thioglycolate, 10 mg hemin, 2 g soluble starch, 2 g FOS/Inulin, 1 g cellobiose, 1 g L-arabinose, 1 g mannitol, 1 Na-lactate, 1 mL Tween 80, 0.6 g MgSO4× 7H2O, 0.6 g CaCl2, 6 g (NH4)2SO4, 3 g KH2PO4, 0.5 g K2HPO4, 33 mM Acetic acid, 9 mM propionic acid, 1 mM Isobutyric acid, 1 mM isovaleric acid, and after autoclaving add 50 mL of 8% NaHCO$_3$ solution and 50 mL 1M MOPS-KOH (pH 7).

Noack-Blaut *Eubacterium* Broth (See Noack et al. J. Nutr. (1998) 128:1385-1391)

BHIS az1/ge2-BHIS az/ge agar (Reeves et. al. Infect. Immun. 80:3786-3794 (2012)) [Brain Heart Infusion Broth (Atlas, Handbook of Microbiological Media, 4th ed, ASM Press, 2010) supplemented with yeast extract 0.5%, cysteine 0.1%, 0.1% cellobiose, 0.1% inulin, 0.1% maltose, aztreonam 1 mg/L, gentamycin 2 mg/L]

BHIS ClnM az1/ge2—BHIS ClnM [Brain Heart Infusion Broth (Atlas, Handbook of Microbiological Media, 4th ed, ASM Press, 2010) supplemented with yeast extract 0.5%, cysteine 0.1%, 0.1% cellobiose, 0.1% inulin, 0.1% maltose, aztreonam 1 mg/L, gentamycin 2 mg/L]

Example 37: High Throughout Screening of Binary Pairs

Construction of binary pairs in a high-throughput 96-well format. To allow high-throughput screening of binary pairs, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed, plates were removed from −80° C. and thawed at room temperature under anaerobic conditions when testing in an In vitro inhibition assay with *Clostridium difficile*.

Construction of ternary combinations in a high-throughput 96-well format. To allow high-throughput screening of ternary combinations, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed for the assay, plates were removed from −80° C. and thawed at room temperature under anaerobic conditions when testing in an In vitro inhibition assay with *Clostridium difficile*.

Construction of an In vitro inhibition Assay to Screen for Ecobiotic™ compositions Inhibitory to the Growth of *Clostridium difficile*. Inhibition of *C. difficile* in this assay may result from competition for nutrients; other mechanisms of inhibition may contribute, as the assay is not limited to a single mechanism.

An overnight culture of *Clostridium difficile* was grown under anaerobic conditions in SweetB-FosIn or other suitable media for the growth of *C. difficile*. SweetB-FosIn is a complex media composed of brain heart infusion, yeast extract, cysteine, cellobiose, maltose, soluble starch, and fructooligosaccharides/inulin, and hemin, and is buffered with MOPs. After 24 hr of growth the culture was diluted 100,000 fold into a complex media such as SweetB-FosIn which is suitable for the growth of a wide variety of anaerobic bacterial species. The diluted *C. difficile* mixture was then aliquoted to wells of a 96-well plate (180 uL to each well). 20 uL of a unique binary pair of potential inhibitory species was then added to each well at a final concentration of 1e6 CFU/mL of each species. Alternatively the assay can be tested with binary pairs at different initial concentrations (1e9 CFU/mL, 1e8 CFU/mL, 1e7 CFU/mL, 1e5 CFU/mL, 1e4 CFU/mL, 1e3 CFU/mL, 1e2 CFU/mL). Control wells only inoculated with *C. difficile* were included for a comparison to the growth of *C. difficile* without inhibition. Additional wells were used for controls that either inhibit or do not inhibit the growth of *C. difficile*. One example of a positive control that inhibits growth was a combination of Blautia *producta, Clostridium bifermentans* and *Escherichia coli*. One example of a control that shows reduced inhibition of *C. difficile* growth as a combination of *Bacteroides* thetalotaomicron, *Bacteroides ovatus* and *Bacteroides* vulgatus. Plates were wrapped with parafilm and incubated for 24 hr at 37° C. under anaerobic conditions. After 24 hr the wells containing *C. difficile* alone were serially diluted and plated to determine titer. The 96-well plate was then frozen at −80 C before quantifying *C. difficile* by qPCR assay.

Construction of an in vitro inhibition Assay to Screen for bacterial compositions that are inhibitory to the growth of *Clostridium difficile* by diffusion mediated mechanisms. The In vitro inhibition assay described above was modified by using a 0.22 uM filter insert (Millipore™ MultiScreen™ 96-Well Assay Plates—Item MAGVS2210) in 96-well format to physically separate *C. difficile* from the bacterial compositions. The *C. difficile* was aliquoted into the 96-well plate while the bacterial compositions were aliquoted into media on the filter overlay. The nutrient media as in contact on both sides of the 0.22 uM filter, allowing exchange of nutrients, small molecules and many macromolecules (e.g., bacteriocins, cell-surface proteins, or polysaccharides) by diffusion. In this embodiment, after 24 hr incubation, the filter insert containing the bacterial compositions was removed. The plate containing *C. difficile* was then transferred to a 96-well plate reader suitable for measuring optical density (OD) at 600 nm. The growth of *C. difficile* in the presence of different bacterial compositions was compared based on the OD measurement.

Construction of an In vitro inhibition Assay to Screen for bacterial compositions inhibitory to the growth of *Clostridium difficile* using *Clostridium difficile* selective media for quantification. The In vitro inhibition assay described above can be modified to determine final *C. difficile* titer by serially diluting and plating to *C. difficile* selective media (Bloedt et al 2009) such as CCFA (cycloserine cefoxitin fructose agar, Anaerobe Systems), CDSA (*Clostridium difficile* selective agar, which is cycloserine cefoxitin mannitol agar, Becton Dickinson).

Example 37. Quantification of *C. difficile* Using Quantitative PCR (aPCR) Standard Curve Preparation The standard curve was generated from a well on each assay plate containing only pathogenic *C. difficile* grown in SweetB+FosIn media as provided herein and quantified by selective spot plating. Serial dilutions of the culture were performed in sterile phosphate-buffered saline. Genomic DNA was extracted from the standard curve samples along with the other wells.

Genomic DNA Extraction

Genomic DNA was extracted from 5 µl of each sample using a dilution, freeze/thaw, and heat lysis protocol. 5 µL of thawed samples were added to 45 µL of UltraPure water (Life Technologies, Carlsbad, Calif.) and mixed by pipetting. The plates with diluted samples were frozen at −20° C. until use for qPCR which includes a heated lysis step prior to amplification. Alternatively the genomic DNA could be isolated using the Mo Bio Powersoil®-htp 96 Well Soil DNA Isolation Kit (Mo Bio Laboratories, Carlsbad, Calif.), Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

qPCR Composition and Conditions

The qPCR reaction mixture contained 1× SsoAdvanced Universal Probes Supermix, 900 nM of Wr-tcdB-F primer (AGCAGTTGAATATAGTGGTTTAGTTAGAGTTG (SEQ ID NO: 2040), IDT, Coralville, Iowa), 900 nM of Wr-tcdB-R primer (CATGCTTITIAGTTTCTGGATTGAA (SEQ ID NO: 2041), IDT, Coralville, Iowa), 250 nM of Wr-tcdB-P probe (6FAM-CATCCAGTCTCAATTGTATATGTTTC-TCCA-MGB (SEQ ID NO: 2042), Life Technologies, Grand Island, N.Y.), and Molecular Biology Grade Water (Mo Bio Laboratories, Carlsbad, Calif.) to 18 µl (Primers adapted from: Wroblewski, D. et al., Rapid Molecular Characterization of *Clostridium difficile* and Assessment of Populations of *C. difficile* in Stool Specimens, Journal of Clinical Microbiology 47:2142-2148 (2009)). This reaction mixture was aliquoted to wells of a Hard-shell Low-Profile Thin Wall 96-well Skirted PCR Plate (BioRad, Hercules, Calif.). To this reaction mixture, 2 µl of diluted, frozen, and thawed samples were added and the plate sealed with a Microseal 'B' Adhesive Seal (BioRad, Hercules, Calif.). The qPCR was performed on a BioRad C1000™ Thermal Cycler equipped with a CFX96™ Real-Time System (BioRad, Hercules, Calif.). The thermocycling conditions were 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

Data Analysis

The Cq value for each well on the FAM channel was determined by the CFX Manager™ 3.0 software. The $\log_{10}$ (cfu/mL) of *C. difficile* each experimental sample was calculated by inputting a given sample's Cq value into a linear regression model generated from the standard curve wells comparing the Cq values of the standard curve wells to the known $\log_{10}$(cfu/mL) of those samples. The log inhibition was calculated for each sample by subtracting the $\log_{10}$(cfu/mL) of *C. difficile* in the sample from the $\log_{10}$(cfu/mL) of *C. difficile* in the sample on each assay plate used for the generation of the standard curve that has no additional bacteria added. The mean log inhibition was calculated for all replicates for each composition.

A histogram of the range and standard deviation of each composition was plotted. Ranges or standard deviations of the log inhibitions that were distinct from the overall distribution were examined as possible outliers. If the removal of a single log inhibition datum from one of the binary pairs that were identified in the histograms would bring the range or standard deviation in line with those from the majority of the samples, that datum was removed as an outlier, and the mean log inhibition was recalculated.

The pooled variance of all samples evaluated in the assay was estimated as the average of the sample variances weighted by the sample's degrees of freedom. The pooled standard error was then calculated as the square root of the pooled variance divided by the square root of the number of samples. Confidence intervals for the null hypothesis were determined by multiplying the pooled standard error to the z score corresponding to a given percentage threshold. Mean log inhibitions outside the confidence interval were considered to be inhibitory if positive or stimulatory if negative with the percent confidence corresponding to the interval used. Samples with mean log inhibition greater than the 99% confidence interval (C.I) of the null hypothesis are reported as ++++, those with a 95%<C.I.<99% as +++, those with a 90%<C.I. <95% as ++, those with a 80%<C.I.<90% as + while samples with mean log inhibition less than the 99% confidence interval (C.I) of the null hypothesis are reported as −−−−, those with a 95%<C.I.<99% as −−−, those with a 90%<C.I.<95% as −−, those with a 80%<C.I.<90% as −.

Many binary pairs inhibit *C. difficile* as shown in Table 5. 622 of 989 combinations show inhibition with a confidence interval >80%; 545 of 989 with a C.I.>90%; 507 of 989 with a C.I.>95%; 430 of 989 with a C.I. of >99%. Non-limiting but exemplary binary pairs include those with mean log reduction greater than 0.366, e.g. *Allistipes shahii* paired with *Blauta producta, Clostridium hathaweyi*, or *Colinsella aerofaciens*, or *Clostidium mayombei* paired with *C. innocuum, C. tertium, Colinsella aerofaciens*, or any of the other 424 combinations shown in Table 5. Equally important, the In vitro inhibition assay describes binary pairs that do not effectively inhibit *C. difficile*. 188 of 989 combinations promote growth with >80% confidence; 52 of 989 show a lack of inhibition with >90% confidence; 22 of 989 show a lack of inhibition with >95% confidence; 3 of 989, including *B. producta* combined with *Coprococcus catus, Alistipes shahii* combined with Dorea formicigenerans, and *Eubacterium rectale* combined with *Roseburia Intestinalis*, show a lack of inhibition with >99% confidence. 249 of 989 combinations are neutral in the assay, meaning they neither promote nor inhibit *C. difficile* growth to the limit of measurement.

Ternary combinations with mean log inhibition greater than 0.312 are reported as ++++(299% confidence interval (C.I.) of the null hypothesis), those with mean log inhibition between 0.221 and 0.312 as +++ (95%<C.I.<99%), those with mean log inhibition between 0.171 and 0.221 as ++ (90%<C.I.<95%), those with mean log inhibition between 0.113 and 0.171 as + (80%<C.I.<90%), those with mean log inhibition between −0.113 and −0.171 as − (80%<C.I.<90%), those with mean log inhibition between −0.171 and −0.221 as −− (90%<C.I.<95%), those with mean log inhibition between −0.221 and −0.312 as −−

(95%<C.I.<99%), and those with mean log inhibition less than −0.312 as -- (99%<C.I.).

The In vitro inhibition assay shows that many ternary combinations inhibit *C. difficile*. 39 of 56 combinations show inhibition with a confidence interval >80%; 36 of 56 with a C.I.>90%; 36 of 56 with a C.I.>95%; 29 of 56 with a C.I. of >99%. Non-limiting but exemplary ternary combinations include those with mean log reduction greater than 0.171, e.g. any combination shown in Table 6 with a score of ++++, such as Colinsella aerofaciens, *Coprococcus comes*, and *Blautia producta*. Equally important, the In vitro inhibition assay describes ternary combinations that do not effectively inhibit *C. difficile*. 5 of 56 combinations promote growth with >80% confidence; 2 of 56 promote growth with >90% confidence; 1 of 56, *Coprococcus comes, Clostridium symbiosum* and *Eubacterium rectale*, promote growth with >95% confidence. 12 of 56 combinations are neutral in the assay, meaning they neither promote nor Inhibit *C. difficile* growth to the limit of measurement.

Unless otherwise indicated, all numbers expressing quantities of ingredients, reaction conditions, and so forth used in the specification, including claims, are to be understood as being modified in all instances by the term "about." Accordingly, unless otherwise Indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby Incorporated by reference in their entirety, for all purposes.

TABLES

Table 1: List of Operational Taxonomic Units (OTU) with Taxonomic Assignments Made to Genus, Species, and Phylogenetic Clads Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a Pathogen or Pathobiont (see Definitions for description of "Pathobiont"). NIAID Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository.

TABLE 1

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Eubacterium saburreum* | 858 | AB525414 | clade__178 | Y | N |
| *Eubacterium* sp. oral clone IR009 | 866 | AY349376 | clade__178 | Y | N |
| Lachnospiraceae bacterium ICM62 | 1061 | HQ616401 | clade__178 | Y | N |
| Lachnospiraceae bacterium MSX33 | 1062 | HQ616384 | clade__178 | Y | N |
| Lachnospiraceae bacterium oral taxon 107 | 1063 | ADDS01000069 | clade__178 | Y | N |
| *Alicyclobacillus acidocaldarius* | 122 | NR__074721 | clade__179 | Y | N |
| *Clostridium baratii* | 555 | NR__029229 | clade__223 | Y | N |
| *Clostridium colicanis* | 576 | FJ957863 | clade__223 | Y | N |
| *Clostridium paraputrificum* | 611 | AB536771 | clade__223 | Y | N |
| *Clostridium sardiniense* | 621 | NR__041006 | clade__223 | Y | N |
| *Eubacterium budayi* | 837 | NR__024682 | clade__223 | Y | N |
| *Eubacterium moniliforme* | 851 | HF558373 | clade__223 | Y | N |
| *Eubacterium multiforme* | 852 | NR__024683 | clade__223 | Y | N |
| *Eubacterium nitritogenes* | 853 | NR__024684 | clade__223 | Y | N |
| *Anoxybacillus flavithermus* | 173 | NR__074667 | clade__238 | Y | N |
| *Bacillus aerophilus* | 196 | NR__042339 | clade__238 | Y | N |
| *Bacillus aestuarii* | 197 | GQ980243 | clade__238 | Y | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Bacillus amyloliquefaciens* | 199 | NR_075005 | clade_238 | Y | N |
| *Bacillus anthracis* | 200 | AAEN01000020 | clade_238 | Y | Category-A |
| *Bacillus atrophaeus* | 201 | NR_075016 | clade_238 | Y | OP |
| *Bacillus badius* | 202 | NR_036893 | clade_238 | Y | OP |
| *Bacillus cereus* | 203 | ABDJ01000015 | clade_238 | Y | OP |
| *Bacillus circulans* | 204 | AB271747 | clade_238 | Y | OP |
| *Bacillus firmus* | 207 | NR_025842 | clade_238 | Y | OP |
| *Bacillus flexus* | 208 | NR_024691 | clade_238 | Y | OP |
| *Bacillus fordii* | 209 | NR_025786 | clade_238 | Y | OP |
| *Bacillus halmapalus* | 211 | NR_026144 | clade_238 | Y | OP |
| *Bacillus herbersteinensis* | 213 | NR_042286 | clade_238 | Y | OP |
| *Bacillus idriensis* | 215 | NR_043268 | clade_238 | Y | OP |
| *Bacillus lentus* | 216 | NR_040792 | clade_238 | Y | OP |
| *Bacillus licheniformis* | 217 | NC_006270 | clade_238 | Y | OP |
| *Bacillus megaterium* | 218 | GU252124 | clade_238 | Y | OP |
| *Bacillus nealsonii* | 219 | NR_044546 | clade_238 | Y | OP |
| *Bacillus niabensis* | 220 | NR_043334 | clade_238 | Y | OP |
| *Bacillus niacini* | 221 | NR_024695 | clade_238 | Y | OP |
| *Bacillus pocheonensis* | 222 | NR_041377 | clade_238 | Y | OP |
| *Bacillus pumilus* | 223 | NR_074977 | clade_238 | Y | OP |
| *Bacillus safensis* | 224 | JQ624766 | clade_238 | Y | OP |
| *Bacillus simplex* | 225 | NR_042136 | clade_238 | Y | OP |
| *Bacillus sonorensis* | 226 | NR_025130 | clade_238 | Y | OP |
| *Bacillus* sp. 10403023 MM10403188 | 227 | CAET01000089 | clade_238 | Y | OP |
| *Bacillus* sp. 2_A_57_CT2 | 230 | ACWD01000095 | clade_238 | Y | OP |
| *Bacillus* sp. 2008724126 | 228 | GU252108 | clade_238 | Y | OP |
| *Bacillus* sp. 2008724139 | 229 | GU252111 | clade_238 | Y | OP |
| *Bacillus* sp. 7_16AIA | 231 | FN397518 | clade_238 | Y | OP |
| *Bacillus* sp. AP8 | 233 | JX101689 | clade_238 | Y | OP |
| *Bacillus* sp. B27(2008) | 234 | EU362173 | clade_238 | Y | OP |
| *Bacillus* sp. BT1B_CT2 | 235 | ACWC01000034 | clade_238 | Y | OP |
| *Bacillus* sp. GB1.1 | 236 | FJ897765 | clade_238 | Y | OP |
| *Bacillus* sp. GB9 | 237 | FJ897766 | clade_238 | Y | OP |
| *Bacillus* sp. HU19.1 | 238 | FJ897769 | clade_238 | Y | OP |
| *Bacillus* sp. HU29 | 239 | FJ897771 | clade_238 | Y | OP |
| *Bacillus* sp. HU33.1 | 240 | FJ897772 | clade_238 | Y | OP |
| *Bacillus* sp. JC6 | 241 | JF824800 | clade_238 | Y | OP |
| *Bacillus* sp. oral taxon F79 | 248 | HM099654 | clade_238 | Y | OP |
| *Bacillus* sp. SRC_DSF1 | 243 | GU797283 | clade_238 | Y | OP |
| *Bacillus* sp. SRC_DSF10 | 242 | GU797292 | clade_238 | Y | OP |
| *Bacillus* sp. SRC_DSF2 | 244 | GU797284 | clade_238 | Y | OP |
| *Bacillus* sp. SRC_DSF6 | 245 | GU797288 | clade_238 | Y | OP |
| *Bacillus* sp. tc09 | 249 | HQ844242 | clade_238 | Y | OP |
| *Bacillus* sp. zh168 | 250 | FJ851424 | clade_238 | Y | OP |
| *Bacillus sphaericus* | 251 | DQ286318 | clade_238 | Y | OP |
| *Bacillus sporothermodurans* | 252 | NR_026010 | clade_238 | Y | OP |
| *Bacillus subtilis* | 253 | EU627588 | clade_238 | Y | OP |
| *Bacillus thermoamylovorans* | 254 | NR_029151 | clade_238 | Y | OP |
| *Bacillus thuringiensis* | 255 | NC_008600 | clade_238 | Y | OP |
| *Bacillus weihenstephanensis* | 256 | NR_074926 | clade_238 | Y | OP |
| *Geobacillus kaustophilus* | 933 | NR_074989 | clade_238 | Y | N |
| *Geobacillus stearothermophilus* | 936 | NR_040794 | clade_238 | Y | N |
| *Geobacillus thermodenitrificans* | 938 | NR_074976 | clade_238 | Y | N |
| *Geobacillus thermoglucosidasius* | 939 | NR_043022 | clade_238 | Y | N |
| *Lysinibacillus sphaericus* | 1193 | NR_074883 | clade_238 | Y | N |
| Clostridiales sp. SS3_4 | 543 | AY305316 | clade_246 | Y | N |
| *Clostridium beijerinckii* | 557 | NR_074434 | clade_252 | Y | N |
| *Clostridium botulinum* | 560 | NC_010723 | clade_252 | Y | Category-A |
| *Clostridium butyricum* | 561 | ABDT01000017 | clade_252 | Y | N |
| *Clostridium chauvoei* | 568 | EU106372 | clade_252 | Y | N |
| *Clostridium favososporum* | 582 | X76749 | clade_252 | Y | N |
| *Clostridium histolyticum* | 592 | HF558362 | clade_252 | Y | N |
| *Clostridium isatidis* | 597 | NR_026347 | clade_252 | Y | N |
| *Clostridium limosum* | 602 | FR870444 | clade_252 | Y | N |
| *Clostridium sartagoforme* | 622 | NR_026490 | clade_252 | Y | N |
| *Clostridium septicum* | 624 | NR_026020 | clade_252 | Y | N |
| *Clostridium* sp. 7_2_43FAA | 626 | ACDK01000101 | clade_252 | Y | N |
| *Clostridium sporogenes* | 645 | ABKW02000003 | clade_252 | Y | N |
| *Clostridium tertium* | 653 | Y18174 | clade_252 | Y | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Clostridium carnis* | 564 | NR_044716 | clade_253 | Y | N |
| *Clostridium celatum* | 565 | X77844 | clade_253 | Y | N |
| *Clostridium disporicum* | 579 | NR_026491 | clade_253 | Y | N |
| *Clostridium gasigenes* | 585 | NR_024945 | clade_253 | Y | N |
| *Clostridium quinii* | 616 | NR_026149 | clade_253 | Y | N |
| *Clostridium hylemonae* | 593 | AB023973 | clade_260 | Y | N |
| *Clostridium scindens* | 623 | AF262238 | clade_260 | Y | N |
| Lachnospiraceae bacterium 5_1_57FAA | 1054 | ACTR01000020 | clade_260 | Y | N |
| *Clostridium glycyrrhizinilyticum* | 588 | AB233029 | clade_262 | Y | N |
| *Clostridium nexile* | 607 | X73443 | clade_262 | Y | N |
| *Coprococcus comes* | 674 | ABVR01000038 | clade_262 | Y | N |
| Lachnospiraceae bacterium 1_1_57FAA | 1048 | ACTM01000065 | clade_262 | Y | N |
| Lachnospiraceae bacterium 1_4_56FAA | 1049 | ACTN01000028 | clade_262 | Y | N |
| Lachnospiraceae bacterium 8_1_57FAA | 1057 | ACWQ01000079 | clade_262 | Y | N |
| *Ruminococcus lactaris* | 1663 | ABOU02000049 | clade_262 | Y | N |
| *Ruminococcus torques* | 1670 | AAVP02000002 | clade_262 | Y | N |
| *Paenibacillus lautus* | 1397 | NR_040882 | clade_270 | Y | N |
| *Paenibacillus polymyxa* | 1399 | NR_037006 | clade_270 | Y | N |
| *Paenibacillus* sp. HGF5 | 1402 | AEXS01000095 | clade_270 | Y | N |
| *Paenibacillus* sp. HGF7 | 1403 | AFDH01000147 | clade_270 | Y | N |
| *Eubacterium* sp. oral clone JI012 | 868 | AY349379 | clade_298 | Y | N |
| *Alicyclobacillus contaminans* | 124 | NR_041475 | clade_301 | Y | N |
| *Alicyclobacillus herbarius* | 126 | NR_024753 | clade_301 | Y | N |
| *Alicyclobacillus pomorum* | 127 | NR_024801 | clade_301 | Y | N |
| *Blautia coccoides* | 373 | AB571656 | clade_309 | Y | N |
| *Blautia glucerasea* | 374 | AB588023 | clade_309 | Y | N |
| *Blautia glucerasei* | 375 | AB439724 | clade_309 | Y | N |
| *Blautia hansenii* | 376 | ABYU02000037 | clade_309 | Y | N |
| *Blautia luti* | 378 | AB691576 | clade_309 | Y | N |
| *Blautia producta* | 379 | AB600998 | clade_309 | Y | N |
| *Blautia schinkii* | 380 | NR_026312 | clade_309 | Y | N |
| *Blautia* sp. M25 | 381 | HM626178 | clade_309 | Y | N |
| *Blautia stercoris* | 382 | HM626177 | clade_309 | Y | N |
| *Blautia wexlerae* | 383 | EF036467 | clade_309 | Y | N |
| *Bryantella formatexigens* | 439 | ACCL02000018 | clade_309 | Y | N |
| *Clostridium coccoides* | 573 | EF025906 | clade_309 | Y | N |
| *Eubacterium cellulosolvens* | 839 | AY178842 | clade_309 | Y | N |
| Lachnospiraceae bacterium 6_1_63FAA | 1056 | ACTV01000014 | clade_309 | Y | N |
| *Ruminococcus hansenii* | 1662 | M59114 | clade_309 | Y | N |
| *Ruminococcus obeum* | 1664 | AY169419 | clade_309 | Y | N |
| *Ruminococcus* sp. 5_1_39BFAA | 1666 | ACII01000172 | clade_309 | Y | N |
| *Ruminococcus* sp. K_1 | 1669 | AB222208 | clade_309 | Y | N |
| *Syntrophococcus sucromutans* | 1911 | NR_036869 | clade_309 | Y | N |
| *Bacillus alcalophilus* | 198 | X76436 | clade_327 | Y | N |
| *Bacillus clausii* | 205 | FN397477 | clade_327 | Y | OP |
| *Bacillus gelatini* | 210 | NR_025595 | clade_327 | Y | OP |
| *Bacillus halodurans* | 212 | AY144582 | clade_327 | Y | OP |
| *Bacillus* sp. oral taxon F26 | 246 | HM099642 | clade_327 | Y | OP |
| *Clostridium innocuum* | 595 | M23732 | clade_351 | Y | N |
| *Clostridium* sp. HGF2 | 628 | AENW01000022 | clade_351 | Y | N |
| *Clostridium perfringens* | 612 | ABDW01000023 | clade_353 | Y | Category-B |
| *Sarcina ventriculi* | 1687 | NR_026146 | clade_353 | Y | N |
| *Clostridium bartlettii* | 556 | ABEZ02000012 | clade_354 | Y | N |
| *Clostridium bifermentans* | 558 | X73437 | clade_354 | Y | N |
| *Clostridium ghonii* | 586 | AB542933 | clade_354 | Y | N |
| *Clostridium glycolicum* | 587 | FJ384385 | clade_354 | Y | N |
| *Clostridium mayombei* | 605 | FR733682 | clade_354 | Y | N |
| *Clostridium sordellii* | 625 | AB448946 | clade_354 | Y | N |
| *Clostridium* sp. MT4 E | 635 | FJ159523 | clade_354 | Y | N |
| *Eubacterium tenue* | 872 | M59118 | clade_354 | Y | N |
| *Clostridium argentinense* | 553 | NR_029232 | clade_355 | Y | N |
| *Clostridium* sp. JC122 | 630 | CAEV01000127 | clade_355 | Y | N |
| *Clostridium* sp. NMBHI_1 | 636 | JN093130 | clade_355 | Y | N |
| *Clostridium subterminale* | 650 | NR_041795 | clade_355 | Y | N |
| *Clostridium sulfidigenes* | 651 | NR_044161 | clade_355 | Y | N |
| *Dorea formicigenerans* | 773 | AAXA02000006 | clade_360 | Y | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Dorea longicatena* | 774 | AJ132842 | clade_360 | Y | N |
| Lachnospiraceae bacterium 2_1_46FAA | 1050 | ADLB01000035 | clade_360 | Y | N |
| Lachnospiraceae bacterium 2_1_58FAA | 1051 | ACTO01000052 | clade_360 | Y | N |
| Lachnospiraceae bacterium 4_1_37FAA | 1053 | ADCR01000030 | clade_360 | Y | N |
| Lachnospiraceae bacterium 9_1_43BFAA | 1058 | ACTX01000023 | clade_360 | Y | N |
| *Ruminococcus gnavus* | 1661 | X94967 | clade_360 | Y | N |
| *Ruminococcus* sp. ID8 | 1668 | AY960564 | clade_360 | Y | N |
| *Blautia hydrogenotrophica* | 377 | ACBZ01000217 | clade_368 | Y | N |
| *Lactonifactor longoviformis* | 1147 | DQ100449 | clade_368 | Y | N |
| *Robinsoniella peoriensis* | 1633 | AF445258 | clade_368 | Y | N |
| *Eubacterium infirmum* | 849 | U13039 | clade_384 | Y | N |
| *Eubacterium* sp. WAL 14571 | 864 | FJ687606 | clade_384 | Y | N |
| Erysipelotrichaceae bacterium 5_2_54FAA | 823 | ACZW01000054 | clade_385 | Y | N |
| *Eubacterium biforme* | 835 | ABYT01000002 | clade_385 | Y | N |
| *Eubacterium cylindroides* | 842 | FP929041 | clade_385 | Y | N |
| *Eubacterium dolichum* | 844 | L34682 | clade_385 | Y | N |
| *Eubacterium* sp. 3_1_31 | 861 | ACTL01000045 | clade_385 | Y | N |
| *Eubacterium tortuosum* | 873 | NR_044648 | clade_385 | Y | N |
| *Bulleidia extructa* | 441 | ADFR01000011 | clade_388 | Y | N |
| *Solobacterium moorei* | 1739 | AECQ01000039 | clade_388 | Y | N |
| *Coprococcus catus* | 673 | EU266552 | clade_393 | Y | N |
| Lachnospiraceae bacterium oral taxon F15 | 1064 | HM099641 | clade_393 | Y | N |
| *Clostridium cochlearium* | 574 | NR_044717 | clade_395 | Y | N |
| *Clostridium malenominatum* | 604 | FR749893 | clade_395 | Y | N |
| *Clostridium tetani* | 654 | NC_004557 | clade_395 | Y | N |
| *Acetivibrio ethanolgignens* | 6 | FR749897 | clade_396 | Y | N |
| *Anaerosporobacter mobilis* | 161 | NR_042953 | clade_396 | Y | N |
| *Bacteroides pectinophilus* | 288 | ABVQ01000036 | clade_396 | Y | N |
| *Clostridium aminovalericum* | 551 | NR_029245 | clade_396 | Y | N |
| *Clostridium phytofermentans* | 613 | NR_074652 | clade_396 | Y | N |
| *Eubacterium hallii* | 848 | L34621 | clade_396 | Y | N |
| *Eubacterium xylanophilum* | 875 | L34628 | clade_396 | Y | N |
| *Ruminococcus callidus* | 1658 | NR_029160 | clade_406 | Y | N |
| *Ruminococcus champanellensis* | 1659 | FP929052 | clade_406 | Y | N |
| *Ruminococcus* sp. 18P13 | 1665 | AJ515913 | clade_406 | Y | N |
| *Ruminococcus* sp. 9SE51 | 1667 | FM954974 | clade_406 | Y | N |
| *Anaerostipes caccae* | 162 | ABAX03000023 | clade_408 | Y | N |
| *Anaerostipes* sp. 3_2_56FAA | 163 | ACWB01000002 | clade_408 | Y | N |
| Clostridiales bacterium 1_7_47FAA | 541 | ABQR01000074 | clade_408 | Y | N |
| Clostridiales sp. SM4_1 | 542 | FP929060 | clade_408 | Y | N |
| Clostridiales sp. SSC_2 | 544 | FP929061 | clade_408 | Y | N |
| *Clostridium aerotolerans* | 546 | X76163 | clade_408 | Y | N |
| *Clostridium aldenense* | 547 | NR_043680 | clade_408 | Y | N |
| *Clostridium algidixylanolyticum* | 550 | NR_028726 | clade_408 | Y | N |
| *Clostridium amygdalinum* | 552 | AY353957 | clade_408 | Y | N |
| *Clostridium asparagiforme* | 554 | ACCJ01000522 | clade_408 | Y | N |
| *Clostridium bolteae* | 559 | ABCC02000039 | clade_408 | Y | N |
| *Clostridium celerecrescens* | 566 | JQ246092 | clade_408 | Y | N |
| *Clostridium citroniae* | 569 | ADLJ01000059 | clade_408 | Y | N |
| *Clostridium clostridiiformes* | 571 | M59089 | clade_408 | Y | N |
| *Clostridium clostridioforme* | 572 | NR_044715 | clade_408 | Y | N |
| *Clostridium hathewayi* | 590 | AY552788 | clade_408 | Y | N |
| *Clostridium indolis* | 594 | AF028351 | clade_408 | Y | N |
| *Clostridium lavalense* | 600 | EF564277 | clade_408 | Y | N |
| *Clostridium saccharolyticum* | 620 | CP002109 | clade_408 | Y | N |
| *Clostridium* sp. M62_1 | 633 | ACFX02000046 | clade_408 | Y | N |
| *Clostridium* sp. SS2_1 | 638 | ABGC03000041 | clade_408 | Y | N |
| *Clostridium sphenoides* | 643 | X73449 | clade_408 | Y | N |
| *Clostridium symbiosum* | 652 | ADLQ01000114 | clade_408 | Y | N |
| *Clostridium xylanolyticum* | 658 | NR_037068 | clade_408 | Y | N |
| *Eubacterium hadrum* | 847 | FR749933 | clade_408 | Y | N |
| Lachnospiraceae bacterium 3_1_57FAA_CT1 | 1052 | ACTP01000124 | clade_408 | Y | N |
| Lachnospiraceae bacterium 5_1_63FAA | 1055 | ACTS01000081 | clade_408 | Y | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Lachnospiraceae bacterium A4 | 1059 | DQ789118 | clade_408 | Y | N |
| Lachnospiraceae bacterium DJF VP30 | 1060 | EU728771 | clade_408 | Y | N |
| Lachnospiraceae genomosp. C1 | 1065 | AY278618 | clade_408 | Y | N |
| *Clostridium difficile* | 578 | NC_013315 | clade_409 | Y | OP |
| *Eubacterium* sp. AS15b | 862 | HQ616364 | clade_428 | Y | N |
| *Eubacterium* sp. OBRC9 | 863 | HQ616354 | clade_428 | Y | N |
| *Eubacterium* sp. oral clone OH3A | 871 | AY947497 | clade_428 | Y | N |
| *Eubacterium yurii* | 876 | AEES01000073 | clade_428 | Y | N |
| *Clostridium acetobutylicum* | 545 | NR_074511 | clade_430 | Y | N |
| *Clostridium algidicarnis* | 549 | NR_041746 | clade_430 | Y | N |
| *Clostridium cadaveris* | 562 | AB542932 | clade_430 | Y | N |
| *Clostridium carboxidivorans* | 563 | FR733710 | clade_430 | Y | N |
| *Clostridium estertheticum* | 580 | NR_042153 | clade_430 | Y | N |
| *Clostridium fallax* | 581 | NR_044714 | clade_430 | Y | N |
| *Clostridium felsineum* | 583 | AF270502 | clade_430 | Y | N |
| *Clostridium frigidicarnis* | 584 | NR_024919 | clade_430 | Y | N |
| *Clostridium kluyveri* | 598 | NR_074165 | clade_430 | Y | N |
| *Clostridium magnum* | 603 | X77835 | clade_430 | Y | N |
| *Clostridium putrefaciens* | 615 | NR_024995 | clade_430 | Y | N |
| *Clostridium* sp. HPB_46 | 629 | AY862516 | clade_430 | Y | N |
| *Clostridium tyrobutyricum* | 656 | NR_044718 | clade_430 | Y | N |
| *Sutterella parvirubra* | 1899 | AB300989 | clade_432 | Y | N |
| *Acetanaerobacterium elongatum* | 4 | NR_042930 | clade_439 | Y | N |
| *Clostridium cellulosi* | 567 | NR_044624 | clade_439 | Y | N |
| *Ethanoligenens harbinense* | 832 | AY675965 | clade_439 | Y | N |
| *Eubacterium rectale* | 856 | FP929042 | clade_444 | Y | N |
| *Eubacterium* sp. oral clone GI038 | 865 | AY349374 | clade_444 | Y | N |
| *Lachnobacterium bovis* | 1045 | GU324407 | clade_444 | Y | N |
| *Roseburia cecicola* | 1634 | GU233441 | clade_444 | Y | N |
| *Roseburia faecalis* | 1635 | AY804149 | clade_444 | Y | N |
| *Roseburia faecis* | 1636 | AY305310 | clade_444 | Y | N |
| *Roseburia hominis* | 1637 | AJ270482 | clade_444 | Y | N |
| *Roseburia intestinalis* | 1638 | FP929050 | clade_444 | Y | N |
| *Roseburia inulinivorans* | 1639 | AJ270473 | clade_444 | Y | N |
| *Brevibacillus brevis* | 410 | NR_041524 | clade_448 | Y | N |
| *Brevibacillus laterosporus* | 414 | NR_037005 | clade_448 | Y | N |
| *Bacillus coagulans* | 206 | DQ297928 | clade_451 | Y | OP |
| *Sporolactobacillus inulinus* | 1752 | NR_040962 | clade_451 | Y | N |
| *Kocuria palustris* | 1041 | EU333884 | clade_453 | Y | N |
| *Nocardia farcinica* | 1353 | NC_006361 | clade_455 | Y | N |
| *Bacillus* sp. oral taxon F28 | 247 | HM099650 | clade_456 | Y | OP |
| *Catenibacterium mitsuokai* | 495 | AB030224 | clade_469 | Y | N |
| *Clostridium* sp. TM_40 | 640 | AB249652 | clade_469 | Y | N |
| *Coprobacillus cateniformis* | 670 | AB030218 | clade_469 | Y | N |
| *Coprobacillus* sp. 29_1 | 671 | ADKX01000057 | clade_469 | Y | N |
| *Clostridium rectum* | 618 | NR_029271 | clade_470 | Y | N |
| *Eubacterium nodatum* | 854 | U13041 | clade_476 | Y | N |
| *Eubacterium saphenum* | 859 | NR_026031 | clade_476 | Y | N |
| *Eubacterium* sp. oral clone JH012 | 867 | AY349373 | clade_476 | Y | N |
| *Eubacterium* sp. oral clone JS001 | 870 | AY349378 | clade_476 | Y | N |
| *Faecalibacterium prausnitzii* | 880 | ACOP02000011 | clade_478 | Y | N |
| *Gemmiger formicilis* | 932 | GU562446 | clade_478 | Y | N |
| *Subdoligranulum variabile* | 1896 | AJ518869 | clade_478 | Y | N |
| Clostridiaceae bacterium JC13 | 532 | JF824807 | clade_479 | Y | N |
| *Clostridium* sp. MLG055 | 634 | AF304435 | clade_479 | Y | N |
| Erysipelotrichaceae bacterium 3_1_53 | 822 | ACTJ01000113 | clade_479 | Y | N |
| *Clostridium cocleatum* | 575 | NR_026495 | clade_481 | Y | N |
| *Clostridium ramosum* | 617 | M23731 | clade_481 | Y | N |
| *Clostridium saccharogumia* | 619 | DQ100445 | clade_481 | Y | N |
| *Clostridium spiroforme* | 644 | X73441 | clade_481 | Y | N |
| *Coprobacillus* sp. D7 | 672 | ACDT01000199 | clade_481 | Y | N |
| Clostridiales bacterium SY8519 | 535 | AB477431 | clade_482 | Y | N |
| *Clostridium* sp. SY8519 | 639 | AP012212 | clade_482 | Y | N |
| *Eubacterium ramulus* | 855 | AJ011522 | clade_482 | Y | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Erysipelothrix inopinata | 819 | NR_025594 | clade_485 | Y | N |
| Erysipelothrix rhusiopathiae | 820 | ACLK01000021 | clade_485 | Y | N |
| Erysipelothrix tonsillarum | 821 | NR_040871 | clade_485 | Y | N |
| Holdemania filiformis | 1004 | Y11466 | clade_485 | Y | N |
| Mollicutes bacterium pACH93 | 1258 | AY297808 | clade_485 | Y | N |
| Coxiella burnetii | 736 | CP000890 | clade_486 | Y | Category-B |
| Clostridium hiranonis | 591 | AB023970 | clade_487 | Y | N |
| Clostridium irregulare | 596 | NR_029249 | clade_487 | Y | N |
| Clostridium orbiscindens | 609 | Y18187 | clade_494 | Y | N |
| Clostridium sp. NML 04A032 | 637 | EU815224 | clade_494 | Y | N |
| Flavonifractor plautii | 886 | AY724678 | clade_494 | Y | N |
| Pseudoflavonifractor capillosus | 1591 | AY136666 | clade_494 | Y | N |
| Ruminococcaceae bacterium D16 | 1655 | ADDX01000083 | clade_494 | Y | N |
| Acetivibrio cellulolyticus | 5 | NR_025917 | clade_495 | Y | N |
| Clostridium aldrichii | 548 | NR_026099 | clade_495 | Y | N |
| Clostridium clariflavum | 570 | NR_041235 | clade_495 | Y | N |
| Clostridium stercorarium | 647 | NR_025100 | clade_495 | Y | N |
| Clostridium straminisolvens | 649 | NR_024829 | clade_495 | Y | N |
| Clostridium thermocellum | 655 | NR_074629 | clade_495 | Y | N |
| Fusobacterium nucleatum | 901 | ADVK01000034 | clade_497 | Y | N |
| Eubacterium barkeri | 834 | NR_044661 | clade_512 | Y | N |
| Eubacterium callanderi | 838 | NR_026330 | clade_512 | Y | N |
| Eubacterium limosum | 850 | CP002273 | clade_512 | Y | N |
| Anaerotruncus colihominis | 164 | ABGD02000021 | clade_516 | Y | N |
| Clostridium methylpentosum | 606 | ACEC01000059 | clade_516 | Y | N |
| Clostridium sp. YIT 12070 | 642 | AB491208 | clade_516 | Y | N |
| Hydrogenoanaerobacterium saccharovorans | 1005 | NR_044425 | clade_516 | Y | N |
| Ruminococcus albus | 1656 | AY445600 | clade_516 | Y | N |
| Ruminococcus flavefaciens | 1660 | NR_025931 | clade_516 | Y | N |
| Clostridium haemolyticum | 589 | NR_024749 | clade_517 | Y | N |
| Clostridium novyi | 608 | NR_074343 | clade_517 | Y | N |
| Clostridium sp. LMG 16094 | 632 | X95274 | clade_517 | Y | N |
| Eubacterium ventriosum | 874 | L34421 | clade_519 | Y | N |
| Bacteroides galacturonicus | 280 | DQ497994 | clade_522 | Y | N |
| Eubacterium eligens | 845 | CP001104 | clade_522 | Y | N |
| Lachnospira multipara | 1046 | FR733699 | clade_522 | Y | N |
| Lachnospira pectinoschiza | 1047 | L14675 | clade_522 | Y | N |
| Lactobacillus rogosae | 1114 | GU269544 | clade_522 | Y | N |
| Bacillus horti | 214 | NR_036860 | clade_527 | Y | OP |
| Bacillus sp. 9_3AIA | 232 | FN397519 | clade_527 | Y | OP |
| Eubacterium brachy | 836 | U13038 | clade_533 | Y | N |
| Filifactor alocis | 881 | CP002390 | clade_533 | Y | N |
| Filifactor villosus | 882 | NR_041928 | clade_533 | Y | N |
| Clostridium leptum | 601 | AJ305238 | clade_537 | Y | N |
| Clostridium sp. YIT 12069 | 641 | AB491207 | clade_537 | Y | N |
| Clostridium sporosphaeroides | 646 | NR_044835 | clade_537 | Y | N |
| Eubacterium coprostanoligenes | 841 | HM037995 | clade_537 | Y | N |
| Ruminococcus bromii | 1657 | EU266549 | clade_537 | Y | N |
| Eubacterium siraeum | 860 | ABCA03000054 | clade_538 | Y | N |
| Clostridium viride | 657 | NR_026204 | clade_540 | Y | N |
| Oscillibacter sp. G2 | 1386 | HM626173 | clade_540 | Y | N |
| Oscillibacter valericigenes | 1387 | NR_074793 | clade_540 | Y | N |
| Oscillospira guilliermondii | 1388 | AB040495 | clade_540 | Y | N |
| Butyrivibrio crossotus | 455 | ABWN01000012 | clade_543 | Y | N |
| Clostridium sp. L2_50 | 631 | AAYW02000018 | clade_543 | Y | N |
| Coprococcus eutactus | 675 | EF031543 | clade_543 | Y | N |
| Coprococcus sp. ART55_1 | 676 | AY350746 | clade_543 | Y | N |
| Eubacterium ruminantium | 857 | NR_024661 | clade_543 | Y | N |
| Collinsella aerofaciens | 659 | AAVN02000007 | clade_553 | Y | N |
| Alkaliphilus metalliredigenes | 137 | AY137848 | clade_554 | Y | N |
| Alkaliphilus oremlandii | 138 | NR_043674 | clade_554 | Y | N |
| Clostridium sticklandii | 648 | L04167 | clade_554 | Y | N |
| Turicibacter sanguinis | 1965 | AF349724 | clade_555 | Y | N |
| Fulvimonas sp. NML 060897 | 892 | EF589680 | clade_557 | Y | N |
| Desulfitobacterium frappieri | 753 | AJ276701 | clade_560 | Y | N |
| Desulfitobacterium hafniense | 754 | NR_074996 | clade_560 | Y | N |
| Desulfotomaculum nigrificans | 756 | NR_044832 | clade_560 | Y | N |
| Lutispora thermophila | 1191 | NR_041236 | clade_564 | Y | N |
| Brachyspira pilosicoli | 405 | NR_075069 | clade_565 | Y | N |
| Eggerthella lenta | 778 | AF292375 | clade_566 | Y | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Streptomyces albus* | 1888 | AJ697941 | clade_566 | Y | N |
| *Chlamydiales bacterium NS11* | 505 | JN606074 | clade_567 | Y | N |
| *Anaerofustis stercorihominis* | 159 | ABIL02000005 | clade_570 | Y | N |
| *Butyricicoccus pullicaecorum* | 453 | HH793440 | clade_572 | Y | N |
| *Eubacterium desmolans* | 843 | NR_044644 | clade_572 | Y | N |
| *Papillibacter cinnamivorans* | 1415 | NR_025025 | clade_572 | Y | N |
| *Sporobacter termitidis* | 1751 | NR_044972 | clade_572 | Y | N |
| *Deferribacteres* sp. oral clone JV006 | 744 | AY349371 | clade_575 | Y | N |
| *Clostridium colinum* | 577 | NR_026151 | clade_576 | Y | N |
| *Clostridium lactatifermentans* | 599 | NR_025651 | clade_576 | Y | N |
| *Clostridium piliforme* | 614 | D14639 | clade_576 | Y | N |
| *Saccharomonospora viridis* | 1671 | X54286 | clade_579 | Y | N |
| *Thermobifida fusca* | 1921 | NC_007333 | clade_579 | Y | N |
| *Leptospira licerasiae* | 1164 | EF612284 | clade_585 | Y | OP |
| *Moorella thermoacetica* | 1259 | NR_075001 | clade_590 | Y | N |
| *Thermoanaerobacter pseudethanolicus* | 1920 | CP000924 | clade_590 | Y | N |
| *Flexistipes sinusarabici* | 888 | NR_074881 | clade_591 | Y | N |
| *Gloeobacter violaceus* | 942 | NR_074282 | clade_596 | Y | N |
| *Eubacterium* sp. oral clone JN088 | 869 | AY349377 | clade_90 | Y | N |
| *Clostridium oroticum* | 610 | FR749922 | clade_96 | Y | N |
| *Clostridium* sp. D5 | 627 | ADBG01000142 | clade_96 | Y | N |
| *Eubacterium contortum* | 840 | FR749946 | clade_96 | Y | N |
| *Eubacterium fissicatena* | 846 | FR749935 | clade_96 | Y | N |
| *Corynebacterium coyleae* | 692 | X96497 | clade_100 | N | N |
| *Corynebacterium mucifaciens* | 711 | NR_026396 | clade_100 | N | N |
| *Corynebacterium ureicelerivorans* | 733 | AM397636 | clade_100 | N | N |
| *Corynebacterium appendicis* | 684 | NR_028951 | clade_102 | N | N |
| *Corynebacterium genitalium* | 698 | ACLJ01000031 | clade_102 | N | N |
| *Corynebacterium glaucum* | 699 | NR_028971 | clade_102 | N | N |
| *Corynebacterium imitans* | 703 | AF537597 | clade_102 | N | N |
| *Corynebacterium riegelii* | 719 | EU848548 | clade_102 | N | N |
| *Corynebacterium* sp. L_2012475 | 723 | HE575405 | clade_102 | N | N |
| *Corynebacterium* sp. NML 93_0481 | 724 | GU238409 | clade_102 | N | N |
| *Corynebacterium sundsvallense* | 728 | Y09655 | clade_102 | N | N |
| *Corynebacterium tuscaniae* | 730 | AY677186 | clade_102 | N | N |
| *Prevotella maculosa* | 1504 | AGEK01000035 | clade_104 | N | N |
| *Prevotella oris* | 1513 | ADDV01000091 | clade_104 | N | N |
| *Prevotella salivae* | 1517 | AB108826 | clade_104 | N | N |
| *Prevotella* sp. ICM55 | 1521 | HQ616399 | clade_104 | N | N |
| *Prevotella* sp. oral clone AA020 | 1528 | AY005057 | clade_104 | N | N |
| *Prevotella* sp. oral clone GI032 | 1538 | AY349396 | clade_104 | N | N |
| *Prevotella* sp. oral taxon G70 | 1558 | GU432179 | clade_104 | N | N |
| *Prevotella corporis* | 1491 | L16465 | clade_105 | N | N |
| *Bacteroides* sp. 4_1_36 | 312 | ACTC01000133 | clade_110 | N | N |
| *Bacteroides* sp. AR20 | 315 | AF139524 | clade_110 | N | N |
| *Bacteroides* sp. D20 | 319 | ACPT01000052 | clade_110 | N | N |
| *Bacteroides* sp. F_4 | 322 | AB470322 | clade_110 | N | N |
| *Bacteroides uniformis* | 329 | AB050110 | clade_110 | N | N |
| *Prevotella nanceiensis* | 1510 | JN867228 | clade_127 | N | N |
| *Prevotella* sp. oral taxon 299 | 1548 | ACWZ01000026 | clade_127 | N | N |
| *Prevotella bergensis* | 1485 | ACKS01000100 | clade_128 | N | N |
| *Prevotella buccalis* | 1489 | JN867261 | clade_129 | N | N |
| *Prevotella timonensis* | 1564 | ADEF01000012 | clade_129 | N | N |
| *Prevotella oralis* | 1512 | AEPE01000021 | clade_130 | N | N |
| *Prevotella* sp. SEQ072 | 1525 | JN867238 | clade_130 | N | N |
| *Leuconostoc carnosum* | 1177 | NR_040811 | clade_135 | N | N |
| *Leuconostoc gasicomitatum* | 1179 | FN822744 | clade_135 | N | N |
| *Leuconostoc inhae* | 1180 | NR_025204 | clade_135 | N | N |
| *Leuconostoc kimchii* | 1181 | NR_075014 | clade_135 | N | N |
| *Edwardsiella tarda* | 777 | CP002154 | clade_139 | N | N |
| *Photorhabdus asymbiotica* | 1466 | Z76752 | clade_139 | N | N |
| *Psychrobacter arcticus* | 1607 | CP000082 | clade_141 | N | N |
| *Psychrobacter cibarius* | 1608 | HQ698586 | clade_141 | N | N |
| *Psychrobacter cryohalolentis* | 1609 | CP000323 | clade_141 | N | N |
| *Psychrobacter faecalis* | 1610 | HQ698566 | clade_141 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Psychrobacter nivimaris* | 1611 | HQ698587 | clade_141 | N | N |
| *Psychrobacter pulmonis* | 1612 | HQ698582 | clade_141 | N | N |
| *Pseudomonas aeruginosa* | 1592 | AABQ07000001 | clade_154 | N | N |
| *Pseudomonas* sp. 2_1_26 | 1600 | ACWU01000257 | clade_154 | N | N |
| *Corynebacterium confusum* | 691 | Y15886 | clade_158 | N | N |
| *Corynebacterium propinquum* | 712 | NR_037038 | clade_158 | N | N |
| *Corynebacterium pseudodiphtheriticum* | 713 | X84258 | clade_158 | N | N |
| *Bartonella bacilliformis* | 338 | NC_008783 | clade_159 | N | N |
| *Bartonella grahamii* | 339 | CP001562 | clade_159 | N | N |
| *Bartonella henselae* | 340 | NC_005956 | clade_159 | N | N |
| *Bartonella quintana* | 341 | BX897700 | clade_159 | N | N |
| *Bartonella tamiae* | 342 | EF672728 | clade_159 | N | N |
| *Bartonella washoensis* | 343 | FJ719017 | clade_159 | N | N |
| *Brucella abortus* | 430 | ACBJ01000075 | clade_159 | N | Category-B |
| *Brucella canis* | 431 | NR_044652 | clade_159 | N | Category-B |
| *Brucella ceti* | 432 | ACJD01000006 | clade_159 | N | Category-B |
| *Brucella melitensis* | 433 | AE009462 | clade_159 | N | Category-B |
| *Brucella microti* | 434 | NR_042549 | clade_159 | N | Category-B |
| *Brucella ovis* | 435 | NC_009504 | clade_159 | N | Category-B |
| *Brucella* sp. 83_13 | 436 | ACBQ01000040 | clade_159 | N | Category-B |
| *Brucella* sp. BO1 | 437 | EU053207 | clade_159 | N | Category-B |
| *Brucella suis* | 438 | ACBK01000034 | clade_159 | N | Category-B |
| *Ochrobactrum anthropi* | 1360 | NC_009667 | clade_159 | N | N |
| *Ochrobactrum intermedium* | 1361 | ACQA01000001 | clade_159 | N | N |
| *Ochrobactrum pseudintermedium* | 1362 | DQ365921 | clade_159 | N | N |
| *Prevotella* genomosp. C2 | 1496 | AY278625 | clade_164 | N | N |
| *Prevotella multisaccharivorax* | 1509 | AFJE01000016 | clade_164 | N | N |
| *Prevotella* sp. oral clone IDR_CEC_0055 | 1543 | AY550997 | clade_164 | N | N |
| *Prevotella* sp. oral taxon 292 | 1547 | GQ422735 | clade_164 | N | N |
| *Prevotella* sp. oral taxon 300 | 1549 | GU409549 | clade_164 | N | N |
| *Prevotella marshii* | 1505 | AEEI01000070 | clade_166 | N | N |
| *Prevotella* sp. oral clone IK053 | 1544 | AY349401 | clade_166 | N | N |
| *Prevotella* sp. oral taxon 781 | 1554 | GQ422744 | clade_166 | N | N |
| *Prevotella stercorea* | 1562 | AB244774 | clade_166 | N | N |
| *Prevotella brevis* | 1487 | NR_041954 | clade_167 | N | N |
| *Prevotella ruminicola* | 1516 | CP002006 | clade_167 | N | N |
| *Prevotella* sp. sp24 | 1560 | AB003384 | clade_167 | N | N |
| *Prevotella* sp. sp34 | 1561 | AB003385 | clade_167 | N | N |
| *Prevotella albensis* | 1483 | NR_025300 | clade_168 | N | N |
| *Prevotella copri* | 1490 | ACBX02000014 | clade_168 | N | N |
| *Prevotella oulorum* | 1514 | L16472 | clade_168 | N | N |
| *Prevotella* sp. BI_42 | 1518 | AJ581354 | clade_168 | N | N |
| *Prevotella* sp. oral clone P4PB_83 P2 | 1546 | AY207050 | clade_168 | N | N |
| *Prevotella* sp. oral taxon G60 | 1557 | GU432133 | clade_168 | N | N |
| *Prevotella amnii* | 1484 | AB547670 | clade_169 | N | N |
| *Bacteroides caccae* | 268 | EU136686 | clade_170 | N | N |
| *Bacteroides finegoldii* | 277 | AB222699 | clade_170 | N | N |
| *Bacteroides intestinalis* | 283 | ABJL02000006 | clade_171 | N | N |
| *Bacteroides* sp. XB44A | 326 | AM230649 | clade_171 | N | N |
| Bifidobacteriaceae genomosp. C1 | 345 | AY278612 | clade_172 | N | N |
| *Bifidobacterium adolescentis* | 346 | AAXD02000018 | clade_172 | N | N |
| *Bifidobacterium angulatum* | 347 | ABYS02000004 | clade_172 | N | N |
| *Bifidobacterium animalis* | 348 | CP001606 | clade_172 | N | N |
| *Bifidobacterium breve* | 350 | CP002743 | clade_172 | N | N |
| *Bifidobacterium catenulatum* | 351 | ABXY01000019 | clade_172 | N | N |
| *Bifidobacterium dentium* | 352 | CP001750 | clade_172 | N | OP |
| *Bifidobacterium gallicum* | 353 | ABXB03000004 | clade_172 | N | N |
| *Bifidobacterium infantis* | 354 | AY151398 | clade_172 | N | N |
| *Bifidobacterium kashiwanohense* | 355 | AB491757 | clade_172 | N | N |
| *Bifidobacterium longum* | 356 | ABQQ01000041 | clade_172 | N | N |
| *Bifidobacterium pseudocatenulatum* | 357 | ABXX02000002 | clade_172 | N | N |
| *Bifidobacterium pseudolongum* | 358 | NR_043442 | clade_172 | N | N |
| *Bifidobacterium scardovii* | 359 | AJ307005 | clade_172 | N | N |
| *Bifidobacterium* sp. HM2 | 360 | AB425276 | clade_172 | N | N |
| *Bifidobacterium* sp. HMLN12 | 361 | JF519685 | clade_172 | N | N |
| *Bifidobacterium* sp. M45 | 362 | HM626176 | clade_172 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Bifidobacterium sp. MSX5B | 363 | HQ616382 | clade_172 | N | N |
| Bifidobacterium sp. TM_7 | 364 | AB218972 | clade_172 | N | N |
| Bifidobacterium thermophilum | 365 | DQ340557 | clade_172 | N | N |
| Leuconostoc citreum | 1178 | AM157444 | clade_175 | N | N |
| Leuconostoc lactis | 1182 | NR_040823 | clade_175 | N | N |
| Alicyclobacillus acidoterrestris | 123 | NR_040844 | clade_179 | N | N |
| Alicyclobacillus cycloheptanicus | 125 | NR_024754 | clade_179 | N | N |
| Acinetobacter baumannii | 27 | ACYQ01000014 | clade_181 | N | N |
| Acinetobacter calcoaceticus | 28 | AM157426 | clade_181 | N | N |
| Acinetobacter genomosp. C1 | 29 | AY278636 | clade_181 | N | N |
| Acinetobacter haemolyticus | 30 | ADMT01000017 | clade_181 | N | N |
| Acinetobacter johnsonii | 31 | ACPL01000162 | clade_181 | N | N |
| Acinetobacter junii | 32 | ACPM01000135 | clade_181 | N | N |
| Acinetobacter lwoffii | 33 | ACPN01000204 | clade_181 | N | N |
| Acinetobacter parvus | 34 | AIEB01000124 | clade_181 | N | N |
| Acinetobacter schindleri | 36 | NR_025412 | clade_181 | N | N |
| Acinetobacter sp. 56A1 | 37 | GQ178049 | clade_181 | N | N |
| Acinetobacter sp. CIP 101934 | 38 | JQ638573 | clade_181 | N | N |
| Acinetobacter sp. CIP 102143 | 39 | JQ638578 | clade_181 | N | N |
| Acinetobacter sp. M16_22 | 41 | HM366447 | clade_181 | N | N |
| Acinetobacter sp. RUH2624 | 42 | ACQF01000094 | clade_181 | N | N |
| Acinetobacter sp. SH024 | 43 | ADCH01000068 | clade_181 | N | N |
| Lactobacillus jensenii | 1092 | ACQD01000066 | clade_182 | N | N |
| Alcaligenes faecalis | 119 | AB680368 | clade_183 | N | N |
| Alcaligenes sp. CO14 | 120 | DQ643040 | clade_183 | N | N |
| Alcaligenes sp. S3 | 121 | HQ262549 | clade_183 | N | N |
| Oligella ureolytica | 1366 | NR_041998 | clade_183 | N | N |
| Oligella urethralis | 1367 | NR_041753 | clade_183 | N | N |
| Eikenella corrodens | 784 | ACEA01000028 | clade_185 | N | N |
| Kingella denitrificans | 1019 | AEWV01000047 | clade_185 | N | N |
| Kingella genomosp. P1 oral cone MB2_C20 | 1020 | DQ003616 | clade_185 | N | N |
| Kingella kingae | 1021 | AFHS01000073 | clade_185 | N | N |
| Kingella oralis | 1022 | ACJW02000005 | clade_185 | N | N |
| Kingella sp. oral clone ID059 | 1023 | AY349381 | clade_185 | N | N |
| Neisseria elongata | 1330 | ADBF01000003 | clade_185 | N | N |
| Neisseria genomosp. P2 oral clone MB5_P15 | 1332 | DQ003630 | clade_185 | N | N |
| Neisseria sp. oral clone JC012 | 1345 | AY349388 | clade_185 | N | N |
| Neisseria sp. SMC_A9199 | 1342 | FJ763637 | clade_185 | N | N |
| Simonsiella muelleri | 1731 | ADCY01000105 | clade_185 | N | N |
| Corynebacterium glucuronolyticum | 700 | ABYP01000081 | clade_193 | N | N |
| Corynebacterium pyruviciproducens | 716 | FJ185225 | clade_193 | N | N |
| Rothia aeria | 1649 | DQ673320 | clade_194 | N | N |
| Rothia dentocariosa | 1650 | ADDW01000024 | clade_194 | N | N |
| Rothia sp. oral taxon 188 | 1653 | GU470892 | clade_194 | N | N |
| Corynebacterium accolens | 681 | ACGD01000048 | clade_195 | N | N |
| Corynebacterium macginleyi | 707 | AB359393 | clade_195 | N | N |
| Corynebacterium pseudogenitalium | 714 | ABYQ01000237 | clade_195 | N | N |
| Corynebacterium tuberculostearicum | 729 | ACVP01000009 | clade_195 | N | N |
| Lactobacillus casei | 1074 | CP000423 | clade_198 | N | N |
| Lactobacillus paracasei | 1106 | ABQV01000067 | clade_198 | N | N |
| Lactobacillus zeae | 1143 | NR_037122 | clade_198 | N | N |
| Prevotella dentalis | 1492 | AB547678 | clade_205 | N | N |
| Prevotella sp. oral clone ASCG10 | 1529 | AY923148 | clade_206 | N | N |
| Prevotella sp. oral clone HF050 | 1541 | AY349399 | clade_206 | N | N |
| Prevotella sp. oral clone ID019 | 1542 | AY349400 | clade_206 | N | N |
| Prevotella sp. oral clone IK062 | 1545 | AY349402 | clade_206 | N | N |
| Prevotella genomosp. P9 oral clone MB7_G16 | 1499 | DQ003633 | clade_207 | N | N |
| Prevotella sp. oral clone AU069 | 1531 | AY005062 | clade_207 | N | N |
| Prevotella sp. oral clone CY006 | 1532 | AY005063 | clade_207 | N | N |
| Prevotella sp. oral clone FL019 | 1534 | AY349392 | clade_207 | N | N |
| Actinomyces genomosp. C1 | 56 | AY278610 | clade_212 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Actinomyces* genomosp. C2 | 57 | AY278611 | clade_212 | N | N |
| *Actinomyces* genomosp. P1 oral clone MB6_C03 | 58 | DQ003632 | clade_212 | N | N |
| *Actinomyces georgiae* | 59 | GU561319 | clade_212 | N | N |
| *Actinomyces israelii* | 60 | AF479270 | clade_212 | N | N |
| *Actinomyces massiliensis* | 61 | AB545934 | clade_212 | N | N |
| *Actinomyces meyeri* | 62 | GU561321 | clade_212 | N | N |
| *Actinomyces odontolyticus* | 66 | ACYT01000123 | clade_212 | N | N |
| *Actinomyces orihominis* | 68 | AJ575186 | clade_212 | N | N |
| *Actinomyces* sp. CCUG 37290 | 71 | AJ234058 | clade_212 | N | N |
| *Actinomyces* sp. ICM34 | 75 | HQ616391 | clade_212 | N | N |
| *Actinomyces* sp. ICM41 | 76 | HQ616392 | clade_212 | N | N |
| *Actinomyces* sp. ICM47 | 77 | HQ616395 | clade_212 | N | N |
| *Actinomyces* sp. ICM54 | 78 | HQ616398 | clade_212 | N | N |
| *Actinomyces* sp. oral clone IP081 | 87 | AY349366 | clade_212 | N | N |
| *Actinomyces* sp. oral taxon 178 | 91 | AEUH01000060 | clade_212 | N | N |
| *Actinomyces* sp. oral taxon 180 | 92 | AEPP01000041 | clade_212 | N | N |
| *Actinomyces* sp. TeJ5 | 80 | GU561315 | clade_212 | N | N |
| *Haematobacter* sp. BC14248 | 968 | GU396991 | clade_213 | N | N |
| *Paracoccus denitrificans* | 1424 | CP000490 | clade_213 | N | N |
| *Paracoccus marcusii* | 1425 | NR_044922 | clade_213 | N | N |
| *Grimontia hollisae* | 967 | ADAQ01000013 | clade_216 | N | N |
| *Shewanella putrefaciens* | 1723 | CP002457 | clade_216 | N | N |
| *Afipia* genomosp. 4 | 111 | EU117385 | clade_217 | N | N |
| *Rhodopseudomonas palustris* | 1626 | CP000301 | clade_217 | N | N |
| *Methylobacterium extorquens* | 1223 | NC_010172 | clade_218 | N | N |
| *Methylobacterium podarium* | 1224 | AY468363 | clade_218 | N | N |
| *Methylobacterium radiotolerans* | 1225 | GU294320 | clade_218 | N | N |
| *Methylobacterium* sp. 1sub | 1226 | AY468371 | clade_218 | N | N |
| *Methylobacterium* sp. MM4 | 1227 | AY468370 | clade_218 | N | N |
| *Achromobacter denitrificans* | 18 | NR_042021 | clade_224 | N | N |
| *Achromobacter piechaudii* | 19 | ADMS01000149 | clade_224 | N | N |
| *Achromobacter xylosoxidans* | 20 | ACRC01000072 | clade_224 | N | N |
| *Bordetella bronchiseptica* | 384 | NR_025949 | clade_224 | N | OP |
| *Bordetella holmesii* | 385 | AB683187 | clade_224 | N | OP |
| *Bordetella parapertussis* | 386 | NR_025950 | clade_224 | N | OP |
| *Bordetella pertussis* | 387 | BX640418 | clade_224 | N | OP |
| *Microbacterium chocolatum* | 1230 | NR_037045 | clade_225 | N | N |
| *Microbacterium flavescens* | 1231 | EU714363 | clade_225 | N | N |
| *Microbacterium lacticum* | 1233 | EU714351 | clade_225 | N | N |
| *Microbacterium oleivorans* | 1234 | EU714381 | clade_225 | N | N |
| *Microbacterium oxydans* | 1235 | EU714348 | clade_225 | N | N |
| *Microbacterium paraoxydans* | 1236 | AJ491806 | clade_225 | N | N |
| *Microbacterium phyllosphaerae* | 1237 | EU714359 | clade_225 | N | N |
| *Microbacterium schleiferi* | 1238 | NR_044936 | clade_225 | N | N |
| *Microbacterium* sp. 768 | 1239 | EU714378 | clade_225 | N | N |
| *Microbacterium* sp. oral strain C24KA | 1240 | AF287752 | clade_225 | N | N |
| *Microbacterium testaceum* | 1241 | EU714365 | clade_225 | N | N |
| *Corynebacterium atypicum* | 686 | NR_025540 | clade_229 | N | N |
| *Corynebacterium mastitidis* | 708 | AB359395 | clade_229 | N | N |
| *Corynebacterium* sp. NML 97_0186 | 725 | GU238411 | clade_229 | N | N |
| *Mycobacterium elephantis* | 1275 | AF385898 | clade_237 | N | OP |
| *Mycobacterium paraterrae* | 1288 | EU919229 | clade_237 | N | OP |
| *Mycobacterium phlei* | 1289 | GU142920 | clade_237 | N | OP |
| *Mycobacterium* sp. 1776 | 1293 | EU703152 | clade_237 | N | N |
| *Mycobacterium* sp. 1781 | 1294 | EU703147 | clade_237 | N | N |
| *Mycobacterium* sp. AQ1GA4 | 1297 | HM210417 | clade_237 | N | N |
| *Mycobacterium* sp. GN_10546 | 1299 | FJ497243 | clade_237 | N | N |
| *Mycobacterium* sp. GN_10827 | 1300 | FJ497247 | clade_237 | N | N |
| *Mycobacterium* sp. GN_11124 | 1301 | FJ652846 | clade_237 | N | N |
| *Mycobacterium* sp. GN_9188 | 1302 | FJ497240 | clade_237 | N | N |
| *Mycobacterium* sp. GR_2007_210 | 1303 | FJ555538 | clade_237 | N | N |
| *Anoxybacillus contaminans* | 172 | NR_029006 | clade_238 | N | N |
| *Bacillus aeolius* | 195 | NR_025557 | clade_238 | N | N |
| *Brevibacterium frigoritolerans* | 422 | NR_042639 | clade_238 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Geobacillus sp. E263 | 934 | DQ647387 | clade_238 | N | N |
| Geobacillus sp. WCH70 | 935 | CP001638 | clade_238 | N | N |
| Geobacillus thermocatenulatus | 937 | NR_043020 | clade_238 | N | N |
| Geobacillus thermoleovorans | 940 | NR_074931 | clade_238 | N | N |
| Lysinibacillus fusiformis | 1192 | FN397522 | clade_238 | N | N |
| Planomicrobium koreense | 1468 | NR_025011 | clade_238 | N | N |
| Sporosarcina newyorkensis | 1754 | AFPZ01000142 | clade_238 | N | N |
| Sporosarcina sp. 2681 | 1755 | GU994081 | clade_238 | N | N |
| Ureibacillus composti | 1968 | NR_043746 | clade_238 | N | N |
| Ureibacillus suwonensis | 1969 | NR_043232 | clade_238 | N | N |
| Ureibacillus terrenus | 1970 | NR_025394 | clade_238 | N | N |
| Ureibacillus thermophilus | 1971 | NR_043747 | clade_238 | N | N |
| Ureibacillus thermosphaericus | 1972 | NR_040961 | clade_238 | N | N |
| Prevotella micans | 1507 | AGWK01000061 | clade_239 | N | N |
| Prevotella sp. oral clone DA058 | 1533 | AY005065 | clade_239 | N | N |
| Prevotella sp. SEQ053 | 1523 | JN867222 | clade_239 | N | N |
| Treponema socranskii | 1937 | NR_024868 | clade_240 | N | OP |
| Treponema sp. 6:H:D15A_4 | 1938 | AY005083 | clade_240 | N | N |
| Treponema sp. oral taxon 265 | 1953 | GU408850 | clade_240 | N | N |
| Treponema sp. oral taxon G85 | 1958 | GU432215 | clade_240 | N | N |
| Porphyromonas endodontalis | 1472 | ACNN01000021 | clade_241 | N | N |
| Porphyromonas sp. oral clone BB134 | 1478 | AY005068 | clade_241 | N | N |
| Porphyromonas sp. oral clone F016 | 1479 | AY005069 | clade_241 | N | N |
| Porphyromonas sp. oral clone P2PB_52 P1 | 1480 | AY207054 | clade_241 | N | N |
| Porphyromonas sp. oral clone P4GB_100 P2 | 1481 | AY207057 | clade_241 | N | N |
| Acidovorax sp. 98_63833 | 26 | AY258065 | clade_245 | N | N |
| Comamonadaceae bacterium NML000135 | 663 | JN585335 | clade_245 | N | N |
| Comamonadaceae bacterium NML790751 | 664 | JN585331 | clade_245 | N | N |
| Comamonadaceae bacterium NML910035 | 665 | JN585332 | clade_245 | N | N |
| Comamonadaceae bacterium NML910036 | 666 | JN585333 | clade_245 | N | N |
| Comamonas sp. NSP5 | 668 | AB076850 | clade_245 | N | N |
| Delftia acidovorans | 748 | CP000884 | clade_245 | N | N |
| Xenophilus aerolatus | 2018 | JN585329 | clade_245 | N | N |
| Oribacterium sp. oral taxon 078 | 1380 | ACIQ02000009 | clade_246 | N | N |
| Oribacterium sp. oral taxon 102 | 1381 | GQ422713 | clade_246 | N | N |
| Weissella cibaria | 2007 | NR_036924 | clade_247 | N | N |
| Weissella confusa | 2008 | NR_040816 | clade_247 | N | N |
| Weissella hellenica | 2009 | AB680902 | clade_247 | N | N |
| Weissella kandleri | 2010 | NR_044659 | clade_247 | N | N |
| Weissella koreensis | 2011 | NR_075058 | clade_247 | N | N |
| Weissella paramesenteroides | 2012 | ACKU01000017 | clade_247 | N | N |
| Weissella sp. KLDS 7.0701 | 2013 | EU600924 | clade_247 | N | N |
| Mobiluncus curtisii | 1251 | AEPZ01000013 | clade_249 | N | N |
| Enhydrobacter aerosaccus | 785 | ACYI01000081 | clade_256 | N | N |
| Moraxella osloensis | 1262 | JN175341 | clade_256 | N | N |
| Moraxella sp. GM2 | 1264 | JF837191 | clade_256 | N | N |
| Brevibacterium casei | 420 | JF951998 | clade_257 | N | N |
| Brevibacterium epidermidis | 421 | NR_029262 | clade_257 | N | N |
| Brevibacterium sanguinis | 426 | NR_028016 | clade_257 | N | N |
| Brevibacterium sp. H15 | 427 | AB177640 | clade_257 | N | N |
| Acinetobacter radioresistens | 35 | ACVR01000010 | clade_261 | N | N |
| Lactobacillus alimentarius | 1068 | NR_044701 | clade_263 | N | N |
| Lactobacillus farciminis | 1082 | NR_044707 | clade_263 | N | N |
| Lactobacillus kimchii | 1097 | NR_025045 | clade_263 | N | N |
| Lactobacillus nodensis | 1101 | NR_041629 | clade_263 | N | N |
| Lactobacillus tucceti | 1138 | NR_042194 | clade_263 | N | N |
| Pseudomonas mendocina | 1595 | AAUL01000021 | clade_265 | N | N |
| Pseudomonas pseudoalcaligenes | 1598 | NR_037000 | clade_265 | N | N |
| Pseudomonas sp. NP522b | 1602 | EU723211 | clade_265 | N | N |
| Pseudomonas stutzeri | 1603 | AM905854 | clade_265 | N | N |
| Paenibacillus barcinonensis | 1390 | NR_042272 | clade_270 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Paenibacillus barengoltzii* | 1391 | NR_042756 | clade_270 | N | N |
| *Paenibacillus chibensis* | 1392 | NR_040885 | clade_270 | N | N |
| *Paenibacillus cookii* | 1393 | NR_025372 | clade_270 | N | N |
| *Paenibacillus durus* | 1394 | NR_037017 | clade_270 | N | N |
| *Paenibacillus glucanolyticus* | 1395 | D78470 | clade_270 | N | N |
| *Paenibacillus lactis* | 1396 | NR_025739 | clade_270 | N | N |
| *Paenibacillus pabuli* | 1398 | NR_040853 | clade_270 | N | N |
| *Paenibacillus popilliae* | 1400 | NR_040888 | clade_270 | N | N |
| *Paenibacillus* sp. CIP 101062 | 1401 | HM212646 | clade_270 | N | N |
| *Paenibacillus* sp. JC66 | 1404 | JF824808 | clade_270 | N | N |
| *Paenibacillus* sp. R_27413 | 1405 | HE586333 | clade_270 | N | N |
| *Paenibacillus* sp. R_27422 | 1406 | HE586338 | clade_270 | N | N |
| *Paenibacillus timonensis* | 1408 | NR_042844 | clade_270 | N | N |
| *Rothia mucilaginosa* | 1651 | ACVO01000020 | clade_271 | N | N |
| *Rothia nasimurium* | 1652 | NR_025310 | clade_271 | N | N |
| *Prevotella* sp. oral taxon 302 | 1550 | ACZK01000043 | clade_280 | N | N |
| *Prevotella* sp. oral taxon F68 | 1556 | HM099652 | clade_280 | N | N |
| *Prevotella tannerae* | 1563 | ACIJ02000018 | clade_280 | N | N |
| Prevotellaceae bacterium P4P_62 P1 | 1566 | AY207061 | clade_280 | N | N |
| *Porphyromonas asaccharolytica* | 1471 | AENO01000048 | clade_281 | N | N |
| *Porphyromonas gingivalis* | 1473 | AE015924 | clade_281 | N | N |
| *Porphyromonas macacae* | 1475 | NR_025908 | clade_281 | N | N |
| *Porphyromonas* sp. UQD 301 | 1477 | EU012301 | clade_281 | N | N |
| *Porphyromonas uenonis* | 1482 | ACLR01000152 | clade_281 | N | N |
| *Leptotrichia buccalis* | 1165 | CP001685 | clade_282 | N | N |
| *Leptotrichia hofstadii* | 1168 | ACVB02000032 | clade_282 | N | N |
| *Leptotrichia* sp. oral clone HE012 | 1173 | AY349386 | clade_282 | N | N |
| *Leptotrichia* sp. oral taxon 223 | 1176 | GU408547 | clade_282 | N | N |
| *Bacteroides fluxus* | 278 | AFBN01000029 | clade_285 | N | N |
| *Bacteroides helcogenes* | 281 | CP002352 | clade_285 | N | N |
| *Parabacteroides johnsonii* | 1419 | ABYH01000014 | clade_286 | N | N |
| *Parabacteroides merdae* | 1420 | EU136685 | clade_286 | N | N |
| *Treponema denticola* | 1926 | ADEC01000002 | clade_288 | N | OP |
| *Treponema* genomosp. P5 oral clone MB3_P23 | 1929 | DQ003624 | clade_288 | N | N |
| *Treponema putidum* | 1935 | AJ543428 | clade_288 | N | OP |
| *Treponema* sp. oral clone P2PB_53 P3 | 1942 | AY207055 | clade_288 | N | N |
| *Treponema* sp. oral taxon 247 | 1949 | GU408748 | clade_288 | N | N |
| *Treponema* sp. oral taxon 250 | 1950 | GU408776 | clade_288 | N | N |
| *Treponema* sp. oral taxon 251 | 1951 | GU408781 | clade_288 | N | N |
| *Anaerococcus hydrogenalis* | 144 | ABXA01000039 | clade_289 | N | N |
| *Anaerococcus* sp. 8404299 | 148 | HM587318 | clade_289 | N | N |
| *Anaerococcus* sp. gpac215 | 156 | AM176540 | clade_289 | N | N |
| *Anaerococcus vaginalis* | 158 | ACXU01000016 | clade_289 | N | N |
| *Propionibacterium acidipropionici* | 1569 | NC_019395 | clade_290 | N | N |
| *Propionibacterium avidum* | 1571 | AJ003055 | clade_290 | N | N |
| *Propionibacterium granulosum* | 1573 | FJ785716 | clade_290 | N | N |
| *Propionibacterium jensenii* | 1574 | NR_042269 | clade_290 | N | N |
| *Propionibacterium propionicum* | 1575 | NR_025277 | clade_290 | N | N |
| *Propionibacterium* sp. H456 | 1577 | AB177643 | clade_290 | N | N |
| *Propionibacterium thoenii* | 1581 | NR_042270 | clade_290 | N | N |
| *Bifidobacterium bifidum* | 349 | ABQP01000027 | clade_293 | N | N |
| *Leuconostoc mesenteroides* | 1183 | ACKV01000113 | clade_295 | N | N |
| *Leuconostoc pseudomesenteroides* | 1184 | NR_040814 | clade_295 | N | N |
| *Johnsonella ignava* | 1016 | X87152 | clade_298 | N | N |
| *Propionibacterium acnes* | 1570 | ADJM01000010 | clade_299 | N | N |
| *Propionibacterium* sp. 434_HC2 | 1576 | AFIL01000035 | clade_299 | N | N |
| *Propionibacterium* sp. LG | 1578 | AY354921 | clade_299 | N | N |
| *Propionibacterium* sp. S555a | 1579 | AB264622 | clade_299 | N | N |
| *Alicyclobacillus* sp. CCUG 53762 | 128 | HE613268 | clade_301 | N | N |
| *Actinomyces cardiffensis* | 53 | GU470888 | clade_303 | N | N |
| *Actinomyces funkei* | 55 | HQ906497 | clade_303 | N | N |
| *Actinomyces* sp. HKU31 | 74 | HQ335393 | clade_303 | N | N |
| *Actinomyces* sp. oral taxon C55 | 94 | HM099646 | clade_303 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Kerstersia gyiorum | 1018 | NR_025669 | clade_307 | N | N |
| Pigmentiphaga daeguensis | 1467 | JN585327 | clade_307 | N | N |
| Aeromonas allosaccharophila | 104 | S39232 | clade_308 | N | N |
| Aeromonas enteropelogenes | 105 | X71121 | clade_308 | N | N |
| Aeromonas hydrophila | 106 | NC_008570 | clade_308 | N | N |
| Aeromonas jandaei | 107 | X60413 | clade_308 | N | N |
| Aeromonas salmonicida | 108 | NC_009348 | clade_308 | N | N |
| Aeromonas trota | 109 | X60415 | clade_308 | N | N |
| Aeromonas veronii | 110 | NR_044845 | clade_308 | N | N |
| Marvinbryantia formatexigens | 1196 | AJ505973 | clade_309 | N | N |
| Rhodobacter sp. oral taxon C30 | 1620 | HM099648 | clade_310 | N | N |
| Rhodobacter sphaeroides | 1621 | CP000144 | clade_310 | N | N |
| Lactobacillus antri | 1071 | ACLL01000037 | clade_313 | N | N |
| Lactobacillus coleohominis | 1076 | ACOH01000030 | clade_313 | N | N |
| Lactobacillus fermentum | 1083 | CP002033 | clade_313 | N | N |
| Lactobacillus gastricus | 1085 | AICN01000060 | clade_313 | N | N |
| Lactobacillus mucosae | 1099 | FR693800 | clade_313 | N | N |
| Lactobacillus oris | 1103 | AEKL01000077 | clade_313 | N | N |
| Lactobacillus pontis | 1111 | HM218420 | clade_313 | N | N |
| Lactobacillus reuteri | 1112 | ACGW02000012 | clade_313 | N | N |
| Lactobacillus sp. KLDS 1.0707 | 1127 | EU600911 | clade_313 | N | N |
| Lactobacillus sp. KLDS 1.0709 | 1128 | EU600913 | clade_313 | N | N |
| Lactobacillus sp. KLDS 1.0711 | 1129 | EU600915 | clade_313 | N | N |
| Lactobacillus sp. KLDS 1.0713 | 1131 | EU600917 | clade_313 | N | N |
| Lactobacillus sp. KLDS 1.0716 | 1132 | EU600921 | clade_313 | N | N |
| Lactobacillus sp. KLDS 1.0718 | 1133 | EU600922 | clade_313 | N | N |
| Lactobacillus sp. oral taxon 052 | 1137 | GQ422710 | clade_313 | N | N |
| Lactobacillus vaginalis | 1140 | ACGV01000168 | clade_313 | N | N |
| Brevibacterium aurantiacum | 419 | NR_044854 | clade_314 | N | N |
| Brevibacterium linens | 423 | AJ315491 | clade_314 | N | N |
| Lactobacillus pentosus | 1108 | JN813103 | clade_315 | N | N |
| Lactobacillus plantarum | 1110 | ACGZ02000033 | clade_315 | N | N |
| Lactobacillus sp. KLDS 1.0702 | 1123 | EU600906 | clade_315 | N | N |
| Lactobacillus sp. KLDS 1.0703 | 1124 | EU600907 | clade_315 | N | N |
| Lactobacillus sp. KLDS 1.0704 | 1125 | EU600908 | clade_315 | N | N |
| Lactobacillus sp. KLDS 1.0705 | 1126 | EU600909 | clade_315 | N | N |
| Agrobacterium radiobacter | 115 | CP000628 | clade_316 | N | N |
| Agrobacterium tumefaciens | 116 | AJ389893 | clade_316 | N | N |
| Corynebacterium argentoratense | 685 | EF463055 | clade_317 | N | N |
| Corynebacterium diphtheriae | 693 | NC_002935 | clade_317 | N | OP |
| Corynebacterium pseudotuberculosis | 715 | NR_037070 | clade_317 | N | N |
| Corynebacterium renale | 717 | NR_037069 | clade_317 | N | N |
| Corynebacterium ulcerans | 731 | NR_074467 | clade_317 | N | N |
| Aurantimonas coralicida | 191 | AY065627 | clade_318 | N | N |
| Aureimonas altamirensis | 192 | FN658986 | clade_318 | N | N |
| Lactobacillus acidipiscis | 1066 | NR_024718 | clade_320 | N | N |
| Lactobacillus salivarius | 1117 | AEBA01000145 | clade_320 | N | N |
| Lactobacillus sp. KLDS 1.0719 | 1134 | EU600923 | clade_320 | N | N |
| Lactobacillus buchneri | 1073 | ACGH01000101 | clade_321 | N | N |
| Lactobacillus genomosp. C1 | 1086 | AY278619 | clade_321 | N | N |
| Lactobacillus genomosp. C2 | 1087 | AY278620 | clade_321 | N | N |
| Lactobacillus hilgardii | 1089 | ACGP01000200 | clade_321 | N | N |
| Lactobacillus kefiri | 1096 | NR_042230 | clade_321 | N | N |
| Lactobacillus parabuchneri | 1105 | NR_041294 | clade_321 | N | N |
| Lactobacillus parakefiri | 1107 | NR_029039 | clade_321 | N | N |
| Lactobacillus curvatus | 1079 | NR_042437 | clade_322 | N | N |
| Lactobacillus sakei | 1116 | DQ989236 | clade_322 | N | N |
| Aneurinibacillus aneurinilyticus | 167 | AB101592 | clade_323 | N | N |
| Aneurinibacillus danicus | 168 | NR_028657 | clade_323 | N | N |
| Aneurinibacillus migulanus | 169 | NR_036799 | clade_323 | N | N |
| Aneurinibacillus terranovensis | 170 | NR_042271 | clade_323 | N | N |
| Staphylococcus aureus | 1757 | CP002643 | clade_325 | N | Category-B |
| Staphylococcus auricularis | 1758 | JQ624774 | clade_325 | N | N |
| Staphylococcus capitis | 1759 | ACFR01000029 | clade_325 | N | N |
| Staphylococcus caprae | 1760 | ACRH01000033 | clade_325 | N | N |
| Staphylococcus carnosus | 1761 | NR_075003 | clade_325 | N | N |
| Staphylococcus cohnii | 1762 | JN175375 | clade_325 | N | N |
| Staphylococcus condimenti | 1763 | NR_029345 | clade_325 | N | N |
| Staphylococcus epidermidis | 1764 | ACHE01000056 | clade_325 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Staphylococcus equorum | 1765 | NR_027520 | clade_325 | N | N |
| Staphylococcus haemolyticus | 1767 | NC_007168 | clade_325 | N | N |
| Staphylococcus hominis | 1768 | AM157418 | clade_325 | N | N |
| Staphylococcus lugdunensis | 1769 | AEQA01000024 | clade_325 | N | N |
| Staphylococcus pasteuri | 1770 | FJ189773 | clade_325 | N | N |
| Staphylococcus pseudintermedius | 1771 | CP002439 | clade_325 | N | N |
| Staphylococcus saccharolyticus | 1772 | NR_029158 | clade_325 | N | N |
| Staphylococcus saprophyticus | 1773 | NC_007350 | clade_325 | N | N |
| Staphylococcus sp. clone bottae7 | 1777 | AF467424 | clade_325 | N | N |
| Staphylococcus sp. H292 | 1775 | AB177642 | clade_325 | N | N |
| Staphylococcus sp. H780 | 1776 | AB177644 | clade_325 | N | N |
| Staphylococcus succinus | 1778 | NR_028667 | clade_325 | N | N |
| Staphylococcus warneri | 1780 | ACPZ01000009 | clade_325 | N | N |
| Staphylococcus xylosus | 1781 | AY395016 | clade_325 | N | N |
| Cardiobacterium hominis | 490 | ACKY01000036 | clade_326 | N | N |
| Cardiobacterium valvarum | 491 | NR_028847 | clade_326 | N | N |
| Pseudomonas fluorescens | 1593 | AY622220 | clade_326 | N | N |
| Pseudomonas gessardii | 1594 | FJ943496 | clade_326 | N | N |
| Pseudomonas monteilii | 1596 | NR_024910 | clade_326 | N | N |
| Pseudomonas poae | 1597 | GU188951 | clade_326 | N | N |
| Pseudomonas putida | 1599 | AF094741 | clade_326 | N | N |
| Pseudomonas sp. G1229 | 1601 | DQ910482 | clade_326 | N | N |
| Pseudomonas tolaasii | 1604 | AF320988 | clade_326 | N | N |
| Pseudomonas viridiflava | 1605 | NR_042764 | clade_326 | N | N |
| Listeria grayi | 1185 | ACCR02000003 | clade_328 | N | OP |
| Listeria innocua | 1186 | JF967625 | clade_328 | N | N |
| Listeria ivanovii | 1187 | X56151 | clade_328 | N | N |
| Listeria monocytogenes | 1188 | CP002003 | clade_328 | N | Category-B |
| Listeria welshimeri | 1189 | AM263198 | clade_328 | N | OP |
| Capnocytophaga sp. oral clone ASCH05 | 484 | AY923149 | clade_333 | N | N |
| Capnocytophaga sputigena | 489 | ABZV01000054 | clade_333 | N | N |
| Leptotrichia genomosp. C1 | 1166 | AY278621 | clade_334 | N | N |
| Leptotrichia shahii | 1169 | AY029806 | clade_334 | N | N |
| Leptotrichia sp. neutropenic Patient | 1170 | AF189244 | clade_334 | N | N |
| Leptotrichia sp. oral clone GT018 | 1171 | AY349384 | clade_334 | N | N |
| Leptotrichia sp. oral clone GT020 | 1172 | AY349385 | clade_334 | N | N |
| Bacteroides sp. 20_3 | 296 | ACRQ01000064 | clade_335 | N | N |
| Bacteroides sp. 3_1_19 | 307 | ADCJ01000062 | clade_335 | N | N |
| Bacteroides sp. 3_2_5 | 311 | ACIB01000079 | clade_335 | N | N |
| Parabacteroides distasonis | 1416 | CP000140 | clade_335 | N | N |
| Parabacteroides goldsteinii | 1417 | AY974070 | clade_335 | N | N |
| Parabacteroides gordonii | 1418 | AB470344 | clade_335 | N | N |
| Parabacteroides sp. D13 | 1421 | ACPW01000017 | clade_335 | N | N |
| Capnocytophaga genomosp. C1 | 477 | AY278613 | clade_336 | N | N |
| Capnocytophaga ochracea | 480 | AEOH01000054 | clade_336 | N | N |
| Capnocytophaga sp. GEJ8 | 481 | GU561335 | clade_336 | N | N |
| Capnocytophaga sp. oral strain A47ROY | 486 | AY005077 | clade_336 | N | N |
| Capnocytophaga sp. S1b | 482 | U42009 | clade_336 | N | N |
| Paraprevotella clara | 1426 | AFFY01000068 | clade_336 | N | N |
| Bacteroides heparinolyticus | 282 | JN867284 | clade_338 | N | N |
| Prevotella heparinolytica | 1500 | GQ422742 | clade_338 | N | N |
| Treponema genomosp. P4 oral clone MB2_G19 | 1928 | DQ003618 | clade_339 | N | N |
| Treponema genomosp. P6 oral clone MB4_G11 | 1930 | DQ003625 | clade_339 | N | N |
| Treponema sp. oral taxon 254 | 1952 | GU408803 | clade_339 | N | N |
| Treponema sp. oral taxon 508 | 1956 | GU413616 | clade_339 | N | N |
| Treponema sp. oral taxon 518 | 1957 | GU413640 | clade_339 | N | N |
| Chlamydia muridarum | 502 | AE002160 | clade_341 | N | OP |
| Chlamydia trachomatis | 504 | U68443 | clade_341 | N | OP |
| Chlamydia psittaci | 503 | NR_036864 | clade_342 | N | Category-B |
| Chlamydophila pneumoniae | 509 | NC_002179 | clade_342 | N | OP |
| Chlamydophila psittaci | 510 | D85712 | clade_342 | N | OP |
| Anaerococcus octavius | 146 | NR_026360 | clade_343 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Anaerococcus* sp. 8405254 | 149 | HM587319 | clade_343 | N | N |
| *Anaerococcus* sp. 9401487 | 150 | HM587322 | clade_343 | N | N |
| *Anaerococcus* sp. 9403502 | 151 | HM587325 | clade_343 | N | N |
| *Gardnerella vaginalis* | 923 | CP001849 | clade_344 | N | N |
| *Campylobacter lari* | 466 | CP000932 | clade_346 | N | OP |
| *Anaerobiospirillum succiniciproducens* | 142 | NR_026075 | clade_347 | N | N |
| *Anaerobiospirillum thomasii* | 143 | AJ420985 | clade_347 | N | N |
| *Ruminobacter amylophilus* | 1654 | NR_026450 | clade_347 | N | N |
| *Succinatimonas hippei* | 1897 | AEVO01000027 | clade_347 | N | N |
| *Actinomyces europaeus* | 54 | NR_026363 | clade_348 | N | N |
| *Actinomyces* sp. oral clone GU009 | 82 | AY349361 | clade_348 | N | N |
| *Moraxella catarrhalis* | 1260 | CP002005 | clade_349 | N | N |
| *Moraxella lincolnii* | 1261 | FR822735 | clade_349 | N | N |
| *Moraxella* sp. 16285 | 1263 | JF682466 | clade_349 | N | N |
| *Psychrobacter* sp. 13983 | 1613 | HM212668 | clade_349 | N | N |
| *Actinobaculum massiliae* | 49 | AF487679 | clade_350 | N | N |
| *Actinobaculum schaalii* | 50 | AY957507 | clade_350 | N | N |
| *Actinobaculum* sp. BM#101342 | 51 | AY282578 | clade_350 | N | N |
| *Actinobaculum* sp. P2P_19 P1 | 52 | AY207066 | clade_350 | N | N |
| *Actinomyces* sp. oral clone IO076 | 84 | AY349363 | clade_350 | N | N |
| *Actinomyces* sp. oral taxon 848 | 93 | ACUY01000072 | clade_350 | N | N |
| *Actinomyces neuii* | 65 | X71862 | clade_352 | N | N |
| *Mobiluncus mulieris* | 1252 | ACKW01000035 | clade_352 | N | N |
| *Blastomonas natatoria* | 372 | NR_040824 | clade_356 | N | N |
| *Novosphingobium aromaticivorans* | 1357 | AAAV03000008 | clade_356 | N | N |
| *Sphingomonas* sp. oral clone FI012 | 1745 | AY349411 | clade_356 | N | N |
| *Sphingopyxis alaskensis* | 1749 | CP000356 | clade_356 | N | N |
| *Oxalobacter formigenes* | 1389 | ACDQ01000020 | clade_357 | N | N |
| *Veillonella atypica* | 1974 | AEDS01000059 | clade_358 | N | N |
| *Veillonella dispar* | 1975 | ACIK02000021 | clade_358 | N | N |
| *Veillonella* genomosp. P1 oral clone MB5_P17 | 1976 | DQ003631 | clade_358 | N | N |
| *Veillonella parvula* | 1978 | ADFU01000009 | clade_358 | N | N |
| *Veillonella* sp. 3_1_44 | 1979 | ADCV01000019 | clade_358 | N | N |
| *Veillonella* sp. 6_1_27 | 1980 | ADCW01000016 | clade_358 | N | N |
| *Veillonella* sp. ACP1 | 1981 | HQ616359 | clade_358 | N | N |
| *Veillonella* sp. AS16 | 1982 | HQ616365 | clade_358 | N | N |
| *Veillonella* sp. BS32b | 1983 | HQ616368 | clade_358 | N | N |
| *Veillonella* sp. ICM51a | 1984 | HQ616396 | clade_358 | N | N |
| *Veillonella* sp. MSA12 | 1985 | HQ616381 | clade_358 | N | N |
| *Veillonella* sp. NVG 100cf | 1986 | EF108443 | clade_358 | N | N |
| *Veillonella* sp. OK11 | 1987 | JN695650 | clade_358 | N | N |
| *Veillonella* sp. oral clone ASCG01 | 1990 | AY923144 | clade_358 | N | N |
| *Veillonella* sp. oral clone ASCG02 | 1991 | AY953257 | clade_358 | N | N |
| *Veillonella* sp. oral clone OH1A | 1992 | AY947495 | clade_358 | N | N |
| *Veillonella* sp. oral taxon 158 | 1993 | AENU01000007 | clade_358 | N | N |
| *Kocuria marina* | 1040 | GQ260086 | clade_365 | N | N |
| *Kocuria rhizophila* | 1042 | AY030315 | clade_365 | N | N |
| *Kocuria rosea* | 1043 | X87756 | clade_365 | N | N |
| *Kocuria varians* | 1044 | AF542074 | clade_365 | N | N |
| Clostridiaceae bacterium END_2 | 531 | EF451053 | clade_368 | N | N |
| *Micrococcus antarcticus* | 1242 | NR_025285 | clade_371 | N | N |
| *Micrococcus luteus* | 1243 | NR_075062 | clade_371 | N | N |
| *Micrococcus lylae* | 1244 | NR_026200 | clade_371 | N | N |
| *Micrococcus* sp. 185 | 1245 | EU714334 | clade_371 | N | N |
| *Lactobacillus brevis* | 1072 | EU194349 | clade_372 | N | N |
| *Lactobacillus parabrevis* | 1104 | NR_042456 | clade_372 | N | N |
| *Pediococcus acidilactici* | 1436 | ACXB01000026 | clade_372 | N | N |
| *Pediococcus pentosaceus* | 1437 | NR_075052 | clade_372 | N | N |
| *Lactobacillus dextrinicus* | 1081 | NR_036861 | clade_373 | N | N |
| *Lactobacillus perolens* | 1109 | NR_029360 | clade_373 | N | N |
| *Lactobacillus rhamnosus* | 1113 | ABWJ01000068 | clade_373 | N | N |
| *Lactobacillus saniviri* | 1118 | AB602569 | clade_373 | N | N |
| *Lactobacillus* sp. BT6 | 1121 | HQ616370 | clade_373 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Mycobacterium mageritense* | 1282 | FR798914 | clade_374 | N | OP |
| *Mycobacterium neoaurum* | 1286 | AF268445 | clade_374 | N | OP |
| *Mycobacterium smegmatis* | 1291 | CP000480 | clade_374 | N | OP |
| *Mycobacterium* sp. HE5 | 1304 | AJ012738 | clade_374 | N | N |
| *Dysgonomonas gadei* | 775 | ADLV01000001 | clade_377 | N | N |
| *Dysgonomonas mossii* | 776 | ADLW01000023 | clade_377 | N | N |
| *Porphyromonas levii* | 1474 | NR_025907 | clade_377 | N | N |
| *Porphyromonas somerae* | 1476 | AB547667 | clade_377 | N | N |
| *Bacteroides barnesiae* | 267 | NR_041446 | clade_378 | N | N |
| *Bacteroides coprocola* | 272 | ABIY02000050 | clade_378 | N | N |
| *Bacteroides coprophilus* | 273 | ACBW01000012 | clade_378 | N | N |
| *Bacteroides dorei* | 274 | ABWZ01000093 | clade_378 | N | N |
| *Bacteroides massiliensis* | 284 | AB200226 | clade_378 | N | N |
| *Bacteroides plebeius* | 289 | AB200218 | clade_378 | N | N |
| *Bacteroides* sp. 3_1_33FAA | 309 | ACPS01000085 | clade_378 | N | N |
| *Bacteroides* sp. 3_1_40A | 310 | ACRT01000136 | clade_378 | N | N |
| *Bacteroides* sp. 4_3_47FAA | 313 | ACDR02000029 | clade_378 | N | N |
| *Bacteroides* sp. 9_1_42FAA | 314 | ACAA01000096 | clade_378 | N | N |
| *Bacteroides* sp. NB_8 | 323 | AB117565 | clade_378 | N | N |
| *Bacteroides vulgatus* | 331 | CP000139 | clade_378 | N | N |
| *Bacteroides ovatus* | 287 | ACWH01000036 | clade_38 | N | N |
| *Bacteroides* sp. 1_1_30 | 294 | ADCL01000128 | clade_38 | N | N |
| *Bacteroides* sp. 2_1_22 | 297 | ACPQ01000117 | clade_38 | N | N |
| *Bacteroides* sp. 2_2_4 | 299 | ABZZ01000168 | clade_38 | N | N |
| *Bacteroides* sp. 3_1_23 | 308 | ACRS01000081 | clade_38 | N | N |
| *Bacteroides* sp. D1 | 318 | ACAB02000030 | clade_38 | N | N |
| *Bacteroides* sp. D2 | 321 | ACGA01000077 | clade_38 | N | N |
| *Bacteroides* sp. D22 | 320 | ADCK01000151 | clade_38 | N | N |
| *Bacteroides xylanisolvens* | 332 | ADKP01000087 | clade_38 | N | N |
| *Treponema lecithinolyticum* | 1931 | NR_026247 | clade_380 | N | OP |
| *Treponema parvum* | 1933 | AF302937 | clade_380 | N | OP |
| *Treponema* sp. oral clone JU025 | 1940 | AY349417 | clade_380 | N | N |
| *Treponema* sp. oral taxon 270 | 1954 | GQ422733 | clade_380 | N | N |
| *Parascardovia denticolens* | 1428 | ADEB01000020 | clade_381 | N | N |
| *Scardovia inopinata* | 1688 | AB029087 | clade_381 | N | N |
| *Scardovia wiggsiae* | 1689 | AY278626 | clade_381 | N | N |
| Clostridiales bacterium 9400853 | 533 | HM587320 | clade_384 | N | N |
| *Mogibacterium diversum* | 1254 | NR_027191 | clade_384 | N | N |
| *Mogibacterium neglectum* | 1255 | NR_027203 | clade_384 | N | N |
| *Mogibacterium pumilum* | 1256 | NR_028608 | clade_384 | N | N |
| *Mogibacterium timidum* | 1257 | Z36296 | clade_384 | N | N |
| *Borrelia burgdorferi* | 389 | ABGI01000001 | clade_386 | N | OP |
| *Borrelia garinii* | 392 | ABJV01000001 | clade_386 | N | OP |
| *Borrelia* sp. NE49 | 397 | AJ224142 | clade_386 | N | OP |
| *Caldimonas manganoxidans* | 457 | NR_040787 | clade_387 | N | N |
| Comamonadaceae bacterium oral taxon F47 | 667 | HM099651 | clade_387 | N | N |
| *Lautropia mirabilis* | 1149 | AEQP01000026 | clade_387 | N | N |
| *Lautropia* sp. oral clone AP009 | 1150 | AY005030 | clade_387 | N | N |
| *Peptoniphilus asaccharolyticus* | 1441 | D14145 | clade_389 | N | N |
| *Peptoniphilus duerdenii* | 1442 | EU526290 | clade_389 | N | N |
| *Peptoniphilus harei* | 1443 | NR_026358 | clade_389 | N | N |
| *Peptoniphilus indolicus* | 1444 | AY153431 | clade_389 | N | N |
| *Peptoniphilus lacrimalis* | 1446 | ADDO01000050 | clade_389 | N | N |
| *Peptoniphilus* sp. gpac077 | 1450 | AM176527 | clade_389 | N | N |
| *Peptoniphilus* sp. JC140 | 1447 | JF824803 | clade_389 | N | N |
| *Peptoniphilus* sp. oral taxon 386 | 1452 | ADCS01000031 | clade_389 | N | N |
| *Peptoniphilus* sp. oral taxon 836 | 1453 | AEAA01000090 | clade_389 | N | N |
| Peptostreptococcaceae bacterium ph1 | 1454 | JN837495 | clade_389 | N | N |
| *Dialister pneumosintes* | 765 | HM596297 | clade_390 | N | N |
| *Dialister* sp. oral taxon 502 | 767 | GQ422739 | clade_390 | N | N |
| *Cupriavidus metallidurans* | 741 | GU230889 | clade_391 | N | N |
| *Herbaspirillum seropedicae* | 1001 | CP002039 | clade_391 | N | N |
| *Herbaspirillum* sp. JC206 | 1002 | JN657219 | clade_391 | N | N |
| *Janthinobacterium* sp. SY12 | 1015 | EF455530 | clade_391 | N | N |
| *Massilia* sp. CCUG 43427A | 1197 | FR773700 | clade_391 | N | N |
| *Ralstonia pickettii* | 1615 | NC_010682 | clade_391 | N | N |
| *Ralstonia* sp. 5_7_47FAA | 1616 | ACUF01000076 | clade_391 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Francisella novicida* | 889 | ABSS01000002 | clade_392 | N | N |
| *Francisella philomiragia* | 890 | AY928394 | clade_392 | N | N |
| *Francisella tularensis* | 891 | ABAZ01000082 | clade_392 | N | Category-A |
| *Ignatzschineria indica* | 1009 | HQ823562 | clade_392 | N | N |
| *Ignatzschineria* sp. NML 95_0260 | 1010 | HQ823559 | clade_392 | N | N |
| *Streptococcus mutans* | 1814 | AP010655 | clade_394 | N | N |
| *Lactobacillus gasseri* | 1084 | ACOZ01000018 | clade_398 | N | N |
| *Lactobacillus hominis* | 1090 | FR681902 | clade_398 | N | N |
| *Lactobacillus iners* | 1091 | AEKJ01000002 | clade_398 | N | N |
| *Lactobacillus johnsonii* | 1093 | AE017198 | clade_398 | N | N |
| *Lactobacillus senioris* | 1119 | AB602570 | clade_398 | N | N |
| *Lactobacillus* sp. oral clone HT002 | 1135 | AY349382 | clade_398 | N | N |
| *Weissella beninensis* | 2006 | EU439435 | clade_398 | N | N |
| *Sphingomonas echinoides* | 1744 | NR_024700 | clade_399 | N | N |
| *Sphingomonas* sp. oral taxon A09 | 1747 | HM099639 | clade_399 | N | N |
| *Sphingomonas* sp. oral taxon F71 | 1748 | HM099645 | clade_399 | N | N |
| *Zymomonas mobilis* | 2032 | NR_074274 | clade_399 | N | N |
| *Arcanobacterium haemolyticum* | 174 | NR_025347 | clade_400 | N | N |
| *Arcanobacterium pyogenes* | 175 | GU585578 | clade_400 | N | N |
| *Trueperella pyogenes* | 1962 | NR_044858 | clade_400 | N | N |
| *Lactococcus garvieae* | 1144 | AF061005 | clade_401 | N | N |
| *Lactococcus lactis* | 1145 | CP002365 | clade_401 | N | N |
| *Brevibacterium mcbrellneri* | 424 | ADNU01000076 | clade_402 | N | N |
| *Brevibacterium paucivorans* | 425 | EU086796 | clade_402 | N | N |
| *Brevibacterium* sp. JC43 | 428 | JF824806 | clade_402 | N | N |
| *Selenomonas artemidis* | 1692 | HM596274 | clade_403 | N | N |
| *Selenomonas* sp. FOBRC9 | 1704 | HQ616378 | clade_403 | N | N |
| *Selenomonas* sp. oral taxon 137 | 1715 | AENV01000007 | clade_403 | N | N |
| *Desmospora activa* | 751 | AM940019 | clade_404 | N | N |
| *Desmospora* sp. 8437 | 752 | AFHT01000143 | clade_404 | N | N |
| *Paenibacillus* sp. oral taxon F45 | 1407 | HM099647 | clade_404 | N | N |
| *Corynebacterium ammoniagenes* | 682 | ADNS01000011 | clade_405 | N | N |
| *Corynebacterium aurimucosum* | 687 | ACLH01000041 | clade_405 | N | N |
| *Corynebacterium bovis* | 688 | AF537590 | clade_405 | N | N |
| *Corynebacterium canis* | 689 | GQ871934 | clade_405 | N | N |
| *Corynebacterium casei* | 690 | NR_025101 | clade_405 | N | N |
| *Corynebacterium durum* | 694 | Z97069 | clade_405 | N | N |
| *Corynebacterium efficiens* | 695 | ACLI01000121 | clade_405 | N | N |
| *Corynebacterium falsenii* | 696 | Y13024 | clade_405 | N | N |
| *Corynebacterium flavescens* | 697 | NR_037040 | clade_405 | N | N |
| *Corynebacterium glutamicum* | 701 | BA000036 | clade_405 | N | N |
| *Corynebacterium jeikeium* | 704 | ACYW01000001 | clade_405 | N | OP |
| *Corynebacterium kroppenstedtii* | 705 | NR_026380 | clade_405 | N | N |
| *Corynebacterium lipophiloflavum* | 706 | ACHJ01000075 | clade_405 | N | N |
| *Corynebacterium matruchotii* | 709 | ACSH02000003 | clade_405 | N | N |
| *Corynebacterium minutissimum* | 710 | X82064 | clade_405 | N | N |
| *Corynebacterium resistens* | 718 | ADGN01000058 | clade_405 | N | N |
| *Corynebacterium simulans* | 720 | AF537604 | clade_405 | N | N |
| *Corynebacterium singulare* | 721 | NR_026394 | clade_405 | N | N |
| *Corynebacterium* sp. 1 ex sheep | 722 | Y13427 | clade_405 | N | N |
| *Corynebacterium* sp. NML 99_0018 | 726 | GU238413 | clade_405 | N | N |
| *Corynebacterium striatum* | 727 | ACGE01000001 | clade_405 | N | OP |
| *Corynebacterium urealyticum* | 732 | X81913 | clade_405 | N | OP |
| *Corynebacterium variabile* | 734 | NR_025314 | clade_405 | N | N |
| *Aerococcus sanguinicola* | 98 | AY837833 | clade_407 | N | N |
| *Aerococcus urinae* | 99 | CP002512 | clade_407 | N | N |
| *Aerococcus urinaeequi* | 100 | NR_043443 | clade_407 | N | N |
| *Aerococcus viridans* | 101 | ADNT01000041 | clade_407 | N | N |
| *Fusobacterium naviforme* | 898 | HQ223106 | clade_408 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Moryella indoligenes | 1268 | AF527773 | clade_408 | N | N |
| Selenomonas genomosp. P5 | 1697 | AY341820 | clade_410 | N | N |
| Selenomonas sp. oral clone IQ048 | 1710 | AY349408 | clade_410 | N | N |
| Selenomonas sputigena | 1717 | ACKP02000033 | clade_410 | N | N |
| Hyphomicrobium sulfonivorans | 1007 | AY468372 | clade_411 | N | N |
| Methylocella silvestris | 1228 | NR_074237 | clade_411 | N | N |
| Legionella pneumophila | 1153 | NC_002942 | clade_412 | N | OP |
| Lactobacillus coryniformis | 1077 | NR_044705 | clade_413 | N | N |
| Arthrobacter agilis | 178 | NR_026198 | clade_414 | N | N |
| Arthrobacter arilaitensis | 179 | NR_074608 | clade_414 | N | N |
| Arthrobacter bergerei | 180 | NR_025612 | clade_414 | N | N |
| Arthrobacter globiformis | 181 | NR_026187 | clade_414 | N | N |
| Arthrobacter nicotianae | 182 | NR_026190 | clade_414 | N | N |
| Mycobacterium abscessus | 1269 | AGQU01000002 | clade_418 | N | OP |
| Mycobacterium chelonae | 1273 | AB548610 | clade_418 | N | OP |
| Bacteroides salanitronis | 291 | CP002530 | clade_419 | N | N |
| Paraprevotella xylaniphila | 1427 | AFBR01000011 | clade_419 | N | N |
| Barnesiella intestinihominis | 336 | AB370251 | clade_420 | N | N |
| Barnesiella viscericola | 337 | NR_041508 | clade_420 | N | N |
| Parabacteroides sp. NS31_3 | 1422 | JN029805 | clade_420 | N | N |
| Porphyromonadaceae bacterium NML 060648 | 1470 | EF184292 | clade_420 | N | N |
| Tannerella forsythia | 1913 | CP003191 | clade_420 | N | N |
| Tannerella sp. 6_1_58FAA_CT1 | 1914 | ACWX01000068 | clade_420 | N | N |
| Mycoplasma amphoriforme | 1311 | AY531656 | clade_421 | N | N |
| Mycoplasma genitalium | 1317 | L43967 | clade_421 | N | N |
| Mycoplasma pneumoniae | 1322 | NC_000912 | clade_421 | N | N |
| Mycoplasma penetrans | 1321 | NC_004432 | clade_422 | N | N |
| Ureaplasma parvum | 1966 | AE002127 | clade_422 | N | N |
| Ureaplasma urealyticum | 1967 | AAYN01000002 | clade_422 | N | N |
| Treponema genomosp. P1 | 1927 | AY341822 | clade_425 | N | N |
| Treponema sp. oral taxon 228 | 1943 | GU408580 | clade_425 | N | N |
| Treponema sp. oral taxon 230 | 1944 | GU408603 | clade_425 | N | N |
| Treponema sp. oral taxon 231 | 1945 | GU408631 | clade_425 | N | N |
| Treponema sp. oral taxon 232 | 1946 | GU408646 | clade_425 | N | N |
| Treponema sp. oral taxon 235 | 1947 | GU408673 | clade_425 | N | N |
| Treponema sp. ovine footrot | 1959 | AJ010951 | clade_425 | N | N |
| Treponema vincentii | 1960 | ACYH01000036 | clade_425 | N | OP |
| Burkholderiales bacterium 1_1_47 | 452 | ADCQ01000066 | clade_432 | N | OP |
| Parasutterella excrementihominis | 1429 | AFBP01000029 | clade_432 | N | N |
| Parasutterella secunda | 1430 | AB491209 | clade_432 | N | N |
| Sutterella morbirenis | 1898 | AJ832129 | clade_432 | N | N |
| Sutterella sanguinus | 1900 | AJ748647 | clade_432 | N | N |
| Sutterella sp. YIT 12072 | 1901 | AB491210 | clade_432 | N | N |
| Sutterella stercoricanis | 1902 | NR_025600 | clade_432 | N | N |
| Sutterella wadsworthensis | 1903 | ADMF01000048 | clade_432 | N | N |
| Propionibacterium freudenreichii | 1572 | NR_036972 | clade_433 | N | N |
| Propionibacterium sp. oral taxon 192 | 1580 | GQ422728 | clade_433 | N | N |
| Tessaracoccus sp. oral taxon F04 | 1917 | HM099640 | clade_433 | N | N |
| Peptoniphilus ivorii | 1445 | Y07840 | clade_434 | N | N |
| Peptoniphilus sp. gpac007 | 1448 | AM176517 | clade_434 | N | N |
| Peptoniphilus sp. gpac018A | 1449 | AM176519 | clade_434 | N | N |
| Peptoniphilus sp. gpac148 | 1451 | AM176535 | clade_434 | N | N |
| Flexispira rappini | 887 | AY126479 | clade_436 | N | N |
| Helicobacter bilis | 993 | ACDN01000023 | clade_436 | N | N |
| Helicobacter cinaedi | 995 | ABQT01000054 | clade_436 | N | N |
| Helicobacter sp. None | 998 | U44756 | clade_436 | N | N |
| Brevundimonas subvibrioides | 429 | CP002102 | clade_438 | N | N |
| Hyphomonas neptunium | 1008 | NR_074092 | clade_438 | N | N |
| Phenylobacterium zucineum | 1465 | AY628697 | clade_438 | N | N |
| Streptococcus downei | 1793 | AEKN01000002 | clade_441 | N | N |
| Streptococcus sp. SHV515 | 1848 | Y07601 | clade_441 | N | N |
| Acinetobacter sp. CIP 53.82 | 40 | JQ638584 | clade_443 | N | N |
| Halomonas elongata | 990 | NR_074782 | clade_443 | N | N |
| Halomonas johnsoniae | 991 | FR775979 | clade_443 | N | N |
| Butyrivibrio fibrisolvens | 456 | U41172 | clade_444 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Roseburia sp. 11SE37 | 1640 | FM954975 | clade_444 | N | N |
| Roseburia sp. 11SE38 | 1641 | FM954976 | clade_444 | N | N |
| Shuttleworthia satelles | 1728 | ACIP02000004 | clade_444 | N | N |
| Shuttleworthia sp. MSX8B | 1729 | HQ616383 | clade_444 | N | N |
| Shuttleworthia sp. oral taxon G69 | 1730 | GU432167 | clade_444 | N | N |
| Bdellovibrio sp. MPA | 344 | AY294215 | clade_445 | N | N |
| Desulfobulbus sp. oral clone CH031 | 755 | AY005036 | clade_445 | N | N |
| Desulfovibrio desulfuricans | 757 | DQ092636 | clade_445 | N | N |
| Desulfovibrio fairfieldensis | 758 | U42221 | clade_445 | N | N |
| Desulfovibrio piger | 759 | AF192152 | clade_445 | N | N |
| Desulfovibrio sp. 3_1_syn3 | 760 | ADDR01000239 | clade_445 | N | N |
| Geobacter bemidjiensis | 941 | CP001124 | clade_445 | N | N |
| Brachybacterium alimentarium | 401 | NR_026269 | clade_446 | N | N |
| Brachybacterium conglomeratum | 402 | AB537169 | clade_446 | N | N |
| Brachybacterium tyrofermentans | 403 | NR_026272 | clade_446 | N | N |
| Dermabacter hominis | 749 | FJ263375 | clade_446 | N | N |
| Aneurinibacillus thermoaerophilus | 171 | NR_029303 | clade_448 | N | N |
| Brevibacillus agri | 409 | NR_040983 | clade_448 | N | N |
| Brevibacillus centrosporus | 411 | NR_043414 | clade_448 | N | N |
| Brevibacillus choshinensis | 412 | NR_040980 | clade_448 | N | N |
| Brevibacillus invocatus | 413 | NR_041836 | clade_448 | N | N |
| Brevibacillus parabrevis | 415 | NR_040981 | clade_448 | N | N |
| Brevibacillus reuszeri | 416 | NR_040982 | clade_448 | N | N |
| Brevibacillus sp. phR | 417 | JN837488 | clade_448 | N | N |
| Brevibacillus thermoruber | 418 | NR_026514 | clade_448 | N | N |
| Lactobacillus murinus | 1100 | NR_042231 | clade_449 | N | N |
| Lactobacillus oeni | 1102 | NR_043095 | clade_449 | N | N |
| Lactobacillus ruminis | 1115 | ACGS02000043 | clade_449 | N | N |
| Lactobacillus vini | 1141 | NR_042196 | clade_449 | N | N |
| Gemella haemolysans | 924 | ACDZ02000012 | clade_450 | N | N |
| Gemella morbillorum | 925 | NR_025904 | clade_450 | N | N |
| Gemella morbillorum | 926 | ACRX01000010 | clade_450 | N | N |
| Gemella sanguinis | 927 | ACRY01000057 | clade_450 | N | N |
| Gemella sp. oral clone ASCE02 | 929 | AY923133 | clade_450 | N | N |
| Gemella sp. oral clone ASCF04 | 930 | AY923139 | clade_450 | N | N |
| Gemella sp. oral clone ASCF12 | 931 | AY923143 | clade_450 | N | N |
| Gemella sp. WAL 1945J | 928 | EU427463 | clade_450 | N | N |
| Sporolactobacillus nakayamae | 1753 | NR_042247 | clade_451 | N | N |
| Gluconacetobacter entanii | 945 | NR_028909 | clade_452 | N | N |
| Gluconacetobacter europaeus | 946 | NR_026513 | clade_452 | N | N |
| Gluconacetobacter hansenii | 947 | NR_026133 | clade_452 | N | N |
| Gluconacetobacter oboediens | 949 | NR_041295 | clade_452 | N | N |
| Gluconacetobacter xylinus | 950 | NR_074338 | clade_452 | N | N |
| Auritibacter ignavus | 193 | FN554542 | clade_453 | N | N |
| Dermacoccus sp. Ellin185 | 750 | AEIQ01000090 | clade_453 | N | N |
| Janibacter limosus | 1013 | NR_026362 | clade_453 | N | N |
| Janibacter melonis | 1014 | EF063716 | clade_453 | N | N |
| Acetobacter aceti | 7 | NR_026121 | clade_454 | N | N |
| Acetobacter fabarum | 8 | NR_042678 | clade_454 | N | N |
| Acetobacter lovaniensis | 9 | NR_040832 | clade_454 | N | N |
| Acetobacter malorum | 10 | NR_025513 | clade_454 | N | N |
| Acetobacter orientalis | 11 | NR_028625 | clade_454 | N | N |
| Acetobacter pasteurianus | 12 | NR_026107 | clade_454 | N | N |
| Acetobacter pomorum | 13 | NR_042112 | clade_454 | N | N |
| Acetobacter syzygii | 14 | NR_040868 | clade_454 | N | N |
| Acetobacter tropicalis | 15 | NR_036881 | clade_454 | N | N |
| Gluconacetobacter azotocaptans | 943 | NR_028767 | clade_454 | N | N |
| Gluconacetobacter diazotrophicus | 944 | NR_074292 | clade_454 | N | N |
| Gluconacetobacter johannae | 948 | NR_024959 | clade_454 | N | N |
| Nocardia brasiliensis | 1351 | AIHV01000038 | clade_455 | N | N |
| Nocardia cyriacigeorgica | 1352 | HQ009486 | clade_455 | N | N |
| Nocardia puris | 1354 | NR_028994 | clade_455 | N | N |
| Nocardia sp. 01_Je_025 | 1355 | GU574059 | clade_455 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Rhodococcus equi* | 1623 | ADNW01000058 | clade_455 | N | N |
| *Oceanobacillus caeni* | 1358 | NR_041533 | clade_456 | N | N |
| *Oceanobacillus* sp. Ndiop | 1359 | CAER01000083 | clade_456 | N | N |
| *Ornithinibacillus bavariensis* | 1384 | NR_044923 | clade_456 | N | N |
| *Ornithinibacillus* sp. 7_10AIA | 1385 | FN397526 | clade_456 | N | N |
| *Virgibacillus proomii* | 2005 | NR_025308 | clade_456 | N | N |
| *Corynebacterium amycolatum* | 683 | ABZU01000033 | clade_457 | N | OP |
| *Corynebacterium hansenii* | 702 | AM946639 | clade_457 | N | N |
| *Corynebacterium xerosis* | 735 | FN179330 | clade_457 | N | OP |
| *Staphylococcaceae* bacterium NML 92_0017 | 1756 | AY841362 | clade_458 | N | N |
| *Staphylococcus fleurettii* | 1766 | NR_041326 | clade_458 | N | N |
| *Staphylococcus sciuri* | 1774 | NR_025520 | clade_458 | N | N |
| *Staphylococcus vitulinus* | 1779 | NR_024670 | clade_458 | N | N |
| *Stenotrophomonas maltophilia* | 1782 | AAVZ01000005 | clade_459 | N | N |
| *Stenotrophomonas* sp. FG_6 | 1783 | EF017810 | clade_459 | N | N |
| *Mycobacterium africanum* | 1270 | AF480605 | clade_46 | N | OP |
| *Mycobacterium alsiensis* | 1271 | AJ938169 | clade_46 | N | OP |
| *Mycobacterium avium* | 1272 | CP000479 | clade_46 | N | OP |
| *Mycobacterium colombiense* | 1274 | AM062764 | clade_46 | N | OP |
| *Mycobacterium gordonae* | 1276 | GU142930 | clade_46 | N | OP |
| *Mycobacterium intracellulare* | 1277 | GQ153276 | clade_46 | N | OP |
| *Mycobacterium kansasii* | 1278 | AF480601 | clade_46 | N | OP |
| *Mycobacterium lacus* | 1279 | NR_025175 | clade_46 | N | OP |
| *Mycobacterium leprae* | 1280 | FM211192 | clade_46 | N | OP |
| *Mycobacterium lepromatosis* | 1281 | EU203590 | clade_46 | N | OP |
| *Mycobacterium mantenii* | 1283 | FJ042897 | clade_46 | N | OP |
| *Mycobacterium marinum* | 1284 | NC_010612 | clade_46 | N | OP |
| *Mycobacterium microti* | 1285 | NR_025234 | clade_46 | N | OP |
| *Mycobacterium parascrofulaceum* | 1287 | ADNV01000350 | clade_46 | N | OP |
| *Mycobacterium seoulense* | 1290 | DQ536403 | clade_46 | N | OP |
| *Mycobacterium* sp. 1761 | 1292 | EU703150 | clade_46 | N | N |
| *Mycobacterium* sp. 1791 | 1295 | EU703148 | clade_46 | N | N |
| *Mycobacterium* sp. 1797 | 1296 | EU703149 | clade_46 | N | N |
| *Mycobacterium* sp. B10_07.09.0206 | 1298 | HQ174245 | clade_46 | N | N |
| *Mycobacterium* sp. NLA001000736 | 1305 | HM627011 | clade_46 | N | N |
| *Mycobacterium* sp. W | 1306 | DQ437715 | clade_46 | N | N |
| *Mycobacterium tuberculosis* | 1307 | CP001658 | clade_46 | N | Category-C |
| *Mycobacterium ulcerans* | 1308 | AB548725 | clade_46 | N | OP |
| *Mycobacterium vulneris* | 1309 | EU834055 | clade_46 | N | OP |
| *Xanthomonas campestris* | 2016 | EF101975 | clade_461 | N | N |
| *Xanthomonas* sp. kmd_489 | 2017 | EU723184 | clade_461 | N | N |
| *Dietzia natronolimnaea* | 769 | GQ870426 | clade_462 | N | N |
| *Dietzia* sp. BBDP51 | 770 | DQ337512 | clade_462 | N | N |
| *Dietzia* sp. CA149 | 771 | GQ870422 | clade_462 | N | N |
| *Dietzia timorensis* | 772 | GQ870424 | clade_462 | N | N |
| *Gordonia bronchialis* | 951 | NR_027594 | clade_463 | N | N |
| *Gordonia polyisoprenivorans* | 952 | DQ385609 | clade_463 | N | N |
| *Gordonia* sp. KTR9 | 953 | DQ068383 | clade_463 | N | N |
| *Gordonia sputi* | 954 | FJ536304 | clade_463 | N | N |
| *Gordonia terrae* | 955 | GQ848239 | clade_463 | N | N |
| *Leptotrichia goodfellowii* | 1167 | ADAD01000110 | clade_465 | N | N |
| *Leptotrichia* sp. oral clone IK040 | 1174 | AY349387 | clade_465 | N | N |
| *Leptotrichia* sp. oral clone P2PB_51 P1 | 1175 | AY207053 | clade_465 | N | N |
| *Bacteroidales* genomosp. P7 oral clone MB3_P19 | 264 | DQ003623 | clade_466 | N | N |
| *Butyricimonas virosa* | 454 | AB443949 | clade_466 | N | N |
| *Odoribacter laneus* | 1363 | AB490805 | clade_466 | N | N |
| *Odoribacter splanchnicus* | 1364 | CP002544 | clade_466 | N | N |
| *Capnocytophaga gingivalis* | 478 | ACLQ01000011 | clade_467 | N | N |
| *Capnocytophaga granulosa* | 479 | X97248 | clade_467 | N | N |
| *Capnocytophaga* sp. oral clone AH015 | 483 | AY005074 | clade_467 | N | N |
| *Capnocytophaga* sp. oral strain S3 | 487 | AY005073 | clade_467 | N | N |
| *Capnocytophaga* sp. oral taxon 338 | 488 | AEXX01000050 | clade_467 | N | N |
| *Capnocytophaga canimorsus* | 476 | CP002113 | clade_468 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Capnocytophaga* sp. oral clone ID062 | 485 | AY349368 | clade_468 | N | N |
| *Lactobacillus catenaformis* | 1075 | M23729 | clade_469 | N | N |
| *Lactobacillus vitulinus* | 1142 | NR_041305 | clade_469 | N | N |
| *Cetobacterium somerae* | 501 | AJ438155 | clade_470 | N | N |
| *Fusobacterium gonidiaformans* | 896 | ACET01000043 | clade_470 | N | N |
| *Fusobacterium mortiferum* | 897 | ACDB02000034 | clade_470 | N | N |
| *Fusobacterium necrogenes* | 899 | X55408 | clade_470 | N | N |
| *Fusobacterium necrophorum* | 900 | AM905356 | clade_470 | N | N |
| *Fusobacterium* sp. 12_1B | 905 | AGWJ01000070 | clade_470 | N | N |
| *Fusobacterium* sp. 3_1_5R | 911 | ACDD01000078 | clade_470 | N | N |
| *Fusobacterium* sp. D12 | 918 | ACDG02000036 | clade_470 | N | N |
| *Fusobacterium ulcerans* | 921 | ACDH01000090 | clade_470 | N | N |
| *Fusobacterium varium* | 922 | ACIE01000009 | clade_470 | N | N |
| *Mycoplasma arthritidis* | 1312 | NC_011025 | clade_473 | N | N |
| *Mycoplasma faucium* | 1314 | NR_024983 | clade_473 | N | N |
| *Mycoplasma hominis* | 1318 | AF443616 | clade_473 | N | N |
| *Mycoplasma orale* | 1319 | AY796060 | clade_473 | N | N |
| *Mycoplasma salivarium* | 1324 | M24661 | clade_473 | N | N |
| *Mitsuokella jalaludinii* | 1247 | NR_028840 | clade_474 | N | N |
| *Mitsuokella multacida* | 1248 | ABWK02000005 | clade_474 | N | N |
| *Mitsuokella* sp. oral taxon 521 | 1249 | GU413658 | clade_474 | N | N |
| *Mitsuokella* sp. oral taxon G68 | 1250 | GU432166 | clade_474 | N | N |
| *Selenomonas* genomosp. C1 | 1695 | AY278627 | clade_474 | N | N |
| *Selenomonas* genomosp. P8 oral clone MB5_P06 | 1700 | DQ003628 | clade_474 | N | N |
| *Selenomonas ruminantium* | 1703 | NR_075026 | clade_474 | N | N |
| Veillonellaceae bacterium oral taxon 131 | 1994 | GU402916 | clade_474 | N | N |
| *Alloscardovia omnicolens* | 139 | NR_042583 | clade_475 | N | N |
| *Alloscardovia* sp. OB7196 | 140 | AB425070 | clade_475 | N | N |
| *Bifidobacterium urinalis* | 366 | AJ278695 | clade_475 | N | N |
| *Prevotella loescheii* | 1503 | JN867231 | clade_48 | N | N |
| *Prevotella* sp. oral clone ASCG12 | 1530 | DQ272511 | clade_48 | N | N |
| *Prevotella* sp. oral clone GU027 | 1540 | AY349398 | clade_48 | N | N |
| *Prevotella* sp. oral taxon 472 | 1553 | ACZS01000106 | clade_48 | N | N |
| *Selenomonas dianae* | 1693 | GQ422719 | clade_480 | N | N |
| *Selenomonas flueggei* | 1694 | AF287803 | clade_480 | N | N |
| *Selenomonas* genomosp. C2 | 1696 | AY278628 | clade_480 | N | N |
| *Selenomonas* genomosp. P6 oral clone MB3_C41 | 1698 | DQ003636 | clade_480 | N | N |
| *Selenomonas* genomosp. P7 oral clone MB5_C08 | 1699 | DQ003627 | clade_480 | N | N |
| *Selenomonas infelix* | 1701 | AF287802 | clade_480 | N | N |
| *Selenomonas noxia* | 1702 | GU470909 | clade_480 | N | N |
| *Selenomonas* sp. oral clone FT050 | 1705 | AY349403 | clade_480 | N | N |
| *Selenomonas* sp. oral clone GI064 | 1706 | AY349404 | clade_480 | N | N |
| *Selenomonas* sp. oral clone GT010 | 1707 | AY349405 | clade_480 | N | N |
| *Selenomonas* sp. oral clone HU051 | 1708 | AY349406 | clade_480 | N | N |
| *Selenomonas* sp. oral clone IK004 | 1709 | AY349407 | clade_480 | N | N |
| *Selenomonas* sp. oral clone JI021 | 1711 | AY349409 | clade_480 | N | N |
| *Selenomonas* sp. oral clone JS031 | 1712 | AY349410 | clade_480 | N | N |
| *Selenomonas* sp. oral clone OH4A | 1713 | AY947498 | clade_480 | N | N |
| *Selenomonas* sp. oral clone P2PA_80 P4 | 1714 | AY207052 | clade_480 | N | N |
| *Selenomonas* sp. oral taxon 149 | 1716 | AEEJ01000007 | clade_480 | N | N |
| Veillonellaceae bacterium oral taxon 155 | 1995 | GU470897 | clade_480 | N | N |
| *Agrococcus jenensis* | 117 | NR_026275 | clade_484 | N | N |
| *Microbacterium gubbeenense* | 1232 | NR_025098 | clade_484 | N | N |
| *Pseudoclavibacter* sp. Timone | 1590 | FJ375951 | clade_484 | N | N |
| *Tropheryma whipplei* | 1961 | BX251412 | clade_484 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Zimmermannella bifida* | 2031 | AB012592 | clade_484 | N | N |
| *Legionella hackeliae* | 1151 | M36028 | clade_486 | N | OP |
| *Legionella longbeachae* | 1152 | M36029 | clade_486 | N | OP |
| *Legionella* sp. D3923 | 1154 | JN380999 | clade_486 | N | OP |
| *Legionella* sp. D4088 | 1155 | JN381012 | clade_486 | N | OP |
| *Legionella* sp. H63 | 1156 | JF831047 | clade_486 | N | OP |
| *Legionella* sp. NML 93L054 | 1157 | GU062706 | clade_486 | N | OP |
| *Legionella steelei* | 1158 | HQ398202 | clade_486 | N | OP |
| *Tatlockia micdadei* | 1915 | M36032 | clade_486 | N | N |
| *Helicobacter pullorum* | 996 | ABQU01000097 | clade_489 | N | N |
| Acetobacteraceae bacterium AT_5844 | 16 | AGEZ01000040 | clade_490 | N | N |
| *Roseomonas cervicalis* | 1643 | ADVL01000363 | clade_490 | N | N |
| *Roseomonas mucosa* | 1644 | NR_028857 | clade_490 | N | N |
| *Roseomonas* sp. NML94_0193 | 1645 | AF533357 | clade_490 | N | N |
| *Roseomonas* sp. NML97_0121 | 1646 | AF533359 | clade_490 | N | N |
| *Roseomonas* sp. NML98_0009 | 1647 | AF533358 | clade_490 | N | N |
| *Roseomonas* sp. NML98_0157 | 1648 | AF533360 | clade_490 | N | N |
| *Rickettsia akari* | 1627 | CP000847 | clade_492 | N | OP |
| *Rickettsia conorii* | 1628 | AE008647 | clade_492 | N | OP |
| *Rickettsia prowazekii* | 1629 | M21789 | clade_492 | N | Category-B |
| *Rickettsia rickettsii* | 1630 | NC_010263 | clade_492 | N | OP |
| *Rickettsia slovaca* | 1631 | L36224 | clade_492 | N | OP |
| *Rickettsia typhi* | 1632 | AE017197 | clade_492 | N | OP |
| *Anaeroglobus geminatus* | 160 | AGCJ01000054 | clade_493 | N | N |
| *Megasphaera* genomosp. C1 | 1201 | AY278622 | clade_493 | N | N |
| *Megasphaera micronuciformis* | 1203 | AECS01000020 | clade_493 | N | N |
| Clostridiales genomosp. BVAB3 | 540 | CP001850 | clade_495 | N | N |
| *Tsukamurella paurometabola* | 1963 | X80628 | clade_496 | N | N |
| *Tsukamurella tyrosinosolvens* | 1964 | AB478958 | clade_496 | N | N |
| *Abiotrophia* para_*adiacens* | 2 | AB022027 | clade_497 | N | N |
| *Carnobacterium divergens* | 492 | NR_044706 | clade_497 | N | N |
| *Carnobacterium maltaromaticum* | 493 | NC_019425 | clade_497 | N | N |
| *Enterococcus avium* | 800 | AF133535 | clade_497 | N | N |
| *Enterococcus caccae* | 801 | AY943820 | clade_497 | N | N |
| *Enterococcus casseliflavus* | 802 | AEWT01000047 | clade_497 | N | N |
| *Enterococcus durans* | 803 | AJ276354 | clade_497 | N | N |
| *Enterococcus faecalis* | 804 | AE016830 | clade_497 | N | N |
| *Enterococcus faecium* | 805 | AM157434 | clade_497 | N | N |
| *Enterococcus gallinarum* | 806 | AB269767 | clade_497 | N | N |
| *Enterococcus gilvus* | 807 | AY033814 | clade_497 | N | N |
| *Enterococcus hawaiiensis* | 808 | AY321377 | clade_497 | N | N |
| *Enterococcus hirae* | 809 | AF061011 | clade_497 | N | N |
| *Enterococcus italicus* | 810 | AEPV01000109 | clade_497 | N | N |
| *Enterococcus mundtii* | 811 | NR_024906 | clade_497 | N | N |
| *Enterococcus raffinosus* | 812 | FN600541 | clade_497 | N | N |
| *Enterococcus* sp. BV2CASA2 | 813 | JN809766 | clade_497 | N | N |
| *Enterococcus* sp. CCRI_16620 | 814 | GU457263 | clade_497 | N | N |
| *Enterococcus* sp. F95 | 815 | FJ463817 | clade_497 | N | N |
| *Enterococcus* sp. RfL6 | 816 | AJ133478 | clade_497 | N | N |
| *Enterococcus thailandicus* | 817 | AY321376 | clade_497 | N | N |
| *Fusobacterium canifelinum* | 893 | AY162222 | clade_497 | N | N |
| *Fusobacterium* genomosp. C1 | 894 | AY278616 | clade_497 | N | N |
| *Fusobacterium* genomosp. C2 | 895 | AY278617 | clade_497 | N | N |
| *Fusobacterium periodonticum* | 902 | ACJY01000002 | clade_497 | N | N |
| *Fusobacterium* sp. 1_1_41FAA | 906 | ADGG01000053 | clade_497 | N | N |
| *Fusobacterium* sp. 11_3_2 | 904 | ACUO01000052 | clade_497 | N | N |
| *Fusobacterium* sp. 2_1_31 | 907 | ACDC02000018 | clade_497 | N | N |
| *Fusobacterium* sp. 3_1_27 | 908 | ADGF01000045 | clade_497 | N | N |
| *Fusobacterium* sp. 3_1_33 | 909 | ACQE01000178 | clade_497 | N | N |
| *Fusobacterium* sp. 3_1_36A2 | 910 | ACPU01000044 | clade_497 | N | N |
| *Fusobacterium* sp. AC18 | 912 | HQ616357 | clade_497 | N | N |
| *Fusobacterium* sp. ACB2 | 913 | HQ616358 | clade_497 | N | N |
| *Fusobacterium* sp. AS2 | 914 | HQ616361 | clade_497 | N | N |
| *Fusobacterium* sp. CM1 | 915 | HQ616371 | clade_497 | N | N |
| *Fusobacterium* sp. CM21 | 916 | HQ616375 | clade_497 | N | N |
| *Fusobacterium* sp. CM22 | 917 | HQ616376 | clade_497 | N | N |
| *Fusobacterium* sp. oral clone ASCF06 | 919 | AY923141 | clade_497 | N | N |
| *Fusobacterium* sp. oral clone ASCF11 | 920 | AY953256 | clade_497 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Granulicatella adiacens* | 959 | ACKZ01000002 | clade_497 | N | N |
| *Granulicatella elegans* | 960 | AB252689 | clade_497 | N | N |
| *Granulicatella paradiacens* | 961 | AY879298 | clade_497 | N | N |
| *Granulicatella* sp. oral clone ASC02 | 963 | AY923126 | clade_497 | N | N |
| *Granulicatella* sp. oral clone ASCA05 | 964 | DQ341469 | clade_497 | N | N |
| *Granulicatella* sp. oral clone ASCB09 | 965 | AY953251 | clade_497 | N | N |
| *Granulicatella* sp. oral clone ASCG05 | 966 | AY923146 | clade_497 | N | N |
| *Tetragenococcus halophilus* | 1918 | NR_075020 | clade_497 | N | N |
| *Tetragenococcus koreensis* | 1919 | NR_043113 | clade_497 | N | N |
| *Vagococcus fluvialis* | 1973 | NR_026489 | clade_497 | N | N |
| *Chryseobacterium anthropi* | 514 | AM982793 | clade_498 | N | N |
| *Chryseobacterium gleum* | 515 | ACKQ02000003 | clade_498 | N | N |
| *Chryseobacterium hominis* | 516 | NR_042517 | clade_498 | N | N |
| *Treponema refringens* | 1936 | AF426101 | clade_499 | N | OP |
| *Treponema* sp. oral clone JU031 | 1941 | AY349416 | clade_499 | N | N |
| *Treponema* sp. oral taxon 239 | 1948 | GU408738 | clade_499 | N | N |
| *Treponema* sp. oral taxon 271 | 1955 | GU408871 | clade_499 | N | N |
| *Alistipes finegoldii* | 129 | NR_043064 | clade_500 | N | N |
| *Alistipes onderdonkii* | 131 | NR_043318 | clade_500 | N | N |
| *Alistipes putredinis* | 132 | ABFK02000017 | clade_500 | N | N |
| *Alistipes shahii* | 133 | FP929032 | clade_500 | N | N |
| *Alistipes* sp. HGB5 | 134 | AENZ01000082 | clade_500 | N | N |
| *Alistipes* sp. JC50 | 135 | JF824804 | clade_500 | N | N |
| *Alistipes* sp. RMA 9912 | 136 | GQ140629 | clade_500 | N | N |
| *Mycoplasma agalactiae* | 1310 | AF010477 | clade_501 | N | N |
| *Mycoplasma bovoculi* | 1313 | NR_025987 | clade_501 | N | N |
| *Mycoplasma fermentans* | 1315 | CP002458 | clade_501 | N | N |
| *Mycoplasma flocculare* | 1316 | X62699 | clade_501 | N | N |
| *Mycoplasma ovipneumoniae* | 1320 | NR_025989 | clade_501 | N | N |
| *Arcobacter butzleri* | 176 | AEPT01000071 | clade_502 | N | N |
| *Arcobacter cryaerophilus* | 177 | NR_025905 | clade_502 | N | N |
| *Campylobacter curvus* | 461 | NC_009715 | clade_502 | N | OP |
| *Campylobacter rectus* | 467 | ACFU01000050 | clade_502 | N | OP |
| *Campylobacter showae* | 468 | ACVQ01000030 | clade_502 | N | OP |
| *Campylobacter* sp. FOBRC14 | 469 | HQ616379 | clade_502 | N | OP |
| *Campylobacter* sp. FOBRC15 | 470 | HQ616380 | clade_502 | N | OP |
| *Campylobacter* sp. oral clone BB120 | 471 | AY005038 | clade_502 | N | OP |
| *Campylobacter sputorum* | 472 | NR_044839 | clade_502 | N | OP |
| *Bacteroides ureolyticus* | 330 | GQ167666 | clade_504 | N | N |
| *Campylobacter gracilis* | 463 | ACYG01000026 | clade_504 | N | OP |
| *Campylobacter hominis* | 464 | NC_009714 | clade_504 | N | OP |
| *Dialister invisus* | 762 | ACIM02000001 | clade_506 | N | N |
| *Dialister micraerophilus* | 763 | AFBB01000028 | clade_506 | N | N |
| *Dialister microaerophilus* | 764 | AENT01000008 | clade_506 | N | N |
| *Dialister propionicifaciens* | 766 | NR_043231 | clade_506 | N | N |
| *Dialister succinatiphilus* | 768 | AB370249 | clade_506 | N | N |
| *Megasphaera elsdenii* | 1200 | AY038996 | clade_506 | N | N |
| *Megasphaera* genomosp. type_1 | 1202 | ADGP01000010 | clade_506 | N | N |
| *Megasphaera* sp. BLPYG_07 | 1204 | HM990964 | clade_506 | N | N |
| *Megasphaera* sp. UPII 199_6 | 1205 | AFIJ01000040 | clade_506 | N | N |
| *Chromobacterium violaceum* | 513 | NC_005085 | clade_507 | N | N |
| *Laribacter hongkongensis* | 1148 | CP001154 | clade_507 | N | N |
| *Methylophilus* sp. ECd5 | 1229 | AY436794 | clade_507 | N | N |
| *Finegoldia magna* | 883 | ACHM02000001 | clade_509 | N | N |
| *Parvimonas micra* | 1431 | AB729072 | clade_509 | N | N |
| *Parvimonas* sp. oral taxon 110 | 1432 | AFII01000002 | clade_509 | N | N |
| *Peptostreptococcus micros* | 1456 | AM176538 | clade_509 | N | N |
| *Peptostreptococcus* sp. oral clone FJ023 | 1460 | AY349390 | clade_509 | N | N |
| *Peptostreptococcus* sp. P4P_31 P3 | 1458 | AY207059 | clade_509 | N | N |
| *Helicobacter pylori* | 997 | CP000012 | clade_510 | N | OP |
| *Anaplasma marginale* | 165 | ABOR01000019 | clade_511 | N | N |
| *Anaplasma phagocytophilum* | 166 | NC_007797 | clade_511 | N | N |
| *Ehrlichia chaffeensis* | 783 | AAIF01000035 | clade_511 | N | OP |
| *Neorickettsia risticii* | 1349 | CP001431 | clade_511 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Neorickettsia sennetsu* | 1350 | NC_007798 | clade_511 | N | N |
| *Pseudoramibacter alactolyticus* | 1606 | AB036759 | clade_512 | N | N |
| *Veillonella montpellierensis* | 1977 | AF473836 | clade_513 | N | N |
| *Veillonella* sp. oral clone ASCA08 | 1988 | AY923118 | clade_513 | N | N |
| *Veillonella* sp. oral clone ASCB03 | 1989 | AY923122 | clade_513 | N | N |
| *Inquilinus limosus* | 1012 | NR_029046 | clade_514 | N | N |
| *Sphingomonas* sp. oral clone FZ016 | 1746 | AY349412 | clade_514 | N | N |
| *Anaerococcus lactolyticus* | 145 | ABYO01000217 | clade_515 | N | N |
| *Anaerococcus prevotii* | 147 | CP001708 | clade_515 | N | N |
| *Anaerococcus* sp. gpac104 | 152 | AM176528 | clade_515 | N | N |
| *Anaerococcus* sp. gpac126 | 153 | AM176530 | clade_515 | N | N |
| *Anaerococcus* sp. gpac155 | 154 | AM176536 | clade_515 | N | N |
| *Anaerococcus* sp. gpac199 | 155 | AM176539 | clade_515 | N | N |
| *Anaerococcus tetradius* | 157 | ACGC01000107 | clade_515 | N | N |
| *Bacteroides coagulans* | 271 | AB547639 | clade_515 | N | N |
| Clostridiales bacterium 9403326 | 534 | HM587324 | clade_515 | N | N |
| Clostridiales bacterium ph2 | 539 | JN837487 | clade_515 | N | N |
| *Peptostreptococcus* sp. 9succ1 | 1457 | X90471 | clade_515 | N | N |
| *Peptostreptococcus* sp. oral clone AP24 | 1459 | AB175072 | clade_515 | N | N |
| *Tissierella praeacuta* | 1924 | NR_044860 | clade_515 | N | N |
| *Helicobacter canadensis* | 994 | ABQS01000108 | clade_518 | N | N |
| *Peptostreptococcus anaerobius* | 1455 | AY326462 | clade_520 | N | N |
| *Peptostreptococcus stomatis* | 1461 | ADGQ01000048 | clade_520 | N | N |
| *Bilophila wadsworthia* | 367 | ADCP01000166 | clade_521 | N | N |
| *Desulfovibrio vulgaris* | 761 | NR_074897 | clade_521 | N | N |
| *Actinomyces nasicola* | 64 | AJ508455 | clade_523 | N | N |
| *Cellulosimicrobium funkei* | 500 | AY501364 | clade_523 | N | N |
| *Lactococcus raffinolactis* | 1146 | NR_044359 | clade_524 | N | N |
| Bacteroidales genomosp. P1 | 258 | AY341819 | clade_529 | N | N |
| Bacteroidales genomosp. P2 oral clone MB1_G13 | 259 | DQ003613 | clade_529 | N | N |
| Bacteroidales genomosp. P3 oral clone MB1_G34 | 260 | DQ003615 | clade_529 | N | N |
| Bacteroidales genomosp. P4 oral clone MB2_G17 | 261 | DQ003617 | clade_529 | N | N |
| Bacteroidales genomosp. P5 oral clone MB2_P04 | 262 | DQ003619 | clade_529 | N | N |
| Bacteroidales genomosp. P6 oral clone MB3_C19 | 263 | DQ003634 | clade_529 | N | N |
| Bacteroidales genomosp. P8 oral clone MB4_G15 | 265 | DQ003626 | clade_529 | N | N |
| Bacteroidetes bacterium oral taxon D27 | 333 | HM099638 | clade_530 | N | N |
| Bacteroidetes bacterium oral taxon F31 | 334 | HM099643 | clade_530 | N | N |
| Bacteroidetes bacterium oral taxon F44 | 335 | HM099649 | clade_530 | N | N |
| *Flavobacterium* sp. NF2_1 | 885 | FJ195988 | clade_530 | N | N |
| *Myroides odoratimimus* | 1326 | NR_042354 | clade_530 | N | N |
| *Myroides* sp. MY15 | 1327 | GU253339 | clade_530 | N | N |
| Chlamydiales bacterium NS16 | 507 | JN606076 | clade_531 | N | N |
| *Chlamydophila pecorum* | 508 | D88317 | clade_531 | N | OP |
| *Parachlamydia* sp. UWE25 | 1423 | BX908798 | clade_531 | N | N |
| *Fusobacterium russii* | 903 | NR_044687 | clade_532 | N | N |
| *Streptobacillus moniliformis* | 1784 | NR_027615 | clade_532 | N | N |
| Eubacteriaceae bacterium P4P_50 P4 | 833 | AY207060 | clade_533 | N | N |
| *Abiotrophia defectiva* | 1 | ACIN02000016 | clade_534 | N | N |
| *Abiotrophia* sp. oral clone P4PA_155 P1 | 3 | AY207063 | clade_534 | N | N |
| *Catonella* genomosp. P1 oral clone MB5_P12 | 496 | DQ003629 | clade_534 | N | N |
| *Catonella morbi* | 497 | ACIL02000016 | clade_534 | N | N |
| *Catonella* sp. oral clone FL037 | 498 | AY349369 | clade_534 | N | N |
| *Eremococcus coleocola* | 818 | AENN01000008 | clade_534 | N | N |
| *Facklamia hominis* | 879 | Y10772 | clade_534 | N | N |
| *Granulicatella* sp. M658_99_3 | 962 | AJ271861 | clade_534 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Campylobacter coli | 459 | AAFL01000004 | clade_535 | N | OP |
| Campylobacter concisus | 460 | CP000792 | clade_535 | N | OP |
| Campylobacter fetus | 462 | ACLG01001177 | clade_535 | N | OP |
| Campylobacter jejuni | 465 | AL139074 | clade_535 | N | Category-B |
| Campylobacter upsaliensis | 473 | AEPU01000040 | clade_535 | N | OP |
| Atopobium minutum | 183 | HM007583 | clade_539 | N | N |
| Atopobium parvulum | 184 | CP001721 | clade_539 | N | N |
| Atopobium rimae | 185 | ACFE01000007 | clade_539 | N | N |
| Atopobium sp. BS2 | 186 | HQ616367 | clade_539 | N | N |
| Atopobium sp. F0209 | 187 | EU592966 | clade_539 | N | N |
| Atopobium sp. ICM42b10 | 188 | HQ616393 | clade_539 | N | N |
| Atopobium sp. ICM57 | 189 | HQ616400 | clade_539 | N | N |
| Atopobium vaginae | 190 | AEDQ01000024 | clade_539 | N | N |
| Coriobacteriaceae bacterium BV3Ac1 | 677 | JN809768 | clade_539 | N | N |
| Actinomyces naeslundii | 63 | X81062 | clade_54 | N | N |
| Actinomyces oricola | 67 | NR_025559 | clade_54 | N | N |
| Actinomyces oris | 69 | BABV01000070 | clade_54 | N | N |
| Actinomyces sp. 7400942 | 70 | EU484334 | clade_54 | N | N |
| Actinomyces sp. ChDC B197 | 72 | AF543275 | clade_54 | N | N |
| Actinomyces sp. GEJ15 | 73 | GU561313 | clade_54 | N | N |
| Actinomyces sp. M2231_94_1 | 79 | AJ234063 | clade_54 | N | N |
| Actinomyces sp. oral clone GU067 | 83 | AY349362 | clade_54 | N | N |
| Actinomyces sp. oral clone IO077 | 85 | AY349364 | clade_54 | N | N |
| Actinomyces sp. oral clone IP073 | 86 | AY349365 | clade_54 | N | N |
| Actinomyces sp. oral clone JA063 | 88 | AY349367 | clade_54 | N | N |
| Actinomyces sp. oral taxon 170 | 89 | AFBL01000010 | clade_54 | N | N |
| Actinomyces sp. oral taxon 171 | 90 | AECW01000034 | clade_54 | N | N |
| Actinomyces urogenitalis | 95 | ACFH01000038 | clade_54 | N | N |
| Actinomyces viscosus | 96 | ACRE01000096 | clade_54 | N | N |
| Orientia tsutsugamushi | 1383 | AP008981 | clade_541 | N | OP |
| Megamonas funiformis | 1198 | AB300988 | clade_542 | N | N |
| Megamonas hypermegale | 1199 | AJ420107 | clade_542 | N | N |
| Aeromicrobium marinum | 102 | NR_025681 | clade_544 | N | N |
| Aeromicrobium sp. JC14 | 103 | JF824798 | clade_544 | N | N |
| Luteococcus sanguinis | 1190 | NR_025507 | clade_544 | N | N |
| Propionibacteriaceae bacterium NML 02_0265 | 1568 | EF599122 | clade_544 | N | N |
| Rhodococcus corynebacterioides | 1622 | X80615 | clade_546 | N | N |
| Rhodococcus erythropolis | 1624 | ACNO01000030 | clade_546 | N | N |
| Rhodococcus fascians | 1625 | NR_037021 | clade_546 | N | N |
| Segniliparus rotundus | 1690 | CP001958 | clade_546 | N | N |
| Segniliparus rugosus | 1691 | ACZI01000025 | clade_546 | N | N |
| Exiguobacterium acetylicum | 878 | FJ970034 | clade_547 | N | N |
| Macrococcus caseolyticus | 1194 | NR_074941 | clade_547 | N | N |
| Streptomyces sp. 1 AIP_2009 | 1890 | FJ176782 | clade_548 | N | N |
| Streptomyces sp. SD 524 | 1892 | EU544234 | clade_548 | N | N |
| Streptomyces sp. SD 528 | 1893 | EU544233 | clade_548 | N | N |
| Streptomyces thermoviolaceus | 1895 | NR_027616 | clade_548 | N | N |
| Borrelia afzelii | 388 | ABCU01000001 | clade_549 | N | OP |
| Borrelia crocidurae | 390 | DQ057990 | clade_549 | N | OP |
| Borrelia duttonii | 391 | NC_011229 | clade_549 | N | OP |
| Borrelia hermsii | 393 | AY597657 | clade_549 | N | OP |
| Borrelia hispanica | 394 | DQ057988 | clade_549 | N | OP |
| Borrelia persica | 395 | HM161645 | clade_549 | N | OP |
| Borrelia recurrentis | 396 | AF107367 | clade_549 | N | OP |
| Borrelia spielmanii | 398 | ABKB01000002 | clade_549 | N | OP |
| Borrelia turicatae | 399 | NC_008710 | clade_549 | N | OP |
| Borrelia valaisiana | 400 | ABCY01000002 | clade_549 | N | OP |
| Providencia alcalifaciens | 1586 | ABXW01000071 | clade_55 | N | N |
| Providencia rettgeri | 1587 | AM040492 | clade_55 | N | N |
| Providencia rustigianii | 1588 | AM040489 | clade_55 | N | N |
| Providencia stuartii | 1589 | AF008581 | clade_55 | N | N |
| Treponema pallidum | 1932 | CP001752 | clade_550 | N | OP |
| Treponema phagedenis | 1934 | AEFH01000172 | clade_550 | N | N |
| Treponema sp. clone DDKL_4 | 1939 | Y08894 | clade_550 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Acholeplasma laidlawii* | 17 | NR_074448 | clade_551 | N | N |
| *Mycoplasma putrefaciens* | 1323 | U26055 | clade_551 | N | N |
| Mycoplasmataceae genomosp. P1 oral clone MB1_G23 | 1325 | DQ003614 | clade_551 | N | N |
| *Spiroplasma insolitum* | 1750 | NR_025705 | clade_551 | N | N |
| *Collinsella intestinalis* | 660 | ABXH02000037 | clade_553 | N | N |
| *Collinsella stercoris* | 661 | ABXJ01000150 | clade_553 | N | N |
| *Collinsella tanakaei* | 662 | AB490807 | clade_553 | N | N |
| *Caminicella sporogenes* | 458 | NR_025485 | clade_554 | N | N |
| *Acidaminococcus fermentans* | 21 | CP001859 | clade_556 | N | N |
| *Acidaminococcus intestini* | 22 | CP003058 | clade_556 | N | N |
| *Acidaminococcus* sp. D21 | 23 | ACGB01000071 | clade_556 | N | N |
| *Phascolarctobacterium faecium* | 1462 | NR_026111 | clade_556 | N | N |
| *Phascolarctobacterium* sp. YIT 12068 | 1463 | AB490812 | clade_556 | N | N |
| *Phascolarctobacterium succinatutens* | 1464 | AB490811 | clade_556 | N | N |
| *Acidithiobacillus ferrivorans* | 25 | NR_074660 | clade_557 | N | N |
| Xanthomonadaceae bacterium NML 03_0222 | 2015 | EU313791 | clade_557 | N | N |
| *Catabacter hongkongensis* | 494 | AB671763 | clade_558 | N | N |
| *Christensenella minuta* | 512 | AB490809 | clade_558 | N | N |
| Clostridiales bacterium oral clone P4PA_66 P1 | 536 | AY207065 | clade_558 | N | N |
| Clostridiales bacterium oral taxon 093 | 537 | GQ422712 | clade_558 | N | N |
| *Heliobacterium modesticaldum* | 1000 | NR_074517 | clade_560 | N | N |
| *Alistipes indistinctus* | 130 | AB490804 | clade_561 | N | N |
| Bacteroidales bacterium ph8 | 257 | JN837494 | clade_561 | N | N |
| *Candidatus Sulcia muelleri* | 475 | CP002163 | clade_561 | N | N |
| *Cytophaga xylanolytica* | 742 | FR733683 | clade_561 | N | N |
| Flavobacteriaceae genomosp. C1 | 884 | AY278614 | clade_561 | N | N |
| *Gramella forsetii* | 958 | NR_074707 | clade_561 | N | N |
| *Sphingobacterium faecium* | 1740 | NR_025537 | clade_562 | N | N |
| *Sphingobacterium mizutaii* | 1741 | JF708889 | clade_562 | N | N |
| *Sphingobacterium multivorum* | 1742 | NR_040953 | clade_562 | N | N |
| *Sphingobacterium spiritivorum* | 1743 | ACHA02000013 | clade_562 | N | N |
| *Jonquetella anthropi* | 1017 | ACOO02000004 | clade_563 | N | N |
| *Pyramidobacter piscolens* | 1614 | AY207056 | clade_563 | N | N |
| *Synergistes* genomosp. C1 | 1904 | AY278615 | clade_563 | N | N |
| *Synergistes* sp. RMA 14551 | 1905 | DQ412722 | clade_563 | N | N |
| Synergistetes bacterium ADV897 | 1906 | GQ258968 | clade_563 | N | N |
| *Candidatus Arthromitus* sp. SFB_mouse_Yit | 474 | NR_074460 | clade_564 | N | N |
| *Gracilibacter thermotolerans* | 957 | NR_043559 | clade_564 | N | N |
| *Brachyspira aalborgi* | 404 | FM178386 | clade_565 | N | N |
| *Brachyspira* sp. HIS3 | 406 | FM178387 | clade_565 | N | N |
| *Brachyspira* sp. HIS4 | 407 | FM178388 | clade_565 | N | N |
| *Brachyspira* sp. HIS5 | 408 | FM178389 | clade_565 | N | N |
| *Adlercreutzia equolifaciens* | 97 | AB306661 | clade_566 | N | N |
| Coriobacteriaceae bacterium JC110 | 678 | CAEM01000062 | clade_566 | N | N |
| Coriobacteriaceae bacterium phI | 679 | JN837493 | clade_566 | N | N |
| *Cryptobacterium curtum* | 740 | GQ422741 | clade_566 | N | N |
| *Eggerthella sinensis* | 779 | AY321958 | clade_566 | N | N |
| *Eggerthella* sp. 1_3_56FAA | 780 | ACWN01000099 | clade_566 | N | N |
| *Eggerthella* sp. HGA1 | 781 | AEXR01000021 | clade_566 | N | N |
| *Eggerthella* sp. YY7918 | 782 | AP012211 | clade_566 | N | N |
| *Gordonibacter pamelaeae* | 680 | AM886059 | clade_566 | N | N |
| *Gordonibacter pamelaeae* | 956 | FP929047 | clade_566 | N | N |
| *Slackia equolifaciens* | 1732 | EU377663 | clade_566 | N | N |
| *Slackia exigua* | 1733 | ACUX01000029 | clade_566 | N | N |
| *Slackia faecicanis* | 1734 | NR_042220 | clade_566 | N | N |
| *Slackia heliotrinireducens* | 1735 | NR_074439 | clade_566 | N | N |
| *Slackia isoflavoniconvertens* | 1736 | AB566418 | clade_566 | N | N |
| *Slackia piriformis* | 1737 | AB490806 | clade_566 | N | N |
| *Slackia* sp. NATTS | 1738 | AB505075 | clade_566 | N | N |
| Chlamydiales bacterium NS13 | 506 | JN606075 | clade_567 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| Victivallaceae bacterium NML 080035 | 2003 | FJ394915 | clade_567 | N | N |
| Victivallis vadensis | 2004 | ABDE02000010 | clade_567 | N | N |
| Streptomyces griseus | 1889 | NR_074787 | clade_573 | N | N |
| Streptomyces sp. SD 511 | 1891 | EU544231 | clade_573 | N | N |
| Streptomyces sp. SD 534 | 1894 | EU544232 | clade_573 | N | N |
| Cloacibacillus evryensis | 530 | GQ258966 | clade_575 | N | N |
| Deferribacteres sp. oral clone JV001 | 743 | AY349370 | clade_575 | N | N |
| Deferribacteres sp. oral clone JV023 | 745 | AY349372 | clade_575 | N | N |
| Synergistetes bacterium LBVCM1157 | 1907 | GQ258969 | clade_575 | N | N |
| Synergistetes bacterium oral taxon 362 | 1909 | GU410752 | clade_575 | N | N |
| Synergistetes bacterium oral taxon D48 | 1910 | GU430992 | clade_575 | N | N |
| Peptococcus sp. oral clone JM048 | 1439 | AY349389 | clade_576 | N | N |
| Helicobacter winghamensis | 999 | ACDO01000013 | clade_577 | N | N |
| Wolinella succinogenes | 2014 | BX571657 | clade_577 | N | N |
| Olsenella genomosp. C1 | 1368 | AY278623 | clade_578 | N | N |
| Olsenella profusa | 1369 | FN178466 | clade_578 | N | N |
| Olsenella sp. F0004 | 1370 | EU592964 | clade_578 | N | N |
| Olsenella sp. oral taxon 809 | 1371 | ACVE01000002 | clade_578 | N | N |
| Olsenella uli | 1372 | CP002106 | clade_578 | N | N |
| Nocardiopsis dassonvillei | 1356 | CP002041 | clade_579 | N | N |
| Peptococcus niger | 1438 | NR_029221 | clade_580 | N | N |
| Peptococcus sp. oral taxon 167 | 1440 | GQ422727 | clade_580 | N | N |
| Akkermansia muciniphila | 118 | CP001071 | clade_583 | N | N |
| Opitutus terrae | 1373 | NR_074978 | clade_583 | N | N |
| Clostridiales bacterium oral taxon F32 | 538 | HM099644 | clade_584 | N | N |
| Leptospira borgpetersenii | 1161 | NC_008508 | clade_585 | N | OP |
| Leptospira broomii | 1162 | NR_043200 | clade_585 | N | OP |
| Leptospira interrogans | 1163 | NC_005823 | clade_585 | N | OP |
| Methanobrevibacter gottschalkii | 1213 | NR_044789 | clade_587 | N | N |
| Methanobrevibacter millerae | 1214 | NR_042785 | clade_587 | N | N |
| Methanobrevibacter oralis | 1216 | HE654003 | clade_587 | N | N |
| Methanobrevibacter thaueri | 1219 | NR_044787 | clade_587 | N | N |
| Methanobrevibacter smithii | 1218 | ABYV02000002 | clade_588 | N | N |
| Deinococcus radiodurans | 746 | AE000513 | clade_589 | N | N |
| Deinococcus sp. R_43890 | 747 | FR682752 | clade_589 | N | N |
| Thermus aquaticus | 1923 | NR_025900 | clade_589 | N | N |
| Actinomyces sp. c109 | 81 | AB167239 | clade_590 | N | N |
| Syntrophomonadaceae genomosp. P1 | 1912 | AY341821 | clade_590 | N | N |
| Anaerobaculum hydrogeniformans | 141 | ACJX02000009 | clade_591 | N | N |
| Microcystis aeruginosa | 1246 | NC_010296 | clade_592 | N | N |
| Prochlorococcus marinus | 1567 | CP000551 | clade_592 | N | N |
| Methanobrevibacter acididurans | 1208 | NR_028779 | clade_593 | N | N |
| Methanobrevibacter arboriphilus | 1209 | NR_042783 | clade_593 | N | N |
| Methanobrevibacter curvatus | 1210 | NR_044796 | clade_593 | N | N |
| Methanobrevibacter cuticularis | 1211 | NR_044776 | clade_593 | N | N |
| Methanobrevibacter filiformis | 1212 | NR_044801 | clade_593 | N | N |
| Methanobrevibacter woesei | 1220 | NR_044788 | clade_593 | N | N |
| Roseiflexus castenholzii | 1642 | CP000804 | clade_594 | N | N |
| Methanobrevibacter olleyae | 1215 | NR_043024 | clade_595 | N | N |
| Methanobrevibacter ruminantium | 1217 | NR_042784 | clade_595 | N | N |
| Methanobrevibacter wolinii | 1221 | NR_044790 | clade_595 | N | N |
| Methanosphaera stadtmanae | 1222 | AY196684 | clade_595 | N | N |
| Chloroflexi genomosp. P1 | 511 | AY331414 | clade_596 | N | N |
| Halorubrum lipolyticum | 992 | AB477978 | clade_597 | N | N |
| Methanobacterium formicicum | 1207 | NR_025028 | clade_597 | N | N |
| Acidilobus saccharovorans | 24 | AY350586 | clade_598 | N | N |
| Hyperthermus butylicus | 1006 | CP000493 | clade_598 | N | N |
| Ignicoccus islandicus | 1011 | X99562 | clade_598 | N | N |

TABLE 1-continued

List of Operational Taxonomic Units (OTU) with
taxonomic assignments made to Genus, Species, and
Phylogenetic Clade

| OTU | SEQ ID Number | Public DB Accession | Clade | Spore Former | Pathogen Status |
|---|---|---|---|---|---|
| *Metallosphaera sedula* | 1206 | D26491 | clade_598 | N | N |
| *Thermofilum pendens* | 1922 | X14835 | clade_598 | N | N |
| *Prevotella melaninogenica* | 1506 | CP002122 | clade_6 | N | N |
| *Prevotella* sp. ICM1 | 1520 | HQ616385 | clade_6 | N | N |
| *Prevotella* sp. oral clone FU048 | 1535 | AY349393 | clade_6 | N | N |
| *Prevotella* sp. oral clone GI030 | 1537 | AY349395 | clade_6 | N | N |
| *Prevotella* sp. SEQ116 | 1526 | JN867246 | clade_6 | N | N |
| *Streptococcus anginosus* | 1787 | AECT01000011 | clade_60 | N | N |
| *Streptococcus milleri* | 1812 | X81023 | clade_60 | N | N |
| *Streptococcus* sp. 16362 | 1829 | JN590019 | clade_60 | N | N |
| *Streptococcus* sp. 69130 | 1832 | X78825 | clade_60 | N | N |
| *Streptococcus* sp. AC15 | 1833 | HQ616356 | clade_60 | N | N |
| *Streptococcus* sp. CM7 | 1839 | HQ616373 | clade_60 | N | N |
| *Streptococcus* sp. OBRC6 | 1847 | HQ616352 | clade_60 | N | N |
| *Burkholderia ambifaria* | 442 | AAUZ01000009 | clade_61 | N | OP |
| *Burkholderia cenocepacia* | 443 | AAHI01000060 | clade_61 | N | OP |
| *Burkholderia cepacia* | 444 | NR_041719 | clade_61 | N | OP |
| *Burkholderia mallei* | 445 | CP000547 | clade_61 | N | Category-B |
| *Burkholderia multivorans* | 446 | NC_010086 | clade_61 | N | OP |
| *Burkholderia oklahomensis* | 447 | DQ108388 | clade_61 | N | OP |
| *Burkholderia pseudomallei* | 448 | CP001408 | clade_61 | N | Category-B |
| *Burkholderia rhizoxinica* | 449 | HQ005410 | clade_61 | N | OP |
| *Burkholderia* sp. 383 | 450 | CP000151 | clade_61 | N | OP |
| *Burkholderia xenovorans* | 451 | U86373 | clade_61 | N | OP |
| *Prevotella buccae* | 1488 | ACRB01000001 | clade_62 | N | N |
| *Prevotella* genomosp. P8 oral clone MB3_P13 | 1498 | DQ003622 | clade_62 | N | N |
| *Prevotella* sp. oral clone FW035 | 1536 | AY349394 | clade_62 | N | N |
| *Prevotella bivia* | 1486 | ADFO01000096 | clade_63 | N | N |
| *Prevotella disiens* | 1494 | AEDO01000026 | clade_64 | N | N |
| *Bacteroides faecis* | 276 | GQ496624 | clade_65 | N | N |
| *Bacteroides fragilis* | 279 | AP006841 | clade_65 | N | N |
| *Bacteroides nordii* | 285 | NR_043017 | clade_65 | N | N |
| *Bacteroides salyersiae* | 292 | EU136690 | clade_65 | N | N |
| *Bacteroides* sp. 1_1_14 | 293 | ACRP01000155 | clade_65 | N | N |
| *Bacteroides* sp. 1_1_6 | 295 | ACIC01000215 | clade_65 | N | N |
| *Bacteroides* sp. 2_1_56FAA | 298 | ACWI01000065 | clade_65 | N | N |
| *Bacteroides* sp. AR29 | 316 | AF139525 | clade_65 | N | N |
| *Bacteroides* sp. B2 | 317 | EU722733 | clade_65 | N | N |
| *Bacteroides thetaiotaomicron* | 328 | NR_074277 | clade_65 | N | N |
| *Actinobacillus minor* | 45 | ACFT01000025 | clade_69 | N | N |
| *Haemophilus parasuis* | 978 | GU226366 | clade_69 | N | N |
| *Vibrio cholerae* | 1996 | AAUR01000095 | clade_71 | N | Category-B |
| *Vibrio fluvialis* | 1997 | X76335 | clade_71 | N | Category-B |
| *Vibrio furnissii* | 1998 | CP002377 | clade_71 | N | Category-B |
| *Vibrio mimicus* | 1999 | ADAF01000001 | clade_71 | N | Category-B |
| *Vibrio parahaemolyticus* | 2000 | AAWQ01000116 | clade_71 | N | Category-B |
| *Vibrio* sp. RC341 | 2001 | ACZT01000024 | clade_71 | N | Category-B |
| *Vibrio vulnificus* | 2002 | AE016796 | clade_71 | N | Category-B |
| *Lactobacillus acidophilus* | 1067 | CP000033 | clade_72 | N | N |
| *Lactobacillus amylolyticus* | 1069 | ADNY01000006 | clade_72 | N | N |
| *Lactobacillus amylovorus* | 1070 | CP002338 | clade_72 | N | N |
| *Lactobacillus crispatus* | 1078 | ACOG01000151 | clade_72 | N | N |
| *Lactobacillus delbrueckii* | 1080 | CP002341 | clade_72 | N | N |
| *Lactobacillus helveticus* | 1088 | ACLM01000202 | clade_72 | N | N |
| *Lactobacillus kalixensis* | 1094 | NR_029083 | clade_72 | N | N |
| *Lactobacillus kefiranofaciens* | 1095 | NR_042440 | clade_72 | N | N |
| *Lactobacillus leichmannii* | 1098 | JX986966 | clade_72 | N | N |
| *Lactobacillus* sp. 66c | 1120 | FR681900 | clade_72 | N | N |
| *Lactobacillus* sp. KLDS 1.0701 | 1122 | EU600905 | clade_72 | N | N |
| *Lactobacillus* sp. KLDS 1.0712 | 1130 | EU600916 | clade_72 | N | N |
| *Lactobacillus* sp. oral clone HT070 | 1136 | AY349383 | clade_72 | N | N |
| *Lactobacillus ultunensis* | 1139 | ACGU01000081 | clade_72 | N | N |
| *Prevotella intermedia* | 1502 | AF414829 | clade_81 | N | N |
| *Prevotella nigrescens* | 1511 | AFPX01000069 | clade_81 | N | N |
| *Prevotella pallens* | 1515 | AFPY01000135 | clade_81 | N | N |
| *Prevotella* sp. oral taxon 310 | 1551 | GQ422737 | clade_81 | N | N |
| *Prevotella* genomosp. C1 | 1495 | AY278624 | clade_82 | N | N |
| *Prevotella* sp. CM38 | 1519 | HQ610181 | clade_82 | N | N |
| *Prevotella* sp. oral taxon 317 | 1552 | ACQH01000158 | clade_82 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Prevotella* sp. SG12 | 1527 | GU561343 | clade_82 | N | N |
| *Prevotella denticola* | 1493 | CP002589 | clade_83 | N | N |
| *Prevotella* genomsp. P7 oral clone MB2_P31 | 1497 | DQ003620 | clade_83 | N | N |
| *Prevotella histicola* | 1501 | JN867315 | clade_83 | N | N |
| *Prevotella multiformis* | 1508 | AEWX01000054 | clade_83 | N | N |
| *Prevotella* sp. JCM 6330 | 1522 | AB547699 | clade_83 | N | N |
| *Prevotella* sp. oral clone GI059 | 1539 | AY349397 | clade_83 | N | N |
| *Prevotella* sp. oral taxon 782 | 1555 | GQ422745 | clade_83 | N | N |
| *Prevotella* sp. oral taxon G71 | 1559 | GU432180 | clade_83 | N | N |
| *Prevotella* sp. SEQ065 | 1524 | JN867234 | clade_83 | N | N |
| *Prevotella veroralis* | 1565 | ACVA01000027 | clade_83 | N | N |
| *Bacteroides acidifaciens* | 266 | NR_028607 | clade_85 | N | N |
| *Bacteroides cellulosilyticus* | 269 | ACCH01000108 | clade_85 | N | N |
| *Bacteroides clarus* | 270 | AFBM01000011 | clade_85 | N | N |
| *Bacteroides eggerthii* | 275 | ACWG01000065 | clade_85 | N | N |
| *Bacteroides oleiciplenus* | 286 | AB547644 | clade_85 | N | N |
| *Bacteroides pyogenes* | 290 | NR_041280 | clade_85 | N | N |
| *Bacteroides* sp. 315_5 | 300 | FJ848547 | clade_85 | N | N |
| *Bacteroides* sp. 31SF15 | 301 | AJ583248 | clade_85 | N | N |
| *Bacteroides* sp. 31SF18 | 302 | AJ583249 | clade_85 | N | N |
| *Bacteroides* sp. 35AE31 | 303 | AJ583244 | clade_85 | N | N |
| *Bacteroides* sp. 35AE37 | 304 | AJ583245 | clade_85 | N | N |
| *Bacteroides* sp. 35BE34 | 305 | AJ583246 | clade_85 | N | N |
| *Bacteroides* sp. 35BE35 | 306 | AJ583247 | clade_85 | N | N |
| *Bacteroides* sp. WH2 | 324 | AY895180 | clade_85 | N | N |
| *Bacteroides* sp. XB12B | 325 | AM230648 | clade_85 | N | N |
| *Bacteroides stercoris* | 327 | ABFZ02000022 | clade_85 | N | N |
| *Actinobacillus pleuropneumoniae* | 46 | NR_074857 | clade_88 | N | N |
| *Actinobacillus ureae* | 48 | AEVG01000167 | clade_88 | N | N |
| *Haemophilus aegyptius* | 969 | AFBC01000053 | clade_88 | N | N |
| *Haemophilus ducreyi* | 970 | AE017143 | clade_88 | N | OP |
| *Haemophilus haemolyticus* | 973 | JN175335 | clade_88 | N | N |
| *Haemophilus influenzae* | 974 | AADP01000001 | clade_88 | N | OP |
| *Haemophilus parahaemolyticus* | 975 | GU561425 | clade_88 | N | N |
| *Haemophilus parainfluenzae* | 976 | AEWU01000024 | clade_88 | N | N |
| *Haemophilus paraphrophaemolyticus* | 977 | M75076 | clade_88 | N | N |
| *Haemophilus somnus* | 979 | NC_008309 | clade_88 | N | N |
| *Haemophilus* sp. 70334 | 980 | HQ680854 | clade_88 | N | N |
| *Haemophilus* sp. HK445 | 981 | FJ685624 | clade_88 | N | N |
| *Haemophilus* sp. oral clone ASCA07 | 982 | AY923117 | clade_88 | N | N |
| *Haemophilus* sp. oral clone ASCG06 | 983 | AY923147 | clade_88 | N | N |
| *Haemophilus* sp. oral clone BJ021 | 984 | AY005034 | clade_88 | N | N |
| *Haemophilus* sp. oral clone BJ095 | 985 | AY005033 | clade_88 | N | N |
| *Haemophilus* sp. oral taxon 851 | 987 | AGRK01000004 | clade_88 | N | N |
| *Haemophilus sputorum* | 988 | AFNK01000005 | clade_88 | N | N |
| *Histophilus somni* | 1003 | AF549387 | clade_88 | N | N |
| *Mannheimia haemolytica* | 1195 | ACZX01000102 | clade_88 | N | N |
| *Pasteurella bettyae* | 1433 | L06088 | clade_88 | N | N |
| *Moellerella wisconsensis* | 1253 | JN175344 | clade_89 | N | N |
| *Morganella morganii* | 1265 | AJ301681 | clade_89 | N | N |
| *Morganella* sp. JB_T16 | 1266 | AJ781005 | clade_89 | N | N |
| *Proteus mirabilis* | 1582 | ACLE01000013 | clade_89 | N | N |
| *Proteus penneri* | 1583 | ABVP01000020 | clade_89 | N | N |
| *Proteus* sp. HS7514 | 1584 | DQ512963 | clade_89 | N | N |
| *Proteus vulgaris* | 1585 | AJ233425 | clade_89 | N | N |
| *Oribacterium sinus* | 1374 | ACKX01000142 | clade_90 | N | N |
| *Oribacterium* sp. ACB1 | 1375 | HM120210 | clade_90 | N | N |
| *Oribacterium* sp. ACB7 | 1376 | HM120211 | clade_90 | N | N |
| *Oribacterium* sp. CM12 | 1377 | HQ616374 | clade_90 | N | N |
| *Oribacterium* sp. ICM51 | 1378 | HQ616397 | clade_90 | N | N |
| *Oribacterium* sp. OBRC12 | 1379 | HQ616355 | clade_90 | N | N |
| *Oribacterium* sp. oral taxon 108 | 1382 | AFIH01000001 | clade_90 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| *Actinobacillus actinomycetemcomitans* | 44 | AY362885 | clade_92 | N | N |
| *Actinobacillus succinogenes* | 47 | CP000746 | clade_92 | N | N |
| *Aggregatibacter actinomycetemcomitans* | 112 | CP001733 | clade_92 | N | N |
| *Aggregatibacter aphrophilus* | 113 | CP001607 | clade_92 | N | N |
| *Aggregatibacter segnis* | 114 | AEPS01000017 | clade_92 | N | N |
| *Averyella dalhousiensis* | 194 | DQ481464 | clade_92 | N | N |
| *Bisgaard Taxon* | 368 | AY683487 | clade_92 | N | N |
| *Bisgaard Taxon* | 369 | AY683489 | clade_92 | N | N |
| *Bisgaard Taxon* | 370 | AY683491 | clade_92 | N | N |
| *Bisgaard Taxon* | 371 | AY683492 | clade_92 | N | N |
| *Buchnera aphidicola* | 440 | NR_074609 | clade_92 | N | N |
| *Cedecea davisae* | 499 | AF493976 | clade_92 | N | N |
| *Citrobacter amalonaticus* | 517 | FR870441 | clade_92 | N | N |
| *Citrobacter braakii* | 518 | NR_028687 | clade_92 | N | N |
| *Citrobacter farmeri* | 519 | AF025371 | clade_92 | N | N |
| *Citrobacter freundii* | 520 | NR_028894 | clade_92 | N | N |
| *Citrobacter gillenii* | 521 | AF025367 | clade_92 | N | N |
| *Citrobacter koseri* | 522 | NC_009792 | clade_92 | N | N |
| *Citrobacter murliniae* | 523 | AF025369 | clade_92 | N | N |
| *Citrobacter rodentium* | 524 | NR_074903 | clade_92 | N | N |
| *Citrobacter sedlakii* | 525 | AF025364 | clade_92 | N | N |
| *Citrobacter* sp. 30_2 | 526 | ACDJ01000053 | clade_92 | N | N |
| *Citrobacter* sp. KMSI_3 | 527 | GQ468398 | clade_92 | N | N |
| *Citrobacter werkmanii* | 528 | AF025373 | clade_92 | N | N |
| *Citrobacter youngae* | 529 | ABWL02000011 | clade_92 | N | N |
| *Cronobacter malonaticus* | 737 | GU122174 | clade_92 | N | N |
| *Cronobacter sakazakii* | 738 | NC_009778 | clade_92 | N | N |
| *Cronobacter turicensis* | 739 | FN543093 | clade_92 | N | N |
| *Enterobacter aerogenes* | 786 | AJ251468 | clade_92 | N | N |
| *Enterobacter asburiae* | 787 | NR_024640 | clade_92 | N | N |
| *Enterobacter cancerogenus* | 788 | Z96078 | clade_92 | N | N |
| *Enterobacter cloacae* | 789 | FP929040 | clade_92 | N | N |
| *Enterobacter cowanii* | 790 | NR_025566 | clade_92 | N | N |
| *Enterobacter hormaechei* | 791 | AFHR01000079 | clade_92 | N | N |
| *Enterobacter* sp. 247BMC | 792 | HQ122932 | clade_92 | N | N |
| *Enterobacter* sp. 638 | 793 | NR_074777 | clade_92 | N | N |
| *Enterobacter* sp. JC163 | 794 | JN657217 | clade_92 | N | N |
| *Enterobacter* sp. SCSS | 795 | HM007811 | clade_92 | N | N |
| *Enterobacter* sp. TSE38 | 796 | HM156134 | clade_92 | N | N |
| Enterobacteriaceae bacterium 9_2_54FAA | 797 | ADCU01000033 | clade_92 | N | N |
| Enterobacteriaceae bacterium CF01Ent_1 | 798 | AJ489826 | clade_92 | N | N |
| Enterobacteriaceae bacterium Smarlab 3302238 | 799 | AY538694 | clade_92 | N | N |
| *Escherichia albertii* | 824 | ABKX01000012 | clade_92 | N | N |
| *Escherichia coli* | 825 | NC_008563 | clade_92 | N | Category-B |
| *Escherichia fergusonii* | 826 | CU928158 | clade_92 | N | N |
| *Escherichia hermannii* | 827 | HQ407266 | clade_92 | N | N |
| *Escherichia* sp. 1_1_43 | 828 | ACID01000033 | clade_92 | N | N |
| *Escherichia* sp. 4_1_40B | 829 | ACDM02000056 | clade_92 | N | N |
| *Escherichia* sp. B4 | 830 | EU722735 | clade_92 | N | N |
| *Escherichia vulneris* | 831 | NR_041927 | clade_92 | N | N |
| *Ewingella americana* | 877 | JN175329 | clade_92 | N | N |
| *Haemophilus* genomosp. P2 oral clone MB3_C24 | 971 | DQ003621 | clade_92 | N | N |
| *Haemophilus* genomosp. P3 oral clone MB3_C38 | 972 | DQ003635 | clade_92 | N | N |
| *Haemophilus* sp. oral clone JM053 | 986 | AY349380 | clade_92 | N | N |
| *Hafnia alvei* | 989 | DQ412565 | clade_92 | N | N |
| *Klebsiella oxytoca* | 1024 | AY292871 | clade_92 | N | OP |
| *Klebsiella pneumoniae* | 1025 | CP000647 | clade_92 | N | OP |
| *Klebsiella* sp. AS10 | 1026 | HQ616362 | clade_92 | N | N |
| *Klebsiella* sp. Co9935 | 1027 | DQ068764 | clade_92 | N | N |
| *Klebsiella* sp. enrichment culture clone SRC_DSD25 | 1036 | HM195210 | clade_92 | N | N |
| *Klebsiella* sp. OBRC7 | 1028 | HQ616353 | clade_92 | N | N |
| *Klebsiella* sp. SP_BA | 1029 | FJ999767 | clade_92 | N | N |
| *Klebsiella* sp. SRC_DSD1 | 1033 | GU797254 | clade_92 | N | N |
| *Klebsiella* sp. SRC_DSD11 | 1030 | GU797263 | clade_92 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Klebsiella sp. SRC_DSD12 | 1031 | GU797264 | clade_92 | N | N |
| Klebsiella sp. SRC_DSD15 | 1032 | GU797267 | clade_92 | N | N |
| Klebsiella sp. SRC_DSD2 | 1034 | GU797253 | clade_92 | N | N |
| Klebsiella sp. SRC_DSD6 | 1035 | GU797258 | clade_92 | N | N |
| Klebsiella variicola | 1037 | CP001891 | clade_92 | N | N |
| Kluyvera ascorbata | 1038 | NR_028677 | clade_92 | N | N |
| Kluyvera cryocrescens | 1039 | NR_028803 | clade_92 | N | N |
| Leminorella grimontii | 1159 | AJ233421 | clade_92 | N | N |
| Leminorella richardii | 1160 | HF558368 | clade_92 | N | N |
| Pantoea agglomerans | 1409 | AY335552 | clade_92 | N | N |
| Pantoea ananatis | 1410 | CP001875 | clade_92 | N | N |
| Pantoea brenneri | 1411 | EU216735 | clade_92 | N | N |
| Pantoea citrea | 1412 | EF688008 | clade_92 | N | N |
| Pantoea conspicua | 1413 | EU216737 | clade_92 | N | N |
| Pantoea septics | 1414 | EU216734 | clade_92 | N | N |
| Pasteurella dagmatis | 1434 | ACZR01000003 | clade_92 | N | N |
| Pasteurella multocida | 1435 | NC_002663 | clade_92 | N | N |
| Plesiomonas shigelloides | 1469 | X60418 | clade_92 | N | N |
| Raoultella ornithinolytica | 1617 | AB364958 | clade_92 | N | N |
| Raoultella planticola | 1618 | AF129443 | clade_92 | N | N |
| Raoultella terrigena | 1619 | NR_037085 | clade_92 | N | N |
| Salmonella bongori | 1683 | NR_041699 | clade_92 | N | Category-B |
| Salmonella enterica | 1672 | NC_011149 | clade_92 | N | Category-B |
| Salmonella enterica | 1673 | NC_011205 | clade_92 | N | Category-B |
| Salmonella enterica | 1674 | DQ344532 | clade_92 | N | Category-B |
| Salmonella enterica | 1675 | ABEH02000004 | clade_92 | N | Category-B |
| Salmonella enterica | 1676 | ABAK02000001 | clade_92 | N | Category-B |
| Salmonella enterica | 1677 | NC_011080 | clade_92 | N | Category-B |
| Salmonella enterica | 1678 | EU118094 | clade_92 | N | Category-B |
| Salmonella enterica | 1679 | NC_011094 | clade_92 | N | Category-B |
| Salmonella enterica | 1680 | AE014613 | clade_92 | N | Category-B |
| Salmonella enterica | 1682 | ABFH02000001 | clade_92 | N | Category-B |
| Salmonella enterica | 1684 | ABEM01000001 | clade_92 | N | Category-B |
| Salmonella enterica | 1685 | ABAM02000001 | clade_92 | N | Category-B |
| Salmonella typhimurium | 1681 | DQ344533 | clade_92 | N | Category-B |
| Salmonella typhimurium | 1686 | AF170176 | clade_92 | N | Category-B |
| Serratia fonticola | 1718 | NR_025339 | clade_92 | N | N |
| Serratia liquefaciens | 1719 | NR_042062 | clade_92 | N | N |
| Serratia marcescens | 1720 | GU826157 | clade_92 | N | N |
| Serratia odorifera | 1721 | ADBY01000001 | clade_92 | N | N |
| Serratia proteamaculans | 1722 | AAUN01000015 | clade_92 | N | N |
| Shigella boydii | 1724 | AAKA01000007 | clade_92 | N | Category-B |
| Shigella dysenteriae | 1725 | NC_007606 | clade_92 | N | Category-B |
| Shigella flexneri | 1726 | AE005674 | clade_92 | N | Category-B |
| Shigella sonnei | 1727 | NC_007384 | clade_92 | N | Category-B |
| Tatumella ptyseos | 1916 | NR_025342 | clade_92 | N | N |
| Trabulsiella guamensis | 1925 | AY373830 | clade_92 | N | N |
| Yersinia aldovae | 2019 | AJ871363 | clade_92 | N | OP |
| Yersinia aleksiciae | 2020 | AJ627597 | clade_92 | N | OP |
| Yersinia bercovieri | 2021 | AF366377 | clade_92 | N | OP |
| Yersinia enterocolitica | 2022 | FR729477 | clade_92 | N | Category-B |
| Yersinia frederiksenii | 2023 | AF366379 | clade_92 | N | OP |
| Yersinia intermedia | 2024 | AF366380 | clade_92 | N | OP |
| Yersinia kristensenii | 2025 | ACCA01000078 | clade_92 | N | OP |
| Yersinia mollaretii | 2026 | NR_027546 | clade_92 | N | OP |
| Yersinia pestis | 2027 | AE013632 | clade_92 | N | Category-A |
| Yersinia pseudotuberculosis | 2028 | NC_009708 | clade_92 | N | OP |
| Yersinia rohdei | 2029 | ACCD01000071 | clade_92 | N | OP |
| Yokenella regensburgei | 2030 | AB273739 | clade_92 | N | N |
| Conchiformibius kuhniae | 669 | NR_041821 | clade_94 | N | N |
| Morococcus cerebrosus | 1267 | JN175352 | clade_94 | N | N |
| Neisseria bacilliformis | 1328 | AFAY01000058 | clade_94 | N | N |
| Neisseria cinerea | 1329 | ACDY01000037 | clade_94 | N | N |
| Neisseria flavescens | 1331 | ACQV01000025 | clade_94 | N | N |
| Neisseria gonorrhoeae | 1333 | CP002440 | clade_94 | N | OP |
| Neisseria lactamica | 1334 | ACEQ01000095 | clade_94 | N | N |
| Neisseria macacae | 1335 | AFQE01000146 | clade_94 | N | N |
| Neisseria meningitidis | 1336 | NC_003112 | clade_94 | N | OP |
| Neisseria mucosa | 1337 | ACDX01000110 | clade_94 | N | N |
| Neisseria pharyngis | 1338 | AJ239281 | clade_94 | N | N |
| Neisseria polysaccharea | 1339 | ADBE01000137 | clade_94 | N | N |
| Neisseria sicca | 1340 | ACKO02000016 | clade_94 | N | N |
| Neisseria sp. KEM232 | 1341 | GQ203291 | clade_94 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Neisseria sp. oral clone AP132 | 1344 | AY005027 | clade_94 | N | N |
| Neisseria sp. oral strain B33KA | 1346 | AY005028 | clade_94 | N | N |
| Neisseria sp. oral taxon 014 | 1347 | ADEA01000039 | clade_94 | N | N |
| Neisseria sp. TM10_1 | 1343 | DQ279352 | clade_94 | N | N |
| Neisseria subflava | 1348 | ACEO01000067 | clade_94 | N | N |
| Okadaella gastrococcus | 1365 | HQ699465 | clade_98 | N | N |
| Streptococcus agalactiae | 1785 | AAJO01000130 | clade_98 | N | N |
| Streptococcus alactolyticus | 1786 | NR_041781 | clade_98 | N | N |
| Streptococcus australis | 1788 | AEQR01000024 | clade_98 | N | N |
| Streptococcus bovis | 1789 | AEEL01000030 | clade_98 | N | N |
| Streptococcus canis | 1790 | AJ413203 | clade_98 | N | N |
| Streptococcus constellatus | 1791 | AY277942 | clade_98 | N | N |
| Streptococcus cristatus | 1792 | AEVC01000028 | clade_98 | N | N |
| Streptococcus dysgalactiae | 1794 | AP010935 | clade_98 | N | N |
| Streptococcus equi | 1795 | CP001129 | clade_98 | N | N |
| Streptococcus equinus | 1796 | AEVB01000043 | clade_98 | N | N |
| Streptococcus gallolyticus | 1797 | FR824043 | clade_98 | N | N |
| Streptococcus genomosp. C1 | 1798 | AY278629 | clade_98 | N | N |
| Streptococcus genomosp. C2 | 1799 | AY278630 | clade_98 | N | N |
| Streptococcus genomosp. C3 | 1800 | AY278631 | clade_98 | N | N |
| Streptococcus genomosp. C4 | 1801 | AY278632 | clade_98 | N | N |
| Streptococcus genomosp. C5 | 1802 | AY278633 | clade_98 | N | N |
| Streptococcus genomosp. C6 | 1803 | AY278634 | clade_98 | N | N |
| Streptococcus genomosp. C7 | 1804 | AY278635 | clade_98 | N | N |
| Streptococcus genomosp. C8 | 1805 | AY278609 | clade_98 | N | N |
| Streptococcus gordonii | 1806 | NC_009785 | clade_98 | N | N |
| Streptococcus infantarius | 1807 | ABJK02000017 | clade_98 | N | N |
| Streptococcus infantis | 1808 | AFNN01000024 | clade_98 | N | N |
| Streptococcus intermedius | 1809 | NR_028736 | clade_98 | N | N |
| Streptococcus lutetiensis | 1810 | NR_037096 | clade_98 | N | N |
| Streptococcus massiliensis | 1811 | AY769997 | clade_98 | N | N |
| Streptococcus mitis | 1813 | AM157420 | clade_98 | N | N |
| Streptococcus oligofermentans | 1815 | AY099095 | clade_98 | N | N |
| Streptococcus oralis | 1816 | ADMV01000001 | clade_98 | N | N |
| Streptococcus parasanguinis | 1817 | AEKM01000012 | clade_98 | N | N |
| Streptococcus pasteurianus | 1818 | AP012054 | clade_98 | N | N |
| Streptococcus peroris | 1819 | AEVF01000016 | clade_98 | N | N |
| Streptococcus pneumoniae | 1820 | AE008537 | clade_98 | N | N |
| Streptococcus porcinus | 1821 | EF121439 | clade_98 | N | N |
| Streptococcus pseudopneumoniae | 1822 | FJ827123 | clade_98 | N | N |
| Streptococcus pseudoporcinus | 1823 | AENS01000003 | clade_98 | N | N |
| Streptococcus pyogenes | 1824 | AE006496 | clade_98 | N | OP |
| Streptococcus ratti | 1825 | X58304 | clade_98 | N | N |
| Streptococcus sanguinis | 1827 | NR_074974 | clade_98 | N | N |
| Streptococcus sinensis | 1828 | AF432857 | clade_98 | N | N |
| Streptococcus sp. 2_1_36FAA | 1831 | ACOI01000028 | clade_98 | N | N |
| Streptococcus sp. 2285_97 | 1830 | AJ131965 | clade_98 | N | N |
| Streptococcus sp. ACS2 | 1834 | HQ616360 | clade_98 | N | N |
| Streptococcus sp. AS20 | 1835 | HQ616366 | clade_98 | N | N |
| Streptococcus sp. BS35a | 1836 | HQ616369 | clade_98 | N | N |
| Streptococcus sp. C150 | 1837 | ACRI01000045 | clade_98 | N | N |
| Streptococcus sp. CM6 | 1838 | HQ616372 | clade_98 | N | N |
| Streptococcus sp. ICM10 | 1840 | HQ616389 | clade_98 | N | N |
| Streptococcus sp. ICM12 | 1841 | HQ616390 | clade_98 | N | N |
| Streptococcus sp. ICM2 | 1842 | HQ616386 | clade_98 | N | N |
| Streptococcus sp. ICM4 | 1844 | HQ616387 | clade_98 | N | N |
| Streptococcus sp. ICM45 | 1843 | HQ616394 | clade_98 | N | N |
| Streptococcus sp. M143 | 1845 | ACRK01000025 | clade_98 | N | N |
| Streptococcus sp. M334 | 1846 | ACRL01000052 | clade_98 | N | N |
| Streptococcus sp. oral clone ASB02 | 1849 | AY923121 | clade_98 | N | N |
| Streptococcus sp. oral clone ASCA03 | 1850 | DQ272504 | clade_98 | N | N |
| Streptococcus sp. oral clone ASCA04 | 1851 | AY923116 | clade_98 | N | N |
| Streptococcus sp. oral clone ASCA09 | 1852 | AY923119 | clade_98 | N | N |
| Streptococcus sp. oral clone ASCB04 | 1853 | AY923123 | clade_98 | N | N |
| Streptococcus sp. oral clone ASCB06 | 1854 | AY923124 | clade_98 | N | N |

TABLE 1-continued

List of Operational Taxonomic Units (OTU) with taxonomic assignments made to Genus, Species, and Phylogenetic Clade

| OTU | SEQ ID Number | Public DB Accession | Clade | Spore Former | Pathogen Status |
|---|---|---|---|---|---|
| Streptococcus sp. oral clone ASCC04 | 1855 | AY923127 | clade_98 | N | N |
| Streptococcus sp. oral clone ASCC05 | 1856 | AY923128 | clade_98 | N | N |
| Streptococcus sp. oral clone ASCC12 | 1857 | DQ272507 | clade_98 | N | N |
| Streptococcus sp. oral clone ASCD01 | 1858 | AY923129 | clade_98 | N | N |
| Streptococcus sp. oral clone ASCD09 | 1859 | AY923130 | clade_98 | N | N |
| Streptococcus sp. oral clone ASCD10 | 1860 | DQ272509 | clade_98 | N | N |
| Streptococcus sp. oral clone ASCE03 | 1861 | AY923134 | clade_98 | N | N |
| Streptococcus sp. oral clone ASCE04 | 1862 | AY953253 | clade_98 | N | N |
| Streptococcus sp. oral clone ASCE05 | 1863 | DQ272510 | clade_98 | N | N |
| Streptococcus sp. oral clone ASCE06 | 1864 | AY923135 | clade_98 | N | N |
| Streptococcus sp. oral clone ASCE09 | 1865 | AY923136 | clade_98 | N | N |
| Streptococcus sp. oral clone ASCE10 | 1866 | AY923137 | clade_98 | N | N |
| Streptococcus sp. oral clone ASCE12 | 1867 | AY923138 | clade_98 | N | N |
| Streptococcus sp. oral clone ASCF05 | 1868 | AY923140 | clade_98 | N | N |
| Streptococcus sp. oral clone ASCF07 | 1869 | AY953255 | clade_98 | N | N |
| Streptococcus sp. oral clone ASCF09 | 1870 | AY923142 | clade_98 | N | N |
| Streptococcus sp. oral clone ASCG04 | 1871 | AY923145 | clade_98 | N | N |
| Streptococcus sp. oral clone BW009 | 1872 | AY005042 | clade_98 | N | N |
| Streptococcus sp. oral clone CH016 | 1873 | AY005044 | clade_98 | N | N |
| Streptococcus sp. oral clone GK051 | 1874 | AY349413 | clade_98 | N | N |
| Streptococcus sp. oral clone GM006 | 1875 | AY349414 | clade_98 | N | N |
| Streptococcus sp. oral clone P2PA_41 P2 | 1876 | AY207051 | clade_98 | N | N |
| Streptococcus sp. oral clone P4PA_30 P4 | 1877 | AY207064 | clade_98 | N | N |
| Streptococcus sp. oral taxon 071 | 1878 | AEEP01000019 | clade_98 | N | N |
| Streptococcus sp. oral taxon G59 | 1879 | GU432132 | clade_98 | N | N |
| Streptococcus sp. oral taxon G62 | 1880 | GU432146 | clade_98 | N | N |
| Streptococcus sp. oral taxon G63 | 1881 | GU432150 | clade_98 | N | N |
| Streptococcus suis | 1882 | FM252032 | clade_98 | N | N |
| Streptococcus thermophilus | 1883 | CP000419 | clade_98 | N | N |
| Streptococcus salivarius | 1826 | AGBV01000001 | clade_98 | N | N |
| Streptococcus uberis | 1884 | HQ391900 | clade_98 | N | N |
| Streptococcus urinalis | 1885 | DQ303194 | clade_98 | N | N |
| Streptococcus vestibularis | 1886 | AEKO01000008 | clade_98 | N | N |
| Streptococcus viridans | 1887 | AF076036 | clade_98 | N | N |
| Synergistetes bacterium oral clone 03 5 D05 | 1908 | GU227192 | clade_98 | N | N |

TABLE 2

Species isolated from ethanol treated spore preparation preparation before (left) and after (right) CsCl gradient step

| Isolates | ethanol treated spore preparation | ethanol treated, gradient purified spore preparation |
|---|---|---|
| Bacillus coagulans | 7 | 2 |
| Blautia luti | 1 | 1 |
| Blautia sp | 14 | 13 |
| Blautia wexlerae | 3 | 1 |
| Ruminococcus obeum | 4 | 2 |
| Clostridiales sp | 1 | 2 |
| Clostridium aerotolerans | 1 | 2 |
| Clostridium disporicum | 0 | 1 |
| Clostridium sp | 1 | 1 |
| Clostridium symbiosum | 0 | 1 |
| Dorea longicatena | 8 | 6 |
| Eubacterium cellulosolvens | 1 | 0 |
| Eubacterium ventriosum | 2 | 2 |
| Gemmiger formicilis | 0 | 1 |
| Robinsoniella peoriensis | 0 | 1 |
| Roseburia hominis | 3 | 6 |
| Roseburia intestinalis | 9 | 7 |
| Ruminococcus sp | 5 | 2 |
| Syntrophococcus sucromutans | 1 | 1 |
| Turicibacter sanguinis | 3 | 4 |
| Clostridiales sp | 7 | 9 |
| Clostridium bartlettii | 8 | 11 |
| Clostridium irregulare | 0 | 1 |
| Clostridium sordellii | 4 | 6 |
| Lachnospiraceae sp | 1 | 0 |

TABLE 3

Mortality and weight change in mice challenged with *C. difficile* with or without ethanol treated, spore product treatment.

| Test article | mortality (n = 10) | % weight change on Day 3 |
|---|---|---|
| vehicle (negative control) | 20% | −10.5% |
| Donor feces (positive control) | 0 | −0.1% |
| EtOH-treated feces 1x | 0 | 2.3% |
| EtOH-treated feces 0.1x | 0 | 2.4% |
| EtOH-treated feces 0.01x | 0 | −3% |
| heat-treated feces | 0 | 0.1% |

TABLE 5

Binary pair inhibition of *C. difficile*

| SPC1 | SPC2 | OTU1 | OTU2 | Result |
|---|---|---|---|---|
| SPC10414 | SPC10414 | Alistipes_shahii | Alistipes_shahii | |
| SPC10211 | SPC10414 | Bacteroides_caccae | Alistipes_shahii | |
| SPC10213 | SPC10414 | Bacteroides_eggerthii | Alistipes_shahii | −− |
| SPC10030 | SPC10414 | Bacteroides_ovatus | Alistipes_shahii | |
| SPC00006 | SPC10414 | Bacteroides_sp_1_1_6 | Alistipes_shahii | ++++ |
| SPC00007 | SPC10414 | Bacteroides_sp_3_1_23 | Alistipes_shahii | + |
| SPC00019 | SPC10414 | Bacteroides_sp_D20 | Alistipes_shahii | − |
| SPC00005 | SPC10414 | Bacteroides_vulgatus | Alistipes_shahii | +++ |
| SPC10081 | SPC10414 | Bacteroides_vulgatus | Alistipes_shahii | + |
| SPC10301 | SPC10414 | Bifidobacterium_adolescentis | Alistipes_shahii | ++++ |
| SPC10298 | SPC10414 | Bifidobacterium_pseudocatenulatum | Alistipes_shahii | |
| SPC00021 | SPC10414 | Blautia_producta | Alistipes_shahii | ++++ |
| SPC10403 | SPC10414 | Blautia_schinkii | Alistipes_shahii | |
| SPC10243 | SPC10414 | Clostridium_hathewayi | Alistipes_shahii | ++++ |
| SPC00026 | SPC10414 | Clostridium_nexile | Alistipes_shahii | |
| SPC00027 | SPC10414 | Clostridium_sp_HGF2 | Alistipes_shahii | |
| SPC10355 | SPC10414 | Clostridium_symbiosum | Alistipes_shahii | |
| SPC10097 | SPC10414 | Collinsella_aerofaciens | Alistipes_shahii | ++++ |
| SPC00009 | SPC10414 | Coprobacillus_sp_D7 | Alistipes_shahii | ++++ |
| SPC00080 | SPC10414 | Coprococcus_catus | Alistipes_shahii | − |
| SPC10304 | SPC10414 | Coprococcus_comes | Alistipes_shahii | |
| SPC00018 | SPC10414 | Dorea_formicigenerans | Alistipes_shahii | −−−− |
| SPC00057 | SPC10414 | Dorea_longicatena | Alistipes_shahii | ++++ |
| SPC00008 | SPC10414 | Enterococcus_faecalis | Alistipes_shahii | ++++ |
| SPC10001 | SPC10414 | Erysipelotrichaceae_bacterium | Alistipes_shahii | −−− |
| SPC00001 | SPC10414 | Escherichia_coli | Alistipes_shahii | ++++ |
| SPC10110 | SPC10414 | Escherichia_coli | Alistipes_shahii | ++++ |
| SPC00022 | SPC10414 | Eubacterium_eligens | Alistipes_shahii | −− |
| SPC10363 | SPC10414 | Eubacterium_rectale | Alistipes_shahii | |
| SPC00054 | SPC10414 | Faecalibacterium_prausnitzii | Alistipes_shahii | |
| SPC10386 | SPC10414 | Faecalibacterium_prausnitzii | Alistipes_shahii | + |
| SPC10390 | SPC10414 | Lachnospiraceae_bacterium_5_1_57FAA | Alistipes_shahii | |
| SPC00056 | SPC10414 | Odoribacter_splanchnicus | Alistipes_shahii | |
| SPC10388 | SPC10414 | Odoribacter_splanchnicus | Alistipes_shahii | |
| SPC10048 | SPC10414 | Parabacteroides_merdae | Alistipes_shahii | |
| SPC00061 | SPC10414 | Roseburia_intestinalis | Alistipes_shahii | − |
| SPC10197 | SPC10414 | Ruminococcus_obeum | Alistipes_shahii | |

TABLE 5-continued

Binary pair inhibition of *C. difficile*

| SPC1 | SPC2 | OTU1 | OTU2 | Result |
|---|---|---|---|---|
| SPC10233 | SPC10414 | Ruminococcus_torques | Alistipes_shahii | |
| SPC00015 | SPC10414 | Streptococcus_thermophilus | Alistipes_shahii | |
| SPC10211 | SPC10211 | Bacteroides_caccae | Bacteroides_caccae | ++++ |
| SPC10030 | SPC10211 | Bacteroides_ovatus | Bacteroides_caccae | |
| SPC00006 | SPC10211 | Bacteroides_sp_1_1_6 | Bacteroides_caccae | ++++ |
| SPC00007 | SPC10211 | Bacteroides_sp_3_1_23 | Bacteroides_caccae | +++ |
| SPC10019 | SPC10211 | Bacteroides_sp_D20 | Bacteroides_caccae | +++ |
| SPC00005 | SPC10211 | Bacteroides_vulgatus | Bacteroides_caccae | ++++ |
| SPC10081 | SPC10211 | Bacteroides_vulgatus | Bacteroides_caccae | + |
| SPC00021 | SPC10211 | Blautia_producta | Bacteroides_caccae | ++++ |
| SPC00026 | SPC10211 | Clostridium_nexile | Bacteroides_caccae | |
| SPC00027 | SPC10211 | Clostridium_sp_HGF2 | Bacteroides_caccae | |
| SPC10097 | SPC10211 | Collinsella_aerofaciens | Bacteroides_caccae | ++++ |
| SPC00009 | SPC10211 | Coprobacillus_sp_D7 | Bacteroides_caccae | +++ |
| SPC00080 | SPC10211 | Coprococcus_catus | Bacteroides_caccae | ++++ |
| SPC00018 | SPC10211 | Dorea_formicigenerans | Bacteroides_caccae | +++ |
| SPC00057 | SPC10211 | Dorea_longicatena | Bacteroides_caccae | |
| SPC00008 | SPC10211 | Enterococcus_faecalis | Bacteroides_caccae | ++++ |
| SPC10001 | SPC10211 | Erysipelotrichaceae_bacterium | Bacteroides_caccae | ++ |
| SPC00001 | SPC10211 | Escherichia_coli | Bacteroides_caccae | ++++ |
| SPC10110 | SPC10211 | Escherichia_coli | Bacteroides_caccae | ++++ |
| SPC00022 | SPC10211 | Eubacterium_eligens | Bacteroides_caccae | ++ |
| SPC00054 | SPC10211 | Faecalibacterium_prausnitzii | Bacteroides_caccae | − |
| SPC00056 | SPC10211 | Odoribacter_splanchnicus | Bacteroides_caccae | |
| SPC10048 | SPC10211 | Parabacteroides_merdae | Bacteroides_caccae | + |
| SPC00061 | SPC10211 | Roseburia_intestinalis | Bacteroides_caccae | + |
| SPC10197 | SPC10211 | Ruminococcus_obeum | Bacteroides_caccae | ++++ |
| SPC00015 | SPC10211 | Streptococcus_thermophilus | Bacteroides_caccae | ++ |
| SPC10211 | SPC10213 | Bacteroides_caccae | Bacteroides_eggerthii | ++++ |
| SPC10213 | SPC10213 | Bacteroides_eggerthii | Bacteroides_eggerthii | ++++ |
| SPC10030 | SPC10213 | Bacteroides_ovatus | Bacteroides_eggerthii | |
| SPC00006 | SPC10213 | Bacteroides_sp_1_1_6 | Bacteroides_eggerthii | +++ |
| SPC00007 | SPC10213 | Bacteroides_sp_3_1_23 | Bacteroides_eggerthii | ++ |
| SPC10019 | SPC10213 | Bacteroides_sp_D20 | Bacteroides_eggerthii | |
| SPC00005 | SPC10213 | Bacteroides_vulgatus | Bacteroides_eggerthii | ++++ |
| SPC10081 | SPC10213 | Bacteroides_vulgatus | Bacteroides_eggerthii | + |
| SPC00021 | SPC10213 | Blautia_producta | Bacteroides_eggerthii | ++++ |
| SPC00026 | SPC10213 | Clostridium_nexile | Bacteroides_eggerthii | |
| SPC00027 | SPC10213 | Clostridium_sp_HGF2 | Bacteroides_eggerthii | − |
| SPC10097 | SPC10213 | Collinsella_aerofaciens | Bacteroides_eggerthii | ++++ |
| SPC00009 | SPC10213 | Coprobacillus_sp_D7 | Bacteroides_eggerthii | |
| SPC00080 | SPC10213 | Coprococcus_catus | Bacteroides_eggerthii | + |
| SPC00018 | SPC10213 | Dorea_formicigenerans | Bacteroides_eggerthii | |
| SPC00057 | SPC10213 | Dorea_longicatena | Bacteroides_eggerthii | − |
| SPC00008 | SPC10213 | Enterococcus_faecalis | Bacteroides_eggerthii | ++++ |
| SPC10001 | SPC10213 | Erysipelotrichaceae_bacterium | Bacteroides_eggerthii | |
| SPC00001 | SPC10213 | Escherichia_coli | Bacteroides_eggerthii | ++++ |
| SPC10110 | SPC10213 | Escherichia_coli | Bacteroides_eggerthii | ++++ |
| SPC00022 | SPC10213 | Eubacterium_eligens | Bacteroides_eggerthii | |
| SPC00054 | SPC10213 | Faecalibacterium_prausnitzii | Bacteroides_eggerthii | |
| SPC00056 | SPC10213 | Odoribacter_splanchnicus | Bacteroides_eggerthii | |
| SPC10048 | SPC10213 | Parabacteroides_merdae | Bacteroides_eggerthii | |
| SPC00061 | SPC10213 | Roseburia_intestinalis | Bacteroides_eggerthii | |
| SPC10197 | SPC10213 | Ruminococcus_obeum | Bacteroides_eggerthii | ++++ |
| SPC00015 | SPC10213 | Streptococcus_thermophilus | Bacteroides_eggerthii | |
| SPC10030 | SPC10030 | Bacteroides_ovatus | Bacteroides_ovatus | +++ |
| SPC00006 | SPC10030 | Bacteroides_sp_1_1_6 | Bacteroides_ovatus | ++++ |
| SPC00007 | SPC10030 | Bacteroides_sp_3_1_23 | Bacteroides_ovatus | |
| SPC10019 | SPC10030 | Bacteroides_sp_D20 | Bacteroides_ovatus | − |
| SPC00005 | SPC10030 | Bacteroides_vulgatus | Bacteroides_ovatus | + |
| SPC00021 | SPC10030 | Blautia_producta | Bacteroides_ovatus | ++++ |
| SPC00026 | SPC10030 | Clostridium_nexile | Bacteroides_ovatus | |
| SPC00027 | SPC10030 | Clostridium_sp_HGF2 | Bacteroides_ovatus | |
| SPC00009 | SPC10030 | Coprobacillus_sp_D7 | Bacteroides_ovatus | |
| SPC00080 | SPC10030 | Coprococcus_catus | Bacteroides_ovatus | |
| SPC00018 | SPC10030 | Dorea_formicigenerans | Bacteroides_ovatus | |
| SPC00057 | SPC10030 | Dorea_longicatena | Bacteroides_ovatus | − |
| SPC00008 | SPC10030 | Enterococcus_faecalis | Bacteroides_ovatus | ++++ |
| SPC10001 | SPC10030 | Erysipelotrichaceae_bacterium | Bacteroides_ovatus | |
| SPC00001 | SPC10030 | Escherichia_coli | Bacteroides_ovatus | ++++ |
| SPC00022 | SPC10030 | Eubacterium_eligens | Bacteroides_ovatus | − |
| SPC00054 | SPC10030 | Faecalibacterium_prausnitzii | Bacteroides_ovatus | |
| SPC00056 | SPC10030 | Odoribacter_splanchnicus | Bacteroides_ovatus | |
| SPC00061 | SPC10030 | Roseburia_intestinalis | Bacteroides_ovatus | |
| SPC00015 | SPC10030 | Streptococcus_thermophilus | Bacteroides_ovatus | ++ |
| SPC00006 | SPC00006 | Bacteroides_sp_1_1_6 | Bacteroides_sp_1_1_6 | ++++ |

TABLE 5-continued

Binary pair inhibition of *C. difficile*

| SPC1 | SPC2 | OTU1 | OTU2 | Result |
|---|---|---|---|---|
| SPC00005 | SPC00006 | Bacteroides_vulgatus | Bacteroides_sp_1_1_6 | ++++ |
| SPC00001 | SPC00006 | Escherichia_coli | Bacteroides_sp_1_1_6 | ++++ |
| SPC00006 | SPC00007 | Bacteroides_sp_1_1_6 | Bacteroides_sp_3_1_23 | ++++ |
| SPC00007 | SPC00007 | Bacteroides_sp_3_1_23 | Bacteroides_sp_3_1_23 | |
| SPC00005 | SPC00007 | Bacteroides_vulgatus | Bacteroides_sp_3_1_23 | +++ |
| SPC00001 | SPC00007 | Escherichia_coli | Bacteroides_sp_3_1_23 | ++++ |
| SPC00006 | SPC10019 | Bacteroides_sp_1_1_6 | Bacteroides_sp_D20 | ++++ |
| SPC00007 | SPC10019 | Bacteroides_sp_3_1_23 | Bacteroides_sp_D20 | ++++ |
| SPC10019 | SPC10019 | Bacteroides_sp_D20 | Bacteroides_sp_D20 | |
| SPC00005 | SPC10019 | Bacteroides_vulgatus | Bacteroides_sp_D20 | + |
| SPC00021 | SPC10019 | Blautia_producta | Bacteroides_sp_D20 | ++++ |
| SPC00026 | SPC10019 | Clostridium_nexile | Bacteroides_sp_D20 | − |
| SPC00027 | SPC10019 | Clostridium_sp_HGF2 | Bacteroides_sp_D20 | |
| SPC00009 | SPC10019 | Coprobacillus_sp_D7 | Bacteroides_sp_D20 | |
| SPC00080 | SPC10019 | Coprococcus_catus | Bacteroides_sp_D20 | |
| SPC00018 | SPC10019 | Dorea_formicigenerans | Bacteroides_sp_D20 | − |
| SPC00057 | SPC10019 | Dorea_longicatena | Bacteroides_sp_D20 | |
| SPC00008 | SPC10019 | Enterococcus_faecalis | Bacteroides_sp_D20 | ++++ |
| SPC10001 | SPC10019 | Erysipelotrichaceae_bacterium | Bacteroides_sp_D20 | |
| SPC00001 | SPC10019 | Escherichia_coli | Bacteroides_sp_D20 | ++++ |
| SPC00022 | SPC10019 | Eubacterium_eligens | Bacteroides_sp_D20 | − |
| SPC00054 | SPC10019 | Faecalibacterium_prausnitzii | Bacteroides_sp_D20 | |
| SPC00056 | SPC10019 | Odoribacter_splanchnicus | Bacteroides_sp_D20 | |
| SPC00061 | SPC10019 | Roseburia_intestinalis | Bacteroides_sp_D20 | − |
| SPC00015 | SPC10019 | Streptococcus_thermophilus | Bacteroides_sp_D20 | + |
| SPC10030 | SPC10081 | Bacteroides_ovatus | Bacteroides_vulgatus | |
| SPC00006 | SPC10081 | Bacteroides_sp_1_1_6 | Bacteroides_vulgatus | |
| SPC00007 | SPC10081 | Bacteroides_sp_3_1_23 | Bacteroides_vulgatus | − |
| SPC10019 | SPC10081 | Bacteroides_sp_D20 | Bacteroides_vulgatus | |
| SPC00005 | SPC00005 | Bacteroides_vulgatus | Bacteroides_vulgatus | + |
| SPC00005 | SPC10081 | Bacteroides_vulgatus | Bacteroides_vulgatus | ++ |
| SPC10081 | SPC10081 | Bacteroides_vulgatus | Bacteroides_vulgatus | |
| SPC00021 | SPC10081 | Blautia_producta | Bacteroides_vulgatus | ++++ |
| SPC00026 | SPC10081 | Clostridium_nexile | Bacteroides_vulgatus | |
| SPC00027 | SPC10081 | Clostridium_sp_HGF2 | Bacteroides_vulgatus | +++ |
| SPC00009 | SPC10081 | Coprobacillus_sp_D7 | Bacteroides_vulgatus | − |
| SPC00080 | SPC10081 | Coprococcus_catus | Bacteroides_vulgatus | ++ |
| SPC00018 | SPC10081 | Dorea_formicigenerans | Bacteroides_vulgatus | |
| SPC00057 | SPC10081 | Dorea_longicatena | Bacteroides_vulgatus | |
| SPC00008 | SPC10081 | Enterococcus_faecalis | Bacteroides_vulgatus | ++++ |
| SPC10001 | SPC10081 | Erysipelotrichaceae_bacterium | Bacteroides_vulgatus | |
| SPC00001 | SPC00005 | Escherichia_coli | Bacteroides_vulgatus | ++++ |
| SPC00001 | SPC10081 | Escherichia_coli | Bacteroides_vulgatus | ++++ |
| SPC00022 | SPC10081 | Eubacterium_eligens | Bacteroides_vulgatus | |
| SPC00054 | SPC10081 | Faecalibacterium_prausnitzii | Bacteroides_vulgatus | |
| SPC00056 | SPC10081 | Odoribacter_splanchnicus | Bacteroides_vulgatus | |
| SPC10048 | SPC10081 | Parabacteroides_merdae | Bacteroides_vulgatus | + |
| SPC00061 | SPC10081 | Roseburia_intestinalis | Bacteroides_vulgatus | |
| SPC00015 | SPC10081 | Streptococcus_thermophilus | Bacteroides_vulgatus | −− |
| SPC10211 | SPC10301 | Bacteroides_caccae | Bifidobacterium_adolescentis | ++++ |
| SPC10213 | SPC10301 | Bacteroides_eggerthii | Bifidobacterium_adolescentis | ++++ |
| SPC10030 | SPC10301 | Bacteroides_ovatus | Bifidobacterium_adolescentis | ++++ |
| SPC00006 | SPC10301 | Bacteroides_sp_1_1_6 | Bifidobacterium_adolescentis | ++++ |
| SPC00007 | SPC10301 | Bacteroides_sp_3_1_23 | Bifidobacterium_adolescentis | ++++ |
| SPC10019 | SPC10301 | Bacteroides_sp_D20 | Bifidobacterium_adolescentis | ++++ |
| SPC00005 | SPC10301 | Bacteroides_vulgatus | Bifidobacterium_adolescentis | ++++ |
| SPC10081 | SPC10301 | Bacteroides_vulgatus | Bifidobacterium_adolescentis | ++++ |
| SPC10301 | SPC10301 | Bifidobacterium_adolescentis | Bifidobacterium_adolescentis | ++++ |
| SPC10298 | SPC10301 | Bifidobacterium_pseudocatenulatum | Bifidobacterium_adolescentis | ++++ |
| SPC00021 | SPC10301 | Blautia_producta | Bifidobacterium_adolescentis | ++++ |
| SPC10243 | SPC10301 | Clostridium_hathewayi | Bifidobacterium_adolescentis | ++++ |
| SPC00026 | SPC10301 | Clostridium_nexile | Bifidobacterium_adolescentis | ++++ |
| SPC00027 | SPC10301 | Clostridium_sp_HGF2 | Bifidobacterium_adolescentis | ++++ |
| SPC10097 | SPC10301 | Collinsella_aerofaciens | Bifidobacterium_adolescentis | ++++ |
| SPC00009 | SPC10301 | Coprobacillus_sp_D7 | Bifidobacterium_adolescentis | ++++ |
| SPC00080 | SPC10301 | Coprococcus_catus | Bifidobacterium_adolescentis | |
| SPC00018 | SPC10301 | Dorea_formicigenerans | Bifidobacterium_adolescentis | ++++ |
| SPC00057 | SPC10301 | Dorea_longicatena | Bifidobacterium_adolescentis | ++++ |
| SPC00008 | SPC10301 | Enterococcus_faecalis | Bifidobacterium_adolescentis | ++++ |
| SPC10001 | SPC10301 | Erysipelotrichaceae_bacterium | Bifidobacterium_adolescentis | ++++ |
| SPC00001 | SPC10301 | Escherichia_coli | Bifidobacterium_adolescentis | ++++ |
| SPC10110 | SPC10301 | Escherichia_coli | Bifidobacterium_adolescentis | ++++ |
| SPC00022 | SPC10301 | Eubacterium_eligens | Bifidobacterium_adolescentis | ++++ |
| SPC00054 | SPC10301 | Faecalibacterium_prausnitzii | Bifidobacterium_adolescentis | + |
| SPC00056 | SPC10301 | Odoribacter_splanchnicus | Bifidobacterium_adolescentis | +++ |
| SPC10048 | SPC10301 | Parabacteroides_merdae | Bifidobacterium_adolescentis | ++++ |

TABLE 5-continued

Binary pair inhibition of *C. difficile*

| SPC1 | SPC2 | OTU1 | OTU2 | Result |
|---|---|---|---|---|
| SPC00061 | SPC10301 | Roseburia_intestinalis | Bifidobacterium_adolescentis | +++ |
| SPC10197 | SPC10301 | Ruminococcus_obeum | Bifidobacterium_adolescentis | ++++ |
| SPC10233 | SPC10301 | Ruminococcus_torques | Bifidobacterium_adolescentis | ++++ |
| SPC00015 | SPC10301 | Streptococcus_thermophilus | Bifidobacterium_adolescentis | ++++ |
| SPC10211 | SPC10298 | Bacteroides_caccae | Bifidobacterium_pseudocatenulatum | ++++ |
| SPC10213 | SPC10298 | Bacteroides_eggerthii | Bifidobacterium_pseudocatenulatum | ++++ |
| SPC10030 | SPC10298 | Bacteroides_ovatus | Bifidobacterium_pseudocatenulatum | ++++ |
| SPC00006 | SPC10298 | Bacteroides_sp_1_1_6 | Bifidobacterium_pseudocatenulatum | ++++ |
| SPC00007 | SPC10298 | Bacteroides_sp_3_1_23 | Bifidobacterium_pseudocatenulatum | ++++ |
| SPC10019 | SPC10298 | Bacteroides_sp_D20 | Bifidobacterium_pseudocatenulatum | -- |
| SPC00005 | SPC10298 | Bacteroides_vulgatus | Bifidobacterium_pseudocatenulatum | ++++ |
| SPC10081 | SPC10298 | Bacteroides_vulgatus | Bifidobacterium_pseudocatenulatum | ++++ |
| SPC10298 | SPC10298 | Bifidobacterium_pseudocatenulatum | Bifidobacterium_pseudocatenulatum | ++++ |
| SPC00021 | SPC10298 | Blautia_producta | Bifidobacterium_pseudocatenulatum | + |
| SPC10243 | SPC10298 | Clostridium_hathewayi | Bifidobacterium_pseudocatenulatum | ++++ |
| SPC00026 | SPC10298 | Clostridium_nexile | Bifidobacterium_pseudocatenulatum | ++++ |
| SPC00027 | SPC10298 | Clostridium_sp_HGF2 | Bifidobacterium_pseudocatenulatum | +++ |
| SPC10097 | SPC10298 | Collinsella_aerofaciens | Bifidobacterium_pseudocatenulatum | ++++ |
| SPC00009 | SPC10298 | Coprobacillus_sp_D7 | Bifidobacterium_pseudocatenulatum | +++ |
| SPC00080 | SPC10298 | Coprococcus_catus | Bifidobacterium_pseudocatenulatum | |
| SPC00018 | SPC10298 | Dorea_formicigenerans | Bifidobacterium_pseudocatenulatum | +++ |
| SPC00057 | SPC10298 | Dorea_longicatena | Bifidobacterium_pseudocatenulatum | ++++ |
| SPC00008 | SPC10298 | Enterococcus_faecalis | Bifidobacterium_pseudocatenulatum | ++++ |
| SPC10001 | SPC10298 | Erysipelotrichaceae_bacterium | Bifidobacterium_pseudocatenulatum | |
| SPC00001 | SPC10298 | Escherichia_coli | Bifidobacterium_pseudocatenulatum | ++++ |
| SPC10110 | SPC10298 | Escherichia_coli | Bifidobacterium_pseudocatenulatum | ++++ |
| SPC00022 | SPC10298 | Eubacterium_eligens | Bifidobacterium_pseudocatenulatum | ++++ |
| SPC00054 | SPC10298 | Faecalibacterium_prausnitzii | Bifidobacterium_pseudocatenulatum | ++ |
| SPC00056 | SPC10298 | Odoribacter_splanchnicus | Bifidobacterium_pseudocatenulatum | + |
| SPC10048 | SPC10298 | Parabacteroides_merdae | Bifidobacterium_pseudocatenulatum | ++++ |
| SPC00061 | SPC10298 | Roseburia_intestinalis | Bifidobacterium_pseudocatenulatum | +++ |
| SPC10197 | SPC10298 | Ruminococcus_obeum | Bifidobacterium_pseudocatenulatum | ++++ |
| SPC10233 | SPC10298 | Ruminococcus_torques | Bifidobacterium_pseudocatenulatum | ++++ |
| SPC00015 | SPC10298 | Streptococcus_thermophilus | Bifidobacterium_pseudocatenulatum | ++++ |
| SPC10414 | SPC10415 | Alistipes_shahii | Blautia_producta | |
| SPC10211 | SPC10415 | Bacteroides_caccae | Blautia_producta | + |
| SPC10213 | SPC10415 | Bacteroides_eggerthii | Blautia_producta | |
| SPC10030 | SPC10415 | Bacteroides_ovatus | Blautia_producta | − |
| SPC00006 | SPC00021 | Bacteroides_sp_1_1_6 | Blautia_producta | ++++ |
| SPC00006 | SPC10415 | Bacteroides_sp_1_1_6 | Blautia_producta | ++++ |
| SPC00007 | SPC00021 | Bacteroides_sp_3_1_23 | Blautia_producta | ++++ |
| SPC00007 | SPC10415 | Bacteroides_sp_3_1_23 | Blautia_producta | ++ |
| SPC10019 | SPC10415 | Bacteroides_sp_D20 | Blautia_producta | |
| SPC00005 | SPC00021 | Bacteroides_vulgatus | Blautia_producta | ++++ |
| SPC00005 | SPC10415 | Bacteroides_vulgatus | Blautia_producta | ++++ |
| SPC10081 | SPC10415 | Bacteroides_vulgatus | Blautia_producta | ++++ |
| SPC10301 | SPC10415 | Bifidobacterium_adolescentis | Blautia_producta | ++++ |
| SPC10298 | SPC10415 | Bifidobacterium_pseudocatenulatum | Blautia_producta | |
| SPC00021 | SPC00021 | Blautia_producta | Blautia_producta | ++++ |
| SPC00021 | SPC10415 | Blautia_producta | Blautia_producta | ++++ |
| SPC10415 | SPC10415 | Blautia_producta | Blautia_producta | + |
| SPC10415 | SPC10415 | Blautia_producta | Blautia_producta | ++++ |
| SPC10403 | SPC10415 | Blautia_schinkii | Blautia_producta | |
| SPC10256 | SPC10415 | *Clostridium butyricum* | Blautia_producta | ++++ |
| SPC10358 | SPC10415 | *Clostridium orbiscindens* | Blautia_producta | ++++ |
| SPC10325 | SPC10415 | Clostridium_bolteae | Blautia_producta | ++++ |
| SPC10167 | SPC10415 | Clostridium_disporicum | Blautia_producta | ++++ |
| SPC10243 | SPC10415 | Clostridium_hathewayi | Blautia_producta | +++ |
| SPC10313 | SPC10415 | Clostridium_hylemonae | Blautia_producta | ++++ |
| SPC10202 | SPC10415 | Clostridium_innocuum | Blautia_producta | ++++ |
| SPC10238 | SPC10415 | Clostridium_mayombei | Blautia_producta | ++++ |
| SPC00026 | SPC10415 | Clostridium_nexile | Blautia_producta | − |
| SPC00027 | SPC10415 | Clostridium_sp_HGF2 | Blautia_producta | |
| SPC10355 | SPC10415 | Clostridium_symbiosum | Blautia_producta | |
| SPC10355 | SPC10415 | Clostridium_symbiosum | Blautia_producta | ++++ |
| SPC10155 | SPC10415 | Clostridium_tertium | Blautia_producta | ++++ |
| SPC10097 | SPC10415 | Collinsella_aerofaciens | Blautia_producta | ++++ |
| SPC10097 | SPC10415 | Collinsella_aerofaciens | Blautia_producta | ++++ |
| SPC00009 | SPC00021 | Coprobacillus_sp_D7 | Blautia_producta | ++++ |
| SPC00009 | SPC10415 | Coprobacillus_sp_D7 | Blautia_producta | ++++ |
| SPC00080 | SPC10415 | Coprococcus_catus | Blautia_producta | ---- |
| SPC10304 | SPC10415 | Coprococcus_comes | Blautia_producta | |
| SPC10304 | SPC10415 | Coprococcus_comes | Blautia_producta | ++++ |
| SPC00018 | SPC00021 | Dorea_formicigenerans | Blautia_producta | ++++ |
| SPC00018 | SPC10415 | Dorea_formicigenerans | Blautia_producta | -- |
| SPC00057 | SPC10415 | Dorea_longicatena | Blautia_producta | +++ |

TABLE 5-continued

Binary pair inhibition of *C. difficile*

| SPC1 | SPC2 | OTU1 | OTU2 | Result |
|---|---|---|---|---|
| SPC00008 | SPC00021 | Enterococcus__faecalis | Blautia__producta | ++++ |
| SPC00008 | SPC10415 | Enterococcus__faecalis | Blautia__producta | ++++ |
| SPC10001 | SPC10415 | Erysipelotrichaceae__bacterium | Blautia__producta | −−− |
| SPC00001 | SPC00021 | Escherichia__coli | Blautia__producta | ++++ |
| SPC00001 | SPC10415 | Escherichia__coli | Blautia__producta | ++++ |
| SPC10110 | SPC10415 | Escherichia__coli | Blautia__producta | ++++ |
| SPC00022 | SPC10415 | Eubacterium__eligens | Blautia__producta | −−− |
| SPC10363 | SPC10415 | Eubacterium__rectale | Blautia__producta | + |
| SPC00054 | SPC10415 | Faecalibacterium__prausnitzii | Blautia__producta | |
| SPC10386 | SPC10415 | Faecalibacterium__prausnitzii | Blautia__producta | + |
| SPC10386 | SPC10415 | Faecalibacterium__prausnitzii | Blautia__producta | ++++ |
| SPC10390 | SPC10415 | Lachnospiraceae__bacterium__5__1__57FAA | Blautia__producta | + |
| SPC10390 | SPC10415 | Lachnospiraceae__bacterium__5__1__57FAA | Blautia__producta | ++++ |
| SPC00056 | SPC10415 | Odoribacter__splanchnicus | Blautia__producta | − |
| SPC10388 | SPC10415 | Odoribacter__splanchnicus | Blautia__producta | + |
| SPC10048 | SPC10415 | Parabacteroides__merdae | Blautia__producta | +++ |
| SPC00061 | SPC10415 | Roseburia__intestinalis | Blautia__producta | −− |
| SPC10468 | SPC10415 | Ruminococcus__gnavus | Blautia__producta | ++++ |
| SPC10197 | SPC10415 | Ruminococcus__obeum | Blautia__producta | |
| SPC10233 | SPC10415 | Ruminococcus__torques | Blautia__producta | |
| SPC00015 | SPC00021 | Streptococcus__thermophilus | Blautia__producta | ++++ |
| SPC00015 | SPC10415 | Streptococcus__thermophilus | Blautia__producta | |
| SPC10211 | SPC10403 | Bacteroides__caccae | Blautia__schinkii | |
| SPC10213 | SPC10403 | Bacteroides__eggerthii | Blautia__schinkii | −− |
| SPC10030 | SPC10403 | Bacteroides__ovatus | Blautia__schinkii | − |
| SPC00006 | SPC10403 | Bacteroides__sp__1__1__6 | Blautia__schinkii | +++ |
| SPC00007 | SPC10403 | Bacteroides__sp__3__1__23 | Blautia__schinkii | + |
| SPC10019 | SPC10403 | Bacteroides__sp__D20 | Blautia__schinkii | −− |
| SPC00005 | SPC10403 | Bacteroides__vulgatus | Blautia__schinkii | ++ |
| SPC10081 | SPC10403 | Bacteroides__vulgatus | Blautia__schinkii | |
| SPC10301 | SPC10403 | Bifidobacterium__adolescentis | Blautia__schinkii | ++ |
| SPC10298 | SPC10403 | Bifidobacterium__pseudocatenulatum | Blautia__schinkii | − |
| SPC00021 | SPC10403 | Blautia__producta | Blautia__schinkii | ++++ |
| SPC10403 | SPC10403 | Blautia__schinkii | Blautia__schinkii | |
| SPC10243 | SPC10403 | Clostridium__hathewayi | Blautia__schinkii | ++++ |
| SPC00026 | SPC10403 | Clostridium__nexile | Blautia__schinkii | −− |
| SPC00027 | SPC10403 | Clostridium__sp__HGF2 | Blautia__schinkii | |
| SPC10355 | SPC10403 | Clostridium__symbiosum | Blautia__schinkii | |
| SPC10097 | SPC10403 | Collinsella__aerofaciens | Blautia__schinkii | ++++ |
| SPC00009 | SPC10403 | Coprobacillus__sp__D7 | Blautia__schinkii | ++++ |
| SPC00080 | SPC10403 | Coprococcus__catus | Blautia__schinkii | −−− |
| SPC10304 | SPC10403 | Coprococcus__comes | Blautia__schinkii | + |
| SPC00018 | SPC10403 | Dorea__formicigenerans | Blautia__schinkii | |
| SPC00057 | SPC10403 | Dorea__longicatena | Blautia__schinkii | +++ |
| SPC00008 | SPC10403 | Enterococcus__faecalis | Blautia__schinkii | ++++ |
| SPC10001 | SPC10403 | Erysipelotrichaceae__bacterium | Blautia__schinkii | −−− |
| SPC00001 | SPC10403 | Escherichia__coli | Blautia__schinkii | ++++ |
| SPC10110 | SPC10403 | Escherichia__coli | Blautia__schinkii | ++++ |
| SPC00022 | SPC10403 | Eubacterium__eligens | Blautia__schinkii | − |
| SPC10363 | SPC10403 | Eubacterium__rectale | Blautia__schinkii | + |
| SPC00054 | SPC10403 | Faecalibacterium__prausnitzii | Blautia__schinkii | |
| SPC10386 | SPC10403 | Faecalibacterium__prausnitzii | Blautia__schinkii | |
| SPC10390 | SPC10403 | Lachnospiraceae__bacterium__5__1__57FAA | Blautia__schinkii | |
| SPC00056 | SPC10403 | Odoribacter__splanchnicus | Blautia__schinkii | − |
| SPC10388 | SPC10403 | Odoribacter__splanchnicus | Blautia__schinkii | |
| SPC10048 | SPC10403 | Parabacteroides__merdae | Blautia__schinkii | |
| SPC00061 | SPC10403 | Roseburia__intestinalis | Blautia__schinkii | − |
| SPC10197 | SPC10403 | Ruminococcus__obeum | Blautia__schinkii | |
| SPC10233 | SPC10403 | Ruminococcus__torques | Blautia__schinkii | |
| SPC00015 | SPC10403 | Streptococcus__thermophilus | Blautia__schinkii | |
| SPC10256 | SPC10256 | *Clostridium butyricum* | *Clostridium butyricum* | ++++ |
| SPC10167 | SPC10256 | Clostridium__disporicum | *Clostridium butyricum* | ++++ |
| SPC10202 | SPC10256 | Clostridium__innocuum | *Clostridium butyricum* | ++++ |
| SPC10238 | SPC10256 | Clostridium__mayombei | *Clostridium butyricum* | ++++ |
| SPC10155 | SPC10256 | Clostridium__tertium | *Clostridium butyricum* | ++++ |
| SPC10097 | SPC10256 | Collinsella__aerofaciens | *Clostridium butyricum* | ++++ |
| SPC10304 | SPC10256 | Coprococcus__comes | *Clostridium butyricum* | ++++ |
| SPC10256 | SPC10358 | *Clostridium butyricum* | *Clostridium orbiscindens* | ++++ |
| SPC10358 | SPC10358 | *Clostridium orbiscindens* | *Clostridium orbiscindens* | + |
| SPC10325 | SPC10358 | Clostridium__bolteae | *Clostridium orbiscindens* | ++++ |
| SPC10167 | SPC10358 | Clostridium__disporicum | *Clostridium orbiscindens* | ++++ |
| SPC10313 | SPC10358 | Clostridium__hylemonae | *Clostridium orbiscindens* | |
| SPC10202 | SPC10358 | Clostridium__innocuum | *Clostridium orbiscindens* | ++++ |
| SPC10238 | SPC10358 | Clostridium__mayombei | *Clostridium orbiscindens* | ++++ |
| SPC10355 | SPC10358 | Clostridium__symbiosum | *Clostridium orbiscindens* | ++++ |
| SPC10155 | SPC10358 | Clostridium__tertium | *Clostridium orbiscindens* | ++++ |

TABLE 5-continued

Binary pair inhibition of *C. difficile*

| SPC1 | SPC2 | OTU1 | OTU2 | Result |
|---|---|---|---|---|
| SPC10097 | SPC10358 | Collinsella_aerofaciens | Clostridium orbiscindens | ++++ |
| SPC10304 | SPC10358 | Coprococcus_comes | Clostridium orbiscindens | ++++ |
| SPC10386 | SPC10358 | Faecalibacterium_prausnitzii | Clostridium orbiscindens | |
| SPC10256 | SPC10325 | *Clostridium butyricum* | Clostridium_bolteae | ++++ |
| SPC10325 | SPC10325 | Clostridium_bolteae | Clostridium_bolteae | ++++ |
| SPC10167 | SPC10325 | Clostridium_disporicum | Clostridium_bolteae | ++++ |
| SPC10313 | SPC10325 | Clostridium_hylemonae | Clostridium_bolteae | |
| SPC10202 | SPC10325 | Clostridium_innocuum | Clostridium_bolteae | ++++ |
| SPC10238 | SPC10325 | Clostridium_mayombei | Clostridium_bolteae | ++++ |
| SPC10355 | SPC10325 | Clostridium_symbiosum | Clostridium_bolteae | ++++ |
| SPC10155 | SPC10325 | Clostridium_tertium | Clostridium_bolteae | ++++ |
| SPC10097 | SPC10325 | Collinsella_aerofaciens | Clostridium_bolteae | ++++ |
| SPC10304 | SPC10325 | Coprococcus_comes | Clostridium_bolteae | ++++ |
| SPC10167 | SPC10167 | Clostridium_disporicum | Clostridium_disporicum | +++ |
| SPC10202 | SPC10167 | Clostridium_innocuum | Clostridium_disporicum | +++ |
| SPC10155 | SPC10167 | Clostridium_tertium | Clostridium_disporicum | ++++ |
| SPC10097 | SPC10167 | Collinsella_aerofaciens | Clostridium_disporicum | − |
| SPC10211 | SPC10243 | Bacteroides_caccae | Clostridium_hathewayi | ++++ |
| SPC10213 | SPC10243 | Bacteroides_eggerthii | Clostridium_hathewayi | ++++ |
| SPC10030 | SPC10243 | Bacteroides_ovatus | Clostridium_hathewayi | ++++ |
| SPC00006 | SPC10243 | Bacteroides_sp_1_1_6 | Clostridium_hathewayi | ++++ |
| SPC00007 | SPC10243 | Bacteroides_sp_3_1_23 | Clostridium_hathewayi | ++++ |
| SPC10019 | SPC10243 | Bacteroides_sp_D20 | Clostridium_hathewayi | ++++ |
| SPC00005 | SPC10243 | Bacteroides_vulgatus | Clostridium_hathewayi | ++++ |
| SPC10081 | SPC10243 | Bacteroides_vulgatus | Clostridium_hathewayi | ++++ |
| SPC00021 | SPC10243 | Blautia_producta | Clostridium_hathewayi | ++++ |
| SPC10243 | SPC10243 | Clostridium_hathewayi | Clostridium_hathewayi | ++++ |
| SPC00026 | SPC10243 | Clostridium_nexile | Clostridium_hathewayi | |
| SPC00027 | SPC10243 | Clostridium_sp_HGF2 | Clostridium_hathewayi | |
| SPC10097 | SPC10243 | Collinsella_aerofaciens | Clostridium_hathewayi | ++++ |
| SPC00009 | SPC10243 | Coprobacillus_sp_D7 | Clostridium_hathewayi | ++++ |
| SPC00080 | SPC10243 | Coprococcus_catus | Clostridium_hathewayi | +++ |
| SPC00018 | SPC10243 | Dorea_formicigenerans | Clostridium_hathewayi | ++++ |
| SPC00057 | SPC10243 | Dorea_longicatena | Clostridium_hathewayi | + |
| SPC00008 | SPC10243 | Enterococcus_faecalis | Clostridium_hathewayi | ++++ |
| SPC10001 | SPC10243 | Erysipelotrichaceae_bacterium | Clostridium_hathewayi | ++++ |
| SPC00001 | SPC10243 | Escherichia_coli | Clostridium_hathewayi | ++++ |
| SPC10110 | SPC10243 | Escherichia_coli | Clostridium_hathewayi | ++++ |
| SPC00022 | SPC10243 | Eubacterium_eligens | Clostridium_hathewayi | + |
| SPC00054 | SPC10243 | Faecalibacterium_prausnitzii | Clostridium_hathewayi | |
| SPC00056 | SPC10243 | Odoribacter_splanchnicus | Clostridium_hathewayi | |
| SPC10048 | SPC10243 | Parabacteroides_merdae | Clostridium_hathewayi | + |
| SPC00061 | SPC10243 | Roseburia_intestinalis | Clostridium_hathewayi | +++ |
| SPC10197 | SPC10243 | Ruminococcus_obeum | Clostridium_hathewayi | ++++ |
| SPC10233 | SPC10243 | Ruminococcus_torques | Clostridium_hathewayi | ++++ |
| SPC00015 | SPC10243 | Streptococcus_thermophilus | Clostridium_hathewayi | ++ |
| SPC10256 | SPC10313 | *Clostridium butyricum* | Clostridium_hylemonae | ++++ |
| SPC10325 | SPC10313 | Clostridium_bolteae | Clostridium_hylemonae | |
| SPC10167 | SPC10313 | Clostridium_disporicum | Clostridium_hylemonae | |
| SPC10313 | SPC10313 | Clostridium_hylemonae | Clostridium_hylemonae | |
| SPC10202 | SPC10313 | Clostridium_innocuum | Clostridium_hylemonae | ++++ |
| SPC10238 | SPC10313 | Clostridium_mayombei | Clostridium_hylemonae | ++++ |
| SPC10155 | SPC10313 | Clostridium_tertium | Clostridium_hylemonae | ++++ |
| SPC10097 | SPC10313 | Collinsella_aerofaciens | Clostridium_hylemonae | +++ |
| SPC10304 | SPC10313 | Coprococcus_comes | Clostridium_hylemonae | + |
| SPC10167 | SPC10202 | Clostridium_disporicum | Clostridium_innocuum | +++ |
| SPC10202 | SPC10202 | Clostridium_innocuum | Clostridium_innocuum | ++++ |
| SPC10238 | SPC10202 | Clostridium_mayombei | Clostridium_innocuum | ++++ |
| SPC10155 | SPC10202 | Clostridium_tertium | Clostridium_innocuum | ++++ |
| SPC10097 | SPC10202 | Collinsella_aerofaciens | Clostridium_innocuum | +++ |
| SPC10256 | SPC10238 | *Clostridium butyricum* | Clostridium_mayombei | ++++ |
| SPC10167 | SPC10238 | Clostridium_disporicum | Clostridium_mayombei | ++++ |
| SPC10202 | SPC10238 | Clostridium_innocuum | Clostridium_mayombei | ++++ |
| SPC10238 | SPC10238 | Clostridium_mayombei | Clostridium_mayombei | ++++ |
| SPC10155 | SPC10238 | Clostridium_tertium | Clostridium_mayombei | ++++ |
| SPC10097 | SPC10238 | Collinsella_aerofaciens | Clostridium_mayombei | ++++ |
| SPC00006 | SPC00026 | Bacteroides_sp_1_1_6 | Clostridium_nexile | ++++ |
| SPC00007 | SPC00026 | Bacteroides_sp_3_1_23 | Clostridium_nexile | ++++ |
| SPC00005 | SPC00026 | Bacteroides_vulgatus | Clostridium_nexile | ++++ |
| SPC00021 | SPC00026 | Blautia_producta | Clostridium_nexile | ++++ |
| SPC00026 | SPC00026 | Clostridium_nexile | Clostridium_nexile | ++ |
| SPC00009 | SPC00026 | Coprobacillus_sp_D7 | Clostridium_nexile | |
| SPC00018 | SPC00026 | Dorea_formicigenerans | Clostridium_nexile | |
| SPC00008 | SPC00026 | Enterococcus_faecalis | Clostridium_nexile | ++++ |
| SPC00001 | SPC00026 | Escherichia_coli | Clostridium_nexile | ++++ |
| SPC00022 | SPC00026 | Eubacterium_eligens | Clostridium_nexile | + |

TABLE 5-continued

Binary pair inhibition of *C. difficile*

| SPC1 | SPC2 | OTU1 | OTU2 | Result |
|---|---|---|---|---|
| SPC00015 | SPC00026 | Streptococcus_thermophilus | Clostridium_nexile | + |
| SPC00006 | SPC00027 | Bacteroides_sp_1_1_6 | Clostridium_sp_HGF2 | ++++ |
| SPC00007 | SPC00027 | Bacteroides_sp_3_1_23 | Clostridium_sp_HGF2 | ++++ |
| SPC00005 | SPC00027 | Bacteroides_vulgatus | Clostridium_sp_HGF2 | ++ |
| SPC00021 | SPC00027 | Blautia_producta | Clostridium_sp_HGF2 | ++++ |
| SPC00026 | SPC00027 | Clostridium_nexile | Clostridium_sp_HGF2 | ++++ |
| SPC00027 | SPC00027 | Clostridium_sp_HGF2 | Clostridium_sp_HGF2 | ++++ |
| SPC00009 | SPC00027 | Coprobacillus_sp_D7 | Clostridium_sp_HGF2 | − |
| SPC00018 | SPC00027 | Dorea_formicigenerans | Clostridium_sp_HGF2 |  |
| SPC00008 | SPC00027 | Enterococcus_faecalis | Clostridium_sp_HGF2 | ++++ |
| SPC00001 | SPC00027 | Escherichia_coli | Clostridium_sp_HGF2 | ++++ |
| SPC00022 | SPC00027 | Eubacterium_eligens | Clostridium_sp_HGF2 |  |
| SPC00015 | SPC00027 | Streptococcus_thermophilus | Clostridium_sp_HGF2 | + |
| SPC10211 | SPC10355 | Bacteroides_caccae | Clostridium_symbiosum | +++ |
| SPC10213 | SPC10355 | Bacteroides_eggerthii | Clostridium_symbiosum | ++++ |
| SPC10030 | SPC10355 | Bacteroides_ovatus | Clostridium_symbiosum |  |
| SPC00006 | SPC10355 | Bacteroides_sp_1_1_6 | Clostridium_symbiosum | ++++ |
| SPC00007 | SPC10355 | Bacteroides_sp_3_1_23 | Clostridium_symbiosum | ++++ |
| SPC10019 | SPC10355 | Bacteroides_sp_D20 | Clostridium_symbiosum |  |
| SPC00005 | SPC10355 | Bacteroides_vulgatus | Clostridium_symbiosum | +++ |
| SPC10081 | SPC10355 | Bacteroides_vulgatus | Clostridium_symbiosum |  |
| SPC10301 | SPC10355 | Bifidobacterium_adolescentis | Clostridium_symbiosum | ++++ |
| SPC10298 | SPC10355 | Bifidobacterium_pseudocatenulatum | Clostridium_symbiosum | + |
| SPC00021 | SPC10355 | Blautia_producta | Clostridium_symbiosum | ++++ |
| SPC10256 | SPC10355 | *Clostridium butyricum* | Clostridium_symbiosum | ++++ |
| SPC10358 | SPC10355 | *Clostridium orbiscindens* | Clostridium_symbiosum | ++++ |
| SPC10325 | SPC10355 | Clostridium_bolteae | Clostridium_symbiosum | ++++ |
| SPC10167 | SPC10355 | Clostridium_disporicum | Clostridium_symbiosum | ++++ |
| SPC10243 | SPC10355 | Clostridium_hathewayi | Clostridium_symbiosum | ++++ |
| SPC10313 | SPC10355 | Clostridium_hylemonae | Clostridium_symbiosum | +++ |
| SPC10202 | SPC10355 | Clostridium_innocuum | Clostridium_symbiosum | ++++ |
| SPC10238 | SPC10355 | Clostridium_mayombei | Clostridium_symbiosum | ++++ |
| SPC00026 | SPC10355 | Clostridium_nexile | Clostridium_symbiosum | + |
| SPC00027 | SPC10355 | Clostridium_sp_HGF2 | Clostridium_symbiosum |  |
| SPC10355 | SPC10355 | Clostridium_symbiosum | Clostridium_symbiosum | + |
| SPC10355 | SPC10355 | Clostridium_symbiosum | Clostridium_symbiosum | ++++ |
| SPC10155 | SPC10355 | Clostridium_tertium | Clostridium_symbiosum | + |
| SPC10097 | SPC10355 | Collinsella_aerofaciens | Clostridium_symbiosum | +++ |
| SPC10097 | SPC10355 | Collinsella_aerofaciens | Clostridium_symbiosum | ++++ |
| SPC00009 | SPC10355 | Coprobacillus_sp_D7 | Clostridium_symbiosum |  |
| SPC00080 | SPC10355 | Coprococcus_catus | Clostridium_symbiosum | − |
| SPC10304 | SPC10355 | Coprococcus_comes | Clostridium_symbiosum |  |
| SPC10304 | SPC10355 | Coprococcus_comes | Clostridium_symbiosum | ++++ |
| SPC00018 | SPC10355 | Dorea_formicigenerans | Clostridium_symbiosum |  |
| SPC00057 | SPC10355 | Dorea_longicatena | Clostridium_symbiosum | ++++ |
| SPC00008 | SPC10355 | Enterococcus_faecalis | Clostridium_symbiosum | ++++ |
| SPC10001 | SPC10355 | Erysipelotrichaceae_bacterium | Clostridium_symbiosum |  |
| SPC00001 | SPC10355 | Escherichia_coli | Clostridium_symbiosum | ++++ |
| SPC10110 | SPC10355 | Escherichia_coli | Clostridium_symbiosum | ++++ |
| SPC00022 | SPC10355 | Eubacterium_eligens | Clostridium_symbiosum | + |
| SPC00054 | SPC10355 | Faecalibacterium_prausnitzii | Clostridium_symbiosum |  |
| SPC00056 | SPC10355 | Odoribacter_splanchnicus | Clostridium_symbiosum |  |
| SPC10048 | SPC10355 | Parabacteroides_merdae | Clostridium_symbiosum | − |
| SPC00061 | SPC10355 | Roseburia_intestinalis | Clostridium_symbiosum | −− |
| SPC10197 | SPC10355 | Ruminococcus_obeum | Clostridium_symbiosum | ++++ |
| SPC10233 | SPC10355 | Ruminococcus_torques | Clostridium_symbiosum | ++ |
| SPC00015 | SPC10355 | Streptococcus_thermophilus | Clostridium_symbiosum |  |
| SPC10167 | SPC10155 | Clostridium_disporicum | Clostridium_tertium | ++++ |
| SPC10155 | SPC10155 | Clostridium_tertium | Clostridium_tertium | ++++ |
| SPC10097 | SPC10155 | Collinsella_aerofaciens | Clostridium_tertium |  |
| SPC10030 | SPC10097 | Bacteroides_ovatus | Collinsella_aerofaciens | ++++ |
| SPC00006 | SPC10097 | Bacteroides_sp_1_1_6 | Collinsella_aerofaciens | ++++ |
| SPC00007 | SPC10097 | Bacteroides_sp_3_1_23 | Collinsella_aerofaciens | ++++ |
| SPC10019 | SPC10097 | Bacteroides_sp_D20 | Collinsella_aerofaciens | ++++ |
| SPC00005 | SPC10097 | Bacteroides_vulgatus | Collinsella_aerofaciens | ++++ |
| SPC10081 | SPC10097 | Bacteroides_vulgatus | Collinsella_aerofaciens | ++++ |
| SPC00021 | SPC10097 | Blautia_producta | Collinsella_aerofaciens | ++++ |
| SPC00026 | SPC10097 | Clostridium_nexile | Collinsella_aerofaciens | + |
| SPC00027 | SPC10097 | Clostridium_sp_HGF2 | Collinsella_aerofaciens | ++++ |
| SPC10155 | SPC10097 | Clostridium_tertium | Collinsella_aerofaciens |  |
| SPC10097 | SPC10097 | Collinsella_aerofaciens | Collinsella_aerofaciens | ++++ |
| SPC10097 | SPC10097 | Collinsella_aerofaciens | Collinsella_aerofaciens |  |
| SPC00009 | SPC10097 | Coprobacillus_sp_D7 | Collinsella_aerofaciens | +++ |
| SPC00080 | SPC10097 | Coprococcus_catus | Collinsella_aerofaciens | ++++ |
| SPC00018 | SPC10097 | Dorea_formicigenerans | Collinsella_aerofaciens | ++ |
| SPC00057 | SPC10097 | Dorea_longicatena | Collinsella_aerofaciens | ++++ |

TABLE 5-continued

Binary pair inhibition of C. difficile

| SPC1 | SPC2 | OTU1 | OTU2 | Result |
|---|---|---|---|---|
| SPC00008 | SPC10097 | Enterococcus_faecalis | Collinsella_aerofaciens | ++++ |
| SPC10001 | SPC10097 | Erysipelotrichaceae_bacterium | Collinsella_aerofaciens | ++++ |
| SPC00001 | SPC10097 | Escherichia_coli | Collinsella_aerofaciens | ++++ |
| SPC00022 | SPC10097 | Eubacterium_eligens | Collinsella_aerofaciens | +++ |
| SPC00054 | SPC10097 | Faecalibacterium_prausnitzii | Collinsella_aerofaciens | +++ |
| SPC00056 | SPC10097 | Odoribacter_splanchnicus | Collinsella_aerofaciens | +++ |
| SPC10048 | SPC10097 | Parabacteroides_merdae | Collinsella_aerofaciens | ++++ |
| SPC00061 | SPC10097 | Roseburia_intestinalis | Collinsella_aerofaciens | ++ |
| SPC00015 | SPC10097 | Streptococcus_thermophilus | Collinsella_aerofaciens | + |
| SPC00006 | SPC00009 | Bacteroides_sp_1_1_6 | Coprobacillus_sp_D7 | +++ |
| SPC00007 | SPC00009 | Bacteroides_sp_3_1_23 | Coprobacillus_sp_D7 | |
| SPC00005 | SPC00009 | Bacteroides_vulgatus | Coprobacillus_sp_D7 | + |
| SPC00009 | SPC00009 | Coprobacillus_sp_D7 | Coprobacillus_sp_D7 | – |
| SPC00008 | SPC00009 | Enterococcus_faecalis | Coprobacillus_sp_D7 | ++++ |
| SPC00001 | SPC00009 | Escherichia_coli | Coprobacillus_sp_D7 | ++ |
| SPC00006 | SPC00080 | Bacteroides_sp_1_1_6 | Coprococcus_catus | ++++ |
| SPC00007 | SPC00080 | Bacteroides_sp_3_1_23 | Coprococcus_catus | |
| SPC00005 | SPC00080 | Bacteroides_vulgatus | Coprococcus_catus | + |
| SPC00021 | SPC00080 | Blautia_producta | Coprococcus_catus | ++++ |
| SPC00026 | SPC00080 | Clostridium_nexile | Coprococcus_catus | |
| SPC00027 | SPC00080 | Clostridium_sp_HGF2 | Coprococcus_catus | --- |
| SPC00009 | SPC00080 | Coprobacillus_sp_D7 | Coprococcus_catus | --- |
| SPC00080 | SPC00080 | Coprococcus_catus | Coprococcus_catus | |
| SPC00018 | SPC00080 | Dorea_formicigenerans | Coprococcus_catus | |
| SPC00057 | SPC00080 | Dorea_longicatena | Coprococcus_catus | |
| SPC00008 | SPC00080 | Enterococcus_faecalis | Coprococcus_catus | ++++ |
| SPC00001 | SPC00080 | Escherichia_coli | Coprococcus_catus | ++++ |
| SPC00022 | SPC00080 | Eubacterium_eligens | Coprococcus_catus | |
| SPC00054 | SPC00080 | Faecalibacterium_prausnitzii | Coprococcus_catus | |
| SPC00056 | SPC00080 | Odoribacter_splanchnicus | Coprococcus_catus | |
| SPC00061 | SPC00080 | Roseburia_intestinalis | Coprococcus_catus | |
| SPC00015 | SPC00080 | Streptococcus_thermophilus | Coprococcus_catus | |
| SPC10211 | SPC10304 | Bacteroides_caccae | Coprococcus_comes | +++ |
| SPC10213 | SPC10304 | Bacteroides_eggerthii | Coprococcus_comes | +++ |
| SPC10030 | SPC10304 | Bacteroides_ovatus | Coprococcus_comes | |
| SPC00006 | SPC10304 | Bacteroides_sp_1_1_6 | Coprococcus_comes | +++ |
| SPC00007 | SPC10304 | Bacteroides_sp_3_1_23 | Coprococcus_comes | ++++ |
| SPC10019 | SPC10304 | Bacteroides_sp_D20 | Coprococcus_comes | |
| SPC00005 | SPC10304 | Bacteroides_vulgatus | Coprococcus_comes | ++++ |
| SPC10081 | SPC10304 | Bacteroides_vulgatus | Coprococcus_comes | |
| SPC10301 | SPC10304 | Bifidobacterium_adolescentis | Coprococcus_comes | ++++ |
| SPC10298 | SPC10304 | Bifidobacterium_pseudocatenulatum | Coprococcus_comes | ++++ |
| SPC00021 | SPC10304 | Blautia_producta | Coprococcus_comes | ++++ |
| SPC10256 | SPC10304 | *Clostridium butyricum* | Coprococcus_comes | ++++ |
| SPC10167 | SPC10304 | Clostridium_disporicum | Coprococcus_comes | ++++ |
| SPC10243 | SPC10304 | Clostridium_hathewayi | Coprococcus_comes | ++++ |
| SPC10313 | SPC10304 | Clostridium_hylemonae | Coprococcus_comes | + |
| SPC10202 | SPC10304 | Clostridium_innocuum | Coprococcus_comes | ++++ |
| SPC10238 | SPC10304 | Clostridium_mayombei | Coprococcus_comes | ++++ |
| SPC00026 | SPC10304 | Clostridium_nexile | Coprococcus_comes | |
| SPC00027 | SPC10304 | Clostridium_sp_HGF2 | Coprococcus_comes | |
| SPC10155 | SPC10304 | Clostridium_tertium | Coprococcus_comes | ++++ |
| SPC10097 | SPC10304 | Collinsella_aerofaciens | Coprococcus_comes | ++++ |
| SPC10097 | SPC10304 | Collinsella_aerofaciens | Coprococcus_comes | +++ |
| SPC00009 | SPC10304 | Coprobacillus_sp_D7 | Coprococcus_comes | +++ |
| SPC00080 | SPC10304 | Coprococcus_catus | Coprococcus_comes | -- |
| SPC10304 | SPC10304 | Coprococcus_comes | Coprococcus_comes | |
| SPC10304 | SPC10304 | Coprococcus_comes | Coprococcus_comes | ++ |
| SPC00018 | SPC10304 | Dorea_formicigenerans | Coprococcus_comes | |
| SPC00057 | SPC10304 | Dorea_longicatena | Coprococcus_comes | |
| SPC00008 | SPC10304 | Enterococcus_faecalis | Coprococcus_comes | ++++ |
| SPC10001 | SPC10304 | Erysipelotrichaceae_bacterium | Coprococcus_comes | – |
| SPC00001 | SPC10304 | Escherichia_coli | Coprococcus_comes | ++++ |
| SPC10110 | SPC10304 | Escherichia_coli | Coprococcus_comes | ++++ |
| SPC00022 | SPC10304 | Eubacterium_eligens | Coprococcus_comes | ++ |
| SPC00054 | SPC10304 | Faecalibacterium_prausnitzii | Coprococcus_comes | |
| SPC00056 | SPC10304 | Odoribacter_splanchnicus | Coprococcus_comes | |
| SPC10048 | SPC10304 | Parabacteroides_merdae | Coprococcus_comes | – |
| SPC00061 | SPC10304 | Roseburia_intestinalis | Coprococcus_comes | – |
| SPC10197 | SPC10304 | Ruminococcus_obeum | Coprococcus_comes | ++++ |
| SPC10233 | SPC10304 | Ruminococcus_torques | Coprococcus_comes | ++++ |
| SPC00015 | SPC10304 | Streptococcus_thermophilus | Coprococcus_comes | ++ |
| SPC00006 | SPC00018 | Bacteroides_sp_1_1_6 | Dorea_formicigenerans | +++ |
| SPC00007 | SPC00018 | Bacteroides_sp_3_1_23 | Dorea_formicigenerans | |
| SPC00005 | SPC00018 | Bacteroides_vulgatus | Dorea_formicigenerans | ++ |
| SPC00009 | SPC00018 | Coprobacillus_sp_D7 | Dorea_formicigenerans | – |

TABLE 5-continued

Binary pair inhibition of *C. difficile*

| SPC1 | SPC2 | OTU1 | OTU2 | Result |
|---|---|---|---|---|
| SPC00018 | SPC00018 | Dorea_formicigenerans | Dorea_formicigenerans | -- |
| SPC00008 | SPC00018 | Enterococcus_faecalis | Dorea_formicigenerans | ++++ |
| SPC00001 | SPC00018 | Escherichia_coli | Dorea_formicigenerans | ++ |
| SPC00015 | SPC00018 | Streptococcus_thermophilus | Dorea_formicigenerans | |
| SPC00006 | SPC00057 | Bacteroides_sp_1_1_6 | Dorea_longicatena | ++++ |
| SPC00007 | SPC00057 | Bacteroides_sp_3_1_23 | Dorea_longicatena | +++ |
| SPC00005 | SPC00057 | Bacteroides_vulgatus | Dorea_longicatena | ++++ |
| SPC00021 | SPC00057 | Blautia_producta | Dorea_longicatena | ++++ |
| SPC00026 | SPC00057 | Clostridium_nexile | Dorea_longicatena | |
| SPC00027 | SPC00057 | Clostridium_sp_HGF2 | Dorea_longicatena | -- |
| SPC00009 | SPC00057 | Coprobacillus_sp_D7 | Dorea_longicatena | |
| SPC00018 | SPC00057 | Dorea_formicigenerans | Dorea_longicatena | ++ |
| SPC00057 | SPC00057 | Dorea_longicatena | Dorea_longicatena | − |
| SPC00008 | SPC00057 | Enterococcus_faecalis | Dorea_longicatena | ++++ |
| SPC00001 | SPC00057 | Escherichia_coli | Dorea_longicatena | ++++ |
| SPC00022 | SPC00057 | Eubacterium_eligens | Dorea_longicatena | ++ |
| SPC00054 | SPC00057 | Faecalibacterium_prausnitzii | Dorea_longicatena | − |
| SPC00056 | SPC00057 | Odoribacter_splanchnicus | Dorea_longicatena | |
| SPC00015 | SPC00057 | Streptococcus_thermophilus | Dorea_longicatena | + |
| SPC00006 | SPC00008 | Bacteroides_sp_1_1_6 | Enterococcus_faecalis | ++++ |
| SPC00007 | SPC00008 | Bacteroides_sp_3_1_23 | Enterococcus_faecalis | ++++ |
| SPC00005 | SPC00008 | Bacteroides_vulgatus | Enterococcus_faecalis | ++++ |
| SPC00008 | SPC00008 | Enterococcus_faecalis | Enterococcus_faecalis | ++++ |
| SPC00001 | SPC00008 | Escherichia_coli | Enterococcus_faecalis | ++++ |
| SPC00006 | SPC10001 | Bacteroides_sp_1_1_6 | Erysipelotrichaceae_bacterium | ++++ |
| SPC00007 | SPC10001 | Bacteroides_sp_3_1_23 | Erysipelotrichaceae_bacterium | |
| SPC00005 | SPC10001 | Bacteroides_vulgatus | Erysipelotrichaceae_bacterium | + |
| SPC00021 | SPC10001 | Blautia_producta | Erysipelotrichaceae_bacterium | ++++ |
| SPC00026 | SPC10001 | Clostridium_nexile | Erysipelotrichaceae_bacterium | |
| SPC00027 | SPC10001 | Clostridium_sp_HGF2 | Erysipelotrichaceae_bacterium | -- |
| SPC00009 | SPC10001 | Coprobacillus_sp_D7 | Erysipelotrichaceae_bacterium | − |
| SPC00080 | SPC10001 | Coprococcus_catus | Erysipelotrichaceae_bacterium | |
| SPC00018 | SPC10001 | Dorea_formicigenerans | Erysipelotrichaceae_bacterium | -- |
| SPC00057 | SPC10001 | Dorea_longicatena | Erysipelotrichaceae_bacterium | |
| SPC00008 | SPC10001 | Enterococcus_faecalis | Erysipelotrichaceae_bacterium | ++++ |
| SPC10001 | SPC10001 | Erysipelotrichaceae_bacterium | Erysipelotrichaceae_bacterium | − |
| SPC00001 | SPC10001 | Escherichia_coli | Erysipelotrichaceae_bacterium | ++++ |
| SPC00022 | SPC10001 | Eubacterium_eligens | Erysipelotrichaceae_bacterium | − |
| SPC00054 | SPC10001 | Faecalibacterium_prausnitzii | Erysipelotrichaceae_bacterium | − |
| SPC00056 | SPC10001 | Odoribacter_splanchnicus | Erysipelotrichaceae_bacterium | |
| SPC00061 | SPC10001 | Roseburia_intestinalis | Erysipelotrichaceae_bacterium | − |
| SPC00015 | SPC10001 | Streptococcus_thermophilus | Erysipelotrichaceae_bacterium | |
| SPC10030 | SPC10110 | Bacteroides_ovatus | Escherichia_coli | ++++ |
| SPC00006 | SPC10110 | Bacteroides_sp_1_1_6 | Escherichia_coli | ++++ |
| SPC00007 | SPC10110 | Bacteroides_sp_3_1_23 | Escherichia_coli | ++++ |
| SPC10019 | SPC10110 | Bacteroides_sp_D20 | Escherichia_coli | ++++ |
| SPC00005 | SPC10110 | Bacteroides_vulgatus | Escherichia_coli | ++++ |
| SPC10081 | SPC10110 | Bacteroides_vulgatus | Escherichia_coli | ++++ |
| SPC00021 | SPC10110 | Blautia_producta | Escherichia_coli | ++++ |
| SPC00026 | SPC10110 | Clostridium_nexile | Escherichia_coli | ++++ |
| SPC00027 | SPC10110 | Clostridium_sp_HGF2 | Escherichia_coli | ++++ |
| SPC10097 | SPC10110 | Collinsella_aerofaciens | Escherichia_coli | ++++ |
| SPC00009 | SPC10110 | Coprobacillus_sp_D7 | Escherichia_coli | ++ |
| SPC00080 | SPC10110 | Coprococcus_catus | Escherichia_coli | ++++ |
| SPC00018 | SPC10110 | Dorea_formicigenerans | Escherichia_coli | ++++ |
| SPC00057 | SPC10110 | Dorea_longicatena | Escherichia_coli | ++++ |
| SPC00008 | SPC10110 | Enterococcus_faecalis | Escherichia_coli | ++++ |
| SPC10001 | SPC10110 | Erysipelotrichaceae_bacterium | Escherichia_coli | ++++ |
| SPC00001 | SPC00001 | Escherichia_coli | Escherichia_coli | ++++ |
| SPC00001 | SPC10110 | Escherichia_coli | Escherichia_coli | ++++ |
| SPC10110 | SPC10110 | Escherichia_coli | Escherichia_coli | ++++ |
| SPC00022 | SPC10110 | Eubacterium_eligens | Escherichia_coli | ++++ |
| SPC00054 | SPC10110 | Faecalibacterium_prausnitzii | Escherichia_coli | +++ |
| SPC00056 | SPC10110 | Odoribacter_splanchnicus | Escherichia_coli | +++ |
| SPC10048 | SPC10110 | Parabacteroides_merdae | Escherichia_coli | ++++ |
| SPC00061 | SPC10110 | Roseburia_intestinalis | Escherichia_coli | +++ |
| SPC00015 | SPC10110 | Streptococcus_thermophilus | Escherichia_coli | +++ |
| SPC00006 | SPC00022 | Bacteroides_sp_1_1_6 | Eubacterium_eligens | ++++ |
| SPC00007 | SPC00022 | Bacteroides_sp_3_1_23 | Eubacterium_eligens | |
| SPC00005 | SPC00022 | Bacteroides_vulgatus | Eubacterium_eligens | +++ |
| SPC00021 | SPC00022 | Blautia_producta | Eubacterium_eligens | ++++ |
| SPC00009 | SPC00022 | Coprobacillus_sp_D7 | Eubacterium_eligens | |
| SPC00018 | SPC00022 | Dorea_formicigenerans | Eubacterium_eligens | -- |
| SPC00008 | SPC00022 | Enterococcus_faecalis | Eubacterium_eligens | ++++ |
| SPC00001 | SPC00022 | Escherichia_coli | Eubacterium_eligens | ++ |
| SPC00022 | SPC00022 | Eubacterium_eligens | Eubacterium_eligens | |

TABLE 5-continued

Binary pair inhibition of *C. difficile*

| SPC1 | SPC2 | OTU1 | OTU2 | Result |
|---|---|---|---|---|
| SPC00015 | SPC00022 | Streptococcus_thermophilus | Eubacterium_eligens | |
| SPC10211 | SPC10363 | Bacteroides_caccae | Eubacterium_rectale | |
| SPC10213 | SPC10363 | Bacteroides_eggerthii | Eubacterium_rectale | |
| SPC10030 | SPC10363 | Bacteroides_ovatus | Eubacterium_rectale | |
| SPC00006 | SPC10363 | Bacteroides_sp_1_1_6 | Eubacterium_rectale | ++++ |
| SPC00007 | SPC10363 | Bacteroides_sp_3_1_23 | Eubacterium_rectale | +++ |
| SPC10019 | SPC10363 | Bacteroides_sp_D20 | Eubacterium_rectale | -- |
| SPC00005 | SPC10363 | Bacteroides_vulgatus | Eubacterium_rectale | ++++ |
| SPC10081 | SPC10363 | Bacteroides_vulgatus | Eubacterium_rectale | |
| SPC10301 | SPC10363 | Bifidobacterium_adolescentis | Eubacterium_rectale | ++++ |
| SPC10298 | SPC10363 | Bifidobacterium_pseudocatenulatum | Eubacterium_rectale | |
| SPC00021 | SPC10363 | Blautia_producta | Eubacterium_rectale | ++++ |
| SPC10415 | SPC10567 | Blautia_producta | Eubacterium_rectale | ++++ |
| SPC10256 | SPC10567 | *Clostridium butyricum* | Eubacterium_rectale | ++++ |
| SPC10358 | SPC10567 | *Clostridium orbiscindens* | Eubacterium_rectale | + |
| SPC10325 | SPC10567 | Clostridium_bolteae | Eubacterium_rectale | ++ |
| SPC10167 | SPC10567 | Clostridium_disporicum | Eubacterium_rectale | ++++ |
| SPC10243 | SPC10363 | Clostridium_hathewayi | Eubacterium_rectale | ++++ |
| SPC10313 | SPC10567 | Clostridium_hylemonae | Eubacterium_rectale | |
| SPC10202 | SPC10567 | Clostridium_innocuum | Eubacterium_rectale | ++++ |
| SPC10238 | SPC10567 | Clostridium_mayombei | Eubacterium_rectale | ++++ |
| SPC00026 | SPC10363 | Clostridium_nexile | Eubacterium_rectale | - |
| SPC00027 | SPC10363 | Clostridium_sp_HGF2 | Eubacterium_rectale | -- |
| SPC10355 | SPC10363 | Clostridium_symbiosum | Eubacterium_rectale | ++ |
| SPC10355 | SPC10567 | Clostridium_symbiosum | Eubacterium_rectale | + |
| SPC10155 | SPC10567 | Clostridium_tertium | Eubacterium_rectale | ++++ |
| SPC10097 | SPC10363 | Collinsella_aerofaciens | Eubacterium_rectale | ++++ |
| SPC10097 | SPC10567 | Collinsella_aerofaciens | Eubacterium_rectale | ++++ |
| SPC00009 | SPC10363 | Coprobacillus_sp_D7 | Eubacterium_rectale | +++ |
| SPC00080 | SPC10363 | Coprococcus_catus | Eubacterium_rectale | --- |
| SPC10304 | SPC10363 | Coprococcus_comes | Eubacterium_rectale | + |
| SPC10304 | SPC10567 | Coprococcus_comes | Eubacterium_rectale | ++++ |
| SPC00018 | SPC10363 | Dorea_formicigenerans | Eubacterium_rectale | - |
| SPC00057 | SPC10363 | Dorea_longicatena | Eubacterium_rectale | ++++ |
| SPC00008 | SPC10363 | Enterococcus_faecalis | Eubacterium_rectale | ++++ |
| SPC10001 | SPC10363 | Erysipelotrichaceae_bacterium | Eubacterium_rectale | - |
| SPC00001 | SPC10363 | Escherichia_coli | Eubacterium_rectale | ++++ |
| SPC10110 | SPC10363 | Escherichia_coli | Eubacterium_rectale | ++++ |
| SPC00022 | SPC10363 | Eubacterium_eligens | Eubacterium_rectale | |
| SPC10363 | SPC10363 | Eubacterium_rectale | Eubacterium_rectale | +++ |
| SPC10567 | SPC10567 | Eubacterium_rectale | Eubacterium_rectale | |
| SPC00054 | SPC10363 | Faecalibacterium_prausnitzii | Eubacterium_rectale | -- |
| SPC10386 | SPC10567 | Faecalibacterium_prausnitzii | Eubacterium_rectale | |
| SPC10390 | SPC10567 | Lachnospiraceae_bacterium_5_1_57FAA | Eubacterium_rectale | +++ |
| SPC00056 | SPC10363 | Odoribacter_splanchnicus | Eubacterium_rectale | - |
| SPC10048 | SPC10363 | Parabacteroides_merdae | Eubacterium_rectale | - |
| SPC00061 | SPC10363 | Roseburia_intestinalis | Eubacterium_rectale | ---- |
| SPC10470 | SPC10567 | Ruminococcus_bromii | Eubacterium_rectale | + |
| SPC10468 | SPC10567 | Ruminococcus_gnavus | Eubacterium_rectale | ++++ |
| SPC10197 | SPC10363 | Ruminococcus_obeum | Eubacterium_rectale | ++ |
| SPC10233 | SPC10363 | Ruminococcus_torques | Eubacterium_rectale | + |
| SPC00015 | SPC10363 | Streptococcus_thermophilus | Eubacterium_rectale | |
| SPC10211 | SPC10386 | Bacteroides_caccae | Faecalibacterium_prausnitzii | |
| SPC10213 | SPC10386 | Bacteroides_eggerthii | Faecalibacterium_prausnitzii | - |
| SPC10030 | SPC10386 | Bacteroides_ovatus | Faecalibacterium_prausnitzii | - |
| SPC00006 | SPC00054 | Bacteroides_sp_1_1_6 | Faecalibacterium_prausnitzii | ++++ |
| SPC00006 | SPC10386 | Bacteroides_sp_1_1_6 | Faecalibacterium_prausnitzii | +++ |
| SPC00007 | SPC00054 | Bacteroides_sp_3_1_23 | Faecalibacterium_prausnitzii | ++ |
| SPC00007 | SPC10386 | Bacteroides_sp_3_1_23 | Faecalibacterium_prausnitzii | |
| SPC10019 | SPC10386 | Bacteroides_sp_D20 | Faecalibacterium_prausnitzii | -- |
| SPC00005 | SPC00054 | Bacteroides_vulgatus | Faecalibacterium_prausnitzii | ++++ |
| SPC00005 | SPC10386 | Bacteroides_vulgatus | Faecalibacterium_prausnitzii | +++ |
| SPC10081 | SPC10386 | Bacteroides_vulgatus | Faecalibacterium_prausnitzii | --- |
| SPC10301 | SPC10386 | Bifidobacterium_adolescentis | Faecalibacterium_prausnitzii | + |
| SPC10298 | SPC10386 | Bifidobacterium_pseudocatenulatum | Faecalibacterium_prausnitzii | |
| SPC00021 | SPC00054 | Blautia_producta | Faecalibacterium_prausnitzii | ++++ |
| SPC00021 | SPC10386 | Blautia_producta | Faecalibacterium_prausnitzii | ++++ |
| SPC10256 | SPC10386 | *Clostridium butyricum* | Faecalibacterium_prausnitzii | ++++ |
| SPC10358 | SPC10386 | *Clostridium orbiscindens* | Faecalibacterium_prausnitzii | |
| SPC10325 | SPC10386 | Clostridium_bolteae | Faecalibacterium_prausnitzii | ++ |
| SPC10167 | SPC10386 | Clostridium_disporicum | Faecalibacterium_prausnitzii | |
| SPC10243 | SPC10386 | Clostridium_hathewayi | Faecalibacterium_prausnitzii | +++ |
| SPC10313 | SPC10386 | Clostridium_hylemonae | Faecalibacterium_prausnitzii | |
| SPC10202 | SPC10386 | Clostridium_innocuum | Faecalibacterium_prausnitzii | ++++ |
| SPC10238 | SPC10386 | Clostridium_mayombei | Faecalibacterium_prausnitzii | ++++ |
| SPC00026 | SPC00054 | Clostridium_nexile | Faecalibacterium_prausnitzii | |

TABLE 5-continued

Binary pair inhibition of *C. difficile*

| SPC1 | SPC2 | OTU1 | OTU2 | Result |
|------|------|------|------|--------|
| SPC00026 | SPC10386 | Clostridium_nexile | Faecalibacterium_prausnitzii | − |
| SPC00027 | SPC00054 | Clostridium_sp_HGF2 | Faecalibacterium_prausnitzii | ++ |
| SPC00027 | SPC10386 | Clostridium_sp_HGF2 | Faecalibacterium_prausnitzii | −− |
| SPC10355 | SPC10386 | Clostridium_symbiosum | Faecalibacterium_prausnitzii | +++ |
| SPC10355 | SPC10386 | Clostridium_symbiosum | Faecalibacterium_prausnitzii | ++++ |
| SPC10155 | SPC10386 | Clostridium_tertium | Faecalibacterium_prausnitzii | ++++ |
| SPC10097 | SPC10386 | Collinsella_aerofaciens | Faecalibacterium_prausnitzii | ++++ |
| SPC10097 | SPC10386 | Collinsella_aerofaciens | Faecalibacterium_prausnitzii | ++++ |
| SPC00009 | SPC00054 | Coprobacillus_sp_D7 | Faecalibacterium_prausnitzii |  |
| SPC00009 | SPC10386 | Coprobacillus_sp_D7 | Faecalibacterium_prausnitzii | −−− |
| SPC00080 | SPC10386 | Coprococcus_catus | Faecalibacterium_prausnitzii | −−− |
| SPC10304 | SPC10386 | Coprococcus_comes | Faecalibacterium_prausnitzii |  |
| SPC10304 | SPC10386 | Coprococcus_comes | Faecalibacterium_prausnitzii | +++ |
| SPC00018 | SPC00054 | Dorea_formicigenerans | Faecalibacterium_prausnitzii |  |
| SPC00018 | SPC10386 | Dorea_formicigenerans | Faecalibacterium_prausnitzii | −−− |
| SPC00057 | SPC10386 | Dorea_longicatena | Faecalibacterium_prausnitzii | +++ |
| SPC00008 | SPC00054 | Enterococcus_faecalis | Faecalibacterium_prausnitzii | ++++ |
| SPC00008 | SPC10386 | Enterococcus_faecalis | Faecalibacterium_prausnitzii | ++++ |
| SPC10001 | SPC10386 | Erysipelotrichaceae_bacterium | Faecalibacterium_prausnitzii | −− |
| SPC00001 | SPC00054 | Escherichia_coli | Faecalibacterium_prausnitzii | ++++ |
| SPC00001 | SPC10386 | Escherichia_coli | Faecalibacterium_prausnitzii | ++++ |
| SPC10110 | SPC10386 | Escherichia_coli | Faecalibacterium_prausnitzii | ++ |
| SPC00022 | SPC00054 | Eubacterium_eligens | Faecalibacterium_prausnitzii |  |
| SPC00022 | SPC10386 | Eubacterium_eligens | Faecalibacterium_prausnitzii |  |
| SPC10363 | SPC10386 | Eubacterium_rectale | Faecalibacterium_prausnitzii | + |
| SPC00054 | SPC00054 | Faecalibacterium_prausnitzii | Faecalibacterium_prausnitzii | + |
| SPC00054 | SPC10386 | Faecalibacterium_prausnitzii | Faecalibacterium_prausnitzii |  |
| SPC10386 | SPC10386 | Faecalibacterium_prausnitzii | Faecalibacterium_prausnitzii | + |
| SPC10386 | SPC10386 | Faecalibacterium_prausnitzii | Faecalibacterium_prausnitzii |  |
| SPC10390 | SPC10386 | Lachnospiraceae_bacterium_5_1_57FAA | Faecalibacterium_prausnitzii | ++++ |
| SPC00056 | SPC10386 | Odoribacter_splanchnicus | Faecalibacterium_prausnitzii | −− |
| SPC10048 | SPC10386 | Parabacteroides_merdae | Faecalibacterium_prausnitzii | − |
| SPC00061 | SPC10386 | Roseburia_intestinalis | Faecalibacterium_prausnitzii |  |
| SPC10197 | SPC10386 | Ruminococcus_obeum | Faecalibacterium_prausnitzii |  |
| SPC10233 | SPC10386 | Ruminococcus_torques | Faecalibacterium_prausnitzii |  |
| SPC00015 | SPC00054 | Streptococcus_thermophilus | Faecalibacterium_prausnitzii |  |
| SPC00015 | SPC10386 | Streptococcus_thermophilus | Faecalibacterium_prausnitzii |  |
| SPC10211 | SPC10390 | Bacteroides_caccae | Lachnospiraceae_bacterium_5_1_57FAA |  |
| SPC10213 | SPC10390 | Bacteroides_eggerthii | Lachnospiraceae_bacterium_5_1_57FAA |  |
| SPC10030 | SPC10390 | Bacteroides_ovatus | Lachnospiraceae_bacterium_5_1_57FAA | − |
| SPC00006 | SPC10390 | Bacteroides_sp_1_1_6 | Lachnospiraceae_bacterium_5_1_57FAA | +++ |
| SPC00007 | SPC10390 | Bacteroides_sp_3_1_23 | Lachnospiraceae_bacterium_5_1_57FAA |  |
| SPC10019 | SPC10390 | Bacteroides_sp_D20 | Lachnospiraceae_bacterium_5_1_57FAA | −−− |
| SPC00005 | SPC10390 | Bacteroides_vulgatus | Lachnospiraceae_bacterium_5_1_57FAA | +++ |
| SPC10081 | SPC10390 | Bacteroides_vulgatus | Lachnospiraceae_bacterium_5_1_57FAA | −− |
| SPC10301 | SPC10390 | Bifidobacterium_adolescentis | Lachnospiraceae_bacterium_5_1_57FAA | ++++ |
| SPC10298 | SPC10390 | Bifidobacterium_pseudocatenulatum | Lachnospiraceae_bacterium_5_1_57FAA |  |
| SPC00021 | SPC10390 | Blautia_producta | Lachnospiraceae_bacterium_5_1_57FAA | ++++ |
| SPC10415 | SPC10390 | Blautia_producta | Lachnospiraceae_bacterium_5_1_57FAA | ++++ |
| SPC10256 | SPC10390 | *Clostridium butyricum* | Lachnospiraceae_bacterium_5_1_57FAA | ++++ |
| SPC10358 | SPC10390 | *Clostridium orbiscindens* | Lachnospiraceae_bacterium_5_1_57FAA | ++++ |
| SPC10325 | SPC10390 | Clostridium_bolteae | Lachnospiraceae_bacterium_5_1_57FAA | ++++ |
| SPC10167 | SPC10390 | Clostridium_disporicum | Lachnospiraceae_bacterium_5_1_57FAA | ++++ |
| SPC10243 | SPC10390 | Clostridium_hathewayi | Lachnospiraceae_bacterium_5_1_57FAA | ++++ |
| SPC10313 | SPC10390 | Clostridium_hylemonae | Lachnospiraceae_bacterium_5_1_57FAA | ++++ |
| SPC10202 | SPC10390 | Clostridium_innocuum | Lachnospiraceae_bacterium_5_1_57FAA | ++++ |
| SPC10238 | SPC10390 | Clostridium_mayombei | Lachnospiraceae_bacterium_5_1_57FAA | ++++ |
| SPC00026 | SPC10390 | Clostridium_nexile | Lachnospiraceae_bacterium_5_1_57FAA | − |
| SPC00027 | SPC10390 | Clostridium_sp_HGF2 | Lachnospiraceae_bacterium_5_1_57FAA | − |
| SPC10355 | SPC10390 | Clostridium_symbiosum | Lachnospiraceae_bacterium_5_1_57FAA | + |
| SPC10355 | SPC10390 | Clostridium_symbiosum | Lachnospiraceae_bacterium_5_1_57FAA | ++++ |
| SPC10155 | SPC10390 | Clostridium_tertium | Lachnospiraceae_bacterium_5_1_57FAA | ++++ |
| SPC10097 | SPC10390 | Collinsella_aerofaciens | Lachnospiraceae_bacterium_5_1_57FAA | ++++ |
| SPC10097 | SPC10390 | Collinsella_aerofaciens | Lachnospiraceae_bacterium_5_1_57FAA | ++++ |
| SPC00009 | SPC10390 | Coprobacillus_sp_D7 | Lachnospiraceae_bacterium_5_1_57FAA | ++++ |
| SPC00080 | SPC10390 | Coprococcus_catus | Lachnospiraceae_bacterium_5_1_57FAA |  |
| SPC10304 | SPC10390 | Coprococcus_comes | Lachnospiraceae_bacterium_5_1_57FAA |  |
| SPC10304 | SPC10390 | Coprococcus_comes | Lachnospiraceae_bacterium_5_1_57FAA | ++++ |
| SPC00018 | SPC10390 | Dorea_formicigenerans | Lachnospiraceae_bacterium_5_1_57FAA | −− |
| SPC00057 | SPC10390 | Dorea_longicatena | Lachnospiraceae_bacterium_5_1_57FAA | ++++ |
| SPC00008 | SPC10390 | Enterococcus_faecalis | Lachnospiraceae_bacterium_5_1_57FAA | ++++ |
| SPC10001 | SPC10390 | Erysipelotrichaceae_bacterium | Lachnospiraceae_bacterium_5_1_57FAA | −−− |
| SPC00001 | SPC10390 | Escherichia_coli | Lachnospiraceae_bacterium_5_1_57FAA | ++++ |
| SPC10110 | SPC10390 | Escherichia_coli | Lachnospiraceae_bacterium_5_1_57FAA | ++++ |
| SPC00022 | SPC10390 | Eubacterium_eligens | Lachnospiraceae_bacterium_5_1_57FAA |  |
| SPC10363 | SPC10390 | Eubacterium_rectale | Lachnospiraceae_bacterium_5_1_57FAA |  |

TABLE 5-continued

Binary pair inhibition of *C. difficile*

| SPC1 | SPC2 | OTU1 | OTU2 | Result |
|---|---|---|---|---|
| SPC00054 | SPC10390 | Faecalibacterium_prausnitzii | Lachnospiraceae_bacterium_5_1_57FAA | |
| SPC10386 | SPC10390 | Faecalibacterium_prausnitzii | Lachnospiraceae_bacterium_5_1_57FAA | |
| SPC10386 | SPC10390 | Faecalibacterium_prausnitzii | Lachnospiraceae_bacterium_5_1_57FAA | ++++ |
| SPC10390 | SPC10390 | Lachnospiraceae_bacterium_5_1_57FAA | Lachnospiraceae_bacterium_5_1_57FAA | |
| SPC10390 | SPC10390 | Lachnospiraceae_bacterium_5_1_57FAA | Lachnospiraceae_bacterium_5_1_57FAA | ++++ |
| SPC00056 | SPC10390 | Odoribacter_splanchnicus | Lachnospiraceae_bacterium_5_1_57FAA | -- |
| SPC10388 | SPC10390 | Odoribacter_splanchnicus | Lachnospiraceae_bacterium_5_1_57FAA | |
| SPC10048 | SPC10390 | Parabacteroides_merdae | Lachnospiraceae_bacterium_5_1_57FAA | - |
| SPC00061 | SPC10390 | Roseburia_intestinalis | Lachnospiraceae_bacterium_5_1_57FAA | |
| SPC10197 | SPC10390 | Ruminococcus_obeum | Lachnospiraceae_bacterium_5_1_57FAA | |
| SPC10233 | SPC10390 | Ruminococcus_torques | Lachnospiraceae_bacterium_5_1_57FAA | |
| SPC00015 | SPC10390 | Streptococcus_thermophilus | Lachnospiraceae_bacterium_5_1_57FAA | |
| SPC10211 | SPC10388 | Bacteroides_caccae | Odoribacter_splanchnicus | |
| SPC10213 | SPC10388 | Bacteroides_eggerthii | Odoribacter_splanchnicus | - |
| SPC10030 | SPC10388 | Bacteroides_ovatus | Odoribacter_splanchnicus | -- |
| SPC00006 | SPC00056 | Bacteroides_sp_1_1_6 | Odoribacter_splanchnicus | ++++ |
| SPC00006 | SPC10388 | Bacteroides_sp_1_1_6 | Odoribacter_splanchnicus | + |
| SPC00007 | SPC00056 | Bacteroides_sp_3_1_23 | Odoribacter_splanchnicus | + |
| SPC00007 | SPC10388 | Bacteroides_sp_3_1_23 | Odoribacter_splanchnicus | |
| SPC10019 | SPC10388 | Bacteroides_sp_D20 | Odoribacter_splanchnicus | --- |
| SPC00005 | SPC00056 | Bacteroides_vulgatus | Odoribacter_splanchnicus | +++ |
| SPC00005 | SPC10388 | Bacteroides_vulgatus | Odoribacter_splanchnicus | +++ |
| SPC10081 | SPC10388 | Bacteroides_vulgatus | Odoribacter_splanchnicus | - |
| SPC10301 | SPC10388 | Bifidobacterium_adolescentis | Odoribacter_splanchnicus | ++++ |
| SPC10298 | SPC10388 | Bifidobacterium_pseudocatenulatum | Odoribacter_splanchnicus | +++ |
| SPC00021 | SPC00056 | Blautia_producta | Odoribacter_splanchnicus | ++++ |
| SPC00021 | SPC10388 | Blautia_producta | Odoribacter_splanchnicus | ++++ |
| SPC10243 | SPC10388 | Clostridium_hathewayi | Odoribacter_splanchnicus | ++++ |
| SPC00026 | SPC00056 | Clostridium_nexile | Odoribacter_splanchnicus | |
| SPC00026 | SPC10388 | Clostridium_nexile | Odoribacter_splanchnicus | --- |
| SPC00027 | SPC00056 | Clostridium_sp_HGF2 | Odoribacter_splanchnicus | |
| SPC00027 | SPC10388 | Clostridium_sp_HGF2 | Odoribacter_splanchnicus | --- |
| SPC10355 | SPC10388 | Clostridium_symbiosum | Odoribacter_splanchnicus | ++ |
| SPC10097 | SPC10388 | Collinsella_aerofaciens | Odoribacter_splanchnicus | ++++ |
| SPC00009 | SPC00056 | Coprobacillus_sp_D7 | Odoribacter_splanchnicus | - |
| SPC00009 | SPC10388 | Coprobacillus_sp_D7 | Odoribacter_splanchnicus | +++ |
| SPC00080 | SPC10388 | Coprococcus_catus | Odoribacter_splanchnicus | -- |
| SPC10304 | SPC10388 | Coprococcus_comes | Odoribacter_splanchnicus | |
| SPC00018 | SPC00056 | Dorea_formicigenerans | Odoribacter_splanchnicus | |
| SPC00018 | SPC10388 | Dorea_formicigenerans | Odoribacter_splanchnicus | - |
| SPC00057 | SPC10388 | Dorea_longicatena | Odoribacter_splanchnicus | ++++ |
| SPC00008 | SPC00056 | Enterococcus_faecalis | Odoribacter_splanchnicus | ++++ |
| SPC00008 | SPC10388 | Enterococcus_faecalis | Odoribacter_splanchnicus | ++++ |
| SPC10001 | SPC10388 | Erysipelotrichaceae_bacterium | Odoribacter_splanchnicus | -- |
| SPC00001 | SPC00056 | Escherichia_coli | Odoribacter_splanchnicus | ++++ |
| SPC00001 | SPC10388 | Escherichia_coli | Odoribacter_splanchnicus | ++++ |
| SPC10110 | SPC10388 | Escherichia_coli | Odoribacter_splanchnicus | ++++ |
| SPC00022 | SPC00056 | Eubacterium_eligens | Odoribacter_splanchnicus | |
| SPC00022 | SPC10388 | Eubacterium_eligens | Odoribacter_splanchnicus | |
| SPC10363 | SPC10388 | Eubacterium_rectale | Odoribacter_splanchnicus | + |
| SPC00054 | SPC00056 | Faecalibacterium_prausnitzii | Odoribacter_splanchnicus | |
| SPC00054 | SPC10388 | Faecalibacterium_prausnitzii | Odoribacter_splanchnicus | - |
| SPC10386 | SPC10388 | Faecalibacterium_prausnitzii | Odoribacter_splanchnicus | + |
| SPC00056 | SPC10388 | Odoribacter_splanchnicus | Odoribacter_splanchnicus | |
| SPC00056 | SPC10388 | Odoribacter_splanchnicus | Odoribacter_splanchnicus | --- |
| SPC10388 | SPC10388 | Odoribacter_splanchnicus | Odoribacter_splanchnicus | + |
| SPC10048 | SPC10388 | Parabacteroides_merdae | Odoribacter_splanchnicus | |
| SPC00061 | SPC10388 | Roseburia_intestinalis | Odoribacter_splanchnicus | |
| SPC10197 | SPC10388 | Ruminococcus_obeum | Odoribacter_splanchnicus | + |
| SPC10233 | SPC10388 | Ruminococcus_torques | Odoribacter_splanchnicus | |
| SPC00015 | SPC00056 | Streptococcus_thermophilus | Odoribacter_splanchnicus | |
| SPC00015 | SPC10388 | Streptococcus_thermophilus | Odoribacter_splanchnicus | + |
| SPC10030 | SPC10048 | Bacteroides_ovatus | Parabacteroides_merdae | |
| SPC00006 | SPC10048 | Bacteroides_sp_1_1_6 | Parabacteroides_merdae | ++++ |
| SPC00007 | SPC10048 | Bacteroides_sp_3_1_23 | Parabacteroides_merdae | +++ |
| SPC10019 | SPC10048 | Bacteroides_sp_D20 | Parabacteroides_merdae | |
| SPC00005 | SPC10048 | Bacteroides_vulgatus | Parabacteroides_merdae | ++++ |
| SPC00021 | SPC10048 | Blautia_producta | Parabacteroides_merdae | ++++ |
| SPC00026 | SPC10048 | Clostridium_nexile | Parabacteroides_merdae | ++ |
| SPC00027 | SPC10048 | Clostridium_sp_HGF2 | Parabacteroides_merdae | +++ |
| SPC00009 | SPC10048 | Coprobacillus_sp_D7 | Parabacteroides_merdae | - |
| SPC00080 | SPC10048 | Coprococcus_catus | Parabacteroides_merdae | +++ |
| SPC00018 | SPC10048 | Dorea_formicigenerans | Parabacteroides_merdae | |
| SPC00057 | SPC10048 | Dorea_longicatena | Parabacteroides_merdae | |
| SPC00008 | SPC10048 | Enterococcus_faecalis | Parabacteroides_merdae | ++++ |
| SPC10001 | SPC10048 | Erysipelotrichaceae_bacterium | Parabacteroides_merdae | |

TABLE 5-continued

Binary pair inhibition of *C. difficile*

| SPC1 | SPC2 | OTU1 | OTU2 | Result |
|---|---|---|---|---|
| SPC00001 | SPC10048 | Escherichia_coli | Parabacteroides_merdae | ++++ |
| SPC00022 | SPC10048 | Eubacterium_eligens | Parabacteroides_merdae | |
| SPC00054 | SPC10048 | Faecalibacterium_prausnitzii | Parabacteroides_merdae | + |
| SPC00056 | SPC10048 | Odoribacter_splanchnicus | Parabacteroides_merdae | |
| SPC10048 | SPC10048 | Parabacteroides_merdae | Parabacteroides_merdae | +++ |
| SPC00061 | SPC10048 | Roseburia_intestinalis | Parabacteroides_merdae | |
| SPC00015 | SPC10048 | Streptococcus_thermophilus | Parabacteroides_merdae | |
| SPC00006 | SPC00061 | Bacteroides_sp_1_1_6 | Roseburia_intestinalis | ++++ |
| SPC00007 | SPC00061 | Bacteroides_sp_3_1_23 | Roseburia_intestinalis | + |
| SPC00005 | SPC00061 | Bacteroides_vulgatus | Roseburia_intestinalis | + |
| SPC00021 | SPC00061 | Blautia_producta | Roseburia_intestinalis | ++++ |
| SPC00026 | SPC00061 | Clostridium_nexile | Roseburia_intestinalis | − |
| SPC00027 | SPC00061 | Clostridium_sp_HGF2 | Roseburia_intestinalis | −−− |
| SPC00009 | SPC00061 | Coprobacillus_sp_D7 | Roseburia_intestinalis | − |
| SPC00018 | SPC00061 | Dorea_formicigenerans | Roseburia_intestinalis | |
| SPC00057 | SPC00061 | Dorea_longicatena | Roseburia_intestinalis | − |
| SPC00008 | SPC00061 | Enterococcus_faecalis | Roseburia_intestinalis | ++++ |
| SPC00001 | SPC00061 | Escherichia_coli | Roseburia_intestinalis | ++++ |
| SPC00022 | SPC00061 | Eubacterium_eligens | Roseburia_intestinalis | |
| SPC00054 | SPC00061 | Faecalibacterium_prausnitzii | Roseburia_intestinalis | |
| SPC00056 | SPC00061 | Odoribacter_splanchnicus | Roseburia_intestinalis | − |
| SPC00061 | SPC00061 | Roseburia_intestinalis | Roseburia_intestinalis | |
| SPC00015 | SPC00061 | Streptococcus_thermophilus | Roseburia_intestinalis | |
| SPC10415 | SPC10470 | Blautia_producta | Ruminococcus_bromii | ++++ |
| SPC10256 | SPC10470 | *Clostridium butyricum* | Ruminococcus_bromii | ++++ |
| SPC10358 | SPC10470 | *Clostridium orbiscindens* | Ruminococcus_bromii | |
| SPC10325 | SPC10470 | Clostridium_bolteae | Ruminococcus_bromii | +++ |
| SPC10167 | SPC10470 | Clostridium_disporicum | Ruminococcus_bromii | |
| SPC10313 | SPC10470 | Clostridium_hylemonae | Ruminococcus_bromii | |
| SPC10202 | SPC10470 | Clostridium_innocuum | Ruminococcus_bromii | ++++ |
| SPC10238 | SPC10470 | Clostridium_mayombei | Ruminococcus_bromii | ++++ |
| SPC10355 | SPC10470 | Clostridium_symbiosum | Ruminococcus_bromii | ++++ |
| SPC10155 | SPC10470 | Clostridium_tertium | Ruminococcus_bromii | ++++ |
| SPC10097 | SPC10470 | Collinsella_aerofaciens | Ruminococcus_bromii | ++++ |
| SPC10304 | SPC10470 | Coprococcus_comes | Ruminococcus_bromii | ++++ |
| SPC10567 | SPC10470 | Eubacterium_rectale | Ruminococcus_bromii | + |
| SPC10386 | SPC10470 | Faecalibacterium_prausnitzii | Ruminococcus_bromii | |
| SPC10390 | SPC10470 | Lachnospiraceae_bacterium_5_1_57FAA | Ruminococcus_bromii | ++++ |
| SPC10470 | SPC10470 | Ruminococcus_bromii | Ruminococcus_bromii | − |
| SPC10468 | SPC10470 | Ruminococcus_gnavus | Ruminococcus_bromii | ++++ |
| SPC10415 | SPC10468 | Blautia_producta | Ruminococcus_gnavus | ++++ |
| SPC10256 | SPC10468 | *Clostridium butyricum* | Ruminococcus_gnavus | ++++ |
| SPC10358 | SPC10468 | *Clostridium orbiscindens* | Ruminococcus_gnavus | ++++ |
| SPC10325 | SPC10468 | Clostridium_bolteae | Ruminococcus_gnavus | ++++ |
| SPC10167 | SPC10468 | Clostridium_disporicum | Ruminococcus_gnavus | ++++ |
| SPC10313 | SPC10468 | Clostridium_hylemonae | Ruminococcus_gnavus | +++ |
| SPC10202 | SPC10468 | Clostridium_innocuum | Ruminococcus_gnavus | ++++ |
| SPC10238 | SPC10468 | Clostridium_mayombei | Ruminococcus_gnavus | ++++ |
| SPC10355 | SPC10468 | Clostridium_symbiosum | Ruminococcus_gnavus | ++++ |
| SPC10155 | SPC10468 | Clostridium_tertium | Ruminococcus_gnavus | ++++ |
| SPC10097 | SPC10468 | Collinsella_aerofaciens | Ruminococcus_gnavus | ++++ |
| SPC10304 | SPC10468 | Coprococcus_comes | Ruminococcus_gnavus | ++++ |
| SPC10386 | SPC10468 | Faecalibacterium_prausnitzii | Ruminococcus_gnavus | ++++ |
| SPC10390 | SPC10468 | Lachnospiraceae_bacterium_5_1_57FAA | Ruminococcus_gnavus | ++++ |
| SPC10470 | SPC10468 | Ruminococcus_bromii | Ruminococcus_gnavus | ++++ |
| SPC10468 | SPC10468 | Ruminococcus_gnavus | Ruminococcus_gnavus | +++ |
| SPC10030 | SPC10197 | Bacteroides_ovatus | Ruminococcus_obeum | |
| SPC00006 | SPC10197 | Bacteroides_sp_1_1_6 | Ruminococcus_obeum | +++ |
| SPC00007 | SPC10197 | Bacteroides_sp_3_1_23 | Ruminococcus_obeum | +++ |
| SPC10019 | SPC10197 | Bacteroides_sp_D20 | Ruminococcus_obeum | |
| SPC00005 | SPC10197 | Bacteroides_vulgatus | Ruminococcus_obeum | ++++ |
| SPC10081 | SPC10197 | Bacteroides_vulgatus | Ruminococcus_obeum | |
| SPC00021 | SPC10197 | Blautia_producta | Ruminococcus_obeum | ++++ |
| SPC00026 | SPC10197 | Clostridium_nexile | Ruminococcus_obeum | − |
| SPC00027 | SPC10197 | Clostridium_sp_HGF2 | Ruminococcus_obeum | −− |
| SPC10097 | SPC10197 | Collinsella_aerofaciens | Ruminococcus_obeum | ++++ |
| SPC00009 | SPC10197 | Coprobacillus_sp_D7 | Ruminococcus_obeum | + |
| SPC00080 | SPC10197 | Coprococcus_catus | Ruminococcus_obeum | |
| SPC00018 | SPC10197 | Dorea_formicigenerans | Ruminococcus_obeum | ++++ |
| SPC00057 | SPC10197 | Dorea_longicatena | Ruminococcus_obeum | − |
| SPC00008 | SPC10197 | Enterococcus_faecalis | Ruminococcus_obeum | ++++ |
| SPC10001 | SPC10197 | Erysipelotrichaceae_bacterium | Ruminococcus_obeum | |
| SPC00001 | SPC10197 | Escherichia_coli | Ruminococcus_obeum | +++ |
| SPC10110 | SPC10197 | Escherichia_coli | Ruminococcus_obeum | ++++ |
| SPC00022 | SPC10197 | Eubacterium_eligens | Ruminococcus_obeum | + |
| SPC00054 | SPC10197 | Faecalibacterium_prausnitzii | Ruminococcus_obeum | |

TABLE 5-continued

Binary pair inhibition of *C. difficile*

| SPC1 | SPC2 | OTU1 | OTU2 | Result |
|---|---|---|---|---|
| SPC00056 | SPC10197 | Odoribacter_splanchnicus | Ruminococcus_obeum | − |
| SPC10048 | SPC10197 | Parabacteroides_merdae | Ruminococcus_obeum | |
| SPC00061 | SPC10197 | Roseburia_intestinalis | Ruminococcus_obeum | |
| SPC10197 | SPC10197 | Ruminococcus_obeum | Ruminococcus_obeum | ++++ |
| SPC00015 | SPC10197 | Streptococcus_thermophilus | Ruminococcus_obeum | +++ |
| SPC10211 | SPC10233 | Bacteroides_caccae | Ruminococcus_torques | ++++ |
| SPC10213 | SPC10233 | Bacteroides_eggerthii | Ruminococcus_torques | ++++ |
| SPC10030 | SPC10233 | Bacteroides_ovatus | Ruminococcus_torques | ++++ |
| SPC00006 | SPC10233 | Bacteroides_sp_1_1_6 | Ruminococcus_torques | ++++ |
| SPC00007 | SPC10233 | Bacteroides_sp_3_1_23 | Ruminococcus_torques | ++++ |
| SPC10019 | SPC10233 | Bacteroides_sp_D20 | Ruminococcus_torques | ++ |
| SPC00005 | SPC10233 | Bacteroides_vulgatus | Ruminococcus_torques | ++++ |
| SPC10081 | SPC10233 | Bacteroides_vulgatus | Ruminococcus_torques | ++++ |
| SPC00021 | SPC10233 | Blautia_producta | Ruminococcus_torques | ++++ |
| SPC00026 | SPC10233 | Clostridium_nexile | Ruminococcus_torques | + |
| SPC00027 | SPC10233 | Clostridium_sp_HGF2 | Ruminococcus_torques | |
| SPC10097 | SPC10233 | Collinsella_aerofaciens | Ruminococcus_torques | ++++ |
| SPC00009 | SPC10233 | Coprobacillus_sp_D7 | Ruminococcus_torques | ++++ |
| SPC00080 | SPC10233 | Coprococcus_catus | Ruminococcus_torques | + |
| SPC00018 | SPC10233 | Dorea_formicigenerans | Ruminococcus_torques | ++++ |
| SPC00057 | SPC10233 | Dorea_longicatena | Ruminococcus_torques | |
| SPC00008 | SPC10233 | Enterococcus_faecalis | Ruminococcus_torques | ++++ |
| SPC10001 | SPC10233 | Erysipelotrichaceae_bacterium | Ruminococcus_torques | + |
| SPC00001 | SPC10233 | Escherichia_coli | Ruminococcus_torques | ++++ |
| SPC10110 | SPC10233 | Escherichia_coli | Ruminococcus_torques | ++++ |
| SPC00022 | SPC10233 | Eubacterium_eligens | Ruminococcus_torques | ++ |
| SPC00054 | SPC10233 | Faecalibacterium_prausnitzii | Ruminococcus_torques | |
| SPC00056 | SPC10233 | Odoribacter_splanchnicus | Ruminococcus_torques | |
| SPC10048 | SPC10233 | Parabacteroides_merdae | Ruminococcus_torques | + |
| SPC00061 | SPC10233 | Roseburia_intestinalis | Ruminococcus_torques | + |
| SPC10197 | SPC10233 | Ruminococcus_obeum | Ruminococcus_torques | ++++ |
| SPC10233 | SPC10233 | Ruminococcus_torques | Ruminococcus_torques | ++++ |
| SPC00015 | SPC10233 | Streptococcus_thermophilus | Ruminococcus_torques | + |
| SPC00006 | SPC00015 | Bacteroides_sp_1_1_6 | Streptococcus_thermophilus | +++ |
| SPC00007 | SPC00015 | Bacteroides_sp_3_1_23 | Streptococcus_thermophilus | +++ |
| SPC00005 | SPC00015 | Bacteroides_vulgatus | Streptococcus_thermophilus | + |
| SPC00009 | SPC00015 | Coprobacillus_sp_D7 | Streptococcus_thermophilus | + |
| SPC00008 | SPC00015 | Enterococcus_faecalis | Streptococcus_thermophilus | ++++ |
| SPC00001 | SPC00015 | Escherichia_coli | Streptococcus_thermophilus | + |
| SPC00015 | SPC00015 | Streptococcus_thermophilus | Streptococcus_thermophilus | |

TABLE 6

Non-limiting but exemplary ternary combinations include those with mean log reduction greater than 0.171, e.g. any combination shown in Table 6.

| SPC1 | SPC2 | SPC3 | OTU1 | OTU2 |
|---|---|---|---|---|
| SPC10325 | SPC10415 | SPC10567 | Clostridium_bolteae | *Blautia producta* |
| SPC10325 | SPC10355 | SPC10415 | Clostridium_bolteae | Clostridium_symbiosum |
| SPC10325 | SPC10355 | SPC10567 | Clostridium_bolteae | Clostridium_symbiosum |
| SPC10325 | SPC10355 | SPC10386 | Clostridium_bolteae | Clostridium_symbiosum |
| SPC10325 | SPC10355 | SPC10390 | Clostridium_bolteae | Clostridium_symbiosum |
| SPC10325 | SPC10386 | SPC10415 | Clostridium_bolteae | Faecalibacterium_prausnitzii |
| SPC10325 | SPC10386 | SPC10567 | Clostridium_bolteae | Faecalibacterium_prausnitzii |
| SPC10325 | SPC10386 | SPC10390 | Clostridium_bolteae | Faecalibacterium_prausnitzii |
| SPC10325 | SPC10390 | SPC10415 | Clostridium_bolteae | Lachnospiraceae_bacterium_5_1_57FAA |
| SPC10325 | SPC10390 | SPC10567 | Clostridium_bolteae | Lachnospiraceae_bacterium_5_1_57FAA |
| SPC10355 | SPC10415 | SPC10567 | Clostridium_symbiosum | *Blautia producta* |
| SPC10355 | SPC10386 | SPC10415 | Clostridium_symbiosum | Faecalibacterium_prausnitzii |
| SPC10355 | SPC10386 | SPC10567 | Clostridium_symbiosum | Faecalibacterium_prausnitzii |
| SPC10355 | SPC10386 | SPC10390 | Clostridium_symbiosum | Faecalibacterium_prausnitzii |
| SPC10355 | SPC10390 | SPC10415 | Clostridium_symbiosum | Lachnospiraceae_bacterium_5_1_57FAA |
| SPC10355 | SPC10390 | SPC10567 | Clostridium_symbiosum | Lachnospiraceae_bacterium_5_1_57FAA |
| SPC10097 | SPC10415 | SPC10567 | Collinsella_aerofaciens | *Blautia producta* |
| SPC10097 | SPC10325 | SPC10415 | Collinsella_aerofaciens | Clostridium_bolteae |
| SPC10097 | SPC10325 | SPC10355 | Collinsella_aerofaciens | Clostridium_bolteae |
| SPC10097 | SPC10325 | SPC10567 | Collinsella_aerofaciens | Clostridium_bolteae |
| SPC10097 | SPC10325 | SPC10386 | Collinsella_aerofaciens | Clostridium_bolteae |
| SPC10097 | SPC10325 | SPC10390 | Collinsella_aerofaciens | Clostridium_bolteae |
| SPC10097 | SPC10355 | SPC10415 | Collinsella_aerofaciens | Clostridium_symbiosum |
| SPC10097 | SPC10355 | SPC10567 | Collinsella_aerofaciens | Clostridium_symbiosum |
| SPC10097 | SPC10355 | SPC10386 | Collinsella_aerofaciens | Clostridium_symbiosum |

TABLE 6-continued

Non-limiting but exemplary ternary combinations include those with mean log reduction greater than 0.171, e.g. any combination shown in Table 6.

| | | | | |
|---|---|---|---|---|
| SPC10097 | SPC10355 | SPC10390 | Collinsella_aerofaciens | Clostridium_symbiosum |
| SPC10097 | SPC10304 | SPC10415 | Collinsella_aerofaciens | Coprococcus_comes |
| SPC10097 | SPC10304 | SPC10325 | Collinsella_aerofaciens | Coprococcus_comes |
| SPC10097 | SPC10304 | SPC10355 | Collinsella_aerofaciens | Coprococcus_comes |
| SPC10097 | SPC10304 | SPC10567 | Collinsella_aerofaciens | Coprococcus_comes |
| SPC10097 | SPC10304 | SPC10386 | Collinsella_aerofaciens | Coprococcus_comes |
| SPC10097 | SPC10304 | SPC10390 | Collinsella_aerofaciens | Coprococcus_comes |
| SPC10097 | SPC10386 | SPC10415 | Collinsella_aerofaciens | Faecalibacterium_prausnitzii |
| SPC10097 | SPC10386 | SPC10567 | Collinsella_aerofaciens | Faecalibacterium_prausnitzii |
| SPC10097 | SPC10386 | SPC10390 | Collinsella_aerofaciens | Faecalibacterium_prausnitzii |
| SPC10097 | SPC10390 | SPC10415 | Collinsella_aerofaciens | Lachnospiraceae_bacterium_5_1_57FAA |
| SPC10097 | SPC10390 | SPC10567 | Collinsella_aerofaciens | Lachnospiraceae_bacterium_5_1_57FAA |
| SPC10304 | SPC10415 | SPC10567 | Coprococcus_comes | *Blautia producta* |
| SPC10304 | SPC10325 | SPC10415 | Coprococcus_comes | Clostridium_bolteae |
| SPC10304 | SPC10325 | SPC10355 | Coprococcus_comes | Clostridium_bolteae |
| SPC10304 | SPC10325 | SPC10567 | Coprococcus_comes | Clostridium_bolteae |
| SPC10304 | SPC10325 | SPC10386 | Coprococcus_comes | Clostridium_bolteae |
| SPC10304 | SPC10325 | SPC10390 | Coprococcus_comes | Clostridium_bolteae |
| SPC10304 | SPC10355 | SPC10415 | Coprococcus_comes | Clostridium_symbiosum |
| SPC10304 | SPC10355 | SPC10567 | Coprococcus_comes | Clostridium_symbiosum |
| SPC10304 | SPC10355 | SPC10386 | Coprococcus_comes | Clostridium_symbiosum |
| SPC10304 | SPC10355 | SPC10390 | Coprococcus_comes | Clostridium_symbiosum |
| SPC10304 | SPC10386 | SPC10415 | Coprococcus_comes | Faecalibacterium_prausnitzii |
| SPC10304 | SPC10386 | SPC10567 | Coprococcus_comes | Faecalibacterium_prausnitzii |
| SPC10304 | SPC10386 | SPC10390 | Coprococcus_comes | Faecalibacterium_prausnitzii |
| SPC10304 | SPC10390 | SPC10415 | Coprococcus_comes | Lachnospiraceae_bacterium_5_1_57FAA |
| SPC10304 | SPC10390 | SPC10567 | Coprococcus_comes | Lachnospiraceae_bacterium_5_1_57FAA |
| SPC10386 | SPC10415 | SPC10567 | Faecalibacterium_prausnitzii | *Blautia producta* |
| SPC10386 | SPC10390 | SPC10415 | Faecalibacterium_prausnitzii | Lachnospiraceae_bacterium_5_1_57FAA |
| SPC10386 | SPC10390 | SPC10567 | Faecalibacterium_prausnitzii | Lachnospiraceae_bacterium_5_1_57FAA |
| SPC10390 | SPC10415 | SPC10567 | Lachnospiraceae_bacterium_5_1_57FAA | *Blautia producta* |

| SPC1 | SPC2 | SPC3 | OTU3 | Results |
|---|---|---|---|---|
| SPC10325 | SPC10415 | SPC10567 | Eubacterium_rectale | ++++ |
| SPC10325 | SPC10355 | SPC10415 | *Blautia producta* | ++++ |
| SPC10325 | SPC10355 | SPC10567 | Eubacterium_rectale | − |
| SPC10325 | SPC10355 | SPC10386 | Faecalibacterium_prausnitzii | − |
| SPC10325 | SPC10355 | SPC10390 | Lachnospiraceae_bacterium_5_1_57FAA | |
| SPC10325 | SPC10386 | SPC10415 | *Blautia producta* | ++++ |
| SPC10325 | SPC10386 | SPC10567 | Eubacterium_rectale | |
| SPC10325 | SPC10386 | SPC10390 | Lachnospiraceae_bacterium_5_1_57FAA | ++++ |
| SPC10325 | SPC10390 | SPC10415 | *Blautia producta* | ++++ |
| SPC10325 | SPC10390 | SPC10567 | Eubacterium_rectale | + |
| SPC10355 | SPC10415 | SPC10567 | Eubacterium_rectale | ++++ |
| SPC10355 | SPC10386 | SPC10415 | *Blautia producta* | ++++ |
| SPC10355 | SPC10386 | SPC10567 | Eubacterium_rectale | |
| SPC10355 | SPC10386 | SPC10390 | Lachnospiraceae_bacterium_5_1_57FAA | + |
| SPC10355 | SPC10390 | SPC10415 | *Blautia producta* | ++++ |
| SPC10355 | SPC10390 | SPC10567 | Eubacterium_rectale | |
| SPC10097 | SPC10415 | SPC10567 | Eubacterium_rectale | ++++ |
| SPC10097 | SPC10325 | SPC10415 | *Blautia producta* | ++++ |
| SPC10097 | SPC10325 | SPC10355 | Clostridium_symbiosum | ++++ |
| SPC10097 | SPC10325 | SPC10567 | Eubacterium_rectale | ++++ |
| SPC10097 | SPC10325 | SPC10386 | Faecalibacterium_prausnitzii | ++++ |
| SPC10097 | SPC10325 | SPC10390 | Lachnospiraceae_bacterium_5_1_57FAA | ++++ |
| SPC10097 | SPC10355 | SPC10415 | *Blautia producta* | ++++ |
| SPC10097 | SPC10355 | SPC10567 | Eubacterium_rectale | |
| SPC10097 | SPC10355 | SPC10386 | Faecalibacterium_prausnitzii | |
| SPC10097 | SPC10355 | SPC10390 | Lachnospiraceae_bacterium_5_1_57FAA | + |
| SPC10097 | SPC10304 | SPC10415 | *Blautia producta* | ++++ |
| SPC10097 | SPC10304 | SPC10325 | Clostridium_bolteae | ++++ |
| SPC10097 | SPC10304 | SPC10355 | Clostridium_symbiosum | +++ |
| SPC10097 | SPC10304 | SPC10567 | Eubacterium_rectale | +++ |
| SPC10097 | SPC10304 | SPC10386 | Faecalibacterium_prausnitzii | ++++ |
| SPC10097 | SPC10304 | SPC10390 | Lachnospiraceae_bacterium_5_1_57FAA | +++ |
| SPC10097 | SPC10386 | SPC10415 | *Blautia producta* | ++++ |
| SPC10097 | SPC10386 | SPC10567 | Eubacterium_rectale | +++ |
| SPC10097 | SPC10386 | SPC10390 | Lachnospiraceae_bacterium_5_1_57FAA | +++ |
| SPC10097 | SPC10390 | SPC10415 | *Blautia producta* | ++++ |
| SPC10097 | SPC10390 | SPC10567 | Eubacterium_rectale | ++++ |
| SPC10304 | SPC10415 | SPC10567 | Eubacterium_rectale | ++++ |
| SPC10304 | SPC10325 | SPC10415 | *Blautia producta* | ++++ |
| SPC10304 | SPC10325 | SPC10355 | Clostridium_symbiosum | |
| SPC10304 | SPC10325 | SPC10567 | Eubacterium_rectale | −− |
| SPC10304 | SPC10325 | SPC10386 | Faecalibacterium_prausnitzii | +++ |
| SPC10304 | SPC10325 | SPC10390 | Lachnospiraceae_bacterium_5_1_57FAA | +++ |

TABLE 6-continued

Non-limiting but exemplary ternary combinations include those with mean log reduction greater than 0.171, e.g. any combination shown in Table 6.

| | | | | |
|---|---|---|---|---|
| SPC10304 | SPC10355 | SPC10415 | Blautia producta | ++++ |
| SPC10304 | SPC10355 | SPC10567 | Eubacterium_rectale | --- |
| SPC10304 | SPC10355 | SPC10386 | Faecalibacterium_prausnitzii | |
| SPC10304 | SPC10355 | SPC10390 | Lachnospiraceae_bacterium_5_1_57FAA | |
| SPC10304 | SPC10386 | SPC10415 | Blautia producta | ++++ |
| SPC10304 | SPC10386 | SPC10567 | Eubacterium_rectale | - |
| SPC10304 | SPC10386 | SPC10390 | Lachnospiraceae_bacterium_5_1_57FAA | |
| SPC10304 | SPC10390 | SPC10415 | Blautia producta | ++++ |
| SPC10304 | SPC10390 | SPC10567 | Eubacterium_rectale | |
| SPC10386 | SPC10415 | SPC10567 | Eubacterium_rectale | ++++ |
| SPC10386 | SPC10390 | SPC10415 | Blautia producta | ++++ |
| SPC10386 | SPC10390 | SPC10567 | Eubacterium_rectale | |
| SPC10390 | SPC10415 | SPC10567 | Eubacterium_rectale | ++++ |

OTUs that comprise an augmented ecology are not present in the patient prior to treatment and/or exist at extremely low frequencies such that they do not comprise a significant fraction of the total microbial carriage and are not detectable by genomic and/or microbiological assay methods. OTUs that are members of the engrafting and augmented ecologies were identified by characterizing the OTUs that increase in their relative abundance post treatment and that respectively are: (i) present in the ethanol treated spore preparation and absent in the patient pretreatment, or (ii) absent in the ethanol treated spore preparation, but increase in their relative abundance through time post treatment with the preparation due to the formation of favorable growth conditions by the treatment. Notably, the latter OTUs can grow from low frequency reservoirs in the patient, or be introduced from exogenous sources such as diet. OTUs that comprise a "core" augmented or engrafted ecology can be defined by the percentage of total patients in which they are observed to engraft and/or augment; the greater this percentage the more likely they are to be part of a core ecology responsible for catalyzing a shift away from a dysbiotic ecology. The dominant OTUs in an ecology can be identified using several methods including but not limited to defining the OTUs that have the greatest relative abundance in either the augmented or engrafted ecologies and defining a total relative abundance threshold. As example, the dominant OTUs in the augmented ecology of Patient-1 were Identified by defining the OTUs with the greatest relative abundance, which together comprise 60% of the microbial carriage in this patient's augmented ecology.

TABLE 16

Bacterial OTUs associated with engraftment and ecological augmentation and establishment of a more diverse microbial ecology in patients treated with an ethanol treated spore preparation.

| OTU | Phylo-genetic Clade | Spore Forming OTU | Dominant OTU in Augmented Ecology |
|---|---|---|---|
| Bacteroides sp. 2_1_22 | clade38 | N | Y |
| Streptococcus anginosus | clade60 | N | |
| Prevotella intermedia | clade81 | N | |
| Prevotella nigrescens | clade81 | N | |
| Oribacterium sp. ACB7 | clade90 | N | |
| Prevotella salivae | clade104 | N | |
| Bacteroides intestinalis | clade171 | N | Y |
| Bifidobacterium dentium | clade172 | N | |
| Alcaligenes faecalis | clade183 | N | |
| Rothia dentocariosa | clade194 | N | |

TABLE 16-continued

Bacterial OTUs associated with engraftment and ecological augmentation and establishment of a more diverse microbial ecology in patients treated with an ethanol treated spore preparation.

| OTU | Phylo-genetic Clade | Spore Forming OTU | Dominant OTU in Augmented Ecology |
|---|---|---|---|
| Peptoniphilus lacrimalis | clade291 | N | |
| Anaerococcus sp. gpac155 | clade294 | N | |
| Sutterella stercoricanis | clade302 | N | Y |
| Bacteroides sp. 3_1_19 | clade335 | N | Y |
| Parabacteroides goldsteinii | clade335 | N | |
| Bacteroides dorei | clade378 | N | Y |
| Bacteroides massiliensis | clade378 | N | |
| Lactobacillus iners | clade398 | N | |
| Granulicatella adiacens | clade460 | N | |
| Eggerthella sp. 1_3_56FAA | clade477 | N | |
| Gordonibacter pamelaeae | clade477 | N | |
| Finegoldia magna | clade509 | N | |
| Actinomyces nasicola | clade523 | N | |
| Streptobacillus moniliformis | clade532 | N | |
| Oscillospira guilliermondii | clade540 | N | |
| Orientia tsutsugamushi | clade541 | N | |
| Christensenella minuta | clade558 | N | |
| Clostridium oroticum | clade96 | Y | |
| Clostridium sp. D5 | clade96 | Y | |
| Clostridium glycyrrhizinilyticum | clade147 | Y | |
| Coprococcus comes | clade147 | Y | |
| Ruminococcus lactaris | clade147 | Y | |
| Ruminococcus torques | clade147 | Y | Y |
| Clostridiales sp. SS3/4 | clade246 | Y | |
| Clostridium hylemonae | clade260 | Y | |
| Clostridium aerotolerans | clade269 | Y | |
| Clostridium asparagiforme | clade300 | Y | Y |
| Clostridium sp. M62/1 | clade300 | Y | |
| Clostridium symbiosum | clade300 | Y | |
| Lachnospiraceae genomosp. C1 | clade300 | Y | |
| Blautia sp. M25 | clade304 | Y | Y |
| Blautia stercoris | clade304 | Y | |
| Ruminococcus hansenii | clade304 | Y | |
| Ruminococcus obeum | clade304 | Y | |
| Ruminococcus sp. 5_1_39BFAA | clade304 | Y | |
| Bryantella formatexigens | clade309 | Y | |
| Eubacterium cellulosolvens | clade309 | Y | |
| Clostridium sp. HGF2 | clade351 | Y | |
| Clostridium bartlettii | clade354 | Y | |
| Clostridium bifermentans | clade354 | Y | |
| Clostridium glycolicum | clade354 | Y | |
| Eubacterium tenue | clade354 | Y | |
| Dorea formicigenerans | clade360 | Y | |
| Dorea longicatena | clade360 | Y | |
| Lachnospiraceae bacterium 2_1_46FAA | clade360 | Y | |
| Lachnospiraceae bacterium 9_1_43BFAA | clade360 | Y | Y |

TABLE 16-continued

Bacterial OTUs associated with engraftment and ecological augmentation and establishment of a more diverse microbial ecology in patients treated with an ethanol treated spore preparation.

| OTU | Phylogenetic Clade | Spore Forming OTU | Dominant OTU in Augmented Ecology |
|---|---|---|---|
| Ruminococcus gnavus | clade360 | Y | |
| Clostridium hathewayi | clade362 | Y | |
| Blautia hydrogenotrophica | clade368 | Y | |
| Clostridiaceae bacterium END-2 | clade368 | Y | |
| Roseburia faecis | clade369 | Y | |
| Roseburia hominis | clade370 | Y | |
| Roseburia intestinalis | clade370 | Y | |
| Eubacterium sp. WAL 14571 | clade384 | Y | |
| Erysipelotrichaceae bacterium 5_2_54FAA | clade385 | Y | |
| Eubacterium biforme | clade385 | Y | |
| Eubacterium dolichum | clade385 | Y | |
| Coprococcus catus | clade393 | Y | |
| Acetivibrio ethanolgignens | clade396 | Y | |
| Anaerosporobacter mobilis | clade396 | Y | |
| Bacteroides pectinophilus | clade396 | Y | |
| Eubacterium hallii | clade396 | Y | |
| Eubacterium xylanophilum | clade396 | Y | |
| Anaerostipes caccae | clade408 | Y | |
| Clostridiales bacterium 1_7_47FAA | clade408 | Y | |
| Clostridium aldenense | clade408 | Y | |
| Clostridium citroniae | clade408 | Y | |
| Eubacterium hadrum | clade408 | Y | Y |
| Acetanaerobacterium elongatum | clade439 | Y | |
| Faecalibacterium prausnitzii | clade478 | Y | |
| Gemmiger formicilis | clade478 | Y | Y |
| Eubacterium ramulus | clade482 | Y | |
| Lachnospiraceae bacterium 3_1_57FAA_CT1 | clade483 | Y | |
| Lachnospiraceae bacterium A4 | clade483 | Y | Y |
| Lachnospiraceae bacterium DJF VP30 | clade483 | Y | |
| Holdemania filiformis | clade485 | Y | |
| Clostridium orbiscindens | clade494 | Y | |
| Pseudoflavonifractor capillosus | clade494 | Y | |
| Ruminococcaceae bacterium D16 | clade494 | Y | |
| Acetivibrio cellulolyticus | clade495 | Y | |
| Eubacterium limosum | clade512 | Y | |
| Anaerotruncus colihominis | clade516 | Y | |
| Clostridium methylpentosum | clade516 | Y | |
| Clostridium sp. YIT 12070 | clade516 | Y | |
| Hydrogenoanaerobacterium saccharovorans | clade516 | Y | |
| Eubacterium ventriosum | clade519 | Y | |
| Eubacterium eligens | clade522 | Y | |
| Lachnospira pectinoschiza | clade522 | Y | |
| Lactobacillus rogosae | clade522 | Y | Y |
| Clostridium leptum | clade537 | Y | |
| Eubacterium coprostanoligenes | clade537 | Y | |
| Ruminococcus bromii | clade537 | Y | |
| Clostridium viride | clade540 | Y | |
| Butyrivibrio crossotus | clade543 | Y | |
| Coprococcus eutactus | clade543 | Y | |
| Eubacterium ruminantium | clade543 | Y | |
| Eubacterium rectale | clade568 | Y | Y |
| Roseburia inulinivorans | clade568 | Y | |
| Butyricicoccus pullicaecorum | clade572 | Y | |
| Eubacterium desmolans | clade572 | Y | |
| Papillibacter cinnamivorans | clade572 | Y | |
| Sporobacter termitidis | clade572 | Y | |
| Clostridium lactatifermentans | clade576 | Y | |

TABLE 18

Reduction in the opportunistic pathogen or pathobiont load by ethanol treated spores.

| | Pretreatment | Day 5 | Day 14 | Day 25 |
|---|---|---|---|---|
| Klebsiella (% of total reads) | 20.27% | 1.32% | 7.62% | 0.00% |
| Fusobacterium (% total of reads) | 19.14% | 3.01% | 0.01% | 0.00% |

TABLE 19

Changes in Enterobacteria as a function of treatment measured on Simmons Citrate Agar

| Patient | Organism | Pretreatment titer (cfu/g) | Day 25 titer (cfu/g) |
|---|---|---|---|
| 1 | Klebsiella pneumoniae | $9 \times 10^6$ | $1 \times 10^3$ |
| 1 | Klebsiella sp. Co9935 | $4 \times 10^6$ | $1 \times 10^3$ |
| 1 | Escherichia coli | $7 \times 10^6$ | $1 \times 10^6$ |
| 2 | Klebsiella sp. Co9935 | $4 \times 10^6$ | $1 \times 10^3$ |
| 4 | Klebsiella pneumoniae | $3 \times 10^8$ | $<1 \times 10^4$ |
| 4 | Klebsiella sp. Co9935 | $6 \times 10^7$ | $<1 \times 10^4$ |
| 5 | Klebsiella pneumoniae | $1 \times 10^6$ | $<1 \times 10^4$ |

TABLE 20

Augmentation of Bacteroides as a function of bacterial composition treatment of Patient 1

| Media | Bacteroides species | Pretreatment titer (cfu/g) | Day 25 titer (cfu/g) |
|---|---|---|---|
| BBE | B. fragilis group | $<2 \times 10^4$ | $3 \times 10^8$ |
| PFA | All Bacteroides | $<2 \times 10^7_{[DC1]}$ | $2 \times 10^{10}$ |

TABLE 21

Bacteroides spp. in Patient 1 post-treatment with the ethanol treated spore preparation based full-length 16S rDNA sequences of isolated strains

| Species | % of total Bacteroides cfu (1.58E10 cfu/g) |
|---|---|
| Bacteroides sp. 4_1_36 | 63% |
| Bacteroides cellulosilyticus | 14% |
| Bacteroides sp. 1_1_30 | 14% |
| Bacteroides uniformis | 4.8% |
| Bacteroides ovatus | 1.7% |
| Bacteroides dorei | 0.91% |
| Bacteroides xylanisolvens | 0.83% |
| Bacteroides sp. 3_1_19 | 0.23% |

TABLE 22

Titers (in cfu/g) of imipenem-resistant M. morganii, P. rettgeri and P. pennerii from Patients B, D & E

| Patient | Organism | Pretreatment titer | Day 28 titer* |
|---|---|---|---|
| Patient 2 | M. morganii | $1 \times 10^4$ | $6 \times 10^2$ |
| Patient 2 | P. rettgeri | $9 \times 10^3$ | $<5 \times 10^1$ |
| Patient 4 | M. morganii | $2 \times 10^4$ | $<5 \times 10^1$ |
| Patient 4 | P. pennerii | $2 \times 10^4$ | $<5 \times 10^1$ |
| Patient 5 | M. morganii | $5 \times 10^3$ | $<5 \times 10^1$ |

*Limit of detection based on plating 200 uL of 10% wt/vol suspension is $5 \times 10^1$

TABLE XXX1

List of representative vitamins, minerals and co-factors

L-glutamine
nickel chloride
$BaCl_2$
hemin
potassium telurite
Fibrinogen
Bacto Vitamin-Free Casamino Acids
cocarboxylase
bovine albumin fraction V
$FeCl_2 \cdot H_2O$
L-cystine•2HCl
Bacto Casamino Acids
Agar
$CuSO_4$
pyridoxine
$SnCl_2 \cdot 2H_2O$
sodium selenite
$CaCl_2$
NaCl
albumin fraction V
vitamin $B_{12}$
folic acid
$ZnCl_2$
$FeSO_4$
oleic acid
$Co(NO_3)_2 \cdot 6H_2O$
L-cystine
$Na_2B_4O_7 \cdot 10H_2O$
$CaSO_4 \cdot 2H_2O$
$AlCl_3$
$SeCl_4$
$Na_2MoO_4 \cdot 2H_2O$
thiamine pyrophosphate
Pyridoxine•HCl
$MnCl_2 \cdot 4H_2O$
aluminum sulphate
$Na_2HPO_4$
$H_3BO_3$
L-cysteine•HCl•$H_2O$
adenine sulfate
long-chain fatty acids
$KNO_3$
sodium metabisulfite
sodium molybdate
$CoCl_2 \cdot 6H_2O$
$Na_2MoO_4$
Castenholz Salts
$NaNO_3$
HCl
L-cysteine
copper sulfate
L-cysteine•HCl
thiamine•HCl
biotin
sodium chloride
thallium acetate
$NiCl_2 \cdot 6H_2O$
$NaVO_3 \cdot H_2O$
nicotinamide adenine dinucleotide
nicotinic acid
$Na_2MoO_4 \cdot H_2O$
$CuCl_2 \cdot 2H_2O$
$FeCl_2 \cdot 4H_2O$
$(NH_4)_2MoO_4$
$MnSO_4$
guanine•HCl
$H_2SO_4$
$CoCl_2$
cholesterol
LiCl
pyridoxine•2HCl
Disodium ethylenediamine tetraacetic acid
Vitamin K1
KBr
alkalinized oleic acid
$ZnSO_4 \cdot 7H_2O$
trypsin inhibitor
KI

TABLE XXX1-continued

List of representative vitamins, minerals and co-factors ethanol
cobalt nitrate
Ethylenediamine tetraacetic acid
$CuSO_4 \cdot 5H_2O$
calcium-D-pathothenate
$Fe(NO_3)_3$
$CaCl_2 \cdot 2H_2O$
Sodium pyruvate
NaOH
p-aminobenzoic acid
a-ketoglutarate
boric acid
casein
Pyridoxine hydrochloride
Dried bovine hemoglobin
$ZnSO_4$
Nicotinamide
$FeCl_3$
$Fe(NO_3)_3 \cdot 6H_2O$
calcium pantothenate
cyanocobalamin
nitrilotriacetic acid
Adenine
sodium tartrate
magnesium sulfate
zinc sulfate
$NaHCO_3$
Glucose
$MgSO_4 \cdot 7H_2O$
$Na_2S \cdot 9H_2O$
riboflavin
ferric pyrophosphate
Essential growth factors V and X
Peptone
$FeSO_4 \cdot 7H_2O$
catalase
$MnSO_4 \cdot 7H_2O$
$CuCl_2$
$Na_2SeO_3 \cdot 5H_2O$
thiamine
$NiCl_2$
sodium tungstate
iron sulfate
calcium chloride
$(NH_4)_6Mo_7O_{24} \cdot 4H_2O$
ACES buffer/KOH
Thioctic acid
succinate
formate
lactate
butyrate
acetate
Vitamin K
Mercaptoethane-sulfonic acid
Lipoic acid
ammonia
heme
S-Adenosylmethionine

TABLE XXX5

List of nitrogen sources.

Ammonia
Nitrite
Nitrate
Urea
Biuret
L-Alanine
L-Arginine
L-Asparagine
L-Aspartic Acid
L-Cysteine
L-Glutamic Acid
Histamine TABLE XXX5-continued

| List of nitrogen sources. |
|---|
| beta-Phenylethyl-amine |
| Tyramine |
| Acetamide |
| Formamide |
| Glucuronamide |
| D,L-Lactamide |
| D-Glucosamine |
| D-Galactosamine |
| D-Mannosamine |
| N-Acetyl-D-Glucosamine |
| N-Acetyl-D-Galactosamine |
| N-Acetyl-D-Mannosamine |
| Adenine |
| Adenosine |
| Cytidine |
| Cytosine |
| Guanine |
| Guanosine |
| Thymine |
| Thymidine |
| Uracil |
| Uridine |
| Inosine |
| Xanthine |
| Xanthosine |
| Acid |
| Alloxan |
| Allantoin |
| Parabanic Acid |
| D,L-alpha-Amino-N-Butyric Acid |
| gamma-Amino-N-Butyric Acid |
| epsilon-Amino-N-Caproic Acid |
| D,L-alpha-Amino-Caprylic Acid |
| delta-Amino-N-Valeric Acid |
| alpha-Amino-N-Valeric Acid |
| Ala-Asp |
| Ala-Gln |
| Ala-Glu |
| Ala-Gly |
| Ala-His |
| Ala-Leu |
| Ala-Thr |
| Gly-Asn |
| Gly-Gln |
| Gly-Glu |
| Gly-Met |
| Met-Ala |
| N-Acetyl-L-Glutamic Acid |
| N-Phthaloyl-L-Glutamic Acid |
| L-Pyroglutamic Acid |
| Hydroxylamine |
| Methylamine |
| N-Amylamine |
| N-Butylamine |
| Ethylamine |
| Ethanolamine |
| Ethylenediamine |
| Putrescine |
| Agmatine |
| L-Glutamine |
| Glycine |
| L-Histidine |
| L-Isoleucine |
| L-Leucine |
| L-Lysine |
| L-Methionine |
| L-Phenylalanine |
| L-Proline |
| L-Serine |
| L-Threonine |
| L-Tryptophan |
| L-Tyrosine |
| L-Valine |
| D-Alanine |
| D-Asparagine |
| D-Aspartic Acid |
| D-Glutamic Acid |
| D-Lysine |
| D-Serine |
| D-Valine |
| L-Citrulline |
| L-Homoserine |
| L-Ornithine |

TABLE X4

| Spore-forming Bacterial Species |
|---|
| *Alkaliphilus metalliredigens* |
| *Ammonifex degensii* |
| *Anaerofustis stercorihominis* |
| *Anaerostipes caccae* |
| *Anaerotruncus colihominis* |
| *Bacillus amyloliquefaciens* |
| *Bacillus anthracis* |
| *Bacillus cellulosilyticus* |
| *Bacillus cereus* |
| *Bacillus clausii* |
| *Bacillus coagulans* |
| *Bacillus cytotoxicus* |
| *Bacillus halodurans* |
| *Bacillus licheniformis* |
| *Bacillus pumilus* |
| *Bacillus subtilis* |
| *Bacillus thuringiensis* |
| *Bacillus weihenstephanensis* |
| *Blautia hansenii* |
| *Brevibacillus brevis* |
| *Bryantella formatexigens* |
| *Caldicellulosiruptor saccharolyticus* |
| *Candidatus Desulforudis audaxviato* |
| *Carboxydibrachium pacificum* |
| *Carboxydothermus hydrogenoformans* |
| *Clostridium acetobutylicum* |
| *Clostridium asparagiforme* |
| *Clostridium bartlettii* |
| *Clostridium beijerinckii* |
| *Clostridium bolteae* |
| *Clostridium botulinum* A str. ATCC 19397 |
| *Clostridium botulinum* B str. Eklund 17B |
| *Clostridium butyricum* pathogenic E4 str. BoNT BL5262 |
| *Clostridium Carboxidivorans* |
| *Clostridium cellulolyticum* |
| *Clostridium cellulovorans* |
| *Clostridium difficile* |
| *Clostridium hathewayi* |
| *Clostridium hylemonae* |
| *Clostridium kluyveri* |
| *Clostridium leptum* |
| *Clostridium methylpentosum* |
| *Clostridium nexile* |
| *Clostridium novyi* NT |
| *Clostridium papyrosolvens* |
| *Clostridium perfringens* |
| *Clostridium phytofermentans* ISDg |
| *Clostridium scindens* |
| *Clostridium* sp. 7_2_43FAA |
| *Clostridium sporogenes* |
| *Clostridium tetani* |
| *Clostridium thermocellum* |
| *Coprococcus comes* |
| *Desulfotomaculum reducens* |
| *Dorea longicatena* |
| *Eubacterium eligens* |
| *Eubacterium hallii* |
| *Eubacterium rectale* |
| *Eubacterium ventriosum* |
| *Faecalibacterium prausnitzii* |
| *Geobacillus kaustophilus* |
| *Geobacillus* sp. G11MC16 |
| *Geobacillus thermodenitrificans* |

TABLE X4-continued

| Spore-forming Bacterial Species |
|---|
| Heliobacterium modesticaldum |
| Lysinibacillus sphaericus |
| Oceanobacillus iheyensis |
| Paenibacillus sp. JDR-2 |
| Pelotomaculum thermopropionicum |
| Roseburia intestinalis |
| Ruminococcus bromii |
| Ruminococcus gnavus |
| Ruminococcus obeum |
| Ruminococcus torques |
| Subdoligranulum variabile |
| Symbiobacterium thermophilum |
| Thermoanaerobacter italicus |
| Thermoanaerobacter tengcongensis |
| Thermoanaerobacterium thermosaccharolyticum |
| Thermosinus carboxydivorans |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11185562B2). An electronic copy of the "Sequence Listing" will also be available from the USPTO upon request and payment of the fee set forth in 37 CFR 1.19(b)(3).

What is claimed is:

1. A composition comprising a population of bacteria, an excipient, and an enteric coating, the composition formulated for oral administration to a mammalian subject, wherein the bacteria consist of spore forming bacteria comprising at least a first and a second spore forming species of bacteria, wherein the first spore forming species of bacteria is *Clostridium bolteae* comprising a 16S sequence having at least 97% sequence identity to SEQ ID No: 559, and the second spore forming species of bacteria is *Clostridium orbiscindens* comprising a 16S sequence having at least 97% sequence identity to SEQ ID No: 609, wherein the first and second spore forming species of bacteria are: (i) isolated, (ii) not identical, and (iii) independently capable of proliferating in a medium comprising a nutrient and having a threshold concentration of the nutrient below a concentration of the nutrient required for *Clostridium difficile* proliferation in the medium.

2. The composition of claim 1, wherein the nutrient comprises a carbohydrate nutrient.

3. The composition of claim 1, wherein the threshold concentration is 90% or less of the concentration of the nutrient required for *Clostridium difficile* proliferation.

4. The composition of claim 1, wherein the threshold concentration is 50% or less of the concentration of the nutrient required for *Clostridium difficile* proliferation.

5. The composition of claim 1, wherein the threshold concentration is 10%, 5%, or 1% of the concentration of the nutrient required for *Clostridium difficile* proliferation.

6. The composition of claim 1, wherein the nutrient comprises a vitamin nutrient.

7. The composition of claim 1, wherein the first and second spore forming species of bacteria are independently capable of proliferating at a rate at least 10% greater than *Clostridium difficile* proliferation rate in the medium, wherein the nutrient comprises one or more carbohydrate nutrients.

8. A method of treating or preventing *Clostridium difficile* infection in a mammalian subject, the method comprising administering to the subject an effective amount of the composition of claim 1, wherein the effective amount prevents or reduces *Clostridium difficile* growth, proliferation, and/or colonization in the subject.

9. The composition of claim 1, wherein the excipient is selected from the group consisting of: a buffering agent, a preservative, a stabilizer, a binder, a compaction agent, a lubricant, a dispersion enhancer, a disintegration agent, a flavoring agent, a sweetener, and a coloring agent.

10. The composition of claim 1, wherein the excipient comprises glycerol.

11. The composition of claim 1, wherein proliferation in the medium is determined by inoculating into the medium at least one bacteria selected from the group consisting of the first spore forming species of bacteria, the second spore forming species of bacteria and *Clostridium difficile*, culturing the at least one bacteria in the medium for a time period, measuring a titer of the at least one bacteria in the medium at several points over the time period, and calculating a growth rate as a difference in the titer over the time period.

12. The composition of claim 11, wherein the medium consists of 0.5% (wt/vol) of a test carbohydrate, 0.125 mg/l biotin, 1 mg/l pyridoxine and pantothenate, 75 mg/l histidine, glycine and tryptophan, 150 mg/l arginine, methionine and threonine, 225 mg/l valine and isoleucine, 300 mg/l leucine, 400 mg/l cysteine, and 450 mg/l proline; and the titer is measured as an OD600; and the growth rate is calculated $\ln(X/X_o)/T$, where X is the OD600 value during a linear portion of growth and T is time (hours).

13. The composition of claim 1, wherein the population of bacteria consists of spores.

14. The composition of claim 1, wherein the spore forming bacteria further comprises a third spore forming species of bacteria, wherein the third spore forming species of bacteria is *Clostridium scindens* comprising a 16S sequence having at least 97% sequence identity to SEQ ID No: 623.

15. The composition of claim 1, wherein the spore forming bacteria further comprises a third spore forming species of bacteria, wherein the third spore forming species of bacteria is *Clostridium symbiosum* comprising a 16S sequence having at least 97% sequence identity to SEQ ID No: 652.

16. The composition of claim 1, wherein the spore forming bacteria further comprises a third and a fourth spore forming species of bacteria, wherein the third spore forming species of bacteria is *Clostridium scindens* comprising a 16S sequence having at least 97% sequence identity to SEQ ID No: 623 and the fourth spore forming species of bacteria is *Clostridium symbiosum* comprising a 16S sequence having at least 97% sequence identity to SEQ ID No: 652.

* * * * *

UNITED STATES PATENT AND TRADEMARK OFFICE
CERTIFICATE OF CORRECTION

PATENT NO. : 11,185,562 B2  
APPLICATION NO. : 14/765814  
DATED : November 30, 2021  
INVENTOR(S) : Cook et al.

Page 1 of 5

It is certified that error appears in the above-identified patent and that said Letters Patent is hereby corrected as shown below:

In the Specification

In Column 5, Line 23, delete "297%" and insert -- $\geq$97% --, therefor.

In Column 5, Line 35, delete "295%" and insert -- $\geq$95% --, therefor.

In Column 6, Lines 5-6, delete "1x10-2%, 1x10-3%, 1x10-4%, 1x10-5%, 1x10-6%, 1x10-7%, 1x10-8" and insert -- $1\times10^{-2}$%, $1\times10^{-3}$%, $1\times10^{-4}$%, $1\times10^{-5}$%, $1\times10^{-6}$%, $1\times10^{-7}$%, $1\times10^{-8}$%, --, therefor.

In Column 7, Line 27, delete "http://www.ncbi.nlm.nih.govlbooks/NBK21090/)," and insert -- ncbi.nlm.nih.gov/books/NBK21090), --, therefor.

In Column 12, Line 47, delete "N-acetyineuraminic" and insert -- N-acetylneuraminic --, therefor.

In Column 14, Line 64, delete "N-acetyineuramic" and insert -- N-acetylneuraminic --, therefor.

In Column 15, Line 11, delete "2930," and insert -- 29, 30, --, therefor.

In Column 15, Line 40, delete "thetaoiotaomicron," and insert -- thetaiotaomicron, --, therefor.

In Column 15, Line 41, delete "Blautda" and insert -- Blautia --, therefor.

In Column 15, Line 51, delete "thetaoiotaomicron," and insert -- thetaiotaomicron, --, therefor.

In Column 15, Lines 64-65, delete "ventriosumi, Faecalibacterum prausnitzli," and insert -- ventriosum, Faecalibacterium prausnitzii, --, therefor.

In Column 15, Line 66, delete "Paracateroides" and insert -- Parabacteroides --, therefor.

In Column 16, Line 1, delete "Rosebura" and insert -- Roseburia --, therefor.

Signed and Sealed this  
Twenty-fifth Day of October, 2022

Katherine Kelly Vidal  
*Director of the United States Patent and Trademark Office*

CERTIFICATE OF CORRECTION (continued)
U.S. Pat. No. 11,185,562 B2

In Column 16, Lines 9-10, delete "reuter;" and insert -- reuteri; --, therefor.

In Column 16, Line 10, delete "hiras," and insert -- hirae, --, therefor.

In Column 16, Line 12, delete "Anserostipes" and insert -- Anaerostipes --, therefor.

In Column 16, Line 38, delete "tertlum," and insert -- tertium, --, therefor.

In Column 16, Line 39, delete "wechii," and insert -- welchii, --, therefor.

In Column 17, Line 8, delete "Bacteroldes" and insert -- Bacteroides --, therefor.

In Column 17, Line 8, delete "eggerthili," and insert -- eggerthii, --, therefor.

In Column 17, Lines 9-10, delete "fragilis-ryhm," and insert -- fragilis-rhyme, --, therefor.

In Column 17, Line 14, delete "thetalotaomicron," and insert -- thetaiotaomicron, --, therefor.

In Column 17, Line 15, delete "Bacteroldes" and insert -- Bacteroides --, therefor.

In Column 17, Line 32, delete "Fusobacterum" and insert -- Fusobacterium --, therefor.

In Column 17, Line 35, delete "bronii," and insert -- bromii, --, therefor.

In Column 17, Line 35, delete "Bifdobacteium" and insert -- Bifidobacterium --, therefor.

In Column 17, Line 45, delete "leichmanii," and insert -- leichmannii, --, therefor.

In Column 17, Line 46, delete "cailidus," and insert -- callidus, --, therefor.

In Column 17, Line 46, delete "Butyrivibro" and insert -- Butyrivibrio --, therefor.

In Column 17, Line 54, delete "Clostidium" and insert -- Clostridium --, therefor.

In Column 17, Line 54, delete "Propionibacterlum" and insert -- Propionibacterium --, therefor.

In Column 17, Line 55, delete "lavefaciens," and insert -- flavefaciens, --, therefor.

In Column 17, Line 59, delete "morbiliorum," and insert -- morbillorum, --, therefor.

In Column 17, Line 65, delete "orails," and insert -- oralis, --, therefor.

In Column 17, Lines 66-67, delete "Desuifomonas" and insert -- Desulfomonas --, therefor.

In Column 17, Line 67, delete "pigr," and insert -- pigra, --, therefor.

CERTIFICATE OF CORRECTION (continued)
U.S. Pat. No. 11,185,562 B2

In Column 18, Line 30, delete "thetaoiotaomicron," and insert -- thetaiotaomicron, --, therefor.

In Column 18, Line 40, delete "ventriosumi," and insert -- ventriosum, --, therefor.

In Column 18, Line 41, delete "prausnitzli," and insert -- prausnitzii, --, therefor.

In Column 18, Line 42, delete "Paracateroides" and insert -- Parabacteroides --, therefor.

In Column 18, Line 49, delete "Enterococus" and insert -- Enterococcus --, therefor.

In Column 19, Line 35, delete "fragilis-ryhm," and insert -- fragilis-rhyme, --, therefor.

In Column 19, Lines 49-50, delete "Thetalotaomicron," and insert -- Thetaiotaomicron, --, therefor.

In Column 19, Line 52, delete "prausnitzil," and insert -- prausnitzii, --, therefor.

In Column 19, Line 65, delete "leichmanii, Ruminococcus cailidus," and insert -- leichmannii, Ruminococcus callidus, --, therefor.

In Column 20, Line 11, delete "morbiliorum," and insert -- morbillorum, --, therefor.

In Column 20, Line 17, delete "orails," and insert -- oralis, --, therefor.

In Column 20, Line 19, delete "spianchnicus," and insert -- splanchnicus, --, therefor.

In Column 20, Line 19, delete "Desuifomonas" and insert -- Desulfomonas --, therefor.

In Column 20, Lines 37-38, delete "Carbapenem-resistent Enterobacterlaceae" and insert -- Carbapenem-resistant Enterobacteriaceae --, therefor.

In Column 20, Line 42, delete "Pleslomonas shlgelloides," and insert -- Plesiomonas shigelloides, --, therefor.

In Column 20, Line 48, delete "Lysteria" and insert -- Listeria --, therefor.

In Column 22, Lines 2-3, delete "$1x10^-_5\%$," and insert -- $1x10^{-5}\%$, --, therefor.

In Column 22, Line 48, delete "Dendrosporobacter" and insert -- Dendrosporobacter, --, therefor.

In Column 23, Line 45, delete "$1x10^6$," and insert -- $1x10^8$, --, therefor.

In Column 26, Line 64, delete "dose" and insert -- close --, therefor.

In Column 29, Line 28, delete "105" and insert -- $10^5$ --, therefor.

In Column 29, Line 32, delete "107" and insert -- $10^7$ --, therefor.

CERTIFICATE OF CORRECTION (continued)
U.S. Pat. No. 11,185,562 B2

In Column 29, Line 34, delete "107" and insert -- $10^7$ --, therefor.

In Column 30, Line 22, delete "fioxin," and insert -- floxin, --, therefor.

In Column 30, Lines 31-32, delete "Foscamet," and insert -- Foscarnet, --, therefor.

In Column 30, Line 33, delete "Lopinavir" and insert -- Lopinavir, --, therefor.

In Column 30, Line 35, delete "Tenofovir" and insert -- Tenofovir, --, therefor.

In Column 30, Line 60, delete "glucocorticolds," and insert -- glucocorticoids, --, therefor.

In Column 31, Line 5, delete "blotin," and insert -- biotin, --, therefor.

In Column 31, Line 59, delete "104" and insert -- $10^4$ --, therefor.

In Column 32, Line 63, delete "MicroAmpe" and insert -- MicroAmp® --, therefor.

In Column 37, Line 59, delete "polyvinylpyrolidone," and insert -- polyvinylpyrrolidone, --, therefor.

In Column 38, Line 42, delete "sylitol," and insert -- xylitol, --, therefor.

In Column 39, Line 55, delete "caranuba" and insert -- carnauba --, therefor.

In Column 42, Line 26, delete "(SPRIME," and insert -- (5PRIME, --, therefor.

In Column 42, Line 65, delete "-1.5 kb" and insert -- ~1.5 kb --, therefor.

In Column 43, Line 13, delete "(SPRIME," and insert -- (5PRIME, --, therefor.

In Column 44, Line 24, delete "DNAcust," and insert -- DNAclust, --, therefor.

In Column 44, Line 39, delete "Wamow" and insert -- Warnow --, therefor.

In Column 47, Line 66, delete "ciprofioxacin" and insert -- ciprofloxacin --, therefor.

In Column 48, Line 53, delete "Borrello" and insert -- Borriello --, therefor.

In Column 51, Line 55, delete "10W" and insert -- $10^6$ --, therefor.

In Column 54, Line 8, delete "104-5" and insert -- $10^{4.5}$ --, therefor.

In Column 59, Line 30, delete "Pheylethyl-amine," and insert -- Phenylethyl-amine, --, therefor.

In Column 60, Line 12, delete "Clostidium" and insert -- Clostridium --, therefor.

CERTIFICATE OF CORRECTION (continued)
U.S. Pat. No. 11,185,562 B2

In Column 60, Lines 60-61, delete "(can we insert a reference for how to perform an RNA-seq experiment?].".

In Column 61, Line 6, delete "201381:3757)," and insert -- 2013 81:3757), --, therefor.

In Column 61, Line 22, delete "(Invitogen," and insert -- (Invitrogen, --, therefor.

In Column 62, Line 66, delete "TbCba)" and insert -- TbCl$_3$) --, therefor.

In Column 66, Line 16, delete "Fusobacterdum" and insert -- Fusobacterium --, therefor.

In Column 67, Line 61, delete "Enterobacterdaceae" and insert -- Enterobacteriaceae --, therefor.

In Columns 67-68, Lines 67-1, delete "rettgert" and insert -- rettgeri --, therefor.

In Column 68, Line 1, delete "pennerii." and insert -- penneri. --, therefor.

In Column 68, Line 12, delete "Enterobactenaceae" and insert -- Enterobacteriaceae --, therefor.

In Column 68, Line 24, delete "pennerii" and insert -- penneri --, therefor.

In Column 80, Line 10, delete "Collineslia" and insert -- Collinsella --, therefor.

In Column 87, Line 23, delete "cystein" and insert -- cysteine --, therefor.

In Column 88, Line 35, delete "thetalotaomicron," and insert -- thetaiotaomicron, --, therefor.

In Column 90, Line 40, delete "Allistipes" and insert -- Alistipes --, therefor.

In Column 90, Line 41, delete "Blauta" and insert -- Blautia --, therefor.

In Column 90, Line 41, delete "hathaweyi," and insert -- hathewayi, --, therefor.

In Column 90, Line 41, delete "Colinsella" and insert -- Collinsella --, therefor.

In Column 90, Line 42, delete "Clostidium" and insert -- Clostridium --, therefor.

In Column 90, Line 43, delete "Colinsella" and insert -- Collinsella --, therefor.

In Column 91, Line 10, delete "Colinsella" and insert -- Collinsella --, therefor.

In Column 190, under "TABLE 22", Line 58, delete "pennerii" and insert -- penneri --, therefor.

In Column 190, under "TABLE 22", Line 64, delete "pennerii" and insert -- penneri --, therefor.